US011739347B2

(12) United States Patent
Gu et al.

(10) Patent No.: US 11,739,347 B2
(45) Date of Patent: Aug. 29, 2023

(54) ADENO-ASSOCIATED VIRUS (AAV) PRODUCER CELL LINE AND RELATED METHODS

(71) Applicant: LONZA WALKERSVILLE, INC., Walkersville, MD (US)

(72) Inventors: Bingnan Gu, Manvel, TX (US); Caitlin M. Guenther, Houston, TX (US); Anandita Seth, Sugar Land, TX (US)

(73) Assignee: LONZA WALKERVILLE, INC., Walkersville, MD (US)

( * ) Notice: Subject to any disclaimer, the term of this patent is extended or adjusted under 35 U.S.C. 154(b) by 753 days.

(21) Appl. No.: 16/719,251

(22) Filed: Dec. 18, 2019

(65) Prior Publication Data

US 2020/0199627 A1 Jun. 25, 2020

Related U.S. Application Data

(60) Provisional application No. 62/866,092, filed on Jun. 25, 2019, provisional application No. 62/783,589, filed on Dec. 21, 2018.

(51) Int. Cl.

*C12N 15/86* (2006.01)
*C12N 15/113* (2010.01)
*C12N 15/864* (2006.01)

(52) U.S. Cl.

CPC ............ *C12N 15/86* (2013.01); *C12N 15/113* (2013.01); *C12N 15/8645* (2013.01); *C12N 2710/10343* (2013.01); *C12N 2830/008* (2013.01)

(58) Field of Classification Search

CPC .................. C12N 15/86; C12N 15/113; C12N 2710/10343

See application file for complete search history.

(56) References Cited

U.S. PATENT DOCUMENTS 5,622,856 A 4/1997 Natsoulis

FOREIGN PATENT DOCUMENTS

WO 2015/162211 A1 10/2015
WO 2018/136566 A1 7/2018
WO 2018/192982 A2 10/2018

OTHER PUBLICATIONS

Smith, R. H., and R. M. Kotin, Apr. 2000, An adeno-associated virus (AAV) initiator protein, Rep78, catalyzes the cleavage and ligation of single-stranded AAV ori DNA, J. Virol. 74(7):3122-3129.*

Li, J., et al., Jul. 1997, Role for highly regulated rep gene expression in adenovirus-associated virus vector production, J. Virol. 71(7):5236-5243.*

Robert et al., "Manufacturing of recombinant adeno-associated viruses using mammalian expression platforms," Biotechnology Journal 12:1600193 (pp. 1-16) (2017).

Nakamura et al., "Development of packaging cell lines for generation of adeno-associated virus vectors by lentiviral gene transfer of trans-complementary components," Eur. J. Haematol. 73:285-294 (2004).

Chu et al., "SV40 DNA Transfection of Cells in Suspension: Analysis of the Efficiency of Transcription and Translation of T Antigen," Gene 13(2): 197-202 (1981).

Clark et al., "Cell Lines for the Production of Recombinant Adeno-Associated Virus," Human Gene Therapy 6:1329-1341 (1995).

Deuschle et al., "Tetracycline-Reversible Silencing of Eukaryotic Promoters," Mol. Cell Biol. 15(4): 1907-1914 (1995).

Graham et al., "A New Technique for the Assay of Infectivity of Human Adenovirus 5 DNA," Virology, 52(2): 456-457 (1973).

Guido et al., "Human bocavirus: Current knowledge and future challenges," World J. Gateroenterol 22:8684-8697, 2016.

Ishibashi et al., "Adenoviruses of animals," The Adenoviruses, Ginsberg, ed., Plenum Press, New York, N.Y., pp. 497-562 (1984).

Kotin, R. M., "Prospects for the Use of Adeno-Associated Virus as a Vector for Human Gene Therapy," Human Gene Therapy 5:793-801 (1994).

Li et al., "Role for Highly Regulated rep Gene Expression in Adeno-Associated Virus Vector Production," Journal of Virology 71:5236-5243 (1997).

Mullick et al., "The cumate gene-switch: a system for regulated expression in mammalian cells," BMC Biotechnology 6:43 (1-18) (2006).

Muzyczka, N., "Use of Adeno-Associated Virus as a General Transduction Vector for Mammalian Cells," Current Topics in Microbiol. and Immunol. 158:97-129 (1992).

Robert et al., "Manufacturing of Recombinant Adeno-Associated Viruses Using Mammalian Expression Platforms," Biotechnology Journal 12(1600193): 1-16 (2017).

Strauss, "Adenovirus infections in humans," In The Adenoviruses, Ginsberg, ed., Plenum Press, New York, N.Y., pp. 451-596 (1984).

Szulc et al., "A versatile tool for conditional gene expression and knockdown," Nature Methods 3:109-116 (2006).

Tordo et al., "A Novel Adeno-Associated Virus Capsid with Enhanced Neurotropism Corrects a Lysosomal Transmembrane Enzyme Deficiency," Brain ePub 141(7): 2014-2031 (2018).

Urabe et al., "Insect Cells as a Factory to Produce Adeno-Associated Virus Type 2 Vectors," Human Gene Therapy 13: 193501943 (2002).

Wiederschain et al., "Single-vector inducible lentiviral RNAi system for oncology target validation," Cell Cycle 8:498-504 (2009).

Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9:1939-1950 (1998).

(Continued)

*Primary Examiner* — Jeffrey S Parkin

(74) *Attorney, Agent, or Firm* — Medler Ferro Woodhouse & Mills PLLC

(57) ABSTRACT

The present disclosure relates to a mammalian cell line for producing adeno-associated virus (AAV), suitably including nucleic acids encoding helper genes and AAV genes, under the control of derepressible promoters. The disclosure also relates to isolated nucleic acid molecules that encode such genes, as well as methods of using the mammalian cells for producing AAVs.

14 Claims, 15 Drawing Sheets

Specification includes a Sequence Listing.

(56) References Cited

OTHER PUBLICATIONS

Huang et al., "Adenovirus early region 4 encodes two gene products with redundant effects in lytic infection," Journal of Virology 63(6):2605-2615 (1989).
Machitani et al., "Development of an adenovirus vector lacking the expression of virus-associates RNAs," Journal of Controlled Release 154(3):285-289 (2011).
Zhou et al., "A New Vector System with Inducible E2a Cell Line for Production of Higher Titer and Safer Adenoviral Vectors," Virology 275(2):348-357 (2000).
Tetracycline On, "Tetracycline (Tet) Inducible Expression". Addgene. Retrieved from https://www.addgene.org/collections/tetracycline/ on Jun. 2, 2023.

* cited by examiner pcDNA3.1-E2A-E4-VA-TetR
11,986 bp pcDNA3.1-E2A-E4-VA-TetR-V2
11,641 bp

| AAV titer (vg/ml) | 1.04E+10 | 1.26E+10 | 1.50E+09 | 3.35E+09 |
|---|---|---|---|---|

PBBG-iHelper-Puro
11,801 bp

PBBG-ITRGFP
7798 bp

PBBG-iRC8
9399 bp

PBBG-iRC9
9393 bp

ADENO-ASSOCIATED VIRUS (AAV) PRODUCER CELL LINE AND RELATED METHODS

CROSS-REFERENCE TO RELATED APPLICATIONS

The present application claims priority to U.S. Provisional Patent Application No. 62/783,589, filed Dec. 21, 2018, and 62/866,092, filed Jun. 25, 2019, the disclosures of each of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Dec. 17, 2019, is named 0132-0049US1 SL.txt and is 364,567 bytes in size.

FIELD OF THE INVENTION

The present disclosure relates to mammalian cell lines for producing adeno-associated virus (AAV). The cells suitably include nucleic acids encoding helper genes and AAV genes, under the control of derepressible promoters. The disclosure also relates to isolated nucleic acid molecules that encode such genes, as well as methods of using the mammalian cells for producing AAVs.

BACKGROUND OF THE INVENTION

The safety profile and long-term expression capacity make adeno-associated virus (AAV) an excellent viral vector for gene therapy in humans. The wildtype AAV genome is composed of a 4.7 kb single-stranded DNA that includes regulatory genes for replication (Rep) and structural genes for Capsid (Cap), flanked by inverted terminal repeats (ITR) for virus replication and packaging. As a dependent virus, AAV replication in host cells requires the coinfection of helper viruses, such as Adenovirus (Ad) and Herpes Simplex virus. Alternatively, the expression of cloned helper genes can also support AAV replication. For instance, recombinant AAV can be produced in HEK293 cells by the co-transfection of three plasmids: pHelper plasmids expressing E2A, E4Orf6 and VA from Adenovirus, pRep-Cap plasmids for Rep and Cap proteins, and AAV transfer plasmids carrying the desired gene of interest (GOI).

Currently, AAV manufacturing relies on several bridging platforms. Besides the triple trasnfection in HEK293 cells noted above, AAV can be produced by co-infection of two baculoviruses expressing Rep-Cap and the GOI, respectively, into insect cells. However, these baculoviruses are unstable at higher passage and are time-consuming to prepare (see, e.g., Urabe et al., "Insect Cells as a Factory to Produce Adeno-Associated Virus Type 2 Vectors," *Human Gene Therapy* 13:1935-1943 (2002)). HeLa packaging cells with stably integrated Rep-Cap and GOI have also been developed. These systems, nevertheless, still require the wildtype Adenovirus as a helper virus, which poses risks of contamination of replicative adenovirus in AAV products (see, e.g., Robert et al., "Manufacturing of recombinant adeno-associated viruses using mammalian expression platforms," *Biotechnology Journal* 12: 1600193 (1-16) (2017).

What are needed, are cell lines and related methods for production of AAV that are easily scalable to large volume production, to provide reproducible and stable results, while limiting contamination and reducing cost.

SUMMARY OF THE INVENTION

In some embodiments, provided herein is a mammalian cell for producing an adeno-associated virus (AAV), comprising a nucleic acid molecule encoding a viral helper gene under control of a first derepressible promoter, a nucleic acid molecule encoding an AAV gene under control of a second derepressible promoter, and a nucleic acid molecule encoding a repressor element of the first and the second derepressible promoters.

In additional embodiments, provided herein is a mammalian cell for producing an adeno-associated virus (AAV), comprising a nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

In further embodiments, provided herein is an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

In still further embodiments, provided herein is a method of producing an adeno-associated virus (AAV) in a mammalian cell comprising transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, and harvesting the AAV.

In further embodiments, provided herein is a method of treatment with an adeno-associated virus (AAV) comprising: transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, harvesting the AAV and administering the AAV to a mammalian patient.

In still further embodiments, provided herein is a method of producing an adeno-associated virus (AAV) comprising: transfecting a mammalian cell stably expressing one or more nucleic acids encoding TetR and/or TetR-KRAB with a first nucleic acid encoding an adenovirus helper gene comprising an E2A gene, a E4Orf gene and a viral-associated non-coding RNA under control of a first derepressible promoter, a second nucleic acid encoding an AAV gene comprising Rep and Cap genes under control of a second derepressible promoter, and, optionally, a third nucleic acid encoding a gene of interest under control of a third derepressible promoter, treating the mammalian cell with a binding partner of the TetR and/or TetR-KRAB, activating the first, second, and third derepressible promoters, producing the AAV, and harvesting the AAV.

In still further embodiments, provided herein is a method for producing an adeno-associated virus (AAV), comprising: stably transfecting a mammalian cell with a nucleic acid encoding a TetR and/or TetR-KRAB repressor, chicken hypersensitive site-4 (cHS4) sequences flanking the TetR and/or TetR-KRAB repressor, and a selection gene, transfecting the stably transfected mammalian cell with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the mammalian cell with a binding partner of the TetR; activating the first, second and third derepressible promoters; producing the AAV; and harvesting the AAV.

DETAILED DESCRIPTION OF THE INVENTION

Figure 1:
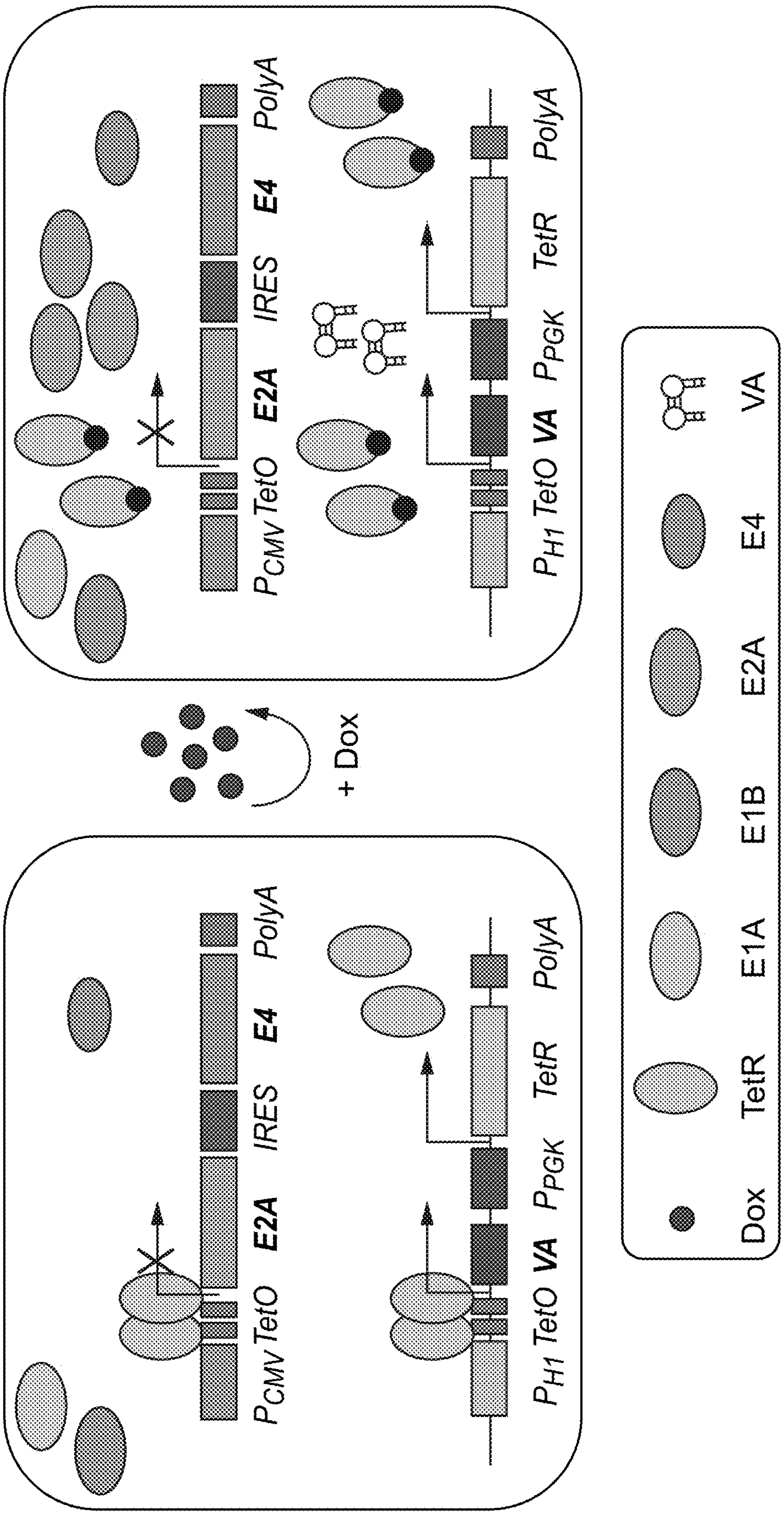
FIG. 1 shows a schematic of the use of derepressible promoters to control the expression of helper and VA genes in accordance with embodiments hereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

Adeno-associated virus (AAV) has emerged as the vector of choice for gene therapy in over 120 clinical trials worldwide. The fast-growing demand of recombinant AAV requires highly efficient and robust manufacturing platforms. However, current methods for AAV production, including transient transfection and helper virus systems, are extremely costly and lab-intensive. Described herein is a plasmid/helper virus-free AAV producer cell line, and methods of use thereof, that provides efficient AAV manufacturing for a long-term solution at significantly reduced cost. The AAV producer cell line described herein represents a next generation platform for both clinical and commercial AAV manufacturing.

Thus, in embodiments, provided herein is a mammalian cell for producing an adeno-associated virus (AAV).

As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g. POTELLIGENT®, Lonza, Slough, UK), a CHOK1SV GS-KO (glutamine synthetase knockout) cell including all variants (e.g., XCEED™ Lonza, Slough, UK). Exemplary human cells include human embryonic kidney (HEK) cells, such as HEK293, a HeLa cell, or a HT1080 cell.

Mammalian cells include mammalian cell cultures which can be either adherent cultures or suspension cultures. Adherent cultures refer to cells that are grown on a substrate surface, for example a plastic plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

As used herein, the term "adeno-associated virus (AAV)" refers to a small sized, replicative-defective nonenveloped virus containing a single stranded DNA of the family Parvoviridae and the genus Dependoparvovirus. Over 10 adeno-associated virus serotypes have been identified so far, with serotype AAV2 being the best characterized. Other non-limiting examples of AAV serotypes are ANC80, AAV1, AAV3, AAV4, AAV5, AAV6, AAV7, AAV8, AAV9, AAV10, and AAV11. In addition to these serotypes, AAV pseudotypes have been developed. An AAV pseudotype contains the capsid of a first serotype and the genome of a second serotype (e.g. the pseudotype AAV2/5 would correspond to an AAV with the genome of serotype AAV2 and the capsid of AAV5).

As referred to herein, the term "adenovirus" refers to a nonenveloped virus with an icosahedral nucleocapsid containing a double stranded DNA of the family Adenoviridae. Over 50 adenoviral subtypes have been isolated from humans and many additional subtypes have been isolated from other mammals and birds. Birds. See, e.g., Ishibashi et al., "Adenoviruses of animals," In *The Adenoviruses*, Ginsberg, ed., Plenum Press, New York, N.Y., pp. 497-562 (1984); Strauss, "Adenovirus infections in humans," In *The Adenoviruses*, Ginsberg, ed., Plenum Press, New York, N.Y., pp. 451-596 (1984). These subtypes belong to the family Adenoviridae, which is currently divided into two genera, namely Mastadenovirus and Aviadenovirus. All adenoviruses are morphologically and structurally similar. In humans, however, adenoviruses show diverging immunological properties and are, therefore, divided into serotypes. Two human serotypes of adenovirus, namely AV2 and AV5, have been studied intensively and have provided the majority of general information about adenoviruses.

In embodiments, the mammalian cell provided herein suitably includes a nucleic acid molecule encoding a viral helper gene under control of a first derepressible promoter, a nucleic acid molecule encoding an AAV gene under control of a second derepressible promoter, and a nucleic acid molecule encoding a repressor element of the first and the second derepressible promoters.

In exemplary embodiments, the nucleic acid molecules encoding the various components for producing an AAV are contained within the mammalian cell in separate nucleic acid molecules, for example separate plasmids or vectors. In other embodiments, the nucleic acid molecules encoding the various components for producing an AAV are included on the same plasmid or vector. In further embodiments, certain of the components are contained on the same nucleic acid molecule (e.g., helper genes and AAV gens), while other genes are contained on separate nucleic acid molecules (e.g., gene encoding the repressor element).

A "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

In the various embodiments described herein, the nucleic acid molecules are capable of encoding the various genes. That is the nucleic acid molecules, when transcribed, produce mRNA for the genes described herein, which is then translated to the desired or required proteins.

As described herein, suitably the mammalian cells include a nucleic acid molecule encoding a viral helper gene. Viral helper genes include various adenoviral virus genes, herpes virus genes and bocavirus genes (see, e.g., Guido et al., "Human bocavirus: Current knowledge and future challenges," *World J. Gateroenterol* 22:8684-8697, the disclosure of which is incorporated by reference herein in its entirety). In exemplary embodiments, the viral helper gene is an adenovirus helper gene. As referred to herein, the term "adenovirus helper gene" or "AV helper gene" refers to a gene that is composed of one or more nucleic acid sequences derived from one or more adenovirus subtypes or serotypes that contributes to Adeno-associated virus replication and packaging. In some embodiments, the Adenovirus helper gene is E1A, E1B, E2A, E4 (including E4Orf6), VA, or a combination thereof or any other adenovirus helper gene. In exemplary embodiments, the adenovirus helper gene comprises both E2A and E4Orf6 genes. Suitably, an internal ribosome entry site (IRES) element is included between the E2A and E4Orf6 genes. The IRES element initiates translation of the E4Orf6 gene after the E2A gene in a single expression cassette, providing stability to the construct.

The various nucleic acid molecules encoding the various genes described herein are suitably under control of a derepressible promoter. As used herein "under control" refers to a gene being regulated by a "promoter," "promoter sequence," or "promoter region," which refers to a DNA regulatory region/sequence capable of binding RNA polymerase and initiating transcription of a downstream coding or non-coding gene sequence. In other words, the promoter and the gene are in operable combination or operably linked. As referred to herein, the terms "in operable combination", "in operable order" and "operably linked" refer to the linkage of nucleic acid sequences in such a manner that a promoter capable of directing the transcription of a given gene and/or the synthesis of a desired protein molecule is produced. The term also refers to the linkage of amino acid sequences in such a manner so that a functional protein is produced.

In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any of the gene products as described herein. In other embodiments as described herein, the promoter is a constitutive promoter, which initiates mRNA synthesis independent of the influence of an external regulation.

Suitably, the promoters used to control the transcription of the various genes for producing the AAVs described herein are derepressible promoters. As used herein, a "derepressible promoter" refers to a structure that includes a functional promoter and additional elements or sequences capable of binding to a repressor element to cause repression of the functional promoter. "Repression" refers to the decrease or inhibition of the initiation of transcription of a downstream coding or non-coding gene sequence by a promoter. A "repressor element" refers to a protein or polypeptide that is capable of binding to a promoter (or near a promoter) so as to decrease or inhibit the activity of the promoter. A repressor element can interact with a substrate or binding partner of the repressor element, such that the repressor element undergoes a conformation change. This conformation change in the repressor element takes away the ability of the repressor element to decrease or inhibit the promoter, resulting in the "derepression" of the promoter, thereby allowing the promoter to proceed with the initiation of transcription. A "functional promoter" refers to a promoter, that absent the action of the repressor element, would be capable of initiation transcription. Various functional promoters that can be used in the practice of the present invention are known in the art, and include for example, $P_{CMV}$, $P_{H1}$, P19, P5, P40 and promoters of Adenovirus helper genes (e.g., E1A, E1B, E2A, E4Orf6, and VA).

Exemplary repressor elements and their corresponding binding partners that can be used as derepressible promoters are known in the art, and include systems such as the cumate gene-switch system (CuO operator, CymR repressor and cumate binding partner) (see, e.g., Mullick et al., "The cumate gene-switch: a system for regulated expression in mammalian cells," *BMC Biotechnology* 6:43 (1-18) (2006), the disclosure of which is incorporated by reference herein in its entirety, including the disclosure of the derepressible promoter system described therein) and the TetO/TetR system described herein (see, e.g., Yao et al., "Tetracycline Repressor, tetR, rather than the tetR-Mammalian Cell Transcription Factor Fusion Derivatives, Regulates Inducible Gene Expression in Mammalian Cells," *Human Gene Therapy* 9:1939-1950 (1998), the disclosure of which is incorporated by reference herein in its entirety).

In exemplary embodiments, the derepressible promoters comprise a functional promoter and two tetracycline operator sequences ($TetO_2$). A schematic showing an exemplary depressible promoter system is provided in FIG. 1. A derepressible promoter including the $P_{CMV}$ promoter, and a derepressible promoter including the $P_{H1}$ promoter, are shown, both including two TetO sequences ($TetO_2$). As illustrated schematically, upon binding of two tetracycline repressor proteins (TetR—the repressor elements for the $TetO_2$ sequences), to the $TetO_2$ sequences, both the $P_{CMV}$ promoter and the $P_{H1}$ promoter are repressed. That is, little or no transcription takes place from these promoters. Upon binding of a binding partner for TetR (suitably Doxycycline (Dox), the TetR proteins change conformation, release from the $TetO_2$ sequences, and the functional promoters begin their normal transcription processes, as they would naturally. As illustrated schematically in FIG. 1, this results in the change of the overall system from an "off" position (where suitably no transcription is taking place from the $P_{CMV}$ promoter and the $P_{H1}$ promoter), to an "on" position when Dox is added, allowing the $P_{CMV}$ promoter and the $P_{H1}$ promoter to return to their natural state of transcribing the genes under their control.

For example, as shown in FIG. 1, the $P_{CMV}$ promoter with $TetO_2$ sequences (suitably the pcDNA4/TO promotor; INVITROGEN®), is in an "off" position when bound by TetR. When Dox is added, the TetR changes conformation, release from the $TetO_2$ sequences of the depressible promoter, and the $P_{CMV}$ promotor proceeds to transcribe the adenoviral helper genes (e.g., E2A and E4).

As described herein, and as illustrated in FIG. 1, the mammalian cell can further comprise a nucleic acid encoding a viral-associated (VA), non-coding RNA under control of a fourth derepressible promoter. As shown in FIG. 1, this derepressible promoter can include the functional promoter PFH, and the $TetO_2$ sequences controlling the expression of the non-coding RNA (see, e.g., Wiederschain et al., "Single-vector inducible lentiviral RNAi system for oncology target validation, *Cell Cycle* 8:498-504 (2009), the disclosure of which is incorporated by reference herein in its entirety, including for the disclosure of the promoter system and sequence). As shown in FIG. 1, the $P_{H1}$ promoter with $TetO_2$ sequences, is in an "off" position when bound by TetR. When Dox is added, the TetR changes conformation, release from the $TetO_2$ sequences of the depressible promoter, and the $P_{H1}$ promotor proceeds to transcribe the VA 1 non-coding RNA.

Figure 2A:
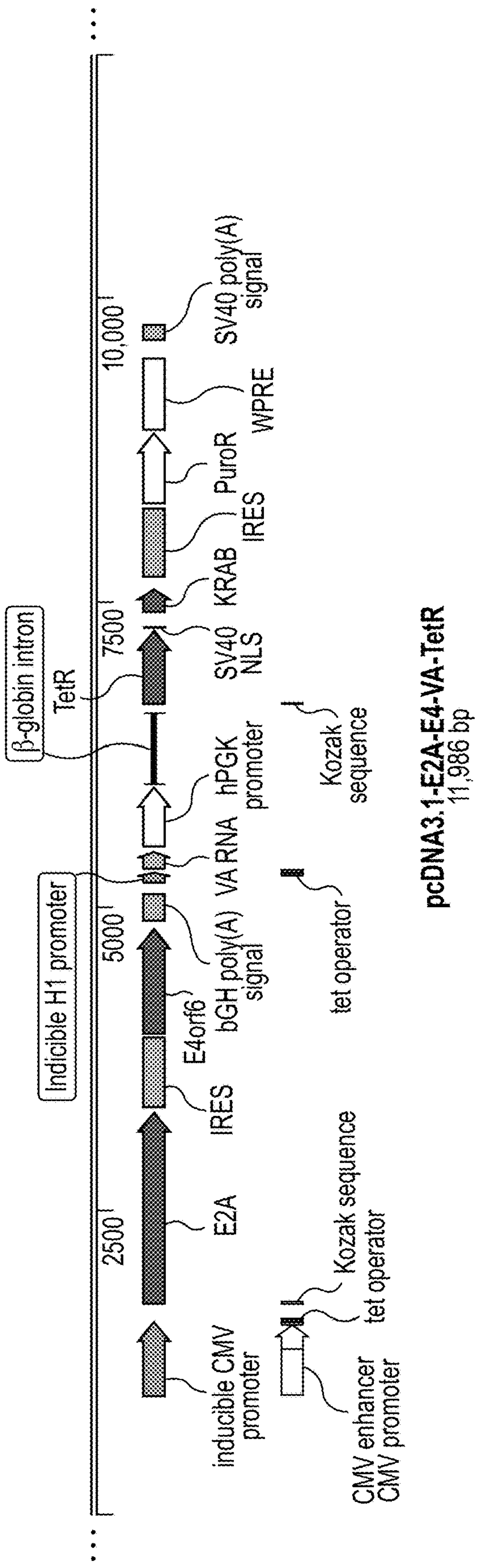
FIGS. 2A and 2B show exemplary nucleic acid molecules for production of helper and VA genes in accordance with embodiments hereof.

FIG. 2A shows an exemplary nucleic acid molecule that can be utilized in the various mammalian cells and methods described herein. As illustrated, a CMV promoter is used upstream of both E2A and E4Orf6 genes, linked via a IRES element. The CMV promoter includes the CMV enhancer and the tet operator ($TetO_2$), for control, via derepression. Also illustrated in FIG. 2A is an exemplary location for the H1 promotor, also including $TetO_2$ sequences, controlling the expression of the VA non-coding RNA.

FIG. 1 and FIG. 2A also illustrate that, in embodiments, the mammalian cells can include the repressor element under control of a constitutive promoter. As described herein, suitably the repressor element that is encoded is a tetracycline repressor protein (TetR). As illustrated in FIG. 1 and FIG. 2A, a suitable promotor for expression of the repressor element is an hPGK promotor. By placing the repressor element under the control of a constitutive promotor, production of the repressor element, suitably TetR, is always active. That is, TetR is being produced upon introduction of the nucleic acid molecule into the mammalian cell. This provides tight control of the various derepressible promoters that are repressed by the TetR binding to the $TetO_2$ sequences.

Figure 2B:
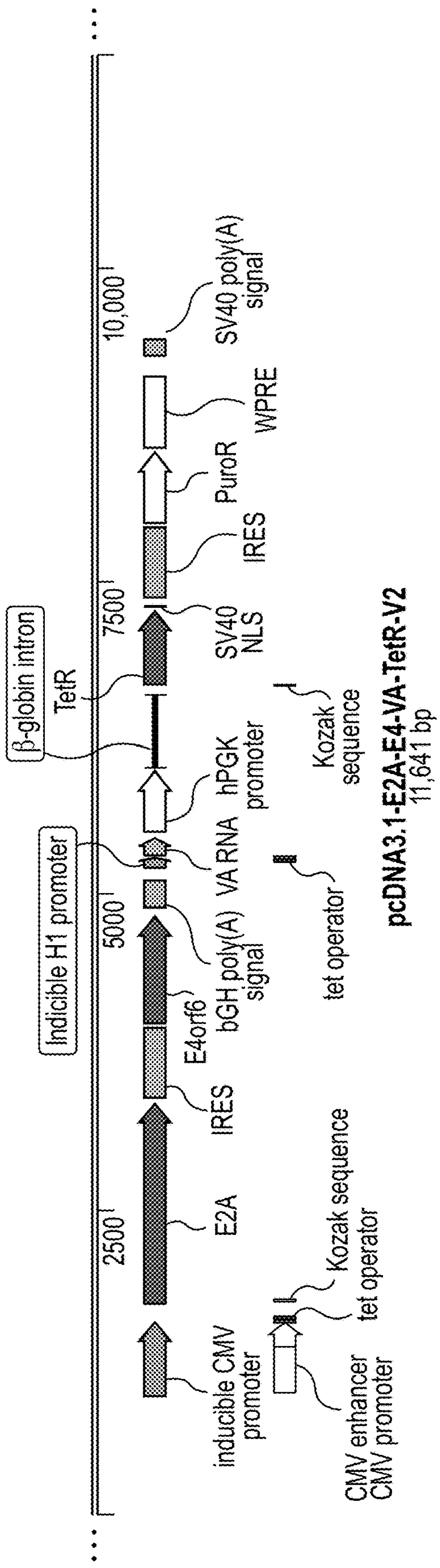
Figure 12A:
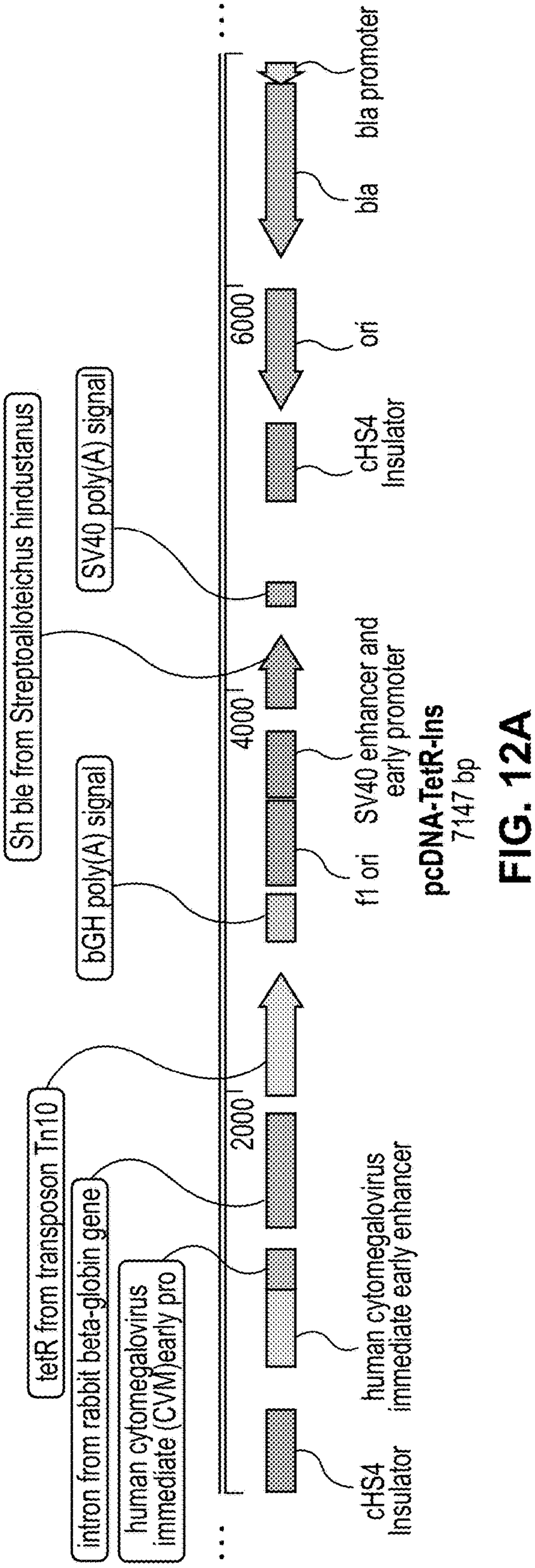
FIGS. 12A-12B show exemplary nucleic acid constructs encoding TetR and TetR-KRAB, in accordance with embodiments hereof.

As shown in FIG. 2A, in exemplary embodiments, a nucleic acid encoding a transcriptional repression domain in frame with the nucleic acid encoding the tetracycline repressor protein, can be included. In FIG. 2A, this transcriptional repression domain is a Krueppel-associated box (KRAB) sequence, fused in frame to the C-terminus of TetR (see, e.g., Szulc et al., "A versatile tool for conditional gene expression and knockdown," *Nature Methods* 3:109-116 (2006)). The use of a KRAB sequence, or other transcriptional repression domain, improves the repressive activity of the TetR when binding to $TetO_2$, thereby minimizing the amount of leakage or basal gene expression prior to derepression (i.e., prior to the addition of Dox). FIG. 2B and FIG. 12A shows an exemplary nucleic acid molecule that lacks the KRAB sequence.

Figure 12B:
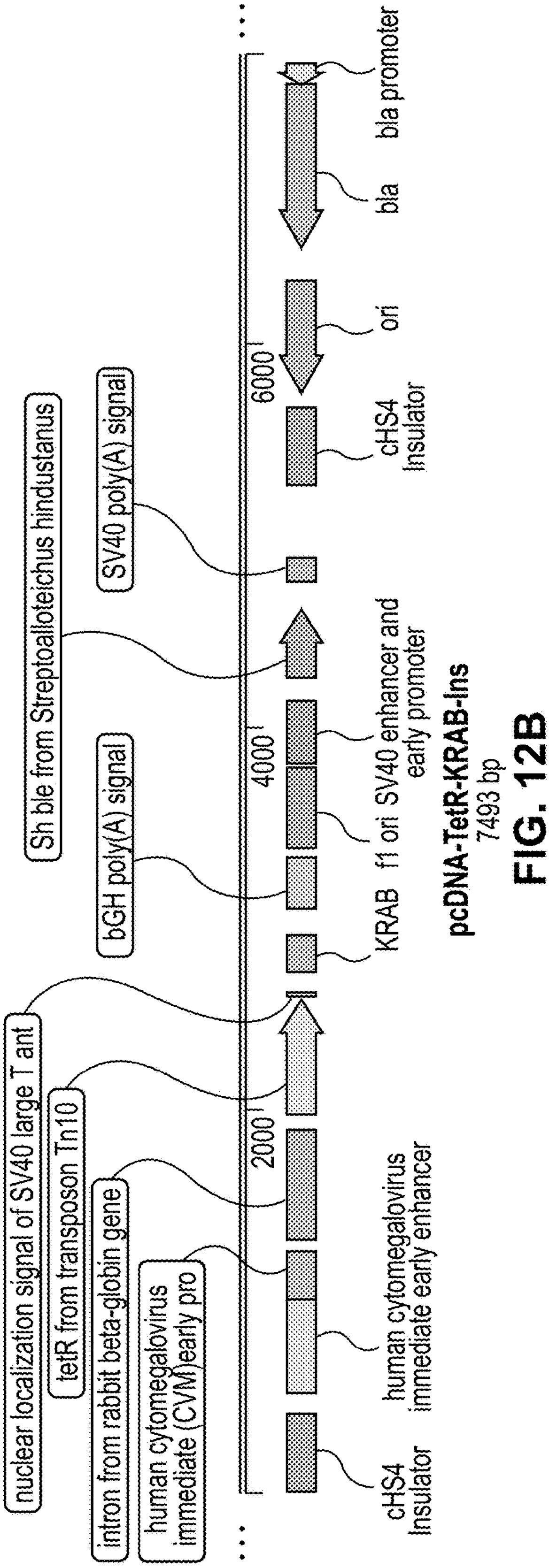

As shown in FIG. 12A, in exemplary embodiments, a nucleic acid encoding the tetracycline repressor protein, can be included or stably expressed within a mammalian cell. In FIG. 2A and FIG. 12B, this transcriptional repression domain is a Krueppel-associated box (KRAB) sequence, fused in frame to the C-terminus of TetR (see, e.g., Szulc et al., "A versatile tool for conditional gene expression and knockdown," *Nature Methods* 3:109-116 (2006)). The use of a KRAB sequence, or other transcriptional repression domain, improves the repressive activity of the TetR when binding to $TetO_2$, thereby minimizing the amount of leakage or basal gene expression prior to derepression (i.e., prior to the addition of Dox). FIG. 2B and FIG. 12A show an exemplary nucleic acid molecule that lacks the KRAB sequence.

In embodiments, the AAV gene that is encoded by the nucleic acid molecule comprises Rep and Cap genes. Other AAV genes that can be encoded by the nucleic acid molecules include any gene from any AAV serotype. In some embodiments, the AAV gene is Rep78, Rep68, Rep 52, Rep40, VP1, VP2, VP3, or a combination thereof. In some embodiments, the AAV gene is from adeno-associated virus type 2. In some embodiments, the AAV gene is from the adeno-associated virus Anc80.

As referred to herein, the term "Rep" gene refers to the art-recognized region of the AAV genome which encodes the replication proteins of the virus which are collectively required for replicating the viral genome, or functional homologues thereof such as the human herpesvirus 6 (HHV-6) rep gene which is also known to mediate AAV-2 DNA replication. Thus, the rep coding region can include the genes encoding for AAV Rep78 and Rep68 (the "long forms of Rep"), and Rep52 and Rep40 (the "short forms of Rep"), or functional homologues thereof. The rep coding region, as used herein, can be derived from any viral serotype, such as the AAV serotypes described herein. The region need not include all wild-type genes but may be altered, (e.g., by insertion, deletion or substitution of nucleotides), so long as the rep genes present provide for sufficient integration functions when expressed in a suitable target cell. See, e.g. Muzyczka, N., *Current Topics in Microbiol. and Immunol.* 158:97-129 (1992); and Kotin, R. M., *Human Gene Therapy* 5:793-801 (1994).

As referred to herein, the term "Cap" gene refers to the art-recognized region of the AAV genome which encodes the capsid proteins of the virus. Illustrative (non-limiting) examples of these capsid proteins are the AAV capsid proteins VP1, VP2, and VP3. Cap genes used in this disclosure can come from any AAV serotype or a combination of AAV serotypes.

Figures 4A, 4B, 4C:
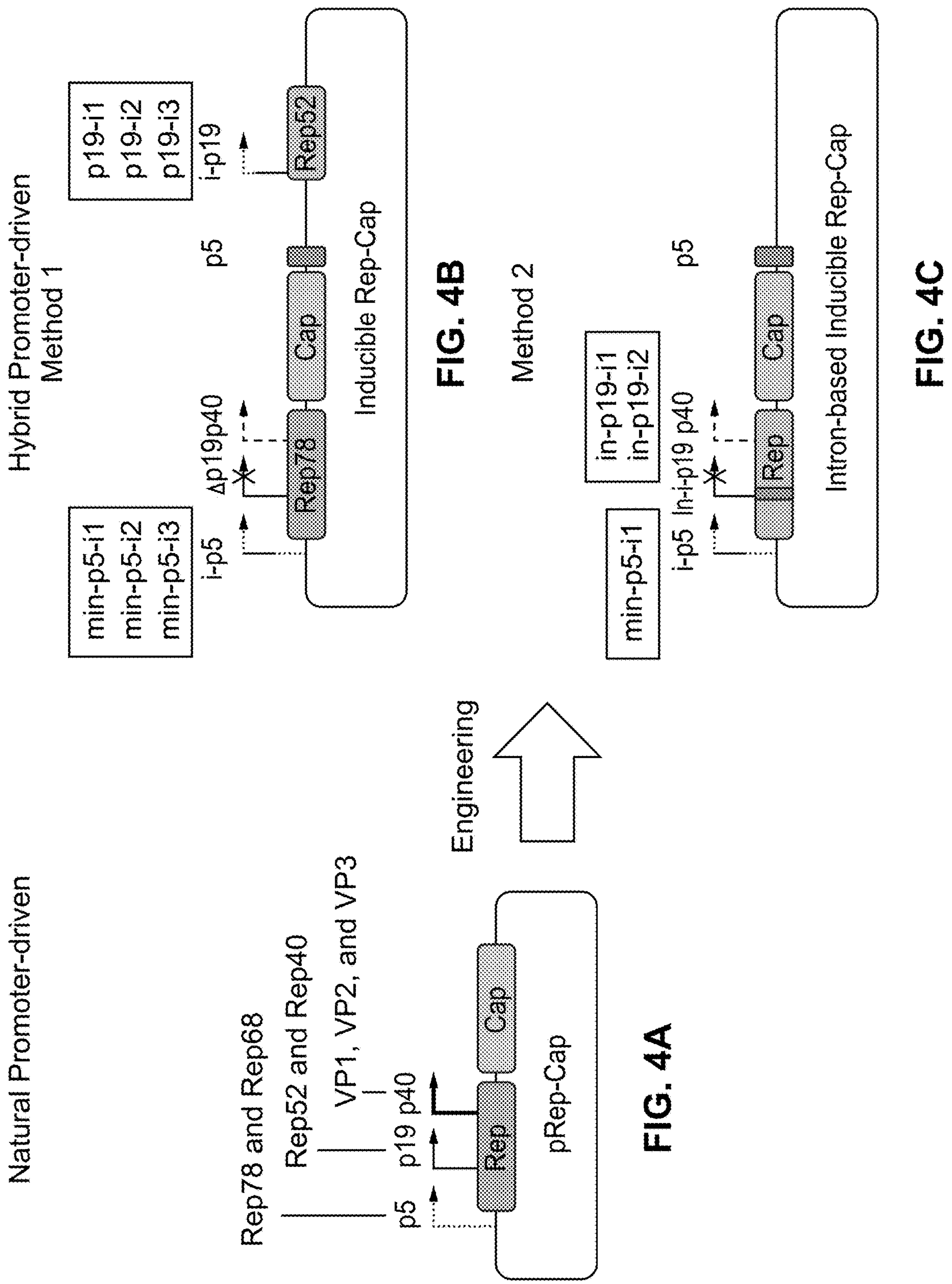
FIGS. 4A-4C shows schematics of derepressible constructs for expression of AAV genes in accordance with embodiments hereof.

FIG. 4A shows the natural location and promoter drivers of Rep and Cap genes. As known in the art, for successful production of AAV, the ratio of Rep78 and Rep52 genes must be maintained at optimum levels. For example, as discussed in Li et al., "Role for Highly Regulated rep Gene Expression in Adeno-Associated Virus Vector Production," *Journal of Virology* 71:5236-5243 (1997) (the disclosure of which is incorporated by reference herein in its entirety), control of the amount of Rep78 production can interference with DNA replication. In addition, Rep78 can be toxic if overly produced in mammalian cells. See, e.g., Clark et al., "Cell Lines for the Production of Recombinant Adeno-Associated Virus," *Human Gene Therapy* 6:1329-1341 (1995), the disclosure of which is incorporated by reference herein in its entirety, discussing that elevate rep protein levels can be associated with cytotoxicity. Also, the location of the promoter for Rep52 expression (p19) is located within the coding region for Rep78. As described herein, various modifications have been made to the natural locations of the Rep genes and promoters to overcome these challenges.

In exemplary embodiments, the mammalian cell can include a nucleic acid encoding a Rep78 gene under control of the second derepressible promoter and a Rep52 gene under control of a third derepressible promoter. As shown in FIG. 4B, one way to achieve this arrangement is to remove the Rep52 gene from within the Rep78 gene, and place it downstream of the Rep78 and Cap genes. The Rep78 gene can be under the control of a derepressible promoter (p5), that includes the $TetO_2$ sequences. In such embodiments, the natural p19 promoter within Rep78 is modified or mutated to be silenced. The removed Rep52 gene is also placed under the control of a derepressible promoter (p19) that includes $TetO_2$ sequences.

Figure 5:
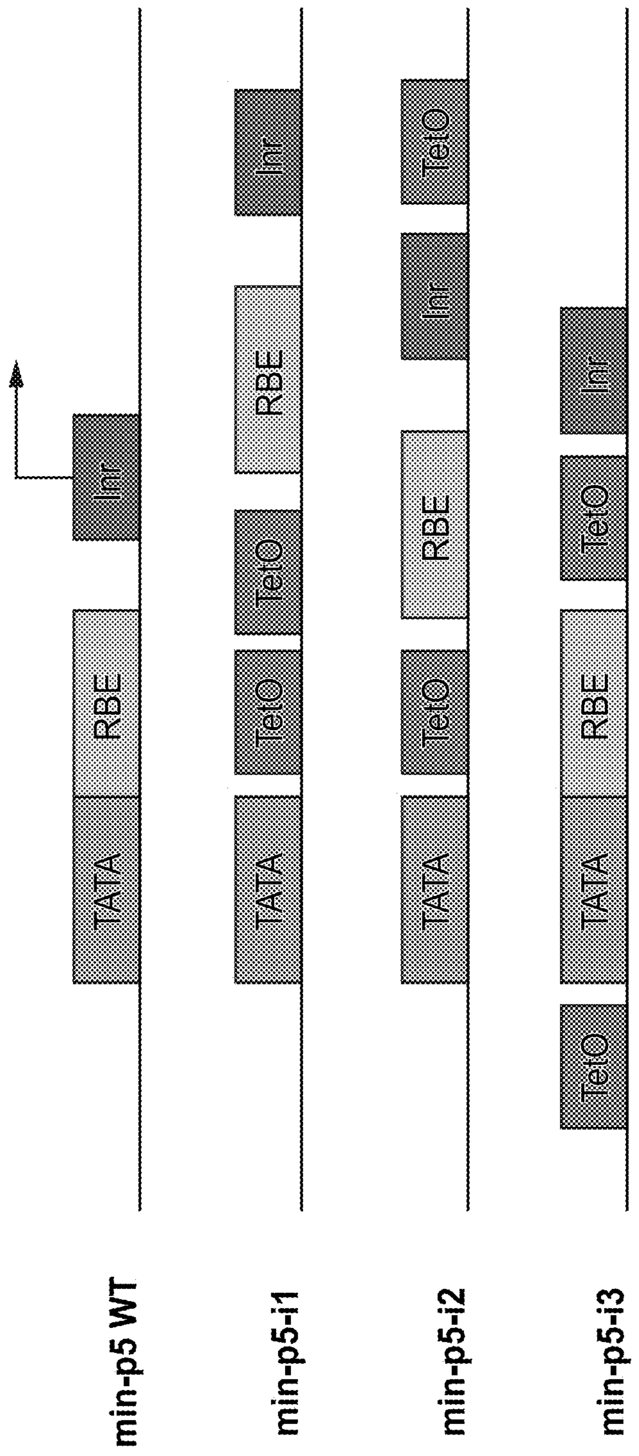
FIG. 5 shows exemplary derepressible p5 promoters in accordance with embodiments hereof.
Figure 6:
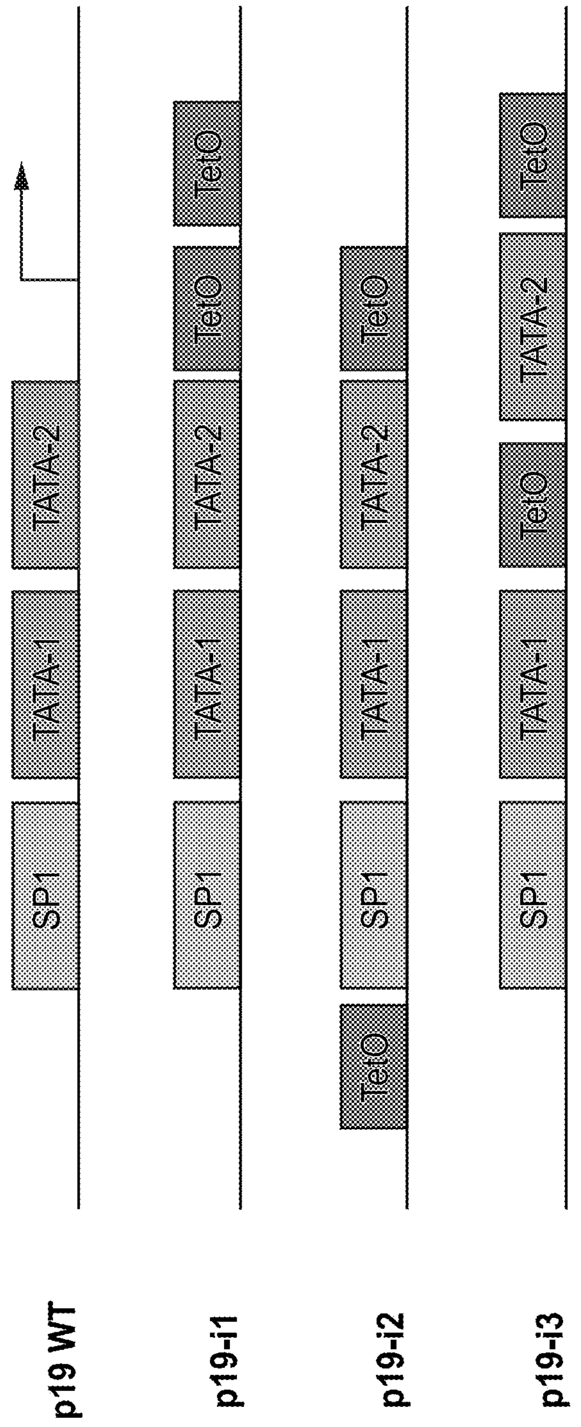
FIG. 6 shows exemplary derepressible p19 promoters in accordance with embodiments hereof.

FIG. 5 shows three potential locations for each of the TetO sequences, relative to the TATA box, rep-binding element (RBE) and initiator element (INR), for modification to the p5 promotor of Rep78. The wild-type p5 promotor is also illustrated schematically. FIG. 6 shows three potential locations for each of the TetO sequences, relative to the TATA boxes and the Spl transcription factor, of the p19 promoter for Rep52. The wild-type p19 promotor is also illustrated schematically. Additional locations of the TetO sequences are also encompassed herein and can readily be envisioned by those of ordinary skill in the art.

In still further embodiments, the Rep78 gene can be under control of a derepressible promoter, and the Rep52 gene can be under control of a derepressible promoter that is contained within an artificial intron. Such an embodiment is represented schematically in FIG. 4C. As illustrated, a derepressible p5 promoter (e.g., including $TetO_2$ sequences as described herein) is placed upstream of a Rep78 gene. A derepressible p19 promoter (e.g., including $TetO_2$ sequences) contained within an intron (designated In-i-p19), controls the expression of Rep52. A schematic of this embodiment is provided in FIG. 7A, where the two tet operator sequences are illustrated within a chimeric intron. This chimeric intron can be inserted at various locations relative to the components of the p19 promoter. For example, as shown in FIG. 7B, the intron sequence is suitably placed downstream of the TATA-2 of the p19 promoter. Spacing can be, for example, between about 1 and 25 base pairs downstream from the TATA-2 sequence.

As described herein, in exemplary embodiments, the Cap gene that is encoded by the nucleic acid molecules is suitably under the control of a native promoter. That is, the Cap gene does not necessarily have to be under the control of a derepressible promoter, though a derepressible promoter can be used if desired. In suitable embodiments, the Cap gene is under the control of a p40 promoter.

In exemplary embodiments, the nucleic acid molecules include two inverted terminal repeat (ITR) sequences. As known in the art, these ITR sequences (i.e., AAV2 ITR) are single stranded sequence of nucleotides, followed downstream by its reverse compliment. ITR sequences represent the minimal sequence required for replication, rescue, packaging and integration of the AAV genome. Suitably, these ITR sequences flank a gene of interest. Thus, in embodiments, the nucleic acid molecules further encode a gene of interest. This gene of interest can be, for example, a reporter gene, a selection gene, or a gene of therapeutic interest, for example.

Figure 10A:
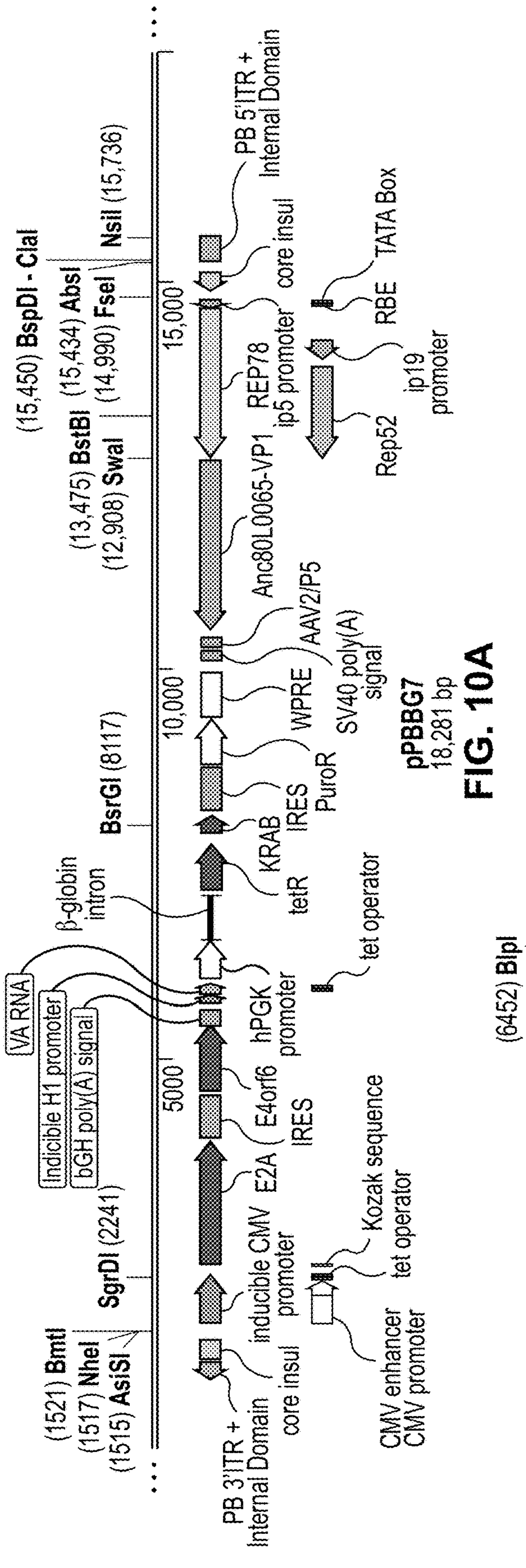
FIGS. 10A-10D show exemplary nucleic acid constructs encoding helper, AAV and VA genes, in accordance with embodiments hereof.
Figure 10B:
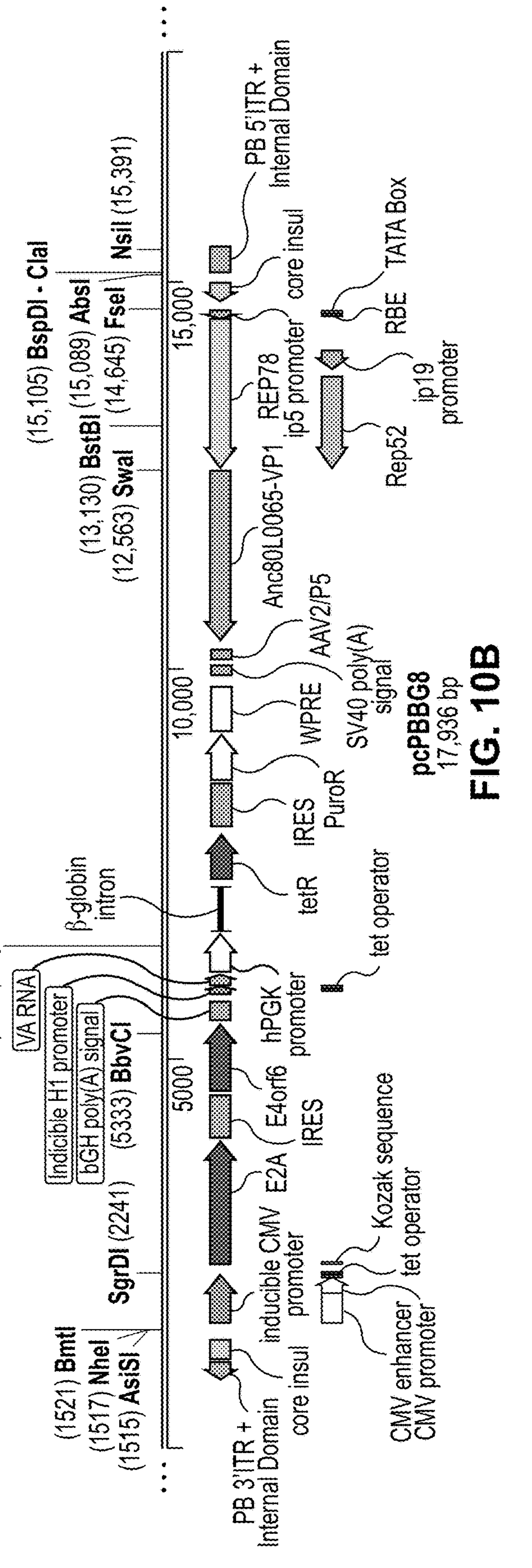
Figure 10C:
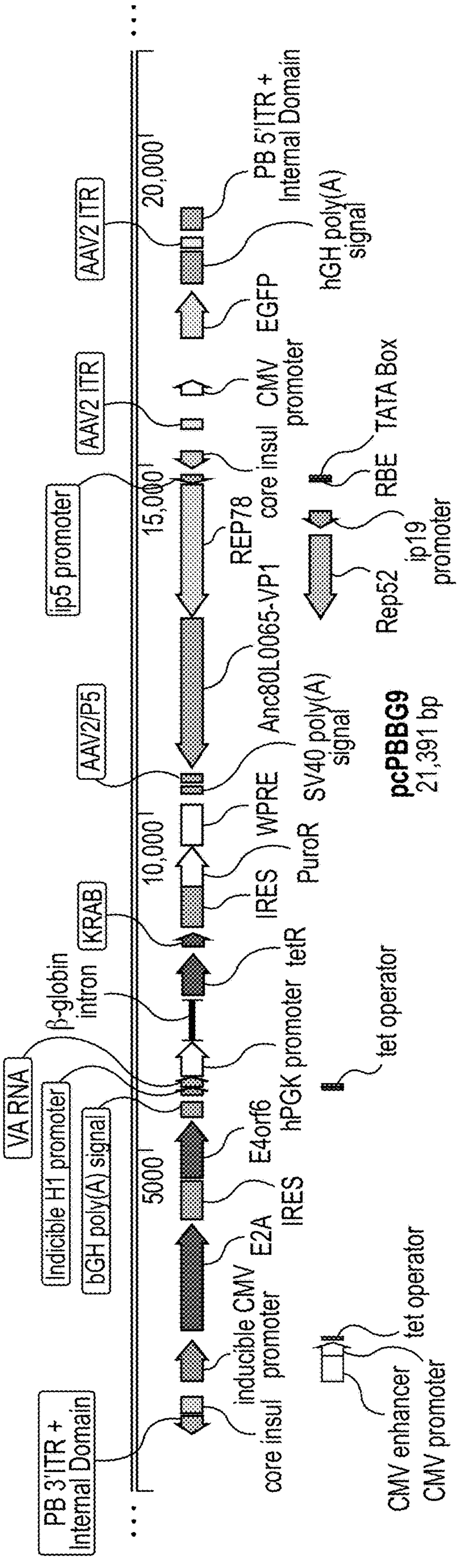

For example, as illustrated in FIG. 10C, a gene of interest, such as the gene encoding green fluorescent protein (EGFP) is flanked by two ITR sequences.

A "gene" refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

As referred to herein, the term "gene of interest" or "GOI" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

As referred to herein, a "reporter gene" is a gene whose expression confers a phenotype upon a cell that can be easily identified and measured. In some embodiments, the reporter gene comprises a fluorescent protein gene. In some embodiments, the reporter gene comprises a selection gene.

As referred to herein, the term "selection gene" refers to the use of a gene which encodes an enzymatic activity that confers the ability to grow in medium lacking what would otherwise be an essential nutrient; in addition, a selection gene may confer resistance to an antibiotic or drug upon the cell in which the selection gene is expressed. A selection gene may be used to confer a particular phenotype upon a host cell. When a host cell must express a selection gene to grow in selective medium, the gene is said to be a positive selection gene. A selection gene can also be used to select against host cells containing a particular gene; a selection gene used in this manner is referred to as a negative selection gene.

As referred to herein, the term "gene of therapeutic interest" refers to any functionally relevant nucleotide sequence. Thus, the gene of therapeutic interest of the present disclosure can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

In some embodiments, the mammalian cells provided herein are substantially free of helper virus. As referred to herein, a "helper virus" is any non-AAV virus that is added to enable the replication and packaging of adeno-associated virus. Representative (non-limiting) examples of helper viruses are adenovirus and herpes virus. In some embodiments, the term substantially free of helper virus refers to a cell that has fewer than 100, fewer than 10, or fewer than 1 helper virus per cell. In some embodiments, the term substantially free of helper virus refers to a cell in which no helper viruses are present or to a population of cells in which no helper viruses are present using detection methods known to those skilled in the art. In some embodiments, no wild-type helper virus is in the cell. In some embodiments, the term wild-type virus refers to any complete-non-AAV virus that can replicate in the cell independently of any other virus.

The AAV producer cells described herein provide a long-term and cost-effective solution for large scale AAV manufacturing. As constitutive expression of either helper or Rep proteins can be cytotoxic, the strategies described herein allow for control of their expression by engineered, derepressible promoters.

In still further embodiments, provided herein is a mammalian cell for producing an adeno-associated virus (AAV), comprising, in a single nucleic acid molecule, sequences encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters. In such embodiments, this single nucleic acid molecule includes all of the various sequences, along with other required elements, to enable the production of an AAV within the cell.

FIGS. 10A and 10B show exemplary nucleic acid molecules including these various sequences that can be utilized in mammalian cells to produce AAVs.

As described herein, suitably the mammalian cells are mammalian cell cultures, and in embodiments, can be suspension cultures. As described herein, the use of suspension cell cultures allows for increased scalability and production of AAV.

As described herein and as shown in FIGS. 1, 2A-2B, and 10A-10B, suitably the single nucleic acid molecule includes an internal ribosome entry site (IRES) element between the E2A and E4Orf6 genes.

Various constructs are described herein for encoding the Rep and Cap genes, including Rep78 and Rep52 genes. In embodiments, a Rep78 gene is under control of the second derepressible promoter and a Rep52 gene is under control of a fourth derepressible promoter (e.g., as shown in FIG. 4B, the Rep52 gene is separate from the Rep78 gene). In additional embodiments, for example as described herein with reference to FIGS. 4C and 7A-7B, a Rep78 gene can be placed under control of the second derepressible promoter and a Rep52 gene can be placed under control of a fourth derepressible promoter contained within an artificial intron. Suitably, the Cap gene is under control of a native promoter.

Various derepressible promoters are described herein, and in embodiments, the derepressible promoters comprise a functional promoter and two tetracycline operator sequences ($TetO_2$). In embodiments, the functional promoter of the first derepressible promoter (i.e., controlling the expression of the adenovirus helper gene comprising E2A and E4Orf6 genes) is a cytomegalovirus (CMV) promoter.

As described herein, in embodiments and as illustrated in FIGS. 1, 2A-2B, and 10A-10D, suitably the repressor element of the derepressible promoter is under control of a constitutive promoter, such that it is produced at all times to limit expression of other genes under the control of the derepressible promoters. Suitably, the repressor element that is encoded is a tetracycline repressor protein, for binding to $TetO_2$ sequences to act as the derepressible promoter. In embodiments, for example as shown in FIGS. 2A, 10A and 10C, a nucleic acid encoding a transcriptional repression domain (e.g., a KRAB sequence) is included in frame with the nucleic acid encoding the tetracycline repressor protein. This transcriptional repression domain provides for improved repressive activity of the TetR when binding to $TetO_2$, thereby minimizing the amount of leakage or basal gene expression prior to derepression.

Exemplary mammalian cells that can be used in the embodiments and methods described herein are described throughout, and include for example, Chinese hamster ovary (CHO) cells, as well as human cells, including human embryonic kidney (HEK, such as HEK293) cells.

Figure 10D:
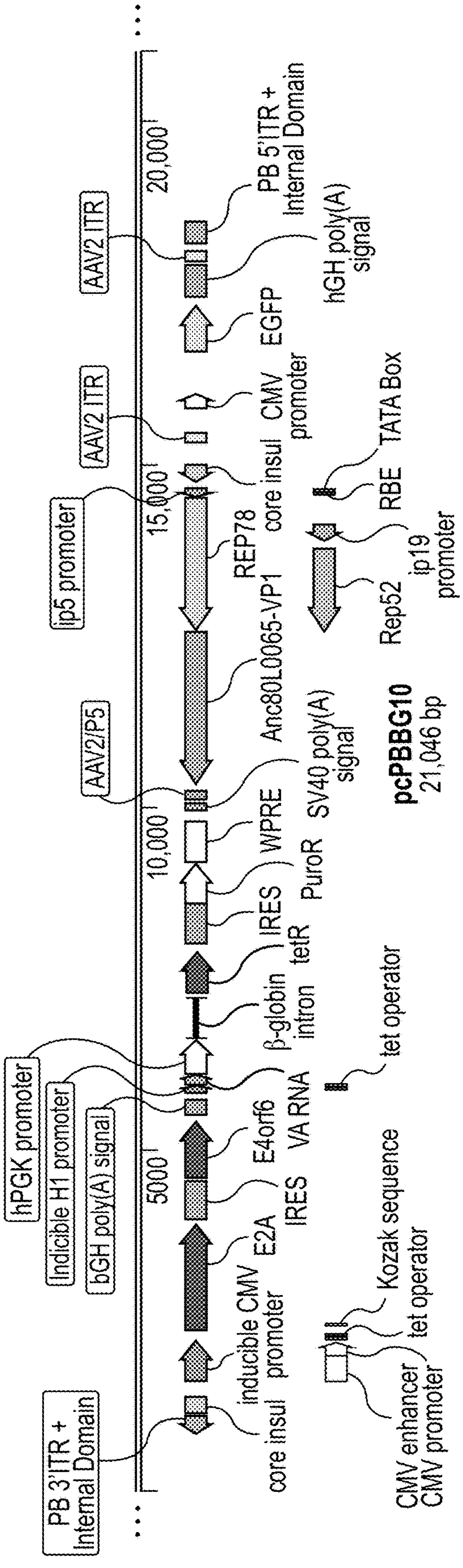

As described herein, suitably the mammalian cells further include a nucleic acid molecule encoding a gene of interest (GOI). As shown in FIGS. 10C-10D, suitably the GOI is included between two ITR sequences.

Also provided herein is an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

As used herein an "isolated nucleic acid molecule" includes vectors and plasmids that can contain the isolated nucleic acid molecule, as well as similar structures where the isolated nucleic acid molecule can be manipulated, stored, shipped, and ultimately utilized in various cell transfection systems. The isolated nucleic acid molecules described herein can be used for production of AAVs as described herein, but can also be utilized in various non-AAV producing cell lines (including transient transfection systems). The isolated nucleic acid molecules described herein suitably further include various additional elements and sequences as required to allow for use in the cellular systems, including mammalian cells, described herein.

For example, as shown in FIGS. 10A-10B, two plasmid constructs are shown. As indicated, in embodiments, an internal ribosome entry site (IRES) element can be included between the E2A and E4Orf6 genes. As described herein with reference to FIG. 4B in embodiments, a Rep78 gene is under control of the second derepressible promoter and a Rep52 gene is under control of a fourth derepressible promoter (i.e., separated from the Rep52 gene).

In further embodiments, as shown with reference to FIGS. 10A-10B, a Rep78 gene is under control of a derepressible promoter (ip5 promoter as shown, and various iterations described in FIG. 5) and a Rep52 gene is under control of a fourth derepressible promoter contained within an artificial intron, illustrated as ip19, and described with reference to FIGS. 7A-7B. The isolated nucleic acid further suitably includes the Cap gene under control of a native promoter (i.e., p40).

As described herein, various derepressible promoters can be included in the isolated nucleic acid molecules, and suitably include a functional promoter and two tetracycline operator sequences ($TetO_2$). As shown in FIGS. 10A and 10B, with regard to the helper genes E2 and E4, suitably this functional promoter is a CMV promoter, which includes the $TetO_2$ sequences. The derepressible promoter for use with the viral-associated, non-coding RNA suitably includes an H1 promoter, as well as the $TetO_2$ sequences.

As described herein and as shown in FIGS. 10A and 10B, the repressor element (e.g., a tetracycline repressor protein), is suitably under the control of a constitutive promoter, for example, a hPGK promoter. As shown in FIGS. 10A and 12B, the isolated nucleic acid molecules can further include a nucleic acid encoding a transcriptional repression domain (e.g., a KRAB sequence) in frame with the nucleic acid encoding the tetracycline repressor protein. As shown in FIGS. 10C-10D and FIG. 11B, the isolated nucleic acid molecules can further include a gene of interest (GOI, e.g., a GFP), suitably between the two ITR sequences.

As described herein and as shown in FIGS. 12A-12B, the repressor element is suitably flanked by an insulator, for example, a chicken hypersensitive site-4 (cHS4) sequence.

In embodiments, a nucleic acid encoding a transcriptional repression domain (such as KRAB) is included in frame with the nucleic acid encoding the tetracycline repressor protein (e.g., TetR-KRAB).

Additional genetic and sequence elements for inclusion in the isolated nucleic acid molecules described herein are known in the art and can be found illustrated schematically in FIGS. 10A-10D and FIGS. 11A-11E.

The terms "sequence identity" or "% identity" in the context of nucleic acid sequences described herein refers to the percentage of residues in the compared sequences that are the same when the sequences are aligned over a specified comparison window. A comparison window can be a segment of at least 10 to over 1000 residues in which the sequences can be aligned and compared. Methods of alignment for determination of sequence identity are well-known can be performed using publicly available databases such as BLAST (blast.ncbi.nlm.nih.gov/Blast. CGI.).

In some embodiments, nucleic acid molecules have at least about 70%, at least about 75%, at least about 80%, at least about 85%, at least about 90%, at least about 95%, at least about 97%, at least about 98%, at least about 99% or about 100% sequence identity with a reference nucleic acid molecule, respectively (or a fragment of the reference polypeptide or nucleic acid molecule). In certain embodiments of the disclosure, polypeptides or nucleic acid molecules have at least 70%, at least 75%, at least 80%, at least 85%, at least 90%, at least 95%, at least 97%, at least 98%, or at least 99% or 100% sequence identity with a reference nucleic acid molecule, respectively (or a fragment of the reference nucleic acid molecule). In some embodiments, nucleic acid molecules have about 90%, 91%, 92%, 93%, 94%, 95%, 96%, 97%, 98%, 99%, 99.5% sequence identity with a reference nucleic acid molecule, respectively.

A "vector" or "expression vector" is a replicon, such as a plasmid, phage, virus, or cosmid, to which a nucleic acid molecule described herein may be attached to bring about the replication and/or expression of the attached nucleic acid molecule in a cell. "Vector" includes episomal (e.g., plasmids) and non-episomal vectors. The term "vector" includes both viral and nonviral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters.

Also provided herein is a method of producing an adeno-associated virus (AAV) in a mammalian cell. Suitably, the methods described herein include transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., *Virology,* 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., *Gene* 13:197 (1981). Such techniques can be used to introduce one or more exogenous DNA moieties, such as an AAV vector cassette, AAV helper constructs, and other nucleic acid molecules, into suitable host cells.

Various methods of transfecting the mammalian cells with the isolated nucleic acid molecules described herein (i.e., vectors), are known in the art and include various chemical and physical methods, for example, electroporation, cell injection, calcium phosphate exposure, liposome or polymer-based carrier systems, etc.

In exemplary embodiments, a vectors such as the PIGGYBAC™ transposon can be used for the stable integration of these nucleic acid molecules, which allows one-step insertion of large nucleic acid sequences in multiple copies randomly in a cell genome. The system consists of a PIGGYBAC™ Vector and the Super PIGGYBAC™ Transposase which recognizes transposon-specific inverted terminal repeats (ITRs) and efficiently integrates the ITRs and intervening DNA into the genome at TTAA sites. The Super PIGGYBAC™ Transposase is delivered to the cell via the Super PIGGYBAC™ Transposase Expression Vector, which is co-transfected with one or more PIGGYBAC™ Vectors.

The methods further include treating the mammalian cell with a binding partner of the repressor element. As described herein, in the presence of a repressor element, the functional promoters of the derepressible promoters controlling the transcription of the various genes encoded by the nucleic acid molecules, are repressed. That is, the genes are not actively being transcribed, and are instead awaiting derepression. As noted herein, the repressor element of the derepressible promoters is suitably under control of constitutive promoter, such that the repressor element is being produced soon after transfection of the nucleic acid molecule into the mammalian cell. Upon treatment with the binding partner of the repressor element, the repressor element binds to the binding partner, changes conformation, and no longer represses the derepressible promoter. This results in the activating of the first, second and third (and additional as needed) derepressible promoters (i.e., the functional promoters of the derepressible promoters) within the mammalian cell.

Following the activation, the various elements are transcribed and translated within the mammalian cell, resulting in the production of the AAV. The AAV is then harvested using methods known in the art.

While the methods described herein can be utilized in any mammalian cell, including a mammalian cell culture, suitably the mammalian cell culture is a suspension culture, including a human cell such as an HEK suspension cell culture.

As described throughout the nucleic acid molecules can further include an internal ribosome entry site (IRES) element between the E2A and E4Orf6 genes. Exemplary constructs related to the Rep78 and Rep 52 genes are described herein, including where a Rep78 gene is under control of the second derepressible promoter and a Rep52 gene is under control of a fourth derepressible promoter. In additional embodiments of the methods, a Rep78 gene is under control of the second derepressible promoter and a Rep52 gene is under control of a fourth derepressible promoter contained within an artificial intron.

As described herein, the use of an artificial intron allows for removal of the fourth derepressible promoter following activating the derepressible promoters and prior to the producing the AAV. As described herein, the derepressible promoter within the intron ensures the repression of Rep52 gene expression before activation, while still allowing for the expression of the Rep78 protein following the removal of the intron during mRNA splicing. In exemplary embodiments of the methods, the Cap gene is under control of a native promoter, such as p40.

In embodiments, the functional promoter of the derepressible promoter controlling the expression of the helper genes is a cytomegalovirus (CMV) promoter. Suitably, the repressor element that is encoded in the methods described herein is a tetracycline repressor protein, and suitably the derepressible promoters comprise a functional promoter and two tetracycline operator sequences (TetO2). In embodiments, the repressor element is under control of a constitutive promoter, such as hPGK, for example when the repressor element that is encoded is a tetracycline repressor protein.

As described herein, in embodiments utilizing the TetR and/or TetR-KRAB repressor element, treating the cells with doxycycline changes the conformation of the TetR and activates the transcription of the various genes.

Various mammalian cells can be utilized in the methods described herein, including human cells such as human embryonic kidney (HEK) cells, or other mammalian cells including Chinese hamster ovary (CHO) cells.

As described throughout, in embodiments, the AAV comprises a nucleic acid molecule encoding a gene of interest. This GOI can be a reporter gene, a selection gene, or any other gene of interest, including a gene of therapeutic interest.

The methods of producing the AAVs can be used in a continuous manufacturing system. In exemplary embodiments, the use of a suspension cell culture allows for the production of large volumes of AAV, with high productivity and prolonged culture conditions to allow for multiple harvests of AAV for each batch of starting cells.

Production methods can utilize any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

In further embodiments, provided herein is a method of treatment with an adeno-associated virus (AAV) comprising: transfecting the mammalian cell with an isolated nucleic acid molecule encoding: an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, harvesting the AAV, and administering the AAV to a mammalian patient.

Suitably, the methods are used to treat a human patient with a gene of interest, including a gene of therapeutic interest. Administration to a human patient can include, for example, inhalation, injection, or intravenous administration, as well as other administration methods known in the art.

The methods of producing the AAV and the use of various derepressible promoters are described herein.

In further embodiments, a method of producing an adeno-associated virus (AAV) is provided and includes transfecting a mammalian cell stably expressing one or more nucleic acids encoding TetR and/or TetR-KRAB with: a first nucleic acid encoding an adenovirus helper gene comprising an E2A gene, a E4Orf gene and a viral-associated non-coding RNA, under control of a first derepressible promoter, a second nucleic acid encoding an AAV gene comprising Rep and Cap genes under control of a second derepressible promoter, optionally, a third nucleic acid encoding a gene of interest under control of a third derepressible promoter; treating the mammalian cell with a binding partner of the TetR; activating the first, second and third derepressible promoters; producing the AAV; and harvesting the AAV.

As described herein, suitably the mammalian cell is a mammalian cell culture, including a suspension culture As described herein, suitably the mammalian cell is a Chinese hamster ovary (CHO) cell or a human cell including a human embryonic kidney (HEK) cell.

As described herein, using 2 or 3 different nucleic acids or transposons to transfect mammalian cells offers advantages over combining the nucleic acids in one plasmid, including the ability to optimize the ratio of separate AAV-producing and packaging components and to exert temporal control over expression of each transposon.

As described herein, suitably the nucleic acid encoding the E2A and E4Orf genes further comprises an internal ribosome entry site (IRES) element between the E2A and E4Orf genes.

As described herein, suitably the derepressible promoters comprise a functional promoter and two tetracycline operator sequences ($TetO_2$).

As described herein, suitably the functional promoter of the first derepressible promoter is a cytomegalovirus (CMV) promoter.

In some embodiments, the mammalian cell used to produce adeno-associated virus (AAV) is stably expressing one or more nucleic acids encoding TetR and/or TetR-KRAB under control of a constitutive promoter.

As described herein, stable expression of a TetR and/or TetR-KRAB in a mammalian cell (prior to insertion of nucleic acids carrying the components of the virus, suitably via transposons) maximizes the repression of potentially cytotoxic AAV genes introduced by transfection and confers increased temporal control over the derepressible promoter elements.

In some embodiments, a KRAB repressor domain is fused in frame with the TetR.

As described herein, fusing a KRAB repressor domain in frame with the TetR ensures that “leaky” expression of the potentially cytotoxic AAV-packaging nucleic acids is less likely to occur. A KRAB repressor domain fused in frame with the TetR repressor domain provides an additional mechanism to accomplish high levels of repression of derepressible promoters.

In some embodiments, the mammalian cell produces a sufficient amounts of TetR. As used herein, a “sufficient” of TetR is defined as the level of amount and/or activity of a repressor (e.g., TetR) to stop expression and/or activity of a repressible and/or derepressible element (i.e., prior to addition of doxycycline).

As described herein, producing sufficient amounts of TetR is necessary for repression of the derepressible promoters under normal conditions (e.g., before addition of doxycycline). If sufficient amounts of TetR are not produced by the mammalian cell, the cell may prematurely transcribe and translate potentially cytotoxic AAV-packaging nucleic acids.

In further embodiments, the mammalian cell further comprises stable expression of one or more nucleic acids encoding chicken hypersensitive site-4 (cHS4) flanking the TetR and/or TetR-KRAB repressor sequences. As described herein, expression of cHS4 sequences flanking the TetR and/or TetR-KRAB repressor sequences prevent the silencing of TetR expression and further improve the stability of integrated repressors in the mammalian cell genome.

In further embodiments, the treating comprises treating with doxycycline to remove repression of derepressible promoters.

In further embodiments, each of the first, second and third nucleic acids are flanked by transposon-specific inverted terminal repeats (ITRs).

In further embodiments, a method for producing an adeno-associated virus (AAV) comprises stably transfecting a mammalian cell with: a nucleic acid encoding a TetR and/or TetR-KRAB repressor, chicken hypersensitive site-4 (cHS4) sequences flanking the TetR and/or TetR-KRAB repressor, and a selection gene; transfecting the stably transfected mammalian cell with a first nucleic acid encoding an adenovirus helper gene comprising an E2A gene, a E4Orf gene and a viral-associated non-coding RNA, under control of a first derepressible promoter, a second nucleic acid encoding an AAV gene comprising Rep and Cap genes under control of a second derepressible promoter, and optionally, a third nucleic acid encoding a gene of interest under control of a third derepressible promoter; treating the mammalian cell with a binding partner of the TetR; activating the first, second and third derepressible promoters; producing the AAV; and harvesting the AAV.

In some embodiments, the mammalian cell further comprises a selection gene, such asa zeocin resistance gene. Additional selection genes include other antibiotic resistance genes, such as kanamycin and geneticin resistance genes. As described herein, expression of a zeocin resistance gene allows for efficient selection of correctly integrated repressors in the mammalian cell genome.

Additional Exemplary Embodiments

Embodiment 1 is a mammalian cell for producing an adeno-associated virus (AAV), comprising a nucleic acid molecule encoding a viral helper gene under control of a first derepressible promoter, a nucleic acid molecule encoding an AAV gene under control of a second derepressible promoter, and a nucleic acid molecule encoding a repressor element of the first and the second derepressible promoters.

Embodiment 2 includes the mammalian cell of embodiment 1, wherein the mammalian cell is a mammalian cell culture.

Embodiment 3 includes the mammalian cell of embodiment 2, wherein the mammalian cell culture is a suspension culture.

Embodiment 4 includes the mammalian cell of any one of embodiments 1-3, wherein the viral helper gene is an adenovirus helper gene.

Embodiment 5 includes the mammalian cell of embodiment 4, wherein the adenovirus helper gene comprises E2A and E4Orf6 genes.

Embodiment 6 includes the mammalian cell of embodiment 5, further comprising an internal ribosome entry site (IRES) element between the E2A and E4Orf6 genes.

Embodiment 7 includes the mammalian cell of any one of embodiments 1-6, wherein the AAV gene comprises Rep and Cap genes.

Embodiment 8 includes the mammalian cell of embodiment 7, wherein a Rep78 gene is under control of the second derepressible promoter and a Rep52 gene is under control of a third derepressible promoter.

Embodiment 9 includes the mammalian cell of embodiment 7, wherein a Rep78 gene is under control of the second derepressible promoter and a Rep52 gene is under control of a third derepressible promoter contained within an artificial intron.

Embodiment 10 includes the mammalian cell of any one of embodiments 8 or 9, wherein the Cap gene is under control of a native promoter.

Embodiment 11 includes the mammalian cell of any one of embodiments 1-10, wherein each of the derepressible promoters comprise a functional promoter and two tetracycline operator sequences (TetO2).

Embodiment 12 includes the mammalian cell of embodiment 11, wherein the functional promoter of the first derepressible promoter is a cytomegalovirus (CMV) promoter.

Embodiment 13 includes the mammalian cell of any one of embodiments 1-12, wherein the repressor element is under control of a constitutive promoter.

Embodiment 14 includes the mammalian cell of any one of embodiments 1-13, wherein the repressor element is a tetracycline repressor protein.

Embodiment 15 includes the mammalian cell of embodiment 14, further comprising a nucleic acid encoding a transcriptional repression domain in frame with the nucleic acid encoding the tetracycline repressor protein.

Embodiment 16 includes the mammalian cell of any one of embodiments 1-15, wherein the mammalian cell is a Chinese hamster ovary (CHO) cell.

Embodiment 17 includes the mammalian cell of any one of embodiments 1-15, wherein the mammalian cell is a human cell.

Embodiment 18 includes the mammalian cell of embodiment 17, wherein the human cell is a human embryonic kidney (HEK) cell.

Embodiment 19 includes the mammalian cell of any one of embodiments 1-18, further comprising a nucleic acid molecule including two inverted terminal repeat (ITR) sequences.

Embodiment 20 includes the mammalian cell of any one of embodiments 1-19, further comprising a nucleic acid molecule encoding a gene of interest.

Embodiment 21 includes the mammalian cell of any one of embodiments 1-20, further comprising a nucleic acid encoding a viral-associated, non-coding RNA under control of a fourth derepressible promoter.

Embodiment 22 is a mammalian cell for producing an adeno-associated virus (AAV), comprising a nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

Embodiment 23 includes mammalian cell of embodiment 22, wherein the mammalian cell is a mammalian cell culture.

Embodiment 24 includes the mammalian cell of embodiment 23, wherein the mammalian cell culture is a suspension culture.

Embodiment 25 includes the mammalian cell of any one of embodiments 22-24, further comprising an internal ribosome entry site (IRES) element between the E2A and E4Orf6 genes.

Embodiment 26 includes the mammalian cell of any one of embodiments 22-25, wherein a Rep78 gene is under control of the second derepressible promoter and a Rep52 gene is under control of a fourth derepressible promoter.

Embodiment 27 includes the mammalian cell of any one of embodiments 22-25, wherein a Rep78 gene is under control of the second derepressible promoter and a Rep52 gene is under control of a fourth derepressible promoter contained within an artificial intron.

Embodiment 28 includes the mammalian cell of any one of embodiments 26 or 27, wherein the Cap gene is under control of a native promoter.

Embodiment 29 includes the mammalian cell of any one of embodiments 22-28, wherein each of the derepressible promoters comprise a functional promoter and two tetracycline operator sequences (TetO2).

Embodiment 30 includes the mammalian cell of embodiment 29, wherein the functional promoter of the first derepressible promoter is a cytomegalovirus (CMV) promoter.

Embodiment 31 includes the mammalian cell of any one of embodiments 22-30, wherein the repressor element is under control of a constitutive promoter.

Embodiment 32 includes the mammalian cell of any one of embodiments 22-31, wherein the repressor element is a tetracycline repressor protein.

Embodiment 33 includes the mammalian cell of embodiment 25, further comprising a nucleic acid encoding a transcriptional repression domain in frame with the nucleic acid encoding the tetracycline repressor protein.

Embodiment 34 includes the mammalian cell of any one of embodiments 22-33, wherein the mammalian cell is a Chinese hamster ovary (CHO) cell.

Embodiment 35 includes the mammalian cell of any one of embodiments 22-33, wherein the mammalian cell is a human cell.

Embodiment 36 includes the mammalian cell embodiment 35, wherein the human cell is a human embryonic kidney (HEK) cell.

Embodiment 37 includes the mammalian cell of any one of embodiments 22-36, further comprising a nucleic acid molecule encoding a gene of interest.

Embodiment 38 is an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

Embodiment 39 includes the isolated nucleic acid of embodiment 38, further comprising an internal ribosome entry site (IRES) element between the E2A and E4Orf6 genes.

Embodiment 40 includes the isolated nucleic acid of any of embodiments 38-39, wherein a Rep78 gene is under control of the second derepressible promoter and a Rep52 gene is under control of a fourth derepressible promoter.

Embodiment 41 includes the isolated nucleic acid of any of embodiments 38-39 wherein a Rep78 gene is under control of the second derepressible promoter and a Rep52 gene is under control of a fourth derepressible promoter contained within an artificial intron.

Embodiment 42 includes the isolated nucleic acid of any of embodiments 40 or 41, wherein the Cap gene is under control of a native promoter.

Embodiment 43 includes the isolated nucleic acid of any of embodiments 38-42, wherein each of the derepressible promoters comprise a functional promoter and two tetracycline operator sequences (TetO2).

Embodiment 44 includes the isolated nucleic acid of embodiment 43, wherein the functional promoter of the first derepressible promoter is a cytomegalovirus (CMV) promoter.

Embodiment 45 includes the isolated nucleic acid of any of embodiments 38-44, wherein the repressor element is under control of a constitutive promoter.

Embodiment 46 includes the isolated nucleic acid of any of embodiments 38-45, wherein the repressor element is a tetracycline repressor protein.

Embodiment 47 includes the isolated nucleic acid of embodiment 46, further comprising a nucleic acid encoding a transcriptional repression domain in frame with the nucleic acid encoding the tetracycline repressor protein.

Embodiment 48 includes the isolated nucleic acid of any of embodiments 38-47, further comprising a gene of interest.

Embodiment 49 is a method of producing an adeno-associated virus (AAV) in a mammalian cell comprising transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, and harvesting the AAV.

Embodiment 50 includes the method of embodiment 49, wherein the mammalian cell is a mammalian cell culture.

Embodiment 51 includes the method of embodiment 50, wherein the mammalian cell culture is a suspension culture.

Embodiment 52 includes the method of any of embodiments 49-51, further comprising an internal ribosome entry site (IRES) element between the E2A and E4Orf6 genes.

Embodiment 53 includes the method of any of embodiments 49-52, wherein a Rep78 gene is under control of the second derepressible promoter and a Rep52 gene is under control of a fourth derepressible promoter.

Embodiment 54 includes the method of any of embodiments 49-52, wherein a Rep78 gene is under control of the second derepressible promoter and a Rep52 gene is under control of a fourth derepressible promoter contained within an artificial intron.

Embodiment 55 includes the method of embodiment 54, wherein the fourth derepressible promoter is removed following the activating the derepressible promoters and prior to the producing the AAV.

Embodiment 56 includes the method of any of embodiments 53 or 54, wherein the Cap gene is under control of a native promoter.

Embodiment 57 includes the method of any of embodiments 49-56, wherein each of the derepressible promoters comprise a functional promoter and two tetracycline operator sequences (TetO2).

Embodiment 58 includes the method of embodiment 57, wherein the functional promoter of the first derepressible promoter is a cytomegalovirus (CMV) promoter.

Embodiment 59 includes the method of any of embodiments 49-58, wherein the repressor element is under control of a constitutive promoter.

Embodiment 60 includes the method of any of embodiments 49-59, wherein the repressor element that is a tetracycline repressor protein.

Embodiment 61 includes the method of embodiment 60, wherein the nucleic acid further comprises a nucleic acid encoding a transcriptional repression domain in frame with the nucleic acid encoding the tetracycline repressor protein.

Embodiment 62 includes the method of any of embodiments 60 or 61, wherein the treating comprises treating with doxycycline.

Embodiment 63 includes the method of any of embodiments 49-62, wherein the mammalian cell is a Chinese hamster ovary (CHO) cell.

Embodiment 64 includes the method of any of embodiments 49-63, wherein the mammalian cell is a human cell.

Embodiment 65 includes the method of embodiment 64, wherein the human cell is a human embryonic kidney (HEK) cell.

Embodiment 66 includes the method of any of embodiments 49-65, wherein the AAV comprises a nucleic acid molecule encoding a gene of interest.

Embodiment 67 includes the method of embodiment 66, wherein the AAV comprises a gene of therapeutic interest.

Embodiment 68 is a method of treatment with an adeno-associated virus (AAV) comprising transfecting the mammalian cell with an isolated nucleic acid molecule encoding, an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences; and a repressor element of the first, second and third derepressible promoters; treating the mammalian cell with a binding partner of the repressor element; activating the first, second and third derepressible promoters; producing the AAV; harvesting the AAV; and administering the AAV to a mammalian patient.

Embodiment 69 includes the method of embodiment 68, wherein the mammalian cell is a mammalian cell culture.

Embodiment 70 includes the method of embodiment 69, wherein the mammalian cell culture is a suspension culture.

Embodiment 71 includes the method of any of embodiments 68-70, further comprising an internal ribosome entry site (IRES) element between the E2A and E4Orf6 genes.

Embodiment 72 includes the method of any of embodiments 68-71, wherein a Rep78 gene is under control of the second derepressible promoter and a Rep52 gene is under control of a fourth derepressible promoter.

Embodiment 73 includes the method of any of embodiments 68-72, wherein a Rep78 gene is under control of the second derepressible promoter and a Rep52 gene is under control of a fourth derepressible promoter contained within an artificial intron.

Embodiment 74 includes the method of embodiment 73, wherein the fourth derepressible promoter is removed following the activating the derepressible promoters and prior to the producing the AAV.

Embodiment 75 includes the method of any of embodiments 73 or 74, wherein the Cap gene is under control of a native promoter.

Embodiment 76 includes the method of any of embodiments 68-75, wherein each of the derepressible promoters comprise a functional promoter and two tetracycline operator sequences ($TetO_2$).

Embodiment 77 includes the method of embodiment 76, wherein the functional promoter of the first derepressible promoter is a cytomegalovirus (CMV) promoter.

Embodiment 78 includes the method of any of embodiments 68-77, wherein the repressor element is under control of a constitutive promoter.

Embodiment 79 includes the method of any of embodiments 68-78, wherein the repressor element that is a tetracycline repressor protein.

Embodiment 80 includes the method of embodiment 79, wherein the nucleic acid further comprises a nucleic acid encoding a transcriptional repression domain in frame with the nucleic acid encoding the tetracycline repressor protein.

Embodiment 81 includes the method of any of embodiments 79 or 80, wherein the treating comprises treating with doxycycline.

Embodiment 82 includes the method of any of embodiments 68-81, wherein the mammalian cell is a Chinese hamster ovary (CHO) cell.

Embodiment 83 includes the method of any of embodiments 68-82, wherein the mammalian cell is a human cell.

Embodiment 84 includes the method of embodiment 83, wherein the human cell is a human embryonic kidney (HEK) cell.

Embodiment 85 includes the method of any of embodiments 68-84, wherein the AAV comprises a nucleic acid molecule encoding a gene of interest.

Embodiment 86 includes the method of embodiment 87, wherein the AAV comprises a gene of therapeutic interest.

Embodiment 87 includes the method of any of embodiments 68-86, wherein the administering comprises inhalation, injection or intravenous administration.

Embodiment 88 is a method of producing an adeno-associated (AAV) virus, comprising: transfecting a mammalian cell stably expressing one or more nucleic acids encoding TetR and/or TetR with a first nucleic acid encoding an adenovirus helper gene comprising an E2A gene, a E4Orf gene and a viral-associated non-coding RNA under control of a first derepressible promoter, a second nucleic acid encoding an AAV gene comprising Rep and Cap genes under control of a second derepressible promoter, and, optionally, a third nucleic acid encoding a gene of interest under control of a third derepressible promoter; treating the mammalian cell with a binding partner of the TetR and/or TetR-KRAB; activating the first, second and third derepressible promoters; producing the AAV; and harvesting the AAV.

Embodiment 89 includes the method of embodiment 88, wherein the mammalian cell is a mammalian cell culture.

Embodiment 90 includes the method of any of embodiments 88-89, wherein the mammalian cell is a Chinese hamster ovary (CHO) cell.

Embodiment 91 includes the method of any of embodiments 88-90, wherein the mammalian cell is a human cell.

Embodiment 92 includes the method of embodiment 91, wherein the human cell is a human embryonic kidney (HEK) cell.

Embodiment 93 includes the method of embodiment 89, wherein the mammalian cell culture is a suspension culture.

Embodiment 94 includes the method of any of embodiments 88-90, wherein the mammalian cell further comprises an internal ribosome entry site (IRES) element between the E2A and E4Orf6 genes.

Embodiment 95 includes the method of any of embodiments 88-91, wherein each of the derepressible promoters comprise a functional promoter and two tetracycline operator sequences ($TetO_2$).

Embodiment 96 includes the method of embodiment 92, wherein the functional promoter of the first derepressible promoter is a cytomegalovirus (CMV) promoter.

Embodiment 97 includes the method of any of embodiments 88-96, wherein the stably expressed TetR and/or TetR-KRAB is under control of a constitutive promoter.

Embodiment 98 includes the method of embodiment 97, wherein the nucleic acid encoding the TetR-KRAB comprises KRAB fused in frame with the TetR.

Embodiment 99 includes the method of any one of embodiments 88-98, wherein the treating comprises treating with doxycycline.

Embodiment 100 includes the method of any one of embodiments 88-99, wherein each of the first, second and third nucleic acids are flanked by transposon-specific inverted terminal repeats (ITRs).

Embodiment 101 includes the method of any of embodiments 88-100, wherein the mammalian cell expresses sufficient amounts of TetR and/or TetR-KRAB.

Embodiment 102 includes the method of any of embodiments 88-101, wherein the AAV comprises a gene of therapeutic interest.

Embodiment 103 includes the method of any of embodiments 88-102, wherein the mammalian cell further comprises stable expression of one or more nucleic acids encoding chicken hypersensitive site-4 (cHS4) flanking the TetR and/or TetR-KRAB repressor sequences.

Embodiment 104 includes the method of any of embodiments 88-103, wherein the mammalian cell further comprises a zeocin resistance gene.

Embodiment 105 is a method for producing an adeno-associated virus (AAV), comprising: stably transfecting a mammalian cell with: a nucleic acid encoding a TetR and/or TetR-KRAB repressor; chicken hypersensitive site-4 (cHS4) sequences flanking the TetR and/or TetR-KRAB repressor; and a selection gene; transfecting the stably transfected mammalian cell with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the stably transfected mammalian cell with a binding partner of the TetR; activating the first, second and third derepressible promoters; producing the AAV; and harvesting the AAV.

Embodiment 106 includes the method of embodiment 105, wherein the stably transfected mammalian cell produces a sufficient amounts of TetR.

Embodiment 107 includes the method of any of embodiments 106 and 107, wherein the KRAB repressor domain is fused in frame with the TetR.

EXAMPLES

Example 1: Design and Validation of Derepressible Helper Genes

To drive the expression of E2A and E4Orf6 genes, a derepressible promoter from the pcDNA4/TO vector (INVITROGEN) was utilized. This promoter includes the complete CMV promoter with an insertion of two Tetracycline operator sequences ($TetO_2$) between the TATA box and transcriptional start site (TSS). In the presence of tetracycline repressor protein (TetR), transcription initiation was blocked by the binding of TetR onto the $TetO_2$ sites. When Tetracycline or Doxycycline is added into the medium, it binds to TetR and changes its conformation. This leads to the release of TetR and derepression/activation of the CMV promoter and results in induced gene expression (FIG. 1 showing OFF and ON conformations of TetR/$TetO_2$ derepressible promoter system).

To simplify the design and improve the stability, an Internal Ribosome Entry Site (IRES) element was used to initiate the translation of E4Orf6 after E2A in a single expression cassette, driven by a single inducible CMV promoter (FIG. 1).

To induce the VA I non-coding RNA, an H1 promoter with $TetO_2$ insertion was applied (see, e.g., Wiederschain et al., "Single-vector inducible lentiviral RNAi system for oncology target validation, *Cell Cycle* 8:498-504 (2009)). Similarly, the addition of Doxycycline releases TetR and turns on VA I expression (FIG. 1).

As mentioned, a TetR gene expression cassette is included for the control of the derepressible promoters (see FIG. 1). A constitutive human PGK promoter is used to drive the expression of TetR, followed by an IRES that directs the expression of puromycin N-acetyltransferase used to select the transposon integrated cells (see FIG. 2A).

To reduce the potential leaky expression from the derepressible promoters, an enhanced version of TetR was also included (see, e.g., Szulc et al., "A versatile tool for conditional gene expression and knockdown," *Nature Methods* 3:109-116 (2006)). Briefly, a strong repressive domain of KRAB was fused in-frame to the C-terminal of original TetR, which improves its repressive activity and minimizes basal gene expression before induction. An SV40 Nuclear Localization Signal (NLS) was inserted as well to facilitate the nuclear entry of the larger TetR-KRAB fusion protein (FIG. 2A, FIGS. 12A-12B).

The sequence of the pcDNA3.1-E2A-E4-VA-TetR vector shown in FIG. 2A is provided below:

```
iHelper 1/pcDNA3.1-E2A-E4-VA-TetR (11, 986 bp)
                                                    (SEQ ID NO: 1)
GACGGATCGGGAGATCTCCCGATCCCCTATGGTGCACTCTCAGTACAATC

TGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAAT

TGCATGAAGAATCTGCTTAGGGTTAGGCGTTTTGCGCTGCTTCGCGATGTACGGGCC

AGATATACGCGTTGACATTGATTATTGACTAGTTATTAATAGTAATCAATTACGGGG

TCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATT

GACGTCAATGACGGTAAATGGCCCGCCTGGCATTATGCCCAGTACATGACCTTATGG
```

-continued

GACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAA
GTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTAC
GGTGGGAGGTCTATATAAGCAGAGCTCTCTGGCTAACTAGAGAACCCACTGCTTACT
GGCTTATCGAAATTAATACGACTCACTATAGGGAGACCCAAGCTGGCTAGCGTTTAA
ACTTAAGCTTGGTACCGAGCTCGGATCCACTAGTCCAGTGTGGTGGAATTCCTGCTT
CGCGATGTACGGGCCAGATATACGCGTTGACATTGATTATTGACTAGTTATTAATAG
TAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCA
ATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCA
AGTACGCCCCCTATTGACGTCAATGACGGTAAATGGCCCGCCTGGCATTATGCCCAG
TACATGACCTTATGGGACTTTCCTACTTGGCAGTACATCTACGTATTAGTCATCGCTA
TTACCATGGTGATGCGGTTTTGGCAGTACATCAATGGGCGTGGATAGCGGTTTGACT
CACGGGGATTTCCAAGTCTCCACCCCATTGACGTCAATGGGAGTTTGTTTTGGAACC
AAAATCAACGGGACTTTCCAAAATGTCGTAACAACTCCGCCCCATTGACGCAAATG
GGCGGTAGGCGTGTACGGTGGGAGGTCTATATAAGCAGAGCTCTCCCTATCAGTGAT
AGAGATCTCCCTATCAGTGATAGAGATCGTCGACGAGCTCGTTTAGTGAACCGTCAG
ATCGCCTGGAGACGCCATCCACGCTGTTTTGACCTCCATAGAAGACACCGGGACCG
ATCCAGCCTCCGGACTCTAGCGTTTAAACTTAAGCTTGCCACCatggccagtcgggaagaggagc
agcgcgaaaccacccccgagcgcggacgcggtgcggcgcgacgtcccccaaccatggaggacgtg
tcgtccccgtccccgtcgccgccgcctccccgggcgcccccaaaaaagcggatgaggcggcgtat
cgagtccgaggacgaggaagactcatcacaagacgcgctggtgccgcgcacacccagcccgcggc
catcgacctcggcggcggatttggccattgcgcccaagaagaaaaagaagcgcccttctcccaag
cccgagcgcccgccatcaccagaggtaatcgtggacagcgaggaagaaagagaagatgtggcgct
acaaatggtgggtttcagcaacccaccggtgctaatcaagcatggcaaaggaggtaagcgcacag
tgcggcggctgaatgaagacgacccagtggcgcgtggtatgcggacgcaagaggaagaggaagag
cccagcgaagcggaaagtgaaattacggtgatgaacccgctgagtgtgccgatcgtgtctgcgtg
ggagaagggcatggaggctgcgcgcgcgctgatggacaagtaccacgtggataacgatctaaagg
cgaacttcaaactactgcctgaccaagtggaagctctggCggccgtatgcaagacctggctgaac
gaggagcaccgcgggttgcagctgaccttcaccagcaacaagacctttgtgacgatgatggggcg
attcctgcaggcgtacctgcagtcgtttgcagaggtgacctacaagcatcacgagcccacgggct
gcgcgttgtggctgcaccgctgcgctgagatcgaaggcgagcttaagtgtctacacggaagcatt
atgataaataaggagcacgtgattgaaatggatgtgacgagcgaaaacgggcagcgcgcgctgaa
ggagcagtctagcaaggccaagatcgtgaagaaccggtggggccgaaatgtggtgcagatctcca
acaccgacgcaaggtgctgcgtgcacgacgcggcctgtccggccaatcagttttccggcaagtct
tgcggcatgttcttctctgaaggcgcaaaggctcaggtggcttttaagcagatcaaggcttttat
gcaggcgctgtatcctaacgcccagaccgggcacggtcaccttttgatgccactacggtgcgagt
gcaactcaaagcctgggcacgcgccctttttgggaaggcagctaccaaagttgactccgttcgcc -continued ctgagcaacgcggaggacctggacgcggatctgatctccgacaagagcgtgctggccagcgtgca
ccacccggcgctgatagtgttccagtgctgcaaccctgtgtatcgcaactcgcgcgcgcagggcg
gaggccccaactgcgacttcaagatatcggcgcccgacctgctaaacgcgttggtgatggtgcgc
agcctgtggagtgaaaacttcaccgagctgccgcggatggttgtgcctgagtttaagtggagcac
taaacaccagtatcgcaacgtgtccctgccagtggcgcatagcgatgcgcggcagaacccctttg
atttttaacccgggagttctagggatctgcccctctccctcccccccccctaacgttactggccg
aagccgcttggaataaggccggtgtgcgtttgtctatatgttattttccaccatattgccgtctt
ttggcaatgtgagggcccggaaacctggccctgtcttcttgacgagcattcctaggggtctttcc
cctctcgccaaaggaatgcaaggtctgttgaatgtcgtgaaggaagcagttcctctggaagcttc
ttgaagacaaacaacgtctgtagcgaccctttgcaggcagcggaaccccccacctggcgacaggt
gcctctgcggccaaaagccacgtgtataagatacacctgcaaaggcggcacaaccccagtgccac
gttgtgagttggatagttgtggaaagagtcaaatggctctcctcaagcgtattcaacaaggggct
gaaggatgcccagaaggtaccccattgtatgggatctgatctggggcctcggtgcacatgcttta
catgtgtttagtcgaggttaaaaaaacgtctaggccccccgaaccacggggacgtggttttcctt
tgaaaaacacgatgataaggatccaccggaggccaccatgactacgtccggcgttccatttggca
tgacactacgaccaacacgatctcggttgtctcggcgcactccgtacagtagggatcgtctacct
ccttttgagacagaaacccgcgctaccatactggaggatcatccgctgctgcccgaatgtaacac
tttgacaatgcacaacgtgagttacgtgcgaggtcttccctgcagtgtgggatttacgctgattc
aggaatgggttgttccctgggatatggttctaacgcgggaggagcttgtaatcctgaggaagtgt
atgcacgtgtgcctgtgttgtgccaacattgatatcatgacgagcatgatgatccatggttacga
gtcctgggctctccactgtcattgttccagtcccggttccctgcagtgtatagccggcgggcagg
ttttggccagctggtttaggatggtggtggatggcgccatgtttaatcagaggtttatatggtac
cgggaggtggtgaattacaacatgccaaaagaggtaatgtttatgtccagcgtgtttatgagggg
tcgccacttaatctacctgcgcttgtggtatgatggccacgtgggttctgtggtccccgccatga
gctttggatacagcgccttgcactgtgggattttgaacaatattgtggtgctgtgctgcagttac
tgtgctgatttaagtgagatcagggtgcgctgctgtgcccggaggacaaggcgccttatgctgcg
ggcggtgcgaatcatcgctgaggagaccactgccatgttgtattcctgcaggacggagcggcggc
ggcagcagtttattcgcgcgctgctgcagcaccaccgccctatcctgatgcacgattatgactct
acccccatgtagGCGGCCGCTCGAGTCTAGAGGGCCCGTTTAAACCCGCTGATCAGCCTCGACTG
TGCCTTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATAGCAGGC
ATGCTGGGGATGCGGTGGGCTCTATGGCTTCTGAGGCGGAAAGAACCAGCTGGGGCTCTAGGGGG
TATCCCCggggttggggttgcgccttttccaaggcATCCAGCACAGTGGCGGCCGCaatatttgc
atgtcgctatgtgttctgggaaatcaccataaacgtgaaatccctatcagtgatagagacttata
agttccctatcagtgatagagaaccggtgggcactcttccgtggtctggtggataaattcgcaag
ggtatcatggcggacgaccggggttcgagccccgtatccggccgtccgccgtgatccatgcggtt
accgcccgcgtgtcgaacccaggtgtgcgacgtcagacaacgggggagtgctcctttttgaattc
cactttggccgcggctcgagggggttggggttgcgccttttccaaggcagccctgggtttgcgca
gggacgcggctgctctgggcgtggttccgggaaacgcagcggcgccgaccctgggtctcgcacat
tcttcacgtccgttcgcagcgtcacccggatcttcgccgctacccttgtgggccccccggcgacg -continued

```
cttcctgctccgcccctaagtcgggaaggttccttgcggttcgcggcgtgccggacgtgacaaac
ggaagccgcacgtctcactagtaccctcgcagacggacagcgccagggagcaatggcagcgcgcc
gaccgcgatgggctgtggccaatagcggctgctcagcagggcgcgccgagagcagcggccgggaa
ggggcggtgcgggaggcggggtgtggggcggtagtgtgggccctgttcctgcccgcgcggtgttc
cgcattctgcaagcctccggagcgcacgtcggcagtcggctccctcgttgaccgaatcaccgacc
tctctccccagggggatctgtgagtttggggacccttgattgttctttctttttcgctattgtaa
aattcatgttatatggagggggcaaagttttcagggtgttgtttagaatgggaagatgtcccttg
tatcaccatggaccctcatgataattttgtttctttcactttctactctgttgacaaccattgtc
tcctcttattttcttttcattttctgtaactttttcgttaaactttagcttgcatttgtaacgaa
tttttaaattcacttttgtttatttgtcagattgtaagtactttctctaatcacttttttttcaa
ggcaatcagggtatattatattgtacttcagcacagttttagagaacaattgttataattaaatg
ataaggtagaatatttctgcatataaattctggctggcgtggaaatattcttattggtagaaaca
actacatcctggtcatcatcctgcctttctctttatggttacaatgatatacactgtttgagatg
aggataaaatactctgagtccaaaccgggcccctctgctaaccatgttcatgccttcttcttttt
cctacagctcctgggcaacgtgctggttattgtgctgtctcatcattttggcaaagaattgtaat
acgactcactatagggcgaGCCACCatggctagattagataaaagtaaagtgattaacagcgcat
tagagctgcttaatgaggtcggaatcgaaggtttaacaacccgtaaactcgcccagaagctaggt
gtagagcagcctacattgtattggcatgtaaaaaataagcgggctttgctcgacgccttagccat
tgagatgttagataggcaccatactcacttttgccctttagaaggggaaagctggcaagattttt
tacgtaataacgctaaaagttttagatgtgctttactaagtcatcgcgatggagcaaaagtacat
ttaggtacacggcctacagaaaaacagtatgaaactctcgaaaatcaattagcctttttatgcca
acaaggtttttcactagagaatgcCttatatgcactcagcgcCgtggggcattttactttaggtt
gcgtattggaagatcaagagcatcaagtcgctaaagaagaaagggaaacacctactactgatagt
atgccgccattattacgacaagctatcgaattatttgatcaccaaggtgcagagccagccttctt
attcggccttgaattgatcatatgcggattagaaaaacaacttaaatgtgaaagtgggtccccaa
aaaagaagagaaaggtcgacggcggtggtgctttgtctcctcagcactctgctgtcactcaagga
agtatcatcaagaacaaggagggcatggatgctaagtcactaactgcctggtcccggacactggt
gaccttcaaggatgtatttgtggacttcaccagggaggagtggaagctgctggacactgctcagc
agatcgtgtacagaaatgtgatgctggagaactataagaacctggtttccttgggttatcagctt
actaagccagatgtgatcctccggttggagaagggagaagagccctggctggtggagagagaaat
tcaccaagagacccatcctgattcagagactgcatttgaaatcaaatcatcagtttaagcgtaca
gcggctcccgggagttctagggatctgcccctctccctcccccccccctaacgttactggccgaa
gccgcttggaataaggccggtgtgcgtttgtctatatgttattttccaccatattgccgtctttt
ggcaatgtgagggcccggaaacctggccctgtcttcttgacgagcattcctaggggtctttcccc
tctcgccaaaggaatgcaaggtctgttgaatgtcgtgaaggaagcagttcctctggaagcttctt
gaagacaaacaacgtctgtagcgaccctttgcaggcagcggaacccccacctggcgacaggtgc
ctctgcggccaaaagccacgtgtataagatacacctgcaaaggcggcacaaccccagtgccacgt
tgtgagttggatagttgtggaaagagtcaaatggctctcctcaagcgtattcaacaaggggctga
aggatgcccagaaggtaccccattgtatgggatctgatctggggcctcggtgcacatgctttaca
tgtgtttagtcgaggttaaaaaaacgtctaggccccccgaaccacggggacgtggttttcctttg
```

-continued aaaaacacgatgataaggatccaccggagGCCACCatgaccgagtacaagcccacggtgcgcctc gccacccgcgacgacgtccccagggccgtacgcaccctcgccgccgcgttcgccgactaccccgc cacgcgccacaccgtcgatccggaccgccacatcgagcgggtcaccgagctgcaagaactcttcc tcacgcgcgtcgggctcgacatcggcaaggtgtgggtcgcggacgacggcgccgcggtggcggtc tggaccacgccggagagcgtcgaagcgggggcggtgttcgccgagatcggcccgcgcatggccga gttgagcggttcccggctggccgcgcagcaacagatggaaggcctcctggcgccgcaccggccca aggagcccgcgtggttcctggccaccgtcggcgtctcgcccgaccaccagggcaagggtctgggc agcgccgtcgtgctccccggagtggaggcggccgagcgcgccggggtgcccgccttcctggagac ctccgcgccccgcaacctccccttctacgagcggctcggcttcaccgtcaccgccgacgtcgagg tgcccgaaggaccgcgcacctggtgcatgacccgcaagcccggtgcctgaCCGCGTCTGGAACAA

TCAACCTCTGGATTACAAAATTTGTGAAAGATTGACTGGTA

TTCTTAACTATGTTGCTCCTTTTACGCTATGTGGATACGCTGCTTTAATGCCTTTGTAT

CATGCTATTGCTTCCCGTATGGCTTTCATTTTCTCCTCCTTGTATAAATCCTGGTTGCT

GTCTCTTTATGAGGAGTTGTGGCCCGTTGTCAGGCAACGTGGCGTGGTGTGCACTGT

GTTTGCTGACGCAACCCCCACTGGTTGGGGCATTGCCACCACCTGTCAGCTCCTTTC

CGGGACTTTCGCTTTCCCCCTCCCTATTGCCACGGCGGAACTCATCGCCGCCTGCCTT

GCCCGCTGCTGGACAGGGGCTCGGCTGTTGGGCACTGACAATTCCGTGGTGTTGTCG

GGGAAGCTGACGTCCTTTCCATGGCTGCTCGCCTGTGTTGCCACCTGGATTCTGCGC

GGGACGTCCTTCTGCTACGTCCCTTCGGCCCTCAATCCAGCGGACCTTCCTTCCCGCG

GCCTGCTGCCGGCTCTGCGGCCTCTTCCGCGTCTTCGCCTTCGCCCTCAGACGAGTCG

GATCTCCCTTTGGGCCGCCTCCCCGCaAAATGACCGACCAAGCGACGCCCAACCTGC

CATCACGAGATTTCGATTCCACCGCCGCCTTCTATGAAAGGTTGGGCTTCGGAATCG

TTTTCCGGGACGCCGGCTGGATGATCCTCCAGCGCGGGGATCTCATGCTGGAGTTCT

TCGCCCACCCCAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAA

ACTCATCAATGTATCTTATCATGTCTGTATACCGTCGACCTCTAGCTAGAGCTTGGCG

TAATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCTGTCGTGC

CAGCTGCATTAATGAATCGGCCAACGCGCGGGGAGAGGCGGTTTGCGTATTGGGCG

CTCTTCCGCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACAAAAATCGA

CGCTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAG

-continued

AACAGTATTTGGTATCTGCGCTCTGCTGAAGCCAGTTACCTTCGGAAAAAGAGTTGG

TAGCTCTTGATCCGGCAAACAAACCACCGCTGGTAGCGGTTTTTTTGTTTGCAAGCA

GCAGATTACGCGCAGAAAAAAAGGATCTCAAGAAGATCCTTTGATCTTTTCTACGGG

GTCTGACGCTCAGTGGAACGAAAACTCACGTTAAGGGATTTTGGTCATGAGATTATC

AAAAAGGATCTTCACCTAGATCCTTTTAAATTAAAAATGAAGTTTTAAATCAATCTA

AAGTATATATGAGTAAACTTGGTCTGACAGTTACCAATGCTTAATCAGTGAGGCACC

TATCTCAGCGATCTGTCTATTTCGTTCATCCATAGTTGCCTGACTCCCCGTCGTGTAG

ATAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAGGG

CCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATTCAGCTCCGG

TTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATG

GTTATGGCAGCACTGCATAATTCTCTTACTGTCATGCCATCCGTAAGATGCTTTTCTG

TGACTGGTGAGTACTCAACCAAGTCATTCTGAGAATAGTGTATGCGGCGACCGAGTT

GCTCTTGCCCGGCGTCAATACGGGATAATACCGCGCCACATAGCAGAACTTTAAAA

GTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTA

CTTTCACCAGCGTTTCTGGGTGAGCAAAAACAGGAAGGCAAAATGCCGCAAAAAAG

GGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAG

AAAAATAAACAAATAGGGGTTCCGCGCACATTTCCCCGAAAAGTGCCACCTGACGTC

The sequence of the pcDNA3.1-E2A-E4-VA-TetR-V2 vector shown in FIG. 2B is provided below:

iHelper2/ pcDNA3.1-E2A-E4-VA-TetR-V2 (11,641 bp)

(SEQ ID NO: 2)

GACGGATCGGGAGATCTCCCGATCCCCTATGGTGCACTCTCAGTACAATC

TGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAAT

TGCATGAAGAATCTGCTTAGGGTTAGGCGTTTTGCGCTGCTTCGCGATGTACGGGCC

AGATATACGCGTTGACATTGATTATTGACTAGTTATTAATAGTAATCAATTACGGGG

TCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATT

GACGTCAATGACGGTAAATGGCCCGCCTGGCATTATGCCCAGTACATGACCTTATGG

GACTTTCCTACTTGGCAGTACATCTACGTATTAGTCATCGCTATTACCATGGTGATGC

GGTTTTGGCAGTACATCAATGGGCGTGGATAGCGGTTTGACTCACGGGGATTTCCAA

GTCTCCACCCCATTGACGTCAATGGGAGTTTGTTTTGGCACCAAAATCAACGGGACT

-continued

```
TTCCAAAATGTCGTAACAACTCCGCCCCATTGACGCAAATGGGCGGTAGGCGTGTAC
GGTGGGAGGTCTATATAAGCAGAGCTCTCTGGCTAACTAGAGAACCCACTGCTTACT
GGCTTATCGAAATTAATACGACTCACTATAGGGAGACCCAAGCTGGCTAGCGTTTAA
ACTTAAGCTTGGTACCGAGCTCGGATCCACTAGTCCAGTGTGGTGGAATTCCTGCTT
CGCGATGTACGGGCCAGATATACGCGTTGACATTGATTATTGACTAGTTATTAATAG
TAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCA
ATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCA
AGTACGCCCCCTATTGACGTCAATGACGGTAAATGGCCCGCCTGGCATTATGCCCAG
TACATGACCTTATGGGACTTTCCTACTTGGCAGTACATCTACGTATTAGTCATCGCTA
TTACCATGGTGATGCGGTTTTGGCAGTACATCAATGGGCGTGGATAGCGGTTTGACT
CACGGGGATTTCCAAGTCTCCACCCCATTGACGTCAATGGGAGTTTGTTTTGGAACC
AAAATCAACGGGACTTTCCAAAATGTCGTAACAACTCCGCCCCATTGACGCAAATG
GGCGGTAGGCGTGTACGGTGGGAGGTCTATATAAGCAGAGCTCTCCCTATCAGTGAT
AGAGATCTCCCTATCAGTGATAGAGATCGTCGACGAGCTCGTTTAGTGAACCGTCAG
ATCGCCTGGAGACGCCATCCACGCTGTTTTGACCTCCATAGAAGACACCGGGACCG
ATCCAGCCTCCGGACTCTAGCGTTTAAACTTAAGCTTGCCACCatggccagtcgggaagaggagc
agcgcgaaaccacccccgagcgcggacgcggtgcggcgcgacgtcccccaaccatggaggacgtgtcgtccccgtccccgtcgccgc
cgcctccccgggcgcccccaaaaaagcggatgaggcggcgtatcgagtccgaggacgaggaagactcatcacaagacgcgctggtgc
cgcgcacacccagcccgcggccatcgacctcggcggcggatttggccattgcgcccaagaagaaaaagaagcgcccttctcccaagcc
cgagcgcccgccatcaccagaggtaatcgtggacagcgaggaagaaagagaagatgtggcgctacaaatggtgggtttcagcaaccca
ccggtgctaatcaagcatggcaaaggaggtaagcgcacagtgcggcggctgaatgaagacgacccagtggcgcgtggtatgcggacgc
aagaggaagaggaagagcccagcgaagcggaaagtgaaattacggtgatgaacccgctgagtgtgccgatcgtgtctgcgtgggagaa
gggcatggaggctgcgcgcgcgctgatggacaagtaccacgtggataacgatctaaaggcgaacttcaaactactgcctgaccaagtgg
aagctctggcggccgtatgcaagacctggctgaacgaggagcaccgcgggttgcagctgaccttcaccagcaacaagacctttgtgacga
tgatggggcgattcctgcaggcgtacctgcagtcgtttgcagaggtgacctacaagcatcacgagcccacgggctgcgcgttgtggctgca
ccgctgcgctgagatcgaaggcgagcttaagtgtctacacggaagcattatgataaataaggagcacgtgattgaaatggatgtgacgagc
gaaaacgggcagcgcgcgctgaaggagcagtctagcaaggccaagatcgtgaagaaccggtggggccgaaatgtggtgcagatctcc
aacaccgacgcaaggtgctgcgtgcacgacgcggcctgtccggccaatcagttttccggcaagtcttgcggcatgttcttctctgaaggcg
caaaggctcaggtggcttttaagcagatcaaggcttttatgcaggcgctgtatcctaacgcccagaccgggcacggtcacctttttgatgccac
tacggtgcgagtgcaactcaaagcctgggcacgcgccctttttgggaaggcagctaccaaagttgactccgttcgccctgagcaacgcgg
aggacctggacgcggatctgatctccgacaagagcgtgctggccagcgtgcaccacccggcgctgatagtgttccagtgctgcaaccctg
tgtatcgcaactcgcgcgcgcagggcggaggccccaactgcgacttcaagatatcggcgcccgacctgctaaacgcgttggtgatggtgc
gcagcctgtggagtgaaaacttcaccgagctgccgcggatggttgtgcctgagtttaagtggagcactaaacaccagtatcgcaacgtgtc
cctgccagtggcgcatagcgatgcgcggcagaacccctttgattttaacccgggagttctagggatctgcccctctccctcccccccccta
acgttactggccgaagccgcttggaataaggccggtgtgcgtttgtctatatgttattttccaccatattgccgtcttttggcaatgtgagggccc
ggaaacctggccctgtcttcttgacgagcattcctaggggtctttcccctctcgccaaaggaatgcaaggtctgttgaatgtcgtgaaggaag
cagttcctctggaagcttcttgaagacaaacaacgtctgtagcgaccctttgcaggcagcggaacccccacctggcgacaggtgcctctg
cggccaaaagccacgtgtataagatacacctgcaaaggcggcacaaccccagtgccacgttgtgagttggatagttgtggaaagagtcaa
atggctctcctcaagcgtattcaacaaggggctgaaggatgcccagaaggtaccccattgtatgggatctgatctggggcctcggtgcacat
```

-continued gctttacatgtgtttagtcgaggttaaaaaaacgtctaggccccccgaaccacggggacgtggttttcctttgaaaaacacgatgataaggat
ccaccggaggccaccatgactacgtccggcgttccatttggcatgacactacgaccaacacgatctcggttgtctcggcgcactccgtaca
gtagggatcgtctacctccttttgagacagaaacccgcgctaccatactggaggatcatccgctgctgcccgaatgtaacactttgacaatgc
acaacgtgagttacgtgcgaggtcttccctgcagtgtgggatttacgctgattcaggaatgggttgttccctgggatatggttctaacgcggga
ggagcttgtaatcctgaggaagtgtatgcacgtgtgcctgtgttgtgccaacattgatatcatgacgagcatgatgatccatggttacgagtcc
tgggctctccactgtcattgttccagtcccggttccctgcagtgtatagccggcgggcaggttttggccagctggtttaggatggtggtggatg
gcgccatgtttaatcagaggtttatatggtaccgggaggtggtgaattacaacatgccaaaagaggtaatgtttatgtccagcgtgtttatgag
gggtcgccacttaatctacctgcgcttgtggtatgatggccacgtgggttctgtggtccccgccatgagctttggatacagcgccttgcactgt
gggattttgaacaatattgtggtgctgtgctgcagttactgtgctgatttaagtgagatcagggtgcgctgctgtgcccggaggacaaggcgc
cttatgctgcgggcggtgcgaatcatcgctgaggagaccactgccatgttgtattcctgcaggacggagcggcggcggcagcagtttattc
gcgcgctgctgcagcaccaccgccctatcctgatgcacgattatgactctacccccatgtagGCGGCCGCTCGAGTCTAG
AGGGCCCGTTTAAACCCGCTGATCAGCCTCGACTGTGCCTTCTAGTTGCCAGCCATC
TGTTGTTTGCCCCTCCCCCGTGCCTTCCTTGACCCTGGAAGGTGCCACTCCCACTGTC
CTTTCCTAATAAAATGAGGAAATTGCATCGCATTGTCTGAGTAGGTGTCATTCTATTC
TGGGGGGTGGGGTGGGGCAGGACAGCAAGGGGGAGGATTGGGAAGACAATAGCAG
GCATGCTGGGGATGCGGTGGGCTCTATGGCTTCTGAGGCGGAAAGAACCAGCTGGG
GCTCTAGGGGGTATCCCCggggttggggttgcgccttttccaaggcATCCAGCACAGTGGCGGCCGCa
atatttgcatgtcgctatgtgttctgggaaatcaccataaacgtgaaatccctatcagtgatagagacttataagttccctatcagtgatagagaa
ccggtgggcactcttccgtggtctggtggataaattcgcaagggtatcatggcggacgaccggggttcgagccccgtatccggccgtccg
ccgtgatccatgcggttaccgcccgcgtgtcgaacccaggtgtgcgacgtcagacaacgggggagtgctccttttttgaattccactttggcc
gcggctcgagggggttggggttgcgccttttccaaggcagccctgggtttgcgcagggacgcggctgctctgggcgtggttccgggaaac
gcagcggcgccgaccctgggtctcgcacattcttcacgtccgttcgcagcgtcacccggatcttcgccgctacccttgtgggccccccggc
gacgcttcctgctccgcccctaagtcgggaaggttccttgcggttcgcggcgtgccggacgtgacaaacggaagccgcacgtctcactagt
accctcgcagacggacagcgccagggagcaatggcagcgcgccgaccgcgatgggctgtggccaatagcggctgctcagcagggcg
cgccgagagcagcggccgggaaggggcggtgcgggaggcggggtgtggggcggtagtgtgggccctgttcctgcccgcgcggtgttc
cgcattctgcaagcctccggagcgcacgtcggcagtcggctccctcgttgaccgaatcaccgacctctctccccagggggatctgtgagttt
ggggacccttgattgttctttctttttcgctattgtaaaattcatgttatatggagggggcaaagttttcagggtgttgtttagaatgggaagatgtc
ccttgtatcaccatggaccctcatgataattttgtttctttcactttctactctgttgacaaccattgtctcctcttattttcttttcattttctgtaac
tttttcgttaaactttagcttgcatttgtaacgaatttttaaattcacttttgtttatttgtcagattgtaagtactttctctaatcacttttttttcaa
ggcaatcagggtatattatattgtacttcagcacagttttagagaacaattgttataattaaatgataaggtagaatatttctgcatataaattctggct
ggcgtggaaatattcttattggtagaaacaactacatcctggtcatcatcctgcctttctctttatggttacaatgatatacactgtttgagatgaggat
aaaatactctgagtccaaaccgggcccctctgctaaccatgttcatgccttcttctttttcctacagctcctgggcaacgtgctggttattgtgctgtct
catcattttggcaaagaattgtaatacgactcactatagggcgaGCCACCatggctagattagataaaagtaaagtgattaacagcgcattaga
gctgcttaatgaggtcggaatcgaaggtttaacaacccgtaaactcgcccagaagctaggtgtagagcagcctacattgtattggcatgtaaa
aaataagcgggctttgctcgacgccttagccattgagatgttagataggcaccatactcacttttgccctttagaaggggaaagctggcaaga
tttttacgtaataacgctaaaagttttagatgtgctttactaagtcatcgcgatggagcaaaagtacatttaggtacacggcctacagaaaaaca
gtatgaaactctcgaaaatcaattagcctttttatgccaacaaggtttttcactagagaatgcCttatatgcactcagcgcCgtggggcatttta
ctttaggttgcgtattggaagatcaagagcatcaagtcgctaaagaagaaagggaaacacctactactgatagtatgccgccattattacgac
aagctatcgaattatttgatcaccaaggtgcagagccagccttatattcggccttgaattgatcatatgcggattagaaaaacaacttaaatgt
gaaagtgggtccccaaaaaagaagagaaaggtcgacggcggtggttcagtttaagcgtacagcggctcccgggagttctagggatctgc -continued ccctctccctcccccccccctaacgttactggccgaagccgcttggaataaggccggtgtgcgtttgtctatatgttattttccaccatattgcc gtcttttggcaatgtgagggcccggaaacctggccctgtcttcttgacgagcattcctaggggtctttcccctctcgccaaaggaatgcaagg tctgttgaatgtcgtgaaggaagcagttcctctggaagcttcttgaagacaaacaacgtctgtagcgaccctttgcaggcagcggaacccccc cacctggcgacaggtgcctctgcggccaaaagccacgtgtataagatacacctgcaaaggcggcacaaccccagtgccacgttgtgagtt ggatagttgtggaaagagtcaaatggctctcctcaagcgtattcaacaaggggctgaaggatgcccagaaggtaccccattgtatgggatct gatctggggcctcggtgcacatgctttacatgtgtttagtcgaggttaaaaaaacgtctaggccccccgaaccacggggacgtggttttccttt gaaaaacacgatgataaggatccaccggagGCCACCatgaccgagtacaagcccacggtgcgcctcgccacccgcgacgacgtc cccagggccgtacgcaccctcgccgccgcgttcgccgactaccccgccacgcgccacaccgtcgatccggaccgccacatcgagcgg gtcaccgagctgcaagaactcttcctcacgcgcgtcgggctcgacatcggcaaggtgtgggtcgcggacgacggcgccgcggtggcgg tctggaccacgccggagagcgtcgaagcgggggcggtgttcgccgagatcggcccgcgcatggccgagttgagcggttcccggctggc cgcgcagcaacagatggaaggcctcctggcgccgcaccggcccaaggagcccgcgtggttcctggccaccgtcggcgtctcgcccga ccaccagggcaagggtctgggcagcgccgtcgtgctccccggagtggaggcggccgagcgcgccggggtgcccgccttcctggagac ctccgcgccccgcaacctccccttctacgagcggctcggcttcaccgtcaccgccgacgtcgaggtgcccgaaggaccgcgcacctggt gcatgacccgcaagcccggtgcctgaCCGCGTCTGGAACAATCAACCTCTGGATTACAAAATTTGT

GAAAGATTGACTGGTATTCTTAACTATGTTGCTCCTTTTACGCTATGTGGATACGCTG

CTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATTGCCACC

ACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACA

ATTCCGTGGTGTTGTCGGGGAAGCTGACGTCCTTTCCATGGCTGCTCGCCTGTGTTGC

CACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTT

CGCCCTCAGACGAGTCGGATCTCCCTTTGGGCCGCCTCCCCGCaAAATGACCGACCA

AGCGACGCCCAACCTGCCATCACGAGATTTCGATTCCACCGCCGCCTTCTATGAAAG

GTTGGGCTTCGGAATCGTTTTCCGGGACGCCGGCTGGATGATCCTCCAGCGCGGGGA

TCTCATGCTGGAGTTCTTCGCCCACCCCAACTTGTTTATTGCAGCTTATAATGGTTAC

AAATAAAGCAATAGCATCACAAATTTCACAAATAAAGCATTTTTTTCACTGCATTCT

AGTTGTGGTTTGTCCAAACTCATCAATGTATCTTATCATGTCTGTATACCGTCGACCT

CTAGCTAGAGCTTGGCGTAATCATGGTCATAGCTGTTTCCTGTGTGAAATTGTTATCC

GCTCACAATTCCACACAACATACGAGCCGGAAGCATAAAGTGTAAAGCCTGGGGTG

CCTAATGAGTGAGCTAACTCACATTAATTGCGTTGCGCTCACTGCCCGCTTTCCAGTC

GGGAAACCTGTCGTGCCAGCTGCATTAATGAATCGGCCAACGCGCGGGGAGAGGCG

GTTTGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCACAG

AATCAGGGGATAACGCAGGAAAGAACATGTGAGCAAAAGGCCAGCAAAAGGCCAG

GAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCATAGC

TCACGCTGTAGGTATCTCAGTTCGGTGTAGGTCGTTCGCTCCAAGCTGGGCTGTGTG

-continued

CACGAACCCCCCGTTCAGCCCGACCGCTGCGCCTTATCCGGTAACTATCGTCTTGAG

TCCAACCCGGTAAGACACGACTTATCGCCACTGGCAGCAGCCACTGGTAACAGGAT

TAGCAGAGCGAGGTATGTAGGCGGTGCTACAGAGTTCTTGAAGTGGTGGCCTAACT

ACGGCTACACTAGAAGAACAGTATTTGGTATCTGCGCTCTGCTGAAGCCAGTTACCT

TCGGAAAAAGAGTTGGTAGCTCTTGATCCGGCAAACAAACCACCGCTGGTAGCGGT

TTTTTTGTTTGCAAGCAGCAGATTACGCGCAGAAAAAAAGGATCTCAAGAAGATCCT

TTGATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAATGA

AGTTTTAAATCAATCTAAAGTATATATGAGTAAACTTGGTCTGACAGTTACCAATGC

TTAATCAGTGAGGCACCTATCTCAGCGATCTGTCTATTTCGTTCATCCATAGTTGCCT

GACTCCCCGTCGTGTAGATAACTACGATACGGGAGGGCTTACCATCTGGCCCCAGTG

CTGCAATGATACCGCGAGACCCACGCTCACCGGCTCCAGATTTATCAGCAATAAACC

AGCCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTTTG

CGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTG

TGCAAAAAAGCGGTTAGCTCCTTCGGTCCTCCGATCGTTGTCAGAAGTAAGTTGGCC

GCAGTGTTATCACTCATGGTTATGGCAGCACTGCATAATTCTCTTACTGTCATGCCAT

CCGTAAGATGCTTTTCTGTGACTGGTGAGTACTCAACCAAGTCATTCTGAGAATAGT

GTATGCGGCGACCGAGTTGCTCTTGCCCGGCGTCAATACGGGATAATACCGCGCCAC

ATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGC

AAAATGCCGCAAAAAAGGGAATAAGGGCGACACGGAAATGTTGAATACTCATACTC

TTCCTTTTTCAATATTATTGAAGCATTTATCAGGGTTATTGTCTCATGAGCGGATACA

TATTTGAATGTATTTAGAAAAATAAACAAATAGGGGTTCCGCGCACATTTCCCCGAA

AAGTGCCACCTGACGTC

Figure 3:
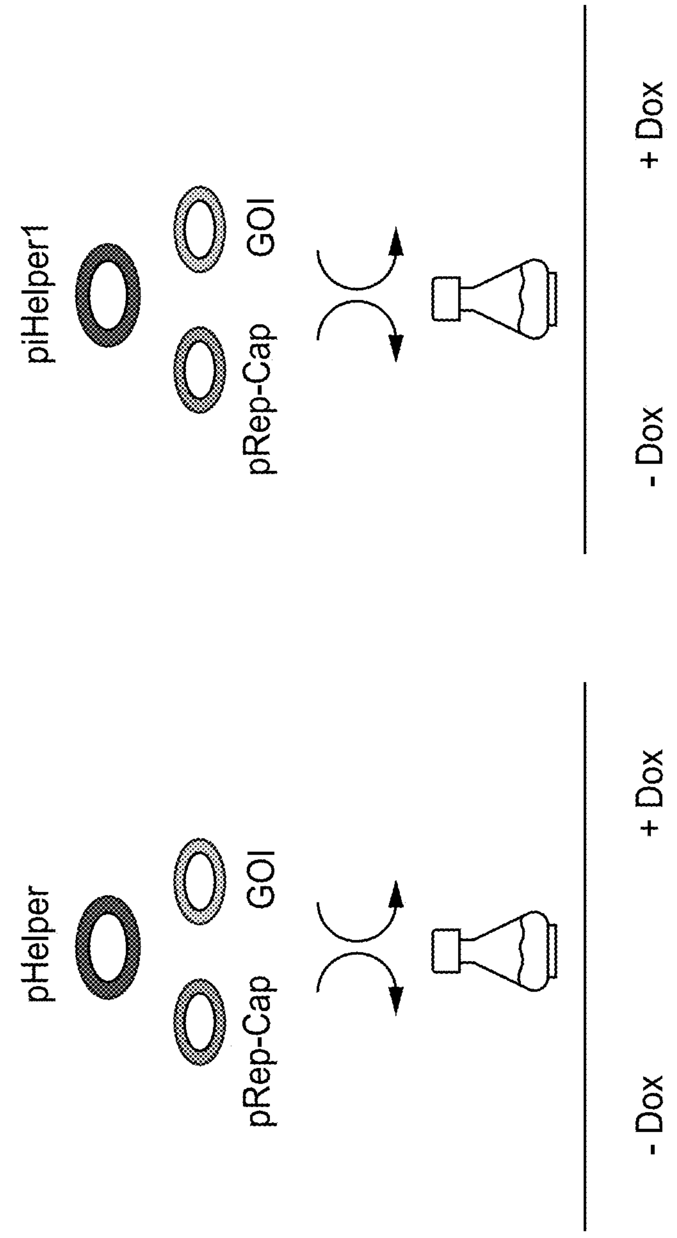
FIG. 3 shows the results of induction of helper and AAV genes in accordance with embodiments hereof.

The entire transfer plasmid including the derepressible Helper (piHelper1) and TetR expression cassettes was tested for use in AAV production by transient transfection. As shown in FIG. 3, when the plasmids were co-transfected with control pRep-Cap and pAAV-GOI plasmids, the addition of Dox activated the production of AAV to the level of approximately 30% of control Helper vectors that supports constitutive helper gene expression. Therefore, the derepressible helper construct was functional for AAV production upon induction.

Example 2: Design and Validation of Derepressible Rep-Cap Genes

Challenges for producing Rep proteins are two-fold. First, the ratio of Rep78 and Rep52 needs to be maintained during induction for high titer AAV production. Second, the p19 promoter required for Rep52 expression is located inside the coding region of Rep78, which creates challenges for including a derepressible promoter. To overcome these challenges, two strategies were developed (FIGS. 4A-4C).

First, to retain the natural regulation of Rep gene expression (see FIG. 4A), the original viral promoters were retained but modified by inserting two TetO sites surround the TATA box and TSS. Two copies of TetO sites was inserted into the upstream truncated p5 promoter with core elements including TATA box, Rep Binding Element (RBE), and YY1 site. In addition, a wildtype copy of p5 promoter, serving as an enhancer, was placed downstream of cap gene to support both Rep and Cap expression (FIG. 5) (See, e.g., U.S. Pat. No. 5,622,856).

The sequences for the derepressible p5 promoters set forth in FIG. 5 are as follows min-p5-i1

(SEQ ID NO: 3)

TATTTAATCTCCCTATCAGTGATAGAGATCTCCCTATCAGTGATAGAGAT

CGCCCGAGTGAGCACGCAGGGTCTCCATTTTGAAGCGGGAGGTTTGAACG

CGCAGCCGCC

-continued min-p5-i2

(SEQ ID NO: 4)

TATTTAAtcTCCCTATCAGTGATAGAGAtcGCCCGAGTGAGCACGCAGGG

TCTCCATTTTGATCCCTATCAGTGATAGAGAAGCGGGAGGTTTGAACGCG

CAGCCGCC min-p5-i3

(SEQ ID NO: 5)

TCCCTATCAGTGATAGAGAtcTATTTAAGCCCGAGTGAGCACGCAGTCCC

TATCAGTGATAGAGAGGTCTCCATTTTGAAGCGGGAGGTTTGAACGCGCA

GCCGCC

Similarly, two copies of TetO sites were also inserted into the p19 promoter next to TSS site (FIG. 6). In order to minimize the interference of such insertion and maximize the original activity of these viral promoters, three ways of insertion of TetO sites were designed for each promoter for best performance. Thus, a total of 9 variations were examined (iRepCap 1 to iRepCap9).

The sequences for the derepressible promoters including p19 illustrated schematically in FIG. 6 are provided below:

p19-i1

(SEQ ID NO: 6)

ccagaaatggcgccggaggcgggaacaaggtggtggatgagtgctacatc cccaattacttgctccccaaaacccagcctgagctccagtgggcgtggac taatatggaacagtatttaagcgcctgTCCCTATCAGTGATAGAGATCTC CCTATCAGTGATAGAGAtttgaatctcacggag p19-i2

(SEQ ID NO: 7)

ccagaaatggcgccggaggcgggaacaaggtggtggatgagtgctacatc cccaattacttgctccccaaaacccagcctgagTCCCTATCAGTGATAGA GActccagtgggcgtggactaatatggaacagtatttaagcgcctgTCCC TATCAGTGATAGAGAtttgaatctcacggag p19-i3

(SEQ ID NO: 8)

ccagaaatggcgccggaggcgggaacaaggtggtggatgagtgctacatc cccaattacttgaccccaaaacccagcctgagctccagtgggcgtggact aatatggaaTCCCTATCAGTGATAGAGAcagtatttaagcgcctgTCCCT ATCAGTGATAGAGAtttgaatctcacggag Two methods were developed for the placement of the derepressible p19 promoters. In the first method, a separate expression cassette for Rep52 was generated, driven by the derepressible p19 promoters. In the first method shown in FIG. 4B, the original p19 promoter in the Rep78 ORF was silenced by changing six nucleotides in three core regulatory elements required for p19 activity (SP1, TATA-1, and TATA-2 sites). These changes did not alter the Rep78 protein sequence. Rep78 was controlled by a derepressible p5 promoter.

In a second method, an artificial intron was created for the insertion of TetO sites in the Rep78 ORF (FIG. 4C). The chimeric intron between introns from human (3-globin and immunoglobulin heavy chain genes was adopted by replacing the non-essential internal sequence with the $TetO_2$ sites (FIG. 7A). The new artificial intron was inserted 1 bp or 25 bp downstream of TATA-2 of p19 promoter in situ (iRepCap-10 and iRepCap 11) (FIG. 4B and FIG. 7B). The new p19 promoter with adjacent TetO-containing intron ensured the repression of Rep52 gene expression before induction, while still allowing for the expression of the Rep78 protein after the removal of the intron during mRNA splicing. The efficiency of splicing is evaluated by PCR analysis for the cDNA.

Figure 7A:
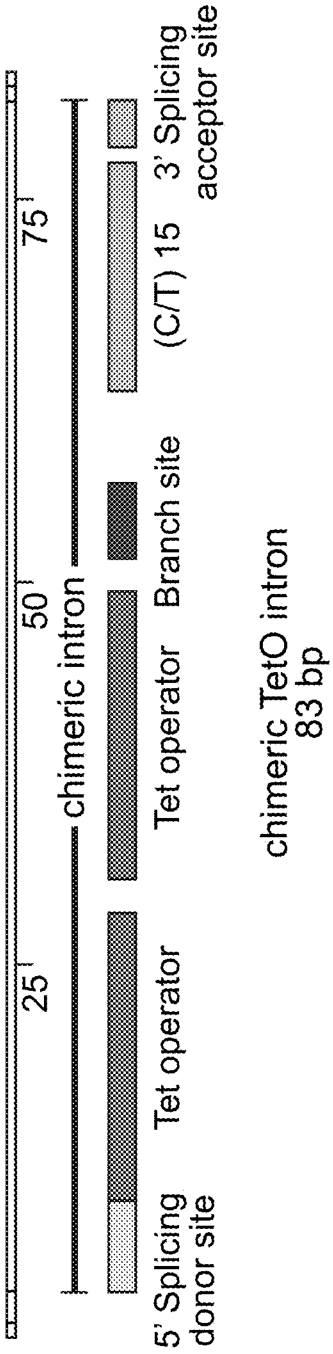
FIG. 7A-7B shows exemplary derepressible p19 promoters, including an artificial intron, in accordance with embodiments hereof.
Figure 7B:
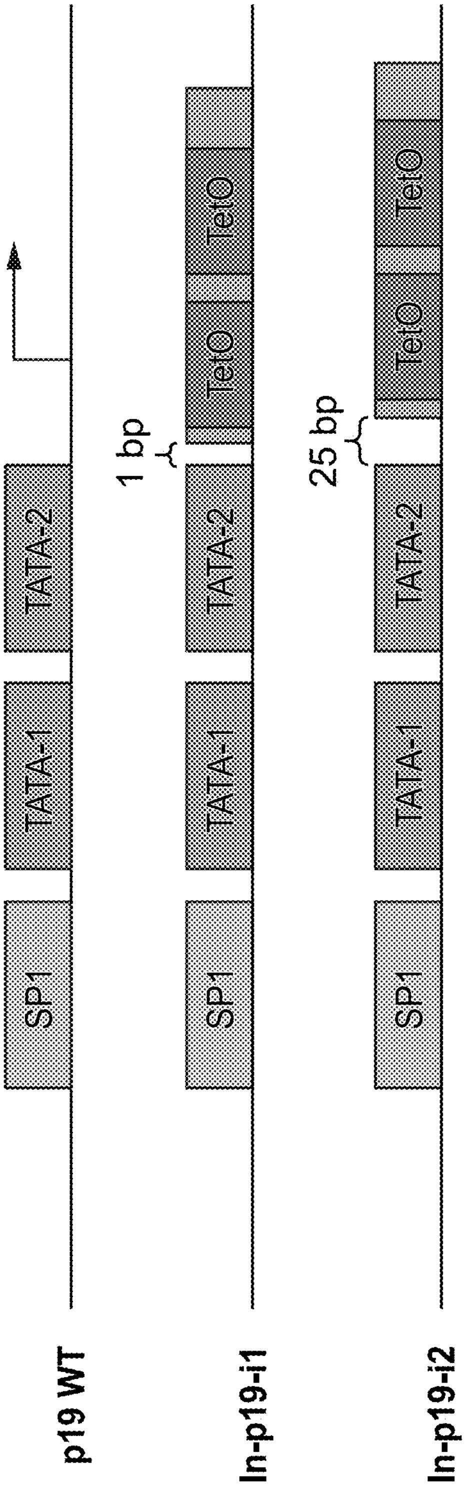

The nucleic acid sequences for the intron-based p19 promoters illustrated in FIGS. 7A-7B are provided below.

In-p19-i1

(SEQ ID NO: 9)

ccagaaatggcgccggaggcgggaacaaggtggtggatgagtgctacatc cccaattacttgctccccaaaacccagcctgagctccagtgggcgtggac taatatggaacagtatttaaggtaagtTCCCTATCAGTGATAGAGATCTC CCTATCAGTGATAGAGAtactgacatccactttgcctttctctccacagc gcctgtttgaatctcacggag In-p19-i2

Figure 8A:
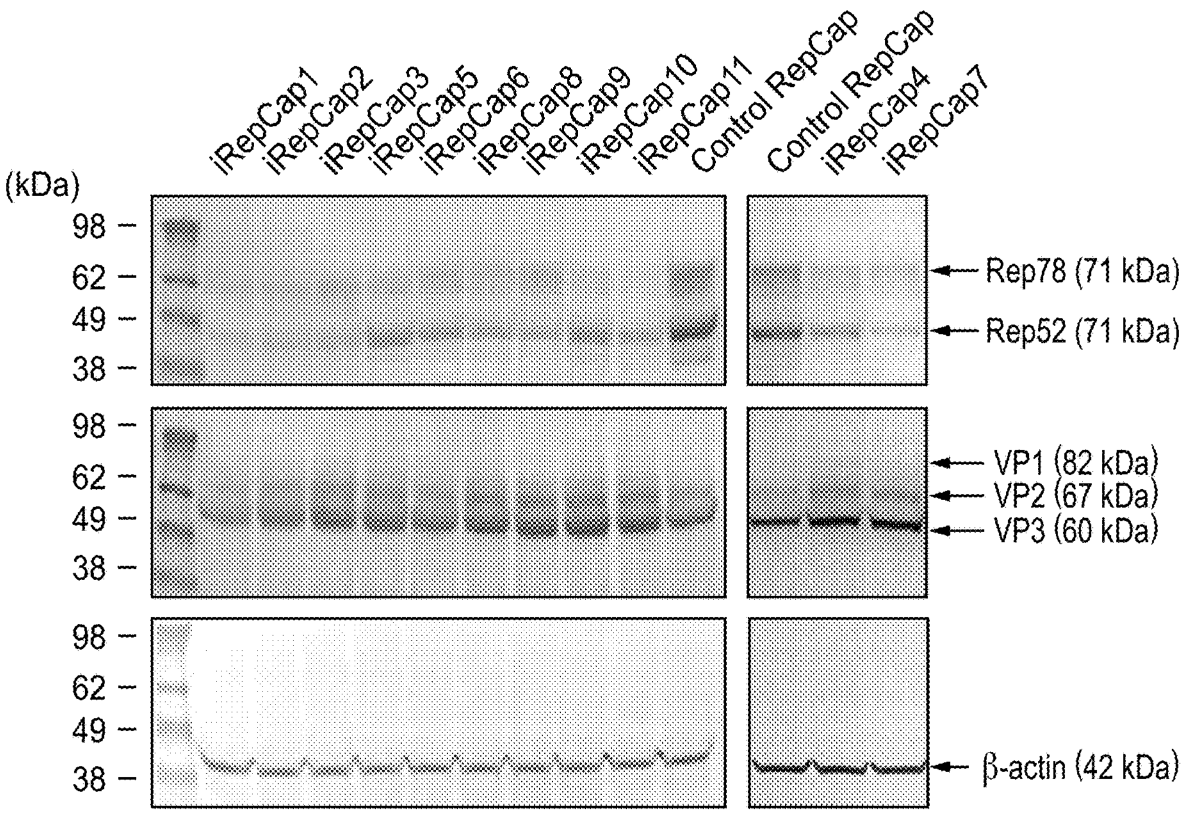
FIGS. 8A-8B show the results of Rep-Cap expression and AAV titers using the Rep-Cap vectors, in accordance with embodiments hereof.
Figure 8B:
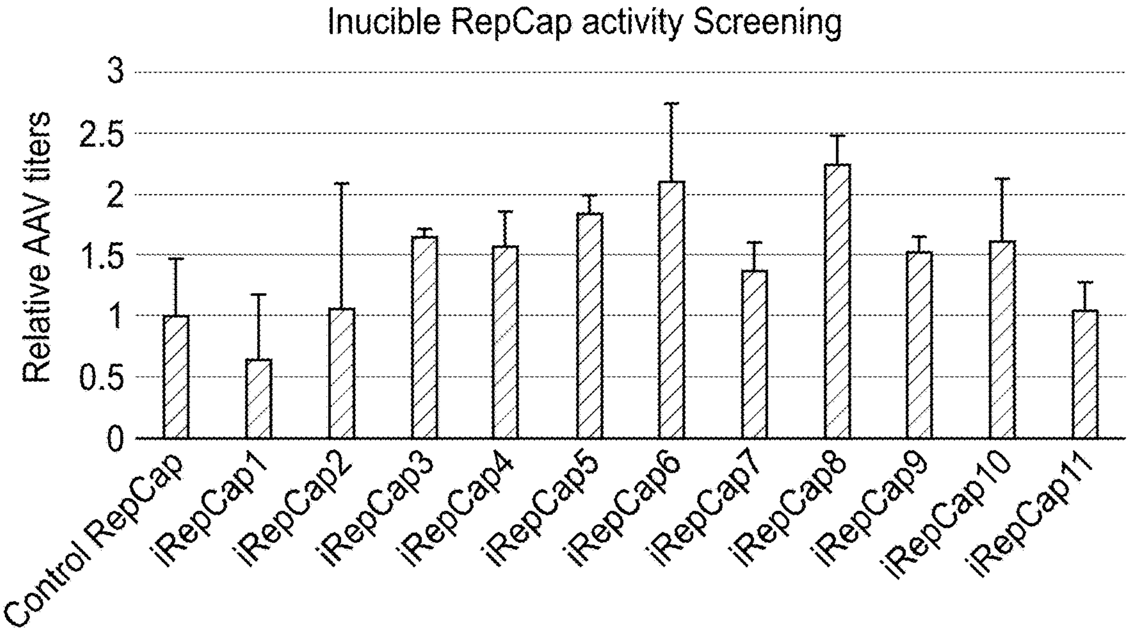

(SEQ ID NO: 10)

ccagaaatggcgccggaggcgggaacaaggtggtggatgagtgctacatc cccaattacttgctccccaaaacccagcctgagctccagtgggcgtggac taatatggaacagtatttaagcgcctgtttgaatctcacggaaaggtaag tTCCCTATCAGTGATAGAGATCTCCCTATCAGTGATAGAGAtactgacat ccactttgcctttctctccacag To test the activity of the 11 inducible Rep-Cap designs, HEK293 cells were transfected with one of the vectors plus standard pHelper and pAAV-GFP for AAV production. Three days after transfection, cells were harvested for Rep-Cap protein expression and AAV titer analysis. Western blot analysis revealed various expression levels of Rep and Cap proteins; many maintained similar ratios of Rep78 vs Rep52 as control RepCap vector (FIG. 8A). qPCR analysis of the AAV titer showed that the designs performed similarly or had higher titers compared to control triple transfection (FIG. 8B).

Figure 9A:
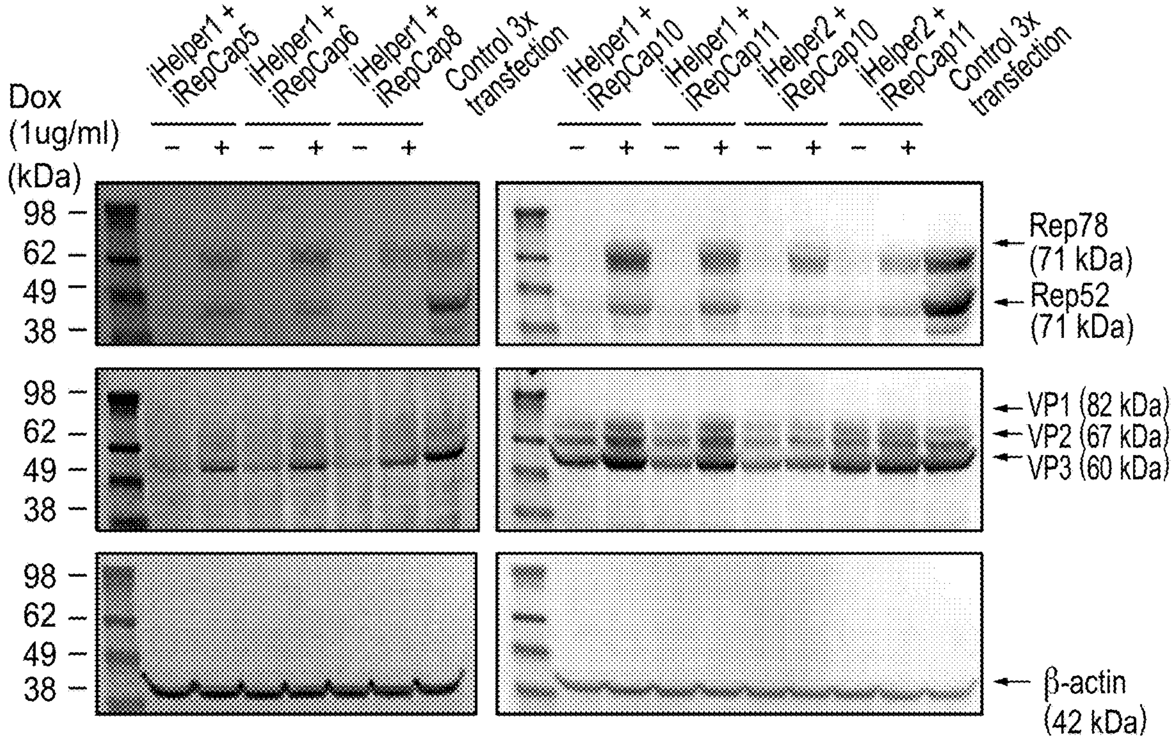
FIGS. 9A-9B show additional results of Rep-Cap expression and AAV titers using the Helpers and Rep-Cap vectors, in accordance with embodiments hereof.
Figure 9B:
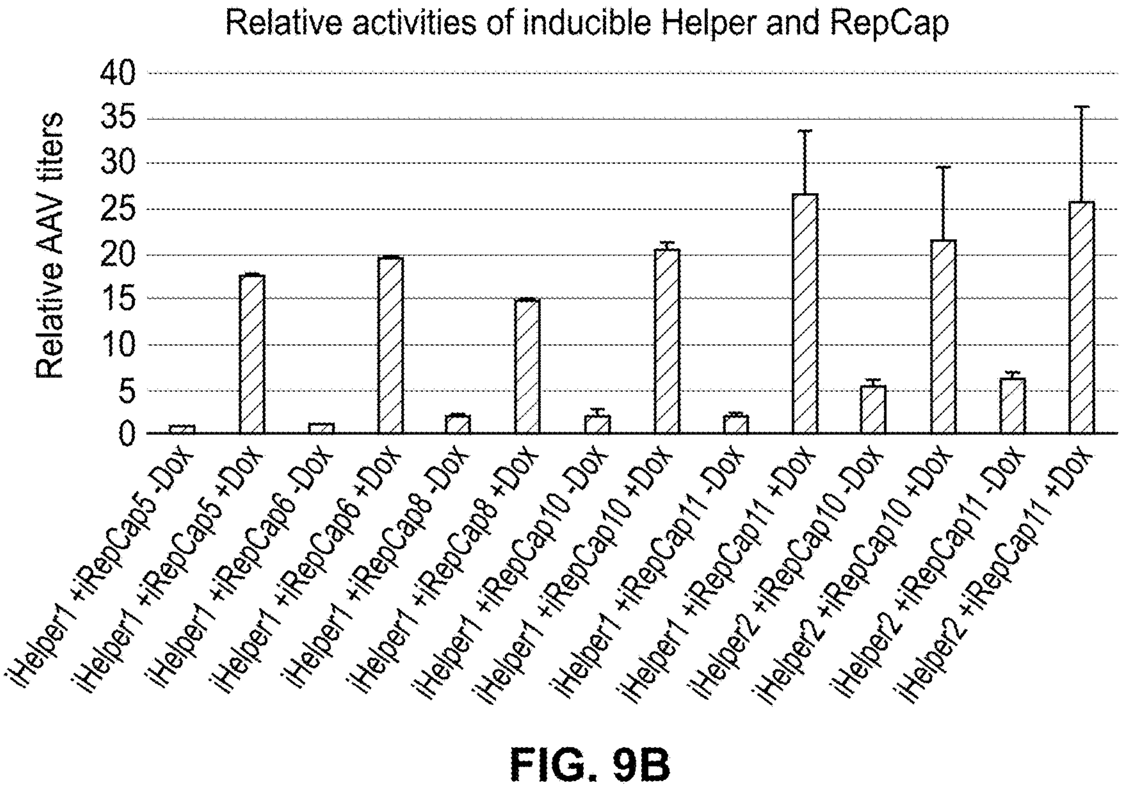

To test the performance of both inducible helpers and inducible Rep-Cap designs together, HEK293 cells were transfected with selected iRepCap vectors, iHelperl/2, and pAAV-GFP, and left untreated or treated with Doxycycline for three days. As shown in FIG. 9A, the protein expression of Rep and Cap was only induced by the addition of Dox, and the derepression of the derepressible promoters. Accordingly, the AAV titer was significantly increased over 10 to 25 fold upon derepression (FIG. 9B).

To stably integrate the iHelper and iRepCap, iHelperl/2 and iRepCap10 were chosen with AAV-GFP to assemble the functional cassettes into a single PIGGYBAC™ transposon transfer vector PB007 (Transposagen, Inc., Lexington, Ky.). FIGS. 10A-10D show the plasmid constructs used for integration into mammalian cells, suitably HEK293 cells. To facilitate the future addition of specific AAV genes of interest, the AAV-GFP was not included in some of the transfer vectors (FIGS. 10A and 10B). HEK293 cells will be transfected with both the transfer vectors and transposase mRNA and the integrated cell pool will be enriched by puromycin selection. The single cell clones will be isolated and screened for AAV production with and without Dox treatment to activate derepression.

The nucleic acid sequence of the vector illustrated in FIG. 10 A is provided below:

PB007-iHelper1-iRepCap10/ PBBG7 (18,281 bp)

(SEQ ID NO: 11)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

-continued

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcacctttttgatgc cactacggtgcgagtgcaactcaaagcctgggcacgcgccctttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgatttttaacccgggagttctagggatctgcccctctccctcccccccc cctaacgttactggccgaagccgcttggaataaggccggtgtgcgtttgtctatatgttattttccaccatattgccgtcttttggcaatgtgagg gcccggaaacctggccctgtcttcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaaccccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg ggaggagcttgtaatcctgaggaagtgtatgcacgtgtgcctgtgttgtgccaacattgatatcatgacgagcatgatgatccatggttacga gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGCTCGAGTCT

AGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACAATAGC

-continued

AGGCATGCTGGGGATGCGGTGGGCTCTATGGCTTCTGAGGCGGAAAGAACCAGCTG

GGGCTCTAGGGGGTATCCCCggggttggggttgcgccttttccaaggcATCCAGCACAGTGGCGGCC

GCaatatttgcatgtcgctatgtgttctgggaaatcaccataaacgtgaaatccctatcagtgatagagacttataagttccctatcagtgatag agaaccggtgggcactcttccgtggtctggtggataaattcgcaagggtatcatggcggacgaccggggttcgagccccgtatccggccg tccgccgtgatccatgcggttaccgcccgcgtgtcgaacccaggtgtgcgacgtcagacaacgggggagtgctccttttggaattccactttg gccgcggctcgaggggggttggggttgcgccttttccaaggcagccctgggtttgcgcagggacgcggctgctctgggcgtggttccggg aaacgcagcggcgccgaccctgggtctcgcacattcttcacgtccgttcgcagcgtcacccggatcttcgccgctacccttgtgggccccc cggcgacgcttcctgctccgcccctaagtcgggaaggttccttgcggttcgcggcgtgccggacgtgacaaacggaagccgcacgtctca ctagtaccctcgcagacggacagcgccagggagcaatggcagcgcgccgaccgcgatgggctgtggccaatagcggctgctcagcag ggcgcgccgagagcagcggccgggaaggggcggtgcgggaggcggggtgtggggcggtagtgtgggccctgttcctgcccgcgcg gtgttccgcattctgcaagcctccggagcgcacgtcggcagtcggctccctcgttgaccgaatcaccgacctctctccccagggggatctgt gagtttggggacccttgattgttctttctttttcgctattgtaaaattcatgttatatggagggggcaaagttttcagggtgttgtttagaatgggaa gatgtcccttgtatcaccatggaccctcatgataatttgtttctttcactttctactctgttgacaaccattgtctcctcttattttcttttcattttct gtaactttttcgttaaactttagcttgcatttgtaacgaatttttaaattcacttttgtttatttgtcagattgtaagtactttctctaatcacttttttt tcaaggcaatcagggtatattatattgtacttcagcacagttttagagaacaattgttataattaaatgataaggtagaatatttctgcatataaattctg gctggcgtggaaatattcttattggtagaaacaactacatcctggtcatcatcctgcctttctctttatggttacaatgatatacactgtttgagatgagg ataaaatactctgagtccaaaccgggcccctctgctaaccatgttcatgccttcttctttttcctacagctcctgggcaacgtgctggttattgtgctg tctcatcattttggcaaagaattgtaatacgactcactatagggcgaGCCACCatggctagattagataaaagtaaagtgattaacagcg cattagagctgcttaatgaggtcggaatcgaaggtttaacaacccgtaaactcgcccagaagctaggtgtagagcagcctacattgtattggc atgtaaaaaataagcgggctttgctcgacgccttagccattgagatgttagataggcaccatactcacttttgccctttagaaggggaaagctg gcaagatttttacgtaataacgctaaaagttttagatgtgctttactaagtcatcgcgatggagcaaaagtacatttaggtacacggcctacag aaaaacagtatgaaactctcgaaaatcaattagcctttttatgccaacaaggtttttcactagagaatgcCttatatgcactcagcgcCgtggg gcattttactttaggttgcgtattggaagatcaagagcatcaagtcgctaaagaagaaagggaaacacctactactgatagtatgccgccatta ttacgacaagctatcgaattatttgatcaccaaggtgcagagccagccttcttattcggccttgaattgatcatatgcggattagaaaaacaactt aaatgtgaaagtgggtccccaaaaaagaagagaaaggtcgacggcggtggtgctttgtctcctcagcactctgctgtcactcaaggaagtat catcaagaacaaggagggcatggatgctaagtcactaactgcctggtcccggacactggtgaccttcaaggatgtatttgtggacttcacca gggaggagtggaagctgctggacactgctcagcagatcgtgtacagaaatgtgatgctggagaactataagaacctggtttccttgggttat cagcttactaagccagatgtgatcctccggttggagaagggagaagagccctggctggtggagagagaaattcaccaagagacccatcct gattcagagactgcatttgaaatcaaatcatcagtttaagcgtacagcggctcccgggagttctagggatctgcccctctccctccccccccc ctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaagg aagcagttcctctggaagcttcttgaagacaaacaacgtctgtagcgaccctttgcaggcagcggaaccccccacctggcgacaggtgcct ctgcggccaaaagccacgtgtataagatacacctgcaaaggcggcacaaccccagtgccacgttgtgagttggatagttgtggaaagagt caaatggctctcctcaagcgtattcaacaaggggctgaaggatgcccagaaggtaccccattgtatgggatctgatctggggcctcggtgc acatgctttacatgtgtttagtcgaggttaaaaaaacgtctaggccccccgaaccacggggacgtggttttcctttgaaaaacacgatgataag gatccaccggagGCCACCatgaccgagtacaagcccacggtgcgcctcgccacccgcgacgacgtccccagggccgtacgcacc ctcgccgccgcgttcgccgactaccccgccacgcgccacaccgtcgatccggaccgccacatcgagcgggtcaccgagctgcaagaac tcttcctcacgcgcgtcgggctcgacatcggcaaggtgtgggtcgcggacgacggcgccgcggtggcggtctggaccacgccggagag cgtcgaagcgggggcggtgttcgccgagatcggcccgcgcatggccgagttgagcggttcccggctggccgcgcagcaacagatgga aggcctcctggcgccgcaccggcccaaggagcccgcgtggttcctggccaccgtcggcgtctcgcccgaccaccagggcaagggtctg ggcagcgccgtcgtgctccccggagtggaggcggccgagcgcgccggggtgcccgccttcctggagacctccgcgccccgcaacctc -continued cccttctacgagcggctcggcttcaccgtcaccgccgacgtcgaggtgcccgaaggaccgcgcacctggtgcatgacccgcaagcccg gtgcctgaCCGCGTCTGGAACAATCAACCTCTGGATTACAAAATTTGTGAAAGATTGACT

GGTATTCTTAACTATGTTGCTCCTTTTACGCTATGTGGATACGCTGCTTTAATGCCTT

TGTATCATGCTATTGCTTCCCGTATGGCTTTCATTTTCTCCTCCTTGTATAAATCCTGG

TTGCTGTCTCTTTATGAGGAGTTGTGGCCCGTTGTCAGGCAACGTGGCGTGGTGTGC

ACTGTGTTTGCTGACGCAACCCCCACTGGTTGGGGCATTGCCACCACCTGTCAGCTC

CTTTCCGGGACTTTCGCTTTCCCCCTCCCTATTGCCACGGCGGAACTCATCGCCGCCT

GCCTTGCCCGCTGCTGGACAGGGGCTCGGCTGTTGGGCACTGACAATTCCGTGGTGT

TGTCGGGGAAGCTGACGTCCTTTCCATGGCTGCTCGCCTGTGTTGCCACCTGGATTCT

GCGCGGGACGTCCTTCTGCTACGTCCCTTCGGCCCTCAATCCAGCGGACCTTCCTTCC

CGCGGCCTGCTGCCGGCTCTGCGGCCTCTTCCGCGTCTTCGCCTTCGCCCTCAGACG

AGTCGGATCTCCCTTTGGGCCGCCTCCCCGCaAAATGACCGACCAAGCGACGCCCAA

CCTGCCATCACGAGATTTCGATTCCACCGCCGCCTTCTATGAAAGGTTGGGCTTCGG

AATCGTTTTCCGGGACGCCGGCTGGATGATCCTCCAGCGCGGGGATCTCATGCTGGA

GTTCTTCGCCCACCCCAACTTGTTTATTGCAGCTTATAATGGTTACAAATAAAGCAAT

AGCATCACAAATTTCACAAATAAAGCATTTTTTTCACTGCATTCTAGTTGTGGTTTGT

CCAAACTCATCAATGTATCTTATCATGTCTGTAGCtGATcaATTgGCGCGCCGAATTCG

TTatctgcagaattcggcttggcggctgcgcgttcaaacctcccgcttcaaaatggagaccctgcgtgctcactcgggcttaaatacccag cgtgaccacatggtgtcgcaaaatgtcgcaaaacactcacgtgacctctaatacaggacctctagagcatggaaactagataagaaagaaa tacgcagagaccaaagttcaactgaaacgaattaaacggtttattgattaacaagcaaactagtttacagattacgggtgaggtaacgggtgc cgatggggcgaggctcagaataaacgccatttgtgtcaacagcaaagtccacatttgtagatttgttgtagttggaagtgtattgaatctctgg gttccagcgtttgctgttttctttctgcagctcccattcaatttccacgctgacctgtccggtgctgtactgcgtgatgaacgacgcaaacttagct ggactgaaggtagttggaggattcgcgggaacaggtgtattcttaatcaggatctgaggaggcgggtgtttcagtccaaagcctcccatcag cggcgagggatgaaagtgtccgtccgtgtgaggaatcttggcccagataggaccctgcaggtacacgtcccggtcctgccagaccatgcc aggtaaggctccttgactgttgacggtccctgtagcaggagcggtgttggccgattgcaggttagtggccaccgtgccgtactcttctgtggc cactgggttggtggtttaatttcttcctcgttggttatcataacgttgtcaaggtccacgttgctatttccagctccctgtttcccaaatattaagact ccgctcatcggaaaaaatttgtcttcgtcgtccttgtgggttgccatagcgggaccgggatttaccagagagtctctgccattcagatgatactt ggtggcaccggtccaggcaaagttgctgttgttattttgattggttgtcttggagacgcgttgctgccggtagcagggcccgggtagccagttt ttggcctgattcgccatgctactaggcccggcctgagaaaattgcaacgtccgatttcctgcggtaccactcgtggtctgagtccgagacag gtagtacaggtactggtcgatgaggggggttcatcagccggtccaggctttggctgtgcgcgtagctgctgtgaaaaggcacgtcctcaaac gtgtagctgaactgaaagttgttgcccgttctcagcatttgagaaggaaagtattccaggcagtagaaggaggaacggcccacggcctgac tgccattgttcagagtcaggtacccgtactgaggaatcatgaagacgtccgccgggaacggaggcaggcagccctggtgcgcagagccg aggacgtacgggagctggtattccgagtccgtaaagacctgaaccgtgctggtaaggttattggcgatggtcgtggtgccatcattcgtcgt gacctccttgacctggatgttgaagagcttgaagttgagcttcttgggccggaatccccagttgttgttgatgagtcgctgccagtcacgtggt gagaagtggcagtggaatctgttaaagtcaaaataccccccaggggggtgctgtagccgaagtaggtgttgtcgttggtgctgcctcccgattg gctggagatttgcttgtagaggtggttgttgtaggtggggagggcccaggttcgggtgctggtggtgatgactctgtcgcccagccatgtgg aatcgcaatgccaatttcctgaggcgttacccactccgtcggcgccttcgttattgtctgccattggagcgccaccgcctgcagccattgtatt agatcccacaccagagggggctgcgggggggttctccgagtggttgagggtcgggcactgactctgagtcgccagtctgcccaaagttga gtctctttctcgcgggctgctggcctttcttgccgatgcccgaagaggagtctggttcctggggtgattgctctaccggtctcttctttccagga gccgtcttagcgccttcctcaaccagaccgagaggttcgagaacccgcttcttggcctggaagactgctcgcccgaggttgcccccaaaag -continued acgtatcttcttgcagacgctcctgaaactcggcgtcggcgtggttataccgcaggtacggattgtcacccgctttgagctgctggtcgtagg ccttgtcgtgctcgagggccgctgcgtccgccgcgttgacgggctccccttgtcgagtccgttgaagggtccgaggtacttgtagccagg aagcaccagaccccggccgtcgtcctgcttttgctggttggctttgggtttcggggctccaggtttcaagtcccaccactcgcgaatgccctc agagaggttgtcctcgagccaatctggaagataaccatcggcagccatacctgatttaaatcatttattgttcaaagatgcagtcatccaaatc cacattgaccagatcgcaggcagtgcaagcgtctggcacctttcccatgatatgatgaatgtagcacagtttctgatacgcctttttgacgaca gaaacgggttgagattctgacacgggaaagcactctaaacagtctttctgtccgtgagtgaagcagatatttgaattctgattcattctctcgca ttgtctgcagggaaacagcatcagattcatgcccacgtgacgagaacatttgttttggtacctgtctgcgtagttgatcgaagcttccgcgtctg acgtcgatggctgcgcaactgactcgcgcacccgtttgggctcacttatatctgcgtcactgggggcgggtcttttcttggctccacccttttg acgtagaattcatgctccacctcaaccacgtgatcctttgcccaccggaaaaagtctttgacttcctgcttggtgaccttcccaaagtcatgatc cagacggcgggtgagttcaaatttgaacatccggtcttgcaacggctgctggtgttcgaaggtcgttgagttcccgtcaatcacggcgcaca tgttggtgttggaggtgacgatcacgggagtcgggtctatctgggccgaggacttgcatttctggtccacgcgcaccttgcttcctccgagaa tggctttggccgactccacgaccttggcggtcatcttcccctcctcccaccagatcaccatcttgtcgacacagtcgttgaagggaaagttctc attggtccagtttacgcacccgtagaagggcacagtgtgggctatggcctccgcgatgttggtcttcccggtagttgcaggcccaaacagcc agatggtgttcctcttgccgaactttttcgtggcccatcccagaaagacggaagccgcatattggggatcgtacccgtttagttccaaaattta taaatccgattgctggaaatgtcctccacgggctgctggcccaccaggtagtcgggggcggttttagtcaggctcataatctttcccgcattgt ccaaggcagccttgatttgggaccgcgagttggaggccgcattgaaggagatgtatgaggcctggtcctcctggatccactgcttctccga ggtaatccccttgtccacgagccacccgaccagctccatgtacctggctgaagtttttgatctgatcaccggcgcatcagaattgggattctga ttctctttgttctgctcctgcgtctgcgacacgtgcgtcagatgctgcgccaccaaccgtttacgctccgtgagattcaaacaggcgctgtgga gagaaaggcaaagtggatgtcagtaTCTCTATCACTGATAGGGAGATCTCTATCACTGATAGGGAac ttaccttaaatactgttccatattagtccacgcccactggagctcaggctgggttttggggagcaagtaattggggatgtagcactcatccacc accttgttcccgcctccggcgccatttctggtctttgtgaccgcgaaccagtttggcaaagtcggctcgatcccgcggtaaattctctgaatca gtttttcgcgaatctgactcaggaaacgtcccaaaaccatggatttcaccccggtggtttccacgagcacgtgcatgtggaagtagctctctcc cttctcaaattgcacaaagaaaagagcctccggggccttactcacacggcgccattccgtcagaaagtcgcgctgcagcttctcggccacg gtcaggggtgcctgctcaatcagattcagatccatgtcagaatctggcggcaactcccattccttctcggccacccagttcacaaagctgtca gaaatgccgggcagatgctcgtcaaggtcgctggggaccttaatcacaatctcgtaaaaccccggcatGGCGGCTGCGCGTT CAAACCTCCCGCTTCAAAATGGAGACCCTGCGTGCTCACTCGGGCgaTCTCTATCACT GATAGGGAGATCTCTATCACTGATAGGGAgaTTAAATAgaatggCTAggATCCGGCCGGc cTGCAggTGTCCTCACAGGAACGAAGTCCCTAAAGAAACAGTGGCAGCCAGGTTTAG

CCCCGGAATTGACTGGATTCCTTTTTTAGGGCCCATTGGTATGGCTTTTTCCCCGTAT

CCCCCCAGGTGTCTGCAGGCTCAAAGAGCAGCGAGAAGCGTTCAGAGGAAAGCGAT

CCCGTGCCACCTTCCCCGTGCCCGGGCTGTCCCCGCACGCTGCCGGCTCGGGGATGC

GGGGGGAGCGCCGGACCGGAGCGGAGCCCCGGGCGGCTCGCTGCTGCCCCCTAGCG

GGGGAGGGACGTAATTACATCCCTGGGGGCTTTGGGGGGGGGCTGTCCCTCTAGAG

CGGCCGCCACCGCGGTGGAGCTCCAGCTTTTGTTCCCTTTAGTGAGGGTTAATTAGA

TCTTAATACGACTCACTATAGGGCGAATTGGGTACCGGGCCCCCCCTCGAGGTCGAC

GGTATCGATAAGCTTGATATCTATAACAAGAAAATATATATATAATAAGTTATCACG

TAAGTAGAACATGAAATAACAATATAATTATCGTATGAGTTAAATCTTAAAAGTCAC

GTAAAAGATAATCATGCGTCATTTTGACTCACGCGGTCGTTATAGTTCAAAATCAGT

GACACTTACCGCATTGACAAGCACGCCTCACGGGAGCTCCAAGCGGCGACTGAGAT

GTCCTAAATGCACAGCGACGGATTCGCGCTATTTAGAAAGAGAGAGCAATATTTCA

AGAATGCATGCGTCAATTTTACGCAGACTATCTTTCTAGGGTTAATCTAGCTGCATC

-continued

AGGATCATATCGTCGGGTCTTTTTTCCGGCTCAGTCATCGCCCAAGCTGGCGCTATCT

GGGCATCGGGGAGGAAGAAGCCCGTGCCTTTTCCCGCGAGGTTGAAGCGGCATGGA

AAGAGTTTGCCGAGGATGACTGCTGCTGCATTGACGTTGAGCGAAAACGCACGTTTA

CCATGATGATTCGGGAAGGTGTGGCCATGCACGCCTTTAACGGTGAACTGTTCGTTC

AGGCCACCTGGGATACCAGTTCGTCGCGGCTTTTCCGGACACAGTTCCGGATGGTCA

GCCCGAAGCGCATCAGCAACCCGAACAATACCGGCGACAGCCGGAACTGCCGTGCC

GGTGTGCAGATTAATGACAGCGGTGCGGCGCTGGGATATTACGTCAGCGAGGACGG

GTATCCTGGCTGGATGCCGCAGAAATGGACATGGATACCCCGTGAGTTACCCGGCG

GGCGCGCTTGGCGTAATCATGGTCATAGCTGTTTCCTGTGTGAAATTGTTATCCGCTC

ACAATTCCACACAACATACGAGCCGGAAGCATAAAGTGTAAAGCCTGGGGTGCCTA

ATGAGTGAGCTAACTCACATTAATTGCGTTGCGCTCACTGCCCGCTTTCCAGTCGGG

AAACCTGTCGTGCCAGCTGCATTAATGAATCGGCCAACGCGCGGGGAGAGGCGGTT

TGCGTATTGGGCGCTCTTCCGCTTCCTCGCTCACTGACTCGCTGCGCTCGGTCGTTCG

GCTGCGGCGAGCGGTATCAGCTCACTCAAAGGCGGTAATACGGTTATCCACAGAAT

CAGGGGATAACGCAGGAAAGAACATGTGAGCAAAAGGCCAGCAAAAGGCCAGGAA

CCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACCCTGCCGCT

TACCGGATACCTGTCCGCCTTTCTCCCTTCGGGAAGCGTGGCGCTTTCTCATAGCTCA

CGCTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGTCC

AACCCGGTAAGACACGACTTATCGCCACTGGCAGCAGCCACTGGTAACAGGATTAG

CAGAGCGAGGTATGTAGGCGGTGCTACAGAGTTCTTGAAGTGGTGGCCTAACTACG

GCTACACTAGAAGGACAGTATTTGGTATCTGCGCTCTGCTGAAGCCAGTTACCTTCG

GAAAAAGAGTTGGTAGCTCTTGATCCGGCAAACAAACCACCGCTGGTAGCGGTGGT

TTTTTTGTTTGCAAGCAGCAGATTACGCGCAGAAAAAAAGGATCTCAAGAAGATCCT

TTGATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAATGA

AGTTTTAAATCAATCTAAAGTATATATGAGTAAACTTGGTCTGACAGTTACCAATGC

TTAATCAGTGAGGCACCTATCTCAGCGATCTGTCTATTTCGTTCATCCATAGTTGCCT

GACTCCCCGTCGTGTAGATAACTACGATACGGGAGGGCTTACCATCTGGCCCCAGTG

CTGCAATGATACCGCGAGACCCACGCTCACCGGCTCCAGATTTATCAGCAATAAACC

AGCCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTTTG

CGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTG

TGCAAAAAAGCGGTTAGCTCCTTCGGTCCTCCGATCGTTGTCAGAAGTAAGTTGGCC

GCAGTGTTATCACTCATGGTTATGGCAGCACTGCATAATTCTCTTACTGTCATGCCAT

CCGTAAGATGCTTTTCTGTGACTGGTGAGTACTCAACCAAGTCATTCTGAGAATAGT

GTATGCGGCGACCGAGTTGCTCTTGCCCGGCGTCAATACGGGATAATACCGCGCCAC

-continued

ATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGC

AAAATGCCGCAAAAAAGGGAATAAGGGCGACACGGAAATGTTGAATACTCAT

The sequence of the vector illustrated in FIG. 10B is provided below.

PB007-iHelper2-iRepCap10/ PBBG8 (17,936 bp)

(SEQ ID NO: 12)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

-continued

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcacctttttgatgc cactacggtgcgagtgcaactcaaagcctgggcacgcgcccttttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgattttaacccgggagttctagggatctgcccctctccctcccccccc cctaacgttactggccgaagccgcttggaataaggccggtgtgcgtttgtctatatgttattttccaccatattgccgtcttttggcaatgtgagg gcccggaaacctggccctgtcttcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaaccccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg ggaggagcttgtaatcctgaggaagtgtatgcacgtgtgcctgtgttgtgccaacattgatatcatgacgagcatgatgatccatggttacga gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca -continued ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGCTCGAGTCT

AGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACAATAGC

AGGCATGCTGGGGATGCGGTGGGCTCTATGGCTTCTGAGGCGGAAAGAACCAGCTG

GGGCTCTAGGGGGTATCCCCggggttggggttgcgccttttccaaggcATCCAGCACAGTGGCGGCC

GCaatatttgcatgtcgctatgtgttctgggaaatcaccataaacgtgaaatccctatcagtgatagagacttataagttccctatcagtgatag agaaccggtgggcactcttccgtggtctggtggataaattcgcaagggtatcatggcggacgaccggggttcgagccccgtatccggccg tccgccgtgatccatgcggttaccgcccgcgtgtcgaacccaggtgtgcgacgtcagacaacgggggagtgctccttttttgaattccactttg gccgcggctcgaggggggttggggttgcgccttttccaaggcagccctgggtttgcgcagggacgcggctgctctgggcgtggttccggg aaacgcagcggcgccgaccctgggtctcgcacattatcacgtccgttcgcagcgtcacccggatcttcgccgctacccttgtgggccccc cggcgacgcttcctgctccgcccctaagtcgggaaggttccttgcggttcgcggcgtgccggacgtgacaaacggaagccgcacgtctca ctagtaccctcgcagacggacagcgccagggagcaatggcagcgcgccgaccgcgatgggctgtggccaatagcggctgctcagcag ggcgcgccgagagcagcggccgggaaggggcggtgcgggaggcggggtgtggggcggtagtgtgggccctgttcctgcccgcgcg gtgttccgcattctgcaagcctccggagcgcacgtcggcagtcggctccctcgttgaccgaatcaccgacctctctccccaggggggatctgt gagtttggggacccttgattgttctttctttttcgctattgtaaaattcatgttatatggagggggcaaagttttcagggtgttgtttagaatgggaa gatgtcctatgtatcaccatggaccctcatgataatttgtttctttcactttctactctgttgacaaccattgtctcctcttattttcttttcattttct gtaactttttcgttaaactttagcttgcatttgtaacgaatttttaaattcacttttgtttatttgtcagattgtaagtactttctctaatcactttttt tcaaggcaatcagggtatattatattgtacttcagcacagttttagagaacaattgttataattaaatgataaggtagaatatttctgcatataaattctg gctggcgtggaaatattcttattggtagaaacaactacatcctggtcatcatcctgcctttctctttatggttacaatgatatacactgtttgagatgagg ataaaatactctgagtccaaaccgggcccctctgctaaccatgttcatgccttcttctttttcctacagctcctgggcaacgtgctggttattgtgctg tctcatcattttggcaaagaattgtaatacgactcactatagggcgaGCCACCatggctagattagataaaagtaaagtgattaacagcg cattagagctgcttaatgaggtcggaatcgaaggtttaacaacccgtaaactcgcccagaagctaggtgtagagcagcctacattgtattggc atgtaaaaaataagcgggctttgctcgacgccttagccattgagatgttagataggcaccatactcacttttgccctttagaaggggaaagctg gcaagatttttacgtaataacgctaaaagttttagatgtgctttactaagtcatcgcgatggagcaaaagtacatttaggtacacggcctacag aaaaacagtatgaaactctcgaaaatcaattagcctttttatgccaacaaggttttcactagagaatgcCttatatgcactcagcgcCgtggg gcattttactttaggttgcgtattggaagatcaagagcatcaagtcgctaaagaagaaagggaaacacctactactgatagtatgccgccatta ttacgacaagctatcgaattatttgatcaccaaggtgcagagccagccttcttattcggccttgaattgatcatatgcggattagaaaaacaactt aaatgtgaaagtgggtccccaaaaaagaagagaaaggtcgacggcggtggttcagtttaagcgtacagcggctcccgggagttctaggg atctgcccctctccctcccccccccctaacgttactggccgaagccgcttggaataaggccggtgtgcgtttgtctatatgttattttccaccata ttgccgtcttttggcaatgtgagggcccggaaacctggccctgtcttcttgacgagcattcctaggggtctttcccctctcgccaaaggaatgc aaggtctgttgaatgtcgtgaaggaagcagttcctctggaagcttcttgaagacaaacaacgtctgtagcgaccctttgcaggcagcggaac cccccacctggcgacaggtgcctctgcggccaaaagccacgtgtataagatacacctgcaaaggcggcacaaccccagtgccacgttgt gagttggatagttgtggaaagagtcaaatggctctcctcaagcgtattcaacaaggggctgaaggatgcccagaaggtaccccattgtatgg gatctgatctggggcctcggtgcacatgctttacatgtgtttagtcgaggttaaaaaaacgtctaggccccccgaaccacggggacgtggttt tcctttgaaaaacacgatgataaggatccaccggagGCCACCatgaccgagtacaagcccacggtgcgcctcgccacccgcgacga cgtccccagggccgtacgcaccctcgccgccgcgttcgccgactaccccgccacgcgccacaccgtcgatccggaccgccacatcgag cgggtcaccgagctgcaagaactcttcctcacgcgcgtcgggctcgacatcggcaaggtgtgggtcgcggacgacggcgccgcggtgg -continued cggtctggaccacgccggagagcgtcgaagcgggggcggtgttcgccgagatcggcccgcgcatggccgagttgagcggttcccggct ggccgcgcagcaacagatggaaggcctcctggcgccgcaccggcccaaggagcccgcgtggttcctggccaccgtcggcgtctcgcc cgaccaccagggcaagggtctgggcagcgccgtcgtgctccccggagtggaggcggccgagcgcgccggggtgcccgccttcctgga gacctccgcgccccgcaacctccccttctacgagcggctcggcttcaccgtcaccgccgacgtcgaggtgcccgaaggaccgcgcacct ggtgcatgacccgcaagcccggtgcctgaCCGCGTCTGGAACAATCAACCTCTGGATTACAAAATTT

GTGAAAGATTGACTGGTATTCTTAACTATGTTGCTCCTTTTACGCTATGTGGATACGC

TGCTTTAATGCCTTTGTATCATGCTATTGCTTCCCGTATGGCTTTCATTTTCTCCTCCT

TGTATAAATCCTGGTTGCTGTCTCTTTATGAGGAGTTGTGGCCCGTTGTCAGGCAAC

GTGGCGTGGTGTGCACTGTGTTTGCTGACGCAACCCCCACTGGTTGGGGCATTGCCA

CCACCTGTCAGCTCCTTTCCGGGACTTTCGCTTTCCCCCTCCCTATTGCCACGGCGGA

ACTCATCGCCGCCTGCCTTGCCCGCTGCTGGACAGGGGCTCGGCTGTTGGGCACTGA

CAATTCCGTGGTGTTGTCGGGGAAGCTGACGTCCTTTCCATGGCTGCTCGCCTGTGTT

GCCACCTGGATTCTGCGCGGGACGTCCTTCTGCTACGTCCCTTCGGCCCTCAATCCA

GCGGACCTTCCTTCCCGCGGCCTGCTGCCGGCTCTGCGGCCTCTTCCGCGTCTTCGCC

TTCGCCCTCAGACGAGTCGGATCTCCCTTTGGGCCGCCTCCCCGCaAAATGACCGAC

CAAGCGACGCCCAACCTGCCATCACGAGATTTCGATTCCACCGCCGCCTTCTATGAA

AGGTTGGGCTTCGGAATCGTTTTCCGGGACGCCGGCTGGATGATCCTCCAGCGCGGG

GATCTCATGCTGGAGTTCTTCGCCCACCCCAACTTGTTTATTGCAGCTTATAATGGTT

ACAAATAAAGCAATAGCATCACAAATTTCACAAATAAAGCATTTTTTTCACTGCATT

CTAGTTGTGGTTTGTCCAAACTCATCAATGTATCTTATCATGTCTGTAGCtGATcaATTg

GCGCGCCGAATTCGTTatctgcagaattcggcttggcggctgcgcgttcaaacctcccgcttcaaaatggagaccctgcgtg ctcactcgggcttaaatacccagcgtgaccacatggtgtcgcaaaatgtcgcaaaacactcacgtgacctctaatacaggacctctagagca tggaaactagataagaaagaaatacgcagagaccaaagttcaactgaaacgaattaaacggtttattgattaacaagcaaactagtttacaga ttacgggtgaggtaacgggtgccgatggggcgaggctcagaataaacgccatttgtgtcaacagcaaagtccacatttgtagatttgttgtag ttggaagtgtattgaatctctgggttccagcgtttgctgttttctttctgcagctcccattcaatttccacgctgacctgtccggtgctgtactgcgt gatgaacgacgcaaacttagctggactgaaggtagttggaggattcgcgggaacaggtgtattcttaatcaggatctgaggaggcgggtgt ttcagtccaaagcctcccatcagcggcgagggatgaaagtgtccgtccgtgtgaggaatcttggcccagataggaccctgcaggtacacgt cccggtcctgccagaccatgccaggtaaggctccttgactgttgacggtccctgtagcaggagcggtgttggccgattgcaggttagtggc caccgtgccgtactcttctgtggccactgggttggtggttttaatttcttcctcgttggttatcataacgttgtcaaggtccacgttgctatttccag ctccctgtttcccaaatattaagactccgctcatcggaaaaaatttgtcttcgtcgtccttgtgggttgccatagcgggaccgggatttaccaga gagtctctgccattcagatgatacttggtggcaccggtccaggcaaagttgctgttgttattttgattggttgtcttggagacgcgttgctgccgg tagcagggcccgggtagccagtttttggcctgattcgccatgctactaggcccggcctgagaaaattgcaacgtccgatttcctgcggtacc actcgtggtctgagtccgagacaggtagtacaggtactggtcgatgaggggttcatcagccggtccaggctttggctgtgcgcgtagctg ctgtgaaaaggcacgtcctcaaacgtgtagctgaactgaaagttgttgcccgttctcagcatttgagaaggaaagtattccaggcagtagaa ggaggaacggcccacggcctgactgccattgttcagagtcaggtacccgtactgaggaatcatgaagacgtccgccgggaacggaggc aggcagccctggtgcgcagagccgaggacgtacgggagctggtattccgagtccgtaaagacctgaaccgtgctggtaaggttattggcg atggtcgtggtgccatcattcgtcgtgacctccttgacctggatgttgaagagcttgaagttgagcttcttgggccggaatccccagttgttgtt gatgagtcgctgccagtcacgtggtgagaagtggcagtggaatctgttaaagtcaaaatacccccaggggggtgctgtagccgaagtaggt gttgtcgttggtgctgcctcccgattggctggagatttgcttgtagaggtggttgttgtaggtggggagggcccaggttcgggtgctggtggt gatgactctgtcgcccagccatgtggaatcgcaatgccaatttcctgaggcgttacccactccgtcggcgccttcgttattgtctgccattgga -continued gcgccaccgcctgcagccattgtattagatcccacaccagagggggctgcgggggttctccgagtggttgagggtcgggcactgactct gagtcgccagtctgcccaaagttgagtctctttctcgcgggctgctggcctttcttgccgatgcccgaagaggagtctggttcctggggtgatt gctctaccggtctcttctttccaggagccgtcttagcgccttcctcaaccagaccgagaggttcgagaacccgcttcttggcctggaagactg ctcgcccgaggttgcccccaaaagacgtatcttcttgcagacgctcctgaaactcggcgtcggcgtggttataccgcaggtacggattgtca cccgctttgagctgctggtcgtaggccttgtcgtgctcgagggccgctgcgtccgccgcgttgacgggctccccccttgtcgagtccgttgaa gggtccgaggtacttgtagccaggaagcaccagaccccggccgtcgtcctgcttttgctggttggctttgggtttcggggctccaggtttcaa gtcccaccactcgcgaatgccctcagagaggttgtcctcgagccaatctggaagataaccatcggcagccatacctgatttaaatcatttattg ttcaaagatgcagtcatccaaatccacattgaccagatcgcaggcagtgcaagcgtctggcacctttcccatgatatgatgaatgtagcacag tttctgatacgcctttttgacgacagaaacgggttgagattctgacacgggaaagcactctaaacagtctttctgtccgtgagtgaagcagatat ttgaattctgattcattctctcgcattgtctgcagggaaacagcatcagattcatgcccacgtgacgagaacatttgttttggtacctgtctgcgta gttgatcgaagcttccgcgtctgacgtcgatggctgcgcaactgactcgcgcacccgtttgggctcacttatatctgcgtcactgggggcgg gtcttttcttggctccacccttttgacgtagaattcatgctccacctcaaccacgtgatcctttgcccaccggaaaaagtctttgacttcctgcttg gtgaccttcccaaagtcatgatccagacggcgggtgagttcaaatttgaacatccggtcttgcaacggctgctggtgttcgaaggtcgttgag ttcccgtcaatcacggcgcacatgttggtgttggaggtgacgatcacgggagtcgggtctatctgggccgaggacttgcatttctggtccac gcgcaccttgcttcctccgagaatggctttggccgactccacgaccttggcggtcatcttcccctcctcccaccagatcaccatcttgtcgaca cagtcgttgaagggaaagttctcattggtccagtttacgcacccgtagaagggcacagtgtgggctatggcctccgcgatgttggtcttcccg gtagttgcaggcccaaacagccagatggtgttcctcttgccgaactttttcgtggcccatcccagaaagacggaagccgcatattggggatc gtacccgtttagttccaaaattttataaatccgattgctggaaatgtcctccacgggctgctggcccaccaggtagtcgggggcggttttagtc aggctcataatctttcccgcattgtccaaggcagccttgatttgggaccgcgagttggaggccgcattgaaggagatgtatgaggcctggtc ctcctggatccactgcttctccgaggtaatccccttgtccacgagccacccgaccagctccatgtacctggctgaagtttttgatctgatcacc ggcgcatcagaattgggattctgattctctttgttctgctcctgcgtctgcgacacgtgcgtcagatgctgcgccaccaaccgtttacgctccgt gagattcaaacaggcgctgtggagagaaaggcaaagtggatgtcagtaTCTCTATCACTGATAGGGAGATCTCT ATCACTGATAGGGAacttaccttaaatactgttccatattagtccacgcccactggagctcaggctgggttttggggagcaagta attggggatgtagcactcatccaccaccttgttcccgcctccggcgccatttctggtctttgtgaccgcgaaccagtttggcaaagtcggctcg atcccgcggtaaattctctgaatcagtttttcgcgaatctgactcaggaaacgtcccaaaaccatggatttcaccccggtggtttccacgagca cgtgcatgtggaagtagctctctcccttctcaaattgcacaaagaaaagagcctccggggccttactcacacggcgccattccgtcagaaag tcgcgctgcagcttctcggccacggtcaggggtgcctgctcaatcagattcagatccatgtcagaatctggcggcaactcccattccttctcg gccacccagttcacaaagctgtcagaaatgccgggcagatgctcgtcaaggtcgctggggaccttaatcacaatctcgtaaaaccccggca tGGCGGCTGCGCGTTCAAACCTCCCGCTTCAAAATGGAGACCCTGCGTGCTCACTCG GGCgaTCTCTATCACTGATAGGGAGATCTCTATCACTGATAGGGAgaTTAAATAgaatgg CTAggATCCGGCCGGccTGCAggTGTCCTCACAGGAACGAAGTCCCTAAAGAAACAGT

GGCAGCCAGGTTTAGCCCCGGAATTGACTGGATTCCTTTTTTAGGGCCCATTGGTAT

GGCTTTTTCCCCGTATCCCCCCAGGTGTCTGCAGGCTCAAAGAGCAGCGAGAAGCGT

TCAGAGGAAAGCGATCCCGTGCCACCTTCCCCGTGCCCGGGCTGTCCCCGCACGCTG

CCGGCTCGGGGATGCGGGGGGAGCGCCGGACCGGAGCGGAGCCCCGGGCGGCTCG

CTGCTGCCCCCTAGCGGGGGAGGGACGTAATTACATCCCTGGGGGCTTTGGGGGGG

GGCTGTCCCTCTAGAGCGGCCGCCACCGCGGTGGAGCTCCAGCTTTTGTTCCCTTTA

GTGAGGGTTAATTAGATCTTAATACGACTCACTATAGGGCGAATTGGGTACCGGGCC

CCCCCTCGAGGTCGACGGTATCGATAAGCTTGATATCTATAACAAGAAAATATATAT

ATAATAAGTTATCACGTAAGTAGAACATGAAATAACAATATAATTATCGTATGAGTT

AAATCTTAAAAGTCACGTAAAAGATAATCATGCGTCATTTTGACTCACGCGGTCGTT

-continued

ATAGTTCAAAATCAGTGACACTTACCGCATTGACAAGCACGCCTCACGGGAGCTCC

AAGCGGCGACTGAGATGTCCTAAATGCACAGCGACGGATTCGCGCTATTTAGAAAG

AGAGAGCAATATTTCAAGAATGCATGCGTCAATTTTACGCAGACTATCTTTCTAGGG

TTAATCTAGCTGCATCAGGATCATATCGTCGGGTCTTTTTTCCGGCTCAGTCATCGCC

CAAGCTGGCGCTATCTGGGCATCGGGGAGGAAGAAGCCCGTGCCTTTTCCCGCGAG

GTTGAAGCGGCATGGAAAGAGTTTGCCGAGGATGACTGCTGCTGCATTGACGTTGA

GCGAAAACGCACGTTTACCATGATGATTCGGGAAGGTGTGGCCATGCACGCCTTTAA

CGGTGAACTGTTCGTTCAGGCCACCTGGGATACCAGTTCGTCGCGGCTTTTCCGGAC

ACAGTTCCGGATGGTCAGCCCGAAGCGCATCAGCAACCCGAACAATACCGGCGACA

GCCGGAACTGCCGTGCCGGTGTGCAGATTAATGACAGCGGTGCGGCGCTGGGATAT

TACGTCAGCGAGGACGGGTATCCTGGCTGGATGCCGCAGAAATGGACATGGATACC

CCGTGAGTTACCCGGCGGGCGCGCTTGGCGTAATCATGGTCATAGCTGTTTCCTGTG

TGAAATTGTTATCCGCTCACAATTCCACACAACATACGAGCCGGAAGCATAAAGTGT

AAAGCCTGGGGTGCCTAATGAGTGAGCTAACTCACATTAATTGCGTTGCGCTCACTG

CCCGCTTTCCAGTCGGGAAACCTGTCGTGCCAGCTGCATTAATGAATCGGCCAACGC

GCGGGGAGAGGCGGTTTGCGTATTGGGCGCTCTTCCGCTTCCTCGCTCACTGACTCG

CTGCGCTCGGTCGTTCGGCTGCGGCGAGCGGTATCAGCTCACTCAAAGGCGGTAATA

CGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAACCC

GACAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTATCCGGTA

ACTATCGTCTTGAGTCCAACCCGGTAAGACACGACTTATCGCCACTGGCAGCAGCCA

CTGGTAACAGGATTAGCAGAGCGAGGTATGTAGGCGGTGCTACAGAGTTCTTGAAG

TGGTGGCCTAACTACGGCTACACTAGAAGGACAGTATTTGGTATCTGCGCTCTGCTG

AAGCCAGTTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGAAAAAAAGG

ATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGGTC

TGACAGTTACCAATGCTTAATCAGTGAGGCACCTATCTCAGCGATCTGTCTATTTCGT

TCATCCATAGTTGCCTGACTCCCCGTCGTGTAGATAACTACGATACGGGAGGGCTTA

CCATCTGGCCCCAGTGCTGCAATGATACCGCGAGACCCACGCTCACCGGCTCCAGAT

TTATCAGCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACG

CTCGTCGTTTGGTATGGCTTCATTCAGCTCCGGTTCCCAACGATCAAGGCGAGTTAC

ATGATCCCCCATGTTGTGCAAAAAAGCGGTTAGCTCCTTCGGTCCTCCGATCGTTGT

-continued

CAGAAGTAAGTTGGCCGCAGTGTTATCACTCATGGTTATGGCAGCACTGCATAATTC

TCTTACTGTCATGCCATCCGTAAGATGCTTTTCTGTGACTGGTGAGTACTCAACCAAG

TCATTCTGAGAATAGTGTATGCGGCGACCGAGTTGCTCTTGCCCGGCGTCAATACGG

GATAATACCGCGCCACATAGCAGAACTTTAAAAGTGCTCATCATTGGAAAACGTTCT

TCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAG

CAAAAACAGGAAGGCAAAATGCCGCAAAAAAGGGAATAAGGGCGACACGGAAATG

TTGAATACTCAT

The sequence of the vector represented in FIG. 10C is provided below.

PB007-iHelper1-iRepCap10-AAV-GFP/ PBBG9 (21,391 bp)

(SEQ ID NO: 13)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

-continued

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcaccttttgatgc cactacggtgcgagtgcaactcaaagcctgggcacgcgcccttttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgattttaacccgggagttctagggatctgcccctctccctcccccccc cctaacgttactggccgaagccgcttggaataaggccggtgtgcgtttgtctatatgttattttccaccatattgccgtatttggcaatgtgagg gcccggaaacctggccctgtcttcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaacccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg -continued ggaggagcttgtaatcctgaggaagtgtatgcacgtgtgcctgtgttgtgccaacattgatatcatgacgagcatgatgatccatggttacga gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGCTCGAGTCT

AGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACAATAGC

AGGCATGCTGGGGATGCGGTGGGCTCTATGGCTTCTGAGGCGGAAAGAACCAGCTG

GGGCTCTAGGGGGTATCCCCggggttggggttgcgccttttccaaggcATCCAGCACAGTGGCGGCC

GCaatatttgcatgtcgctatgtgttctgggaaatcaccataaacgtgaaatccctatcagtgatagagacttataagttccctatcagtgatag agaaccggtgggcactcttccgtggtctggtggataaattcgcaagggtatcatggcggacgaccggggttcgagccccgtatccggccg tccgccgtgatccatgcggttaccgcccgcgtgtcgaacccaggtgtgcgacgtcagacaacgggggagtgctccttttttgaattccactttg gccgcggctcgaggggggttggggttgcgccttttccaaggcagccctgggtttgcgcagggacgcggctgctctgggcgtggttccggg aaacgcagcggcgccgaccctgggtctcgcacattatcacgtccgttcgcagcgtcacccggatcttcgccgctacccttgtgggccccc cggcgacgcttcctgctccgcccctaagtcgggaaggttccttgcggttcgcggcgtgccggacgtgacaaacggaagccgcacgtctca ctagtaccctcgcagacggacagcgccagggagcaatggcagcgcgccgaccgcgatgggctgtggccaatagcggctgctcagcag ggcgcgccgagagcagcggccgggaaggggcggtgcgggaggcggggtgtggggcggtagtgtgggccctgttcctgcccgcgcg gtgttccgcattctgcaagcctccggagcgcacgtcggcagtcggctccctcgttgaccgaatcaccgacctctctccccaggggggatctgt gagtttggggacccttgattgttctttattttcgctattgtaaaattcatgttatatggagggggcaaagttttcagggtgttgtttagaatgggaa gatgtcccttgtatcaccatggaccctcatgataatttgtttctttcactttctactctgttgacaaccattgtctcctcttattttcttttcatt ttctgtaactttttcgttaaactttagcttgcatttgtaacgaatttttaaattcactttgtttatttgtcagattgtaagtactttctctaatcact tttttttcaaggcaatcagggtatattatattgtacttcagcacagttttagagaacaattgttataattaaatgataaggtagaatatttctgcatat aaattctggctggcgtggaaatattcttattggtagaaacaactacatcctggtcatcatcctgcctttctctttatggttacaatgatatacactgtt tgagatgaggataaaatactctgagtccaaaccgggcccctctgctaaccatgttcatgccttcttctttttcctacagctcctgggcaacgtgctggt tattgtgctgtctcatcattttggcaaagaattgtaatacgactcactatagggcgaGCCACCatggctagattagataaaagtaaagtgattaacagcg cattagagctgcttaatgaggtcggaatcgaaggtttaacaacccgtaaactcgcccagaagctaggtgtagagcagcctacattgtattggc atgtaaaaaataagcgggctttgctcgacgccttagccattgagatgttagataggcaccatactcacttttgccctttagaaggggaaagctg gcaagatttttacgtaataacgctaaaagttttagatgtgctttactaagtcatcgcgatggagcaaaagtacatttaggtacacggcctacag aaaaacagtatgaaactctcgaaaatcaattagcctttttatgccaacaaggtttttcactagagaatgcCttatatgcactcagcgcCgtggg gcattttactttaggttgcgtattggaagatcaagagcatcaagtcgctaaagaagaaagggaaacacctactactgatagtatgccgccatta ttacgacaagctatcgaattatttgatcaccaaggtgcagagccagccttcttattcggccttgaattgatcatatgcggattagaaaaacaactt aaatgtgaaagtgggtccccaaaaaagaagagaaaggtcgacggcggtggtgctttgtctcctcagcactctgctgtcactcaaggaagtat catcaagaacaaggagggcatggatgctaagtcactaactgcctggtcccggacactggtgaccttcaaggatgtatttgtggacttcacca gggaggagtggaagctgctggacactgctcagcagatcgtgtacagaaatgtgatgctggagaactataagaacctggtttccttgggttat cagcttactaagccagatgtgatcctccggttggagaagggagaagagccctggctggtggagagagaaattcaccaagagacccatcct gattcagagactgcatttgaaatcaaatcatcagtttaagcgtacagcggctcccgggagttctagggatctgcccctctccctccccccccc ctaacgttactggccgaagccgcttggaataaggccggtgtgcgtttgtctatatgttattttccaccatattgccgtcttttggcaatgtgaggg -continued cccggaaacctggccctgtcttcttgacgagcattcctaggggtctttcccctctcgccaaaggaatgcaaggtctgttgaatgtcgtgaagg aagcagttcctctggaagcttcttgaagacaaacaacgtctgtagcgaccctttgcaggcagcggaaccccccacctggcgacaggtgcct ctgcggccaaaagccacgtgtataagatacacctgcaaaggcggcacaaccccagtgccacgttgtgagttggatagttgtggaaagagt caaatggctctcctcaagcgtattcaacaaggggctgaaggatgcccagaaggtaccccattgtatgggatctgatctggggcctcggtgc acatgctttacatgtgtttagtcgaggttaaaaaaacgtctaggccccccgaaccacggggacgtggttttcctttgaaaaacacgatgataag gatccaccggagGCCACCatgaccgagtacaagcccacggtgcgcctcgccacccgcgacgacgtccccagggccgtacgcacc ctcgccgccgcgttcgccgactaccccgccacgcgccacaccgtcgatccggaccgccacatcgagcgggtcaccgagctgcaagaac tcttcctcacgcgcgtcgggctcgacatcggcaaggtgtgggtcgcggacgacggcgccgcggtggcggtctggaccacgccggagag cgtcgaagcgggggcggtgttcgccgagatcggcccgcgcatggccgagttgagcggttcccggctggccgcgcagcaacagatgga aggcctcctggcgccgcaccggcccaaggagcccgcgtggttcctggccaccgtcggcgtctcgcccgaccaccagggcaagggtctg ggcagcgccgtcgtgctccccggagtggaggcggccgagcgcgccggggtgcccgccttcctggagacctccgcgccccgcaacctc cccttctacgagcggctcggcttcaccgtcaccgccgacgtcgaggtgcccgaaggaccgcgcacctggtgcatgacccgcaagcccg gtgcctgaCCGCGTCTGGAACAATCAACCTCTGGATTACAAAATTTGTGAAAGATTGACT

GGTATTCTTAACTATGTTGCTCCTTTTACGCTATGTGGATACGCTGCTTTAATGCCTT

TGTATCATGCTATTGCTTCCCGTATGGCTTTCATTTTCTCCTCCTTGTATAAATCCTGG

TTGCTGTCTCTTTATGAGGAGTTGTGGCCCGTTGTCAGGCAACGTGGCGTGGTGTGC

ACTGTGTTTGCTGACGCAACCCCCACTGGTTGGGGCATTGCCACCACCTGTCAGCTC

CTTTCCGGGACTTTCGCTTTCCCCCTCCCTATTGCCACGGCGGAACTCATCGCCGCCT

GCCTTGCCCGCTGCTGGACAGGGGCTCGGCTGTTGGGCACTGACAATTCCGTGGTGT

TGTCGGGGAAGCTGACGTCCTTTCCATGGCTGCTCGCCTGTGTTGCCACCTGGATTCT

GCGCGGGACGTCCTTCTGCTACGTCCCTTCGGCCCTCAATCCAGCGGACCTTCCTTCC

CGCGGCCTGCTGCCGGCTCTGCGGCCTCTTCCGCGTCTTCGCCTTCGCCCTCAGACG

AGTCGGATCTCCCTTTGGGCCGCCTCCCCGCaAAATGACCGACCAAGCGACGCCCAA

CCTGCCATCACGAGATTTCGATTCCACCGCCGCCTTCTATGAAAGGTTGGGCTTCGG

AATCGTTTTCCGGGACGCCGGCTGGATGATCCTCCAGCGCGGGGATCTCATGCTGGA

GTTCTTCGCCCACCCCAACTTGTTTATTGCAGCTTATAATGGTTACAAATAAAGCAAT

AGCATCACAAATTTCACAAATAAAGCATTTTTTTCACTGCATTCTAGTTGTGGTTTGT

CCAAACTCATCAATGTATCTTATCATGTCTGTAGCtGATcaATTgGCGCGCCGAATTCG

TTatctgcagaattcggcttggcggctgcgcgttcaaacctcccgcttcaaaatggagaccctgcgtgctcactcgggcttaaatacccag cgtgaccacatggtgtcgcaaaatgtcgcaaaacactcacgtgacctctaatacaggacctctagagcatggaaactagataagaaagaaa tacgcagagaccaaagttcaactgaaacgaattaaacggtttattgattaacaagcaaactagtttacagattacgggtgaggtaacgggtgc cgatggggcgaggctcagaataaacgccatttgtgtcaacagcaaagtccacatttgtagatttgttgtagttggaagtgtattgaatctctgg gttccagcgtttgctgttttctttctgcagctcccattcaatttccacgctgacctgtccggtgctgtactgcgtgatgaacgacgcaaacttagct ggactgaaggtagttggaggattcgcgggaacaggtgtattcttaatcaggatctgaggaggcgggtgtttcagtccaaagcctcccatcag cggcgagggatgaaagtgtccgtccgtgtgaggaatcttggcccagataggaccctgcaggtacacgtcccggtcctgccagaccatgcc aggtaaggctccttgactgttgacggtccctgtagcaggagcggtgttggccgattgcaggttagtggccaccgtgccgtactcttctgtggc cactgggttggtggttttaatttcttcctcgttggttatcataacgttgtcaaggtccacgttgctatttccagctccctgtttcccaaatattaagact ccgctcatcggaaaaaatttgtcttcgtcgtccttgtgggttgccatagcgggaccgggatttaccagagagtctctgccattcagatgatactt ggtggcaccggtccaggcaaagttgctgttgttattttgattggttgtcttggagacgcgttgctgccggtagcagggcccgggtagccagttt ttggcctgattcgccatgctactaggcccggcctgagaaaattgcaacgtccgatttcctgcggtaccactcgtggtctgagtccgagacag -continued gtagtacaggtactggtcgatgaggggttcatcagccggtccaggctttggctgtgcgcgtagctgctgtgaaaaggcacgtcctcaaac gtgtagctgaactgaaagttgttgcccgttctcagcatttgagaaggaaagtattccaggcagtagaaggaggaacggcccacggcctgac tgccattgttcagagtcaggtacccgtactgaggaatcatgaagacgtccgccgggaacggaggcaggcagccctggtgcgcagagccg aggacgtacgggagctggtattccgagtccgtaaagacctgaaccgtgctggtaaggttattggcgatggtcgtggtgccatcattcgtcgt gacctccttgacctggatgttgaagagcttgaagttgagcttcttgggccggaatccccagttgttgttgatgagtcgctgccagtcacgtggt gagaagtggcagtggaatctgttaaagtcaaaatacccccaggggggtgctgtagccgaagtaggtgttgtcgttggtgctgcctcccgattg gctggagatttgcttgtagaggtggttgttgtaggtggggagggcccaggttcgggtgctggtggtgatgactctgtcgcccagccatgtgg aatcgcaatgccaatttcctgaggcgttacccactccgtcggcgccttcgttattgtctgccattggagcgccaccgcctgcagccattgtatt agatcccacaccagagggggctgcgggggggttctccgagtggttgagggtcgggcactgactctgagtcgccagtctgcccaaagttga gtctctttctcgcgggctgctggcctttcttgccgatgcccgaagaggagtctggttcctggggtgattgctctaccggtctcttctttccagga gccgtatagcgccttcctcaaccagaccgagaggttcgagaacccgcttcttggcctggaagactgctcgcccgaggttgcccccaaaag acgtatcttcttgcagacgctcctgaaactcggcgtcggcgtggttataccgcaggtacggattgtcacccgctttgagctgctggtcgtagg ccttgtcgtgctcgagggccgctgcgtccgccgcgttgacgggctccccccttgtcgagtccgttgaagggtccgaggtacttgtagccagg aagcaccagaccccggccgtcgtcctgcttttgctggttggctttgggtttcggggctccaggtttcaagtcccaccactcgcgaatgccctc agagaggttgtcctcgagccaatctggaagataaccatcggcagccatacctgatttaaatcatttattgttcaaagatgcagtcatccaaatc cacattgaccagatcgcaggcagtgcaagcgtctggcacctttcccatgatatgatgaatgtagcacagtttctgatacgcctttttgacgaca gaaacgggttgagattctgacacgggaaagcactctaaacagtctttctgtccgtgagtgaagcagatatttgaattctgattcattctctcgca ttgtctgcagggaaacagcatcagattcatgcccacgtgacgagaacatttgttttggtacctgtctgcgtagttgatcgaagcttccgcgtctg acgtcgatggctgcgcaactgactcgcgcacccgtttgggctcacttatatctgcgtcactgggggcgggtcttttcttggctccaccctttttg acgtagaattcatgctccacctcaaccacgtgatcctttgcccaccggaaaaagtctttgacttcctgcttggtgaccttcccaaagtcatgatc cagacggcgggtgagttcaaatttgaacatccggtcttgcaacggctgctggtgttcgaaggtcgttgagttcccgtcaatcacggcgcaca tgttggtgttggaggtgacgatcacgggagtcgggtctatctgggccgaggacttgcatttctggtccacgcgcaccttgcttcctccgagaa tggctttggccgactccacgaccttggcggtcatcttcccctcctcccaccagatcaccatcttgtcgacacagtcgttgaagggaaagttctc attggtccagtttacgcacccgtagaagggcacagtgtgggctatggcctccgcgatgttggtcttcccggtagttgcaggcccaaacagcc agatggtgttcctcttgccgaactttttcgtggcccatcccagaaagacggaagccgcatattggggatcgtacccgtttagttccaaaattta taaatccgattgctggaaatgtcctccacgggctgctggcccaccaggtagtcgggggcggttttagtcaggctcataatctttcccgcattgt ccaaggcagccttgatttgggaccgcgagttggaggccgcattgaaggagatgtatgaggcctggtcctcctggatccactgcttctccga ggtaatccccttgtccacgagccacccgaccagctccatgtacctggctgaagtttttgatctgatcaccggcgcatcagaattgggattctga ttctctttgttctgctcctgcgtctgcgacacgtgcgtcagatgctgcgccaccaaccgtttacgctccgtgagattcaaacaggcgctgtgga gagaaaggcaaagtggatgtcagtaTCTCTATCACTGATAGGGAGATCTCTATCACTGATAGGGAac ttaccttaaatactgttccatattagtccacgcccactggagctcaggctgggttttggggagcaagtaattggggatgtagcactcatccacc accttgttcccgcctccggcgccatttctggtctttgtgaccgcgaaccagtttggcaaagtcggctcgatcccgcggtaaattctctgaatca gtttttcgcgaatctgactcaggaaacgtcccaaaaccatggatttcaccccggtggtttccacgagcacgtgcatgtggaagtagctctctcc cttctcaaattgcacaaagaaaagagcctccggggccttactcacacggcgccattccgtcagaaagtcgcgctgcagcttctcggccacg gtcaggggtgcctgctcaatcagattcagatccatgtcagaatctggcggcaactcccattccttctcggccacccagttcacaaagctgtca gaaatgccgggcagatgctcgtcaaggtcgctggggaccttaatcacaatctcgtaaaaccccggcatGGCGGCTGCGCGTT CAAACCTCCCGCTTCAAAATGGAGACCCTGCGTGCTCACTCGGGCgaTCTCTATCACT GATAGGGAGATCTCTATCACTGATAGGGAgaTTAAATAgaatggCTAggATCCGGCCGGc cTGCAggTGTCCTCACAGGAACGAAGTCCCTAAAGAAACAGTGGCAGCCAGGTTTAG

CCCCGGAATTGACTGGATTCCTTTTTTAGGGCCCATTGGTATGGCTTTTTCCCCGTAT

CCCCCCAGGTGTCTGCAGGCTCAAAGAGCAGCGAGAAGCGTTCAGAGGAAAGCGAT

-continued

CCCGTGCCACCTTCCCCGTGCCCGGGCTGTCCCCGCACGCTGCCGGCTCGGGGATGC
GGGGGGAGCGCCGGACCGGAGCGGAGCCCCGGGCGGCTCGCTGCTGCCCCCTAGCG
GGGGAGGGACGTAATTACATCCCTGGGGGCTTTGGGGGGGGGCTGTCCCTCTAGAG
CGGCCGCCACCGCGGTGGAGCTCCAGCTTTTGTTCCCTTTAGTGAGGGTTAATTAGA
TCTTAATACGACTCACTATAGGGCGAATTGGGTACCGGGCCCCCCCTCGAGGTCGAC
GGTATCGCCTCCAAGGCCAGCTTCCCACAATAAGTTGGGTGAATTTTGGCTCATTCC
TCCTTTCTATAGGATTGAGGTCAGAGCTTTGTGATGGGAATTCTGTGGAATGTGTGT
CAGTTAGGGTGTGGAAAGTCCCgcGATCgcTAGcAAACGCCAGCAACGCGGCCTTTTT
ACGGTTCCTGGCCTTTTGCTGGCCTTTTGCTCACATGTCCTGCAGGCAGCTGCGCGCT
CGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGCCAACTCCATCACTA
GGGGTTCCTGCGGCCGCACGCGTGGAGCTAGTTATTAATAGTAATCAATTACGGGGT
CATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTC
CCATAGTAACGTCAATAGGGACTTTCCATTGACGTCAATGGGTGGAGTATTTACGGT
AAACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCG
GTTTTGGCAGTACATCAATGGGCGTGGATAGCGGTTTGACTCACGGGGATTTCCAAG
TCTCCACCCCATTGACGTCAATGGGAGTTTGTTTTGCACCAAAATCAACGGGACTTT
CCAAAATGTCGTAACAACTCCGCCCCATTGACGCAAATGGGCGGTAGGCGTGTACG
GTGGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCCGCG
GATTCGAATCCCGGCCGGGAACGGTGCATTGGAACGCGGATTCCCCGTGCCAAGAG
TGACGTAAGTACCGCCTATAGAGTCTATAGGCCCACAAAAAATGCTTTCTTCTTTTA
ATATACTTTTTTGTTTATCTTATTTCTAATACTTTCCCTAATCTCTTTCTTTCAGGGCA
ATAATGATACAATGTATCATGCCTCTTTGCACCATTCTAAAGAATAACAGTGATAAT
TTCTGGGTTAAGGCAATAGCAATATTTCTGCATATAAATATTTCTGCATATAAATTGT
AACTGATGTAAGAGGTTTCATATTGCTAATAGCAGCTACAATCCAGCTACCATTCTG
CTTTTATTTTATGGTTGGGATAAGGCTGGATTATTCTGAGTCCAAGCTAGGCCCTTTT
GCTAATCATGTTCATACCTCTTATCTTCCTCCCACAGCTCCTGGGCAACGTGCTGGTC
TGTGTGCTGGCCCATCACTTTGGCAAAGAATTGGGATTCGAACATCGATTGAATTCT
GAATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGCGA
TGCCACCTACGGCAAGCTGACCCTGAAGTTCATCTGCACCACCGGCAAGCTGCCCGT
GCCCTGGCCCACCCTCGTGACCACCCTGACCTACGGCGTGCAGTGCTTCAGCCGCTA
CCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGG
TGAAGTTCGAGGGCGACACCCTGGTGAACCGCATCGAGCTGAAGGGCATCGACTTC
AAGGAGGACGGCAACATCCTGGGGCACAAGCTGGAGTACAACTACAACAGCCACA

-continued

ACGTCTATATCATGGCCGACAAGCAGAAGAACGGCATCAAGGTGAACTTCAAGATC

CGCCACAACATCGAGGACGGCAGCGTGCAGCTCGCCGACCACTACCAGCAGAACAC

CCCCATCGGCGACGGCCCCGTGCTGCTGCCCGACAACCACTACCTGAGCACCCAGTC

CGCCCTGAGCAAAGACCCCAACGAGAAGCGCGATCACATGGTCCTGCTGGAGTTCG

TGACCGCCGCCGGGATCACTCTCGGCATGGACGAGCTGTACAAGTACTCAGATCTCG

AGCTCAAGTAGGGATCCTCTAGAGTCGACCTGCAGAAGCTTGCCTCGAGCAGCGCT

GCTCGAGAGATCTACGGGTGGCATCCCTGTGACCCCTCCCCAGTGCCTCTCCTGGCC

CTGGAAGTTGCCACTCCAGTGCCCACCAGCCTTGTCCTAATAAAATTAAGTTGCATC

ATTTTGTCTGACTAGGTGTCCTTCTATAATATTATGGGGTGGAGGGGGGTGGTATGG

AGCAAGGGGCAAGTTGGGAAGACAACCTGTAGGGCCTGCGGGGTCTATTGGGAACC

AAGCTGGAGTGCAGTGGCACAATCTTGGCTCACTGCAATCTCCGCCTCCTGGGTTCA

AGCGATTCTCCTGCCTCAGCCTCCCGAGTTGTTGGGATTCCAGGCATGCATGACCAG

GCTCAGCTAATTTTTGTTTTTTTGGTAGAGACGGGGTTTCACCATATTGGCCAGGCTG

GTCTCCAACTCCTAATCTCAGGTGATCTACCCACCTTGGCCTCCCAAATTGCTGGGA

TTACAGGCGTGAACCACTGCTCCCTTCCCTGTCCTTCTGATTTTGTAGGTAACCACGT

GCGGACCGAGCGGCCGCAGGAACCCCTAGTGATGGAGTTGGCCACTCCCTCTCTGC

GCGCTCGCTCGCTCACTGAGGCCGGGCGACCAAAGGTCGCCCGACGCCCGGGCTTT

GCCCGGGCGGCCTCAGTGAGCGAGCGAGCGCGCAGCTGCCTGCAGGGGCGCCTGAT

GCGGTATTTTCTCCTTACGCATCTGTGCGGTATTTCACACCGCATACGTCgtaGCtGATc aATTgGCGCGCCGAATTCGTTAACAAGCTtTAATTAaCGCgtAcgATAAGCTTGATATCT

ATAACAAGAAAATATATATATAATAAGTTATCACGTAAGTAGAACATGAAATAACA

ATATAATTATCGTATGAGTTAAATCTTAAAAGTCACGTAAAAGATAATCATGCGTCA

TTTTGACTCACGCGGTCGTTATAGTTCAAAATCAGTGACACTTACCGCATTGACAAG

CACGCCTCACGGGAGCTCCAAGCGGCGACTGAGATGTCCTAAATGCACAGCGACGG

ATTCGCGCTATTTAGAAAGAGAGAGCAATATTTCAAGAATGCATGCGTCAATTTTAC

GCAGACTATCTTTCTAGGGTTAATCTAGCTGCATCAGGATCATATCGTCGGGTCTTTT

TTCCGGCTCAGTCATCGCCCAAGCTGGCGCTATCTGGGCATCGGGGAGGAAGAAGC

CCGTGCCTTTTCCCGCGAGGTTGAAGCGGCATGGAAAGAGTTTGCCGAGGATGACTG

CTGCTGCATTGACGTTGAGCGAAAACGCACGTTTACCATGATGATTCGGGAAGGTGT

GGCCATGCACGCCTTTAACGGTGAACTGTTCGTTCAGGCCACCTGGGATACCAGTTC

GTCGCGGCTTTTCCGGACACAGTTCCGGATGGTCAGCCCGAAGCGCATCAGCAACCC

GAACAATACCGGCGACAGCCGGAACTGCCGTGCCGGTGTGCAGATTAATGACAGCG

GTGCGGCGCTGGGATATTACGTCAGCGAGGACGGGTATCCTGGCTGGATGCCGCAG

AAATGGACATGGATACCCCGTGAGTTACCCGGCGGGCGCGCTTGGCGTAATCATGG

TCATAGCTGTTTCCTGTGTGAAATTGTTATCCGCTCACAATTCCACACAACATACGA

GCCGGAAGCATAAAGTGTAAAGCCTGGGGTGCCTAATGAGTGAGCTAACTCACATT

AATTGCGTTGCGCTCACTGCCCGCTTTCCAGTCGGGAAACCTGTCGTGCCAGCTGCA

TTAATGAATCGGCCAACGCGCGGGGAGAGGCGGTTTGCGTATTGGGCGCTCTTCCGC

TTCCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCT

-continued

GGCGTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTT

TCTCCCTTCGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGGCGG

TGCTACAGAGTTCTTGAAGTGGTGGCCTAACTACGGCTACACTAGAAGGACAGTATT

TGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGGTCTGA

CGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTA

TATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGG

GAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTC

TTGCCCGGCGTCAATACGGGATAATACCGCGCCACATAGCAGAACTTTAAAAGTGCT

CATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTC

ACCAGCGTTTCTGGGTGAGCAAAAACAGGAAGGCAAAATGCCGCAAAAAAGGGAA

TAAGGGCGACACGGAAATGTTGAATACTCAT

The sequence of the vector illustrated in FIG. 10D is provided below.

PB007-iHelper2-iRepCap10-AAV-GFP/ PBB G10 (21,046 bp)

(SEQ ID NO: 14)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

-continued

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga -continued gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcaccttttgatgc cactacggtgcgagtgcaactcaaagcctgggcacgcgcccttttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgatttttaacccgggagttctagggatctgcccctctccctcccccccc cctaacgttactggccgaagccgcttggaataaggccggtgtgcgtttgtctatatgttattttccaccatattgccgtcttttggcaatgtgagg gcccggaaacctggccctgtatcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaaccccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg ggaggagcttgtaatcctgaggaagtgtatgcacgtgtgcctgtgttgtgccaacattgatatcatgacgagcatgatgatccatggttacga gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGCTCGAGTCT

AGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACAATAGC

AGGCATGCTGGGGATGCGGTGGGCTCTATGGCTTCTGAGGCGGAAAGAACCAGCTG

GGGCTCTAGGGGGTATCCCCggggttggggttgcgccttttccaaggcATCCAGCACAGTGGCGGCC

GCaatatttgcatgtcgctatgtgttctgggaaatcaccataaacgtgaaatccctatcagtgatagagacttataagttccctatcagtgatag agaaccggtgggcactcttccgtggtctggtggataaattcgcaagggtatcatggcggacgaccggggttcgagccccgtatccggccg tccgccgtgatccatgcggttaccgcccgcgtgtcgaacccaggtgtgcgacgtcagacaacgggggagtgctcctttttgaattccactttg gccgcggctcgaggggggttggggttgcgccttttccaaggcagccctgggtttgcgcagggacgcggctgctctgggcgtggttccggg aaacgcagcggcgccgaccctgggtctcgcacattcttcacgtccgttcgcagcgtcacccggatcttcgccgctacccttgtgggccccc cggcgacgcttcctgctccgcccctaagtcgggaaggttccttgcggttcgcggcgtgccggacgtgacaaacggaagccgcacgtctca -continued ctagtaccctcgcagacggacagcgccagggagcaatggcagcgcgccgaccgcgatgggctgtggccaatagcggctgctcagcag ggcgcgccgagagcagcggccgggaaggggcggtgcgggaggcggggtgtggggcggtagtgtgggccctgttcctgcccgcgcg gtgttccgcattctgcaagcctccggagcgcacgtcggcagtcggctccctcgttgaccgaatcaccgacctctctccccagggggatctgt gagtttggggacccttgattgttctttctttttcgctattgtaaaattcatgttatatggagggggcaaagttttcagggtgttgtttagaatgggaa gatgtcccttgtatcaccatggaccctcatgataatttgtttctttcactttctactctgttgacaaccattgtctcctcttattttcttttcattt tctgtaactttttcgttaaactttagcttgcatttgtaacgaatttttaaattcacttttgtttatttgtcagattgtaagtactttctctaatcact ttttttcaaggcaatcagggtatattatattgtacttcagcacagttttagagaacaattgttataattaaatgataaggtagaatatttctgcata taaattctggctggcgtggaaatattcttattggtagaaacaactacatcctggtcatcatcctgcctttctctttatggttacaatgatatacactg tttgagatgaggataaaatactctgagtccaaaccgggcccctctgctaaccatgttcatgccttcttctttttcctacagctcctgggcaacgtgct ggttattgtgctgtctcatcattttggcaaagaattgtaatacgactcactatagggcgaGCCACCatggctagattagataaaagtaaagtgattaa cagcgcattagagctgcttaatgaggtcggaatcgaaggtttaacaacccgtaaactcgcccagaagctaggtgtagagcagcctacattgtattggc atgtaaaaaataagcgggctttgctcgacgccttagccattgagatgttagataggcaccatactcacttttgccctttagaaggggaaagctg gcaagatttttacgtaataacgctaaaagttttagatgtgctttactaagtcatcgcgatggagcaaaagtacatttaggtacacggcctacag aaaaacagtatgaaactctcgaaaatcaattagcctttttatgccaacaaggtttttcactagagaatgcCttatatgcactcagcgcCgtggg gcatttactttaggttgcgtattggaagatcaagagcatcaagtcgctaaagaagaaagggaaacacctactactgatagtatgccgccatta ttacgacaagctatcgaattatttgatcaccaaggtgcagagccagccttcttattcggccttgaattgatcatatgcggattagaaaaacaactt aaatgtgaaagtgggtccccaaaaaagaagagaaaggtcgacggcggtggttcagtttaagcgtacagcggctcccgggagttctaggg atctgcccctctccctcccccccccctaacgttactggccgaagccgcttggaataaggccggtgtgcgtttgtctatatgttattttccaccata ttgccgtcttttggcaatgtgagggcccggaaacctggccctgtcttcttgacgagcattcctaggggtctttcccctctcgccaaaggaatgc aaggtctgttgaatgtcgtgaaggaagcagttcctctggaagcttcttgaagacaaacaacgtctgtagcgaccctttgcaggcagcggaac cccccacctggcgacaggtgcctctgcggccaaaagccacgtgtataagatacacctgcaaaggcggcacaaccccagtgccacgttgt gagttggatagttgtggaaagagtcaaatggctctcctcaagcgtattcaacaaggggctgaaggatgcccagaaggtaccccattgtatgg gatctgatctggggcctcggtgcacatgctttacatgtgtttagtcgaggttaaaaaaacgtctaggccccccgaaccacggggacgtggttt tcctttgaaaaacacgatgataaggatccaccggagGCCACCatgaccgagtacaagcccacggtgcgcctcgccacccgcgacga cgtccccagggccgtacgcaccctcgccgccgcgttcgccgactaccccgccacgcgccacaccgtcgatccggaccgccacatcgag cgggtcaccgagctgcaagaactcttcctcacgcgcgtcgggctcgacatcggcaaggtgtgggtcgcggacgacggcgccgcggtgg cggtctggaccacgccggagagcgtcgaagcgggggcggtgttcgccgagatcggcccgcgcatggccgagttgagcggttcccggct ggccgcgcagcaacagatggaaggcctcctggcgccgcaccggcccaaggagcccgcgtggttcctggccaccgtcggcgtctcgcc cgaccaccagggcaagggtctgggcagcgccgtcgtgctccccggagtggaggcggccgagcgcgccggggtgcccgccttcctgga gacctccgcgccccgcaacctccccttctacgagcggctcggcttcaccgtcaccgccgacgtcgaggtgcccgaaggaccgcgcacct ggtgcatgacccgcaagcccggtgcctgaCCGCGTCTGGAACAATCAACCTCTGGATTACAAAATTT

GTGAAAGATTGACTGGTATTCTTAACTATGTTGCTCCTTTTACGCTATGTGGATACGC

TGCTTTAATGCCTTTGTATCATGCTATTGCTTCCCGTATGGCTTTCATTTTCTCCTCCT

TGTATAAATCCTGGTTGCTGTCTCTTTATGAGGAGTTGTGGCCCGTTGTCAGGCAAC

GTGGCGTGGTGTGCACTGTGTTTGCTGACGCAACCCCCACTGGTTGGGGCATTGCCA

CCACCTGTCAGCTCCTTTCCGGGACTTTCGCTTTCCCCCTCCCTATTGCCACGGCGGA

ACTCATCGCCGCCTGCCTTGCCCGCTGCTGGACAGGGGCTCGGCTGTTGGGCACTGA

CAATTCCGTGGTGTTGTCGGGGAAGCTGACGTCCTTTCCATGGCTGCTCGCCTGTGTT

GCCACCTGGATTCTGCGCGGGACGTCCTTCTGCTACGTCCCTTCGGCCCTCAATCCA

GCGGACCTTCCTTCCCGCGGCCTGCTGCCGGCTCTGCGGCCTCTTCCGCGTCTTCGCC

TTCGCCCTCAGACGAGTCGGATCTCCCTTTGGGCCGCCTCCCCGCaAAATGACCGAC

-continued

CAAGCGACGCCCAACCTGCCATCACGAGATTTCGATTCCACCGCCGCCTTCTATGAA

AGGTTGGGCTTCGGAATCGTTTTCCGGGACGCCGGCTGGATGATCCTCCAGCGCGGG

GATCTCATGCTGGAGTTCTTCGCCCACCCCAACTTGTTTATTGCAGCTTATAATGGTT

ACAAATAAAGCAATAGCATCACAAATTTCACAAATAAAGCATTTTTTTCACTGCATT

CTAGTTGTGGTTTGTCCAAACTCATCAATGTATCTTATCATGTCTGTAGCtGATcaATTg

GCGCGCCGAATTCGTTatctgcagaattcggcttggcggctgcgcgttcaaacctcccgcttcaaaatggagaccctgcgtg ctcactcgggcttaaatacccagcgtgaccacatggtgtcgcaaaatgtcgcaaaacactcacgtgacctctaatacaggacctctagagca tggaaactagataagaaagaaatacgcagagaccaaagttcaactgaaacgaattaaacggtttattgattaacaagcaaactagtttacaga ttacgggtgaggtaacgggtgccgatggggcgaggctcagaataaacgccatttgtgtcaacagcaaagtccacatttgtagatttgttgtag ttggaagtgtattgaatctctgggttccagcgtttgctgttttctttctgcagctcccattcaatttccacgctgacctgtccggtgctgtactgcgt gatgaacgacgcaaacttagctggactgaaggtagttggaggattcgcgggaacaggtgtattcttaatcaggatctgaggaggcgggtgt ttcagtccaaagcctcccatcagcggcgagggatgaaagtgtccgtccgtgtgaggaatcttggcccagataggaccctgcaggtacacgt cccggtcctgccagaccatgccaggtaaggctccttgactgttgacggtccctgtagcaggagcggtgttggccgattgcaggttagtggc caccgtgccgtactcttctgtggccactgggttggtggttttaatttcttcctcgttggttatcataacgttgtcaaggtccacgttgctatttccag ctccctgtttcccaaatattaagactccgctcatcggaaaaaatttgtcttcgtcgtccttgtgggttgccatagcgggaccgggatttaccaga gagtctctgccattcagatgatacttggtggcaccggtccaggcaaagttgctgttgttattttgattggttgtcttggagacgcgttgctgccgg tagcagggcccgggtagccagtttttggcctgattcgccatgctactaggcccggcctgagaaaattgcaacgtccgatttcctgcggtacc actcgtggtctgagtccgagacaggtagtacaggtactggtcgatgaggggttcatcagccggtccaggctttggctgtgcgcgtagctg ctgtgaaaaggcacgtcctcaaacgtgtagctgaactgaaagttgttgcccgttctcagcatttgagaaggaaagtattccaggcagtagaa ggaggaacggcccacggcctgactgccattgttcagagtcaggtacccgtactgaggaatcatgaagacgtccgccgggaacggaggc aggcagccctggtgcgcagagccgaggacgtacgggagctggtattccgagtccgtaaagacctgaaccgtgctggtaaggttattggcg atggtcgtggtgccatcattcgtcgtgacctccttgacctggatgttgaagagcttgaagttgagcttcttgggccggaatccccagttgttgtt gatgagtcgctgccagtcacgtggtgagaagtggcagtggaatctgttaaagtcaaaatacccccaggggggtgctgtagccgaagtaggt gttgtcgttggtgctgcctcccgattggctggagatttgcttgtagaggtggttgttgtaggtggggagggcccaggttcgggtgctggtggt gatgactctgtcgcccagccatgtggaatcgcaatgccaatttcctgaggcgttacccactccgtcggcgccttcgttattgtctgccattgga gcgccaccgcctgcagccattgtattagatcccacaccagagggggctgcgggggggttctccgagtggttgagggtcgggcactgactct gagtcgccagtctgcccaaagttgagtctctttctcgcgggctgctggcctttcttgccgatgcccgaagaggagtctggttcctggggtgatt gctctaccggtctcttctttccaggagccgtcttagcgccttcctcaaccagaccgagaggttcgagaacccgcttcttggcctggaagactg ctcgcccgaggttgcccccaaaagacgtatcttcttgcagacgctcctgaaactcggcgtcggcgtggttataccgcaggtacggattgtca cccgctttgagctgctggtcgtaggccttgtcgtgctcgagggccgctgcgtccgccgcgttgacgggctccccccttgtcgagtccgttgaa gggtccgaggtacttgtagccaggaagcaccagaccccggccgtcgtcctgcttttgctggttggctttgggtttcggggctccaggtttcaa gtcccaccactcgcgaatgccctcagagaggttgtcctcgagccaatctggaagataaccatcggcagccatacctgatttaaatcatttattg ttcaaagatgcagtcatccaaatccacattgaccagatcgcaggcagtgcaagcgtctggcacctttcccatgatatgatgaatgtagcacag tttctgatacgccttttttgacgacagaaacgggttgagattctgacacgggaaagcactctaaacagtctttctgtccgtgagtgaagcagatat ttgaattctgattcattctctcgcattgtctgcagggaaacagcatcagattcatgcccacgtgacgagaacatttgttttggtacctgtctgcgta gttgatcgaagcttccgcgtctgacgtcgatggctgcgcaactgactcgcgcacccgtttgggctcacttatatctgcgtcactgggggcgg gtcttttcttggctccaccctttttgacgtagaattcatgctccacctcaaccacgtgatcctttgcccaccggaaaaagtctttgacttcctgcttg gtgaccttcccaaagtcatgatccagacggcgggtgagttcaaatttgaacatccggtcttgcaacggctgctggtgttcgaaggtcgttgag ttcccgtcaatcacggcgcacatgttggtgttggaggtgacgatcacgggagtcgggtctatctgggccgaggacttgcatttctggtccac gcgcaccttgcttcctccgagaatggctttggccgactccacgaccttggcggtcatcttcccctcctcccaccagatcaccatcttgtcgaca -continued cagtcgttgaagggaaagttctcattggtccagtttacgcacccgtagaagggcacagtgtgggctatggcctccgcgatgttggtcttcccg
gtagttgcaggcccaaacagccagatggtgttcctcttgccgaactttttcgtggcccatcccagaaagacggaagccgcatattggggatc
gtacccgtttagttccaaaattttataaatccgattgctggaaatgtcctccacgggctgctggcccaccaggtagtcgggggcggttttagtc
aggctcataatctttcccgcattgtccaaggcagccttgatttgggaccgcgagttggaggccgcattgaaggagatgtatgaggcctggtc
ctcctggatccactgcttctccgaggtaatccccttgtccacgagccacccgaccagctccatgtacctggctgaagtttttgatctgatcacc
ggcgcatcagaattgggattctgattctctttgttctgctcctgcgtctgcgacacgtgcgtcagatgctgcgccaccaaccgtttacgctccgt
gagattcaaacaggcgctgtggagagaaaggcaaagtggatgtcagtaTCTCTATCACTGATAGGGAGATCTCT
ATCACTGATAGGGAacttaccttaaatactgttccatattagtccacgcccactggagctcaggctgggttttggggagcaagta
attggggatgtagcactcatccaccaccttgttcccgcctccggcgccatttctggtctttgtgaccgcgaaccagtttggcaaagtcggctcg
atcccgcggtaaattctctgaatcagtttttcgcgaatctgactcaggaaacgtcccaaaaccatggatttcaccccggtggtttccacgagca
cgtgcatgtggaagtagctctctcccttctcaaattgcacaaagaaaagagcctccggggccttactcacacggcgccattccgtcagaaag
tcgcgctgcagcttctcggccacggtcaggggtgcctgctcaatcagattcagatccatgtcagaatctggcggcaactcccattccttctcg
gccacccagttcacaaagctgtcagaaatgccgggcagatgctcgtcaaggtcgctggggaccttaatcacaatctcgtaaaccccggca
tGGCGGCTGCGCGTTCAAACCTCCCGCTTCAAAATGGAGACCCTGCGTGCTCACTCG
GGCgaTCTCTATCACTGATAGGGAGATCTCTATCACTGATAGGGAgaTTAAATAgaatgg
CTAggATCCGGCCGGccTGCAggTGTCCTCACAGGAACGAAGTCCCTAAAGAAACAGT
GGCAGCCAGGTTTAGCCCCGGAATTGACTGGATTCCTTTTTTAGGGCCCATTGGTAT
GGCTTTTTCCCCGTATCCCCCCAGGTGTCTGCAGGCTCAAAGAGCAGCGAGAAGCGT
TCAGAGGAAAGCGATCCCGTGCCACCTTCCCCGTGCCCGGGCTGTCCCCGCACGCTG
CCGGCTCGGGGATGCGGGGGGAGCGCCGGACCGGAGCGGAGCCCCGGGCGGCTCG
CTGCTGCCCCCTAGCGGGGGAGGGACGTAATTACATCCCTGGGGGCTTTGGGGGGG
GGCTGTCCCTCTAGAGCGGCCGCCACCGCGGTGGAGCTCCAGCTTTTGTTCCCTTTA
GTGAGGGTTAATTAGATCTTAATACGACTCACTATAGGGCGAATTGGGTACCGGGCC
CCCCCTCGAGGTCGACGGTATCGCCTCCAAGGCCAGCTTCCCACAATAAGTTGGGTG
AATTTTGGCTCATTCCTCCTTTCTATAGGATTGAGGTCAGAGCTTTGTGATGGGAATT
CTGTGGAATGTGTGTCAGTTAGGGTGTGGAAAGTCCCgcGATCgcTAGcAAACGCCAG
CAACGCGGCCTTTTTACGGTTCCTGGCCTTTTGCTGGCCTTTTGCTCACATGTCCTGC
AGGCAGCTGCGCGCTCGCTCGCTCACTGAGGCCGCCCGGGCAAAGCCCGGGCGTCG
GGCGACCTTTGGTCGCCCGGCCTCAGTGAGCGAGCGAGCGCGCAGAGAGGGAGTGG
CCAACTCCATCACTAGGGGTTCCTGCGGCCGCACGCGTGGAGCTAGTTATTAATAGT
AATCAATTACGGGGTCATTAGTTCATAGCCCATATATGGAGTTCCGCGTTACATAAC
TTACGGTAAATGGCCCGCCTGGCTGACCGCCCAACGACCCCCGCCCATTGACGTCAA
TAATGACGTATGTTCCCATAGTAACGTCAATAGGGACTTTCCATTGACGTCAATGGG
TGGAGTATTTACGGTAAACTGCCCACTTGGCAGTACATCAAGTGTATCATATGCCAA
GTACGCCCCCTATTGACGTCAATGACGGTAAATGGCCCGCCTGGCATTATGCCCAGT
ACATGACCTTATGGGACTTTCCTACTTGGCAGTACATCTACGTATTAGTCATCGCTAT
TACCATGGTGATGCGGTTTTGGCAGTACATCAATGGGCGTGGATAGCGGTTTGACTC
ACGGGGATTTCCAAGTCTCCACCCCATTGACGTCAATGGGAGTTTGTTTTGCACCAA
AATCAACGGGACTTTCCAAAATGTCGTAACAACTCCGCCCCATTGACGCAAATGGG
CGGTAGGCGTGTACGGTGGGAGGTCTATATAAGCAGAGCTCGTTTAGTGAACCGTC
AGATCGCCTGGAGACGCCATCCACGCTGTTTTGACCTCCATAGAAGACACCGGGAC -continued

CGATCCAGCCTCCGCGGATTCGAATCCCGGCCGGGAACGGTGCATTGGAACGCGGA

TTCCCCGTGCCAAGAGTGACGTAAGTACCGCCTATAGAGTCTATAGGCCCACAAAA

AATGCTTTCTTCTTTTAATATACTTTTTTGTTTATCTTATTTCTAATACTTTCCCTAATC

TCTTTCTTTCAGGGCAATAATGATACAATGTATCATGCCTCTTTGCACCATTCTAAAG

AATAACAGTGATAATTTCTGGGTTAAGGCAATAGCAATATTTCTGCATATAAATATT

TCTGCATATAAATTGTAACTGATGTAAGAGGTTTCATATTGCTAATAGCAGCTACAA

TCCAGCTACCATTCTGCTTTTATTTTATGGTTGGGATAAGGCTGGATTATTCTGAGTC

CAAGCTAGGCCCTTTTGCTAATCATGTTCATACCTCTTATCTTCCTCCCACAGCTCCT

GGGCAACGTGCTGGTCTGTGTGCTGGCCCATCACTTTGGCAAAGAATTGGGATTCGA

ACATCGATTGAATTCTGAATGGTGAGCAAGGGCGAGGAGCTGTTCACCGGGGTGGT

GCCCATCCTGGTCGAGCTGGACGGCGACGTAAACGGCCACAAGTTCAGCGTGTCCG

GCGAGGGCGAGGGCGATGCCACCTACGGCAAGCTGACCCTGAAGTTCATCTGCACC

ACCGGCAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGTCCGCC

ATGCCCGAAGGCTACGTCCAGGAGCGCACCATCTTCTTCAAGGACGACGGCAACTA

CAAGACCCGCGCCGAGGTGAAGTTCGAGGGCGACACCCTGGTGAACCGCATCGAGC

TGAAGGGCATCGACTTCAAGGAGGACGGCAACATCCTGGGGCACAAGCTGGAGTAC

AACTACAACAGCCACAACGTCTATATCATGGCCGACAAGCAGAAGAACGGCATCAA

GGTGAACTTCAAGATCCGCCACAACATCGAGGACGGCAGCGTGCAGCTCGCCGACC

ACTACCAGCAGAACACCCCCATCGGCGACGGCCCCGTGCTGCTGCCCGACAACCAC

TACCTGAGCACCCAGTCCGCCCTGAGCAAAGACCCCAACGAGAAGCGCGATCACAT

GGTCCTGCTGGAGTTCGTGACCGCCGCCGGGATCACTCTCGGCATGGACGAGCTGTA

CAAGTACTCAGATCTCGAGCTCAAGTAGGGATCCTCTAGAGTCGACCTGCAGAAGCT

TGCCTCGAGCAGCGCTGCTCGAGAGATCTACGGGTGGCATCCCTGTGACCCCTCCCC

AGTGCCTCTCCTGGCCCTGGAAGTTGCCACTCCAGTGCCCACCAGCCTTGTCCTAAT

AAAATTAAGTTGCATCATTTTGTCTGACTAGGTGTCCTTCTATAATATTATGGGGTGG

AGGGGGGTGGTATGGAGCAAGGGGCAAGTTGGGAAGACAACCTGTAGGGCCTGCG

GGGTCTATTGGGAACCAAGCTGGAGTGCAGTGGCACAATCTTGGCTCACTGCAATCT

CCGCCTCCTGGGTTCAAGCGATTCTCCTGCCTCAGCCTCCCGAGTTGTTGGGATTCCA

GGCATGCATGACCAGGCTCAGCTAATTTTTGTTTTTTTGGTAGAGACGGGGTTTCAC

CATATTGGCCAGGCTGGTCTCCAACTCCTAATCTCAGGTGATCTACCCACCTTGGCC

TCCCAAATTGCTGGGATTACAGGCGTGAACCACTGCTCCCTTCCCTGTCCTTCTGATT

TTGTAGGTAACCACGTGCGGACCGAGCGGCCGCAGGAACCCCTAGTGATGGAGTTG

GCCACTCCCTCTCTGCGCGCTCGCTCGCTCACTGAGGCCGGGCGACCAAAGGTCGCC

CGACGCCCGGGCTTTGCCCGGGCGGCCTCAGTGAGCGAGCGAGCGCGCAGCTGCCT

GCAGGGGCGCCTGATGCGGTATTTTCTCCTTACGCATCTGTGCGGTATTTCACACCG

CATACGTCgtaGCtGATcaATTgGCGCGCCGAATTCGTTAACAAGCTtTAATTAaCGCgtAc gATAAGCTTGATATCTATAACAAGAAAATATATATATAATAAGTTATCACGTAAGTA

GAACATGAAATAACAATATAATTATCGTATGAGTTAAATCTTAAAAGTCACGTAAA

AGATAATCATGCGTCATTTTGACTCACGCGGTCGTTATAGTTCAAAATCAGTGACAC

-continued

TTACCGCATTGACAAGCACGCCTCACGGGAGCTCCAAGCGGCGACTGAGATGTCCT

AAATGCACAGCGACGGATTCGCGCTATTTAGAAAGAGAGAGCAATATTTCAAGAAT

GCATGCGTCAATTTTACGCAGACTATCTTTCTAGGGTTAATCTAGCTGCATCAGGAT

CATATCGTCGGGTCTTTTTTCCGGCTCAGTCATCGCCCAAGCTGGCGCTATCTGGGCA

TCGGGGAGGAAGAAGCCCGTGCCTTTTCCCGCGAGGTTGAAGCGGCATGGAAAGAG

TTTGCCGAGGATGACTGCTGCTGCATTGACGTTGAGCGAAAACGCACGTTTACCATG

ATGATTCGGGAAGGTGTGGCCATGCACGCCTTTAACGGTGAACTGTTCGTTCAGGCC

ACCTGGGATACCAGTTCGTCGCGGCTTTTCCGGACACAGTTCCGGATGGTCAGCCCG

AAGCGCATCAGCAACCCGAACAATACCGGCGACAGCCGGAACTGCCGTGCCGGTGT

GCAGATTAATGACAGCGGTGCGGCGCTGGGATATTACGTCAGCGAGGACGGGTATC

CTGGCTGGATGCCGCAGAAATGGACATGGATACCCCGTGAGTTACCCGGCGGGCGC

GCTTGGCGTAATCATGGTCATAGCTGTTTCCTGTGTGAAATTGTTATCCGCTCACAAT

TCCACACAACATACGAGCCGGAAGCATAAAGTGTAAAGCCTGGGGTGCCTAATGAG

TGAGCTAACTCACATTAATTGCGTTGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTTCCGCTTCCTCGCTCACTGACTCGCTGCGCTCGGTCGTTCGGCTGC

GGCGAGCGGTATCAGCTCACTCAAAGGCGGTAATACGGTTATCCACAGAATCAGGG

GATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACA

AAAATCGACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGTCCAACCC

GGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACA

CTAGAAGGACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAA

TGATACCGCGAGACCCACGCTCACCGGCTCCAGATTTATCAGCAATAAACCAGCCA

GCCGGAAGGGCCGAGCGCAGAAGTGGTCCTGCAACTTTATCCGCCTCCATCCAGTCT

ATTAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTCAT

TCAGCTCCGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCCGCAGTGT

TATCACTCATGGTTATGGCAGCACTGCATAATTCTCTTACTGTCATGCCATCCGTAAG

-continued

ATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAAGGGAATAAGGGCGACACGGAAATGTTGAATACTCAT

Sequences of additional vectors for use in the practice of the present invention:

iRepCap1/pKan-Anc80-RepCap-p5i1-p19i1 (10,497 bp)

(SEQ ID NO: 15)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccaAtgggcAtggacCaaCatggaaca gtaCCtCagcgcctgtttgaatctcacggagcgtaaacggttggtggcgcagcatctgacgcacgtgtcgcagacgcaggagcagaac aaagagaatcagaatcccaattctgatgcgccggtgatcagatcaaaaacttcagccaggtacatggagctggtcgggtggctcgtggaca aggggattacctcggagaagcagtggatccaggaggaccaggcctcatacatctccttcaatgcggcctccaactcgcggtcccaaatca aggctgccttggacaatgcgggaaagattatgagcctgactaaaaccgcccccgactacctggtgggccagcagcccgtggaggacattt ccagcaatcggatttataaaattttggaactaaacgggtacgatccccaatatgcggcttccgtctttctgggatgggccacgaaaaagttcg gcaagaggaacaccatctggctgtttgggcctgcaactaccgggaagaccaacatcgcggaggccatagcccacactgtgcccttctacg ggtgcgtaaactggaccaatgagaactttcccttcaacgactgtgtcgacaagatggtgatctggtgggaggaggggaagatgaccgcca aggtcgtggagtcggccaaagccattctcggaggaagcaaggtgcgcgtggaccagaaatgcaagtcctcggcccagatagacccgact cccgtgatcgtcacctccaacaccaacatgtgcgccgtgattgacgggaactcaacgaccttcgaacaccagcagccgttgcaagaccgg atgttcaaatttgaactcacccgccgtctggatcatgactttgggaaggtcaccaagcaggaagtcaaagactttttccggtgggcaaaggat cacgtggttgaggtggagcatgaattctacgtcaaaaagggtggagccaagaaaagacccgcccccagtgacgcagatataagtgagcc caaacgggtgcgcgagtcagttgcgcagccatcgacgtcagacgcggaagcttcgatcaactacgcagacaggtaccaaaacaaatgttc tcgtcacgtgggcatgaatctgatgctgtttccctgcagacaatgcgagagaatgaatcagaattcaaatatctgcttcactcacggacagaa agactgtttagagtgctttcccgtgtcagaatctcaacccgtttctgtcgtcaaaaaggcgtatcagaaactgtgctacattcatcatatcatggg aaaggtgccagacgcttgcactgcctgcgatctggtcaatgtggatttggatgactgcatctttgaacaataaatgatttaaatcaggtatggct gccgatggttatcttccagattggctcgaggacaacctctctgagggcattcgcgagtggtgggacttgaaacctggagccccgaaaccca aagccaaccagcaaaagcaggacgacggccggggtctggtgcttcctggctacaagtacctcggacccttcaacggactcgacaaggg ggagcccgtcaacgcggcggacgcagcggccctcgagcacgacaaggcctacgaccagcagctcaaagcgggtgacaatccgtacct gcggtataaccacgccgacgccgagtttcaggagcgtctgcaagaagatacgtcttttgggggcaacctcgggcgagcagtcttccaggc caagaagcgggttctcgaacctctcggtctggttgaggaaggcgctaagacggctcctggaaagaagagaccggtagagcaatcacccc aggaaccagactcctcttcgggcatcggcaagaaaggccagcagcccgcgagaaagagactcaactttgggcagactggcgactcaga gtcagtgcccgaccctcaaccactcggagaacccccgcagcccctctggtgtgggatctaatacaatggctgcaggcggtggcgctcc -continued aatggcagacaataacgaaggcgccgacggagtgggtaacgcctcaggaaattggcattgcgattccacatggctgggcgacagagtca tcaccaccagcacccgaacctgggccctccccacctacaacaaccacctctacaagcaaatctccagccaatcgggaggcagcaccaac gacaacacctacttcggctacagcaccccctgggggtattttgactttaacagattccactgccacttctcaccacgtgactggcagcgactc atcaacaacaactggggattccggcccaagaagctcaacttcaagctcttcaacatccaggtcaaggaggtcacgacgaatgatggcacc acgaccatcgccaataaccttaccagcacggttcaggtctttacggactcggaataccagctcccgtacgtcctcggctctgcgcaccagg gctgcctgcctccgttcccggcggacgtcttcatgattcctcagtacgggtacctgactctgaacaatggcagtcaggccgtgggccgttcct ccttctactgcctggaatactttccttctcaaatgctgagaacgggcaacaactttcagttcagctacacgtttgaggacgtgccttttcacagca gctacgcgcacagccaaagcctggaccggctgatgaacccctcatcgaccagtacctgtactacctgtctcggactcagaccacgagtg gtaccgcaggaaatcggacgttgcaattttctcaggccgggcctagtagcatggcgaatcaggccaaaaactggctacccgggccctgct accggcagcaacgcgtctccaagacaaccaatcaaaataacaacagcaactttgcctggaccggtgccaccaagtatcatctgaatggca gagactctctggtaaatcccggtcccgctatggcaacccacaaggacgacgaagacaaatttttttccgatgagcggagtcttaatatttggga aacagggagctggaaatagcaacgtggaccttgacaacgttatgataaccaacgaggaagaaattaaaaccaccaacccagtggccaca gaagagtacggcacggtggccactaacctgcaatcggccaacaccgctcctgctacagggaccgtcaacagtcaaggagccttacctgg catggtctggcaggaccgggacgtgtacctgcagggtcctatctgggccaagattcctcacacggacggacactttcatccctcgccgctg atgggaggctttggactgaaacacccgcctcctcagatcctgattaagaatacacctgttcccgcgaatcctccaactaccttcagtccagct aagtttgcgtcgttcatcacgcagtacagcaccggacaggtcagcgtggaaattgaatgggagctgcagaaagaaaacagcaaacgctgg aacccagagattcaatacacttccaactacaacaaatctacaaatgtggactttgctgttgacacaaatggcgtttattctgagcctcgccccat cggcacccgttacctcacccgtaatctgtaaactagtttgcttgttaatcaataaaccgtttaattcgtttcagttgaactttggtctctgcgtatttct ttcttatctagtttccatgctctagaggtcctgtattagaggtcacgtgagtgttttgcgacattttgcgacaccatgtggtcacgctgggtatttaa gcccgagtgagcacgcagggtctccattttgaagcgggaggtttgaacgcgcagccgccaagccgaattctgcagatatcggggttgggg ttgcgccttttccaaggcagccctgggtttgcgcagggacgcggctgctctgggcgtggttccgggaaacgcagcggcgccgaccctgg gtctcgcacattcttcacgtccgttcgcagcgtcacccggatcttcgccgctacccttgtgggccccccggcgacgcttcctgctccgcccct aagtcgggaaggttccttgcggttcgcggcgtgccggacgtgacaaacggaagccgcacgtctcactagtaccctcgcagacggacagc gccagggagcaatggcagcgcgccgaccgcgatgggctgtggccaatagcggctgctcagcagggcgcgcccgagagcagcggccg ggaaggggcggtgcgggaggcggggtgtggggcggtagtgtgggccctgttcctgcccgcgcggtgttccgcattctgcaagcctccg gagcgcacgtcggcagtcggctccctcgttgaccgaatcaccgacctctctccccagAAGCTCCCGGGAGCTTGTATA

TCCATTTTCGGATCTGATCAGCACGTGTTGACAATTAATCATCGGCATAGTATATCG

GCATAGTATAATACGACAAGGTGAGGAACgccaccATGGCCAAGCCTTTGTCTCAAGA

AGAATCCACCCTCATTGAAAGAGCAACGGCTACAATCAACAGCATCCCCATCTCTG

AAGACTACAGCGTCGCCAGCGCAGCTCTCTCTAGCGACGGCCGCATCTTCACTGGTG

TCAATGTATATCATTTTACTGGGGACCTTGTGCAGAACTCGTGGTGCTGGGCACTG

CTGCTGCTGCGGCAGCTGGCAACCTGACTTGTATCGTCGCGATCGGAAATGAGAACA

GGGGCATCTTGAGCCCCTGCGGACGGTGCCGACAGGTGCTTCTCGATCTGCATCCTG

GGATCAAAGCCATAGTGAAGGACAGTGATGGACAGCCGACGGCAGTTGGGATTCGT

GAATTGCTGCCCTCTGGTTATGTGTGGGAGGGCTAAGCACTTCGTGGCCGAGGAGCA

GGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCAT

GCTGGAGTTCTTCGCCCACCCCAACTTGTTTATTGCAGCTTATAATGGTTACAAATAA

AGCAATAGCATCACAAATTTCACAAATAAAGCATTTTTTTCACTGCATTCTAGTTGT

GGTTTGTCCAAACTCATCAATGTATCTTAGCGCTCACTGCCCGCTTTCCAGTCGGGA

AACCTGTCGTGCCAGCTGCATTAATGAATCGGCCAACGCGCGGGGAGAGGCGGTTT

-continued

GCGTATTGGGCGCTCTCCTAGGccagaaatggcgccggaggcgggaacaaggtggtggatgagtgctacatcccca attacttgctccccaaaacccagcctgagctccagtgggcgtggactaatatggaacagtatttaagcgcctgTCCCTATCAGTG ATAGAGATCTCCCTATCAGTGATAGAGAtttgaatctcacggagcgtaaacggttggtggcgcagcatctGTT TAAACgcagacgcaggagcagaacaaagagaatcagaatcccaattctgatgcgccggtgatcagatcaaaaacttcagccaggtac atggagctggtcgggtggctcgtggacaaggggattacctcggagaagcagtggattcaggaggaccaggcctcatacatctccttcaatg cggcctccaactcgcggtcccaaatcaaggctgccttggacaatgcgggaaagattatgagcctgactaaaaccgcccccgactacctggt gggccagcagcccgtggaggacatttccagcaatcggatttataaaattttggaactaaacgggtacgatccccaatatgcggcttccgtctt tctgggatgggccacgaaaaagttcggcaagaggaacaccatctggctgtttgggcctgcaactaccgggaagaccaacatcgcggagg ccatagcccacactgtgcccttctacgggtgcgtaaactggaccaatgagaactttcccttcaacgactgtgtcgacaagatggtgatctggt gggaggaggggaagatgaccgccaaggtcgtggagtcggccaaagccattctcggaggaagcaaggtgcgcgtggaccagaaatgca agtcctcggcccagatagacccgactcccgtgatcgtcacctccaacaccaacatgtgcgccgtgattgacgggaactcaacgaccttcga acaccagcagccgttgcaagaccggatgttcaaatttgaactcacccgccgtctggatcatgactttgggaaggtcaccaagcaggaagtc aaagactttttccggtgggcaaaggatcacgtggttgaggtggagcatgaattctacgtcaaaaagggtggagccaagaaaagacccgcc cccagtgacgcagatataagtgagcccaaacgggtgcgcgagtcagttgcgcagccatcgacgtcagacgcggaagcttcgatcaacta cgcagacaggtaccaaaacaaatgttctcgtcacgtgggcatgaatctgatgctgtttccctgcagacaatgcgagagaatgaatcagaatt caaatatctgcttcactcacggacagaaagactgtttagagtgctttcccgtgtcagaatctcaacccgtttctgtcgtcaaaaaggcgtatcag aaactgtgctacattcatcatatcatgggaaaggtgccagacgcttgcactgcctgcgatctggtcaatgtggatttggatgactgcatctttga acaataaACTAGTTTGCTTGTTAATCAATAAACCGTTTAATTCGTTTCAGTTGAACTTTGG TCTCTGCGTATTTCTTTCTTATCTAGTTTCCATGCTCTAGAGTATACgatatccatcacactggcg gccgctcgactagagcggccgccaccgcggtggagctccagcttttgttcgcgcgcttggcgtaatcatggtcatagctgtttcctgtgtgaa attccacagcctggggtgcctaattgcgttgcgctcactgcccgctttccagtcgggaaacctgtcgtgccagctgcattaatgaatcggcca acgcgcggggagaggcggtttgcgtattgggcgctcttccgcttcctcgctcactgactcgctgcgctcggtcgttcggctgcggcgagcg gtatcagctcactcaaaggcggtaatacggttatccacagaatcaggggataacgcaggaaagaacatgtgagcaaaaggccagcaaaa ggccaggaaccgtaaaaaggccgcgttgctggcgtttttccataggctccgcccccctgacgagcatcacaaaaatcgacgctcaagtca gaggtggcgaaacccgacaggactataaagataccaggcgtttccccctggaagctccctcgtgcgctctcctgttccgaccctgccgctta ccggatacctgtccgcctttctcccttcgggaagcgtggcgctttctcatagctcacgctgtaggtatctcagttcggtgtaggtcgttcgctcc aagctgggctgtgtgcacgaaccccccgttcagcccgaccgctgcgccttatccggtaactatcgtcttgagtccaacccggtaagacacg acttatcgccactggcagcagccactggtaacaggattagcagagcgaggtatgtaggcggtgctacagagttcttgaagtggtggcctaa ctacggctacactagaagaacagtatttggtatctgcgctctgctgaagccagttaccttcggaaaaagagttggtagctcttgatccggcaa acaaaccaccgctggtagcggtggtttttttgtttgcaagcagcagattacgcgcagaaaaaaaggatctcaagaagatcctttgatcttttcta cggggtctgacgctcagtggaacgaaaactcacgttaagggattttggtcatgagattatcaaaaaggatcttcacctagatccttttaaattaa aaatgaagttttaaatcaatctaaagtatatatgagtaaacttggtctgacagaaataataaaaaagccggattaataatctggctttttatattctc tctctagtatataaacgcagaaaggcccacccgaaggtgagccagtgtgactctagtattattagaaaaactcatcgagcatcaaatgaaact gcaatttattcatatcaggattatcaataccatatttttgaaaaagccgtttctgtaatgaaggagaaaactcaccgaggcagttccaaagaatg gcaaggtcctggtaacggtctgcgattccgacccgtccaacatcaatacaacctattaatttcccctcgtcaaaaataaggttatcaagtgaga aatcaccatgagtgacgactgaatccggtgagaatggcaagagcttgtgcatttattccagacttgttcaacaggccagccattacgctcgtc atcaaaatcactcgcatcaaccaaaccgttattcatgcgtgattgcgcctgagcaagacgaaatacacgatcgctgttaaaaggacaattaca aacaggaatcgaatgtaaccggcgcaggaacacggccagcgcatcaacaatattttcacctgaatcaggatattcttctaatacctggaagg ctgttttcccaggaatcgcggtggtgagtaaccacgcatcatcaggagtacggataaaatgcttgatggtcgggagaggcataaactccgtc agccagttgagacggaccatctcatctgtaacatcattggcaacgctacctttgccatgtttcagaaacaactctggcgcatcgggcttcccat -continued acaagcgatagattgtcgcacctgattgcccgacattatcgcgagcccatttatacccatataaatcagcgtccatgttggagtttaagcgcgg acgggagcaagacgtttcccgttgaatatggctcataacaccccttgtattactgtttatgtaagcagacagttttattgttcatgatgatatattttt atcttgtgcaatgtaacatcagagattttgagacacaacgtggctttgttgaataaatcgaacttttgctgagttgaaggatcagctctagtaaaa taataaaaaagccggattaataatctggctttttatattctctctctagtatataaacgcagaaaggcccacccgaaggtgagccagtgtgacg gcacatttccccgaaaagtgccacctaaattgtaagcgttaatattttgttaaaattcgcgttaaatttttgttaaatcagctcattttttaaccaatag gccgaaatcggcaaaatcccttataaatcaaaagaatagaccgagatagggttgagtgttgttccagtttggaacaagagtccactattaaag aacgtggactccaacgtcaaagggcgaaaaaccgtctatcagggcgatggcccactacgtgaaccatcaccctaatcaagttttttggggtc gaggtgccgtaaagcactaaatcggaaccctaaagggagcccccgatttagagcttgacggggaaagccggcgaacgtggcgagaaag gaagggaagaaagcgaaaggagcgggcgctagggcgctggcaagtgtagcggtcacgctgcgcgtaaccaccacacccgccgcgctt aatgcgccgctacagggcgcgtcccattcgccattcaggctgcgcaactgttgggaagggcgatcggtgcgggcctcttcgctattacgcc agctggcgaaagggggatgtgctgcaaggcgattaagttgggtaacgccagggttttcccagtcacgacgttgtaaaacgacggccagtg agcgcgcggcgaattgggtaccgggccccc iRepCap2/ pKan-Anc80-RepCap-p5i2-p19i1 (10,495 bp)

(SEQ ID NO: 16)

cctcgaggGCTAGCcattcTATTTAAtcTCCCTATCAGTGATAGAGAtcGCCCGAGT

GAGCACGCAGGGTCTCCATTTTGATCCCTATCAGTGATAGAGAAGCGGGAGGTTTGA

ACGCGCAGCCGCCatgccggggttttacgagattgtgattaaggtccccagcgaccttgacgagcatctgcccggcatttctgac agctttgtgaactgggtggccgagaaggaatgggagttgccgccagattctgacatggatctgaatctgattgagcaggcacccctgaccg tggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg -continued aaccagactcctcttcgggcatcggcaagaaaggccagcagcccgcgagaaagagactcaactttgggcagactggcgactcagagtca
gtgcccgaccctcaaccactcggagaaccccccgcagcccccctctggtgtgggatctaatacaatggctgcaggcggtggcgctccaatg
gcagacaataacgaaggcgccgacggagtgggtaacgcctcaggaaattggcattgcgattccacatggctgggcgacagagtcatcac
caccagcacccgaacctgggccctccccacctacaacaaccacctctacaagcaaatctccagccaatcgggaggcagcaccaacgaca
acacctacttcggctacagcaccccctgggggtattttgactttaacagattccactgccacttctcaccacgtgactggcagcgactcatcaa
caacaactggggattccggcccaagaagctcaacttcaagctcttcaacatccaggtcaaggaggtcacgacgaatgatggcaccacgac
catcgccaataaccttaccagcacggttcaggtctttacggactcggaataccagctcccgtacgtcctcggctctgcgcaccagggctgcc
tgcctccgttcccggcggacgtcttcatgattcctcagtacgggtacctgactctgaacaatggcagtcaggccgtgggccgttcctccttcta
ctgcctggaatactttccttctcaaatgctgagaacgggcaacaactttcagttcagctacacgtttgaggacgtgccttttcacagcagctacg
cgcacagccaaagcctggaccggctgatgaacccccctcatcgaccagtacctgtactacctgtctcggactcagaccacgagtggtaccg
caggaaatcggacgttgcaattttctcaggccgggcctagtagcatggcgaatcaggccaaaaactggctacccgggccctgctaccggc
agcaacgcgtctccaagacaaccaatcaaaataacaacagcaactttgcctggaccggtgccaccaagtatcatctgaatggcagagactc
tctggtaaatcccggtcccgctatggcaacccacaaggacgacgaagacaaatttttttccgatgagcggagtcttaatatttgggaaacagg
gagctggaaatagcaacgtggaccttgacaacgttatgataaccaacgaggaagaaattaaaaccaccaacccagtggccacagaagagt
acggcacggtggccactaacctgcaatcggccaacaccgctcctgctacagggaccgtcaacagtcaaggagccttacctggcatggtct
ggcaggaccgggacgtgtacctgcagggtcctatctgggccaagattcctcacacggacggacactttcatccctcgccgctgatgggag
gctttggactgaaacacccgcctcctcagatcctgattaagaatacacctgttcccgcgaatcctccaactaccttcagtccagctaagtttgc
gtcgttcatcacgcagtacagcaccggacaggtcagcgtggaaattgaatgggagctgcagaaagaaaacagcaaacgctggaacccag
agattcaatacacttccaactacaacaaatctacaaatgtggactttgctgttgacacaaatggcgtttattctgagcctcgccccatcggcacc
cgttacctcacccgtaatctgtaaactagtttgcttgttaatcaataaaccgtttaattcgtttcagttgaactttggtctctgcgtatttctttcttat
ctagtttccatgctctagaggtcctgtattagaggtcacgtgagtgttttgcgacattttgcgacaccatgtggtcacgctgggtatttaagcccga
gtgagcacgcagggtctccattttgaagcgggaggtttgaacgcgcagccgccaagccgaattctgcagatatcggggttggggttgcgc
cttttccaaggcagccctgggtttgcgcagggacgcggctgctctgggcgtggttccgggaaacgcagcggcgccgaccctgggtctcg
cacattcttcacgtccgttcgcagcgtcacccggatcttcgccgctacccttgtgggccccccggcgacgcttcctgctccgcccctaagtcg
ggaaggttccttgcggttcgcggcgtgccggacgtgacaaacggaagccgcacgtctcactagtaccctcgcagacggacagcgccag
ggagcaatggcagcgcgccgaccgcgatgggctgtggccaatagcggctgctcagcagggcgcgccgagagcagcggccgggaag
gggcggtgcgggaggcggggtgtggggcggtagtgtgggccctgttcctgcccgcgcggtgttccgcattctgcaagcctccggagcgc
acgtcggcagtcggctccctcgttgaccgaatcaccgacctctctccccagAAGCTCCCGGGAGCTTGTATATCCA
TTTTCGGATCTGATCAGCACGTGTTGACAATTAATCATCGGCATAGTATATCGGCAT
AGTATAATACGACAAGGTGAGGAACgccaccATGGCCAAGCCTTTGTCTCAAGAAGAA
TCCACCCTCATTGAAAGAGCAACGGCTACAATCAACAGCATCCCCATCTCTGAAGAC
TACAGCGTCGCCAGCGCAGCTCTCTCTAGCGACGGCCGCATCTTCACTGGTGTCAAT
GTATATCATTTTACTGGGGGACCTTGTGCAGAACTCGTGGTGCTGGGCACTGCTGCT
GCTGCGGCAGCTGGCAACCTGACTTGTATCGTCGCGATCGGAAATGAGAACAGGGG
CATCTTGAGCCCCTGCGGACGGTGCCGACAGGTGCTTCTCGATCTGCATCCTGGGAT
CAAAGCCATAGTGAAGGACAGTGATGGACAGCCGACGGCAGTTGGGATTCGTGAAT
TGCTGCCCTCTGGTTATGTGTGGGAGGGCTAAGCACTTCGTGGCCGAGGAGCAGGAC
TGACACGTGCTACGAGATTTCGATTCCACCGCCGCCTTCTATGAAAGGTTGGGCTTC
GGAATCGTTTTCCGGGACGCCGGCTGGATGATCCTCCAGCGCGGGGATCTCATGCTG
GAGTTCTTCGCCCACCCCAACTTGTTTATTGCAGCTTATAATGGTTACAAATAAAGC -continued

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaacagtatttaagcgcctgTCCCTATCAGTGATAG AGATCTCCCTATCAGTGATAGAGAtttgaatctcacggagcgtaaacggttggtggcgcagcatctGTTTAAA Cgcagacgcaggagcagaacaaagagaatcagaatcccaattctgatgcgccggtgatcagatcaaaaacttcagccaggtacatggag ctggtcgggtggctcgtggacaaggggattacctcggagaagcagtggattcaggaggaccaggcctcatacatctccttcaatgcggcct ccaactcgcggtcccaaatcaaggctgccttggacaatgcgggaaagattatgagcctgactaaaaccgcccccgactacctggtgggcc agcagcccgtggaggacatttccagcaatcggatttataaaattttggaactaaacgggtacgatccccaatatgcggcttccgtctttctggg atgggccacgaaaaagttcggcaagaggaacaccatctggctgtttgggcctgcaactaccgggaagaccaacatcgcggaggccatag cccacactgtgcccttctacgggtgcgtaaactggaccaatgagaactttcccttcaacgactgtgtcgacaagatggtgatctggtgggag gaggggaagatgaccgccaaggtcgtggagtcggccaaagccattctcggaggaagcaaggtgcgcgtggaccagaaatgcaagtcct cggcccagatagacccgactcccgtgatcgtcacctccaacaccaacatgtgcgccgtgattgacgggaactcaacgaccttcgaacacc agcagccgttgcaagaccggatgttcaaatttgaactcacccgccgtctggatcatgactttgggaaggtcaccaagcaggaagtcaaaga ctttttccggtgggcaaaggatcacgtggttgaggtggagcatgaattctacgtcaaaaagggtggagccaagaaaagacccgcccccagt gacgcagatataagtgagcccaaacgggtgcgcgagtcagttgcgcagccatcgacgtcagacgcggaagcttcgatcaactacgcaga caggtaccaaaacaaatgttctcgtcacgtgggcatgaatctgatgctgtttccctgcagacaatgcgagagaatgaatcagaattcaaatat ctgcttcactcacggacagaaagactgtttagagtgctttcccgtgtcagaatctcaacccgtttctgtcgtcaaaaaggcgtatcagaaactgt gctacattcatcatatcatgggaaaggtgccagacgcttgcactgcctgcgatctggtcaatgtggatttggatgactgcatctttgaacaataa

ACTAGTTTGCTTGTTAATCAATAAACCGTTTAATTCGTTTCAGTTGAACTTTGGTCTC

TGCGTATTTCTTTCTTATCTAGTTTCCATGCTCTAGAGTATACgatatccatcacactggcggccgct cgactagagcggccgccaccgcggtggagctccagcttttgttcgcgcgcttggcgtaatcatggtcatagctgtttcctgtgtgaaattcca cagcctggggtgcctaattgcgttgcgctcactgcccgctttccagtcgggaaacctgtcgtgccagctgcattaatgaatcggccaacgcg cggggagaggcggtttgcgtattgggcgctcttccgcttcctcgctcactgactcgctgcgctcggtcgttcggctgcggcgagcggtatca gctcactcaaaggcggtaatacggttatccacagaatcaggggataacgcaggaaagaacatgtgagcaaaaggccagcaaaaggcca ggaaccgtaaaaaggccgcgttgctggcgtttttccataggctccgcccccctgacgagcatcacaaaaatcgacgctcaagtcagaggtg gcgaaacccgacaggactataaagataccaggcgtttccccctggaagctccctcgtgcgctctcctgttccgaccctgccgcttaccggat acctgtccgcctttctcccttcgggaagcgtggcgctttctcatagctcacgctgtaggtatctcagttcggtgtaggtcgttcgctccaagctg ggctgtgtgcacgaaccccccgttcagcccgaccgctgcgccttatccggtaactatcgtcttgagtccaacccggtaagacacgacttatc gccactggcagcagccactggtaacaggattagcagagcgaggtatgtaggcggtgctacagagttcttgaagtggtggcctaactacgg ctacactagaagaacagtatttggtatctgcgctctgctgaagccagttaccttcggaaaaagagttggtagctcttgatccggcaaacaaac caccgctggtagcggtggtttttttgtttgcaagcagcagattacgcgcagaaaaaaaggatctcaagaagatcctttgatcttttctacggggt ctgacgctcagtggaacgaaaactcacgttaagggattttggtcatgagattatcaaaaaggatcttcacctagatccttttaaattaaaaatga agttttaaatcaatctaaagtatatatgagtaaacttggtctgacagaaataataaaaaagccggattaataatctggctttttatattctctctctag tatataaacgcagaaaggcccacccgaaggtgagccagtgtgactctagtattattagaaaaactcatcgagcatcaaatgaaactgcaattt attcatatcaggattatcaataccatatttttgaaaaagccgtttctgtaatgaaggagaaaactcaccgaggcagttccaaagaatggcaagg tcctggtaacggtctgcgattccgacccgtccaacatcaatacaacctattaatttcccctcgtcaaaaataaggttatcaagtgagaaatcacc atgagtgacgactgaatccggtgagaatggcaagagcttgtgcatttctttccagacttgttcaacaggccagccattacgctcgtcatcaaaa tcactcgcatcaaccaaaccgttattcatgcgtgattgcgcctgagcaagacgaaatacacgatcgctgttaaaaggacaattacaaacagg aatcgaatgtaaccggcgcaggaacacggccagcgcatcaacaatattttcacctgaatcaggatattcttctaatacctggaaggctgttttc -continued ccaggaatcgcggtggtgagtaaccacgcatcatcaggagtacggataaaatgcttgatggtcgggagaggcataaactccgtcagccag ttgagacggaccatctcatctgtaacatcattggcaacgctacctttgccatgtttcagaaacaactctggcgcatcgggcttcccatacaagc gatagattgtcgcacctgattgcccgacattatcgcgagcccatttatacccatataaatcagcgtccatgttggagtttaagcgcggacggg agcaagacgtttcccgttgaatatggctcataacaccccttgtattactgtttatgtaagcagacagttttattgttcatgatgatatatttttatcttgt gcaatgtaacatcagagattttgagacacaacgtggctttgttgaataaatcgaacttttgctgagttgaaggatcagctctagtaaaataataa aaaagccggattaataatctggctttttatattctctctctagtatataaacgcagaaaggcccacccgaaggtgagccagtgtgacggcacat ttccccgaaaagtgccacctaaattgtaagcgttaatattttgttaaaattcgcgttaaatttttgttaaatcagctcattttttaaccaataggccga aatcggcaaaatcccttataaatcaaaagaatagaccgagatagggttgagtgttgttccagtttggaacaagagtccactattaaagaacgt ggactccaacgtcaaagggcgaaaaaccgtctatcagggcgatggcccactacgtgaaccatcaccctaatcaagttttttggggtcgagg tgccgtaaagcactaaatcggaaccctaaagggagcccccgatttagagcttgacggggaaagccggcgaacgtggcgagaaaggaag ggaagaaagcgaaaggagcgggcgctagggcgctggcaagtgtagcggtcacgctgcgcgtaaccaccacacccgccgcgcttaatg cgccgctacagggcgcgtcccattcgccattcaggctgcgcaactgttgggaagggcgatcggtgcgggcctcttcgctattacgccagct ggcgaaagggggatgtgctgcaaggcgattaagttgggtaacgccagggttttcccagtcacgacgttgtaaaacgacggccagtgagcg cgcggcgaattgggtaccgggccccc iRepCap3/ pKan-Anc80-RepCap-p5i3-p19i1 (10,493 bp)

(SEQ ID NO: 17)

cctcgaggGCTAGCcattcTCCCTATCAGTGATAGAGAtcTATTTAAGCCCGAGTG

AGCACGCAGTCCCTATCAGTGATAGAGAGGTCTCCATTTTGAAGCGGGAGGTTTGAA

CGCGCAGCCGCCatgccggggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga -continued gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaacccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttcttat ctagtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

-continued

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaacagtatttaagcgcctgTCCCTATCAGTGATAG AGATCTCCCTATCAGTGATAGAGAtttgaatctcacggagcgtaaacggttggtggcgcagcatctGTTTAAA Cgcagacgcaggagcagaacaaagagaatcagaatcccaattctgatgcgccggtgatcagatcaaaaacttcagccaggtacatggag ctggtcgggtggctcgtggacaaggggattacctcggagaagcagtggattcaggaggaccaggcctcatacatctccttcaatgcggcct ccaactcgcggtcccaaatcaaggctgccttggacaatgcgggaaagattatgagcctgactaaaaccgcccccgactacctggtgggcc agcagcccgtggaggacatttccagcaatcggatttataaaattttggaactaaacgggtacgatccccaatatgcggcttccgtctttctggg atgggccacgaaaaagttcggcaagaggaacaccatctggctgtttgggcctgcaactaccgggaagaccaacatcgcggaggccatag cccacactgtgcccttctacgggtgcgtaaactggaccaatgagaactttcccttcaacgactgtgtcgacaagatggtgatctggtgggag gaggggaagatgaccgccaaggtcgtggagtcggccaaagccattctcggaggaagcaaggtgcgcgtggaccagaaatgcaagtcct cggcccagatagacccgactcccgtgatcgtcacctccaacaccaacatgtgcgccgtgattgacgggaactcaacgaccttcgaacacc agcagccgttgcaagaccggatgttcaaatttgaactcacccgccgtctggatcatgactttgggaaggtcaccaagcaggaagtcaaaga ctttttccggtgggcaaaggatcacgtggttgaggtggagcatgaattctacgtcaaaaagggtggagccaagaaaagacccgcccccagt gacgcagatataagtgagcccaaacgggtgcgcgagtcagttgcgcagccatcgacgtcagacgcggaagcttcgatcaactacgcaga caggtaccaaaacaaatgttctcgtcacgtgggcatgaatctgatgctgtttccctgcagacaatgcgagagaatgaatcagaattcaaatat ctgcttcactcacggacagaaagactgtttagagtgctttcccgtgtcagaatctcaacccgtttctgtcgtcaaaaaggcgtatcagaaactgt gctacattcatcatatcatgggaaaggtgccagacgcttgcactgcctgcgatctggtcaatgtggatttggatgactgcatctttgaacaataa

ACTAGTTTGCTTGTTAATCAATAAACCGTTTAATTCGTTTCAGTTGAACTTTGGTCTC

TGCGTATTTCTTTCTTATCTAGTTTCCATGCTCTAGAGTATACgatatccatcacactggcggccgct cgactagagcggccgccaccgcggtggagctccagcttttgttcgcgcgcttggcgtaatcatggtcatagctgtttcctgtgtgaaattcca cagcctggggtgcctaattgcgttgcgctcactgcccgctttccagtcgggaaacctgtcgtgccagctgcattaatgaatcggccaacgcg cggggagaggcggtttgcgtattgggcgctcttccgcttcctcgctcactgactcgctgcgctcggtcgttcggctgcggcgagcggtatca gctcactcaaaggcggtaatacggttatccacagaatcaggggataacgcaggaaagaacatgtgagcaaaaggccagcaaaaggcca ggaaccgtaaaaaggccgcgttgctggcgtttttccataggctccgcccccctgacgagcatcacaaaaatcgacgctcaagtcagaggtg gcgaaacccgacaggactataaagataccaggcgtttccccctggaagctccctcgtgcgctctcctgttccgaccctgccgcttaccggat acctgtccgcctttctcccttcgggaagcgtggcgctttctcatagctcacgctgtaggtatctcagttcggtgtaggtcgttcgctccaagctg ggctgtgtgcacgaaccccccgttcagcccgaccgctgcgccttatccggtaactatcgtcttgagtccaacccggtaagacacgacttatc gccactggcagcagccactggtaacaggattagcagagcgaggtatgtaggcggtgctacagagttcttgaagtggtggcctaactacgg ctacactagaagaacagtatttggtatctgcgctctgctgaagccagttaccttcggaaaaagagttggtagctcttgatccggcaaacaaac caccgctggtagcggtggtttttttgtttgcaagcagcagattacgcgcagaaaaaaaggatctcaagaagatcctttgatcttttctacggggt ctgacgctcagtggaacgaaaactcacgttaagggattttggtcatgagattatcaaaaaggatcttcacctagatccttttaaattaaaaatga agttttaaatcaatctaaagtatatatgagtaaacttggtctgacagaaataataaaaaagccggattaataatctggctttttatattctctctctag tatataaacgcagaaaggcccacccgaaggtgagccagtgtgactctagtattattagaaaaactcatcgagcatcaaatgaaactgcaattt attcatatcaggattatcaataccatatttttgaaaaagccgtttctgtaatgaaggagaaaactcaccgaggcagttccaaagaatggcaagg tcctggtaacggtctgcgattccgacccgtccaacatcaatacaacctattaatttcccctcgtcaaaaataaggttatcaagtgagaaatcacc -continued atgagtgacgactgaatccggtgagaatggcaagagcttgtgcatttctttccagacttgttcaacaggccagccattacgctcgtcatcaaaa tcactcgcatcaaccaaaccgttattcatgcgtgattgcgcctgagcaagacgaaatacacgatcgctgttaaaaggacaattacaaacagg aatcgaatgtaaccggcgcaggaacacggccagcgcatcaacaatattttcacctgaatcaggatattcttctaatacctggaaggctgttttc ccaggaatcgcggtggtgagtaaccacgcatcatcaggagtacggataaaatgcttgatggtcgggagaggcataaactccgtcagccag ttgagacggaccatctcatctgtaacatcattggcaacgctacctttgccatgtttcagaaacaactctggcgcatcgggcttcccatacaagc gatagattgtcgcacctgattgcccgacattatcgcgagcccatttatacccatataaatcagcgtccatgttggagtttaagcgcggacggg agcaagacgtttcccgttgaatatggctcataacaccccttgtattactgtttatgtaagcagacagttttattgttcatgatgatatatttttatcttgt gcaatgtaacatcagagattttgagacacaacgtggctttgttgaataaatcgaacttttgctgagttgaaggatcagctctagtaaaataataa aaaagccggattaataatctggctttttatattctctctctagtatataaacgcagaaaggcccacccgaaggtgagccagtgtgacggcacat ttccccgaaaagtgccacctaaattgtaagcgttaatattttgttaaaattcgcgttaaatttttgttaaatcagctcattttttaaccaataggccga aatcggcaaaatcccttataaatcaaaagaatagaccgagatagggttgagtgttgttccagtttggaacaagagtccactattaaagaacgt ggactccaacgtcaaagggcgaaaaaccgtctatcagggcgatggcccactacgtgaaccatcaccctaatcaagttttttggggtcgagg tgccgtaaagcactaaatcggaaccctaaagggagcccccgatttagagcttgacggggaaagccggcgaacgtggcgagaaaggaag ggaagaaagcgaaaggagcgggcgctagggcgctggcaagtgtagcggtcacgctgcgcgtaaccaccacacccgccgcgcttaatg cgccgctacagggcgcgtcccattcgccattcaggctgcgcaactgttgggaagggcgatcggtgcgggcctcttcgctattacgccagct ggcgaaagggggatgtgctgcaaggcgattaagttgggtaacgccagggttttcccagtcacgacgttgtaaaacgacggccagtgagcg cgcggcgaattgggtaccgggccccc iRepCap4/ pKan-Anc80-RepCap-p5i1-p19i2 (10,495 bp)

(SEQ ID NO: 18)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccaAtgggcAtggacCaaCatggaaca gtaCCtCagcgcctgtttgaatctcacggagcgtaaacggttggtggcgcagcatctgacgcacgtgtcgcagacgcaggagcagaac aaagagaatcagaatcccaattctgatgcgccggtgatcagatcaaaaacttcagccaggtacatggagctggtcgggtggctcgtggaca aggggattacctcggagaagcagtggatccaggaggaccaggcctcatacatctccttcaatgcggcctccaactcgcggtcccaaatca aggctgccttggacaatgcgggaaagattatgagcctgactaaaaccgcccccgactacctggtgggccagcagcccgtggaggacattt ccagcaatcggatttataaaattttggaactaaacgggtacgatccccaatatgcggcttccgtctttctgggatgggccacgaaaaagttcg gcaagaggaacaccatctggctgtttgggcctgcaactaccgggaagaccaacatcgcggaggccatagcccacactgtgcccttctacg ggtgcgtaaactggaccaatgagaactttcccttcaacgactgtgtcgacaagatggtgatctggtgggaggaggggaagatgaccgcca aggtcgtggagtcggccaaagccattctcggaggaagcaaggtgcgcgtggaccagaaatgcaagtcctcggcccagatagacccgact cccgtgatcgtcacctccaacaccaacatgtgcgccgtgattgacgggaactcaacgaccttcgaacaccagcagccgttgcaagaccgg atgttcaaatttgaactcacccgccgtctggatcatgactttgggaaggtcaccaagcaggaagtcaaagactttttccggtgggcaaaggat cacgtggttgaggtggagcatgaattctacgtcaaaaagggtggagccaagaaaagacccgcccccagtgacgcagatataagtgagcc caaacgggtgcgcgagtcagttgcgcagccatcgacgtcagacgcggaagcttcgatcaactacgcagacaggtaccaaaacaaatgttc tcgtcacgtgggcatgaatctgatgctgtttccctgcagacaatgcgagagaatgaatcagaattcaaatatctgcttcactcacggacagaa agactgtttagagtgctttcccgtgtcagaatctcaacccgtttctgtcgtcaaaaaggcgtatcagaaactgtgctacattcatcatatcatggg aaaggtgccagacgcttgcactgcctgcgatctggtcaatgtggatttggatgactgcatctttgaacaataaatgatttaaatcaggtatggct -continued gccgatggttatcttccagattggctcgaggacaacctctctgagggcattcgcgagtggtgggacttgaaacctggagccccgaaaccca
aagccaaccagcaaaagcaggacgacggccggggtctggtgcttcctggctacaagtacctcggacccttcaacggactcgacaaggg
ggagcccgtcaacgcggcggacgcagcggccctcgagcacgacaaggcctacgaccagcagctcaaagcgggtgacaatccgtacct
gcggtataaccacgccgacgccgagtttcaggagcgtctgcaagaagatacgtcttttgggggcaacctcgggcgagcagtcttccaggc
caagaagcgggttctcgaacctctcggtctggttgaggaaggcgctaagacggctcctggaaagaagagaccggtagagcaatcacccc
aggaaccagactcctcttcgggcatcggcaagaaaggccagcagcccgcgagaaagagactcaactttgggcagactggcgactcaga
gtcagtgcccgaccctcaaccactcggagaaccccccgcagcccccctctggtgtgggatctaatacaatggctgcaggcggtggcgctcc
aatggcagacaataacgaaggcgccgacggagtgggtaacgcctcaggaaattggcattgcgattccacatggctgggcgacagagtca
tcaccaccagcacccgaacctgggccctccccacctacaacaaccacctctacaagcaaatctccagccaatcgggaggcagcaccaac
gacaacacctacttcggctacagcaccccctgggggtattttgactttaacagattccactgccacttctcaccacgtgactggcagcgactc
atcaacaacaactggggattccggcccaagaagctcaacttcaagctcttcaacatccaggtcaaggaggtcacgacgaatgatggcacc
acgaccatcgccaataaccttaccagcacggttcaggtctttacggactcggaataccagctcccgtacgtcctcggctctgcgcaccagg
gctgcctgcctccgttcccggcggacgtcttcatgattcctcagtacgggtacctgactctgaacaatggcagtcaggccgtgggccgttcct
ccttctactgcctggaatactttccttctcaaatgctgagaacgggcaacaactttcagttcagctacacgtttgaggacgtgccttttcacagca
gctacgcgcacagccaaagcctggaccggctgatgaacccccctcatcgaccagtacctgtactacctgtctcggactcagaccacgagtg
gtaccgcaggaaatcggacgttgcaattttctcaggccgggcctagtagcatggcgaatcaggccaaaaactggctacccgggccctgct
accggcagcaacgcgtctccaagacaaccaatcaaaataacaacagcaactttgcctggaccggtgccaccaagtatcatctgaatggca
gagactctctggtaaatcccggtcccgctatggcaacccacaaggacgacgaagacaaatttttttccgatgagcggagtcttaatatttggga
aacagggagctggaaatagcaacgtggaccttgacaacgttatgataaccaacgaggaagaaattaaaaccaccaacccagtggccaca
gaagagtacggcacggtggccactaacctgcaatcggccaacaccgctcctgctacagggaccgtcaacagtcaaggagccttacctgg
catggtctggcaggaccgggacgtgtacctgcagggtcctatctgggccaagattcctcacacggacggacactttcatccctcgccgctg
atgggaggctttggactgaaacacccgcctcctcagatcctgattaagaatacacctgttcccgcgaatcctccaactaccttcagtccagct
aagtttgcgtcgttcatcacgcagtacagcaccggacaggtcagcgtggaaattgaatgggagctgcagaaagaaaacagcaaacgctgg
aacccagagattcaatacacttccaactacaacaaatctacaaatgtggactttgctgttgacacaaatggcgtttattctgagcctcgccccat
cggcacccgttacctcacccgtaatctgtaaactagtttgcttgttaatcaataaaccgtttaattcgtttcagttgaactttggtctctgcgtatttct
ttcttatctagtttccatgctctagaggtcctgtattagaggtcacgtgagtgttttgcgacattttgcgacaccatgtggtcacgctgggtatttaa
gcccgagtgagcacgcagggtctccattttgaagcgggaggtttgaacgcgcagccgccaagccgaattctgcagatatcggggttgggg
ttgcgccttttccaaggcagccctgggtttgcgcagggacgcggctgctctgggcgtggttccgggaaacgcagcggcgccgaccctgg
gtctcgcacattcttcacgtccgttcgcagcgtcacccggatcttcgccgctacccttgtgggccccccggcgacgcttcctgctccgcccct
aagtcgggaaggttccttgcggttcgcggcgtgccggacgtgacaaacggaagccgcacgtctcactagtaccctcgcagacggacagc
gccagggagcaatggcagcgcgccgaccgcgatgggctgtggccaatagcggctgctcagcagggcgcgccgagagcagcggccg
ggaaggggcggtgcgggaggcggggtgtggggcggtagtgtgggccctgttcctgcccgcgcggtgttccgcattctgcaagcctccg
gagcgcacgtcggcagtcggctccctcgttgaccgaatcaccgacctctctccccagAAGCTCCCGGGAGCTTGTATA
TCCATTTTCGGATCTGATCAGCACGTGTTGACAATTAATCATCGGCATAGTATATCG
GCATAGTATAATACGACAAGGTGAGGAACgccaccATGGCCAAGCCTTTGTCTCAAGA
AGAATCCACCCTCATTGAAAGAGCAACGGCTACAATCAACAGCATCCCCATCTCTG
AAGACTACAGCGTCGCCAGCGCAGCTCTCTCTAGCGACGGCCGCATCTTCACTGGTG
TCAATGTATATCATTTTACTGGGGGACCTTGTGCAGAACTCGTGGTGCTGGGCACTG
CTGCTGCTGCGGCAGCTGGCAACCTGACTTGTATCGTCGCGATCGGAAATGAGAACA
GGGGCATCTTGAGCCCCTGCGGACGGTGCCGACAGGTGCTTCTCGATCTGCATCCTG -continued

GGATCAAAGCCATAGTGAAGGACAGTGATGGACAGCCGACGGCAGTTGGGATTCGT

GAATTGCTGCCCTCTGGTTATGTGTGGGAGGGCTAAGCACTTCGTGGCCGAGGAGCA

GGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCAT

GCTGGAGTTCTTCGCCCACCCCAACTTGTTTATTGCAGCTTATAATGGTTACAAATAA

AGCAATAGCATCACAAATTTCACAAATAAAGCATTTTTTTCACTGCATTCTAGTTGT

GGTTTGTCCAAACTCATCAATGTATCTTAGCGCTCACTGCCCGCTTTCCAGTCGGGA

AACCTGTCGTGCCAGCTGCATTAATGAATCGGCCAACGCGCGGGGAGAGGCGGTTT

GCGTATTGGGCGCTCTCCTAGGccagaaatggcgccggaggcgggaacaaggtggtggatgagtgctacatcccca attacttgctccccaaaacccagcctgagTCCCTATCAGTGATAGAGActccagtgggcgtggactaatatggaacagtat ttaagcgcctgTCCCTATCAGTGATAGAGAtttgaatctcacggagcgtaaacggttggtggcgcagcatctGTTTA AACgcagacgcaggagcagaacaaagagaatcagaatcccaattctgatgcgccggtgatcagatcaaaaacttcagccaggtacatg gagctggtcgggtggctcgtggacaaggggattacctcggagaagcagtggattcaggaggaccaggcctcatacatctccttcaatgcg gcctccaactcgcggtcccaaatcaaggctgccttggacaatgcgggaaagattatgagcctgactaaaaccgcccccgactacctggtg ggccagcagcccgtggaggacatttccagcaatcggatttataaaattttggaactaaacgggtacgatccccaatatgcggcttccgtctttc tgggatgggccacgaaaaagttcggcaagaggaacaccatctggctgtttgggcctgcaactaccgggaagaccaacatcgcggaggcc atagcccacactgtgcccttctacgggtgcgtaaactggaccaatgagaactttcccttcaacgactgtgtcgacaagatggtgatctggtgg gaggaggggaagatgaccgccaaggtcgtggagtcggccaaagccattctcggaggaagcaaggtgcgcgtggaccagaaatgcaag tcctcggcccagatagacccgactcccgtgatcgtcacctccaacaccaacatgtgcgccgtgattgacgggaactcaacgaccttcgaac accagcagccgttgcaagaccggatgttcaaatttgaactcacccgccgtctggatcatgactttgggaaggtcaccaagcaggaagtcaa agactttttccggtgggcaaaggatcacgtggttgaggtggagcatgaattctacgtcaaaaagggtggagccaagaaaagacccgcccc cagtgacgcagatataagtgagcccaaacgggtgcgcgagtcagttgcgcagccatcgacgtcagacgcggaagcttcgatcaactacg cagacaggtaccaaaacaaatgttctcgtcacgtgggcatgaatctgatgctgtttccctgcagacaatgcgagagaatgaatcagaattcaa atatctgcttcactcacggacagaaagactgtttagagtgctttcccgtgtcagaatctcaacccgtttctgtcgtcaaaaaggcgtatcagaaa ctgtgctacattcatcatatcatgggaaaggtgccagacgcttgcactgcctgcgatctggtcaatgtggatttggatgactgcatctttgaaca ataaACTAGTTTGCTTGTTAATCAATAAACCGTTTAATTCGTTTCAGTTGAACTTTGGTC TCTGCGTATTTCTTTCTTATCTAGTTTCCATGCTCTAGAGTATACgatatccatcacactggcggcc gctcgactagagcggccgccaccgcggtggagctccagcttttgttcgcgcgcttggcgtaatcatggtcatagctgtttcctgtgtgaaattc cacagcctggggtgcctaattgcgttgcgctcactgcccgctttccagtcgggaaacctgtcgtgccagctgcattaatgaatcggccaacg cgcggggagaggcggtttgcgtattgggcgctcttccgcttcctcgctcactgactcgctgcgctcggtcgttcggctgcggcgagcggtat cagctcactcaaaggcggtaatacggttatccacagaatcaggggataacgcaggaaagaacatgtgagcaaaaggccagcaaaaggc caggaaccgtaaaaaggccgcgttgctggcgtttttccataggctccgcccccctgacgagcatcacaaaaatcgacgctcaagtcagag gtggcgaaacccgacaggactataaagataccaggcgtttccccctggaagctccctcgtgcgctctcctgttccgaccctgccgcttaccg gatacctgtccgcctttctcccttcgggaagcgtggcgctttctcatagctcacgctgtaggtatctcagttcggtgtaggtcgttcgctccaag ctgggctgtgtgcacgaaccccccgttcagcccgaccgctgcgccttatccggtaactatcgtcttgagtccaacccggtaagacacgactt atcgccactggcagcagccactggtaacaggattagcagagcgaggtatgtaggcggtgctacagagttcttgaagtggtggcctaactac ggctacactagaagaacagtatttggtatctgcgctctgctgaagccagttaccttcggaaaaagagttggtagctcttgatccggcaaacaa accaccgctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaattaaaaa tgaagttttaaatcaatctaaagtatatatgagtaaacttggtctgacagaaataataaaaaagccggattaataatctggctttttatattctctctc tagtatataaacgcagaaaggcccacccgaaggtgagccagtgtgactctagtattattagaaaaactcatcgagcatcaaatgaaactgca -continued atttattcatatcaggattatcaataccatatttttgaaaaagccgtttctgtaatgaaggagaaaactcaccgaggcagttccaaagaatggca aggtcctggtaacggtctgcgattccgacccgtccaacatcaatacaacctattaatttcccctcgtcaaaaataaggttatcaagtgagaaat caccatgagtgacgactgaatccggtgagaatggcaagagcttgtgcatttctttccagacttgttcaacaggccagccattacgctcgtcatc aaaatcactcgcatcaaccaaaccgttattcatgcgtgattgcgcctgagcaagacgaaatacacgatcgctgttaaaaggacaattacaaa caggaatcgaatgtaaccggcgcaggaacacggccagcgcatcaacaatattttcacctgaatcaggatattcttctaatacctggaaggct gttttcccaggaatcgcggtggtgagtaaccacgcatcatcaggagtacggataaaatgcttgatggtcgggagaggcataaactccgtca gccagttgagacggaccatctcatctgtaacatcattggcaacgctacctttgccatgtttcagaaacaactctggcgcatcgggcttcccata caagcgatagattgtcgcacctgattgcccgacattatcgcgagcccatttatacccatataaatcagcgtccatgttggagtttaagcgcgga cgggagcaagacgtttcccgttgaatatggctcataacaccccttgtattactgtttatgtaagcagacagttttattgttcatgatgatatattttta tcttgtgcaatgtaacatcagagattttgagacacaacgtggctttgttgaataaatcgaacttttgctgagttgaaggatcagctctagtaaaat aataaaaaagccggattaataatctggctttttatattctctctctagtatataaacgcagaaaggcccacccgaaggtgagccagtgtgacgg cacatttccccgaaaagtgccacctaaattgtaagcgttaatattttgttaaaattcgcgttaaatttttgttaaatcagctcattttttaaccaatagg ccgaaatcggcaaaatcccttataaatcaaaagaatagaccgagatagggttgagtgttgttccagtttggaacaagagtccactattaaaga acgtggactccaacgtcaaagggcgaaaaaccgtctatcagggcgatggcccactacgtgaaccatcaccctaatcaagttttttggggtcg aggtgccgtaaagcactaaatcggaaccctaaagggagcccccgatttagagcttgacggggaaagccggcgaacgtggcgagaaagg aagggaagaaagcgaaaggagcgggcgctagggcgctggcaagtgtagcggtcacgctgcgcgtaaccaccacacccgccgcgctta atgcgccgctacagggcgcgtcccattcgccattcaggctgcgcaactgttgggaagggcgatcggtgcgggcctcttcgctattacgcca gctggcgaaagggggatgtgctgcaaggcgattaagttgggtaacgccagggttttcccagtcacgacgttgtaaaacgacggccagtga gcgcgcggcgaattgggtaccgggccccc iRepCap5/ pKan-Anc80-RepCap-p5i2-p19i2 (10,493 bp)

(SEQ ID NO: 19)

cctcgaggGCTAGCcattcTATTTAAtcTCCCTATCAGTGATAGAGAtcGCCCGAGT

GAGCACGCAGGGTCTCCATTTTGATCCCTATCAGTGATAGAGAAGCGGGAGGTTTGA

ACGCGCAGCCGCCatgccggggttttacgagattgtgattaaggtccccagcgaccttgacgagcatctgcccggcatttctgac agctttgtgaactgggtggccgagaaggaatgggagttgccgccagattctgacatggatctgaatctgattgagcaggcacccctgaccg tggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgcccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg -continued tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaacccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttcccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgatgttaatcaataaaccgtttaattcgtttcagttgaactttggtctctgcgtatttctttcttatct agtttccatgctctagaggtcctgtattagaggtcacgtgagtgttttgcgacattttgcgacaccatgtggtcacgctgggtatttaagcccga gtgagcacgcagggtctccatttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

-continued

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagTCCCTATCAGTGATAGAGActccagtgggcgtggactaatatggaacagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagactttttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag gtaccaaaacaaatgttctcgtcacgtgggcatgaatctgatgctgtttccctgcagacaatgcgagagaatgaatcagaattcaaatatctgc ttcactcacggacagaaagactgtttagagtgctttcccgtgtcagaatctcaacccgtttctgtcgtcaaaaaggcgtatcagaaactgtgcta cattcatcatatcatgggaaaggtgccagacgcttgcactgcctgcgatctggtcaatgtggatttggatgactgcatctttgaacaataaAC

TAGTTTGCTTGTTAATCAATAAACCGTTTAATTCGTTTCAGTTGAACTTTGGTCTCTG

CGTATTTCTTTCTTATCTAGTTTCCATGCTCTAGAGTATACgatatccatcacactggcggccgctcga ctagagcggccgccaccgcggtggagctccagcttttgttcgcgcgcttggcgtaatcatggtcatagctgtttcctgtgtgaaattccacag cctggggtgcctaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggtatcagct cactcaaaggcggtaatacggttatccacagaatcaggggataacgcaggaaagaacatgtgagcaaaaggccagcaaaaggccagga accgtaaaaaggccgcgttgctggcgtttttccataggctccgcccccctgacgagcatcacaaaaatcgacgctcaagtcagaggtggcg aaacccgacaggactataaagataccaggcgtttccccctggaagctccctcgtgcgctctcctgttccgaccctgccgcttaccggatacc tgtccgcctttctcccttcgggaagcgtggcgctttctcatagctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcctaactacggctac actagaagaacagtatttggtatctgcgctctgctgaagccagttaccttcggaaaaagagttggtagctcttgatccggcaaacaaaccacc gctggtagcggtggtttttttgtttgcaagcagcagattacgcgcagaaaaaaaggatctcaagaagatcctttgatcttttctacggggtctga -continued cgctcagtggaacgaaaactcacgttaagggattttggtcatgagattatcaaaaaggatcttcacctagatccttttaaattaaaaatgaagttt taaatcaatctaaagtatatatgagtaaacttggtctgacagaaataataaaaaagccggattaataatctggctttttatattctctctctagtatat aaacgcagaaaggcccacccgaaggtgagccagtgtgactctagtattattagaaaaactcatcgagcatcaaatgaaactgcaatttattca tatcaggattatcaataccatatttttgaaaaagccgtttctgtaatgaaggagaaaactcaccgaggcagttccaaagaatggcaaggtcctg gtaacggtctgcgattccgacccgtccaacatcaatacaacctattaatttcccctcgtcaaaaataaggttatcaagtgagaaatcaccatga gtgacgactgaatccggtgagaatggcaagagcttgtgcatttctttccagacttgttcaacaggccagccattacgctcgtcatcaaaatcac tcgcatcaaccaaaccgttattcatgcgtgattgcgcctgagcaagacgaaatacacgatcgctgttaaaaggacaattacaaacaggaatc gaatgtaaccggcgcaggaacacggccagcgcatcaacaatattttcacctgaatcaggatattcttctaatacctggaaggctgttttccca ggaatcgcggtggtgagtaaccacgcatcatcaggagtacggataaaatgcttgatggtcgggagaggcataaactccgtcagccagttg agacggaccatctcatctgtaacatcattggcaacgctacctttgccatgtttcagaaacaactctggcgcatcgggcttcccatacaagcgat agattgtcgcacctgattgcccgacattatcgcgagcccatttatacccatataaatcagcgtccatgttggagtttaagcgcggacgggagc aagacgtttcccgttgaatatggctcataacaccccttgtattactgtttatgtaagcagacagttttattgttcatgatgatatatttttatcttgtgca atgtaacatcagagattttgagacacaacgtggctttgttgaataaatcgaacttttgctgagttgaaggatcagctctagtaaaataataaaaa agccggattaataatctggattttatattctctctctagtatataaacgcagaaaggcccacccgaaggtgagccagtgtgacggcacatttcc ccgaaaagtgccacctaaattgtaagcgttaatattttgttaaaattcgcgttaaatttttgttaaatcagctcattttttaaccaataggccgaaatc ggcaaaatcccttataaatcaaaagaatagaccgagatagggttgagtgttgttccagtttggaacaagagtccactattaaagaacgtggac tccaacgtcaaagggcgaaaaaccgtctatcagggcgatggcccactacgtgaaccatcaccctaatcaagttttttggggtcgaggtgcc gtaaagcactaaatcggaaccctaaagggagcccccgatttagagcttgacggggaaagccggcgaacgtggcgagaaaggaaggga agaaagcgaaaggagcgggcgctagggcgctggcaagtgtagcggtcacgctgcgcgtaaccaccacacccgccgcgcttaatgcgc cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap6/ pKan-Anc80-RepCap-p5i3-p19i2 (10,491 bp)

(SEQ ID NO: 20)

cctcgaggGCTAGCcattcTCCCTATCAGTGATAGAGAtcTATTTAAGCCCGAGTG

AGCACGCAGTCCCTATCAGTGATAGAGAGGTCTCCATTTTGAAGCGGGAGGTTTGAA

CGCGCAGCCGCCatgccggggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac -continued gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaacccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttcttat ctagtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

-continued

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagTCCCTATCAGTGATAGAGActccagtgggcgtggactaatatggaacagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagacttttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag gtaccaaaacaaatgttctcgtcacgtgggcatgaatctgatgctgtttccctgcagacaatgcgagagaatgaatcagaattcaaatatctgc ttcactcacggacagaaagactgtttagagtgctttcccgtgtcagaatctcaacccgtttctgtcgtcaaaaaggcgtatcagaaactgtgcta cattcatcatatcatgggaaaggtgccagacgcttgcactgcctgcgatctggtcaatgtggatttggatgactgcatctttgaacaataaAC

TAGTTTGCTTGTTAATCAATAAACCGTTTAATTCGTTTCAGTTGAACTTTGGTCTCTG

CGTATTTCTTTCTTATCTAGTTTCCATGCTCTAGAGTATACgatatccatcacactggcggccgctcga ctagagcggccgccaccgcggtggagctccagcttttgttcgcgcgcttggcgtaatcatggtcatagctgtttcctgtgtgaaattccacag cctggggtgcctaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggtatcagct cactcaaaggcggtaatacggttatccacagaatcaggggataacgcaggaaagaacatgtgagcaaaaggccagcaaaaggccagga accgtaaaaaggccgcgttgctggcgtttttccataggctccgcccccctgacgagcatcacaaaaatcgacgctcaagtcagaggtggcg aaacccgacaggactataaagataccaggcgtttccccctggaagctccctcgtgcgctctcctgttccgaccctgccgcttaccggatacc tgtccgcctttctcccttcgggaagcgtggcgctttctcatagctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcctaactacggctac -continued actagaagaacagtatttggtatctgcgctctgctgaagccagttaccttcggaaaaagagttggtagctcttgatccggcaaacaaaccacc gctggtagcggtggtttttttgtttgcaagcagcagattacgcgcagaaaaaaaggatctcaagaagatcctttgatcttttctacggggtctga cgctcagtggaacgaaaactcacgttaagggattttggtcatgagattatcaaaaaggatcttcacctagatccttttaaattaaaaatgaagttt taaatcaatctaaagtatatatgagtaaacttggtctgacagaaataataaaaaagccggattaataatctggcttttttatattctctctctagtatat aaacgcagaaaggcccacccgaaggtgagccagtgtgactctagtattattagaaaaactcatcgagcatcaaatgaaactgcaatttattca tatcaggattatcaataccatatttttgaaaaagccgtttctgtaatgaaggagaaaactcaccgaggcagttccaaagaatggcaaggtcctg gtaacggtctgcgattccgacccgtccaacatcaatacaacctattaatttcccctcgtcaaaaataaggttatcaagtgagaaatcaccatga gtgacgactgaatccggtgagaatggcaagagcttgtgcatttattccagacttgttcaacaggccagccattacgctcgtcatcaaaatcac tcgcatcaaccaaaccgttattcatgcgtgattgcgcctgagcaagacgaaatacacgatcgctgttaaaaggacaattacaaacaggaatc gaatgtaaccggcgcaggaacacggccagcgcatcaacaatattttcacctgaatcaggatattcttctaatacctggaaggctgttttccca ggaatcgcggtggtgagtaaccacgcatcatcaggagtacggataaaatgcttgatggtcgggagaggcataaactccgtcagccagttg agacggaccatctcatctgtaacatcattggcaacgctacctttgccatgtttcagaaacaactctggcgcatcgggcttcccatacaagcgat agattgtcgcacctgattgcccgacattatcgcgagcccatttatacccatataaatcagcgtccatgttggagtttaagcgcggacgggagc aagacgtttcccgttgaatatggctcataacacccactgtattactgtttatgtaagcagacagttttattgttcatgatgatatatttttatcttgtgca atgtaacatcagagattttgagacacaacgtggctttgttgaataaatcgaacttttgctgagttgaaggatcagctctagtaaaataataaaaa agccggattaataatctggcttttttatattctctctctagtatataaacgcagaaaggcccacccgaaggtgagccagtgtgacggcacatttcc ccgaaaagtgccacctaaattgtaagcgttaatattttgttaaaattcgcgttaaatttttgttaaatcagctcattttttaaccaataggccgaaatc ggcaaaatcccttataaatcaaaagaatagaccgagatagggttgagtgttgttccagtttggaacaagagtccactattaaagaacgtggac tccaacgtcaaagggcgaaaaaccgtctatcagggcgatggcccactacgtgaaccatcaccctaatcaagttttttggggtcgaggtgcc gtaaagcactaaatcggaaccctaaagggagcccccgatttagagcttgacggggaaagccggcgaacgtggcgagaaaggaaggga agaaagcgaaaggagcgggcgctagggcgctggcaagtgtagcggtcacgctgcgcgtaaccaccacacccgccgcgcttaatgcgc cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap7/ pKan-Anc80-RepCap-p5i1-p19i3 (10,495 bp)

(SEQ ID NO: 21)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccaAtgggcAtggacCaaCatggaaca gtaCCtCagcgcctgtttgaatctcacggagcgtaaacggttggtggcgcagcatctgacgcacgtgtcgcagacgcaggagcagaac aaagagaatcagaatcccaattctgatgcgccggtgatcagatcaaaaacttcagccaggtacatggagctggtcgggtggctcgtggaca aggggattacctcggagaagcagtggatccaggaggaccaggcctcatacatctccttcaatgcggcctccaactcgcggtcccaaatca aggctgccttggacaatgcgggaaagattatgagcctgactaaaaccgcccccgactacctggtgggccagcagcccgtggaggacattt ccagcaatcggatttataaaattttggaactaaacgggtacgatccccaatatgcggcttccgtctttctgggatgggccacgaaaaagttcg gcaagaggaacaccatctggctgtttgggcctgcaactaccgggaagaccaacatcgcggaggccatagcccacactgtgcccttctacg ggtgcgtaaactggaccaatgagaactttcccttcaacgactgtgtcgacaagatggtgatctggtgggaggaggggaagatgaccgcca -continued aggtcgtggagtcggccaaagccattctcggaggaagcaaggtgcgcgtggaccagaaatgcaagtcctcggcccagatagacccgact cccgtgatcgtcacctccaacaccaacatgtgcgccgtgattgacgggaactcaacgaccttcgaacaccagcagccgttgcaagaccgg atgttcaaatttgaactcacccgccgtctggatcatgactttgggaaggtcaccaagcaggaagtcaaagactttttccggtgggcaaaggat cacgtggttgaggtggagcatgaattctacgtcaaaaagggtggagccaagaaaagacccgcccccagtgacgcagatataagtgagcc caaacgggtgcgcgagtcagttgcgcagccatcgacgtcagacgcggaagcttcgatcaactacgcagacaggtaccaaaacaaatgttc tcgtcacgtgggcatgaatctgatgctgtttccctgcagacaatgcgagagaatgaatcagaattcaaatatctgcttcactcacggacagaa agactgtttagagtgctttcccgtgtcagaatctcaacccgtttctgtcgtcaaaaaggcgtatcagaaactgtgctacattcatcatatcatggg aaaggtgccagacgcttgcactgcctgcgatctggtcaatgtggatttggatgactgcatctttgaacaataaatgatttaaatcaggtatggct gccgatggttatcttccagattggctcgaggacaacctctctgagggcattcgcgagtggtgggacttgaaacctggagccccgaaaccca aagccaaccagcaaaagcaggacgacggccggggtctggtgcttcctggctacaagtacctcggacccttcaacggactcgacaaggg ggagcccgtcaacgcggcggacgcagcggccctcgagcacgacaaggcctacgaccagcagctcaaagcgggtgacaatccgtacct gcggtataaccacgccgacgccgagtttcaggagcgtctgcaagaagatacgtcttttgggggcaacctcgggcgagcagtcttccaggc caagaagcgggttctcgaacctctcggtctggttgaggaaggcgctaagacggctcctggaaagaagagaccggtagagcaatcacccc aggaaccagactcctcttcgggcatcggcaagaaaggccagcagcccgcgagaaagagactcaactttgggcagactggcgactcaga gtcagtgcccgaccctcaaccactcggagaacccccgcagcccccctctggtgtgggatctaatacaatggctgcaggcggtggcgctcc aatggcagacaataacgaaggcgccgacggagtgggtaacgcctcaggaaattggcattgcgattccacatggctgggcgacagagtca tcaccaccagcacccgaacctgggccctccccacctacaacaaccacctctacaagcaaatctccagccaatcgggaggcagcaccaac gacaacacctacttcggctacagcaccccctgggggtattttgactttaacagattccactgccacttctcaccacgtgactggcagcgactc atcaacaacaactggggattccggcccaagaagctcaacttcaagctcttcaacatccaggtcaaggaggtcacgacgaatgatggcacc acgaccatcgccaataaccttaccagcacggttcaggtctttacggactcggaataccagctcccgtacgtcctcggctctgcgcaccagg gctgcctgcctccgttcccggcggacgtcttcatgattcctcagtacgggtacctgactctgaacaatggcagtcaggccgtgggccgttcct ccttctactgcctggaatactttccttctcaaatgctgagaacgggcaacaactttcagttcagctacacgtttgaggacgtgccttttcacagca gctacgcgcacagccaaagcctggaccggctgatgaacccccctcatcgaccagtacctgtactacctgtctcggactcagaccacgagtg gtaccgcaggaaatcggacgttgcaattttctcaggccgggcctagtagcatggcgaatcaggccaaaaactggctacccgggccctgct accggcagcaacgcgtctccaagacaaccaatcaaaataacaacagcaactttgcctggaccggtgccaccaagtatcatctgaatggca gagactctctggtaaatcccggtcccgctatggcaacccacaaggacgacgaagacaaatttttttccgatgagcggagtcttaatatttggga aacagggagctggaaatagcaacgtggaccttgacaacgttatgataaccaacgaggaagaaattaaaaccaccaacccagtggccaca gaagagtacggcacggtggccactaacctgcaatcggccaacaccgctcctgctacagggaccgtcaacagtcaaggagccttacctgg catggtctggcaggaccgggacgtgtacctgcagggtcctatctgggccaagattcctcacacggacggacacttttcatccctcgccgctg atgggaggctttggactgaaacacccgcctcctcagatcctgattaagaatacacctgttcccgcgaatcctccaactaccttcagtccagct aagtttgcgtcgttcatcacgcagtacagcaccggacaggtcagcgtggaaattgaatgggagctgcagaaagaaaacagcaaacgctgg aacccagagattcaatacacttccaactacaacaaatctacaaatgtggactttgctgttgacacaaatggcgtttattctgagcctcgccccat cggcacccgttacctcacccgtaatctgtaaactagtttgcttgttaatcaataaaccgtttaattcgtttcagttgaactttggtctctgcgtatttct ttcttatctagtttccatgctctagaggtcctgtattagaggtcacgtgagtgttttgcgacattttgcgacaccatgtggtcacgctgggtatttaa gcccgagtgagcacgcagggtctccattttgaagcgggaggtttgaacgcgcagccgccaagccgaattctgcagatatcggggttgggg ttgcgccttttccaaggcagccctgggtttgcgcagggacgcggctgctctgggcgtggttccgggaaacgcagcggcgccgaccctgg gtctcgcacattcttcacgtccgttcgcagcgtcacccggatcttcgccgctacccttgtgggccccccggcgacgcttcctgctccgcccct aagtcgggaaggttccttgcggttcgcggcgtgccggacgtgacaaacggaagccgcacgtctcactagtaccctcgcagacggacagc gccagggagcaatggcagcgcgccgaccgcgatgggctgtggccaatagcggctgctcagcagggcgcgcccgagagcagcggccg ggaaggggcggtgcgggaggcggggtgtggggcggtagtgtgggccctgttcctgcccgcgcggtgttccgcattctgcaagcctccg gagcgcacgtcggcagtcggctccctcgttgaccgaatcaccgacctctctccccagAAGCTCCCGGGAGCTTGTATA -continued

TCCATTTTCGGATCTGATCAGCACGTGTTGACAATTAATCATCGGCATAGTATATCG

GCATAGTATAATACGACAAGGTGAGGAACgccaccATGGCCAAGCCTTTGTCTCAAGA

AGAATCCACCCTCATTGAAAGAGCAACGGCTACAATCAACAGCATCCCCATCTCTG

AAGACTACAGCGTCGCCAGCGCAGCTCTCTCTAGCGACGGCCGCATCTTCACTGGTG

TCAATGTATATCATTTTACTGGGGGACCTTGTGCAGAACTCGTGGTGCTGGGCACTG

CTGCTGCTGCGGCAGCTGGCAACCTGACTTGTATCGTCGCGATCGGAAATGAGAACA

GGGGCATCTTGAGCCCCTGCGGACGGTGCCGACAGGTGCTTCTCGATCTGCATCCTG

GGATCAAAGCCATAGTGAAGGACAGTGATGGACAGCCGACGGCAGTTGGGATTCGT

GAATTGCTGCCCTCTGGTTATGTGTGGGAGGGCTAAGCACTTCGTGGCCGAGGAGCA

GGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCAT

GCTGGAGTTCTTCGCCCACCCCAACTTGTTTATTGCAGCTTATAATGGTTACAAATAA

AGCAATAGCATCACAAATTTCACAAATAAAGCATTTTTTTCACTGCATTCTAGTTGT

GGTTTGTCCAAACTCATCAATGTATCTTAGCGCTCACTGCCCGCTTTCCAGTCGGGA

AACCTGTCGTGCCAGCTGCATTAATGAATCGGCCAACGCGCGGGGAGAGGCGGTTT

GCGTATTGGGCGCTCTCCTAGGccagaaatggcgccggaggcgggaacaaggtggtggatgagtgctacatcccca attacttgctccccaaaacccagcctgagctccagtgggcgtggactaatatggaaTCCCTATCAGTGATAGAGAcagtat ttaagcgcctgTCCCTATCAGTGATAGAGAtttgaatctcacggagcgtaaacggttggtggcgcagcatctGTTTA AACgcagacgcaggagcagaacaaagagaatcagaatcccaattctgatgcgccggtgatcagatcaaaaacttcagccaggtacatg gagctggtcgggtggctcgtggacaaggggattacctcggagaagcagtggattcaggaggaccaggcctcatacatctccttcaatgcg gcctccaactcgcggtcccaaatcaaggctgccttggacaatgcgggaaagattatgagcctgactaaaaccgcccccgactacctggtg ggccagcagcccgtggaggacatttccagcaatcggatttataaaattttggaactaaacgggtacgatccccaatatgcggcttccgtctttc tgggatgggccacgaaaaagttcggcaagaggaacaccatctggctgtttggcctgcaactaccgggaagaccaacatcgcggaggcc atagcccacactgtgcccttctacgggtgcgtaaactggaccaatgagaactttcccttcaacgactgtgtcgacaagatggtgatctggtgg gaggaggggaagatgaccgccaaggtcgtggagtcggccaaagccattctcggaggaagcaaggtgcgcgtggaccagaaatgcaag tcctcggcccagatagacccgactcccgtgatcgtcacctccaacaccaacatgtgcgccgtgattgacgggaactcaacgaccttcgaac accagcagccgttgcaagaccggatgttcaaatttgaactcacccgccgtctggatcatgactttgggaaggtcaccaagcaggaagtcaa agactttttccggtgggcaaaggatcacgtggttgaggtggagcatgaattctacgtcaaaaagggtggagccaagaaaagacccgcccc cagtgacgcagatataagtgagcccaaacgggtgcgcgagtcagttgcgcagccatcgacgtcagacgcggaagcttcgatcaactacg cagacaggtaccaaaacaaatgttctcgtcacgtgggcatgaatctgatgctgtttccctgcagacaatgcgagagaatgaatcagaattcaa atatctgcttcactcacggacagaaagactgtttagagtgctttcccgtgtcagaatctcaacccgtttctgtcgtcaaaaaggcgtatcagaaa ctgtgctacattcatcatatcatgggaaaggtgccagacgcttgcactgcctgcgatctggtcaatgtggatttggatgactgcatctttgaaca ataaACTAGTTTGCTTGTTAATCAATAAACCGTTTAATTCGTTTCAGTTGAACTTTGGTC TCTGCGTATTTCTTTCTTATCTAGTTTCCATGCTCTAGAGTATACgatatccatcacactggcggcc gctcgactagagcggccgccaccgcggtggagctccagcttttgttcgcgcgcttggcgtaatcatggtcatagctgtttcctgtgtgaaattc cacagcctggggtgcctaattgcgttgcgctcactgcccgctttccagtcgggaaacctgtcgtgccagctgcattaatgaatcggccaacg cgcggggagaggcggtttgcgtattgggcgctcttccgcttcctcgctcactgactcgctgcgctcggtcgttcggctgcggcgagcggtat cagctcactcaaaggcggtaatacggttatccacagaatcaggggataacgcaggaaagaacatgtgagcaaaaggccagcaaaaggc caggaaccgtaaaaaggccgcgttgctggcgtttttccataggctccgcccccctgacgagcatcacaaaaatcgacgctcaagtcagag gtggcgaaacccgacaggactataaagataccaggcgtttccccctggaagctccctcgtgcgctctcctgttccgaccctgccgcttaccg -continued gatacctgtccgcctttctcccttcgggaagcgtggcgctttctcatagctcacgctgtaggtatctcagttcggtgtaggtcgttcgctccaag ctgggctgtgtgcacgaaccccccgttcagcccgaccgctgcgccttatccggtaactatcgtcttgagtccaacccggtaagacacgactt atcgccactggcagcagccactggtaacaggattagcagagcgaggtatgtaggcggtgctacagagttcttgaagtggtggcctaactac ggctacactagaagaacagtatttggtatctgcgctctgctgaagccagttaccttcggaaaaagagttggtagctcttgatccggcaaacaa accaccgctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaattaaaaa tgaagttttaaatcaatctaaagtatatatgagtaaacttggtctgacagaaataataaaaaagccggattaataatctggcttttatattctctctc tagtatataaacgcagaaaggcccacccgaaggtgagccagtgtgactctagtattattagaaaaactcatcgagcatcaaatgaaactgca atttattcatatcaggattatcaataccatatttttgaaaaagccgtttctgtaatgaaggagaaaactcaccgaggcagttccaaagaatggca aggtcctggtaacggtctgcgattccgacccgtccaacatcaatacaacctattaatttcccctcgtcaaaaataaggttatcaagtgagaaat caccatgagtgacgactgaatccggtgagaatggcaagagcttgtgcatttctttccagacttgttcaacaggccagccattacgctcgtcatc aaaatcactcgcatcaaccaaaccgttattcatgcgtgattgcgcctgagcaagacgaaatacacgatcgctgttaaaaggacaattacaaa caggaatcgaatgtaaccggcgcaggaacacggccagcgcatcaacaatattttcacctgaatcaggatattcttctaatacctggaaggct gttttcccaggaatcgcggtggtgagtaaccacgcatcatcaggagtacggataaaatgcttgatggtcgggagaggcataaactccgtca gccagttgagacggaccatctcatctgtaacatcattggcaacgctacctttgccatgtttcagaaacaactctggcgcatcgggcttcccata caagcgatagattgtcgcacctgattgcccgacattatcgcgagcccatttatacccatataaatcagcgtccatgttggagtttaagcgcgga cgggagcaagacgtttcccgttgaatatggctcataacaccccttgtattactgtttatgtaagcagacagttttattgttcatgatgatatattttta tcttgtgcaatgtaacatcagagattttgagacacaacgtggctttgttgaataaatcgaacttttgctgagttgaaggatcagctctagtaaaat aataaaaaagccggattaataatctggcttttatattctctctctagtatataaacgcagaaaggcccacccgaaggtgagccagtgtgacgg cacatttccccgaaaagtgccacctaaattgtaagcgttaatattttgttaaaattcgcgttaaatttttgttaaatcagctcattttttaaccaatagg ccgaaatcggcaaaatcccttataaatcaaaagaatagaccgagatagggttgagtgttgttccagtttggaacaagagtccactattaaaga acgtggactccaacgtcaaagggcgaaaaaccgtctatcagggcgatggcccactacgtgaaccatcaccctaatcaagttttttggggtcg aggtgccgtaaagcactaaatcggaaccctaaagggagcccccgatttagagcttgacggggaaagccggcgaacgtggcgagaaagg aagggaagaaagcgaaaggagcgggcgctagggcgctggcaagtgtagcggtcacgctgcgcgtaaccaccacacccgccgcgctta atgcgccgctacagggcgcgtcccattcgccattcaggctgcgcaactgttgggaagggcgatcggtgcgggcctcttcgctattacgcca gctggcgaaagggggatgtgctgcaaggcgattaagttgggtaacgccagggttttcccagtcacgacgttgtaaaacgacggccagtga gcgcgcggcgaattgggtaccgggccccc iRepCap8/ pKan-Anc80-RepCap-p5i2-p19i3 (10,493 bp)

(SEQ ID NO: 22)

cctcgaggGCTAGCcattcTATTTAAtcTCCCTATCAGTGATAGAGAtcGCCCGAGT

GAGCACGCAGGGTCTCCATTTTGATCCCTATCAGTGATAGAGAAGCGGGAGGTTTGA

ACGCGCAGCCGCCatgccggggttttacgagattgtgattaaggtccccagcgaccttgacgagcatctgcccggcatttctgac agctttgtgaactgggtggccgagaaggaatgggagttgccgccagattctgacatggatctgaatctgattgagcaggcacccctgaccg tggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca -continued agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaacccccgcagcccccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgatgttaatcaataaaccgtttaattcgtttcagttgaactttggtctctgcgtatttctttcttatct agtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag -continued ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaaTCCCTATCAGTGATAGAGAcagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagactttttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag gtaccaaaacaaatgttctcgtcacgtgggcatgaatctgatgctgtttccctgcagacaatgcgagagaatgaatcagaattcaaatatctgc ttcactcacggacagaaagactgtttagagtgctttcccgtgtcagaatctcaacccgtttctgtcgtcaaaaaggcgtatcagaaactgtgcta cattcatcatatcatgggaaaggtgccagacgcttgcactgcctgcgatctggtcaatgtggatttggatgactgcatctttgaacaataaAC

TAGTTTGCTTGTTAATCAATAAACCGTTTAATTCGTTTCAGTTGAACTTTGGTCTCTG

CGTATTTCTTTCTTATCTAGTTTCCATGCTCTAGAGTATACgatatccatcacactggcggccgctcga ctagagcggccgccaccgcggtggagctccagcttttgttcgcgcgcttggcgtaatcatggtcatagctgtttcctgtgtgaaattccacag cctggggtgcctaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggtatcagct cactcaaaggcggtaatacggttatccacagaatcaggggataacgcaggaaagaacatgtgagcaaaaggccagcaaaaggccagga -continued accgtaaaaaggccgcgttgctggcgtttttccataggctccgcccccctgacgagcatcacaaaaatcgacgctcaagtcagaggtggcg aaacccgacaggactataaagataccaggcgtttccccctggaagctccctcgtgcgctctcctgttccgaccctgccgcttaccggatacc tgtccgcctttctcccttcgggaagcgtggcgctttctcatagctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcctaactacggctac actagaagaacagtatttggtatctgcgctctgctgaagccagttaccttcggaaaaagagttggtagctcttgatccggcaaacaaaccacc gctggtagcggtggtttttttgtttgcaagcagcagattacgcgcagaaaaaaaggatctcaagaagatcctttgatcttttctacggggtctga cgctcagtggaacgaaaactcacgttaagggattttggtcatgagattatcaaaaaggatcttcacctagatccttttaaattaaaaatgaagttt taaatcaatctaaagtatatatgagtaaacttggtctgacagaaataataaaaaagccggattaataatctggcttttttatattctctctctagtatat aaacgcagaaaggcccacccgaaggtgagccagtgtgactctagtattattagaaaaactcatcgagcatcaaatgaaactgcaatttattca tatcaggattatcaataccatatttttgaaaaagccgtttctgtaatgaaggagaaaactcaccgaggcagttccaaagaatggcaaggtcctg gtaacggtctgcgattccgacccgtccaacatcaatacaacctattaatttcccctcgtcaaaaataaggttatcaagtgagaaatcaccatga gtgacgactgaatccggtgagaatggcaagagcttgtgcatttctttccagacttgttcaacaggccagccattacgctcgtcatcaaaatcac tcgcatcaaccaaaccgttattcatgcgtgattgcgcctgagcaagacgaaatacacgatcgctgttaaaaggacaattacaaacaggaatc gaatgtaaccggcgcaggaacacggccagcgcatcaacaatattttcacctgaatcaggatattcttctaatacctggaaggctgttttccca ggaatcgcggtggtgagtaaccacgcatcatcaggagtacggataaaatgcttgatggtcgggagaggcataaactccgtcagccagttg agacggaccatctcatctgtaacatcattggcaacgctacctttgccatgtttcagaaacaactctggcgcatcgggcttcccatacaagcgat agattgtcgcacctgattgcccgacattatcgcgagcccatttatacccatataaatcagcgtccatgttggagtttaagcgcggacgggagc aagacgtttcccgttgaatatggctcataacaccccttgtattactgtttatgtaagcagacagttttattgttcatgatgatatatttttatcttgtgca atgtaacatcagagattttgagacacaacgtggctttgttgaataaatcgaacttttgctgagttgaaggatcagctctagtaaaataataaaaa agccggattaataatctggcttttttatattctctctctagtatataaacgcagaaaggcccacccgaaggtgagccagtgtgacggcacatttcc ccgaaaagtgccacctaaattgtaagcgttaatattttgttaaaattcgcgttaaatttttgttaaatcagctcattttttaaccaataggccgaaatc ggcaaaatcccttataaatcaaaagaatagaccgagatagggttgagtgttgttccagtttggaacaagagtccactattaaagaacgtggac tccaacgtcaaagggcgaaaaaccgtctatcagggcgatggcccactacgtgaaccatcaccctaatcaagttttttggggtcgaggtgcc gtaaagcactaaatcggaaccctaaagggagcccccgatttagagcttgacggggaaagccggcgaacgtggcgagaaaggaaggga agaaagcgaaaggagcgggcgctagggcgctggcaagtgtagcggtcacgctgcgcgtaaccaccacacccgccgcgcttaatgcgc cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap9/ pKan-Anc80-RepCap-p5i3-p19i3 (10,491 bp)

(SEQ ID NO: 23)

cctcgaggGCTAGCcattcTCCCTATCAGTGATAGAGAtcTATTTAAGCCCGAGTG

AGCACGCAGTCCCTATCAGTGATAGAGAGGTCTCCATTTTGAAGCGGGAGGTTTGAA

CGCGCAGCCGCCatgccggggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg -continued ggattacctcggagaagcagtggatccaggaggaccaggcctcatacatctccttcaatgcggcctccaactcgcggtcccaaatcaagg
ctgccttggacaatgcgggaaagattatgagcctgactaaaaccgcccccgactacctggtgggccagcagcccgtggaggacatttcca
gcaatcggatttataaaattttggaactaaacgggtacgatccccaatatgcggcttccgtctttctgggatgggccacgaaaaagttcggca
agaggaacaccatctggctgtttgggcctgcaactaccgggaagaccaacatcgcggaggccatagcccacactgtgcccttctacgggt
gcgtaaactggaccaatgagaactttcccttcaacgactgtgtcgacaagatggtgatctggtgggaggaggggaagatgaccgccaagg
tcgtggagtcggccaaagccattctcggaggaagcaaggtgcgcgtggaccagaaatgcaagtcctcggcccagatagacccgactccc
gtgatcgtcacctccaacaccaacatgtgcgccgtgattgacgggaactcaacgaccttcgaacaccagcagccgttgcaagaccggatgt
tcaaatttgaactcacccgccgtctggatcatgactttgggaaggtcaccaagcaggaagtcaaagactttttccggtgggcaaaggatcac
gtggttgaggtggagcatgaattctacgtcaaaaagggtggagccaagaaaagacccgcccccagtgacgcagatataagtgagcccaa
acgggtgcgcgagtcagttgcgcagccatcgacgtcagacgcggaagcttcgatcaactacgcagacaggtaccaaaacaaatgttctcg
tcacgtgggcatgaatctgatgctgtttccctgcagacaatgcgagagaatgaatcagaattcaaatatctgcttcactcacggacagaaaga
ctgtttagagtgctttcccgtgtcagaatctcaacccgtttctgtcgtcaaaaaggcgtatcagaaactgtgctacattcatcatatcatgggaaa
ggtgccagacgcttgcactgcctgcgatctggtcaatgtggatttggatgactgcatctttgaacaataaatgatttaaatcaggtatggctgcc
gatggttatcttccagattggctcgaggacaacctctctgagggcattcgcgagtggtgggacttgaaacctggagccccgaaacccaaag
ccaaccagcaaaagcaggacgacggccggggtctggtgcttcctggctacaagtacctcggacccttcaacggactcgacaaggggga
gcccgtcaacgcggcggacgcagcggccctcgagcacgacaaggcctacgaccagcagctcaaagcgggtgacaatccgtacctgcg
gtataaccacgccgacgccgagtttcaggagcgtctgcaagaagatacgtcttttgggggcaacctcgggcgagcagtcttccaggccaa
gaagcgggttctcgaacctctcggtctggttgaggaaggcgctaagacggctcctggaaagaagagaccggtagagcaatcaccccagg
aaccagactcctcttcgggcatcggcaagaaaggccagcagcccgcgagaaagagactcaactttgggcagactggcgactcagagtca
gtgcccgaccctcaaccactcggagaaccccccgcagcccccctctggtgtgggatctaatacaatggctgcaggcggtggcgctccaatg
gcagacaataacgaaggcgccgacggagtgggtaacgcctcaggaaattggcattgcgattccacatggctgggcgacagagtcatcac
caccagcacccgaacctgggccctccccacctacaacaaccacctctacaagcaaatctccagccaatcgggaggcagcaccaacgaca
acacctacttcggctacagcaccccctgggggtattttgactttaacagattccactgccacttctcaccacgtgactggcagcgactcatcaa
caacaactggggattccggcccaagaagctcaacttcaagctcttcaacatccaggtcaaggaggtcacgacgaatgatggcaccacgac
catcgccaataaccttaccagcacggttcaggtctttacggactcggaataccagctcccgtacgtcctcggctctgcgcaccagggctgcc
tgcctccgttcccggcggacgtcttcatgattcctcagtacgggtacctgactctgaacaatggcagtcaggccgtgggccgttcctccttcta
ctgcctggaatactttccttctcaaatgctgagaacgggcaacaactttcagttcagctacacgtttgaggacgtgccttttcacagcagctacg
cgcacagccaaagcctggaccggctgatgaacccccctcatcgaccagtacctgtactacctgtctcggactcagaccacgagtggtaccg
caggaaatcggacgttgcaattttctcaggccgggcctagtagcatggcgaatcaggccaaaaactggctacccgggccctgctaccggc
agcaacgcgtctccaagacaaccaatcaaaataacaacagcaactttgcctggaccggtgccaccaagtatcatctgaatggcagagactc
tctggtaaatcccggtcccgctatggcaacccacaaggacgacgaagacaaatttttttccgatgagcggagtcttaatatttgggaaacagg
gagctggaaatagcaacgtggaccttgacaacgttatgataaccaacgaggaagaaattaaaaccaccaacccagtggccacagaagagt
acggcacggtggccactaacctgcaatcggccaacaccgctcctgctacagggaccgtcaacagtcaaggagccttacctggcatggtct
ggcaggaccgggacgtgtacctgcagggtcctatctgggccaagattcctcacacggacggacactttcatccctcgccgctgatgggag
gctttggactgaaacacccgcctcctcagatcctgattaagaatacacctgttcccgcgaatcctccaactaccttcagtccagctaagtttgc
gtcgttcatcacgcagtacagcaccggacaggtcagcgtggaaattgaatgggagctgcagaaagaaaacagcaaacgctggaacccag
agattcaatacacttccaactacaacaaatctacaaatgtggactttgctgttgacacaaatggcgtttattctgagcctcgccccatcggcacc
cgttacctcacccgtaatctgtaaactagtttgcttgttaatcaataaaccgtttaattcgtttcagttgaactttggtctctgcgtatttctttcttat
ctagtttccatgctctagaggtcctgtattagaggtcacgtgagtgttttgcgacattttgcgacaccatgtggtcacgctgggtatttaagcccga
gtgagcacgcagggtctccattttgaagcgggaggtttgaacgcgcagccgccaagccgaattctgcagatatcggggttggggttgcgc
cttttccaaggcagccctgggtttgcgcagggacgcggctgctctgggcgtggttccgggaaacgcagcggcgccgaccctgggtctcg -continued cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaaTCCCTATCAGTGATAGAGAcagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagactttttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag gtaccaaaacaaatgttctcgtcacgtgggcatgaatctgatgctgtttccctgcagacaatgcgagagaatgaatcagaattcaaatatctgc ttcactcacggacagaaagactgtttagagtgctttcccgtgtcagaatctcaacccgtttctgtcgtcaaaaaggcgtatcagaaactgtgcta cattcatcatatcatgggaaaggtgccagacgcttgcactgcctgcgatctggtcaatgtggatttggatgactgcatctttgaacaataaAC

TAGTTTGCTTGTTAATCAATAAACCGTTTAATTCGTTTCAGTTGAACTTTGGTCTCTG

CGTATTTCTTTCTTATCTAGTTTCCATGCTCTAGAGTATACgatatccatcacactggcggccgctcga ctagagcggccgccaccgcggtggagctccagcttttgttcgcgcgcttggcgtaatcatggtcatagctgtttcctgtgtgaaattccacag -continued cctggggtgcctaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggtatcagct cactcaaaggcggtaatacggttatccacagaatcaggggataacgcaggaaagaacatgtgagcaaaaggccagcaaaaggccagga accgtaaaaaggccgcgttgctggcgtttttccataggctccgcccccctgacgagcatcacaaaaatcgacgctcaagtcagaggtggcg aaacccgacaggactataaagataccaggcgtttccccctggaagctccctcgtgcgctctcctgttccgaccctgccgcttaccggatacc tgtccgcctttctcccttcgggaagcgtggcgctttctcatagctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcctaactacggctac actagaagaacagtatttggtatctgcgctctgctgaagccagttaccttcggaaaaagagttggtagctcttgatccggcaaacaaaccacc gctggtagcggtggtttttttgtttgcaagcagcagattacgcgcagaaaaaaaggatctcaagaagatcctttgatcttttctacggggtctga cgctcagtggaacgaaaactcacgttaagggattttggtcatgagattatcaaaaaggatcttcacctagatccttttaaattaaaaatgaagttt taaatcaatctaaagtatatatgagtaaacttggtctgacagaaataataaaaagccggattaataatctggcttttatattctctctctagtatat aaacgcagaaaggcccacccgaaggtgagccagtgtgactctagtattattagaaaaactcatcgagcatcaaatgaaactgcaatttattca tatcaggattatcaataccatatttttgaaaaagccgtttctgtaatgaaggagaaaactcaccgaggcagttccaaagaatggcaaggtcctg gtaacggtctgcgattccgacccgtccaacatcaatacaacctattaatttcccctcgtcaaaaataaggttatcaagtgagaaatcaccatga gtgacgactgaatccggtgagaatggcaagagcttgtgcatttctttccagacttgttcaacaggccagccattacgctcgtcatcaaaatcac tcgcatcaaccaaaccgttattcatgcgtgattgcgcctgagcaagacgaaatacacgatcgctgttaaaaggacaattacaaacaggaatc gaatgtaaccggcgcaggaacacggccagcgcatcaacaatattttcacctgaatcaggatattcttctaatacctggaaggctgttttccca ggaatcgcggtggtgagtaaccacgcatcatcaggagtacggataaaatgcttgatggtcgggagaggcataaactccgtcagccagttg agacggaccatctcatctgtaacatcattggcaacgctacctttgccatgtttcagaaacaactctggcgcatcgggcttcccatacaagcgat agattgtcgcacctgattgcccgacattatcgcgagcccatttatacccatataaatcagcgtccatgttggagtttaagcgcggacgggagc aagacgtttcccgttgaatatggctcataacaccccttgtattactgtttatgtaagcagacagttttattgttcatgatgatatatttttatcttgtgca atgtaacatcagagattttgagacacaacgtggattgttgaataaatcgaacttttgctgagttgaaggatcagctctagtaaaataataaaaa agccggattaataatctggcttttatattctctctctagtatataaacgcagaaaggcccacccgaaggtgagccagtgtgacggcacatttcc ccgaaaagtgccacctaaattgtaagcgttaatattttgttaaaattcgcgttaaatttttgttaaatcagctcattttttaaccaataggccgaaatc ggcaaaatcccttataaatcaaaagaatagaccgagatagggttgagtgttgttccagtttggaacaagagtccactattaaagaacgtggac tccaacgtcaaagggcgaaaaaccgtctatcagggcgatggcccactacgtgaaccatcaccctaatcaagttttttggggtcgaggtgcc gtaaagcactaaatcggaaccctaaagggagcccccgatttagagcttgacggggaaagccggcgaacgtggcgagaaaggaaggga agaaagcgaaaggagcgggcgctagggcgctggcaagtgtagcggtcacgctgcgcgtaaccaccacacccgccgcgcttaatgcgc cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap10/ pKan-Anc80-intron-inducibleRepCap (7,567 bp)

(SEQ ID NO: 24)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccagtgggcgtggactaatatggaacagtat -continued ttaaggtaagtTCCCTATCAGTGATAGAGATCTCCCTATCAGTGATAGAGAtactgacatccactttgc ctttctctccacagcgcctgtttgaatctcacggagcgtaaacggttggtggcgcagcatctgacgcacgtgtcgcagacgcaggagcaga acaaagagaatcagaatcccaattctgatgcgccggtgatcagatcaaaaacttcagccaggtacatggagctggtcgggtggctcgtgga caaggggattacctcggagaagcagtggatccaggaggaccaggcctcatacatctccttcaatgcggcctccaactcgcggtcccaaat caaggctgccttggacaatgcgggaaagattatgagcctgactaaaaccgcccccgactacctggtgggccagcagcccgtggaggaca tttccagcaatcggatttataaaattttggaactaaacgggtacgatccccaatatgcggcttccgtctttctgggatgggccacgaaaaagttc ggcaagaggaacaccatctggctgtttgggcctgcaactaccgggaagaccaacatcgcggaggccatagcccacactgtgcccttctac gggtgcgtaaactggaccaatgagaactttcccttcaacgactgtgtcgacaagatggtgatctggtgggaggaggggaagatgaccgcc aaggtcgtggagtcggccaaagccattctcggaggaagcaaggtgcgcgtggaccagaaatgcaagtcctcggcccagatagacccga ctcccgtgatcgtcacctccaacaccaacatgtgcgccgtgattgacgggaactcaacgaccttcgaacaccagcagccgttgcaagacc ggatgttcaaatttgaactcacccgccgtctggatcatgactttgggaaggtcaccaagcaggaagtcaaagactttttccggtgggcaaag gatcacgtggttgaggtggagcatgaattctacgtcaaaaagggtggagccaagaaaagacccgcccccagtgacgcagatataagtga gcccaaacgggtgcgcgagtcagttgcgcagccatcgacgtcagacgcggaagcttcgatcaactacgcagacaggtaccaaaacaaat gttctcgtcacgtgggcatgaatctgatgctgtttccctgcagacaatgcgagagaatgaatcagaattcaaatatctgcttcactcacggaca gaaagactgtttagagtgctttcccgtgtcagaatctcaacccgtttctgtcgtcaaaaaggcgtatcagaaactgtgctacattcatcatatcat gggaaaggtgccagacgcttgcactgcctgcgatctggtcaatgtggatttggatgactgcatctttgaacaataaatgatttaaatcaggtat ggctgccgatggttatcttccagattggctcgaggacaacctctctgagggcattcgcgagtggtgggacttgaaacctggagccccgaaa cccaaagccaaccagcaaaagcaggacgacggccggggtctggtgcttcctggctacaagtacctcggacccttcaacggactcgacaa gggggagcccgtcaacgcggcggacgcagcggccctcgagcacgacaaggcctacgaccagcagctcaaagcgggtgacaatccgt acctgcggtataaccacgccgacgccgagtttcaggagcgtctgcaagaagatacgtcttttgggggcaacctcgggcgagcagtcttcca ggccaagaagcgggttctcgaacctctcggtctggttgaggaaggcgctaagacggctcctggaaagaagagaccggtagagcaatcac cccaggaaccagactcctcttcgggcatcggcaagaaaggccagcagcccgcgagaaagagactcaactttgggcagactggcgactc agagtcagtgcccgaccctcaaccactcggagaacccccgcagcccctctggtgtgggatctaatacaatggctgcaggcggtggcg ctccaatggcagacaataacgaaggcgccgacggagtgggtaacgcctcaggaaattggcattgcgattccacatggctgggcgacaga gtcatcaccaccagcacccgaacctgggccctccccacctacaacaaccacctctacaagcaaatctccagccaatcgggaggcagcac caacgacaacacctacttcggctacagcaccccctgggggtattttgactttaacagattccactgccacttctcaccacgtgactggcagcg actcatcaacaacaactggggattccggcccaagaagctcaacttcaagctcttcaacatccaggtcaaggaggtcacgacgaatgatggc accacgaccatcgccaataaccttaccagcacggttcaggtctttacggactcggaataccagctcccgtacgtcctcggctctgcgcacca gggctgcctgcctccgttcccggcggacgtcttcatgattcctcagtacgggtacctgactctgaacaatggcagtcaggccgtgggccgtt cctccttctactgcctggaatactttccttctcaaatgctgagaacgggcaacaactttcagttcagctacacgtttgaggacgtgccttttcaca gcagctacgcgcacagccaaagcctggaccggctgatgaacccccctcatcgaccagtacctgtactacctgtctcggactcagaccacga gtggtaccgcaggaaatcggacgttgcaattttctcaggccgggcctagtagcatggcgaatcaggccaaaaactggctacccgggccct gctaccggcagcaacgcgtctccaagacaaccaatcaaaataacaacagcaactttgcctggaccggtgccaccaagtatcatctgaatgg cagagactctctggtaaatcccggtcccgctatggcaacccacaaggacgacgaagacaaatttttccgatgagcggagtcttaatatttgg gaaacagggagctggaaatagcaacgtggaccttgacaacgttatgataaccaacgaggaagaaattaaaaccaccaacccagtggcca cagaagagtacggcacggtggccactaacctgcaatcggccaacaccgctcctgctacagggaccgtcaacagtcaaggagccttacct ggcatggtctggcaggaccgggacgtgtacctgcagggtcctatctgggccaagattcctcacacggacggacactttcatccctcgccgc tgatgggaggctttggactgaaacacccgcctcctcagatcctgattaagaatacacctgttcccgcgaatcctccaactaccttcagtccag ctaagtttgcgtcgttcatcacgcagtacagcaccggacaggtcagcgtggaaattgaatgggagctgcagaaagaaaacagcaaacgct ggaacccagagattcaatacacttccaactacaacaaatctacaaatgtggactttgctgttgacacaaatggcgtttattctgagcctcgccc -continued catcggcacccgttacctcacccgtaatctgtaaactagtttgcttgttaatcaataaaccgtttaattcgtttcagttgaactttggtctctgcgtat ttctttcttatctagtttccatgctctagaggtcctgtattagaggtcacgtgagtgttttgcgacattttgcgacaccatgtggtcacgctgggtatt taagcccgagtgagcacgcagggtctccatttgaagcgggaggtttgaacgcgcagccgccaagccgaattctgcagatatccatcacac tggcggccgctcgactagagcggccgccaccgcggtggagctccagcttttgttcgcgcgcttggcgtaatcatggtcatagctgtttcctgt gtgaaattccacagcctggggtgcctaattgcgttgcgctcactgcccgctttccagtcgggaaacctgtcgtgccagctgcattaatgaatc ggccaacgcgcggggagaggcggtttgcgtattgggcgctcttccgcttcctcgctcactgactcgctgcgctcggtcgttcggctgcggc gagcggtatcagctcactcaaaggcggtaatacggttatccacagaatcaggggataacgcaggaaagaacatgtgagcaaaaggccag caaaaggccaggaaccgtaaaaaggccgcgttgctggcgtttttccataggctccgcccccctgacgagcatcacaaaaatcgacgctca agtcagaggtggcgaaacccgacaggactataaagataccaggcgtttccccctggaagctccctcgtgcgctctcctgttccgaccctgc cgcttaccggatacctgtccgcctttctcccttcgggaagcgtggcgctttctcatagctcacgctgtaggtatctcagttcggtgtaggtcgtt cgctccaagctgggctgtgtgcacgaaccccccgttcagcccgaccgctgcgccttatccggtaactatcgtcttgagtccaacccggtaag acacgacttatcgccactggcagcagccactggtaacaggattagcagagcgaggtatgtaggcggtgctacagagttcttgaagtggtgg cctaactacggctacactagaagaacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaagaagatcctttgatctt ttctacggggtctgacgctcagtggaacgaaaactcacgttaagggattttggtcatgagattatcaaaaaggatcttcacctagatccttttaa attaaaaatgaagttttaaatcaatctaaagtatatatgagtaaacttggtctgacagaaataataaaaaagccggattaataatctggctttttata ttctctctctagtatataaacgcagaaaggcccacccgaaggtgagccagtgtgactctagtattattagaaaaactcatcgagcatcaaatga aactgcaatttattcatatcaggattatcaataccatatttttgaaaaagccgtttctgtaatgaaggagaaaactcaccgaggcagttccaaag aatggcaaggtcctggtaacggtctgcgattccgacccgtccaacatcaatacaacctattaatttcccctcgtcaaaaataaggttatcaagt gagaaatcaccatgagtgacgactgaatccggtgagaatggcaagagcttgtgcatttattccagacttgttcaacaggccagccattacgc tcgtcatcaaaatcactcgcatcaaccaaaccgttattcatgcgtgattgcgcctgagcaagacgaaatacacgatcgctgttaaaaggacaa ttacaaacaggaatcgaatgtaaccggcgcaggaacacggccagcgcatcaacaatattttcacctgaatcaggatattcttctaatacctgg aaggctgttttcccaggaatcgcggtggtgagtaaccacgcatcatcaggagtacggataaaatgcttgatggtcgggagaggcataaact ccgtcagccagttgagacggaccatctcatctgtaacatcattggcaacgctacctttgccatgtttcagaaacaactctggcgcatcgggctt cccatacaagcgatagattgtcgcacctgattgcccgacattatcgcgagcccatttatacccatataaatcagcgtccatgttggagtttaag cgcggacgggagcaagacgtttcccgttgaatatggctcataacaccccttgtattactgtttatgtaagcagacagttttattgttcatgatgat atatttttatcttgtgcaatgtaacatcagagattttgagacacaacgtggctttgttgaataaatcgaacttttgctgagttgaaggatcagctcta gtaaaataataaaaaagccggattaataatctggcttttatattctctctctagtatataaacgcagaaaggcccacccgaaggtgagccagt gtgacggcacatttccccgaaaagtgccacctaaattgtaagcgttaatattttgttaaaattcgcgttaaatttttgttaaatcagctcatttttaa ccaataggccgaaatcggcaaaatcccttataaatcaaaagaatagaccgagatagggttgagtgttgttccagtttggaacaagagtccact attaaagaacgtggactccaacgtcaaagggcgaaaaaccgtctatcagggcgatggcccactacgtgaaccatcaccctaatcaagtttt tggggtcgaggtgccgtaaagcactaaatcggaaccctaaagggagcccccgatttagagcttgacggggaaagccggcgaacgtggc gagaaaggaagggaagaaagcgaaaggagcgggcgctagggcgctggcaagtgtagcggtcacgctgcgcgtaaccaccacacccg ccgcgcttaatgcgccgctacagggcgcgtcccattcgccattcaggctgcgcaactgttgggaagggcgatcggtgcgggcctcttcgct attacgccagctggcgaaagggggatgtgctgcaaggcgattaagttgggtaacgccagggttttcccagtcacgacgttgtaaaacgacg gccagtgagcgcgcggcgaattgggtaccgggccccc iRepCap11/ pKan-Anc80-intron-inducibleRepCap-d2 (7,567 bp)

(SEQ ID NO: 25)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

Figure 11A:
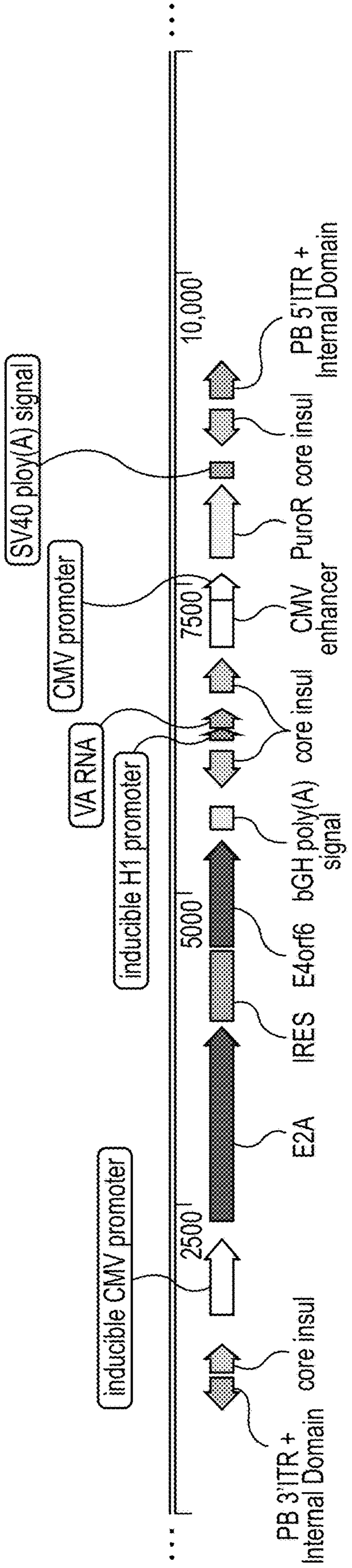
FIGS. 11A-11E show exemplary nucleic acid constructs encoding helper, AAV, gene of interest, and Rep-Cap vectors, in accordance with embodiments hereof.
Figure 11B:
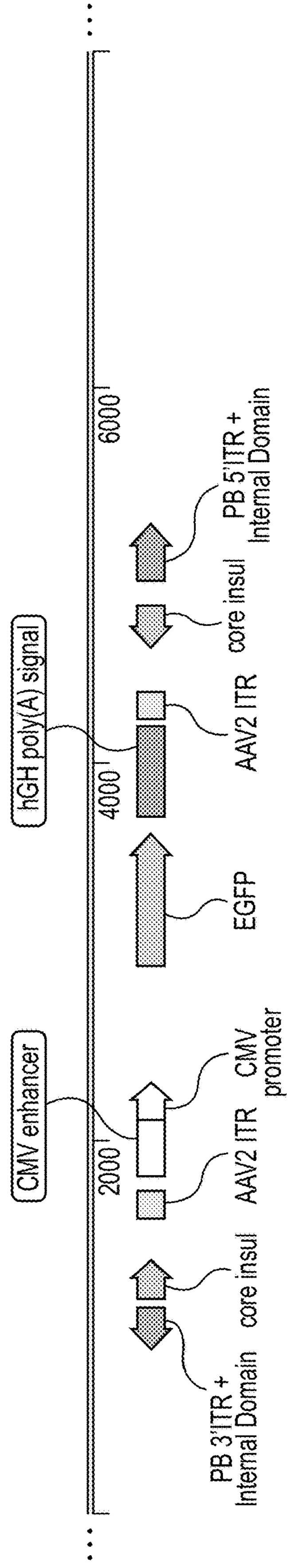

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga -continued ccgtggccgagaagctgcagcgcgactttctgacggaatggcgccgtgtgagtaaggccccggaggctcttttctttgtgcaatttgagaag
ggagagagctacttccacatgcacgtgctcgtggaaaccaccggggtgaaatccatggttttgggacgtttcctgagtcagattcgcgaaaa
actgattcagagaatttaccgcgggatcgagccgactttgccaaactggttcgcggtcacaaagaccagaaatggcgccggaggcggga
acaaggtggtggatgagtgctacatccccaattacttgctccccaaaacccagcctgagctccagtgggcgtggactaatatggaacagtat
ttaagcgcctgtttgaatctcacggaaaggtaagtTCCCTATCAGTGATAGAGATCTCCCTATCAGTGATA
GAGAtactgacatccactttgcctttctctccacaggaaacggttggtggcgcagcatctgacgcacgtgtcgcagacgcaggagcaga
acaaagagaatcagaatcccaattctgatgcgccggtgatcagatcaaaaacttcagccaggtacatggagctggtcgggtggctcgtgga
caaggggattacctcggagaagcagtggatccaggaggaccaggcctcatacatctccttcaatgcggcctccaactcgcggtcccaaat
caaggctgccttggacaatgcgggaaagattatgagcctgactaaaaccgcccccgactacctggtgggccagcagcccgtggaggaca
tttccagcaatcggatttataaaattttggaactaaacgggtacgatccccaatatgcggcttccgtctttctgggatgggccacgaaaaagttc
ggcaagaggaacaccatctggctgtttgggcctgcaactaccgggaagaccaacatcgcggaggccatagcccacactgtgcccttctac
gggtgcgtaaactggaccaatgagaactttcccttcaacgactgtgtcgacaagatggtgatctggtgggaggaggggaagatgaccgcc
aaggtcgtggagtcggccaaagccattctcggaggaagcaaggtgcgcgtggaccagaaatgcaagtcctcggcccagatagacccga
ctcccgtgatcgtcacctccaacaccaacatgtgcgccgtgattgacgggaactcaacgaccttcgaacaccagcagccgttgcaagacc
ggatgttcaaatttgaactcacccgccgtctggatcatgactttgggaaggtcaccaagcaggaagtcaaagactttttccggtgggcaaag
gatcacgtggttgaggtggagcatgaattctacgtcaaaaagggtggagccaagaaaagacccgcccccagtgacgcagatataagtga
gcccaaacgggtgcgcgagtcagttgcgcagccatcgacgtcagacgcggaagcttcgatcaactacgcagacaggtaccaaaacaaat
gttctcgtcacgtgggcatgaatctgatgctgtttccctgcagacaatgcgagagaatgaatcagaattcaaatatctgcttcactcacggaca
gaaagactgtttagagtgctttcccgtgtcagaatctcaacccgtttctgtcgtcaaaaaggcgtatcagaaactgtgctacattcatcatatcat
gggaaaggtgccagacgcttgcactgcctgcgatctggtcaatgtggatttggatgactgcatctttgaacaataaatgatttaaatcaggtat
ggctgccgatggttatcttccagattggctcgaggacaacctctctgagggcattcgcgagtggtgggacttgaaacctggagccccgaaa
cccaaagccaaccagcaaaagcaggacgacggccggggtctggtgcttcctggctacaagtacctcggacccttcaacggactcgacaa
gggggagcccgtcaacgcggcggacgcagcggccctcgagcacgacaaggcctacgaccagcagctcaaagcgggtgacaatccgt
acctgcggtataaccacgccgacgccgagtttcaggagcgtctgcaagaagatacgtcttttgggggcaacctcgggcgagcagtcttcca
ggccaagaagcgggttctcgaacctctcggtctggttgaggaaggcgctaagacggctcctggaaagaagagaccggtagagcaatcac
cccaggaaccagactcctcttcgggcatcggcaagaaaggccagcagcccgcgagaaagagactcaactttgggcagactggcgactc
agagtcagtgcccgaccctcaaccactcggagaaccccccgcagcccctctggtgtgggatctaatacaatggctgcaggcggtggcg
ctccaatggcagacaataacgaaggcgccgacggagtgggtaacgcctcaggaaattggcattgcgattccacatggctgggcgacaga
gtcatcaccaccagcacccgaacctgggccctcccacctacaacaaccacctctacaagcaaatctccagccaatcgggaggcagcac
caacgacaacacctacttcggctacagcaccccctgggggtattttgactttaacagattccactgccacttctcaccacgtgactggcagcg
actcatcaacaacaactggggattccggcccaagaagctcaacttcaagctcttcaacatccaggtcaaggaggtcacgacgaatgatggc
accacgaccatcgccaataaccttaccagcacggttcaggtctttacggactcggaataccagctcccgtacgtcctcggctctgcgcacca
gggctgcctgcctccgttcccggcggacgtcttcatgattcctcagtacgggtacctgactctgaacaatggcagtcaggccgtgggccgtt
cctccttctactgcctggaatactttccttctcaaatgctgagaacgggcaacaactttcagttcagctacacgtttgaggacgtgccttttcaca
gcagctacgcgcacagccaaagcctggaccggctgatgaacccccctcatcgaccagtacctgtactacctgtctcggactcagaccacga
gtggtaccgcaggaaatcggacgttgcaattttctcaggccgggcctagtagcatggcgaatcaggccaaaaactggctacccgggccct
gctaccggcagcaacgcgtctccaagacaaccaatcaaaataacaacagcaactttgcctggaccggtgccaccaagtatcatctgaatgg
cagagactctctggtaaatcccggtcccgctatggcaacccacaaggacgacgaagacaaatttttttccgatgagcggagtcttaatatttgg
gaaacagggagctggaaatagcaacgtggaccttgacaacgttatgataaccaacgaggaagaaattaaaaccaccaacccagtggcca
cagaagagtacggcacggtggccactaacctgcaatcggccaacaccgctcctgctacagggaccgtcaacagtcaaggagccttacct -continued ggcatggtctggcaggaccgggacgtgtacctgcagggtcctatctgggccaagattcctcacacggacggacactttcatccctcgccgc tgatgggaggctttggactgaaacacccgcctcctcagatcctgattaagaatacacctgttcccgcgaatcctccaactaccttcagtccag ctaagtttgcgtcgttcatcacgcagtacagcaccggacaggtcagcgtggaaattgaatgggagctgcagaaagaaaacagcaaacgct ggaacccagagattcaatacacttccaactacaacaaatctacaaatgtggactttgctgttgacacaaatggcgtttattctgagcctcgccc catcggcacccgttacctcacccgtaatctgtaaactagtttgcttgttaatcaataaaccgtttaattcgtttcagttgaactttggtctctgcgtat ttctttcttatctagtttccatgctctagaggtcctgtattagaggtcacgtgagtgttttgcgacattttgcgacaccatgtggtcacgctgggtatt taagcccgagtgagcacgcagggtctccattttgaagcgggaggtttgaacgcgcagccgccaagccgaattctgcagatatccatcacac tggcggccgctcgactagagcggccgccaccgcggtggagctccagcttttgttcgcgcgcttggcgtaatcatggtcatagctgtttcctgt gtgaaattccacagcctggggtgcctaattgcgttgcgctcactgcccgctttccagtcgggaaacctgtcgtgccagctgcattaatgaatc ggccaacgcgcggggagaggcggtttgcgtattgggcgctcttccgcttcctcgctcactgactcgctgcgctcggtcgttcggctgcggc gagcggtatcagctcactcaaaggcggtaatacggttatccacagaatcaggggataacgcaggaaagaacatgtgagcaaaaggccag caaaaggccaggaaccgtaaaaaggccgcgttgctggcgtttttccataggctccgcccccctgacgagcatcacaaaaatcgacgctca agtcagaggtggcgaaacccgacaggactataaagataccaggcgtttccccctggaagctccctcgtgcgctctcctgttccgaccctgc cgcttaccggatacctgtccgcctttctcccttcgggaagcgtggcgctttctcatagctcacgctgtaggtatctcagttcggtgtaggtcgtt cgctccaagctgggctgtgtgcacgaaccccccgttcagcccgaccgctgcgccttatccggtaactatcgtcttgagtccaacccggtaag acacgacttatcgccactggcagcagccactggtaacaggattagcagagcgaggtatgtaggcggtgctacagagttcttgaagtggtgg cctaactacggctacactagaagaacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaagaagatcctttgatctt ttctacggggtctgacgctcagtggaacgaaaactcacgttaagggattttggtcatgagattatcaaaaaggatcttcacctagatccttttaa attaaaaatgaagttttaaatcaatctaaagtatatatgagtaaacttggtctgacagaaataataaaaaagccggattaataatctggcttttata ttctctctctagtatataaacgcagaaaggcccacccgaaggtgagccagtgtgactctagtattattagaaaaactcatcgagcatcaaatga aactgcaatttattcatatcaggattatcaataccatatttttgaaaaagccgtttctgtaatgaaggagaaaactcaccgaggcagttccaaag aatggcaaggtcctggtaacggtctgcgattccgacccgtccaacatcaatacaacctattaatttcccctcgtcaaaaataaggttatcaagt gagaaatcaccatgagtgacgactgaatccggtgagaatggcaagagcttgtgcatttctttccagacttgttcaacaggccagccattacgc tcgtcatcaaaatcactcgcatcaaccaaaccgttattcatgcgtgattgcgcctgagcaagacgaaatacacgatcgctgttaaaaggacaa ttacaaacaggaatcgaatgtaaccggcgcaggaacacggccagcgcatcaacaatattttcacctgaatcaggatattcttctaatacctgg aaggctgttttcccaggaatcgcggtggtgagtaaccacgcatcatcaggagtacggataaaatgcttgatggtcgggagaggcataaact ccgtcagccagttgagacggaccatctcatctgtaacatcattggcaacgctacctttgccatgtttcagaaacaactctggcgcatcgggctt cccatacaagcgatagattgtcgcacctgattgcccgacattatcgcgagcccatttatacccatataaatcagcgtccatgttggagtttaag cgcggacgggagcaagacgtttcccgttgaatatggctcataacaccccttgtattactgtttatgtaagcagacagttttattgttcatgatgat atatttttatcttgtgcaatgtaacatcagagattttgagacacaacgtggctttgttgaataaatcgaacttttgctgagttgaaggatcagctcta gtaaaataataaaaaagccggattaataatctggcttttatattctctctctagtatataaacgcagaaaggcccacccgaaggtgagccagt gtgacggcacatttccccgaaaagtgccacctaaattgtaagcgttaatattttgttaaaattcgcgttaaatttttgttaaatcagctcattttttaa ccaataggccgaaatcggcaaaatcccttataaatcaaaagaatagaccgagatagggttgagtgttgttccagtttggaacaagagtccact attaaagaacgtggactccaacgtcaaagggcgaaaaaccgtctatcagggcgatggcccactacgtgaaccatcaccctaatcaagtttt tggggtcgaggtgccgtaaagcactaaatcggaaccctaaagggagcccccgatttagagcttgacggggaaagccggcgaacgtggc gagaaaggaagggaagaaagcgaaaggagcgggcgctagggcgctggcaagtgtagcggtcacgctgcgcgtaaccaccacacccg ccgcgcttaatgcgccgctacagggcgcgtcccattcgccattcaggctgcgcaactgttgggaagggcgatcggtgcgggcctcttcgct attacgccagctggcgaaagggggatgtgctgcaaggcgattaagttgggtaacgccagggttttcccagtcacgacgttgtaaaacgacg gccagtgagcgcgcggcgaattgggtaccgggccccc The sequence for the PBBG-iHelper-Puro construct illustrated in in FIG. 11A is shown below:

PBBG-iHelper-Puro (11,801 bp)

(SEQ ID NO: 26)

ACTCTTCCTTTTTCAATATTATTGAAGCATTTATCAGGGTTATTGTCTCA

TGAGCGGATACATATTTGAATGTATTTAGAAAAATAAACAAATAGGGGTT

CCGCGCACATTTCCCCGAAAAGTGCCACCTAAATTGTAAGCGTTAATATT

TTGTTAAAATTCGCGTTAAATTTTTGTTAAATCAGCTCATTTTTTAACCA

ATAGGCCGAAATCGGCAAAATCCCTTATAAATCAAAAGAATAGACCGAGA

TAGGGTTGAGTGTTGTTCCAGTTTGGAACAAGAGTCCACTATTAAAGAAC

GTGGACTCCAACGTCAAAGGGCGAAAAACCGTCTATCAGGGCGATGGCCC

ACTACGTGAACCATCACCCTAATCAAGTTTTTTGGGGTCGAGGTGCCGTA

AAGCACTAAATCGGAACCCTAAAGGGAGCCCCCGATTTAGAGCTTGACGG

GGAAAGCCGGCGAACGTGGCGAGAAAGGAAGGGAAGAAAGCGAAAGGAGC

GGGCGCTAGGGCGCTGGCAAGTGTAGCGGTCACGCTGCGCGTAACCACCA

CACCCGCCGCGCTTAATGCGCCGCTACAGGGCGCGTCCCATTCGCCATTC

AGGCTGCGCAACTGTTGGGAAGGGCGATCGGTGCGGGCCTCTTCGCTATT

ACGCCAGCTGGCGAAAGGGGGATGTGCTGCAAGGCGATTAAGTTGGGTAA

CGCCAGGGTTTTCCCAGTCACGACGTTGTAAAACGACGGCCAGTGAGCGC

GCCTCGTTCATTCACGTTTTTGAACCCGTGGAGGACGGGCAGACTCGCGG

TGCAAATGTGTTTTACAGCGTGATGGAGCAGATGAAGATGCTCGACACGC

TGCAGAACACGCAGCTAGATTAACCCTAGAAAGATAATCATATTGTGACG

TACGTTAAAGATAATCATGCGTAAAATTGACGCATGTGTTTTATCGGTCT

GTATATCGAGGTTTATTTATTAATTTGAATAGATATTAAGTTTTATTATA

TTTACACTTACATACTAATAATAAATTCAACAAACAATTTATTTATGTTT

ATTTATTTATTAAAAAAAAACAAAAACTCAAAATTTCTTCTATAAAGTAA

CAAAACTTTTATCGAATTCCTGCAGCCCGGGGGATCCACTAGTTCTAGAG

GGACAGCCCCCCCCCAAAGCCCCCAGGGATGTAATTACGTCCCTCCCCCG

CTAGGGGGCAGCAGCGAGCCGCCCGGGGCTCCGCTCCGGTCCGGCGCTCC

CCCCGCATCCCCGAGCCGGCAGCGTGCGGGGACAGCCCGGGCACGGGGAA

GGTGGCACGGGATCGCTTTCCTCTGAACGCTTCTCGCTGCTCTTTGAGCC

TGCAGACACCTGGGGGGATACGGGGAAAAGGCCTCCAAGGCCAGCTTCCC

ACAATAAGTTGGGTGAATTTTGGCTCATTCCTCCTTTCTATAGGATTGAG

GTCAGAGCTTTGTGATGGGAATTCTGTGGAATGTGTGTCAGTTAGGGTGT

GGAAAGTCCCgcGATCgcTAGcGTTTAAACTTAAGCTTGGTACCGAGCTC

GGATCCACTAGTCCAGTGTGGTGGAATTCCTGCTTCGCGATGTACGGGCC

AGATATACGCGTTGACATTGATTATTGACTAGTTATTAATAGTAATCAAT

TACGGGGTCATTAGTTCATAGCCCATATATGGAGTTCCGCGTTACATAAC

TTACGGTAAATGGCCCGCCTGGCTGACCGCCCAACGACCCCCGCCCATTG

ACGTCAATAATGACGTATGTTCCCATAGTAACGCCAATAGGGACTTTCCA

TTGACGTCAATGGGTGGAGTATTTACGGTAAACTGCCCACTTGGCAGTAC

ATCAAGTGTATCATATGCCAAGTACGCCCCCTATTGACGTCAATGACGGT

-continued

AAATGGCCCGCCTGGCATTATGCCCAGTACATGACCTTATGGGACTTTCC

TACTTGGCAGTACATCTACGTATTAGTCATCGCTATTACCATGGTGATGC

GGTTTTGGCAGTACATCAATGGGCGTGGATAGCGGTTTGACTCACGGGGA

TTTCCAAGTCTCCACCCCATTGACGTCAATGGGAGTTTGTTTTGGAACCA

AAATCAACGGGACTTTCCAAAATGTCGTAACAACTCCGCCCCATTGACGC

AAATGGGCGGTAGGCGTGTACGGTGGGAGGTCTATATAAGCAGAGCTCTC

CCTATCAGTGATAGAGATCTCCCTATCAGTGATAGAGATCGTCGACGAGC

TCGTTTAGTGAACCGTCAGATCGCCTGGAGACGCCATCCACGCTGTTTTG

ACCTCCATAGAAGACACCGGGACCGATCCAGCCTCCGGACTCTAGCGTTT

AAACTTAAGCTTGCCACCatggccagtcgggaagaggagcagcgcgaaac cacccccgagcgcggacgcggtgcggcgcgacgtcccccaaccatggagg acgtgtcgtccccgtccccgtcgccgccgcctcccccgggcgcccccaaaa aagcggatgaggcggcgtatcgagtccgaggacgaggaagactcatcaca agacgcgctggtgccgcgcacacccagcccgcggccatcgacctcggcgg cggatttggccattgcgcccaagaagaaaaagaagcgcccttctcccaag cccgagcgcccgccatcaccagaggtaatcgtggacagcgaggaagaaag agaagatgtggcgctacaaatggtgggtttcagcaacccaccggtgctaa tcaagcatggcaaaggaggtaagcgcacagtgcggcggctgaatgaagac gacccagtggcgcgtggtatgcggacgcaagaggaagaggaagagcccag cgaagcggaaagtgaaattacggtgatgaacccgctgagtgtgccgatcg tgtctgcgtgggagaagggcatggaggctgcgcgcgcgctgatggacaag taccacgtggataacgatctaaaggcgaacttcaaactactgcctgacca agtggaagctctggcggccgtatgcaagacctggctgaacgaggagcacc gcgggttgcagctgaccttcaccagcaacaagacctttgtgacgatgatg gggcgattcctgcaggcgtacctgcagtcgtttgcagaggtgacctacaa gcatcacgagcccacgggctgcgcgttgtggctgcaccgctgcgctgaga tcgaaggcgagcttaagtgtctacacggaagcattatgataaataaggag cacgtgattgaaatggatgtgacgagcgaaaacgggcagcgcgcgctgaa ggagcagtctagcaaggccaagatcgtgaagaaccggtggggccgaaatg tggtgcagatctccaacaccgacgcaaggtgctgcgtgcacgacgcggcc tgtccggccaatcagttttccggcaagtcttgcggcatgttcttctctga aggcgcaaaggctcaggtggcttttaagcagatcaaggcttttatgcagg cgctgtatcctaacgcccagaccgggcacggtcaccttttgatgccacta cggtgcgagtgcaactcaaagcctgggcacgcgcccttttttgggaaggca gctaccaaagttgactccgttcgccctgagcaacgcggaggacctggacg cggatctgatctccgacaagagcgtgctggccagcgtgcaccacccggcg ctgatagtgttccagtgctgcaaccctgtgtatcgcaactcgcgcgcgca gggcggaggccccaactgcgacttcaagatatcggcgcccgacctgctaa acgcgttggtgatggtgcgcagcctgtggagtgaaaacttcaccgagctg ccgcggatggttgtgcctgagtttaagtggagcactaaacaccagtatcg -continued caacgtgtccctgccagtggcgcatagcgatgcgcggcagaacccctttg atttttaacccgggagttctagggatctgcccctctccctcccccccccc taacgttactggccgaagccgcttggaataaggccggtgtgcgtttgtct atatgttattttccaccatattgccgtatttggcaatgtgagggcccgga aacctggccctgtatcttgacgagcattcctaggggtctttcccctctcg ccaaaggaatgcaaggtctgttgaatgtcgtgaaggaagcagttcctctg gaagatcttgaagacaaacaacgtctgtagcgaccctttgcaggcagcgg aaccccccacctggcgacaggtgcctctgcggccaaaagccacgtgtata agatacacctgcaaaggcggcacaaccccagtgccacgttgtgagttgga tagttgtggaaagagtcaaatggctctcctcaagcgtattcaacaagggg ctgaaggatgcccagaaggtaccccattgtatgggatctgatctggggcc tcggtgcacatgctttacatgtgtttagtcgaggttaaaaaaacgtctag gccccccgaaccacggggacgtggttttcctttgaaaaacacgatgataa ggatccaccggaggccaccatgactacgtccggcgttccatttggcatga cactacgaccaacacgatctcggttgtctcggcgcactccgtacagtagg gatcgtctacctccttttgagacagaaacccgcgctaccatactggagga tcatccgctgctgcccgaatgtaacactttgacaatgcacaacgtgagtt acgtgcgaggtcttccctgcagtgtgggatttacgctgattcaggaatgg gttgttccctgggatatggttctaacgcgggaggagcttgtaatcctgag gaagtgtatgcacgtgtgcctgtgttgtgccaacattgatatcatgacga gcatgatgatccatggttacgagtcctgggctctccactgtcattgttcc agtcccggttccctgcagtgtatagccggcgggcaggttttggccagctg gtttaggatggtggtggatggcgccatgtttaatcagaggtttatatggt accgggaggtggtgaattacaacatgccaaaagaggtaatgtttatgtcc agcgtgtttatgaggggtcgccacttaatctacctgcgcttgtggtatga tggccacgtgggttctgtggtccccgccatgagctttggatacagcgcct tgcactgtgggattttgaacaatattgtggtgctgtgctgcagttactgt gctgatttaagtgagatcagggtgcgctgctgtgcccggaggacaaggcg ccttatgctgcgggcggtgcgaatcatcgctgaggagaccactgccatgt tgtattcctgcaggacggagcggcggcggcagcagtttattcgcgcgctg ctgcagcaccaccgccctatcctgatgcacgattatgactctacccccat gtagGCGGCCGTCGAGTCTAGAGGGCCCGTTTAAACCCGCTGATCAGCCT

CGACTGTGCCTTCTAGTTGCCAGCCATCTGTTGTTTGCCCCTCCCCCGTG

CCTTCCTTGACCCTGGAAGGTGCCACTCCCACTGTCCTTTCCTAATAAAA

TGAGGAAATTGCATCGCATTGTCTGAGTAGGTGTCATTCTATTCTGGGGG

GTGGGGTGGGGCAGGACAGCAAGGGGGAGGATTGGGAAGACAATAGCAGG

CATGCTGGGGATGCGGTGGGCTCTATGGCTTCTGAGGCGGAAAGAACCAG

CTGGGGCTCTAGGGGGTATCCCCGGCGCGCCggggtTGAGCTATTCCAGA

AGTAGTGAAGAGGCTTTTTTGGAGGCCTAGGCTTTTGCAAAAAGCTCCGG

ATCGATtggggttgcgccttttccaaggcTTTTCCCCGTATCCCCCCAGG

TGTCTGCAGGCTCAAAGAGCAGCGAGAAGCGTTCAGAGGAAAGCGATCCC

-continued

GTGCCACCTTCCCCGTGCCCGGGCTGTCCCCGCACGCTGCCGGCTCGGGG

ATGCGGGGGGAGCGCCGGACCGGAGCGGAGCCCCGGGCGGCTCGCTGCTG

CCCCCTAGCGGGGGAGGGACGTAATTACATCCCTGGGGGCTTTGGGGGGG

GGCTGTCCCTCTAGGGGATCCTCTAGGGCCTCTGAGCTATTCCAGAAGTA

GTGAAGAGGCTTTTTTGGAGGCCTAGGCTTTTGCAAAAAGCTCCGGATCG

ATCGAGCGGATCCAGCACAGTGGCGGCCGCaatatttgcatgtcgctatg tgttctgggaaatcaccataaacgtgaaatccctatcagtgatagagact tataagttccctatcagtgatagagaaccggtgggcactatccgtggtct ggtggataaattcgcaagggtatcatggcggacgaccggggttcgagccc cgtatccggccgtccgccgtgatccatgcggttaccgcccgcgtgtcgaa cccaggtgtgcgacgtcagacaacgggggagtgctcattttgaattccac tttggccgcggctcgagTGAGCTATTCCAGAAGTAGTGAAGAGGCTTTTT

TGGAGGCCTAGGCTTTTGCAAAAAGCTCCGGATCGATGCCCGGGGGATCC

ACTAGTTCTAGAGGGACAGCCCCCCCCCAAAGCCCCCAGGGATGTAATTA

CGTCCCTCCCCCGCTAGGGGGCAGCAGCGAGCCGCCCGGGGCTCCGCTCC

GGTCCGGCGCTCCCCCCGCATCCCCGAGCCGGCAGCGTGCGGGGACAGCC

CGGGCACGGGGAAGGTGGCACGGGATCGCTTTCCTCTGAACGCTTCTCGC

TGCTCTTTGAGCCTGCAGACACCTGGGGGGATACGGGGAAAAGGCCTCCA

AGGCCAGCTTCCCACAATAAGTTGGGTGAATTTTGGCTGAGCTATTCCAG

AAGTAGTGAAGAGGCTTTTTTGGAGGCCTAGGCTTTTGCAAAAAGCTCCG

GATCGATCATATATGGCAGATATACGCGTTGACATTGATTATTGACTAGT

TATTAATAGTAATCAATTACGGGGTCATTAGTTCATAGCCCATATATGGA

GTTCCGCGTTACATAACTTACGGTAAATGGCCCGCCTGGCTGACCGCCCA

ACGACCCCCGCCCATTGACGTCAATAATGACGTATGTTCCCATAGTAACG

CCAATAGGGACTTTCCATTGACGTCAATGGGTGGAGTATTTACGGTAAAC

TGCCCACTTGGCAGTACATCAAGTGTATCATATGCCAAGTACGCCCCCTA

TTGACGTCAATGACGGTAAATGGCCCGCCTGGCATTATGCCCAGTACATG

ACCTTATGGGACTTTCCTACTTGGCAGTACATCTACGTATTAGTCATCGC

TATTACCATGGTGATGCGGTTTTGGCAGTACATCAATGGGCGTGGATAGC

GGTTTGACTCACGGGGATTTCCAAGTCTCCACCCCATTGACGTCAATGGG

AGTTTGTTTTGGCACCAAAATCAACGGGACTTTCCAAAATGTCGTAACAA

CTCCGCCCCATTGACGCAAATGGGCGGTAGGCGTGTACGGTGGGAGGTCT

ATATAAGCAGAGCTCTCTGGCTAACTATCGTCGACGAGCTCGTTTAGTGA

ACCGTCAGATCGCCTGGAGACGCCATCCACGCTGTTTTGACCTCCATAGA

AGACACCGGGACCGATCCAGCCTCCGGACTCTAGCGTTTAAACTTAAGCT

TGCCACCatgaccgagtacaagcccacggtgcgcctcgccacccgcgacg acgtccccagggccgtacgcaccctcgccgccgcgttcgccgactacccc gccacgcgccacaccgtcgatccggaccgccacatcgagcgggtcaccga gctgcaagaactatcctcacgcgcgtcgggctcgacatcggcaaggtgtg ggtcgcggacgacggcgccgcggtggcggtctggaccacgccggagagcg -continued tcgaagcgggggcggtgttcgccgagatcggcccgcgcatggccgagttg agcggttcccggctggccgcgcagcaacagatggaaggcctcctggcgcc gcaccggcccaaggagcccgcgtggttcctggccaccgtcggcgtctcgc ccgaccaccagggcaagggtctgggcagcgccgtcgtgctccccggagtg gaggcggccgagcgcgccggggtgcccgccttcctggagacctccgcgcc ccgcaacctccccttctacgagcggctcggcttcaccgtcaccgccgacg tcgaggtgcccgaaggaccgcgcacctggtgcatgacccgcaagcccggt gcctgaAGCGCGGGGATCTCATGCTGGAGTTCTTCGCCCACCCCAACTTG

TTTATTGCAGCTTATAATGGTTACAAATAAAGCAATAGCATCACAAATTT

CACAAATAAAGCATTTTTTTCACTGCATTCTAGTTGTGGTTTGTCCAAAC

TCATCAATGTATCTTATCATGTCTGTAGCtGATgtATAcCTAggATCCGG

CCGGccTGCAggTGTCCTCACAGGAACGAAGTCCCTAAAGAAACAGTGGC

AGCCAGGTTTAGCCCCGGAATTGACTGGATTCCTTTTTTAGGGCCCATTG

GTATGGCTTTTTCCCCGTATCCCCCCAGGTGTCTGCAGGCTCAAAGAGCA

GCGAGAAGCGTTCAGAGGAAAGCGATCCCGTGCCACCTTCCCCGTGCCCG

GGCTGTCCCCGCACGCTGCCGGCTCGGGGATGCGGGGGGAGCGCCGGACC

GGAGCGGAGCCCCGGGCGGCTCGCTGCTGCCCCCTAGCGGGGGAGGGACG

TAATTACATCCCTGGGGGCTTTGGGGGGGGGCTGTCCCTCTAGAGCGGCC

GCCACCGCGGTGGAGCTCCAGCTTTTGTTCCCTTTAGTGAGGGTTAATTA

GATCTTAATACGACTCACTATAGGGCGAATTGGGTACCGGGCCCCCCCTC

GAGGTCGACGGTATCGATAAGCTTGATATCTATAACAAGAAAATATATAT

ATAATAAGTTATCACGTAAGTAGAACATGAAATAACAATATAATTATCGT

ATGAGTTAAATCTTAAAAGTCACGTAAAAGATAATCATGCGTCATTTTGA

CTCACGCGGTCGTTATAGTTCAAAATCAGTGACACTTACCGCATTGACAA

GCACGCCTCACGGGAGCTCCAAGCGGCGACTGAGATGTCCTAAATGCACA

GCGACGGATTCGCGCTATTTAGAAAGAGAGAGCAATATTTCAAGAATGCA

TGCGTCAATTTTACGCAGACTATCTTTCTAGGGTTAATCTAGCTGCATCA

GGATCATATCGTCGGGTCTTTTTTCCGGCTCAGTCATCGCCCAAGCTGGC

GCTATCTGGGCATCGGGGAGGAAGAAGCCCGTGCCTTTTCCCGCGAGGTT

GAAGCGGCATGGAAAGAGTTTGCCGAGGATGACTGCTGCTGCATTGACGT

TGAGCGAAAACGCACGTTTACCATGATGATTCGGGAAGGTGTGGCCATGC

ACGCCTTTAACGGTGAACTGTTCGTTCAGGCCACCTGGGATACCAGTTCG

TCGCGGCTTTTCCGGACACAGTTCCGGATGGTCAGCCCGAAGCGCATCAG

CAACCCGAACAATACCGGCGACAGCCGGAACTGCCGTGCCGGTGTGCAGA

TTAATGACAGCGGTGCGGCGCTGGGATATTACGTCAGCGAGGACGGGTAT

CCTGGCTGGATGCCGCAGAAATGGACATGGATACCCCGTGAGTTACCCGG

CGGGCGCGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCTGCATTAATG

AATCGGCCAACGCGCGGGGAGAGGCGGTTTGCGTATTGGGCGCTCTTCCG

-continued

CTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGA

TAACGCAGGAAAGAACATGTGAGCAAAAGGCCAGCAAAAGGCCAGGAACC

GTAAAAAGGCCGCGTTGCTGGCGTTTTTCCATAGGCTCCGCCCCCCTGAC

GAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTC

CTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGT

GTAGGTCGTTCGCTCCAAGCTGGGCTGTGTGCACGAACCCCCCGTTCAGC

CCGACCGCTGCGCCTTATCCGGTAACTATCGTCTTGAGTCCAACCCGGTA

AGACACGACTTATCGCCACTGGCAGCAGCCACTGGTAACAGGATTAGCAG

AGCGAGGTATGTAGGCGGTGCTACAGAGTTCTTGAAGTGGTGGCCTAACT

ACGGCTACACTAGAAGGACAGTATTTGGTATCTGCGCTCTGCTGAAGCCA

GTTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGAA

AAAAAGGATCTCAAGAAGATCCTTTGATCTTTTCTACGGGGTCTGACGCT

CAGTGGAACGAAAACTCACGTTAAGGGATTTTGGTCATGAGATTATCAAA

AAGGATCTTCACCTAGATCCTTTTAAATTAAAAATGAAGTTTTAAATCAA

TCTAAAGTATATATGAGTAAACTTGGTCTGACAGTTACCAATGCTTAATC

AGTGAGGCACCTATCTCAGCGATCTGTCTATTTCGTTCATCCATAGTTGC

CTGACTCCCCGTCGTGTAGATAACTACGATACGGGAGGGCTTACCATCTG

GCCCCAGTGCTGCAATGATACCGCGAGACCCACGCTCACCGGCTCCAGAT

TTATCAGCAATAAACCAGCCAGCCGGAAGGGCCGAGCGCAGAAGTGGTCC

TGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTC

CGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCC

GCAGTGTTATCACTCATGGTTATGGCAGCACTGCATAATTCTCTTACTGT

CATGCCATCCGTAAGATGCTTTTCTGTGACTGGTGAGTACTCAACCAAGT

CATTCTGAGAATAGTGTATGCGGCGACCGAGTTGCTCTTGCCCGGCGTCA

ATACGGGATAATACCGCGCCACATAGCAGAACTTTAAAAGTGCTCATCAT

TGGAAAACGTTCTTCGGGGCGAAAACTCTCAAGGATCTTACCGCTGTTGA

GATCCAGTTCGATGTAACCCACTCGTGCACCCAACTGATCTTCAGCATCT

TTTACTTTCACCAGCGTTTCTGGGTGAGCAAAAACAGGAAGGCAAAATGC

CGCAAAAAAGGGAATAAGGGCGACACGGAAATGTTGAATACTCAT

The sequence for the PBBG-ITRGFP construct illustrated in in FIG. 11B is shown below:

-continued

PBBG-ITRGFP (7,798 bp)

(SEQ ID NO: 27)

ACTCTTCCTTTTTCAATATTATTGAAGCATTTATCAGGGTTATTGTCTCA

TGAGCGGATACATATTTGAATGTATTTAGAAAAATAAACAAATAGGGGTT

CCGCGCACATTTCCCCGAAAAGTGCCACCTAAATTGTAAGCGTTAATATT

TTGTTAAAATTCGCGTTAAATTTTTGTTAAATCAGCTCATTTTTTAACCA

ATAGGCCGAAATCGGCAAAATCCCTTATAAATCAAAAGAATAGACCGAGA

TAGGGTTGAGTGTTGTTCCAGTTTGGAACAAGAGTCCACTATTAAAGAAC

GTGGACTCCAACGTCAAAGGGCGAAAAACCGTCTATCAGGGCGATGGCCC

ACTACGTGAACCATCACCCTAATCAAGTTTTTTGGGGTCGAGGTGCCGTA

AAGCACTAAATCGGAACCCTAAAGGGAGCCCCCGATTTAGAGCTTGACGG

GGAAAGCCGGCGAACGTGGCGAGAAAGGAAGGGAAGAAAGCGAAAGGAGC

GGGCGCTAGGGCGCTGGCAAGTGTAGCGGTCACGCTGCGCGTAACCACCA

CACCCGCCGCGCTTAATGCGCCGCTACAGGGCGCGTCCCATTCGCCATTC

AGGCTGCGCAACTGTTGGGAAGGGCGATCGGTGCGGGCCTCTTCGCTATT

ACGCCAGCTGGCGAAAGGGGGATGTGCTGCAAGGCGATTAAGTTGGGTAA

CGCCAGGGTTTTCCCAGTCACGACGTTGTAAAACGACGGCCAGTGAGCGC

GCCTCGTTCATTCACGTTTTTGAACCCGTGGAGGACGGGCAGACTCGCGG

TGCAAATGTGTTTTACAGCGTGATGGAGCAGATGAAGATGCTCGACACGC

TGCAGAACACGCAGCTAGATTAACCCTAGAAAGATAATCATATTGTGACG

TACGTTAAAGATAATCATGCGTAAAATTGACGCATGTGTTTTATCGGTCT

GTATATCGAGGTTTATTTATTAATTTGAATAGATATTAAGTTTTATTATA

TTTACACTTACATACTAATAATAAATTCAACAAACAATTTATTTATGTTT

ATTTATTTATTAAAAAAAAACAAAAACTCAAAATTTCTTCTATAAAGTAA

CAAAACTTTTATCGAATTCCTGCAGCCCGGGGGATCCACTAGTTCTAGAG

GGACAGCCCCCCCCCAAAGCCCCCAGGGATGTAATTACGTCCCTCCCCCG

CTAGGGGGCAGCAGCGAGCCGCCCGGGGCTCCGCTCCGGTCCGGCGCTCC

CCCCGCATCCCCGAGCCGGCAGCGTGCGGGGACAGCCCGGGCACGGGGAA

GGTGGCACGGGATCGCTTTCCTCTGAACGCTTCTCGCTGCTCTTTGAGCC

TGCAGACACCTGGGGGGATACGGGGAAAAGGCCTCCAAGGCCAGCTTCCC

ACAATAAGTTGGGTGAATTTTGGCTCATTCCTCCTTTCTATAGGATTGAG

GTCAGAGCTTTGTGATGGGAATTCTGTGGAATGTGTGTCAGTTAGGGTGT

GGAAAGTCCCgcGATCgcTAGcAAACGCCAGCAACGCGGCCTTTTTACGG

TTCCTGGCCTTTTGCTGGCCTTTTGCTCACATGTCCTGCAGGCAGCTGCG

CGCTCGCTCGCTCACTGAGGCCGCCCGGGCAAAGCCCGGGCGTCGGGCGA

CCTTTGGTCGCCCGGCCTCAGTGAGCGAGCGAGCGCGCAGAGAGGGAGTG

GCCAACTCCATCACTAGGGGTTCCTGCGGCCGCACGCGTGGAGCTAGTTA

TTAATAGTAATCAATTACGGGGTCATTAGTTCATAGCCCATATATGGAGT

TCCGCGTTACATAACTTACGGTAAATGGCCCGCCTGGCTGACCGCCCAAC

GACCCCCGCCCATTGACGTCAATAATGACGTATGTTCCCATAGTAACGTC

AATAGGGACTTTCCATTGACGTCAATGGGTGGAGTATTTACGGTAAACTG

CCCACTTGGCAGTACATCAAGTGTATCATATGCCAAGTACGCCCCCTATT

GACGTCAATGACGGTAAATGGCCCGCCTGGCATTATGCCCAGTACATGAC

CTTATGGGACTTTCCTACTTGGCAGTACATCTACGTATTAGTCATCGCTA

TTACCATGGTGATGCGGTTTTGGCAGTACATCAATGGGCGTGGATAGCGG

TTTGACTCACGGGGATTTCCAAGTCTCCACCCCATTGACGTCAATGGGAG

TTTGTTTTGCACCAAAATCAACGGGACTTTCCAAAATGTCGTAACAACTC

CGCCCCATTGACGCAAATGGGCGGTAGGCGTGTACGGTGGGAGGTCTATA

TAAGCAGAGCTCGTTTAGTGAACCGTCAGATCGCCTGGAGACGCCATCCA

CGCTGTTTTGACCTCCATAGAAGACACCGGGACCGATCCAGCCTCCGCGG

ATTCGAATCCCGGCCGGGAACGGTGCATTGGAACGCGGATTCCCCGTGCC

AAGAGTGACGTAAGTACCGCCTATAGAGTCTATAGGCCCACAAAAAATGC

TTTCTTCTTTTAATATACTTTTTTGTTTATCTTATTTCTAATACTTTCCC

TAATCTCTTTCTTTCAGGGCAATAATGATACAATGTATCATGCCTCTTTG

CACCATTCTAAAGAATAACAGTGATAATTTCTGGGTTAAGGCAATAGCAA

TATTTCTGCATATAAATATTTCTGCATATAAATTGTAACTGATGTAAGAG

GTTTCATATTGCTAATAGCAGCTACAATCCAGCTACCATTCTGCTTTTAT

TTTATGGTTGGGATAAGGCTGGATTATTCTGAGTCCAAGCTAGGCCCTTT

TGCTAATCATGTTCATACCTCTTATCTTCCTCCCACAGCTCCTGGGCAAC

GTGCTGGTCTGTGTGCTGGCCCATCACTTTGGCAAAGAATTGGGATTCGA

ACATCGATTGAATTCTGAATGGTGAGCAAGGGCGAGGAGCTGTTCACCGG

GGTGGTGCCCATCCTGGTCGAGCTGGACGGCGACGTAAACGGCCACAAGT

TCAGCGTGTCCGGCGAGGGCGAGGGCGATGCCACCTACGGCAAGCTGACC

CTGAAGTTCATCTGCACCACCGGCAAGCTGCCCGTGCCCTGGCCCACCCT

CGTGACCACCCTGACCTACGGCGTGCAGTGCTTCAGCCGCTACCCCGACC

ACATGAAGCAGCACGACTTCTTCAAGTCCGCCATGCCCGAAGGCTACGTC

CAGGAGCGCACCATCTTCTTCAAGGACGACGGCAACTACAAGACCCGCGC

CGAGGTGAAGTTCGAGGGCGACACCCTGGTGAACCGCATCGAGCTGAAGG

GCATCGACTTCAAGGAGGACGGCAACATCCTGGGGCACAAGCTGGAGTAC

AACTACAACAGCCACAACGTCTATATCATGGCCGACAAGCAGAAGAACGG

CATCAAGGTGAACTTCAAGATCCGCCACAACATCGAGGACGGCAGCGTGC

AGCTCGCCGACCACTACCAGCAGAACACCCCCATCGGCGACGGCCCCGTG

CTGCTGCCCGACAACCACTACCTGAGCACCCAGTCCGCCCTGAGCAAAGA

CCCCAACGAGAAGCGCGATCACATGGTCCTGCTGGAGTTCGTGACCGCCG

CCGGGATCACTCTCGGCATGGACGAGCTGTACAAGTACTCAGATCTCGAG

CTCAAGTAGGGATCCTCTAGAGTCGACCTGCAGAAGCTTGCCTCGAGCAG

CGCTGCTCGAGAGATCTACGGGTGGCATCCCTGTGACCCCTCCCCAGTGC

CTCTCCTGGCCCTGGAAGTTGCCACTCCAGTGCCCACCAGCCTTGTCCTA

ATAAAATTAAGTTGCATCATTTTGTCTGACTAGGTGTCCTTCTATAATAT

TATGGGGTGGAGGGGGGTGGTATGGAGCAAGGGGCAAGTTGGGAAGACAA

CCTGTAGGGCCTGCGGGGTCTATTGGGAACCAAGCTGGAGTGCAGTGGCA

CAATCTTGGCTCACTGCAATCTCCGCCTCCTGGGTTCAAGCGATTCTCCT

-continued

GCCTCAGCCTCCCGAGTTGTTGGGATTCCAGGCATGCATGACCAGGCTCA

GCTAATTTTTGTTTTTTTGGTAGAGACGGGGTTTCACCATATTGGCCAGG

CTGGTCTCCAACTCCTAATCTCAGGTGATCTACCCACCTTGGCCTCCCAA

ATTGCTGGGATTACAGGCGTGAACCACTGCTCCCTTCCCTGTCCTTCTGA

TTTTGTAGGTAACCACGTGCGGACCGAGCGGCCGCAGGAACCCCTAGTGA

TGGAGTTGGCCACTCCCTCTCTGCGCGCTCGCTCGCTCACTGAGGCCGGG

CGACCAAAGGTCGCCCGACGCCCGGGCTTTGCCCGGGCGGCCTCAGTGAG

CGAGCGAGCGCGCAGCTGCCTGCAGGGGCGCCTGATGCGGTATTTTCTCC

TTACGCATCTGTGCGGTATTTCACACCGCATACGTCgtaGCtGATcaATT gGCGCGCCGAATTCGTTAACAAGCTtTAATTAaCGCgtATAcCTAggATC CGGCCGGccTGCAggTGTCCTCACAGGAACGAAGTCCCTAAAGAAACAGT

GGCAGCCAGGTTTAGCCCCGGAATTGACTGGATTCCTTTTTTAGGGCCCA

TTGGTATGGCTTTTTCCCCGTATCCCCCCAGGTGTCTGCAGGCTCAAAGA

GCAGCGAGAAGCGTTCAGAGGAAAGCGATCCCGTGCCACCTTCCCCGTGC

CCGGGCTGTCCCCGCACGCTGCCGGCTCGGGGATGCGGGGGGAGCGCCGG

ACCGGAGCGGAGCCCCGGGCGGCTCGCTGCTGCCCCCTAGCGGGGGAGGG

ACGTAATTACATCCCTGGGGGCTTTGGGGGGGGGCTGTCCCTCTAGAGCG

GCCGCCACCGCGGTGGAGCTCCAGCTTTTGTTCCCTTTAGTGAGGGTTAA

TTAGATCTTAATACGACTCACTATAGGGCGAATTGGGTACCGGGCCCCCC

CTCGAGGTCGACGGTATCGATAAGCTTGATATCTATAACAAGAAAATATA

TATATAATAAGTTATCACGTAAGTAGAACATGAAATAACAATATAATTAT

CGTATGAGTTAAATCTTAAAAGTCACGTAAAAGATAATCATGCGTCATTT

TGACTCACGCGGTCGTTATAGTTCAAAATCAGTGACACTTACCGCATTGA

CAAGCACGCCTCACGGGAGCTCCAAGCGGCGACTGAGATGTCCTAAATGC

ACAGCGACGGATTCGCGCTATTTAGAAAGAGAGAGCAATATTTCAAGAAT

GCATGCGTCAATTTTACGCAGACTATCTTTCTAGGGTTAATCTAGCTGCA

TCAGGATCATATCGTCGGGTCTTTTTTCCGGCTCAGTCATCGCCCAAGCT

GGCGCTATCTGGGCATCGGGGAGGAAGAAGCCCGTGCCTTTTCCCGCGAG

GTTGAAGCGGCATGGAAAGAGTTTGCCGAGGATGACTGCTGCTGCATTGA

CGTTGAGCGAAAACGCACGTTTACCATGATGATTCGGGAAGGTGTGGCCA

TGCACGCCTTTAACGGTGAACTGTTCGTTCAGGCCACCTGGGATACCAGT

TCGTCGCGGCTTTTCCGGACACAGTTCCGGATGGTCAGCCCGAAGCGCAT

CAGCAACCCGAACAATACCGGCGACAGCCGGAACTGCCGTGCCGGTGTGC

AGATTAATGACAGCGGTGCGGCGCTGGGATATTACGTCAGCGAGGACGGG

TATCCTGGCTGGATGCCGCAGAAATGGACATGGATACCCCGTGAGTTACC

CGGCGGGCGCGCTTGGCGTAATCATGGTCATAGCTGTTTCCTGTGTGAAA

TTGTTATCCGCTCACAATTCCACACAACATACGAGCCGGAAGCATAAAGT

GTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTA

ATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGA

-continued

GCGGTATCAGCTCACTCAAAGGCGGTAATACGGTTATCCACAGAATCAGG

GGATAACGCAGGAAAGAACATGTGAGCAAAAGGCCAGCAAAAGGCCAGGA

ACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGAC

AGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCT

TCGGGAAGCGTGGCGCTTTCTCATAGCTCACGCTGTAGGTATCTCAGTTC

GGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCG

GTAAGACACGACTTATCGCCACTGGCAGCAGCCACTGGTAACAGGATTAG

CAGAGCGAGGTATGTAGGCGGTGCTACAGAGTTCTTGAAGTGGTGGCCTA

ACTACGGCTACACTAGAAGGACAGTATTTGGTATCTGCGCTCTGCTGAAG

CCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCA

GAAAAAAAGGATCTCAAGAAGATCCTTTGATCTTTTCTACGGGGTCTGAC

GCTCAGTGGAACGAAAACTCACGTTAAGGGATTTTGGTCATGAGATTATC

AAAAAGGATCTTCACCTAGATCCTTTTAAATTAAAAATGAAGTTTTAAAT

CAATCTAAAGTATATATGAGTAAACTTGGTCTGACAGTTACCAATGCTTA

ATCAGTGAGGCACCTATCTCAGCGATCTGTCTATTTCGTTCATCCATAGT

TGCCTGACTCCCCGTCGTGTAGATAACTACGATACGGGAGGGCTTACCAT

CTGGCCCCAGTGCTGCAATGATACCGCGAGACCCACGCTCACCGGCTCCA

GATTTATCAGCAATAAACCAGCCAGCCGGAAGGGCCGAGCGCAGAAGTGG

TCCTGCAACTTTATCCGCCTCCATCCAGTCTATTAATTGTTGCCGGGAAG

CTAGAGTAAGTAGTTCGCCAGTTAATAGTTTGCGCAACGTTGTTGCCATT

GCTACAGGCATCGTGGTGTCACGCTCGTCGTTTGGTATGGCTTCATTCAG

CTCCGGTTCCCAACGATCAAGGCGAGTTACATGATCCCCCATGTTGTGCA

AAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTAC

TGTCATGCCATCCGTAAGATGCTTTTCTGTGACTGGTGAGTACTCAACCA

AGTCATTCTGAGAATAGTGTATGCGGCGACCGAGTTGCTCTTGCCCGGCG

TCAATACGGGATAATACCGCGCCACATAGCAGAACTTTAAAAGTGCTCAT

CATTGGAAAACGTTCTTCGGGGCGAAAACTCTCAAGGATCTTACCGCTGT

TGAGATCCAGTTCGATGTAACCCACTCGTGCACCCAACTGATCTTCAGCA

TCTTTTACTTTCACCAGCGTTTCTGGGTGAGCAAAAACAGGAAGGCAAAA

TGCCGCAAAAAAGGGAATAAGGGCGACACGGAAATGTTGAATACTCAT

Figure 11C:
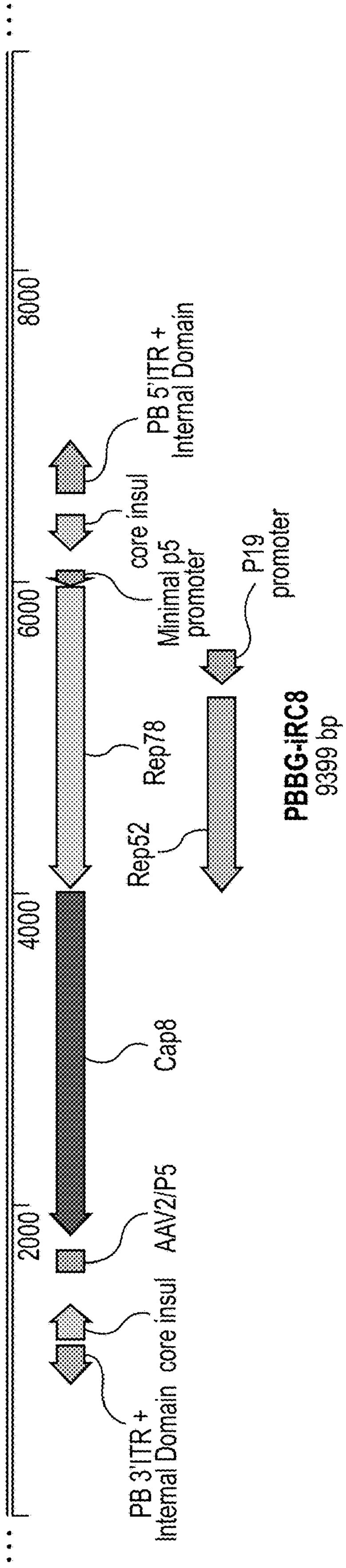

The sequence for the PBBG-iRC8 construct illustrated in in FIG. 11C is shown below:

PBBG-iRC8 (9,399 bp)

(SEQ ID NO: 28)

ACTCTTCCTTTTTCAATATTATTGAAGCATTTATCAGGGTTATTGTCTCA

TGAGCGGATACATATTTGAATGTATTTAGAAAAATAAACAAATAGGGGTT

-continued

CCGCGCACATTTCCCCGAAAAGTGCCACCTAAATTGTAAGCGTTAATATT
TTGTTAAAATTCGCGTTAAATTTTTGTTAAATCAGCTCATTTTTTAACCA
ATAGGCCGAAATCGGCAAAATCCCTTATAAATCAAAAGAATAGACCGAGA
TAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCCC
ACTACGTGAACCATCACCCTAATCAAGTTTTTTGGGGTCGAGGTGCCGTA
AAGCACTAAATCGGAACCCTAAAGGGAGCCCCCGATTTAGAGCTTGACGG
GGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCA
CACCCGCCGCGCTTAATGCGCCGCTACAGGGCGCGTCCCATTCGCCATTC
AGGCTGCGCAACTGTTGGGAAGGGCGATCGGTGCGGGCCTCTTCGCTATT
ACGCCAGCTGGCGAAAGGGGGATGTGCTGCAAGGCGATTAAGTTGGGTAA
CGCCAGGGTTTTCCCAGTCACGACGTTGTAAAACGACGGCCAGTGAGCGC
GCCTCGTTCATTCACGTTTTTGAACCCGTGGAGGACGGGCAGACTCGCGG
TGCAAATGTGTTTTACAGCGTGATGGAGCAGATGAAGATGCTCGACACGC
TGCAGAACACGCAGCTAGATTAACCCTAGAAAGATAATCATATTGTGACG
TACGTTAAAGATAATCATGCGTAAAATTGACGCATGTGTTTTATCGGTCT
GTATATCGAGGTTTATTTATTAATTTGAATAGATATTAAGTTTTATTATA
TTTACACTTACATACTAATAATAAATTCAACAAACAATTTATTTATGTTT
ATTTATTTATTAAAAAAAAACAAAAACTCAAAATTTCTTCTATAAAGTAA
CAAAACTTTTATCGAATTCCTGCAGCCCGGGGGATCCACTAGTTCTAGAG
GGACAGCCCCCCCCCAAAGCCCCCAGGGATGTAATTACGTCCCTCCCCCG
CTAGGGGGCAGCAGCGAGCCGCCCGGGGCTCCGCTCCGGTCCGGCGCTCC
CCCCGCATCCCCGAGCCGGCAGCGTGCGGGGACAGCCCGGGCACGGGGAA
GGTGGCACGGGATCGCTTTCCTCTGAACGCTTCTCGCTGCTCTTTGAGCC
TGCAGACACCTGGGGGGATACGGGGAAAAGGCCTCCAAGGCCAGCTTCCC
ACAATAAGTTGGGTGAATTTTGGCTCATTCCTCCTTTCTATAGGATTGAG
GTCAGAGCTTTGTGATGGGAATTCTGTGGAATGTGTGTCAGTTAGGGTGT
GGAAAGTCCCgcGATCgcTAGcTTAagCGCtGATcaATTgGCGCGCCGAA
TTCGTTatctgcagaattcggcttggcggctgcgcgttcaaacctcccgc
ttcaaaatggagaccctgcgtgctcactcgggcttaaatacccagcgtga
ccacatggtgtcgcaaaatgtcgcaaaacactcacgtgacctctaataca
ggacctctagagcatggaaactagataagaaagaaatacgcagagaccaa
agttcaactgaaacgaattaaacggtttattgattaacaagcaaactagt
ttacagattacgggtgaggtaacgggtgccaatggggcggggttcagagt
acacgccttctgtattaacagcaaagtccacacttgtagatttgtagtag
ttggaggtgtactggatctcggggttccagcgcttgctgttttccttctg
cagctcccattcaatttccacgctgacctgtccggtgctgtattgcgtga
tgaaagagttcagctttgactggttgaaggtggtcggaggatccgcaggt
acaggcgtgttcttgatcaggatctgaggcggaggatgtttcaggccaaa -continued gccgcccatcagcggagacgggtggaagttgccgtccgtgtgaggaatct
tggcccagatgggaccctgcaggtacacgtcccggttctgccagaccata
ccgggtaaggcccccctggctgttgacagttccaatttgaggagccgtgtt
ttgctgctgcaagttatctgccacgataccgtattcctctgtagccacag
ggttagtggttttgatttcttcctcgctggtgagcatgacatcgctgtaa
tccgcattgtctctggcagcattttgtttgccaaaaatcaggatcccgtt
actgggaaaaaaacgctcctcgtcgtctttgtgtgttgccatagcgatgc
caggattagccaatgaatttcttccattcagatggtatttggtcccagca
gtccaggcaaagttgctattgttgttttgcccggttgtcgttgagacgcg
ttgttggcggtaacagggtcctggcagccagttctttgcctgattggcca
ttgtattaggcccaccttggctgaagcccagagtctgcgtatttgccgtg
cctcctgttgtttgagtccgagacaagtagtacaggtactggtcaatcag
aggattcatcagccggtccaagctctggctgtgggcgtagctgctgtgga
aaggcacgtcctcgaaggtgtaagtaaactggaagttgttgccggttctc
agcatctgcgaaggaaagtattccaggcagtagaaggaggagcgtcccac
ggcctgactaccgttgttgagtgttaggtagccgtactggggaatcatga
acacgtccgccgggaacggaggcaggcagccctggtgggcagagccgaga
acgtacggcagctggtactccgagtccgtaaacacctggatggtgctggt
gaggttattggcgatggtcttggtgccttcattctgcgtgacctccttga
cctggatgttgaagagcttgaagctgagtctcttgggccggaatccccag
ttgttgttgatgagtcgctgccagtcacgtggtgaaaagtggcagtggaa
tctgttaaagtcaaaatacccccagggggtgctgtagccgaagtaggtgt
tgtcgttggtggctcctcccgatgtcccgttggagatttgcttgtagagg
tggttgttgtaggtgggcagggcccaggttcgggtgctggtggtgatgac
tctgtcgcccagccatgtggaatcgcaatgccaatttcccgaggaactac
ccactccgtcggcgccttcgttattgtctgccattggtgcgccaccgcct
gcagccattgtattaggtcccacaccagagggcgctgctggaggttctcc
gagaggttgagggtctggaactgactctgagtcgccagtctgaccaaaat
tgagtctttttctggcgggctgttggcctttcttgccgatgcccgtagag
gagtctggagaacgctggggtgatggctctaccggtctcttctttccagg
agccgtcttagcgccttcctcaaccagaccgagaggttcgagaacccgct
tcttggcctggaagactgctcgcccgaggttgcccccaaaagacgtatct
tcttgcagacgctcctgaaactcggcgtcggcgtggttataccgcaggta
cggattgtcacccgcctgcagctgctggtcgtaggccttgtcgtgctcga
gggccgctgcgtccgccgcgttgacgggctccccccttgtcgagtccgttg
aagggtccgaggtacttgtagccaggaagcaccagaccccggccgtcgtc
ctgcttttgctggttggctttgggcttcggggctccaggtttcagcgccc
accactcgcgaatgccctcagagaggttgtcctcgagccaatctggaaga
taaccatcggcagccatacctgatttaaatcatttattgttcaaagatgc
agtcatccaaatccacattgaccagatcgcaggcagtgcaagcgtctggc
acctttcccatgatatgatgaatgtagcacagtttctgatacgcctttttt -continued gacgacagaaacgggttgagattctgacacgggaaagcactctaaacagt
ctttctgtccgtgagtgaagcagatatttgaattctgattcattctctcg
cattgtctgcagggaaacagcatcagattcatgcccacgtgacgagaaca
tttgttttggtacctgtctgcgtagttgatcgaagcttccgcgtctgacg
tcgatggctgcgcaactgactcgcgcacccgtttgggctcacttatatct
gcgtcactgggggcgggtcttttcttggctccacccttttgacgtagaa
ttcatgctccacctcaaccacgtgatcctttgcccaccggaaaaagtctt
tgacttcctgcttggtgaccttcccaaagtcatgatccagacggcgggtg
agttcaaatttgaacatccggtcttgcaacggctgctggtgttcgaaggt
cgttgagttcccgtcaatcacggcgcacatgttggtgttggaggtgacga
tcacgggagtcgggtctatctgggccgaggacttgcatttctggtccacg
cgcaccttgcttcctccgagaatggctttggccgactccacgaccttggc
ggtcatcttcccctcctcccaccagatcaccatcttgtcgacacagtcgt
tgaagggaaagttctcattggtccagtttacgcacccgtagaagggcaca
gtgtgggctatggcctccgcgatgttggtcttcccggtagttgcaggccc
aaacagccagatggtgttcctcttgccgaactttttcgtggcccatccca
gaaagacggaagccgcatattggggatcgtacccgtttagttccaaaatt
ttataaatccgattgctggaaatgtcctccacgggctgctggcccaccag
gtagtcgggggcggttttagtcaggctcataatctttcccgcattgtcca
aggcagccttgatttgggaccgcgagttggaggccgcattgaaggagatg
tatgaggcctggtcctcctggatccactgcttctccgaggtaatcccctt
gtccacgagccacccgaccagctccatgtacctggctgaagtttttgatc
tgatcaccggcgcatcagaattgggattctgattctctttgttctgctcc
tgcgtctgcgacacgtgcgtcagatgctgcgccaccaaccgtttacgctc
cgtgagattcaaacaggcgctgtggagagaaaggcaaagtggatgtcagt
aTCTCTATCACTGATAGGGAGATCTCTATCACTGATAGGGAacttacctt
aaatactgttccatattagtccacgcccactggagctcaggctgggtttt
ggggagcaagtaattggggatgtagcactcatccaccaccttgttcccgc
ctccggcgccatttctggtctttgtgaccgcgaaccagtttggcaaagtc
ggctcgatcccgcggtaaattctctgaatcagtttttcgcgaatctgact
caggaaacgtcccaaaaccatggatttcaccccggtggtttccacgagca
cgtgcatgtggaagtagctctctcccttctcaaattgcacaaagaaaaga
gcctccggggccttactcacacggcgccattccgtcagaaagtcgcgctg
cagcttctcggccacggtcaggggtgcctgctcaatcagattcagatcca
tgtcagaatctggcggcaactcccattccttctcggccacccagttcaca
aagctgtcagaaatgccgggcagatgctcgtcaaggtcgctggggacctt
aatcacaatctcgtaaaaccccggcatGGCGGCTGCGCGTTCAAACCTCC
CGCTTCAAAATGGAGACCCTGCGTGCTCACTCGGGCgaTCTCTATCACTG
ATAGGGAGATCTCTATCACTGATAGGGAgaTTAAATAgaatggCTAggAT
CCGGCCGGccTGCAggTGTCCTCACAGGAACGAAGTCCCTAAAGAAACAG -continued TGGCAGCCAGGTTTAGCCCCGGAATTGACTGGATTCCTTTTTTAGGGCCC
ATTGGTATGGCTTTTTCCCCGTATCCCCCCAGGTGTCTGCAGGCTCAAAG
AGCAGCGAGAAGCGTTCAGAGGAAAGCGATCCCGTGCCACCTTCCCCGTG
CCCGGGCTGTCCCCGCACGCTGCCGGCTCGGGGATGCGGGGGGAGCGCCG
GACCGGAGCGGAGCCCCGGGCGGCTCGCTGCTGCCCCCTAGCGGGGGAGG
GACGTAATTACATCCCTGGGGGCTTTGGGGGGGGGCTGTCCCTCTAGAGC
GGCCGCCACCGCGGTGGAGCTCCAGCTTTTGTTCCCTTTAGTGAGGGTTA
ATTAGATCTTAATACGACTCACTATAGGGCGAATTGGGTACCGGGCCCCC
CCTCGAGGTCGACGGTATCGATAAGCTTGATATCTATAACAAGAAAATAT
ATATATAATAAGTTATCACGTAAGTAGAACATGAAATAACAATATAATTA
TCGTATGAGTTAAATCTTAAAAGTCACGTAAAAGATAATCATGCGTCATT
TTGACTCACGCGGTCGTTATAGTTCAAAATCAGTGACACTTACCGCATTG
ACAAGCACGCCTCACGGGAGCTCCAAGCGGCGACTGAGATGTCCTAAATG
CACAGCGACGGATTCGCGCTATTTAGAAAGAGAGAGCAATATTTCAAGAA
TGCATGCGTCAATTTTACGCAGACTATCTTTCTAGGGTTAATCTAGCTGC
ATCAGGATCATATCGTCGGGTCTTTTTTCCGGCTCAGTCATCGCCCAAGC
TGGCGCTATCTGGGCATCGGGGAGGAAGAAGCCCGTGCCTTTTCCCGCGA
GGTTGAAGCGGCATGGAAAGAGTTTGCCGAGGATGACTGCTGCTGCATTG
ACGTTGAGCGAAAACGCACGTTTACCATGATGATTCGGGAAGGTGTGGCC
ATGCACGCCTTTAACGGTGAACTGTTCGTTCAGGCCACCTGGGATACCAG
TTCGTCGCGGCTTTTCCGGACACAGTTCCGGATGGTCAGCCCGAAGCGCA
TCAGCAACCCGAACAATACCGGCGACAGCCGGAACTGCCGTGCCGGTGTG
CAGATTAATGACAGCGGTGCGGCGCTGGGATATTACGTCAGCGAGGACGG
GTATCCTGGCTGGATGCCGCAGAAATGGACATGGATACCCCGTGAGTTAC
CCGGCGGGCGCGCTTGGCGTAATCATGGTCATAGCTGTTTCCTGTGTGAA
ATTGTTATCCGCTCACAATTCCACACAACATACGAGCCGGAAGCATAAAG
TGTAAAGCCTGGGGTGCCTAATGAGTGAGCTAACTCACATTAATTGCGTT
GCGCTCACTGCCCGCTTTCCAGTCGGGAAACCTGTCGTGCCAGCTGCATT
AATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAG
GGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGA
CAGGACTATAAAGATACCAGGCGTTTCCCCCTGGAAGCTCCCTCGTGCGC
TCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCC
GGTAAGACACGACTTATCGCCACTGGCAGCAGCCACTGGTAACAGGATTA
GCAGAGCGAGGTATGTAGGCGGTGCTACAGAGTTCTTGAAGTGGTGGCCT -continued

AACTACGGCTACACTAGAAGGACAGTATTTGGTATCTGCGCTCTGCTGAA

GCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGC

AGAAAAAAAGGATCTCAAGAAGATCCTTTGATCTTTTCTACGGGGTCTGA

CGCTCAGTGGAACGAAAACTCACGTTAAGGGATTTTGGTCATGAGATTAT

CAAAAAGGATCTTCACCTAGATCCTTTTAAATTAAAAATGAAGTTTTAAA

TCAATCTAAAGTATATATGAGTAAACTTGGTCTGACAGTTACCAATGCTT

AATCAGTGAGGCACCTATCTCAGCGATCTGTCTATTTCGTTCATCCATAG

TTGCCTGACTCCCCGTCGTGTAGATAACTACGATACGGGAGGGCTTACCA

TCTGGCCCCAGTGCTGCAATGATACCGCGAGACCCACGCTCACCGGCTCC

AGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAA

GCTAGAGTAAGTAGTTCGCCAGTTAATAGTTTGCGCAACGTTGTTGCCAT

TGCTACAGGCATCGTGGTGTCACGCTCGTCGTTTGGTATGGCTTCATTCA

GCTCCGGTTCCCAACGATCAAGGCGAGTTACATGATCCCCCATGTTGTGC

AAAAAAGCGGTTAGCTCCTTCGGTCCTCCGATCGTTGTCAGAAGTAAGTT

GGCCGCAGTGTTATCACTCATGGTTATGGCAGCACTGCATAATTCTCTTA

CTGTCATGCCATCCGTAAGATGCTTTTCTGTGACTGGTGAGTACTCAACC

AAGTCATTCTGAGAATAGTGTATGCGGCGACCGAGTTGCTCTTGCCCGGC

GTCAATACGGGATAATACCGCGCCACATAGCAGAACTTTAAAAGTGCTCA

TCATTGGAAAACGTTCTTCGGGGCGAAAACTCTCAAGGATCTTACCGCTG

TTGAGATCCAGTTCGATGTAACCCACTCGTGCACCCAACTGATCTTCAGC

ATCTTTTACTTTCACCAGCGTTTCTGGGTGAGCAAAAACAGGAAGGCAAA

ATGCCGCAAAAAAGGGAATAAGGGCGACACGGAAATGTTGAATACTCAT

Figure 11D:
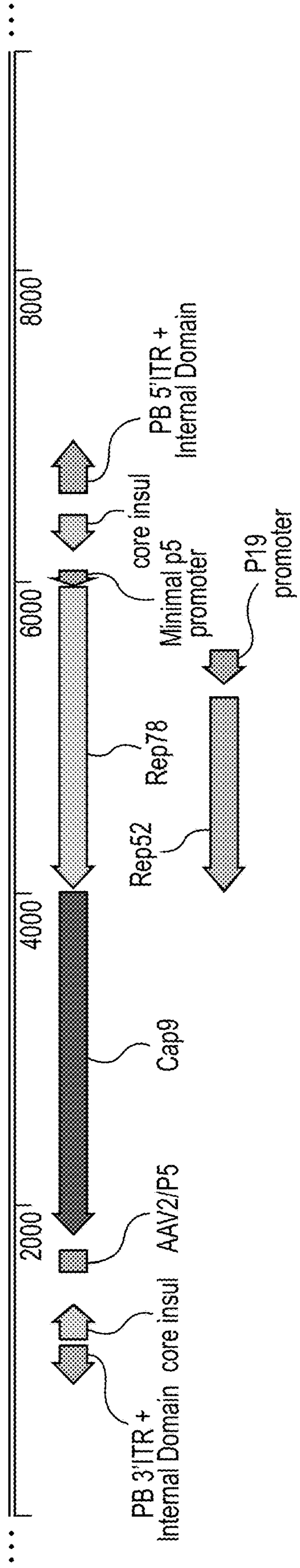

The sequence for the PBBG-iRC9 construct illustrated in in FIG. 11D is shown below:

PBBG-iRC9 (9,393 bp)

(SEQ ID NO: 29)

ACTCTTCCTTTTTCAATATTATTGAAGCATTTATCAGGGTTATTGTCTCA

TGAGCGGATACATATTTGAATGTATTTAGAAAAATAAACAAATAGGGGTT

CCGCGCACATTTCCCCGAAAAGTGCCACCTAAATTGTAAGCGTTAATATT

TTGTTAAAATTCGCGTTAAATTTTTGTTAAATCAGCTCATTTTTTAACCA

ATAGGCCGAAATCGGCAAAATCCCTTATAAATCAAAAGAATAGACCGAGA

TAGGGTTGAGTGTTGTTCCAGTTTGGAACAAGAGTCCACTATTAAAGAAC

GTGGACTCCAACGTCAAAGGGCGAAAAACCGTCTATCAGGGCGATGGCCC

ACTACGTGAACCATCACCCTAATCAAGTTTTTTGGGGTCGAGGTGCCGTA

AAGCACTAAATCGGAACCCTAAAGGGAGCCCCCGATTTAGAGCTTGACGG

GGAAAGCCGGCGAACGTGGCGAGAAAGGAAGGGAAGAAAGCGAAAGGAGC

GGGCGCTAGGGCGCTGGCAAGTGTAGCGGTCACGCTGCGCGTAACCACCA

CACCCGCCGCGCTTAATGCGCCGCTACAGGGCGCGTCCCATTCGCCATTC

AGGCTGCGCAACTGTTGGGAAGGGCGATCGGTGCGGGCCTCTTCGCTATT

-continued

ACGCCAGCTGGCGAAAGGGGGATGTGCTGCAAGGCGATTAAGTTGGGTAA

CGCCAGGGTTTTCCCAGTCACGACGTTGTAAAACGACGGCCAGTGAGCGC

GCCTCGTTCATTCACGTTTTTGAACCCGTGGAGGACGGGCAGACTCGCGG

TGCAAATGTGTTTTACAGCGTGATGGAGCAGATGAAGATGCTCGACACGC

TGCAGAACACGCAGCTAGATTAACCCTAGAAAGATAATCATATTGTGACG

TACGTTAAAGATAATCATGCGTAAAATTGACGCATGTGTTTTATCGGTCT

GTATATCGAGGTTTATTTATTAATTTGAATAGATATTAAGTTTTATTATA

TTTACACTTACATACTAATAATAAATTCAACAAACAATTTATTTATGTTT

ATTTATTTATTAAAAAAAAACAAAAACTCAAAATTTCTTCTATAAAGTAA

CAAAACTTTTATCGAATTCCTGCAGCCCGGGGGATCCACTAGTTCTAGAG

GGACAGCCCCCCCCCAAAGCCCCCAGGGATGTAATTACGTCCCTCCCCCG

CTAGGGGGCAGCAGCGAGCCGCCCGGGGCTCCGCTCCGGTCCGGCGCTCC

CCCCGCATCCCCGAGCCGGCAGCGTGCGGGGACAGCCCGGGCACGGGGAA

GGTGGCACGGGATCGCTTTCCTCTGAACGCTTCTCGCTGCTCTTTGAGCC

TGCAGACACCTGGGGGGATACGGGGAAAAGGCCTCCAAGGCCAGCTTCCC

ACAATAAGTTGGGTGAATTTTGGCTCATTCCTCCTTTCTATAGGATTGAG

GTCAGAGCTTTGTGATGGGAATTCTGTGGAATGTGTGTCAGTTAGGGTGT

GGAAAGTCCCgcGATCgcTAGcTTAagCGCtGATcaATTgGCGCGCCGAA

TTCGTTatctgcagaattcggcttggcggctgcgcgttcaaacctcccgc ttcaaaatggagaccctgcgtgctcactcgggcttaaatacccagcgtga ccacatggtgtcgcaaaatgtcgcaaaacactcacgtgacctctaataca ggacctctagagcatggaaactagataagaaagaaatacgcagagaccaa agttcaactgaaacgaattaaacggtttattgattaacaagcaaactagt

TTACAGATTACGAGTCAGGTATCTGGTGCCAATGGGGCGGGGTTCACTAT

ATACACCTTCAGTATTAACAGCAAATTCAACATTATTAGACTTGTAATAG

TTGGAAGTGTACTGGATCTCCGGGTTCCAGCGCTTGCTGTTTTCCTTCTG

CAGCTCCCACTCGATCTCCACGCTGACTTGGCCAGTAGAATACTGGGTGA

TGAAAGAGTTCAGCTTGTCCTTGTTGAAGGCCGTTGGAGGATCCGCAGGT

ACAGGTGTGTTTTTGATGAGGATCTGAGGAGGCGGGTGCTTCATTCCAAA

CCCTCCCATCAGCGGAGAAGGGTGAAAGTTGCCGTCCGTGTGAGGAATTT

TGGCCCAAATGGGTCCTTGCAGGTACACATCTCTGTCCTGCCAAACCATA

CCCGGAAGTATTCCTTGGTTTTGAACCCAGCCGGTCTGCGCCTGTGCTTG

GGCACTCTGGTGGTTTGTGGCCACTTGTCCATAGGACTCCGTTGCTACCG

GGTTAGTAGTTTTAATTTCTTCTTCGTTGGTTATCATGACTTTGTCCGCA

TCCACGTTGTCTCTTCCAGTTCCTTGTTTGCCAAAAATTAAAGATCCAGA

CAAAGGAAAGAAACGGTCCTCTCCTTCTTTGTGGCTGGCCATAGCAGGTC

CAGGATTCATCAAGCTATTACGTCCATTGAGAGCCCAAGAAGAAGCTCCA

GGCCAAGCAAATTCGCTGTTGTTGTTTTGAGTCACAGTGGTTGAGACACG

TTGTTGTCGGTAGCTGGGTCCAGGTATGTAGTTTCTTCCCTGGACAGCCA

TGTTGCTGGGTCCGGCCACACTGAATTTTAGCGTTTGTTGATTCTGTCCA

-continued

GAACCGTTAATAGTCTTTGAGAGATAGTACAAGTATTGGTCGATGAGTGG

ATTCATTAGTCGGTCCAGGCTTTGGCTGTGAGCGTAGCTGCTATGGAAAG

GTACGTTCTCAAACTCGTAGCTGAACTGGAAGTTGTTACCCGTTCTTAGC

ATTTGCGACGGGAAATATTCCAGGCAGTAAAAGGACGAACGACCCACGGC

CTGGCTTCCATCATTAAGCGTCAGATACCCGTACTGAGGAATCATGAAAA

CGTCCGCTGGGAACGGCGGGAGGCAGCCCTCGTGAGCCGACCCGAGCACG

TACGGGAGCTGATAGTCTGAGTCCGTGAAGACCTGGACCGTGCTGGTAAG

GTTATTGGCGATGGTCTTGACTCCATTGTTGTCCGTAACCTCTTTGACCT

GAATGTTGAAGAGCTTGAAGTTGAGTCGCTTAGGCCGGAATCCCCAGTTG

TTGTTGATGAGTCGCTGCCAGTCACGTGGTGAGAAGTGGCAGTGGAATCT

GTTGAAGTCAAAATACCCCCAGGGGGTGCTGTAGCCGAAGTAGGCGTTGT

CATTTGAAGATCCTCCAGATGTGCTGTTGGAGATTTGCTTGTAGAGGTGA

TTGTTGTAGGTGGGCAGGGCCCAGGTTCGGGTGCTGGTGGTGATGACTCT

GTCCCCCAGCCATTGGGAATCGCAATGCCAATTTCCCGAGGAACTACCCA

CTCCATCGGCACCTTCGTTATTGTCTGCCACTGGTGCGCCACCACCTGAA

GCCATTGTAAGAGATCCCACACCTGAGGGGGCTGCGGGAGGTTCTCCGAT

TGGTTGAGGGTCTGGGACTGACTCTGTGTCGCCAGTCTGACCGAAATTGA

GTCTCTTTTTAGCGGGCTGTGCACCCGATTTGCCAATACCCGCGGAGGAG

TCCGGTTCCTGAGGAGACTGCTCTACAGGCCTCTTCTTTCCAGGAGCCGT

CTTAGCCGCTTCCTCAACCAGACCAAGAGGTTCAAGAAGCCTCTTTTTGG

CCTGGAAGACTGCTCGCCCGAGGTTGCCCCCAAAAGACGTATCTTCTTTG

AGCCGCTCCTGGAACTCGGCGTCGGCGTGGTTGTACTTGAGGTACGGGTT

GTCTCCGGCCTTGAGCTGCTGGTCGTAGGCCTTGTCGTGCTCGAGGGCCG

CCGCGTCTGCTGCGTTGACCGGCTCCCCCTTGTCGAGTCCGTTGCCGGGT

CCAAGGTATTTGTAACCCGGAAGCACAAGACCTCGAGCGTTGTCTTGATG

TTGTTGATTTGCCTTGGGTTGAGGGGCTCCAGGTTTCAAAGCCCACCACT

CGCGAATTCCTTCACTAAGGTTGTCCTCGAGCCAATCTGGAAGATAACCA

TCGGCAGCCATacctgatttaaatcatttattgttcaaagatgcagtcat ccaaatccacattgaccagatcgcaggcagtgcaagcgtctggcaccttt cccatgatatgatgaatgtagcacagtttctgatacgcctttttgacgac agaaacgggttgagattctgacacgggaaagcactctaaacagtctttct gtccgtgagtgaagcagatatttgaattctgattcattctctcgcattgt ctgcagggaaacagcatcagattcatgcccacgtgacgagaacatttgtt ttggtacctgtctgcgtagttgatcgaagcttccgcgtctgacgtcgatg gctgcgcaactgactcgcgcacccgtttgggctcacttatatctgcgtca ctgggggcgggtcttttcttggctccacccttttttgacgtagaattcatg ctccacctcaaccacgtgatcctttgcccaccggaaaaagtctttgactt cctgcttggtgaccttcccaaagtcatgatccagacggcgggtgagttca aatttgaacatccggtcttgcaacggctgctggtgttcgaaggtcgttga gttcccgtcaatcacggcgcacatgttggtgttggaggtgacgatcacgg gagtcgggtctatctgggccgaggacttgcatttctggtccacgcgcacc -continued ttgcttcctccgagaatggctttggccgactccacgaccttggcggtcat cttcccctcctcccaccagatcaccatcttgtcgacacagtcgttgaagg gaaagttctcattggtccagtttacgcacccgtagaagggcacagtgtgg gctatggcctccgcgatgttggtcttcccggtagttgcaggcccaaacag ccagatggtgttcctcttgccgaactttttcgtggcccatcccagaaaga cggaagccgcatattggggatcgtacccgtttagttccaaaattttataa atccgattgctggaaatgtcctccacgggctgctggcccaccaggtagtc gggggcggttttagtcaggctcataatctttcccgcattgtccaaggcag ccttgatttgggaccgcgagttggaggccgcattgaaggagatgtatgag gcctggtcctcctggatccactgcttctccgaggtaatccccttgtccac gagccacccgaccagctccatgtacctggctgaagtttttgatctgatca ccggcgcatcagaattgggattctgattctctttgttctgctcctgcgtc tgcgacacgtgcgtcagatgctgcgccaccaaccgtttacgctccgtgag attcaaacaggcgctgtggagagaaaggcaaagtggatgtcagtaTCTCT ATCACTGATAGGGAGATCTCTATCACTGATAGGGAacttaccttaaatac tgttccatattagtccacgcccactggagctcaggctgggttttggggag caagtaattggggatgtagcactcatccaccaccttgttcccgcctccgg cgccatttctggtctttgtgaccgcgaaccagtttggcaaagtcggctcg atcccgcggtaaattctctgaatcagtttttcgcgaatctgactcaggaa acgtcccaaaaccatggatttcaccccggtggtttccacgagcacgtgca tgtggaagtagctctctcccttctcaaattgcacaaagaaaagagcctcc ggggccttactcacacggcgccattccgtcagaaagtcgcgctgcagctt ctcggccacggtcaggggtgcctgctcaatcagattcagatccatgtcag aatctggcggcaactcccattccttctcggccacccagttcacaaagctg tcagaaatgccgggcagatgctcgtcaaggtcgctggggaccttaatcac aatctcgtaaaaccccggcatGGCGGCTGCGCGTTCAAACCTCCCGCTTC AAAATGGAGACCCTGCGTGCTCACTCGGGCgaTCTCTATCACTGATAGGG AGATCTCTATCACTGATAGGGAgaTTAAATAgaatggCTAggATCCGGCC GGccTGCAggTGTCCTCACAGGAACGAAGTCCCTAAAGAAACAGTGGCAG

CCAGGTTTAGCCCCGGAATTGACTGGATTCCTTTTTTAGGGCCCATTGGT

ATGGCTTTTTCCCCGTATCCCCCCAGGTGTCTGCAGGCTCAAAGAGCAGC

GAGAAGCGTTCAGAGGAAAGCGATCCCGTGCCACCTTCCCCGTGCCCGGG

CTGTCCCCGCACGCTGCCGGCTCGGGGATGCGGGGGGAGCGCCGGACCGG

AGCGGAGCCCCGGGCGGCTCGCTGCTGCCCCCTAGCGGGGGAGGGACGTA

ATTACATCCCTGGGGGCTTTGGGGGGGGGCTGTCCCTCTAGAGCGGCCGC

CACCGCGGTGGAGCTCCAGCTTTTGTTCCCTTTAGTGAGGGTTAATTAGA

TCTTAATACGACTCACTATAGGGCGAATTGGGTACCGGGCCCCCCCTCGA

GGTCGACGGTATCGATAAGCTTGATATCTATAACAAGAAAATATATATAT

AATAAGTTATCACGTAAGTAGAACATGAAATAACAATATAATTATCGTAT

GAGTTAAATCTTAAAAGTCACGTAAAAGATAATCATGCGTCATTTTGACT

-continued

CACGCGGTCGTTATAGTTCAAAATCAGTGACACTTACCGCATTGACAAGC

ACGCCTCACGGGAGCTCCAAGCGGCGACTGAGATGTCCTAAATGCACAGC

GACGGATTCGCGCTATTTAGAAAGAGAGAGCAATATTTCAAGAATGCATG

CGTCAATTTTACGCAGACTATCTTTCTAGGGTTAATCTAGCTGCATCAGG

ATCATATCGTCGGGTCTTTTTTCCGGCTCAGTCATCGCCCAAGCTGGCGC

TATCTGGGCATCGGGGAGGAAGAAGCCCGTGCCTTTTCCCGCGAGGTTGA

AGCGGCATGGAAAGAGTTTGCCGAGGATGACTGCTGCTGCATTGACGTTG

AGCGAAAACGCACGTTTACCATGATGATTCGGGAAGGTGTGGCCATGCAC

GCCTTTAACGGTGAACTGTTCGTTCAGGCCACCTGGGATACCAGTTCGTC

GCGGCTTTTCCGGACACAGTTCCGGATGGTCAGCCCGAAGCGCATCAGCA

ACCCGAACAATACCGGCGACAGCCGGAACTGCCGTGCCGGTGTGCAGATT

AATGACAGCGGTGCGGCGCTGGGATATTACGTCAGCGAGGACGGGTATCC

TGGCTGGATGCCGCAGAAATGGACATGGATACCCCGTGAGTTACCCGGCG

GGCGCGCTTGGCGTAATCATGGTCATAGCTGTTTCCTGTGTGAAATTGTT

ATCCGCTCACAATTCCACACAACATACGAGCCGGAAGCATAAAGTGTAAA

GCCTGGGGTGCCTAATGAGTGAGCTAACTCACATTAATTGCGTTGCGCTC

ACTGCCCGCTTTCCAGTCGGGAAACCTGTCGTGCCAGCTGCATTAATGAA

TCGGCCAACGCGCGGGGAGAGGCGGTTTGCGTATTGGGCGCTCTTCCGCT

TCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATA

ACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCT

GTTCCGACCCTGCCGCTTACCGGATACCTGTCCGCCTTTCTCCCTTCGGG

AAGCGTGGCGCTTTCTCATAGCTCACGCTGTAGGTATCTCAGTTCGGTGT

AGGTCGTTCGCTCCAAGCTGGGCTGTGTGCACGAACCCCCCGTTCAGCCC

GACCGCTGCGCCTTATCCGGTAACTATCGTCTTGAGTCCAACCCGGTAAG

ACACGACTTATCGCCACTGGCAGCAGCCACTGGTAACAGGATTAGCAGAG

CGAGGTATGTAGGCGGTGCTACAGAGTTCTTGAAGTGGTGGCCTAACTAC

GGCTACACTAGAAGGACAGTATTTGGTATCTGCGCTCTGCTGAAGCCAGT

TACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCA

GTGGAACGAAAACTCACGTTAAGGGATTTTGGTCATGAGATTATCAAAAA

GGATCTTCACCTAGATCCTTTTAAATTAAAAATGAAGTTTTAAATCAATC

TAAAGTATATATGAGTAAACTTGGTCTGACAGTTACCAATGCTTAATCAG

TGAGGCACCTATCTCAGCGATCTGTCTATTTCGTTCATCCATAGTTGCCT

GACTCCCCGTCGTGTAGATAACTACGATACGGGAGGGCTTACCATCTGGC

CCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTG

-continued

CAACTTTATCCGCCTCCATCCAGTCTATTAATTGTTGCCGGGAAGCTAGA

GTAAGTAGTTCGCCAGTTAATAGTTTGCGCAACGTTGTTGCCATTGCTAC

AGGCATCGTGGTGTCACGCTCGTCGTTTGGTATGGCTTCATTCAGCTCCG

GTTCCCAACGATCAAGGCGAGTTACATGATCCCCCATGTTGTGCAAAAAA

GCGGTTAGCTCCTTCGGTCCTCCGATCGTTGTCAGAAGTAAGTTGGCCGC

AGTGTTATCACTCATGGTTATGGCAGCACTGCATAATTCTCTTACTGTCA

TGCCATCCGTAAGATGCTTTTCTGTGACTGGTGAGTACTCAACCAAGTCA

TTCTGAGAATAGTGTATGCGGCGACCGAGTTGCTCTTGCCCGGCGTCAAT

ACGGGATAATACCGCGCCACATAGCAGAACTTTAAAAGTGCTCATCATTG

GAAAACGTTCTTCGGGGCGAAAACTCTCAAGGATCTTACCGCTGTTGAGA

TCCAGTTCGATGTAACCCACTCGTGCACCCAACTGATCTTCAGCATCTTT

TACTTTCACCAGCGTTTCTGGGTGAGCAAAAACAGGAAGGCAAAATGCCG

CAAAAAAGGGAATAAGGGCGACACGGAAATGTTGAATACTCAT

Figure 11E:
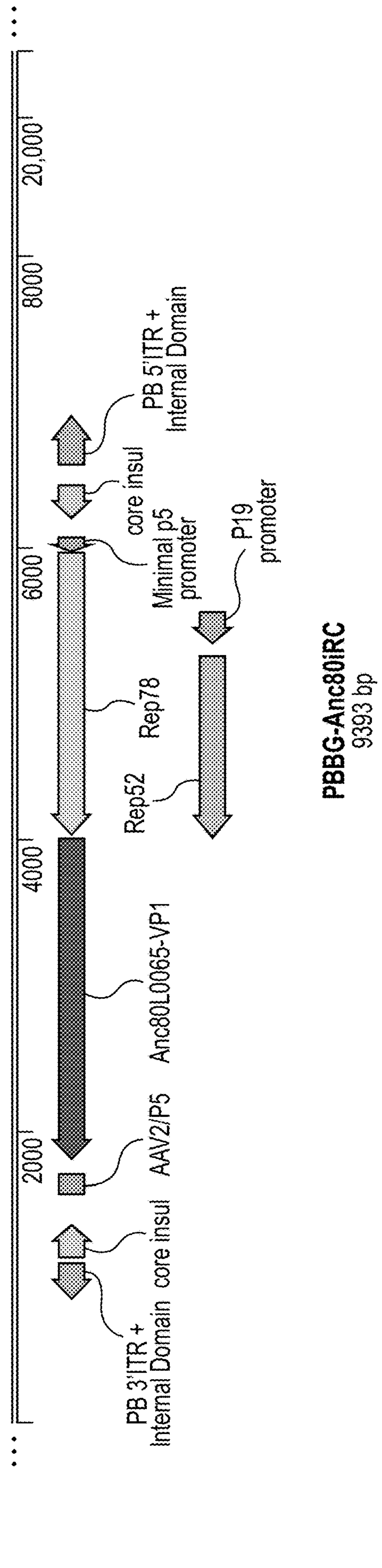

The sequence for the PBBG-Anc80iRC construct illustrated in in FIG. 11E is shown below:

PBBG-Anc80iRC (9,393 bp)
(SEQ ID NO: 30)

ACTCTTCCTTTTTCAATATTATTGAAGCATTTATCAGGGTTATTGTCTCA

TGAGCGGATACATATTTGAATGTATTTAGAAAAATAAACAAATAGGGGTT

CCGCGCACATTTCCCCGAAAAGTGCCACCTAAATTGTAAGCGTTAATATT

TTGTTAAAATTCGCGTTAAATTTTTGTTAAATCAGCTCATTTTTTAACCA

ATAGGCCGAAATCGGCAAAATCCCTTATAAATCAAAAGAATAGACCGAGA

TAGGGTTGAGTGTTGTTCCAGTTTGGAACAAGAGTCCACTATTAAAGAAC

GTGGACTCCAACGTCAAAGGGCGAAAAACCGTCTATCAGGGCGATGGCCC

ACTACGTGAACCATCACCCTAATCAAGTTTTTTGGGGTCGAGGTGCCGTA

AAGCACTAAATCGGAACCCTAAAGGGAGCCCCCGATTTAGAGCTTGACGG

GGAAAGCCGGCGAACGTGGCGAGAAAGGAAGGGAAGAAAGCGAAAGGAGC

GGGCGCTAGGGCGCTGGCAAGTGTAGCGGTCACGCTGCGCGTAACCACCA

CACCCGCCGCGCTTAATGCGCCGCTACAGGGCGCGTCCCATTCGCCATTC

AGGCTGCGCAACTGTTGGGAAGGGCGATCGGTGCGGGCCTCTTCGCTATT

ACGCCAGCTGGCGAAAGGGGGATGTGCTGCAAGGCGATTAAGTTGGGTAA

CGCCAGGGTTTTCCCAGTCACGACGTTGTAAAACGACGGCCAGTGAGCGC

GCCTCGTTCATTCACGTTTTTGAACCCGTGGAGGACGGGCAGACTCGCGG

TGCAAATGTGTTTTACAGCGTGATGGAGCAGATGAAGATGCTCGACACGC

TGCAGAACACGCAGCTAGATTAACCCTAGAAAGATAATCATATTGTGACG

TACGTTAAAGATAATCATGCGTAAAATTGACGCATGTGTTTTATCGGTCT

GTATATCGAGGTTTATTTATTAATTTGAATAGATATTAAGTTTTATTATA

TTTACACTTACATACTAATAATAAATTCAACAAACAATTTATTTATGTTT

ATTTATTTATTAAAAAAAAACAAAAACTCAAAATTTCTTCTATAAAGTAA

CAAAACTTTTATCGAATTCCTGCAGCCCGGGGGATCCACTAGTTCTAGAG

GGACAGCCCCCCCCCAAAGCCCCCAGGGATGTAATTACGTCCCTCCCCCG

-continued

CTAGGGGGCAGCAGCGAGCCGCCCGGGGCTCCGCTCCGGTCCGGCGCTCC
CCCCGCATCCCCGAGCCGGCAGCGTGCGGGGACAGCCCGGGCACGGGGAA
GGTGGCACGGGATCGCTTTCCTCTGAACGCTTCTCGCTGCTCTTTGAGCC
TGCAGACACCTGGGGGGATACGGGGAAAAGGCCTCCAAGGCCAGCTTCCC
ACAATAAGTTGGGTGAATTTTGGCTCATTCCTCCTTTCTATAGGATTGAG
GTCAGAGCTTTGTGATGGGAATTCTGTGGAATGTGTGTCAGTTAGGGTGT
GGAAAGTCCCgcGATCgcTAGcTTAagCGCtGATcaATTgGCGCGCCGAA
TTCGTTatctgcagaattcggcttggcggctgcgcgttcaaacctcccgc
ttcaaaatggagaccctgcgtgctcactcgggcttaaatacccagcgtga
ccacatggtgtcgcaaaatgtcgcaaaacactcacgtgacctctaataca
ggacctctagagcatggaaactagataagaaagaaatacgcagagaccaa
agttcaactgaaacgaattaaacggtttattgattaacaagcaaactagt
ttacagattacgggtgaggtaacgggtgccgatggggcgaggctcagaat
aaacgccatttgtgtcaacagcaaagtccacatttgtagatttgttgtag
ttggaagtgtattgaatctctgggttccagcgtttgctgttttctttctg
cagctcccattcaatttccacgctgacctgtccggtgctgtactgcgtga
tgaacgacgcaaacttagctggactgaaggtagttggaggattcgcggga
acaggtgtattcttaatcaggatctgaggaggcgggtgtttcagtccaaa
gcctcccatcagcggcgagggatgaaagtgtccgtccgtgtgaggaatct
tggcccagataggaccctgcaggtacacgtcccggtcctgccagaccatg
ccaggtaaggctccttgactgttgacggtccctgtagcaggagcggtgtt
ggccgattgcaggttagtggccaccgtgccgtactcttctgtggccactg
ggttggtggttttaatttcttcctcgttggttatcataacgttgtcaagg
tccacgttgctatttccagctccctgtttcccaaatattaagactccgct
catcggaaaaaatttgtcttcgtcgtccttgtgggttgccatagcgggac
cgggatttaccagagagtctctgccattcagatgatacttggtggcaccg
gtccaggcaaagttgctgttgttattttgattggttgtcttggagacgcg
ttgctgccggtagcagggcccgggtagccagtttttggcctgattcgcca
tgctactaggcccggcctgagaaaattgcaacgtccgatttcctgcggta
ccactcgtggtctgagtccgagacaggtagtacaggtactggtcgatgag
gggttcatcagccggtccaggctttggctgtgcgcgtagctgctgtgaa
aaggcacgtcctcaaacgtgtagctgaactgaaagttgttgcccgttctc
agcatttgagaaggaaagtattccaggcagtagaaggaggaacggcccac
ggcctgactgccattgttcagagtcaggtacccgtactgaggaatcatga
agacgtccgccgggaacggaggcaggcagccctggtgcgcagagccgagg
acgtacgggagctggtattccgagtccgtaaagacctgaaccgtgctggt
aaggttattggcgatggtcgtggtgccatcattcgtcgtgacctccttga
cctggatgttgaagagcttgaagttgagcttcttgggccggaatccccag
ttgttgttgatgagtcgctgccagtcacgtggtgagaagtggcagtggaa
tctgttaaagtcaaaatacccccaggggggtgctgtagccgaagtaggtgt -continued tgtcgttggtgctgcctcccgattggctggagatttgcttgtagaggtgg
ttgttgtaggtggggagggcccaggttcgggtgctggtggtgatgactct
gtcgcccagccatgtggaatcgcaatgccaatttcctgaggcgttaccca
ctccgtcggcgccttcgttattgtctgccattggagcgccaccgcctgca
gccattgtattagatcccacaccagaggggggctgcggggggttctccgag
tggttgagggtcgggcactgactctgagtcgccagtctgcccaaagttga
gtctctttctcgcgggctgctggcctttcttgccgatgcccgaagaggag
tctggttcctggggtgattgctctaccggtctcttctttccaggagccgt
cttagcgccttcctcaaccagaccgagaggttcgagaacccgcttcttgg
cctggaagactgctcgcccgaggttgcccccaaaagacgtatcttcttgc
agacgctcctgaaactcggcgtcggcgtggttataccgcaggtacggatt
gtcacccgctttgagctgctggtcgtaggccttgtcgtgctcgagggccg
ctgcgtccgccgcgttgacgggctccccccttgtcgagtccgttgaagggt
ccgaggtacttgtagccaggaagcaccagaccccggccgtcgtcctgctt
ttgctggttggctttgggtttcggggctccaggtttcaagtcccaccact
cgcgaatgccctcagagaggttgtcctcgagccaatctggaagataacca
tcggcagccatacctgatttaaatcatttattgttcaaagatgcagtcat
ccaaatccacattgaccagatcgcaggcagtgcaagcgtctggcaccttt
cccatgatatgatgaatgtagcacagtttctgatacgcctttttgacgac
agaaacgggttgagattctgacacgggaaagcactctaaacagtctttct
gtccgtgagtgaagcagatatttgaattctgattcattctctcgcattgt
ctgcagggaaacagcatcagattcatgcccacgtgacgagaacatttgtt
ttggtacctgtctgcgtagttgatcgaagcttccgcgtctgacgtcgatg
gctgcgcaactgactcgcgcacccgtttgggctcacttatatctgcgtca
ctgggggcgggtcttttcttggctccaccctttttgacgtagaattcatg
ctccacctcaaccacgtgatcctttgcccaccggaaaaagtctttgactt
cctgcttggtgaccttcccaaagtcatgatccagacggcgggtgagttca
aatttgaacatccggtcttgcaacggctgctggtgttcgaaggtcgttga
gttcccgtcaatcacggcgcacatgttggtgttggaggtgacgatcacgg
gagtcgggtctatctgggccgaggacttgcatttctggtccacgcgcacc
ttgcttcctccgagaatggctttggccgactccacgaccttggcggtcat
cttcccctcctcccaccagatcaccatcttgtcgacacagtcgttgaagg
gaaagttctcattggtccagtttacgcacccgtagaagggcacagtgtgg
gctatggcctccgcgatgttggtcttcccggtagttgcaggcccaaacag
ccagatggtgttcctcttgccgaactttttcgtggcccatcccagaaaga
cggaagccgcatattggggatcgtacccgtttagttccaaaattttataa
atccgattgctggaaatgtcctccacgggctgctggcccaccaggtagtc
gggggcggttttagtcaggctcataatctttcccgcattgtccaaggcag
ccttgatttgggaccgcgagttggaggccgcattgaaggagatgtatgag
gcctggtcctcctggatccactgcttctccgaggtaatccccttgtccac
gagccacccgaccagctccatgtacctggctgaagtttttgatctgatca -continued ccggcgcatcagaattgggattctgattctctttgttctgctcctgcgtc
tgcgacacgtgcgtcagatgctgcgccaccaaccgtttacgctccgtgag
attcaaacaggcgctgtggagagaaaggcaaagtggatgtcagtaTCTCT
ATCACTGATAGGGAGATCTCTATCACTGATAGGGAacttaccttaaatac
tgttccatattagtccacgcccactggagctcaggctgggttttggggag
caagtaattggggatgtagcactcatccaccaccttgttcccgcctccgg
cgccatttctggtctttgtgaccgcgaaccagtttggcaaagtcggctcg
atcccgcggtaaattctctgaatcagtttttcgcgaatctgactcaggaa
acgtcccaaaaccatggatttcaccccggtggtttccacgagcacgtgca
tgtggaagtagctctctcccttctcaaattgcacaaagaaaagagcctcc
ggggccttactcacacggcgccattccgtcagaaagtcgcgctgcagctt
ctcggccacggtcaggggtgcctgctcaatcagattcagatccatgtcag
aatctggcggcaactcccattccttctcggccacccagttcacaaagctg
tcagaaatgccgggcagatgctcgtcaaggtcgctggggaccttaatcac
aatctcgtaaaaccccggcatGGCGGCTGCGCGTTCAAACCTCCCGCTTC
AAAATGGAGACCCTGCGTGCTCACTCGGGCgaTCTCTATCACTGATAGGG
AGATCTCTATCACTGATAGGGAgaTTAAATAgaatggCTAggATCCGGCC
GGccTGCAggTGTCCTCACAGGAACGAAGTCCCTAAAGAAACAGTGGCAG
CCAGGTTTAGCCCCGGAATTGACTGGATTCCTTTTTTAGGGCCCATTGGT
ATGGCTTTTTCCCCGTATCCCCCCAGGTGTCTGCAGGCTCAAAGAGCAGC
GAGAAGCGTTCAGAGGAAAGCGATCCCGTGCCACCTTCCCCGTGCCCGGG
CTGTCCCCGCACGCTGCCGGCTCGGGGATGCGGGGGGAGCGCCGGACCGG
AGCGGAGCCCCGGGCGGCTCGCTGCTGCCCCCTAGCGGGGGAGGGACGTA
ATTACATCCCTGGGGGCTTTGGGGGGGGGCTGTCCCTCTAGAGCGGCCGC
CACCGCGGTGGAGCTCCAGCTTTTGTTCCCTTTAGTGAGGGTTAATTAGA
TCTTAATACGACTCACTATAGGGCGAATTGGGTACCGGGCCCCCCCTCGA
GGTCGACGGTATCGATAAGCTTGATATCTATAACAAGAAAATATATATAT
AATAAGTTATCACGTAAGTAGAACATGAAATAACAATATAATTATCGTAT
GAGTTAAATCTTAAAAGTCACGTAAAAGATAATCATGCGTCATTTTGACT
CACGCGGTCGTTATAGTTCAAAATCAGTGACACTTACCGCATTGACAAGC
ACGCCTCACGGGAGCTCCAAGCGGCGACTGAGATGTCCTAAATGCACAGC
GACGGATTCGCGCTATTTAGAAAGAGAGAGCAATATTTCAAGAATGCATG
CGTCAATTTTACGCAGACTATCTTTCTAGGGTTAATCTAGCTGCATCAGG
ATCATATCGTCGGGTCTTTTTTCCGGCTCAGTCATCGCCCAAGCTGGCGC
TATCTGGGCATCGGGGAGGAAGAAGCCCGTGCCTTTTCCCGCGAGGTTGA
AGCGGCATGGAAAGAGTTTGCCGAGGATGACTGCTGCTGCATTGACGTTG
AGCGAAAACGCACGTTTACCATGATGATTCGGGAAGGTGTGGCCATGCAC
GCCTTTAACGGTGAACTGTTCGTTCAGGCCACCTGGGATACCAGTTCGTC
GCGGCTTTTCCGGACACAGTTCCGGATGGTCAGCCCGAAGCGCATCAGCA
ACCCGAACAATACCGGCGACAGCCGGAACTGCCGTGCCGGTGTGCAGATT -continued AATGACAGCGGTGCGGCGCTGGGATATTACGTCAGCGAGGACGGGTATCC
TGGCTGGATGCCGCAGAAATGGACATGGATACCCCGTGAGTTACCCGGCG
GGCGCGCTTGGCGTAATCATGGTCATAGCTGTTTCCTGTGTGAAATTGTT
ATCCGCTCACAATTCCACACAACATACGAGCCGGAAGCATAAAGTGTAAA
GCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAA
TCGGCCAACGCGCGGGGAGAGGCGGTTTGCGTATTGGGCGCTCTTCCGCT
TCCTCGCTCACTGACTCGCTGCGCTCGGTCGTTCGGCTGCGGCGAGCGGT
ATCAGCTCACTCAAAGGCGGTAATACGGTTATCCACAGAATCAGGGGATA
ACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAG
ACACGACTTATCGCCACTGGCAGCAGCCACTGGTAACAGGATTAGCAGAG
CGAGGTATGTAGGCGGTGCTACAGAGTTCTTGAAGTGGTGGCCTAACTAC
GGCTACACTAGAAGGACAGTATTTGGTATCTGCGCTCTGCTGAAGCCAGT
TACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCA
GTGGAACGAAAACTCACGTTAAGGGATTTTGGTCATGAGATTATCAAAAA
GGATCTTCACCTAGATCCTTTTAAATTAAAAATGAAGTTTTAAATCAATC
TAAAGTATATATGAGTAAACTTGGTCTGACAGTTACCAATGCTTAATCAG
TGAGGCACCTATCTCAGCGATCTGTCTATTTCGTTCATCCATAGTTGCCT
GACTCCCCGTCGTGTAGATAACTACGATACGGGAGGGCTTACCATCTGGC
CCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGA
GTAAGTAGTTCGCCAGTTAATAGTTTGCGCAACGTTGTTGCCATTGCTAC
AGGCATCGTGGTGTCACGCTCGTCGTTTGGTATGGCTTCATTCAGCTCCG
GTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCA
TGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAAT -continued

ACGGGATAATACCGCGCCACATAGCAGAACTTTAAAAGTGCTCATCATTG

GAAAACGTTCTTCGGGGCGAAAACTCTCAAGGATCTTACCGCTGTTGAGA

TCCAGTTCGATGTAACCCACTCGTGCACCCAACTGATCTTCAGCATCTTT

TACTTTCACCAGCGTTTCTGGGTGAGCAAAAACAGGAAGGCAAAATGCCG

CAAAAAAGGGAATAAGGGCGACACGGAAATGTTGAATACTCAT

The sequence for the pcDNA-TetR-Ins construct illustrated in in FIG. 12A is shown below:

pcDNA-TetR-Ins (7147 bp)

(SEQ ID NO: 31)

gacggatcgggagatctgagctcacggggacagcccccccccaaagcccccagggatgtaattacgtccctcccccgct agggggcagcagcgagccgcccggggctccgctccggtccggcgctccccccgcatccccgagccggcagcgtgcgggg acagcccgggcacggggaaggtggcacgggatcgctttcctctgaacgcttctcgctgctctttgagcctgcagacacc tggggggatacggggaaaaagctttaggctgaaagagagatttagaatgacagaatcatagaacggcctgggttgcaaa ggagcacagtgctcatccagatccaacccccctgctatgtgcagggtcatcaaccagcagcccaggctgcccagagccac atccagcctggccttgaatgcctgcaggcccgatcccctatggtcgactctcagtacaatctgctctgatgccgcatag ttaagccagtatctgctccctgcttgtgtgttggaggtcgctgagtagtgcgcgagcaaaatttaagctacaacaaggc aaggcttgaccgacaattgcatgaagaatctgcttagggttaggcgttttgcgctgcttcgcgatgtacgggccagata tacgcgttgacattgattattgactagttattaatagtaatcaattacggggtcattagttcatagcccatatatggag ttccgcgttacataacttacggtaaatggcccgcctggctgaccgcccaacgacccccgcccattgacgtcaataatga cgtatgttcccatagtaacgccaatagggactttccattgacgtcaatgggtggactatttacggtaaactgcccactt ggcagtacatcaagtgtatcatatgccaagtacgccccctattgacgtcaatgacggtaaatggcccgcctggcattat gcccagtacatgaccttatgggactttcctacttggcagtacatctacgtattagtcatcgctattaccatggtgatgc ggttttggcagtacatcaatgggcgtggatagcggtttgactcacggggatttccaagtctccaccccattgacgtcaa tgggagtttgttttggcaccaaaatcaacgggactttccaaaatgtcgtaacaactccgccccattgacgcaaatgggc ggtaggcgtgtacggtgggaggtctatataagcagagctctctggctaactagagaacccactgcttactggcttatcg aaattaatacgactcactatagggagacccaagctggctagcgtttaaacttaagctttctgtgagtttggggaccctt gattgttctttctttttcgctattgtaaaattcatgttatatggaggggggcaaagttttcagggtgttgtttagaatgg gaagatgtcccttgtatcaccatggaccctcatgataattttgtttctttcactttctactctgttgacaaccattgtc tcctcttattttcttttcattttctgtaactttttcgttaaactttagcttgcatttgtaacgaatttttaaattcact tttgtttatttgtcagattgtaagtactttctctaatcactttttttcaaggcaatcagggtatattatattgtactt cagcacagttttagagaacaattgttataattaaatgataaggtagaatatttctgcatataaattctggctggcgtgg aaatattcttattggtagaaacaactacatcctggtcatcatcctgcctttctctttatggttacaatgatatacactg tttgagatgaggataaaatactctgagtccaaaccgggcccctctgctaaccatgttcatgccttcttctttttcctac agctcctgggcaacgtgctggttattgtgctgtctcatcattttggcaaagaattgtaatacgactcactatagggcga gccaccatggctagattagataaaagtaaagtgattaacagcgcattagagctgcttaatgaggtcggaatcgaaggtt taacaacccgtaaactcgcccagaagctaggtgtagagcagcctacattgtattggcatgtaaaaaataagcgggcttt gctcgacgccttagccattgagatgttagataggcaccatactcacttttgccctttagaaggggaaagctggcaagat tttttacgtaataacgctaaaagttttagatgtgctttactaagtcatcgcgatggagcaaaagtacatttaggtacac ggcctacagaaaaacagtatgaaactctcgaaaatcaattagcctttttatgccaacaaggtttttcactagagaatgc cttatatgcactcagcgccgtggggcattttactttaggttgcgtattggaagatcaagagcatcaagtcgctaaagaa gaaagggaaacacctactactgatagtatgccgccattattacgacaagctatcgaattatttgatcaccaaggtgcag agccagccttcttattcggccttgaattgatcatatgcggattagaaaaacaacttaaatgtgaaagtgggtccccaaa aaagaagagaaaggtcgacggcggtggttcagtttaagcgtacagcgggatccactagtccagtgtggtggaattctgc agatatccagcacagtggcggccgctcgagtctagagggcccgtttaaacccgctgatcagcctcgactgtgccttcta -continued gttgccagccatctgttgtttgcccctcccccgtgccttccttgaccctggaaggtgccactcccactgtcctttccta ataaaatgaggaaattgcatcgcattgtctgagtaggtgtcattctattctggggggtggggtggggcaggacagcaag ggggaggattgggaagacaatagcaggcatgctggggatgcggtgggctctatggcttctgaggcggaaagaaccagct ggggctctagggggtatccccacgcgccctgtagcggcgcattaagcgcggcgggtgtggtggttacgcgcagcgtgac cgctacacttgccagcgccctagcgcccgctcctttcgctttcttcccttcctttctcgccacgttcgccggctttccc cgtcaagctctaaatcggggcatccctttagggttccgatttagtgctttacggcacctcgaccccaaaaaacttgatt agggtgatggttcacgtagtgggccatcgccctgatagacggtttttcgccctttgacgttggagtccacgttctttaa tagtggactcttgttccaaactggaacaacactcaaccctatctcggtctattcttttgatttataagggattttgggg atttcggcctattggttaaaaaatgagctgatttaacaaaaatttaacgcgaattaattctgtggaatgtgtgtcagtt agggtgtggaaagtccccaggctccccaggcaggcagaagtatgcaaagcatgcatctcaattagtcagcaaccaggtg tggaaagtccccaggctccccagcaggcagaagtatgcaaagcatgcatctcaattagtcagcaaccatagtcccgccc ctaactccgcccatcccgcccctaactccgcccagttccgcccattctccgccccatggctgactaattttttttattt atgcagaggccgaggccgcctctgcctctgagctattccagaagtagtgaggaggcttttttggaggcctaggcttttg caaaaagctcccgggagcttgtatatccattttcggatctgatcagcacgtgttgacaattaatcatcggcatagtata tcggcatagtataatacgacaaggtgaggaactaaaccatggccaagttgaccagtgccgttccggtgctcaccgcgcg cgacgtcgccggagcggtcgagttctggaccgaccggctcgggttctcccgggacttcgtggaggacgacttcgccggt gtggtccgggacgacgtgaccctgttcatcagcgcggtccaggaccaggtggtgccggacaacaccctggcctgggtgt gggtgcgcggcctggacgagctgtacgccgagtggtcggaggtcgtgtccacgaacttccgggacgcctccgggccggc catgaccgagatcggcgagcagccgtgggggcgggagttcgccctgcgcgacccggccggcaactgcgtgcacttcgtg gccgaggagcaggactgacacgtgctacgagatttcgattccaccgccgccttctatgaaaggttgggcttcggaatcg ttttccgggacgccggctggatgatcctccagcgcggggatctcatgctggagttcttcgcccaccccaacttgtttat tgcagcttataatggttacaaataaagcaatagcatcacaaatttcacaaataaagcatttttttcactgcattctagt tgtggtttgtccaaactcatcaatgtatcttatcatgtctgtataccgtcgacctctagctagagcttggcgtaatcat ggtcatagctgtttcctgtgtgaaattgttatccgctcacaattccacacaacatacgagccggaagcataaagtgtaa agcctggggtgcctaatgagtgagctaactcacattaattgcgttgcgctcactgcccgctttccagtcgggaaacctg tcgtgccagctgcattaatgaatcggccaacgcgcggggagaggcggtttgcgtattgggcgctcttccgcttcctcgc tcactgactcgctgcgctcggtcgttcggctgcggcgagcggtatcagctcactcaaaggcggtaatacggttatccac agaatcaggggataacgcaggaaagagagctcacggggacagcccccccccaaagcccccagggatgtaattacgtccc tcccccgctagggggcagcagcgagccgcccggggctccgctccggtccggcgctccccccgcatccccgagccggcag cgtgcggggacagcccgggcacggggaaggtggcacgggatcgctttcctctgaacgcttctcgctgctctttgagcct gcagacacctgggggggatacggggaaaaagctttaggctgaaagagagatttagaatgacagaatcatagaacggcctg ggttgcaaaggagcacagtgctcatccagatccaacccccctgctatgtgcagggtcatcaaccagcagcccaggctgcc cagagccacatccagcctggccttgaatgcctgcaggacatgtgagcaaaaggccagcaaaaggccaggaaccgtaaaa aggccgcgttgctggcgtttttccataggctccgcccccctgacgagcatcacaaaaatcgacgctcaagtcagaggtg gcgaaacccgacaggactataaagataccaggcgtttccccctggaagctccctcgtgcgctctcctgttccgaccctg ccgcttaccggatacctgtccgcctttctcccttcgggaagcgtggcgctttctcaatgctcacgctgtaggtatctca gttcggtgtaggtcgttcgctccaagctgggctgtgtgcacgaaccccccgttcagcccgaccgctgcgccttatccgg taactatcgtcttgagtccaacccggtaagacacgacttatcgccactggcagcagccactggtaacaggattagcaga gcgaggtatgtaggcggtgctacagagttcttgaagtggtggcctaactacggctacactagaaggacagtatttggta tctgcgctctgctgaagccagttaccttcggaaaaagagttggtagctcttgatccggcaaacaaaccaccgctggtag -continued

```
cggtggtttttttgtttgcaagcagcagattacgcgcagaaaaaaaggatctcaagaagatcctttgatcttttctacg

gggtctgacgctcagtggaacgaaaactcacgttaagggattttggtcatgagattatcaaaaaggatcttcacctaga

tccttttaaattaaaaatgaagttttaaatcaatctaaagtatatatgagtaaacttggtctgacagttaccaatgctt

aatcagtgaggcacctatctcagcgatctgtctatttcgttcatccatagttgcctgactccccgtcgtgtagataact

acgatacgggagggcttaccatctggccccagtgctgcaatgataccgcgagacccacgctcaccggctccagatttat

cagcaataaaccagccagccggaagggccgagcgcagaagtggtcctgcaactttatccgcctccatccagtctattaa

ttgttgccgggaagctagagtaagtagttcgccagttaatagtttgcgcaacgttgttgccattgctacaggcatcgtg

gtgtcacgctcgtcgtttggtatggcttcattcagctccggttcccaacgatcaaggcgagttacatgatcccccatgt

tgtgcaaaaaagcggttagctccttcggtcctccgatcgttgtcagaagtaagttggccgcagtgttatcactcatggt

tatggcagcactgcataattctcttactgtcatgccatccgtaagatgcttttctgtgactggtgagtactcaaccaag

tcattctgagaatagtgtatgcggcgaccgagttgctcttgcccggcgtcaatacgggataataccgcgccacatagca

gaactttaaaagtgctcatcattggaaaacgttcttcggggcgaaaactctcaaggatcttaccgctgttgagatccag

ttcgatgtaacccactcgtgcacccaactgatcttcagcatcttttactttcaccagcgtttctgggtgagcaaaaaca

ggaaggcaaaatgccgcaaaaaagggaataagggcgacacggaaatgttgaatactcatactcttcctttttcaatatt

attgaagcatttatcagggttattgtctcatgagcggatacatatttgaatgtatttagaaaaataaacaaataggggt

tccgcgcacatttccccgaaaagtgccacctgacgtc
```

The sequence for the pcDNA-TetR-KRAB-Ins construct illustrated in in FIG. 12B is shown below:

```
pcDNA-TetR-KRAB-Ins (7493 bp)
                                                          (SEQ ID NO: 32)
gacggatcgggagatctgagctcacggggacagcccccccccaaagcccccagggatgtaattacgtccctcccccgct

agggggcagcagcgagccgcccggggctccgctccggtccggcgctccccccgcatccccgagccggcagcgtgcgggg

acagcccgggcacggggaaggtggcacgggatcgctttcctctgaacgcttctcgctgctctttgagcctgcagacacc

tgggggggatacggggaaaaagctttaggctgaaagagagatttagaatgacagaatcatagaacggcctgggttgcaaa

ggagcacagtgctcatccagatccaacccccctgctatgtgcagggtcatcaaccagcagcccaggctgcccagagccac

atccagcctggccttgaatgcctgcaggcccgatcccctatggtcgactctcagtacaatctgctctgatgccgcatag

ttaagccagtatctgctccctgcttgtgtgttggaggtcgctgagtagtgcgcgagcaaaatttaagctacaacaaggc

aaggcttgaccgacaattgcatgaagaatctgcttagggttaggcgttttgcgctgcttcgcgatgtacgggccagata

tacgcgttgacattgattattgactagttattaatagtaatcaattacggggtcattagttcatagcccatatatggag

ttccgcgttacataacttacggtaaatggcccgcctggctgaccgcccaacgacccccgcccattgacgtcaataatga

cgtatgttcccatagtaacgccaatagggactttccattgacgtcaatgggtggactatttacggtaaactgcccactt

ggcagtacatcaagtgtatcatatgccaagtacgccccctattgacgtcaatgacggtaaatggcccgcctggcattat

gcccagtacatgaccttatgggactttcctacttggcagtacatctacgtattagtcatcgctattaccatggtgatgc

ggttttggcagtacatcaatgggcgtggatagcggtttgactcacggggatttccaagtctccaccccattgacgtcaa

tgggagtttgttttggcaccaaaatcaacgggactttccaaaatgtcgtaacaactccgccccattgacgcaaatgggc

ggtaggcgtgtacggtgggaggtctatataagcagagctctctggctaactagagaacccactgcttactggcttatcg

aaattaatacgactcactatagggagacccaagctggctagcgtttaaacttaagctttctgtgagtttggggaccctt

gattgttctttctttttcgctattgtaaaattcatgttatatggagggggcaaagttttcagggtgttgtttagaatgg

gaagatgtcccttgtatcaccatggaccctcatgataattttgtttctttcactttctactctgttgacaaccattgtc

tcctcttattttcttttcattttctgtaactttttcgttaaactttagcttgcatttgtaacgaatttttaaattcact

tttgtttatttgtcagattgtaagtactttctctaatcacttttttttcaaggcaatcagggtatattatattgtactt
```

-continued cagcacagttttagagaacaattgttataattaaatgataaggtagaatatttctgcatataaattctggctggcgtgg aaatattcttattggtagaaacaactacatcctggtcatcatcctgcctttctctttatggttacaatgatatacactg tttgagatgaggataaaatactctgagtccaaaccgggcccctctgctaaccatgttcatgccttcttctttttcctac agctcctgggcaacgtgctggttattgtgctgtctcatcattttggcaaagaattgtaatacgactcactatagggcga gccaccatggctagattagataaaagtaaagtgattaacagcgcattagagctgcttaatgaggtcggaatcgaaggtt taacaacccgtaaactcgcccagaagctaggtgtagagcagcctacattgtattggcatgtaaaaaataagcgggcttt gctcgacgccttagccattgagatgttagataggcaccatactcacttttgccctttagaaggggaaagctggcaagat tttttacgtaataacgctaaaagttttagatgtgctttactaagtcatcgcgatggagcaaaagtacatttaggtacac ggcctacagaaaaacagtatgaaactctcgaaaatcaattagcctttttatgccaacaaggtttttcactagagaatgc cttatatgcactcagcgccgtggggcattttactttaggttgcgtattggaagatcaagagcatcaagtcgctaaagaa gaaagggaaacacctactactgatagtatgccgccattattacgacaagctatcgaattatttgatcaccaaggtgcag agccagccttcttattcggccttgaattgatcatatgcggattagaaaaacaacttaaatgtgaaagtgggtccccaaa aaagaagagaaaggtcgacggcggtggtgctttgtctcctcagcactctgctgtcactcaaggaagtatcatcaagaac aaggagggcatggatgctaagtcactaactgcctggtcccggacactggtgaccttcaaggatgtatttgtggacttca ccagggaggagtggaagctgctggacactgctcagcagatcgtgtacagaaatgtgatgctggagaactataagaacct ggtttccttgggttatcagcttactaagccagatgtgatcctccggttggagaagggagaagagccctggctggtggag agagaaattcaccaagagacccatcctgattcagagactgcatttgaaatcaaatcatcagtttaagcgtacagcgggg atccactagtccagtgtggtggaattctgcagatatccagcacagtggcggccgctcgagtctagagggcccgtttaaa cccgctgatcagcctcgactgtgccttctagttgccagccatctgttgtttgcccctcccccgtgccttccttgaccct ggaaggtgccactcccactgtcctttcctaataaaatgaggaaattgcatcgcattgtctgagtaggtgtcattctatt ctggggggtggggtggggcaggacagcaagggggaggattgggaagacaatagcaggcatgctggggatgcggtgggct ctatggcttctgaggcggaaagaaccagctggggctctagggggtatccccacgcgccctgtagcggcgcattaagcgc ggcgggtgtggtggttacgcgcagcgtgaccgctacacttgccagcgccctagcgcccgctcctttcgctttcttccct tcctttctcgccacgttcgccggctttccccgtcaagctctaaatcgggggcatccctttagggttccgatttagtgctt tacggcacctcgaccccaaaaaacttgattagggtgatggttcacgtagtgggccatcgccctgatagacggtttttcg ccctttgacgttggagtccacgttctttaatagtggactcttgttccaaactggaacaacactcaaccctatctcggtc tattcttttgatttataagggattttggggatttcggcctattggttaaaaaatgagctgatttaacaaaaatttaacg cgaattaattctgtggaatgtgtgtcagttagggtgtggaaagtccccaggctccccaggcaggcagaagtatgcaaag catgcatctcaattagtcagcaaccaggtgtggaaagtccccaggctccccagcaggcagaagtatgcaaagcatgcat ctcaattagtcagcaaccatagtcccgcccctaactccgcccatcccgcccctaactccgcccagttccgcccattctc cgccccatggctgactaattttttttatttatgcagaggccgaggccgcctctgcctctgagctattccagaagtagtg aggaggcttttttggaggcctaggcttttgcaaaaagctcccgggagcttgtatatccattttcggatctgatcagcac gtgttgacaattaatcatcggcatagtatatcggcatagtataatacgacaaggtgaggaactaaaccatggccaagtt gaccagtgccgttccggtgctcaccgcgcgcgacgtcgccggagcggtcgagttctggaccgaccggctcgggttctcc cgggacttcgtggaggacgacttcgccggtgtggtccgggacgacgtgaccctgttcatcagcgcggtccaggaccagg tggtgccggacaacaccctggcctgggtgtgggtgcgcggcctggacgagctgtacgccgagtggtcggaggtcgtgtc cacgaacttccgggacgcctccgggccggccatgaccgagatcggcgagcagccgtgggggcgggagttcgccctgcgc gacccggccggcaactgcgtgcacttcgtggccgaggagcaggactgacacgtgctacgagatttcgattccaccgccg ccttctatgaaaggttgggcttcggaatcgttttccgggacgccggctggatgatcctccagcgcggggatctcatgct ggagttcttcgcccaccccaacttgtttattgcagcttataatggttacaaataaagcaatagcatcacaaatttcaca -continued aataaagcatttttttcactgcattctagttgtggtttgtccaaactcatcaatgtatcttatcatgtctgtataccgt cgacctctagctagagcttggcgtaatcatggtcatagctgtttcctgtgtgaaattgttatccgctcacaattccaca caacatacgagccggaagcataaagtgtaaagcctggggtgcctaatgagtgagctaactcacattaattgcgttgcgc tcactgcccgctttccagtcgggaaacctgtcgtgccagctgcattaatgaatcggccaacgcgcggggagaggcggtt tgcgtattgggcgctcttccgcttcctcgctcactgactcgctgcgctcggtcgttcggctgcggcgagcggtatcagc tcactcaaaggcggtaatacggttatccacagaatcaggggataacgcaggaaagagagctcacggggacagcccccc ccaaagcccccagggatgtaattacgtccctcccccgctagggggcagcagcgagccgcccggggctccgctccggtcc ggcgctcccccgcatccccgagccggcagcgtgcggggacagcccgggcacggggaaggtggcacgggatcgctttcc tctgaacgcttctcgctgctctttgagcctgcagacacctgggggggatacggggaaaaagctttaggctgaaagagaga tttagaatgacagaatcatagaacggcctgggttgcaaaggagcacagtgctcatccagatccaacccctgctatgtg cagggtcatcaaccagcagcccaggctgcccagagccacatccagcctggccttgaatgcctgcaggacatgtgagcaa aaggccagcaaaaggccaggaaccgtaaaaaggccgcgttgctggcgtttttccataggctccgcccccctgacgagca tcacaaaaatcgacgctcaagtcagaggtggcgaaacccgacaggactataaagataccaggcgtttccccctggaagc tccctcgtgcgctctcctgttccgaccctgccgcttaccggatacctgtccgcctttctcccttcgggaagcgtggcgc tttctcaatgctcacgctgtaggtatctcagttcggtgtaggtcgttcgctccaagctgggctgtgtgcacgaacccc cgttcagcccgaccgctgcgccttatccggtaactatcgtcttgagtccaacccggtaagacacgacttatcgccactg gcagcagccactggtaacaggattagcagagcgaggtatgtaggcggtgctacagagttcttgaagtggtggcctaact acggctacactagaaggacagtatttggtatctgcgctctgctgaagccagttaccttcggaaaaagagttggtagctc ttgatccggcaaacaaaccaccgctggtagcggtggtttttttgtttgcaagcagcagattacgcgcagaaaaaaagga tctcaagaagatcctttgatcttttctacggggtctgacgctcagtggaacgaaaactcacgttaagggattttggtca tgagattatcaaaaaggatcttcacctagatccttttaaattaaaaatgaagttttaaatcaatctaaagtatatatga gtaaacttggtctgacagttaccaatgcttaatcagtgaggcacctatctcagcgatctgtctatttcgttcatccata gttgcctgactccccgtcgtgtagataactacgatacgggagggcttaccatctggccccagtgctgcaatgataccgc gagacccacgctcaccggctccagatttatcagcaataaaccagccagccggaagggccgagcgcagaagtggtcctgc aactttatccgcctccatccagtctattaattgttgccgggaagctagagtaagtagttcgccagttaatagtttgcgc aacgttgttgccattgctacaggcatcgtggtgtcacgctcgtcgtttggtatggcttcattcagctccggttcccaac gatcaaggcgagttacatgatcccccatgttgtgcaaaaaagcggttagctccttcggtcctccgatcgttgtcagaag taagttggccgcagtgttatcactcatggttatggcagcactgcataattctcttactgtcatgccatccgtaagatgc ttttctgtgactggtgagtactcaaccaagtcattctgagaatagtgtatgcggcgaccgagttgctcttgcccggcgt caatacgggataataccgcgccacatagcagaactttaaaagtgctcatcattggaaaacgttcttcggggcgaaaact ctcaaggatcttaccgctgttgagatccagttcgatgtaacccactcgtgcacccaactgatcttcagcatcttttact ttcaccagcgtttctgggtgagcaaaaacaggaaggcaaaatgccgcaaaaaagggaataagggcgacacggaaatgtt gaatactcatactcttcctttttcaatattattgaagcatttatcagggttattgtctcatgagcggatacatatttga atgtatttagaaaaataaacaaataggggttccgcgcacatttccccgaaaagtgccacctgacgtc It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. An isolated nucleic acid molecule comprising a plasmid encoding, in operable order:

a. a derepressible p5 promoter;

b. a rep78 gene, including a silenced p19 promoter located within the rep78 gene coding region, wherein the silenced p19 promoter comprises mutations in the SP1, TATA-1, and TATA-2 sites of a p19 promoter;

c. a cap gene;

d. a p5 promoter;

e. a derepressible p19 promoter;

f. a rep52 gene; and;

h. an antibiotic resistance gene.

2. The isolated nucleic acid molecule of claim 1, wherein the cap gene is a cap gene from an AAV serotype selected from the group consisting of ANC80, AAV1, AAV2, AAV3, AAV4, AAV5, AAV6, AAV7, AAV8, AAV9, AAV10, and AAV11.

3. The isolated nucleic acid molecule of claim 2, wherein the cap gene is an ANC80 cap gene.

4. The isolated nucleic acid molecule of claim 1, wherein the derepressible p5 promoter comprises a functional p5 promoter and two tetracycline operator sequences ($TetO_2$).

5. The isolated nucleic acid molecule of claim 4, wherein the derepressible p5 promoter comprises SEQ ID NO:5.

6. The isolated nucleic acid molecule of claim 1, wherein the derepressible p19 promoter comprises a functional p19 promoter and two tetracycline operator sequences ($TetO_2$).

7. The isolated nucleic acid molecule of claim 6, wherein the derepressible p19 promoter comprises SEQ ID NO: 7.

8. The isolated nucleic acid molecule of claim 1, wherein the antibiotic resistance gene is a kanamycin resistance gene.

9. The isolated nucleic acid molecule of claim 1, further comprising an inoperable antibiotic resistance gene.

10. An isolated nucleic acid molecule comprising a plasmid encoding, in operable order:

a. a derepressible p5 promoter comprising a functional p5 promoter and two tetracycline operator sequences ($TetO_2$);

b. a rep78 gene, including a silenced p19 promoter located within the rep78 gene coding region, wherein the silenced p19 promoter comprises mutations in the SP1, TATA-1, and TATA-2 sites of a p19 promoter;

c. a viral associated (VA I) non-coding DNA;

d. a p5 promoter;

e. a derepressible p19 promoter comprising a functional p19 promoter and two tetracycline operator sequences ($TetO_2$);

f. a rep52 gene; and;

h. an antibiotic resistance gene.

11. The isolated nucleic acid molecule of claim 10, wherein the derepressible p5 promoter comprises SEQ ID NO:5.

12. The isolated nucleic acid molecule of claim 10, wherein the derepressible p19 promoter comprises SEQ ID NO: 7.

13. The isolated nucleic acid molecule of claim 10, wherein the antibiotic resistance gene is a kanamycin resistance gene.

14. The isolated nucleic acid molecule of claim 10, further comprising an inoperable antibiotic resistance gene.

* * * * *

SEQUENCE LISTING

<160> NUMBER OF SEQ ID NOS: 32

<210> SEQ ID NO 1
<211> LENGTH: 11986
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cttcgcgatg tacgggccag atatacgcgt tgacattgat tattgactag ttattaatag 1020
taatcaatta cggggtcatt agttcatagc ccatatatgg agttccgcgt tacataactt 1080
acggtaaatg gcccgcctgg ctgaccgccc aacgaccccc gcccattgac gtcaataatg 1140
acgtatgttc ccatagtaac gccaataggg actttccatt gacgtcaatg ggtggagtat 1200
ttacggtaaa ctgcccactt ggcagtacat caagtgtatc atatgccaag tacgccccct 1260
attgacgtca atgacggtaa atggcccgcc tggcattatg cccagtacat gaccttatgg 1320
gactttccta cttggcagta catctacgta ttagtcatcg ctattaccat ggtgatgcgg 1380
ttttggcagt acatcaatgg gcgtggatag cggtttgact cacggggatt tccaagtctc 1440
caccccattg acgtcaatgg gagtttgttt tggaaccaaa atcaacggga ctttccaaaa 1500
tgtcgtaaca actccgcccc attgacgcaa atgggcggta ggcgtgtacg gtgggaggtc 1560
tatataagca gagctctccc tatcagtgat agagatctcc ctatcagtga tagagatcgt 1620
cgacgagctc gtttagtgaa ccgtcagatc gcctggagac gccatccacg ctgttttgac 1680
ctccatagaa gacaccggga ccgatccagc ctccggactc tagcgtttaa acttaagctt 1740
gccaccatgg ccagtcggga agaggagcag cgcgaaacca cccccgagcg cggacgcggt 1800
gcggcgcgac gtcccccaac catggaggac gtgtcgtccc cgtccccgtc gccgccgcct 1860
ccccgggcgc ccccaaaaaa gcggatgagg cggcgtatcg agtccgagga cgaggaagac 1920
tcatcacaag acgcgctggt gccgcgcaca cccagcccgc ggccatcgac ctcggcggcg 1980

-continued

```
gatttggcca ttgcgcccaa gaagaaaaag aagcgccctt ctcccaagcc cgagcgcccg   2040
ccatcaccag aggtaatcgt ggacagcgag gaagaaagag aagatgtggc gctacaaatg   2100
gtgggtttca gcaacccacc ggtgctaatc aagcatggca aaggaggtaa gcgcacagtg   2160
cggcggctga atgaagacga cccagtggcg cgtggtatgc ggacgcaaga ggaagaggaa   2220
gagcccagcg aagcggaaag tgaaattacg gtgatgaacc cgctgagtgt gccgatcgtg   2280
tctgcgtggg agaagggcat ggaggctgcg cgcgcgctga tggacaagta ccacgtggat   2340
aacgatctaa aggcgaactt caaactactg cctgaccaag tggaagctct ggcggccgta   2400
tgcaagacct ggctgaacga ggagcaccgc gggttgcagc tgaccttcac cagcaacaag   2460
acctttgtga cgatgatggg gcgattcctg caggcgtacc tgcagtcgtt tgcagaggtg   2520
acctacaagc atcacgagcc cacgggctgc gcgttgtggc tgcaccgctg cgctgagatc   2580
gaaggcgagc ttaagtgtct acacggaagc attatgataa ataaggagca cgtgattgaa   2640
atggatgtga cgagcgaaaa cgggcagcgc gcgctgaagg agcagtctag caaggccaag   2700
atcgtgaaga accggtgggg ccgaaatgtg gtgcagatct ccaacaccga cgcaaggtgc   2760
tgcgtgcacg acgcggcctg tccggccaat cagttttccg gcaagtcttg cggcatgttc   2820
ttctctgaag gcgcaaaggc tcaggtggct tttaagcaga tcaaggcttt tatgcaggcg   2880
ctgtatccta acgcccagac cgggcacggt caccttttga tgccactacg gtgcgagtgc   2940
aactcaaagc ctgggcacgc gcccttttg ggaaggcagc taccaaagtt gactccgttc    3000
gccctgagca acgcggagga cctggacgcg gatctgatct ccgacaagag cgtgctggcc   3060
agcgtgcacc acccggcgct gatagtgttc cagtgctgca accctgtgta tcgcaactcg   3120
cgcgcgcagg gcggaggccc caactgcgac ttcaagatat cggcgcccga cctgctaaac   3180
gcgttggtga tggtgcgcag cctgtggagt gaaaacttca ccgagctgcc gcggatggtt   3240
gtgcctgagt ttaagtggag cactaaacac cagtatcgca acgtgtccct gccagtggcg   3300
catagcgatg cgcggcagaa cccctttgat ttttaacccg ggagttctag ggatctgccc   3360
ctctccctcc cccccccta acgttactgg ccgaagccgc ttggaataag gccggtgtgc    3420
gtttgtctat atgttatttt ccaccatatt gccgtctttt ggcaatgtga gggcccggaa   3480
acctggccct gtcttcttga cgagcattcc taggggtctt tcccctctcg ccaaaggaat   3540
gcaaggtctg ttgaatgtcg tgaaggaagc agttcctctg gaagcttctt gaagacaaac   3600
aacgtctgta gcgacccttt gcaggcagcg gaacccccca cctggcgaca ggtgcctctg   3660
cggccaaaag ccacgtgtat aagatacacc tgcaaaggcg gcacaacccc agtgccacgt   3720
tgtgagttgg atagttgtgg aaagagtcaa atggctctcc tcaagcgtat tcaacaaggg   3780
gctgaaggat gcccagaagg taccccattg tatgggatct gatctggggc ctcggtgcac   3840
atgctttaca tgtgtttagt cgaggttaaa aaaacgtcta ggccccccga accacgggga   3900
cgtggttttc ctttgaaaaa cacgatgata aggatccacc ggaggccacc atgactacgt   3960
ccggcgttcc atttggcatg acactacgac caacacgatc tcggttgtct cggcgcactc   4020
cgtacagtag ggatcgtcta cctccttttg agacagaaac ccgcgctacc atactggagg   4080
atcatccgct gctgcccgaa tgtaacactt tgacaatgca caacgtgagt tacgtgcgag   4140
gtcttccctg cagtgtggga tttacgctga ttcaggaatg ggttgttccc tgggatatgg   4200
ttctaacgcg ggaggagctt gtaatcctga ggaagtgtat gcacgtgtgc ctgtgttgtg   4260
ccaacattga tatcatgacg agcatgatga tccatggtta cgagtcctgg gctctccact   4320
gtcattgttc cagtcccggt tccctgcagt gtatagccgg cgggcaggtt ttggccagct   4380
```

-continued ggtttaggat ggtggtggat ggcgccatgt ttaatcagag gtttatatgg taccgggagg 4440
tggtgaatta caacatgcca aaagaggtaa tgtttatgtc cagcgtgttt atgaggggtc 4500
gccacttaat ctacctgcgc ttgtggtatg atggccacgt gggttctgtg gtccccgcca 4560
tgagctttgg atacagcgcc ttgcactgtg ggattttgaa caatattgtg gtgctgtgct 4620
gcagttactg tgctgattta agtgagatca gggtgcgctg ctgtgcccgg aggacaaggc 4680
gccttatgct gcgggcggtg cgaatcatcg ctgaggagac cactgccatg ttgtattcct 4740
gcaggacgga gcggcggcgg cagcagttta ttcgcgcgct gctgcagcac caccgcccta 4800
tcctgatgca cgattatgac tctaccccca tgtaggcggc cgctcgagtc tagagggccc 4860
gtttaaaccc gctgatcagc ctcgactgtg ccttctagtt gccagccatc tgttgtttgc 4920
ccctcccccg tgccttcctt gaccctggaa ggtgccactc ccactgtcct ttcctaataa 4980
aatgaggaaa ttgcatcgca ttgtctgagt aggtgtcatt ctattctggg gggtggggtg 5040
gggcaggaca gcaaggggga ggattgggaa gacaatagca ggcatgctgg ggatgcggtg 5100
ggctctatgg cttctgaggc ggaaagaacc agctggggct ctagggggta tccccggggt 5160
tggggttgcg ccttttccaa ggcatccagc acagtggcgg ccgcaatatt tgcatgtcgc 5220
tatgtgttct gggaaatcac cataaacgtg aaatccctat cagtgataga gacttataag 5280
ttccctatca gtgatagaga accggtgggc actcttccgt ggtctggtgg ataaattcgc 5340
aagggtatca tggcggacga ccggggttcg agccccgtat ccggccgtcc gccgtgatcc 5400
atgcggttac cgcccgcgtg tcgaacccag gtgtgcgacg tcagacaacg ggggagtgct 5460
ccttttggaa ttccactttg gccgcggctc gagggggttg ggggttgcgcc ttttccaagg 5520
cagccctggg tttgcgcagg gacgcggctg ctctgggcgt ggttccggga aacgcagcgg 5580
cgccgaccct gggtctcgca cattcttcac gtccgttcgc agcgtcaccc ggatcttcgc 5640
cgctaccctt gtgggccccc cggcgacgct tcctgctccg cccctaagtc gggaaggttc 5700
cttgcggttc gcggcgtgcc ggacgtgaca aacggaagcc gcacgtctca ctagtaccct 5760
cgcagacgga cagcgccagg gagcaatggc agcgcgccga ccgcgatggg ctgtggccaa 5820
tagcggctgc tcagcagggc gcgccgagag cagcggccgg gaaggggcgg tgcgggaggc 5880
ggggtgtggg gcggtagtgt gggccctgtt cctgcccgcg cggtgttccg cattctgcaa 5940
gcctccggag cgcacgtcgg cagtcggctc cctcgttgac cgaatcaccg acctctctcc 6000
ccagggggat ctgtgagttt ggggaccctt gattgttctt tctttttcgc tattgtaaaa 6060
ttcatgttat atggaggggg caaagttttc agggtgttgt ttagaatggg aagatgtccc 6120
ttgtatcacc atggaccctc atgataattt tgtttctttc actttctact ctgttgacaa 6180
ccattgtctc ctcttatttt cttttcattt tctgtaactt tttcgttaaa ctttagcttg 6240
catttgtaac gaatttttaa attcactttt gtttatttgt cagattgtaa gtactttctc 6300
taatcacttt tttttcaagg caatcagggt atattatatt gtacttcagc acagttttag 6360
agaacaattg ttataattaa atgataaggt agaatatttc tgcatataaa ttctggctgg 6420
cgtggaaata ttcttattgg tagaaacaac tacatcctgg tcatcatcct gcctttctct 6480
ttatggttac aatgatatac actgtttgag atgaggataa aatactctga gtccaaaccg 6540
ggcccctctg ctaaccatgt tcatgccttc ttctttttcc tacagctcct gggcaacgtg 6600
ctggttattg tgctgtctca tcattttggc aaagaattgt aatacgactc actatagggc 6660
gagccaccat ggctagatta gataaaagta aagtgattaa cagcgcatta gagctgctta 6720

-continued atgaggtcgg aatcgaaggt ttaacaaccc gtaaactcgc ccagaagcta ggtgtagagc 6780
agcctacatt gtattggcat gtaaaaaata agcgggcttt gctcgacgcc ttagccattg 6840
agatgttaga taggcaccat actcactttt gccctttaga aggggaaagc tggcaagatt 6900
ttttacgtaa taacgctaaa agttttagat gtgctttact aagtcatcgc gatggagcaa 6960
aagtacattt aggtacacgg cctacagaaa aacagtatga aactctcgaa aatcaattag 7020
cctttttatg ccaacaaggt ttttcactag agaatgcctt atatgcactc agcgccgtgg 7080
ggcattttac tttaggttgc gtattggaag atcaagagca tcaagtcgct aaagaagaaa 7140
gggaaacacc tactactgat agtatgccgc cattattacg acaagctatc gaattatttg 7200
atcaccaagg tgcagagcca gccttcttat tcggccttga attgatcata tgcggattag 7260
aaaaacaact taaatgtgaa agtgggtccc caaaaaagaa gagaaaggtc gacggcggtg 7320
gtgctttgtc tcctcagcac tctgctgtca ctcaaggaag tatcatcaag aacaaggagg 7380
gcatggatgc taagtcacta actgcctggt cccggacact ggtgaccttc aaggatgtat 7440
ttgtggactt caccagggag gagtggaagc tgctggacac tgctcagcag atcgtgtaca 7500
gaaatgtgat gctggagaac tataagaacc tggtttcctt gggttatcag cttactaagc 7560
cagatgtgat cctccggttg gagaagggag aagagccctg gctggtggag agagaaattc 7620
accaagagac ccatcctgat tcagagactg catttgaaat caaatcatca gtttaagcgt 7680
acagcggctc ccgggagttc tagggatctg cccctctccc tcccccccc ctaacgttac 7740
tggccgaagc cgcttggaat aaggccggtg tgcgtttgtc tatatgttat tttccaccat 7800
attgccgtct tttggcaatg tgagggcccg gaaacctggc cctgtcttct tgacgagcat 7860
tcctaggggt ctttcccctc tcgccaaagg aatgcaaggt ctgttgaatg tcgtgaagga 7920
agcagttcct ctggaagctt cttgaagaca aacaacgtct gtagcgaccc tttgcaggca 7980
gcggaacccc ccacctggcg acaggtgcct ctgcggccaa aagccacgtg tataagatac 8040
acctgcaaag gcggcacaac cccagtgcca cgttgtgagt tggatagttg tggaaagagt 8100
caaatggctc tcctcaagcg tattcaacaa ggggctgaag gatgcccaga aggtacccca 8160
ttgtatggga tctgatctgg ggcctcggtg cacatgcttt acatgtgttt agtcgaggtt 8220
aaaaaaacgt ctaggccccc cgaaccacgg ggacgtggtt ttcctttgaa aaacacgatg 8280
ataaggatcc accggaggcc accatgaccg agtacaagcc cacggtgcgc ctcgccaccc 8340
gcgacgacgt ccccagggcc gtacgcaccc tcgccgccgc gttcgccgac taccccgcca 8400
cgcgccacac cgtcgatccg gaccgccaca tcgagcgggt caccgagctg caagaactct 8460
tcctcacgcg cgtcgggctc gacatcggca aggtgtgggt cgcggacgac ggcgccgcgg 8520
tggcggtctg gaccacgccg gagagcgtcg aagcgggggc ggtgttcgcc gagatcggcc 8580
cgcgcatggc cgagttgagc ggttcccggc tggccgcgca gcaacagatg gaaggcctcc 8640
tggcgccgca ccggcccaag gagcccgcgt ggttcctggc caccgtcggc gtctcgcccg 8700
accaccaggg caagggtctg ggcagcgccg tcgtgctccc cggagtggag gcggccgagc 8760
gcgccggggt gcccgccttc ctggagacct ccgcgccccg caacctcccc ttctacgagc 8820
ggctcggctt caccgtcacc gccgacgtcg aggtgcccga aggaccgcgc acctggtgca 8880
tgacccgcaa gcccggtgcc tgaccgcgtc tggaacaatc aacctctgga ttacaaaatt 8940
tgtgaaagat tgactggtat tcttaactat gttgctcctt ttacgctatg tggatacgct 9000
gctttaatgc ctttgtatca tgctattgct tcccgtatgg ctttcatttt ctcctccttg 9060
tataaatcct ggttgctgtc tctttatgag gagttgtggc ccgttgtcag gcaacgtggc 9120

-continued

```
gtggtgtgca ctgtgtttgc tgacgcaacc cccactggtt ggggcattgc caccacctgt   9180
cagctccttt ccgggacttt cgctttcccc ctccctattg ccacggcgga actcatcgcc   9240
gcctgccttg cccgctgctg gacaggggct cggctgttgg gcactgacaa ttccgtggtg   9300
ttgtcgggga agctgacgtc ctttccatgg ctgctcgcct gtgttgccac ctggattctg   9360
cgcgggacgt ccttctgcta cgtcccttcg gccctcaatc cagcggacct tccttcccgc   9420
ggcctgctgc cggctctgcg gcctcttccg cgtcttcgcc ttcgccctca gacgagtcgg   9480
atctcccttt gggccgcctc cccgcaaaat gaccgaccaa gcgacgccca acctgccatc   9540
acgagatttc gattccaccg ccgccttcta tgaaaggttg ggcttcggaa tcgttttccg   9600
ggacgccggc tggatgatcc tccagcgcgg ggatctcatg ctggagttct tcgcccaccc   9660
caacttgttt attgcagctt ataatggtta caaataaagc aatagcatca caaatttcac   9720
aaataaagca tttttttcac tgcattctag ttgtggtttg tccaaactca tcaatgtatc   9780
ttatcatgtc tgtataccgt cgacctctag ctagagcttg gcgtaatcat ggtcatagct   9840
gtttcctgtg tgaaattgtt atccgctcac aattccacac aacatacgag ccggaagcat   9900
aaagtgtaaa gcctggggtg cctaatgagt gagctaactc acattaattg cgttgcgctc   9960
actgcccgct ttccagtcgg gaaacctgtc gtgccagctg cattaatgaa tcggccaacg  10020
cgcggggaga ggcggtttgc gtattgggcg ctcttccgct tcctcgctca ctgactcgct  10080
gcgctcggtc gttcggctgc ggcgagcggt atcagctcac tcaaaggcgg taatacggtt  10140
atccacagaa tcaggggata acgcaggaaa gaacatgtga gcaaaaggcc agcaaaaggc  10200
caggaaccgt aaaaaggccg cgttgctggc gtttttccat aggctccgcc cccctgacga  10260
gcatcacaaa aatcgacgct caagtcagag gtggcgaaac ccgacaggac tataaagata  10320
ccaggcgttt ccccctggaa gctccctcgt gcgctctcct gttccgaccc tgccgcttac  10380
cggatacctg tccgcctttc tcccttcggg aagcgtggcg ctttctcata gctcacgctg  10440
taggtatctc agttcggtgt aggtcgttcg ctccaagctg ggctgtgtgc acgaaccccc  10500
cgttcagccc gaccgctgcg ccttatccgg taactatcgt cttgagtcca acccggtaag  10560
acacgactta tcgccactgg cagcagccac tggtaacagg attagcagag cgaggtatgt  10620
aggcggtgct acagagttct tgaagtggtg gcctaactac ggctacacta gaagaacagt  10680
atttggtatc tgcgctctgc tgaagccagt taccttcgga aaaagagttg gtagctcttg  10740
atccggcaaa caaaccaccg ctggtagcgg tttttttgtt tgcaagcagc agattacgcg  10800
cagaaaaaaa ggatctcaag aagatccttt gatcttttct acggggtctg acgctcagtg  10860
gaacgaaaac tcacgttaag ggattttggt catgagatta tcaaaaagga tcttcaccta  10920
gatcctttta aattaaaaat gaagttttaa atcaatctaa agtatatatg agtaaacttg  10980
gtctgacagt taccaatgct taatcagtga ggcacctatc tcagcgatct gtctatttcg  11040
ttcatccata gttgcctgac tccccgtcgt gtagataact acgatacggg agggcttacc  11100
atctggcccc agtgctgcaa tgataccgcg agacccacgc tcaccggctc cagatttatc  11160
agcaataaac cagccagccg gaagggccga gcgcagaagt ggtcctgcaa ctttatccgc  11220
ctccatccag tctattaatt gttgccggga agctagagta agtagttcgc cagttaatag  11280
tttgcgcaac gttgttgcca ttgctacagg catcgtggtg tcacgctcgt cgtttggtat  11340
ggcttcattc agctccggtt cccaacgatc aaggcgagtt acatgatccc ccatgttgtg  11400
caaaaaagcg gttagctcct tcggtcctcc gatcgttgtc agaagtaagt tggccgcagt  11460
```

-continued gttatcactc atggttatgg cagcactgca taattctctt actgtcatgc catccgtaag 11520
atgcttttct gtgactggtg agtactcaac caagtcattc tgagaatagt gtatgcggcg 11580
accgagttgc tcttgcccgg cgtcaatacg ggataatacc gcgccacata gcagaacttt 11640
aaaagtgctc atcattggaa aacgttcttc ggggcgaaaa ctctcaagga tcttaccgct 11700
gttgagatcc agttcgatgt aacccactcg tgcacccaac tgatcttcag catcttttac 11760
tttcaccagc gtttctgggt gagcaaaaac aggaaggcaa aatgccgcaa aaaagggaat 11820
aagggcgaca cggaaatgtt gaatactcat actcttcctt tttcaatatt attgaagcat 11880
ttatcagggt tattgtctca tgagcggata catatttgaa tgtatttaga aaaataaaca 11940
aataggggtt ccgcgcacat ttccccgaaa agtgccacct gacgtc 11986

<210> SEQ ID NO 2
<211> LENGTH: 11641
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cttcgcgatg tacgggccag atatacgcgt tgacattgat tattgactag ttattaatag 1020
taatcaatta cggggtcatt agttcatagc ccatatatgg agttccgcgt tacataactt 1080
acggtaaatg gcccgcctgg ctgaccgccc aacgaccccc gcccattgac gtcaataatg 1140
acgtatgttc ccatagtaac gccaataggg actttccatt gacgtcaatg ggtggagtat 1200
ttacggtaaa ctgcccactt ggcagtacat caagtgtatc atatgccaag tacgcccct 1260 attgacgtca atgacggtaa atggcccgcc tggcattatg cccagtacat gaccttatgg 1320
gactttccta cttggcagta catctacgta ttagtcatcg ctattaccat ggtgatgcgg 1380
ttttggcagt acatcaatgg gcgtggatag cggtttgact cacggggatt tccaagtctc 1440
caccccattg acgtcaatgg gagtttgttt tggaaccaaa atcaacggga ctttccaaaa 1500

-continued

```
tgtcgtaaca actccgcccc attgacgcaa atgggcggta ggcgtgtacg gtgggaggtc   1560
tatataagca gagctctccc tatcagtgat agagatctcc ctatcagtga tagagatcgt   1620
cgacgagctc gtttagtgaa ccgtcagatc gcctggagac gccatccacg ctgttttgac   1680
ctccatagaa gacaccggga ccgatccagc ctccggactc tagcgtttaa acttaagctt   1740
gccaccatgg ccagtcggga agaggagcag cgcgaaacca cccccgagcg cggacgcggt   1800
gcggcgcgac gtcccccaac catggaggac gtgtcgtccc cgtccccgtc gccgccgcct   1860
ccccgggcgc ccccaaaaaa gcggatgagg cggcgtatcg agtccgagga cgaggaagac   1920
tcatcacaag acgcgctggt gccgcgcaca cccagcccgc ggccatcgac ctcggcggcg   1980
gatttggcca ttgcgcccaa gaagaaaaag aagcgccctt ctcccaagcc cgagcgcccg   2040
ccatcaccag aggtaatcgt ggacagcgag gaagaaagag aagatgtggc gctacaaatg   2100
gtgggtttca gcaacccacc ggtgctaatc aagcatggca aaggaggtaa gcgcacagtg   2160
cggcggctga atgaagacga cccagtggcg cgtggtatgc ggacgcaaga ggaagaggaa   2220
gagcccagcg aagcggaaag tgaaattacg gtgatgaacc cgctgagtgt gccgatcgtg   2280
tctgcgtggg agaagggcat ggaggctgcg cgcgcgctga tggacaagta ccacgtggat   2340
aacgatctaa aggcgaactt caaactactg cctgaccaag tggaagctct ggcggccgta   2400
tgcaagacct ggctgaacga ggagcaccgc gggttgcagc tgaccttcac cagcaacaag   2460
acctttgtga cgatgatggg gcgattcctg caggcgtacc tgcagtcgtt tgcagaggtg   2520
acctacaagc atcacgagcc cacgggctgc gcgttgtggc tgcaccgctg cgctgagatc   2580
gaaggcgagc ttaagtgtct acacggaagc attatgataa ataaggagca cgtgattgaa   2640
atggatgtga cgagcgaaaa cgggcagcgc gcgctgaagg agcagtctag caaggccaag   2700
atcgtgaaga accggtgggg ccgaaatgtg gtgcagatct ccaacaccga cgcaaggtgc   2760
tgcgtgcacg acgcggcctg tccggccaat cagttttccg gcaagtcttg cggcatgttc   2820
ttctctgaag gcgcaaaggc tcaggtggct tttaagcaga tcaaggcttt tatgcaggcg   2880
ctgtatccta acgcccagac cgggcacggt cacctttga tgccactacg gtgcgagtgc   2940
aactcaaagc ctgggcacgc gcccttttg ggaaggcagc taccaaagtt gactccgttc   3000
gccctgagca acgcggagga cctggacgcg gatctgatct ccgacaagag cgtgctggcc   3060
agcgtgcacc acccggcgct gatagtgttc cagtgctgca accctgtgta tcgcaactcg   3120
cgcgcgcagg gcggaggccc caactgcgac ttcaagatat cggcgcccga cctgctaaac   3180
gcgttggtga tggtgcgcag cctgtggagt gaaaacttca ccgagctgcc gcggatggtt   3240
gtgcctgagt ttaagtggag cactaaacac cagtatcgca acgtgtccct gccagtggcg   3300
catagcgatg cgcggcagaa cccctttgat ttttaacccg ggagttctag ggatctgccc   3360
ctctccctcc ccccccccta acgttactgg ccgaagccgc ttggaataag gccggtgtgc   3420
gtttgtctat atgttatttt ccaccatatt gccgtctttt ggcaatgtga gggcccggaa   3480
acctggccct gtcttcttga cgagcattcc taggggtctt tcccctctcg ccaaaggaat   3540
gcaaggtctg ttgaatgtcg tgaaggaagc agttcctctg gaagcttctt gaagacaaac   3600
aacgtctgta gcgacccttt gcaggcagcg gaacccccca cctggcgaca ggtgcctctg   3660
cggccaaaag ccacgtgtat aagatacacc tgcaaaggcg gcacaacccc agtgccacgt   3720
tgtgagttgg atagttgtgg aaagagtcaa atggctctcc tcaagcgtat tcaacaaggg   3780
gctgaaggat gcccagaagg taccccattg tatgggatct gatctggggc ctcggtgcac   3840
atgctttaca tgtgtttagt cgaggttaaa aaaacgtcta ggccccccga accacgggga   3900
```

```
cgtggttttc ctttgaaaaa cacgatgata aggatccacc ggaggccacc atgactacgt   3960
ccggcgttcc atttggcatg acactacgac caacacgatc tcggttgtct cggcgcactc   4020
cgtacagtag ggatcgtcta cctccttttg agacagaaac ccgcgctacc atactggagg   4080
atcatccgct gctgcccgaa tgtaacactt tgacaatgca caacgtgagt tacgtgcgag   4140
gtcttccctg cagtgtggga tttacgctga ttcaggaatg ggttgttccc tgggatatgg   4200
ttctaacgcg ggaggagctt gtaatcctga ggaagtgtat gcacgtgtgc ctgtgttgtg   4260
ccaacattga tatcatgacg agcatgatga tccatggtta cgagtcctgg gctctccact   4320
gtcattgttc cagtcccggt tccctgcagt gtatagccgg cgggcaggtt ttggccagct   4380
ggtttaggat ggtggtggat ggcgccatgt ttaatcagag gtttatatgg taccgggagg   4440
tggtgaatta caacatgcca aaagaggtaa tgtttatgtc cagcgtgttt atgaggggtc   4500
gccacttaat ctacctgcgc ttgtggtatg atggccacgt gggttctgtg gtccccgcca   4560
tgagctttgg atacagcgcc ttgcactgtg ggattttgaa caatattgtg gtgctgtgct   4620
gcagttactg tgctgattta agtgagatca gggtgcgctg ctgtgcccgg aggacaaggc   4680
gccttatgct gcgggcggtg cgaatcatcg ctgaggagac cactgccatg ttgtattcct   4740
gcaggacgga gcggcggcgg cagcagttta ttcgcgcgct gctgcagcac caccgcccta   4800
tcctgatgca cgattatgac tctaccccca tgtaggcggc cgctcgagtc tagagggccc   4860
gtttaaaccc gctgatcagc ctcgactgtg ccttctagtt gccagccatc tgttgtttgc   4920
ccctcccccg tgccttcctt gaccctggaa ggtgccactc ccactgtcct ttcctaataa   4980
aatgaggaaa ttgcatcgca ttgtctgagt aggtgtcatt ctattctggg gggtggggtg   5040
gggcaggaca gcaaggggga ggattgggaa gacaatagca ggcatgctgg ggatgcggtg   5100
ggctctatgg cttctgaggc ggaaagaacc agctggggct ctagggggta tccccggggt   5160
tggggttgcg ccttttccaa ggcatccagc acagtggcgg ccgcaatatt tgcatgtcgc   5220
tatgtgttct gggaaatcac cataaacgtg aaatccctat cagtgataga gacttataag   5280
ttccctatca gtgatagaga accggtgggc actcttccgt ggtctggtgg ataaattcgc   5340
aagggtatca tggcggacga ccggggttcg agccccgtat ccggccgtcc gccgtgatcc   5400
atgcggttac cgcccgcgtg tcgaacccag gtgtgcgacg tcagacaacg gggggagtgct  5460
ccttttttgaa ttccactttg gccgcggctc gagggggttg gggttgcgcc ttttccaagg  5520
cagccctggg tttgcgcagg gacgcggctg ctctgggcgt ggttccggga aacgcagcgg   5580
cgccgaccct gggtctcgca cattcttcac gtccgttcgc agcgtcaccc ggatcttcgc   5640
cgctaccctt gtgggccccc cggcgacgct tcctgctccg cccctaagtc gggaaggttc   5700
cttgcggttc gcggcgtgcc ggacgtgaca aacggaagcc gcacgtctca ctagtaccct   5760
cgcagacgga cagcgccagg gagcaatggc agcgcgccga ccgcgatggg ctgtggccaa   5820
tagcggctgc tcagcagggc gcgccgagag cagcggccgg gaaggggcgg tgcgggaggc   5880
ggggtgtggg gcggtagtgt gggccctgtt cctgcccgcg cggtgttccg cattctgcaa   5940
gcctccggag cgcacgtcgg cagtcggctc cctcgttgac cgaatcaccg acctctctcc   6000
ccagggggat ctgtgagttt ggggaccctt gattgttctt tctttttcgc tattgtaaaa   6060
ttcatgttat atggaggggg caaagttttc agggtgttgt ttagaatggg aagatgtccc   6120
ttgtatcacc atggaccctc atgataattt tgtttctttc actttctact ctgttgacaa   6180
ccattgtctc ctcttatttt cttttcattt tctgtaactt tttcgttaaa ctttagcttg   6240
```

-continued

```
catttgtaac gaatttttaa attcactttt gtttatttgt cagattgtaa gtactttctc   6300
taatcacttt tttttcaagg caatcagggt atattatatt gtacttcagc acagttttag   6360
agaacaattg ttataattaa atgataaggt agaatatttc tgcatataaa ttctggctgg   6420
cgtggaaata ttcttattgg tagaaacaac tacatcctgg tcatcatcct gcctttctct   6480
ttatggttac aatgatatac actgtttgag atgaggataa aatactctga gtccaaaccg   6540
ggcccctctg ctaaccatgt tcatgccttc ttctttttcc tacagctcct gggcaacgtg   6600
ctggttattg tgctgtctca tcattttggc aaagaattgt aatacgactc actatagggc   6660
gagccaccat ggctagatta gataaaagta aagtgattaa cagcgcatta gagctgctta   6720
atgaggtcgg aatcgaaggt ttaacaaccc gtaaactcgc ccagaagcta ggtgtagagc   6780
agcctacatt gtattggcat gtaaaaaata agcgggcttt gctcgacgcc ttagccattg   6840
agatgttaga taggcaccat actcactttt gccctttaga aggggaaagc tggcaagatt   6900
ttttacgtaa taacgctaaa agttttagat gtgctttact aagtcatcgc gatggagcaa   6960
aagtacattt aggtacacgg cctacagaaa aacagtatga aactctcgaa aatcaattag   7020
cctttttatg ccaacaaggt ttttcactag agaatgcctt atatgcactc agcgccgtgg   7080
ggcattttac tttaggttgc gtattggaag atcaagagca tcaagtcgct aaagaagaaa   7140
gggaaacacc tactactgat agtatgccgc cattattacg acaagctatc gaattatttg   7200
atcaccaagg tgcagagcca gccttcttat tcggccttga attgatcata tgcggattag   7260
aaaaacaact taaatgtgaa agtgggtccc caaaaaagaa gagaaaggtc gacggcggtg   7320
gttcagttta agcgtacagc ggctcccggg agttctaggg atctgcccct ctccctcccc   7380
ccccctaac gttactggcc gaagccgctt ggaataaggc cggtgtgcgt ttgtctatat   7440
gttattttcc accatattgc cgtcttttgg caatgtgagg gcccggaaac ctggccctgt   7500
cttcttgacg agcattccta ggggtctttc ccctctcgcc aaaggaatgc aaggtctgtt   7560
gaatgtcgtg aaggaagcag ttcctctgga agcttcttga agacaaacaa cgtctgtagc   7620
gaccctttgc aggcagcgga acccccacc tggcgacagg tgcctctgcg gccaaaagcc   7680
acgtgtataa gatacacctg caaaggcggc acaaccccag tgccacgttg tgagttggat   7740
agttgtggaa agagtcaaat ggctctcctc aagcgtattc aacaaggggc tgaaggatgc   7800
ccagaaggta ccccattgta tgggatctga tctggggcct cggtgcacat gctttacatg   7860
tgtttagtcg aggttaaaaa aacgtctagg ccccccgaac cacggggacg tggttttcct   7920
ttgaaaaaca cgatgataag gatccaccgg aggccaccat gaccgagtac aagcccacgg   7980
tgcgcctcgc caccgcgac gacgtcccca gggccgtacg caccctcgcc gccgcgttcg   8040
ccgactaccc cgccacgcgc cacaccgtcg atccggaccg ccacatcgag cgggtcaccg   8100
agctgcaaga actcttcctc acgcgcgtcg ggctcgacat cggcaaggtg tgggtcgcgg   8160
acgacggcgc cgcggtggcg gtctggacca cgccggagag cgtcgaagcg ggggcggtgt   8220
tcgccgagat cggcccgcgc atggccgagt tgagcggttc ccggctggcc gcgcagcaac   8280
agatggaagg cctcctggcg ccgcaccggc ccaaggagcc cgcgtggttc ctggccaccg   8340
tcggcgtctc gcccgaccac cagggcaagg gtctgggcag cgccgtcgtg ctccccggag   8400
tggaggcggc cgagcgcgcc ggggtgcccg ccttcctgga gacctccgcg ccccgcaacc   8460
tccccttcta cgagcggctc ggcttcaccg tcaccgccga cgtcgaggtg cccgaaggac   8520
cgcgcacctg gtgcatgacc cgcaagcccg gtgcctgacc gcgtctggaa caatcaacct   8580
ctggattaca aaatttgtga aagattgact ggtattctta actatgttgc tccttttacg   8640
```

ctatgtggat acgctgcttt aatgcctttg tatcatgcta ttgcttcccg tatggctttc 8700
attttctcct ccttgtataa atcctggttg ctgtctcttt atgaggagtt gtggcccgtt 8760
gtcaggcaac gtggcgtggt gtgcactgtg tttgctgacg caacccccac tggttggggc 8820
attgccacca cctgtcagct cctttccggg actttcgctt tccccctccc tattgccacg 8880
gcggaactca tcgccgcctg ccttgcccgc tgctggacag gggctcggct gttgggcact 8940
gacaattccg tggtgttgtc ggggaagctg acgtcctttc catggctgct cgcctgtgtt 9000
gccacctgga ttctgcgcgg gacgtccttc tgctacgtcc cttcggccct caatccagcg 9060
gaccttcctt cccgcggcct gctgccggct ctgcggcctc ttccgcgtct tcgccttcgc 9120
cctcagacga gtcggatctc cctttgggcc gcctccccgc aaaatgaccg accaagcgac 9180
gcccaacctg ccatcacgag atttcgattc caccgccgcc ttctatgaaa ggttgggctt 9240
cggaatcgtt ttccgggacg ccggctggat gatcctccag cgcggggatc tcatgctgga 9300
gttcttcgcc caccccaact tgtttattgc agcttataat ggttacaaat aaagcaatag 9360
catcacaaat ttcacaaata aagcattttt ttcactgcat tctagttgtg gtttgtccaa 9420
actcatcaat gtatcttatc atgtctgtat accgtcgacc tctagctaga gcttggcgta 9480
atcatggtca tagctgtttc ctgtgtgaaa ttgttatccg ctcacaattc cacacaacat 9540
acgagccgga agcataaagt gtaaagcctg gggtgcctaa tgagtgagct aactcacatt 9600
aattgcgttg cgctcactgc ccgctttcca gtcgggaaac ctgtcgtgcc agctgcatta 9660
atgaatcggc caacgcgcgg ggagaggcgg tttgcgtatt gggcgctctt ccgcttcctc 9720
gctcactgac tcgctgcgct cggtcgttcg gctgcggcga gcggtatcag ctcactcaaa 9780
ggcggtaata cggttatcca cagaatcagg ggataacgca ggaaagaaca tgtgagcaaa 9840
aggccagcaa aaggccagga accgtaaaaa ggccgcgttg ctggcgtttt tccataggct 9900
ccgcccccct gacgagcatc acaaaaatcg acgctcaagt cagaggtggc gaaacccgac 9960
aggactataa agataccagg cgtttccccc tggaagctcc ctcgtgcgct ctcctgttcc 10020
gaccctgccg cttaccggat acctgtccgc ctttctccct tcgggaagcg tggcgctttc 10080
tcatagctca cgctgtaggt atctcagttc ggtgtaggtc gttcgctcca agctgggctg 10140
tgtgcacgaa ccccccgttc agcccgaccg ctgcgcctta tccggtaact atcgtcttga 10200
gtccaacccg gtaagacacg acttatcgcc actggcagca gccactggta acaggattag 10260
cagagcgagg tatgtaggcg gtgctacaga gttcttgaag tggtggccta actacggcta 10320
cactagaaga acagtatttg gtatctgcgc tctgctgaag ccagttacct tcggaaaaag 10380
agttggtagc tcttgatccg gcaaacaaac caccgctggt agcggttttt ttgtttgcaa 10440
gcagcagatt acgcgcagaa aaaaaggatc tcaagaagat cctttgatct tttctacggg 10500
gtctgacgct cagtggaacg aaaactcacg ttaagggatt ttggtcatga gattatcaaa 10560
aaggatcttc acctagatcc ttttaaatta aaaatgaagt tttaaatcaa tctaaagtat 10620
atatgagtaa acttggtctg acagttacca atgcttaatc agtgaggcac ctatctcagc 10680
gatctgtcta tttcgttcat ccatagttgc ctgactcccc gtcgtgtaga taactacgat 10740
acgggagggc ttaccatctg gccccagtgc tgcaatgata ccgcgagacc cacgctcacc 10800
ggctccagat ttatcagcaa taaaccagcc agccggaagg gccgagcgca gaagtggtcc 10860
tgcaacttta tccgcctcca tccagtctat taattgttgc cgggaagcta gagtaagtag 10920
ttcgccagtt aatagtttgc gcaacgttgt tgccattgct acaggcatcg tggtgtcacg 10980
ctcgtcgttt ggtatggctt cattcagctc cggttcccaa cgatcaaggc gagttacatg 11040
atcccccatg ttgtgcaaaa aagcggttag ctccttcggt cctccgatcg ttgtcagaag 11100
taagttggcc gcagtgttat cactcatggt tatggcagca ctgcataatt ctcttactgt 11160
catgccatcc gtaagatgct tttctgtgac tggtgagtac tcaaccaagt cattctgaga 11220
atagtgtatg cggcgaccga gttgctcttg cccggcgtca atacgggata ataccgcgcc 11280
acatagcaga actttaaaag tgctcatcat tggaaaacgt tcttcggggc gaaaactctc 11340
aaggatctta ccgctgttga gatccagttc gatgtaaccc actcgtgcac ccaactgatc 11400
ttcagcatct tttactttca ccagcgtttc tgggtgagca aaaacaggaa ggcaaaatgc 11460
cgcaaaaaag ggaataaggg cgacacggaa atgttgaata ctcatactct tcctttttca 11520
atattattga agcatttatc agggttattg tctcatgagc ggatacatat ttgaatgtat 11580
ttagaaaaat aaacaaatag gggttccgcg cacatttccc cgaaaagtgc cacctgacgt 11640
c 11641

<210> SEQ ID NO 3
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
tatttaatct ccctatcagt gatagagatc tccctatcag tgatagagat cgcccgagtg 60
agcacgcagg gtctccattt tgaagcggga ggtttgaacg cgcagccgcc 110

<210> SEQ ID NO 4
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
tatttaatct ccctatcagt gatagagatc gcccgagtga gcacgcaggg tctccatttt 60
gatccctatc agtgatagag aagcgggagg tttgaacgcg cagccgcc 108

<210> SEQ ID NO 5
<211> LENGTH: 106
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
tccctatcag tgatagagat ctatttaagc ccgagtgagc acgcagtccc tatcagtgat 60
agagaggtct ccattttgaa gcgggaggtt tgaacgcgca gccgcc 106

<210> SEQ ID NO 6
<211> LENGTH: 183
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6
ccagaaatgg cgccggaggc gggaacaagg tggtggatga gtgctacatc cccaattact 60
tgctccccaa aacccagcct gagctccagt gggcgtggac taatatggaa cagtatttaa 120
gcgcctgtcc ctatcagtga tagagatctc cctatcagtg atagagattt gaatctcacg 180
gag 183

<210> SEQ ID NO 7
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
ccagaaatgg cgccggaggc gggaacaagg tggtggatga gtgctacatc cccaattact 60
tgctccccaa aacccagcct gagtccctat cagtgataga gactccagtg ggcgtggact 120
aatatggaac agtatttaag cgcctgtccc tatcagtgat agagatttga atctcacgga 180
g 181

<210> SEQ ID NO 8
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
ccagaaatgg cgccggaggc gggaacaagg tggtggatga gtgctacatc cccaattact 60
tgctccccaa aacccagcct gagctccagt gggcgtggac taatatggaa tccctatcag 120
tgatagagac agtatttaag cgcctgtccc tatcagtgat agagatttga atctcacgga 180
g 181

<210> SEQ ID NO 9
<211> LENGTH: 221
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
ccagaaatgg cgccggaggc gggaacaagg tggtggatga gtgctacatc cccaattact 60
tgctccccaa aacccagcct gagctccagt gggcgtggac taatatggaa cagtatttaa 120
ggtaagttcc ctatcagtga tagagatctc cctatcagtg atagagatac tgacatccac 180
tttgcctttc tctccacagc gcctgtttga atctcacgga g 221

<210> SEQ ID NO 10
<211> LENGTH: 223
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
ccagaaatgg cgccggaggc gggaacaagg tggtggatga gtgctacatc cccaattact 60
tgctccccaa aacccagcct gagctccagt gggcgtggac taatatggaa cagtatttaa 120
gcgcctgttt gaatctcacg gaaaggtaag ttccctatca gtgatagaga tctccctatc 180
agtgatagag atactgacat ccactttgcc tttctctcca cag 223

<210> SEQ ID NO 11
<211> LENGTH: 18281
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct aaattgtaag cgttaatatt ttgttaaaat tcgcgttaaa tttttgttaa 180
atcagctcat tttttaacca ataggccgaa atcggcaaaa tcccttataa atcaaaagaa 240
tagaccgaga tagggttgag tgttgttcca gtttggaaca agagtccact attaaagaac 300
gtggactcca acgtcaaagg gcgaaaaacc gtctatcagg gcgatggccc actacgtgaa 360
ccatcaccct aatcaagttt tttggggtcg aggtgccgta aagcactaaa tcggaaccct 420
aaagggagcc cccgatttag agcttgacgg ggaaagccgg cgaacgtggc gagaaaggaa 480
gggaagaaag cgaaaggagc gggcgctagg gcgctggcaa gtgtagcggt cacgctgcgc 540
gtaaccacca cacccgccgc gcttaatgcg ccgctacagg gcgcgtccca ttcgccattc 600
aggctgcgca actgttggga agggcgatcg gtgcgggcct cttcgctatt acgccagctg 660
gcgaaagggg gatgtgctgc aaggcgatta agttgggtaa cgccagggtt ttcccagtca 720
cgacgttgta aaacgacggc cagtgagcgc gcctcgttca ttcacgtttt tgaacccgtg 780
gaggacgggc agactcgcgg tgcaaatgtg ttttacagcg tgatggagca gatgaagatg 840
ctcgacacgc tgcagaacac gcagctagat taaccctaga aagataatca tattgtgacg 900
tacgttaaag ataatcatgc gtaaaattga cgcatgtgtt ttatcggtct gtatatcgag 960
gtttatttat taatttgaat agatattaag ttttattata tttacactta catactaata 1020
ataaattcaa caaacaattt atttatgttt atttatttat taaaaaaaaa caaaaactca 1080
aaatttcttc tataaagtaa caaaactttt atcgaattcc tgcagcccgg gggatccact 1140
agttctagag ggacagcccc cccccaaagc ccccagggat gtaattacgt ccctcccccg 1200
ctagggggca gcagcgagcc gcccggggct ccgctccggt ccggcgctcc ccccgcatcc 1260
ccgagccggc agcgtgcggg gacagcccgg gcacggggaa ggtggcacgg gatcgctttc 1320
ctctgaacgc ttctcgctgc tctttgagcc tgcagacacc tgggggggata cggggaaaag 1380 gcctccaagg ccagcttccc acaataagtt gggtgaattt tggctcattc ctcctttcta 1440
taggattgag gtcagagctt tgtgatggga attctgtgga atgtgtgtca gttagggtgt 1500
ggaaagtccc gcgatcgcta gcgtttaaac ttaagcttgg taccgagctc ggatccacta 1560
gtccagtgtg gtggaattcc tgcttcgcga tgtacgggcc agatatacgc gttgacattg 1620
attattgact agttattaat agtaatcaat tacggggtca ttagttcata gcccatatat 1680
ggagttccgc gttacataac ttacggtaaa tggcccgcct ggctgaccgc ccaacgaccc 1740
ccgcccattg acgtcaataa tgacgtatgt tcccatagta acgccaatag ggactttcca 1800
ttgacgtcaa tgggtggagt atttacggta aactgcccac ttggcagtac atcaagtgta 1860

-continued

```
tcatatgcca agtacgcccc ctattgacgt caatgacggt aaatggcccg cctggcatta   1920
tgcccagtac atgaccttat gggactttcc tacttggcag tacatctacg tattagtcat   1980
cgctattacc atggtgatgc ggttttggca gtacatcaat gggcgtggat agcggtttga   2040
ctcacgggga tttccaagtc tccaccccat tgacgtcaat gggagtttgt tttggaacca   2100
aaatcaacgg gactttccaa aatgtcgtaa caactccgcc ccattgacgc aaatgggcgg   2160
taggcgtgta cggtgggagg tctatataag cagagctctc cctatcagtg atagagatct   2220
ccctatcagt gatagagatc gtcgacgagc tcgtttagtg aaccgtcaga tcgcctggag   2280
acgccatcca cgctgttttg acctccatag aagacaccgg gaccgatcca gcctccggac   2340
tctagcgttt aaacttaagc ttgccaccat ggccagtcgg gaagaggagc agcgcgaaac   2400
cacccccgag cgcggacgcg gtgcggcgcg acgtccccca accatggagg acgtgtcgtc   2460
cccgtccccg tcgccgccgc ctccccgggc gcccccaaaa aagcggatga ggcggcgtat   2520
cgagtccgag gacgaggaag actcatcaca agacgcgctg gtgccgcgca cacccagccc   2580
gcggccatcg acctcggcgg cggatttggc cattgcgccc aagaagaaaa agaagcgccc   2640
ttctcccaag cccgagcgcc cgccatcacc agaggtaatc gtggacagcg aggaagaaag   2700
agaagatgtg gcgctacaaa tggtgggttt cagcaaccca ccggtgctaa tcaagcatgg   2760
caaaggaggt aagcgcacag tgcggcggct gaatgaagac gacccagtgg cgcgtggtat   2820
gcggacgcaa gaggaagagg aagagcccag cgaagcggaa agtgaaatta cggtgatgaa   2880
cccgctgagt gtgccgatcg tgtctgcgtg ggagaagggc atggaggctg cgcgcgcgct   2940
gatggacaag taccacgtgg ataacgatct aaaggcgaac ttcaaactac tgcctgacca   3000
agtggaagct ctggcggccg tatgcaagac ctggctgaac gaggagcacc gcgggttgca   3060
gctgaccttc accagcaaca agacctttgt gacgatgatg gggcgattcc tgcaggcgta   3120
cctgcagtcg tttgcagagg tgacctacaa gcatcacgag cccacgggct gcgcgttgtg   3180
gctgcaccgc tgcgctgaga tcgaaggcga gcttaagtgt ctacacggaa gcattatgat   3240
aaataaggag cacgtgattg aaatggatgt gacgagcgaa aacgggcagc gcgcgctgaa   3300
ggagcagtct agcaaggcca agatcgtgaa gaaccggtgg ggccgaaatg tggtgcagat   3360
ctccaacacc gacgcaaggt gctgcgtgca cgacgcggcc tgtccggcca atcagttttc   3420
cggcaagtct tgcggcatgt tcttctctga aggcgcaaag gctcaggtgg cttttaagca   3480
gatcaaggct tttatgcagg cgctgtatcc taacgcccag accgggcacg gtcacctttt   3540
gatgccacta cggtgcgagt gcaactcaaa gcctgggcac gcgccctttt tgggaaggca   3600
gctaccaaag ttgactccgt tcgccctgag caacgcggag gacctggacg cggatctgat   3660
ctccgacaag agcgtgctgg ccagcgtgca ccacccggcg ctgatagtgt tccagtgctg   3720
caaccctgtg tatcgcaact cgcgcgcgca gggcggaggc cccaactgcg acttcaagat   3780
atcggcgccc gacctgctaa acgcgttggt gatggtgcgc agcctgtgga gtgaaaactt   3840
caccgagctg ccgcggatgg ttgtgcctga gtttaagtgg agcactaaac accagtatcg   3900
caacgtgtcc ctgccagtgg cgcatagcga tgcgcggcag aacccctttg atttttaacc   3960
cgggagttct agggatctgc cctctccct cccccccccc taacgttact ggccgaagcc   4020
gcttggaata aggccggtgt gcgtttgtct atatgttatt ttccaccata ttgccgtctt   4080
ttggcaatgt gagggcccgg aaacctggcc ctgtcttctt gacgagcatt cctaggggtc   4140
tttcccctct cgccaaagga atgcaaggtc tgttgaatgt cgtgaaggaa gcagttcctc   4200
tggaagcttc ttgaagacaa acaacgtctg tagcgaccct ttgcaggcag cggaaccccc   4260
```

```
cacctggcga caggtgcctc tgcggccaaa agccacgtgt ataagataca cctgcaaagg   4320
cggcacaacc ccagtgccac gttgtgagtt ggatagttgt ggaaagagtc aaatggctct   4380
cctcaagcgt attcaacaag gggctgaagg atgcccagaa ggtaccccat tgtatgggat   4440
ctgatctggg gcctcggtgc acatgcttta catgtgttta gtcgaggtta aaaaaacgtc   4500
taggcccccc gaaccacggg gacgtggttt tcctttgaaa aacacgatga taaggatcca   4560
ccggaggcca ccatgactac gtccggcgtt ccatttggca tgacactacg accaacacga   4620
tctcggttgt ctcggcgcac tccgtacagt agggatcgtc tacctccttt tgagacagaa   4680
acccgcgcta ccatactgga ggatcatccg ctgctgcccg aatgtaacac tttgacaatg   4740
cacaacgtga gttacgtgcg aggtcttccc tgcagtgtgg gatttacgct gattcaggaa   4800
tgggttgttc cctgggatat ggttctaacg cgggaggagc ttgtaatcct gaggaagtgt   4860
atgcacgtgt gcctgtgttg tgccaacatt gatatcatga cgagcatgat gatccatggt   4920
tacgagtcct gggctctcca ctgtcattgt tccagtcccg gttccctgca gtgtatagcc   4980
ggcgggcagg ttttggccag ctggtttagg atggtggtgg atggcgccat gtttaatcag   5040
aggtttatat ggtaccggga ggtggtgaat tacaacatgc caaaagaggt aatgtttatg   5100
tccagcgtgt ttatgagggg tcgccactta atctacctgc gcttgtggta tgatggccac   5160
gtgggttctg tggtccccgc catgagcttt ggatacagcg ccttgcactg tgggattttg   5220
aacaatattg tggtgctgtg ctgcagttac tgtgctgatt taagtgagat cagggtgcgc   5280
tgctgtgccc ggaggacaag gcgccttatg ctgcgggcgg tgcgaatcat cgctgaggag   5340
accactgcca tgttgtattc ctgcaggacg gagcggcggc ggcagcagtt tattcgcgcg   5400
ctgctgcagc accaccgccc tatcctgatg cacgattatg actctacccc catgtaggcg   5460
gccgctcgag tctagagggc ccgtttaaac ccgctgatca gcctcgactg tgccttctag   5520
ttgccagcca tctgttgttt gcccctcccc cgtgccttcc ttgaccctgg aaggtgccac   5580
tcccactgtc ctttcctaat aaaatgagga aattgcatcg cattgtctga gtaggtgtca   5640
ttctattctg gggggtgggg tggggcagga cagcaagggg gaggattggg aagacaatag   5700
caggcatgct ggggatgcgg tgggctctat ggcttctgag gcggaaagaa ccagctgggg   5760
ctctaggggg tatccccggg gttggggttg cgcctttttcc aaggcatcca gcacagtggc   5820
ggccgcaata tttgcatgtc gctatgtgtt ctgggaaatc accataaacg tgaaatccct   5880
atcagtgata gagacttata agttccctat cagtgataga gaaccggtgg gcactcttcc   5940
gtggtctggt ggataaattc gcaagggtat catggcggac gaccggggtt cgagccccgt   6000
atccggccgt ccgccgtgat ccatgcggtt accgcccgcg tgtcgaaccc aggtgtgcga   6060
cgtcagacaa cgggggagtg ctcctttttg aattccactt tggccgcggc tcgagggggt   6120
tggggttgcg cctttttccaa ggcagccctg ggtttgcgca gggacgcggc tgctctgggc   6180
gtggttccgg gaaacgcagc ggcgccgacc ctgggtctcg cacattcttc acgtccgttc   6240
gcagcgtcac ccggatcttc gccgctaccc ttgtgggccc cccggcgacg cttcctgctc   6300
cgcccctaag tcgggaaggt tccttgcggt tcgcggcgtg ccggacgtga caaacggaag   6360
ccgcacgtct cactagtacc ctcgcagacg gacagcgcca gggagcaatg gcagcgcgcc   6420
gaccgcgatg ggctgtggcc aatagcggct gctcagcagg gcgcgccgag agcagcggcc   6480
gggaaggggc ggtgcgggag gcggggtgtg gggcggtagt gtgggccctg ttcctgcccg   6540
cgcggtgttc cgcattctgc aagcctccgg agcgcacgtc ggcagtcggc tccctcgttg   6600
```

```
accgaatcac cgacctctct ccccaggggg atctgtgagt ttggggaccc ttgattgttc   6660
tttcttttttc gctattgtaa aattcatgtt atatggaggg ggcaaagttt tcagggtgtt   6720
gtttagaatg ggaagatgtc ccttgtatca ccatggaccc tcatgataat tttgtttctt   6780
tcactttcta ctctgttgac aaccattgtc tcctcttatt ttcttttcat tttctgtaac   6840
tttttcgtta aactttagct tgcatttgta acgaattttt aaattcactt ttgtttattt   6900
gtcagattgt aagtactttc tctaatcact tttttttcaa ggcaatcagg gtatattata   6960
ttgtacttca gcacagtttt agagaacaat tgttataatt aaatgataag gtagaatatt   7020
tctgcatata aattctggct ggcgtggaaa tattcttatt ggtagaaaca actacatcct   7080
ggtcatcatc ctgcctttct ctttatggtt acaatgatat acactgtttg agatgaggat   7140
aaaatactct gagtccaaac cgggcccctc tgctaaccat gttcatgcct tcttcttttt   7200
cctacagctc ctgggcaacg tgctggttat tgtgctgtct catcattttg gcaaagaatt   7260
gtaatacgac tcactatagg gcgagccacc atggctagat tagataaaag taaagtgatt   7320
aacagcgcat tagagctgct taatgaggtc ggaatcgaag gtttaacaac ccgtaaactc   7380
gcccagaagc taggtgtaga gcagcctaca ttgtattggc atgtaaaaaa taagcgggct   7440
ttgctcgacg ccttagccat tgagatgtta gataggcacc atactcactt ttgcccttta   7500
gaaggggaaa gctggcaaga tttttttacgt aataacgcta aaagttttag atgtgcttta   7560
ctaagtcatc gcgatggagc aaaagtacat ttaggtacac ggcctacaga aaaacagtat   7620
gaaactctcg aaaatcaatt agcctttttta tgccaacaag gtttttcact agagaatgcc   7680
ttatatgcac tcagcgccgt ggggcatttt actttaggtt gcgtattgga agatcaagag   7740
catcaagtcg ctaaagaaga aagggaaaca cctactactg atagtatgcc gccattatta   7800
cgacaagcta tcgaattatt tgatcaccaa ggtgcagagc cagccttctt attcggcctt   7860
gaattgatca tatgcggatt agaaaaacaa cttaaatgtg aaagtgggtc cccaaaaaag   7920
aagagaaagg tcgacggcgg tggtgctttg tctcctcagc actctgctgt cactcaagga   7980
agtatcatca agaacaagga gggcatggat gctaagtcac taactgcctg gtcccggaca   8040
ctggtgacct tcaaggatgt atttgtggac ttcaccaggg aggagtggaa gctgctggac   8100
actgctcagc agatcgtgta cagaaatgtg atgctggaga actataagaa cctggtttcc   8160
ttgggttatc agcttactaa gccagatgtg atcctccggt tggagaaggg agaagagccc   8220
tggctggtgg agagagaaat tcaccaagag acccatcctg attcagagac tgcatttgaa   8280
atcaaatcat cagtttaagc gtacagcggc tcccgggagt tctagggatc tgcccctctc   8340
cctcccccccc ccctaacgtt actggccgaa gccgcttgga ataaggccgg tgtgcgtttg   8400
tctatatgtt attttccacc atattgccgt cttttggcaa tgtgagggcc cggaaacctg   8460
gccctgtctt cttgacgagc attcctaggg gtctttcccc tctcgccaaa ggaatgcaag   8520
gtctgttgaa tgtcgtgaag gaagcagttc ctctggaagc ttcttgaaga caaacaacgt   8580
ctgtagcgac cctttgcagg cagcggaacc ccccacctgg cgacaggtgc ctctgcggcc   8640
aaaagccacg tgtataagat acacctgcaa aggcggcaca accccagtgc cacgttgtga   8700
gttggatagt tgtggaaaga gtcaaatggc tctcctcaag cgtattcaac aaggggctga   8760
aggatgccca gaaggtaccc cattgtatgg gatctgatct ggggcctcgg tgcacatgct   8820
ttacatgtgt ttagtcgagg ttaaaaaaac gtctaggccc cccgaaccac ggggacgtgg   8880
ttttcctttg aaaaacacga tgataaggat ccaccggagg ccaccatgac cgagtacaag   8940
cccacggtgc gcctcgccac ccgcgacgac gtccccaggg ccgtacgcac cctcgccgcc   9000
```

-continued

```
gcgttcgccg actaccccgc cacgcgccac accgtcgatc cggaccgcca catcgagcgg   9060
gtcaccgagc tgcaagaact cttcctcacg cgcgtcgggc tcgacatcgg caaggtgtgg   9120
gtcgcggacg acggcgccgc ggtggcggtc tggaccacgc cggagagcgt cgaagcgggg   9180
gcggtgttcg ccgagatcgg cccgcgcatg gccgagttga gcggttcccg gctggccgcg   9240
cagcaacaga tggaaggcct cctggcgccg caccggccca aggagcccgc gtggttcctg   9300
gccaccgtcg gcgtctcgcc cgaccaccag ggcaagggtc tgggcagcgc cgtcgtgctc   9360
cccggagtgg aggcggccga gcgcgccggg gtgcccgcct tcctggagac ctccgcgccc   9420
cgcaacctcc ccttctacga gcggctcggc ttcaccgtca ccgccgacgt cgaggtgccc   9480
gaaggaccgc gcacctggtg catgacccgc aagcccggtg cctgaccgcg tctggaacaa   9540
tcaacctctg gattacaaaa tttgtgaaag attgactggt attcttaact atgttgctcc   9600
ttttacgcta tgtggatacg ctgctttaat gcctttgtat catgctattg cttcccgtat   9660
ggctttcatt ttctcctcct tgtataaatc ctggttgctg tctctttatg aggagttgtg   9720
gcccgttgtc aggcaacgtg gcgtggtgtg cactgtgttt gctgacgcaa cccccactgg   9780
ttggggcatt gccaccacct gtcagctcct ttccgggact ttcgctttcc ccctccctat   9840
tgccacggcg gaactcatcg ccgcctgcct tgcccgctgc tggacagggg ctcggctgtt   9900
gggcactgac aattccgtgg tgttgtcggg gaagctgacg tcctttccat ggctgctcgc   9960
ctgtgttgcc acctggattc tgcgcgggac gtccttctgc tacgtccctt cggccctcaa  10020
tccagcggac cttccttccc gcggcctgct gccggctctg cggcctcttc cgcgtcttcg  10080
ccttcgccct cagacgagtc ggatctccct ttgggccgcc tccccgcaaa atgaccgacc  10140
aagcgacgcc caacctgcca tcacgagatt tcgattccac cgccgccttc tatgaaaggt  10200
tgggcttcgg aatcgttttc cgggacgccg gctggatgat cctccagcgc ggggatctca  10260
tgctggagtt cttcgcccac cccaacttgt ttattgcagc ttataatggt tacaaataaa  10320
gcaatagcat cacaaatttc acaaataaag catttttttc actgcattct agttgtggtt  10380
tgtccaaact catcaatgta tcttatcatg tctgtagctg atcaattggc gcgccgaatt  10440
cgttatctgc agaattcggc ttggcggctg cgcgttcaaa cctcccgctt caaaatggag  10500
accctgcgtg ctcactcggg cttaaatacc cagcgtgacc acatggtgtc gcaaaatgtc  10560
gcaaaacact cacgtgacct ctaatacagg acctctagag catggaaact agataagaaa  10620
gaaatacgca gagaccaaag ttcaactgaa acgaattaaa cggtttattg attaacaagc  10680
aaactagttt acagattacg ggtgaggtaa cgggtgccga tggggcgagg ctcagaataa  10740
acgccatttg tgtcaacagc aaagtccaca tttgtagatt tgttgtagtt ggaagtgtat  10800
tgaatctctg ggttccagcg tttgctgttt tctttctgca gctcccattc aatttccacg  10860
ctgacctgtc cggtgctgta ctgcgtgatg aacgacgcaa acttagctgg actgaaggta  10920
gttggaggat tcgcgggaac aggtgtattc ttaatcagga tctgaggagg cgggtgtttc  10980
agtccaaagc ctcccatcag cggcgaggga tgaaagtgtc cgtccgtgtg aggaatcttg  11040
gcccagatag gaccctgcag gtacacgtcc cggtcctgcc agaccatgcc aggtaaggct  11100
ccttgactgt tgacggtccc tgtagcagga gcggtgttgg ccgattgcag gttagtggcc  11160
accgtgccgt actcttctgt ggccactggg ttggtggttt taatttcttc ctcgttggtt  11220
atcataacgt tgtcaaggtc cacgttgcta tttccagctc cctgtttccc aaatattaag  11280
actccgctca tcggaaaaaa tttgtcttcg tcgtccttgt gggttgccat agcgggaccg  11340
```

-continued ggatttacca gagagtctct gccattcaga tgatacttgg tggcaccggt ccaggcaaag 11400
ttgctgttgt tattttgatt ggttgtcttg gagacgcgtt gctgccggta gcagggcccg 11460
ggtagccagt ttttggcctg attcgccatg ctactaggcc cggcctgaga aaattgcaac 11520
gtccgatttc ctgcggtacc actcgtggtc tgagtccgag acaggtagta caggtactgg 11580
tcgatgaggg ggttcatcag ccggtccagg ctttggctgt gcgcgtagct gctgtgaaaa 11640
ggcacgtcct caaacgtgta gctgaactga aagttgttgc ccgttctcag catttgagaa 11700
ggaaagtatt ccaggcagta gaaggaggaa cggcccacgg cctgactgcc attgttcaga 11760
gtcaggtacc cgtactgagg aatcatgaag acgtccgccg ggaacggagg caggcagccc 11820
tggtgcgcag agccgaggac gtacgggagc tggtattccg agtccgtaaa gacctgaacc 11880
gtgctggtaa ggttattggc gatggtcgtg gtgccatcat tcgtcgtgac ctccttgacc 11940
tggatgttga agagcttgaa gttgagcttc ttgggccgga atccccagtt gttgttgatg 12000
agtcgctgcc agtcacgtgg tgagaagtgg cagtggaatc tgttaaagtc aaaatacccc 12060
cagggggtgc tgtagccgaa gtaggtgttg tcgttggtgc tgcctcccga ttggctggag 12120
atttgcttgt agaggtggtt gttgtaggtg gggagggccc aggttcgggt gctggtggtg 12180
atgactctgt cgcccagcca tgtggaatcg caatgccaat ttcctgaggc gttacccact 12240
ccgtcggcgc cttcgttatt gtctgccatt ggagcgccac cgcctgcagc cattgtatta 12300
gatcccacac cagagggggc tgcggggggt tctccgagtg gttgagggtc gggcactgac 12360
tctgagtcgc cagtctgccc aaagttgagt ctctttctcg cgggctgctg gcctttcttg 12420
ccgatgcccg aagaggagtc tggttcctgg ggtgattgct ctaccggtct cttctttcca 12480
ggagccgtct tagcgccttc ctcaaccaga ccgagaggtt cgagaacccg cttcttggcc 12540
tggaagactg ctcgcccgag gttgccccca aaagacgtat cttcttgcag acgctcctga 12600
aactcggcgt cggcgtggtt ataccgcagg tacggattgt cacccgcttt gagctgctgg 12660
tcgtaggcct tgtcgtgctc gagggccgct gcgtccgccg cgttgacggg ctccccccttg 12720 tcgagtccgt tgaagggtcc gaggtacttg tagccaggaa gcaccagacc ccggccgtcg 12780
tcctgctttt gctggttggc tttgggtttc ggggctccag gtttcaagtc ccaccactcg 12840
cgaatgccct cagagaggtt gtcctcgagc caatctggaa gataaccatc ggcagccata 12900
cctgatttaa atcatttatt gttcaaagat gcagtcatcc aaatccacat tgaccagatc 12960
gcaggcagtg caagcgtctg gcacctttcc catgatatga tgaatgtagc acagtttctg 13020
atacgccttt ttgacgacag aaacgggttg agattctgac acgggaaagc actctaaaca 13080
gtctttctgt ccgtgagtga agcagatatt tgaattctga ttcattctct cgcattgtct 13140
gcagggaaac agcatcagat tcatgcccac gtgacgagaa catttgtttt ggtacctgtc 13200
tgcgtagttg atcgaagctt ccgcgtctga cgtcgatggc tgcgcaactg actcgcgcac 13260
ccgtttgggc tcacttatat ctgcgtcact gggggcgggt cttttcttgg ctccaccctt 13320
tttgacgtag aattcatgct ccacctcaac cacgtgatcc tttgcccacc ggaaaaagtc 13380
tttgacttcc tgcttggtga ccttcccaaa gtcatgatcc agacggcggg tgagttcaaa 13440
tttgaacatc cggtcttgca acggctgctg gtgttcgaag gtcgttgagt tcccgtcaat 13500
cacggcgcac atgttggtgt tggaggtgac gatcacggga gtcgggtcta tctgggccga 13560
ggacttgcat ttctggtcca cgcgcacctt gcttcctccg agaatggctt tggccgactc 13620
cacgaccttg gcggtcatct tcccctcctc ccaccagatc accatcttgt cgacacagtc 13680
gttgaaggga aagttctcat tggtccagtt tacgcacccg tagaagggca cagtgtgggc 13740

-continued

```
tatggcctcc gcgatgttgg tcttcccggt agttgcaggc ccaaacagcc agatggtgtt  13800
cctcttgccg aactttttcg tggcccatcc cagaaagacg gaagccgcat attggggatc  13860
gtacccgttt agttccaaaa ttttataaat ccgattgctg gaaatgtcct ccacgggctg  13920
ctggcccacc aggtagtcgg gggcggtttt agtcaggctc ataatctttc ccgcattgtc  13980
caaggcagcc ttgatttggg accgcgagtt ggaggccgca ttgaaggaga tgtatgaggc  14040
ctggtcctcc tggatccact gcttctccga ggtaatcccc ttgtccacga gccacccgac  14100
cagctccatg tacctggctg aagtttttga tctgatcacc ggcgcatcag aattgggatt  14160
ctgattctct ttgttctgct cctgcgtctg cgacacgtgc gtcagatgct gcgccaccaa  14220
ccgtttacgc tccgtgagat tcaaacaggc gctgtggaga gaaaggcaaa gtggatgtca  14280
gtatctctat cactgatagg gagatctcta tcactgatag ggaacttacc ttaaatactg  14340
ttccatatta gtccacgccc actggagctc aggctgggtt ttggggagca agtaattggg  14400
gatgtagcac tcatccacca ccttgttccc gcctccggcg ccatttctgg tctttgtgac  14460
cgcgaaccag tttggcaaag tcggctcgat cccgcggtaa attctctgaa tcagtttttc  14520
gcgaatctga ctcaggaaac gtcccaaaac catggatttc accccggtgg tttccacgag  14580
cacgtgcatg tggaagtagc tctctccctt ctcaaattgc acaaagaaaa gagcctccgg  14640
ggccttactc acacggcgcc attccgtcag aaagtcgcgc tgcagcttct cggccacggt  14700
caggggtgcc tgctcaatca gattcagatc catgtcagaa tctggcggca actcccattc  14760
cttctcggcc acccagttca caaagctgtc agaaatgccg ggcagatgct cgtcaaggtc  14820
gctggggacc ttaatcacaa tctcgtaaaa ccccggcatg gcggctgcgc gttcaaacct  14880
cccgcttcaa aatggagacc ctgcgtgctc actcgggcga tctctatcac tgatagggag  14940
atctctatca ctgataggga gattaaatag aatggctagg atccggccgg cctgcaggtg  15000
tcctcacagg aacgaagtcc ctaaagaaac agtggcagcc aggtttagcc ccggaattga  15060
ctggattcct tttttagggc ccattggtat ggctttttcc ccgtatcccc ccaggtgtct  15120
gcaggctcaa agagcagcga gaagcgttca gaggaaagcg atcccgtgcc accttccccg  15180
tgcccgggct gtccccgcac gctgccggct cggggatgcg gggggagcgc cggaccggag  15240
cggagccccg ggcggctcgc tgctgccccc tagcggggga gggacgtaat tacatccctg  15300
ggggctttgg ggggggctg tccctctaga gcggccgcca ccgcggtgga gctccagctt  15360
ttgttccctt tagtgagggt taattagatc ttaatacgac tcactatagg gcgaattggg  15420
taccgggccc cccctcgagg tcgacggtat cgataagctt gatatctata acaagaaaat  15480
atatatataa taagttatca cgtaagtaga acatgaaata acaatataat tatcgtatga  15540
gttaaatctt aaaagtcacg taaaagataa tcatgcgtca ttttgactca cgcggtcgtt  15600
atagttcaaa atcagtgaca cttaccgcat tgacaagcac gcctcacggg agctccaagc  15660
ggcgactgag atgtcctaaa tgcacagcga cggattcgcg ctatttagaa agagagagca  15720
atatttcaag aatgcatgcg tcaattttac gcagactatc tttctagggt taatctagct  15780
gcatcaggat catatcgtcg ggtctttttt ccggctcagt catcgcccaa gctggcgcta  15840
tctgggcatc ggggaggaag aagcccgtgc cttttcccgc gaggttgaag cggcatggaa  15900
agagtttgcc gaggatgact gctgctgcat tgacgttgag cgaaaacgca cgtttaccat  15960
gatgattcgg gaaggtgtgg ccatgcacgc ctttaacggt gaactgttcg ttcaggccac  16020
ctgggatacc agttcgtcgc ggcttttccg gacacagttc cggatggtca gcccgaagcg  16080
```

-continued catcagcaac ccgaacaata ccggcgacag ccggaactgc cgtgccggtg tgcagattaa 16140
tgacagcggt gcggcgctgg gatattacgt cagcgaggac gggtatcctg gctggatgcc 16200
gcagaaatgg acatggatac cccgtgagtt acccggcggg cgcgcttggc gtaatcatgg 16260
tcatagctgt ttcctgtgtg aaattgttat ccgctcacaa ttccacacaa catacgagcc 16320
ggaagcataa agtgtaaagc ctggggtgcc taatgagtga gctaactcac attaattgcg 16380
ttgcgctcac tgcccgcttt ccagtcggga aacctgtcgt gccagctgca ttaatgaatc 16440
ggccaacgcg cggggagagg cggtttgcgt attgggcgct cttccgcttc ctcgctcact 16500
gactcgctgc gctcggtcgt tcggctgcgg cgagcggtat cagctcactc aaaggcggta 16560
atacggttat ccacagaatc aggggataac gcaggaaaga acatgtgagc aaaaggccag 16620
caaaaggcca ggaaccgtaa aaaggccgcg ttgctggcgt ttttccatag gctccgcccc 16680
cctgacgagc atcacaaaaa tcgacgctca agtcagaggt ggcgaaaccc gacaggacta 16740
taaagatacc aggcgtttcc ccctggaagc tccctcgtgc gctctcctgt tccgaccctg 16800
ccgcttaccg gatacctgtc cgcctttctc ccttcgggaa gcgtggcgct ttctcatagc 16860
tcacgctgta ggtatctcag ttcggtgtag gtcgttcgct ccaagctggg ctgtgtgcac 16920
gaaccccccg ttcagcccga ccgctgcgcc ttatccggta actatcgtct tgagtccaac 16980
ccggtaagac acgacttatc gccactggca gcagccactg gtaacaggat tagcagagcg 17040
aggtatgtag gcggtgctac agagttcttg aagtggtggc ctaactacgg ctacactaga 17100
aggacagtat ttggtatctg cgctctgctg aagccagtta ccttcggaaa aagagttggt 17160
agctcttgat ccggcaaaca aaccaccgct ggtagcggtg gtttttttgt ttgcaagcag 17220
cagattacgc gcagaaaaaa aggatctcaa gaagatcctt tgatcttttc tacggggtct 17280
gacgctcagt ggaacgaaaa ctcacgttaa gggattttgg tcatgagatt atcaaaaagg 17340
atcttcacct agatcctttt aaattaaaaa tgaagtttta aatcaatcta aagtatatat 17400
gagtaaactt ggtctgacag ttaccaatgc ttaatcagtg aggcacctat ctcagcgatc 17460
tgtctatttc gttcatccat agttgcctga ctccccgtcg tgtagataac tacgatacgg 17520
gagggcttac catctggccc cagtgctgca atgataccgc gagacccacg ctcaccggct 17580
ccagatttat cagcaataaa ccagccagcc ggaagggccg agcgcagaag tggtcctgca 17640
actttatccg cctccatcca gtctattaat tgttgccggg aagctagagt aagtagttcg 17700
ccagttaata gtttgcgcaa cgttgttgcc attgctacag gcatcgtggt gtcacgctcg 17760
tcgtttggta tggcttcatt cagctccggt tcccaacgat caaggcgagt tacatgatcc 17820
cccatgttgt gcaaaaaagc ggttagctcc ttcggtcctc cgatcgttgt cagaagtaag 17880
ttggccgcag tgttatcact catggttatg gcagcactgc ataattctct tactgtcatg 17940
ccatccgtaa gatgcttttc tgtgactggt gagtactcaa ccaagtcatt ctgagaatag 18000
tgtatgcggc gaccgagttg ctcttgcccg gcgtcaatac gggataatac cgcgccacat 18060
agcagaactt taaaagtgct catcattgga aaacgttctt cggggcgaaa actctcaagg 18120
atcttaccgc tgttgagatc cagttcgatg taacccactc gtgcacccaa ctgatcttca 18180
gcatctttta ctttcaccag cgtttctggg tgagcaaaaa caggaaggca aaatgccgca 18240
aaaaagggaa taagggcgac acggaaatgt tgaatactca t 18281

<210> SEQ ID NO 12
<211> LENGTH: 17936
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12

```
actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct aaattgtaag cgttaatatt ttgttaaaat tcgcgttaaa tttttgttaa    180

atcagctcat tttttaacca ataggccgaa atcggcaaaa tcccttataa atcaaaagaa    240

tagaccgaga tagggttgag tgttgttcca gtttggaaca agagtccact attaaagaac    300

gtggactcca acgtcaaagg gcgaaaaacc gtctatcagg gcgatggccc actacgtgaa    360

ccatcaccct aatcaagttt tttggggtcg aggtgccgta aagcactaaa tcggaaccct    420

aaagggagcc cccgatttag agcttgacgg ggaaagccgg cgaacgtggc gagaaaggaa    480

gggaagaaag cgaaaggagc gggcgctagg gcgctggcaa gtgtagcggt cacgctgcgc    540

gtaaccacca cacccgccgc gcttaatgcg ccgctacagg gcgcgtccca ttcgccattc    600

aggctgcgca actgttggga agggcgatcg gtgcgggcct cttcgctatt acgccagctg    660

gcgaaagggg gatgtgctgc aaggcgatta agttgggtaa cgccagggtt ttcccagtca    720

cgacgttgta aaacgacggc cagtgagcgc gcctcgttca ttcacgtttt tgaacccgtg    780

gaggacgggc agactcgcgg tgcaaatgtg ttttacagcg tgatggagca gatgaagatg    840

ctcgacacgc tgcagaacac gcagctagat taaccctaga aagataatca tattgtgacg    900

tacgttaaag ataatcatgc gtaaaattga cgcatgtgtt ttatcggtct gtatatcgag    960

gtttatttat taatttgaat agatattaag ttttattata tttacactta catactaata   1020

ataaattcaa caaacaattt atttatgttt atttatttat taaaaaaaaa caaaaactca   1080

aaatttcttc tataaagtaa caaaactttt atcgaattcc tgcagcccgg gggatccact   1140

agttctagag ggacagcccc cccccaaagc ccccagggat gtaattacgt ccctcccccg   1200

ctagggggca gcagcgagcc gcccggggct ccgctccggt ccggcgctcc ccccgcatcc   1260

ccgagccggc agcgtgcggg gacagcccgg gcacggggaa ggtggcacgg gatcgctttc   1320

ctctgaacgc ttctcgctgc tctttgagcc tgcagacacc tgggggggata cggggaaaag   1380

gcctccaagg ccagcttccc acaataagtt gggtgaattt tggctcattc ctcctttcta   1440

taggattgag gtcagagctt tgtgatggga attctgtgga atgtgtgtca gttagggtgt   1500

ggaaagtccc gcgatcgcta gcgtttaaac ttaagcttgg taccgagctc ggatccacta   1560

gtccagtgtg gtggaattcc tgcttcgcga tgtacgggcc agatatacgc gttgacattg   1620

attattgact agttattaat agtaatcaat tacggggtca ttagttcata gcccatatat   1680

ggagttccgc gttacataac ttacggtaaa tggcccgcct ggctgaccgc ccaacgaccc   1740

ccgcccattg acgtcaataa tgacgtatgt tcccatagta acgccaatag ggactttcca   1800

ttgacgtcaa tgggtggagt atttacggta aactgcccac ttggcagtac atcaagtgta   1860

tcatatgcca agtacgcccc ctattgacgt caatgacggt aaatggcccg cctggcatta   1920

tgcccagtac atgaccttat gggactttcc tacttggcag tacatctacg tattagtcat   1980

cgctattacc atggtgatgc ggttttggca gtacatcaat gggcgtggat agcggtttga   2040

ctcacgggga tttccaagtc tccaccccat tgacgtcaat gggagtttgt tttggaacca   2100

aaatcaacgg gactttccaa aatgtcgtaa caactccgcc ccattgacgc aaatgggcgg   2160

taggcgtgta cggtgggagg tctatataag cagagctctc cctatcagtg atagagatct   2220
```

```
ccctatcagt gatagagatc gtcgacgagc tcgtttagtg aaccgtcaga tcgcctggag   2280
acgccatcca cgctgttttg acctccatag aagacaccgg gaccgatcca gcctccggac   2340
tctagcgttt aaacttaagc ttgccaccat ggccagtcgg gaagaggagc agcgcgaaac   2400
cacccccgag cgcggacgcg gtgcggcgcg acgtccccca accatggagg acgtgtcgtc   2460
cccgtccccg tcgccgccgc ctccccgggc gcccccaaaa aagcggatga ggcggcgtat   2520
cgagtccgag gacgaggaag actcatcaca agacgcgctg gtgccgcgca cacccagccc   2580
gcggccatcg acctcggcgg cggatttggc cattgcgccc aagaagaaaa agaagcgccc   2640
ttctcccaag cccgagcgcc cgccatcacc agaggtaatc gtggacagcg aggaagaaag   2700
agaagatgtg gcgctacaaa tggtgggttt cagcaaccca ccggtgctaa tcaagcatgg   2760
caaaggaggt aagcgcacag tgcggcggct gaatgaagac gacccagtgg cgcgtggtat   2820
gcggacgcaa gaggaagagg aagagcccag cgaagcggaa agtgaaatta cggtgatgaa   2880
cccgctgagt gtgccgatcg tgtctgcgtg ggagaagggc atggaggctg cgcgcgcgct   2940
gatggacaag taccacgtgg ataacgatct aaaggcgaac ttcaaactac tgcctgacca   3000
agtggaagct ctggcggccg tatgcaagac ctggctgaac gaggagcacc gcgggttgca   3060
gctgaccttc accagcaaca agacctttgt gacgatgatg gggcgattcc tgcaggcgta   3120
cctgcagtcg tttgcagagg tgacctacaa gcatcacgag cccacgggct gcgcgttgtg   3180
gctgcaccgc tgcgctgaga tcgaaggcga gcttaagtgt ctacacggaa gcattatgat   3240
aaataaggag cacgtgattg aaatggatgt gacgagcgaa aacgggcagc gcgcgctgaa   3300
ggagcagtct agcaaggcca agatcgtgaa gaaccggtgg ggccgaaatg tggtgcagat   3360
ctccaacacc gacgcaaggt gctgcgtgca cgacgcggcc tgtccggcca atcagttttc   3420
cggcaagtct tgcggcatgt tcttctctga aggcgcaaag gctcaggtgg cttttaagca   3480
gatcaaggct tttatgcagg cgctgtatcc taacgcccag accgggcacg gtcacctttt   3540
gatgccacta cggtgcgagt gcaactcaaa gcctgggcac gcgccctttt tgggaaggca   3600
gctaccaaag ttgactccgt tcgccctgag caacgcggag gacctggacg cggatctgat   3660
ctccgacaag agcgtgctgg ccagcgtgca ccacccggcg ctgatagtgt tccagtgctg   3720
caaccctgtg tatcgcaact cgcgcgcgca gggcggaggc cccaactgcg acttcaagat   3780
atcggcgccc gacctgctaa acgcgttggt gatggtgcgc agcctgtgga gtgaaaactt   3840
caccgagctg ccgcggatgg ttgtgcctga gtttaagtgg agcactaaac accagtatcg   3900
caacgtgtcc ctgccagtgg cgcatagcga tgcgcggcag aaccccttttg atttttaacc   3960
cgggagttct agggatctgc ccctctccct cccccccccc taacgttact ggccgaagcc   4020
gcttggaata aggccggtgt gcgtttgtct atatgttatt ttccaccata ttgccgtctt   4080
ttggcaatgt gagggcccgg aaacctggcc ctgtcttctt gacgagcatt cctaggggtc   4140
tttcccctct cgccaaagga atgcaaggtc tgttgaatgt cgtgaaggaa gcagttcctc   4200
tggaagcttc ttgaagacaa acaacgtctg tagcgaccct ttgcaggcag cggaaccccc   4260
cacctggcga caggtgcctc tgcggccaaa agccacgtgt ataagataca cctgcaaagg   4320
cggcacaacc ccagtgccac gttgtgagtt ggatagttgt ggaaagagtc aaatggctct   4380
cctcaagcgt attcaacaag gggctgaagg atgcccagaa ggtaccccat tgtatgggat   4440
ctgatctggg gcctcggtgc acatgcttta catgtgttta gtcgaggtta aaaaaacgtc   4500
taggcccccc gaaccacggg gacgtggttt tcctttgaaa aacacgatga taaggatcca   4560
```

-continued

```
ccggaggcca ccatgactac gtccggcgtt ccatttggca tgacactacg accaacacga   4620
tctcggttgt ctcggcgcac tccgtacagt agggatcgtc tacctccttt tgagacagaa   4680
acccgcgcta ccatactgga ggatcatccg ctgctgcccg aatgtaacac tttgacaatg   4740
cacaacgtga gttacgtgcg aggtcttccc tgcagtgtgg gatttacgct gattcaggaa   4800
tgggttgttc cctgggatat ggttctaacg cgggaggagc ttgtaatcct gaggaagtgt   4860
atgcacgtgt gcctgtgttg tgccaacatt gatatcatga cgagcatgat gatccatggt   4920
tacgagtcct gggctctcca ctgtcattgt tccagtcccg gttccctgca gtgtatagcc   4980
ggcgggcagg ttttggccag ctggtttagg atggtggtgg atggcgccat gtttaatcag   5040
aggtttatat ggtaccggga ggtggtgaat tacaacatgc caaaagaggt aatgtttatg   5100
tccagcgtgt ttatgagggg tcgccactta atctacctgc gcttgtggta tgatggccac   5160
gtgggttctg tggtccccgc catgagcttt ggatacagcg ccttgcactg tgggattttg   5220
aacaatattg tggtgctgtg ctgcagttac tgtgctgatt taagtgagat cagggtgcgc   5280
tgctgtgccc ggaggacaag gcgccttatg ctgcgggcgg tgcgaatcat cgctgaggag   5340
accactgcca tgttgtattc ctgcaggacg gagcggcggc ggcagcagtt tattcgcgcg   5400
ctgctgcagc accaccgccc tatcctgatg cacgattatg actctacccc catgtaggcg   5460
gccgctcgag tctagagggc ccgtttaaac ccgctgatca gcctcgactg tgccttctag   5520
ttgccagcca tctgttgttt gcccctcccc cgtgccttcc ttgaccctgg aaggtgccac   5580
tcccactgtc ctttcctaat aaaatgagga aattgcatcg cattgtctga gtaggtgtca   5640
ttctattctg gggggtgggg tggggcagga cagcaagggg gaggattggg aagacaatag   5700
caggcatgct ggggatgcgg tgggctctat ggcttctgag gcggaaagaa ccagctgggg   5760
ctctaggggg tatccccggg gttggggttg cgccttttcc aaggcatcca gcacagtggc   5820
ggccgcaata tttgcatgtc gctatgtgtt ctgggaaatc accataaacg tgaaatccct   5880
atcagtgata gagacttata agttccctat cagtgataga gaaccggtgg gcactcttcc   5940
gtggtctggt ggataaattc gcaagggtat catggcggac gaccggggtt cgagccccgt   6000
atccggccgt ccgccgtgat ccatgcggtt accgcccgcg tgtcgaaccc aggtgtgcga   6060
cgtcagacaa cgggggagtg ctcctttttg aattccactt tggccgcggc tcgagggggt   6120
tggggttgcg ccttttccaa ggcagccctg ggtttgcgca gggacgcggc tgctctgggc   6180
gtggttccgg gaaacgcagc ggcgccgacc ctgggtctcg cacattcttc acgtccgttc   6240
gcagcgtcac ccggatcttc gccgctaccc ttgtgggccc cccggcgacg cttcctgctc   6300
cgcccctaag tcgggaaggt tccttgcggt tcgcggcgtg ccggacgtga caaacggaag   6360
ccgcacgtct cactagtacc ctcgcagacg gacagcgcca gggagcaatg gcagcgcgcc   6420
gaccgcgatg ggctgtggcc aatagcggct gctcagcagg gcgcgccgag agcagcggcc   6480
gggaaggggc ggtgcgggag gcggggtgtg gggcggtagt gtgggccctg ttcctgcccg   6540
cgcggtgttc cgcattctgc aagcctccgg agcgcacgtc ggcagtcggc tccctcgttg   6600
accgaatcac cgacctctct ccccaggggg atctgtgagt ttggggaccc ttgattgttc   6660
tttctttttc gctattgtaa aattcatgtt atatggaggg ggcaaagttt tcagggtgtt   6720
gtttagaatg ggaagatgtc ccttgtatca ccatggaccc tcatgataat tttgtttctt   6780
tcactttcta ctctgttgac aaccattgtc tcctcttatt ttcttttcat tttctgtaac   6840
tttttcgtta aactttagct tgcatttgta acgaattttt aaattcactt ttgtttattt   6900
gtcagattgt aagtactttc tctaatcact ttttttcaa ggcaatcagg gtatattata   6960
```

ttgtacttca gcacagtttt agagaacaat tgttataatt aaatgataag gtagaatatt 7020
tctgcatata aattctggct ggcgtggaaa tattcttatt ggtagaaaca actacatcct 7080
ggtcatcatc ctgcctttct ctttatggtt acaatgatat acactgtttg agatgaggat 7140
aaaatactct gagtccaaac cgggcccctc tgctaaccat gttcatgcct tcttcttttt 7200
cctacagctc ctgggcaacg tgctggttat tgtgctgtct catcattttg gcaaagaatt 7260
gtaatacgac tcactatagg gcgagccacc atggctagat tagataaaag taaagtgatt 7320
aacagcgcat tagagctgct taatgaggtc ggaatcgaag gtttaacaac ccgtaaactc 7380
gcccagaagc taggtgtaga gcagcctaca ttgtattggc atgtaaaaaa taagcgggct 7440
ttgctcgacg ccttagccat tgagatgtta gataggcacc atactcactt ttgcccttta 7500
gaaggggaaa gctggcaaga tttttacgt aataacgcta aaagttttag atgtgcttta 7560
ctaagtcatc gcgatggagc aaaagtacat ttaggtacac ggcctacaga aaaacagtat 7620
gaaactctcg aaaatcaatt agcctttta tgccaacaag gtttttcact agagaatgcc 7680
ttatatgcac tcagcgccgt ggggcatttt actttaggtt gcgtattgga agatcaagag 7740
catcaagtcg ctaaagaaga aagggaaaca cctactactg atagtatgcc gccattatta 7800
cgacaagcta tcgaattatt tgatcaccaa ggtgcagagc cagccttctt attcggcctt 7860
gaattgatca tatgcggatt agaaaaacaa cttaaatgtg aaagtgggtc cccaaaaaag 7920
aagagaaagg tcgacggcgg tggttcagtt taagcgtaca gcggctcccg ggagttctag 7980
ggatctgccc ctctccctcc cccccccta acgttactgg ccgaagccgc ttggaataag 8040
gccggtgtgc gtttgtctat atgttatttt ccaccatatt gccgtctttt ggcaatgtga 8100
gggcccggaa acctggccct gtcttcttga cgagcattcc taggggtctt tcccctctcg 8160
ccaaaggaat gcaaggtctg ttgaatgtcg tgaaggaagc agttcctctg gaagcttctt 8220
gaagacaaac aacgtctgta gcgacccttt gcaggcagcg gaacccccca cctggcgaca 8280
ggtgcctctg cggccaaaag ccacgtgtat aagatacacc tgcaaaggcg gcacaacccc 8340
agtgccacgt tgtgagttgg atagttgtgg aaagagtcaa atggctctcc tcaagcgtat 8400
tcaacaaggg gctgaaggat gcccagaagg taccccattg tatgggatct gatctggggc 8460
ctcggtgcac atgctttaca tgtgtttagt cgaggttaaa aaaacgtcta ggccccccga 8520
accacgggga cgtggttttc ctttgaaaaa cacgatgata aggatccacc ggaggccacc 8580
atgaccgagt acaagcccac ggtgcgcctc gccacccgcg acgacgtccc cagggccgta 8640
cgcaccctcg ccgccgcgtt cgccgactac cccgccacgc gccacaccgt cgatccggac 8700
cgccacatcg agcgggtcac cgagctgcaa gaactcttcc tcacgcgcgt cgggctcgac 8760
atcggcaagg tgtgggtcgc ggacgacggc gccgcggtgg cggtctggac cacgccggag 8820
agcgtcgaag cgggggcggt gttcgccgag atcggcccgc gcatggccga gttgagcggt 8880
tcccggctgg ccgcgcagca acagatggaa ggcctcctgg cgccgcaccg gcccaaggag 8940
cccgcgtggt tcctggccac cgtcggcgtc tcgcccgacc accagggcaa gggtctgggc 9000
agcgccgtcg tgctccccgg agtggaggcg gccgagcgcg ccggggtgcc cgccttcctg 9060
gagacctccg cgccccgcaa cctccccttc tacgagcggc tcggcttcac cgtcaccgcc 9120
gacgtcgagg tgcccgaagg accgcgcacc tggtgcatga cccgcaagcc cggtgcctga 9180
ccgcgtctgg aacaatcaac ctctggatta caaaatttgt gaaagattga ctggtattct 9240
taactatgtt gctcctttta cgctatgtgg atacgctgct ttaatgcctt tgtatcatgc 9300

-continued

```
tattgcttcc cgtatggctt tcattttctc ctccttgtat aaatcctggt tgctgtctct   9360
ttatgaggag ttgtggcccg ttgtcaggca acgtggcgtg gtgtgcactg tgtttgctga   9420
cgcaaccccc actggttggg gcattgccac cacctgtcag ctcctttccg ggactttcgc   9480
tttccccctc cctattgcca cggcggaact catcgccgcc tgccttgccc gctgctggac   9540
aggggctcgg ctgttgggca ctgacaattc cgtggtgttg tcggggaagc tgacgtcctt   9600
tccatggctg ctcgcctgtg ttgccacctg gattctgcgc gggacgtcct tctgctacgt   9660
cccttcggcc ctcaatccag cggaccttcc ttcccgcggc ctgctgccgg ctctgcggcc   9720
tcttccgcgt cttcgccttc gccctcagac gagtcggatc tccctttggg ccgcctcccc   9780
gcaaaatgac cgaccaagcg acgcccaacc tgccatcacg agatttcgat tccaccgccg   9840
ccttctatga aaggttgggc ttcggaatcg ttttccggga cgccggctgg atgatcctcc   9900
agcgcgggga tctcatgctg gagttcttcg cccaccccaa cttgtttatt gcagcttata   9960
atggttacaa ataaagcaat agcatcacaa atttcacaaa taaagcattt ttttcactgc  10020
attctagttg tggtttgtcc aaactcatca atgtatctta tcatgtctgt agctgatcaa  10080
ttggcgcgcc gaattcgtta tctgcagaat tcggcttggc ggctgcgcgt tcaaacctcc  10140
cgcttcaaaa tggagaccct gcgtgctcac tcgggcttaa atacccagcg tgaccacatg  10200
gtgtcgcaaa atgtcgcaaa acactcacgt gacctctaat acaggacctc tagagcatgg  10260
aaactagata agaaagaaat acgcagagac caaagttcaa ctgaaacgaa ttaaacggtt  10320
tattgattaa caagcaaact agtttacaga ttacgggtga ggtaacgggt gccgatgggg  10380
cgaggctcag aataaacgcc atttgtgtca acagcaaagt ccacatttgt agatttgttg  10440
tagttggaag tgtattgaat ctctgggttc cagcgtttgc tgttttcttt ctgcagctcc  10500
cattcaattt ccacgctgac ctgtccggtg ctgtactgcg tgatgaacga cgcaaactta  10560
gctggactga aggtagttgg aggattcgcg ggaacaggtg tattcttaat caggatctga  10620
ggaggcgggt gtttcagtcc aaagcctccc atcagcggcg agggatgaaa gtgtccgtcc  10680
gtgtgaggaa tcttggccca gataggaccc tgcaggtaca cgtcccggtc ctgccagacc  10740
atgccaggta aggctccttg actgttgacg gtccctgtag caggagcggt gttggccgat  10800
tgcaggttag tggccaccgt gccgtactct tctgtggcca ctgggttggt ggttttaatt  10860
tcttcctcgt tggttatcat aacgttgtca aggtccacgt tgctatttcc agctccctgt  10920
ttcccaaata ttaagactcc gctcatcgga aaaaatttgt cttcgtcgtc cttgtgggtt  10980
gccatagcgg gaccgggatt taccagagag tctctgccat tcagatgata cttggtggca  11040
ccggtccagg caaagttgct gttgttattt tgattggttg tcttggagac gcgttgctgc  11100
cggtagcagg gcccgggtag ccagtttttg gcctgattcg ccatgctact aggcccggcc  11160
tgagaaaatt gcaacgtccg atttcctgcg gtaccactcg tggtctgagt ccgagacagg  11220
tagtacaggt actggtcgat gagggggttc atcagccggt ccaggctttg gctgtgcgcg  11280
tagctgctgt gaaaaggcac gtcctcaaac gtgtagctga actgaaagtt gttgcccgtt  11340
ctcagcattt gagaaggaaa gtattccagg cagtagaagg aggaacggcc cacggcctga  11400
ctgccattgt tcagagtcag gtacccgtac tgaggaatca tgaagacgtc cgccgggaac  11460
ggaggcaggc agccctggtg cgcagagccg aggacgtacg ggagctggta ttccgagtcc  11520
gtaaagacct gaaccgtgct ggtaaggtta ttggcgatgg tcgtggtgcc atcattcgtc  11580
gtgacctcct tgacctggat gttgaagagc ttgaagttga gcttcttggg ccggaatccc  11640
cagttgttgt tgatgagtcg ctgccagtca cgtggtgaga agtggcagtg gaatctgtta  11700
```

aagtcaaaat acccccaggg ggtgctgtag ccgaagtagg tgttgtcgtt ggtgctgcct 11760
cccgattggc tggagatttg cttgtagagg tggttgttgt aggtggggag ggcccaggtt 11820
cgggtgctgg tggtgatgac tctgtcgccc agccatgtgg aatcgcaatg ccaatttcct 11880
gaggcgttac ccactccgtc ggcgccttcg ttattgtctg ccattggagc gccaccgcct 11940
gcagccattg tattagatcc cacaccagag ggggctgcgg ggggttctcc gagtggttga 12000
gggtcgggca ctgactctga gtcgccagtc tgcccaaagt tgagtctctt tctcgcgggc 12060
tgctggcctt tcttgccgat gcccgaagag gagtctggtt cctggggtga ttgctctacc 12120
ggtctcttct ttccaggagc cgtcttagcg ccttcctcaa ccagaccgag aggttcgaga 12180
acccgcttct tggcctggaa gactgctcgc ccgaggttgc ccccaaaaga cgtatcttct 12240
tgcagacgct cctgaaactc ggcgtcggcg tggttatacc gcaggtacgg attgtcaccc 12300
gctttgagct gctggtcgta ggccttgtcg tgctcgaggg ccgctgcgtc cgccgcgttg 12360
acgggctccc ccttgtcgag tccgttgaag ggtccgaggt acttgtagcc aggaagcacc 12420
agaccccggc cgtcgtcctg cttttgctgg ttggctttgg gtttcggggc tccaggtttc 12480
aagtcccacc actcgcgaat gccctcagag aggttgtcct cgagccaatc tggaagataa 12540
ccatcggcag ccatacctga tttaaatcat ttattgttca aagatgcagt catccaaatc 12600
cacattgacc agatcgcagg cagtgcaagc gtctggcacc tttcccatga tatgatgaat 12660
gtagcacagt ttctgatacg ccttttttgac gacagaaacg ggttgagatt ctgacacggg 12720
aaagcactct aaacagtctt tctgtccgtg agtgaagcag atatttgaat tctgattcat 12780
tctctcgcat tgtctgcagg gaaacagcat cagattcatg cccacgtgac gagaacattt 12840
gttttggtac ctgtctgcgt agttgatcga agcttccgcg tctgacgtcg atggctgcgc 12900
aactgactcg cgcacccgtt tgggctcact tatatctgcg tcactggggg cgggtctttt 12960
cttggctcca cccttttttga cgtagaattc atgctccacc tcaaccacgt gatcctttgc 13020
ccaccggaaa aagtctttga cttcctgctt ggtgaccttc ccaaagtcat gatccagacg 13080
gcgggtgagt tcaaatttga acatccggtc ttgcaacggc tgctggtgtt cgaaggtcgt 13140
tgagttcccg tcaatcacgg cgcacatgtt ggtgttggag gtgacgatca cgggagtcgg 13200
gtctatctgg gccgaggact tgcatttctg gtccacgcgc accttgcttc ctccgagaat 13260
ggctttggcc gactccacga ccttggcggt catcttcccc tcctcccacc agatcaccat 13320
cttgtcgaca cagtcgttga agggaaagtt ctcattggtc cagtttacgc acccgtagaa 13380
gggcacagtg tgggctatgg cctccgcgat gttggtcttc ccggtagttg caggcccaaa 13440
cagccagatg gtgttcctct tgccgaactt tttcgtggcc catcccagaa agacggaagc 13500
cgcatattgg ggatcgtacc cgtttagttc caaaatttta taaatccgat tgctggaaat 13560
gtcctccacg ggctgctggc ccaccaggta gtcgggggcg gttttagtca ggctcataat 13620
ctttcccgca ttgtccaagg cagccttgat ttgggaccgc gagttggagg ccgcattgaa 13680
ggagatgtat gaggcctggt cctcctggat ccactgcttc tccgaggtaa tccccttgtc 13740
cacgagccac ccgaccagct ccatgtacct ggctgaagtt tttgatctga tcaccggcgc 13800
atcagaattg ggattctgat tctctttgtt ctgctcctgc gtctgcgaca cgtgcgtcag 13860
atgctgcgcc accaaccgtt tacgctccgt gagattcaaa caggcgctgt ggagagaaag 13920
gcaaagtgga tgtcagtatc tctatcactg atagggagat ctctatcact gatagggaac 13980
ttaccttaaa tactgttcca tattagtcca cgcccactgg agctcaggct gggttttggg 14040

-continued

```
gagcaagtaa ttggggatgt agcactcatc caccaccttg ttcccgcctc cggcgccatt  14100
tctggtcttt gtgaccgcga accagtttgg caaagtcggc tcgatcccgc ggtaaattct  14160
ctgaatcagt tttcgcgaa tctgactcag gaaacgtccc aaaaccatgg atttcacccc  14220
ggtggtttcc acgagcacgt gcatgtggaa gtagctctct cccttctcaa attgcacaaa  14280
gaaaagagcc tccggggcct tactcacacg gcgccattcc gtcagaaagt cgcgctgcag  14340
cttctcggcc acggtcaggg gtgcctgctc aatcagattc agatccatgt cagaatctgg  14400
cggcaactcc cattccttct cggccaccca gttcacaaag ctgtcagaaa tgccgggcag  14460
atgctcgtca aggtcgctgg ggaccttaat cacaatctcg taaaaccccg gcatggcggc  14520
tgcgcgttca aacctcccgc ttcaaaatgg agaccctgcg tgctcactcg ggcgatctct  14580
atcactgata gggagatctc tatcactgat agggagatta aatagaatgg ctaggatccg  14640
gccggcctgc aggtgtcctc acaggaacga agtccctaaa gaaacagtgg cagccaggtt  14700
tagccccgga attgactgga ttcctttttt agggcccatt ggtatggctt tttccccgta  14760
tccccccagg tgtctgcagg ctcaaagagc agcgagaagc gttcagagga aagcgatccc  14820
gtgccacctt ccccgtgccc gggctgtccc cgcacgctgc cggctcgggg atgcgggggg  14880
agcgccggac cggagcggag ccccgggcgg ctcgctgctg ccccctagcg ggggagggac  14940
gtaattacat ccctgggggc tttggggggg ggctgtccct ctagagcggc cgccaccgcg  15000
gtggagctcc agcttttgtt ccctttagtg agggttaatt agatcttaat acgactcact  15060
atagggcgaa ttgggtaccg ggcccccccct cgaggtcgac ggtatcgata agcttgatat  15120
ctataacaag aaaatatata tataataagt tatcacgtaa gtagaacatg aaataacaat  15180
ataattatcg tatgagttaa atcttaaaag tcacgtaaaa gataatcatg cgtcattttg  15240
actcacgcgg tcgttatagt tcaaaatcag tgacacttac cgcattgaca agcacgcctc  15300
acgggagctc caagcggcga ctgagatgtc ctaaatgcac agcgacggat tcgcgctatt  15360
tagaaagaga gagcaatatt tcaagaatgc atgcgtcaat tttacgcaga ctatctttct  15420
agggttaatc tagctgcatc aggatcatat cgtcgggtct tttttccggc tcagtcatcg  15480
cccaagctgg cgctatctgg gcatcgggga ggaagaagcc cgtgcctttt cccgcgaggt  15540
tgaagcggca tggaaagagt ttgccgagga tgactgctgc tgcattgacg ttgagcgaaa  15600
acgcacgttt accatgatga ttcgggaagg tgtggccatg cacgccttta acggtgaact  15660
gttcgttcag gccacctggg ataccagttc gtcgcggctt ttccggacac agttccggat  15720
ggtcagcccg aagcgcatca gcaacccgaa caataccggc gacagccgga actgccgtgc  15780
cggtgtgcag attaatgaca gcggtgcggc gctgggatat tacgtcagcg aggacgggta  15840
tcctggctgg atgccgcaga aatggacatg gataccccgt gagttacccg gcgggcgcgc  15900
ttggcgtaat catggtcata gctgtttcct gtgtgaaatt gttatccgct cacaattcca  15960
cacaacatac gagccggaag cataaagtgt aaagcctggg gtgcctaatg agtgagctaa  16020
ctcacattaa ttgcgttgcg ctcactgccc gctttccagt cgggaaacct gtcgtgccag  16080
ctgcattaat gaatcggcca acgcgcgggg agaggcggtt tgcgtattgg gcgctcttcc  16140
gcttcctcgc tcactgactc gctgcgctcg gtcgttcggc tgcggcgagc ggtatcagct  16200
cactcaaagg cggtaatacg gttatccaca gaatcagggg ataacgcagg aaagaacatg  16260
tgagcaaaag gccagcaaaa ggccaggaac cgtaaaaagg ccgcgttgct ggcgtttttc  16320
cataggctcc gcccccctga cgagcatcac aaaaatcgac gctcaagtca gaggtggcga  16380
aacccgacag gactataaag ataccaggcg tttccccctg gaagctccct cgtgcgctct  16440
```

cctgttccga ccctgccgct taccggatac ctgtccgcct ttctcccttc gggaagcgtg 16500
gcgctttctc atagctcacg ctgtaggtat ctcagttcgg tgtaggtcgt tcgctccaag 16560
ctgggctgtg tgcacgaacc ccccgttcag cccgaccgct gcgccttatc cggtaactat 16620
cgtcttgagt ccaacccggt aagacacgac ttatcgccac tggcagcagc cactggtaac 16680
aggattagca gagcgaggta tgtaggcggt gctacagagt tcttgaagtg gtggcctaac 16740
tacggctaca ctagaaggac agtatttggt atctgcgctc tgctgaagcc agttaccttc 16800
ggaaaaagag ttggtagctc ttgatccggc aaacaaacca ccgctggtag cggtggtttt 16860
tttgtttgca agcagcagat tacgcgcaga aaaaaaggat ctcaagaaga tcctttgatc 16920
ttttctacgg ggtctgacgc tcagtggaac gaaaactcac gttaagggat tttggtcatg 16980
agattatcaa aaaggatctt cacctagatc cttttaaatt aaaaatgaag ttttaaatca 17040
atctaaagta tatatgagta aacttggtct gacagttacc aatgcttaat cagtgaggca 17100
cctatctcag cgatctgtct atttcgttca tccatagttg cctgactccc cgtcgtgtag 17160
ataactacga tacgggaggg cttaccatct ggccccagtg ctgcaatgat accgcgagac 17220
ccacgctcac cggctccaga tttatcagca ataaaccagc cagccggaag ggccgagcgc 17280
agaagtggtc ctgcaacttt atccgcctcc atccagtcta ttaattgttg ccgggaagct 17340
agagtaagta gttcgccagt taatagtttg cgcaacgttg ttgccattgc tacaggcatc 17400
gtggtgtcac gctcgtcgtt tggtatggct tcattcagct ccggttccca acgatcaagg 17460
cgagttacat gatcccccat gttgtgcaaa aaagcggtta gctccttcgg tcctccgatc 17520
gttgtcagaa gtaagttggc cgcagtgtta tcactcatgg ttatggcagc actgcataat 17580
tctcttactg tcatgccatc cgtaagatgc ttttctgtga ctggtgagta ctcaaccaag 17640
tcattctgag aatagtgtat gcggcgaccg agttgctctt gcccggcgtc aatacgggat 17700
aataccgcgc cacatagcag aactttaaaa gtgctcatca ttggaaaacg ttcttcgggg 17760
cgaaaactct caaggatctt accgctgttg agatccagtt cgatgtaacc cactcgtgca 17820
cccaactgat cttcagcatc ttttactttc accagcgttt ctgggtgagc aaaaacagga 17880
aggcaaaatg ccgcaaaaaa gggaataagg gcgacacgga aatgttgaat actcat 17936

<210> SEQ ID NO 13
<211> LENGTH: 21391
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct aaattgtaag cgttaatatt ttgttaaaat tcgcgttaaa tttttgttaa 180
atcagctcat tttttaacca ataggccgaa atcggcaaaa tcccttataa atcaaaagaa 240
tagaccgaga tagggttgag tgttgttcca gtttggaaca agagtccact attaaagaac 300
gtggactcca acgtcaaagg gcgaaaaacc gtctatcagg gcgatggccc actacgtgaa 360
ccatcaccct aatcaagttt tttggggtcg aggtgccgta aagcactaaa tcggaaccct 420
aaagggagcc cccgatttag agcttgacgg ggaaagccgg cgaacgtggc gagaaaggaa 480
gggaagaaag cgaaaggagc gggcgctagg gcgctggcaa gtgtagcggt cacgctgcgc 540

-continued

```
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaactttt atcgaattcc tgcagcccgg gggatccact   1140
agttctagag ggacagcccc cccccaaagc ccccagggat gtaattacgt ccctcccccg   1200
ctagggggca gcagcgagcc gcccggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tgggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc agatatacgc gttgacattg   1620
attattgact agttattaat agtaatcaat tacggggtca ttagttcata gcccatatat   1680
ggagttccgc gttacataac ttacggtaaa tggcccgcct ggctgaccgc ccaacgaccc   1740
ccgcccattg acgtcaataa tgacgtatgt tcccatagta acgccaatag ggactttcca   1800
ttgacgtcaa tgggtggagt atttacggta aactgcccac ttggcagtac atcaagtgta   1860
tcatatgcca agtacgcccc ctattgacgt caatgacggt aaatggcccg cctggcatta   1920
tgcccagtac atgaccttat gggactttcc tacttggcag tacatctacg tattagtcat   1980
cgctattacc atggtgatgc ggttttggca gtacatcaat gggcgtggat agcggtttga   2040
ctcacgggga tttccaagtc tccaccccat tgacgtcaat gggagtttgt tttggaacca   2100
aaatcaacgg gactttccaa aatgtcgtaa caactccgcc ccattgacgc aaatgggcgg   2160
taggcgtgta cggtgggagg tctatataag cagagctctc cctatcagtg atagagatct   2220
ccctatcagt gatagagatc gtcgacgagc tcgtttagtg aaccgtcaga tcgcctggag   2280
acgccatcca cgctgttttg acctccatag aagacaccgg gaccgatcca gcctccggac   2340
tctagcgttt aaacttaagc ttgccaccat ggccagtcgg gaagaggagc agcgcgaaac   2400
cacccccgag cgcggacgcg gtgcggcgcg acgtccccca accatggagg acgtgtcgtc   2460
cccgtccccg tcgccgccgc ctccccgggc gcccccaaaa aagcggatga ggcggcgtat   2520
cgagtccgag gacgaggaag actcatcaca agacgcgctg gtgccgcgca cacccagccc   2580
gcggccatcg acctcggcgg cggatttggc cattgcgccc aagaagaaaa agaagcgccc   2640
ttctcccaag cccgagcgcc cgccatcacc agaggtaatc gtggacagcg aggaagaaag   2700
agaagatgtg gcgctacaaa tggtgggttt cagcaaccca ccggtgctaa tcaagcatgg   2760
caaaggaggt aagcgcacag tgcggcggct gaatgaagac gacccagtgg cgcgtggtat   2820
gcggacgcaa gaggaagagg aagagcccag cgaagcggaa agtgaaatta cggtgatgaa   2880
```

-continued

```
cccgctgagt gtgccgatcg tgtctgcgtg ggagaagggc atggaggctg cgcgcgcgct   2940
gatggacaag taccacgtgg ataacgatct aaaggcgaac ttcaaactac tgcctgacca   3000
agtggaagct ctggcggccg tatgcaagac ctggctgaac gaggagcacc gcgggttgca   3060
gctgaccttc accagcaaca agacctttgt gacgatgatg gggcgattcc tgcaggcgta   3120
cctgcagtcg tttgcagagg tgacctacaa gcatcacgag cccacgggct gcgcgttgtg   3180
gctgcaccgc tgcgctgaga tcgaaggcga gcttaagtgt ctacacggaa gcattatgat   3240
aaataaggag cacgtgattg aaatggatgt gacgagcgaa aacgggcagc gcgcgctgaa   3300
ggagcagtct agcaaggcca agatcgtgaa gaaccggtgg ggccgaaatg tggtgcagat   3360
ctccaacacc gacgcaaggt gctgcgtgca cgacgcggcc tgtccggcca atcagttttc   3420
cggcaagtct tgcggcatgt tcttctctga aggcgcaaag gctcaggtgg cttttaagca   3480
gatcaaggct tttatgcagg cgctgtatcc taacgcccag accgggcacg gtcacctttt   3540
gatgccacta cggtgcgagt gcaactcaaa gcctgggcac gcgccctttt tgggaaggca   3600
gctaccaaag ttgactccgt tcgccctgag caacgcggag gacctggacg cggatctgat   3660
ctccgacaag agcgtgctgg ccagcgtgca ccacccggcg ctgatagtgt tccagtgctg   3720
caaccctgtg tatcgcaact cgcgcgcgca gggcggaggc cccaactgcg acttcaagat   3780
atcggcgccc gacctgctaa acgcgttggt gatggtgcgc agcctgtgga gtgaaaactt   3840
caccgagctg ccgcggatgg ttgtgcctga gtttaagtgg agcactaaac accagtatcg   3900
caacgtgtcc ctgccagtgg cgcatagcga tgcgcggcag aaccccttg atttttaacc   3960
cgggagttct agggatctgc cctctccct cccccccccc taacgttact ggccgaagcc   4020
gcttggaata aggccggtgt gcgtttgtct atatgttatt ttccaccata ttgccgtctt   4080
ttggcaatgt gagggcccgg aaacctggcc ctgtcttctt gacgagcatt cctaggggtc   4140
tttcccctct cgccaaagga atgcaaggtc tgttgaatgt cgtgaaggaa gcagttcctc   4200
tggaagcttc ttgaagacaa acaacgtctg tagcgaccct ttgcaggcag cggaaccccc   4260
cacctggcga caggtgcctc tgcggccaaa agccacgtgt ataagataca cctgcaaagg   4320
cggcacaacc ccagtgccac gttgtgagtt ggatagttgt ggaaagagtc aaatggctct   4380
cctcaagcgt attcaacaag gggctgaagg atgcccagaa ggtaccccat tgtatgggat   4440
ctgatctggg gcctcggtgc acatgcttta catgtgttta gtcgaggtta aaaaaacgtc   4500
taggcccccc gaaccacggg gacgtggttt tcctttgaaa aacacgatga taaggatcca   4560
ccggaggcca ccatgactac gtccggcgtt ccatttggca tgacactacg accaacacga   4620
tctcggttgt ctcggcgcac tccgtacagt agggatcgtc tacctccttt tgagacagaa   4680
acccgcgcta ccatactgga ggatcatccg ctgctgcccg aatgtaacac tttgacaatg   4740
cacaacgtga gttacgtgcg aggtcttccc tgcagtgtgg gatttacgct gattcaggaa   4800
tgggttgttc cctgggatat ggttctaacg cgggaggagc ttgtaatcct gaggaagtgt   4860
atgcacgtgt gcctgtgttg tgccaacatt gatatcatga cgagcatgat gatccatggt   4920
tacgagtcct gggctctcca ctgtcattgt tccagtcccg gttccctgca gtgtatagcc   4980
ggcgggcagg ttttggccag ctggtttagg atggtggtgg atggcgccat gtttaatcag   5040
aggtttatat ggtaccggga ggtggtgaat tacaacatgc caaaagaggt aatgtttatg   5100
tccagcgtgt ttatgagggg tcgccactta atctacctgc gcttgtggta tgatggccac   5160
gtgggttctg tggtccccgc catgagcttt ggatacagcg ccttgcactg tgggattttg   5220
aacaatattg tggtgctgtg ctgcagttac tgtgctgatt taagtgagat cagggtgcgc   5280
```

-continued tgctgtgccc ggaggacaag gcgccttatg ctgcgggcgg tgcgaatcat cgctgaggag 5340
accactgcca tgttgtattc ctgcaggacg gagcggcggc ggcagcagtt tattcgcgcg 5400
ctgctgcagc accaccgccc tatcctgatg cacgattatg actctacccc catgtaggcg 5460
gccgctcgag tctagagggc ccgtttaaac ccgctgatca gcctcgactg tgccttctag 5520
ttgccagcca tctgttgttt gcccctcccc cgtgccttcc ttgaccctgg aaggtgccac 5580
tcccactgtc ctttcctaat aaaatgagga aattgcatcg cattgtctga gtaggtgtca 5640
ttctattctg gggggtgggg tggggcagga cagcaagggg gaggattggg aagacaatag 5700
caggcatgct ggggatgcgg tgggctctat ggcttctgag gcggaaagaa ccagctgggg 5760
ctctaggggg tatccccggg gttggggttg cgccttttcc aaggcatcca gcacagtggc 5820
ggccgcaata tttgcatgtc gctatgtgtt ctgggaaatc accataaacg tgaaatccct 5880
atcagtgata gagacttata agttccctat cagtgataga gaaccggtgg gcactcttcc 5940
gtggtctggt ggataaattc gcaagggtat catggcggac gaccggggtt cgagccccgt 6000
atccggccgt ccgccgtgat ccatgcggtt accgcccgcg tgtcgaaccc aggtgtgcga 6060
cgtcagacaa cgggggagtg ctcctttttg aattccactt tggccgcggc tcgagggggt 6120
tggggttgcg ccttttccaa ggcagccctg ggtttgcgca gggacgcggc tgctctgggc 6180
gtggttccgg gaaacgcagc ggcgccgacc ctgggtctcg cacattcttc acgtccgttc 6240
gcagcgtcac ccggatcttc gccgctaccc ttgtgggccc cccggcgacg cttcctgctc 6300
cgcccctaag tcgggaaggt tccttgcggt tcgcggcgtg ccggacgtga caaacggaag 6360
ccgcacgtct cactagtacc ctcgcagacg gacagcgcca gggagcaatg gcagcgcgcc 6420
gaccgcgatg ggctgtggcc aatagcggct gctcagcagg gcgcgccgag agcagcggcc 6480
gggaaggggc ggtgcgggag gcggggtgtg gggcggtagt gtgggccctg ttcctgcccg 6540
cgcggtgttc cgcattctgc aagcctccgg agcgcacgtc ggcagtcggc tccctcgttg 6600
accgaatcac cgacctctct ccccaggggg atctgtgagt ttggggaccc ttgattgttc 6660
tttctttttc gctattgtaa aattcatgtt atatggaggg ggcaaagttt tcagggtgtt 6720
gtttagaatg ggaagatgtc ccttgtatca ccatggaccc tcatgataat tttgtttctt 6780
tcactttcta ctctgttgac aaccattgtc tcctcttatt ttcttttcat tttctgtaac 6840
tttttcgtta aactttagct tgcatttgta acgaattttt aaattcactt ttgtttattt 6900
gtcagattgt aagtactttc tctaatcact ttttttcaa ggcaatcagg gtatattata 6960
ttgtacttca gcacagtttt agagaacaat tgttataatt aaatgataag gtagaatatt 7020
tctgcatata aattctggct ggcgtggaaa tattcttatt ggtagaaaca actacatcct 7080
ggtcatcatc ctgcctttct ctttatggtt acaatgatat acactgtttg agatgaggat 7140
aaaatactct gagtccaaac cgggcccctc tgctaaccat gttcatgcct tcttcttttt 7200
cctacagctc ctgggcaacg tgctggttat tgtgctgtct catcattttg gcaaagaatt 7260
gtaatacgac tcactatagg gcgagccacc atggctagat tagataaaag taaagtgatt 7320
aacagcgcat tagagctgct taatgaggtc ggaatcgaag gtttaacaac ccgtaaactc 7380
gcccagaagc taggtgtaga gcagcctaca ttgtattggc atgtaaaaaa taagcgggct 7440
ttgctcgacg ccttagccat tgagatgtta gataggcacc atactcactt ttgcccttta 7500
gaaggggaaa gctggcaaga tttttacgt aataacgcta aaagttttag atgtgcttta 7560
ctaagtcatc gcgatggagc aaaagtacat ttaggtacac ggcctacaga aaaacagtat 7620
gaaactctcg aaaatcaatt agccttttta tgccaacaag gtttttcact agagaatgcc 7680
ttatatgcac tcagcgccgt ggggcatttt actttaggtt gcgtattgga agatcaagag 7740
catcaagtcg ctaaagaaga aagggaaaca cctactactg atagtatgcc gccattatta 7800
cgacaagcta tcgaattatt tgatcaccaa ggtgcagagc cagccttctt attcggcctt 7860
gaattgatca tatgcggatt agaaaaacaa cttaaatgtg aaagtgggtc ccaaaaaaag 7920
aagagaaagg tcgacggcgg tggtgctttg tctcctcagc actctgctgt cactcaagga 7980
agtatcatca agaacaagga gggcatggat gctaagtcac taactgcctg gtcccggaca 8040
ctggtgacct tcaaggatgt atttgtggac ttcaccaggg aggagtggaa gctgctggac 8100
actgctcagc agatcgtgta cagaaatgtg atgctggaga actataagaa cctggtttcc 8160
ttgggttatc agcttactaa gccagatgtg atcctccggt tggagaaggg agaagagccc 8220
tggctggtgg agagagaaat tcaccaagag acccatcctg attcagagac tgcatttgaa 8280
atcaaatcat cagtttaagc gtacagcggc tcccgggagt tctagggatc tgcccctctc 8340
cctccccccc ccctaacgtt actggccgaa gccgcttgga ataaggccgg tgtgcgtttg 8400
tctatatgtt attttccacc atattgccgt cttttggcaa tgtgagggcc cggaaacctg 8460
gccctgtctt cttgacgagc attcctaggg gtctttcccc tctcgccaaa ggaatgcaag 8520
gtctgttgaa tgtcgtgaag gaagcagttc ctctggaagc ttcttgaaga caaacaacgt 8580
ctgtagcgac cctttgcagg cagcggaacc ccccacctgg cgacaggtgc ctctgcggcc 8640
aaaagccacg tgtataagat acacctgcaa aggcggcaca accccagtgc cacgttgtga 8700
gttggatagt tgtggaaaga gtcaaatggc tctcctcaag cgtattcaac aaggggctga 8760
aggatgccca gaaggtaccc cattgtatgg gatctgatct ggggcctcgg tgcacatgct 8820
ttacatgtgt ttagtcgagg ttaaaaaaac gtctaggccc cccgaaccac ggggacgtgg 8880
ttttcctttg aaaaacacga tgataaggat ccaccggagg ccaccatgac cgagtacaag 8940
cccacggtgc gcctcgccac ccgcgacgac gtccccaggg ccgtacgcac cctcgccgcc 9000
gcgttcgccg actaccccgc cacgcgccac accgtcgatc cggaccgcca catcgagcgg 9060
gtcaccgagc tgcaagaact cttcctcacg cgcgtcgggc tcgacatcgg caaggtgtgg 9120
gtcgcggacg acggcgccgc ggtggcggtc tggaccacgc cggagagcgt cgaagcgggg 9180
gcggtgttcg ccgagatcgg cccgcgcatg gccgagttga gcggttcccg gctggccgcg 9240
cagcaacaga tggaaggcct cctggcgccg caccggccca aggagcccgc gtggttcctg 9300
gccaccgtcg gcgtctcgcc cgaccaccag ggcaagggtc tgggcagcgc cgtcgtgctc 9360
cccggagtgg aggcggccga gcgcgccggg gtgcccgcct tcctggagac ctccgcgccc 9420
cgcaacctcc ccttctacga gcggctcggc ttcaccgtca ccgccgacgt cgaggtgccc 9480
gaaggaccgc gcacctggtg catgacccgc aagcccggtg cctgaccgcg tctggaacaa 9540
tcaacctctg gattacaaaa tttgtgaaag attgactggt attcttaact atgttgctcc 9600
ttttacgcta tgtggatacg ctgctttaat gcctttgtat catgctattg cttcccgtat 9660
ggctttcatt ttctcctcct tgtataaatc ctggttgctg tctctttatg aggagttgtg 9720
gcccgttgtc aggcaacgtg gcgtggtgtg cactgtgttt gctgacgcaa cccccactgg 9780
ttggggcatt gccaccacct gtcagctcct ttccgggact ttcgctttcc ccctccctat 9840
tgccacggcg gaactcatcg ccgcctgcct tgcccgctgc tggacagggg ctcggctgtt 9900
gggcactgac aattccgtgg tgttgtcggg gaagctgacg tcctttccat ggctgctcgc 9960
ctgtgttgcc acctggattc tgcgcgggac gtccttctgc tacgtccctt cggccctcaa 10020

```
tccagcggac cttccttccc gcggcctgct gccggctctg cggcctcttc cgcgtcttcg  10080
ccttcgccct cagacgagtc ggatctccct ttgggccgcc tccccgcaaa atgaccgacc  10140
aagcgacgcc caacctgcca tcacgagatt tcgattccac cgccgccttc tatgaaaggt  10200
tgggcttcgg aatcgttttc cgggacgccg gctggatgat cctccagcgc ggggatctca  10260
tgctggagtt cttcgcccac cccaacttgt ttattgcagc ttataatggt tacaaataaa  10320
gcaatagcat cacaaatttc acaaataaag cattttttc actgcattct agttgtggtt  10380
tgtccaaact catcaatgta tcttatcatg tctgtagctg atcaattggc gcgccgaatt  10440
cgttatctgc agaattcggc ttggcggctg cgcgttcaaa cctcccgctt caaaatggag  10500
accctgcgtg ctcactcggg cttaaatacc cagcgtgacc acatggtgtc gcaaaatgtc  10560
gcaaaacact cacgtgacct ctaatacagg acctctagag catggaaact agataagaaa  10620
gaaatacgca gagaccaaag ttcaactgaa acgaattaaa cggtttattg attaacaagc  10680
aaactagttt acagattacg ggtgaggtaa cgggtgccga tggggcgagg ctcagaataa  10740
acgccatttg tgtcaacagc aaagtccaca tttgtagatt tgttgtagtt ggaagtgtat  10800
tgaatctctg ggttccagcg tttgctgttt tctttctgca gctcccattc aatttccacg  10860
ctgacctgtc cggtgctgta ctgcgtgatg aacgacgcaa acttagctgg actgaaggta  10920
gttggaggat tcgcgggaac aggtgtattc ttaatcagga tctgaggagg cgggtgtttc  10980
agtccaaagc ctcccatcag cggcgaggga tgaaagtgtc cgtccgtgtg aggaatcttg  11040
gcccagatag gaccctgcag gtacacgtcc cggtcctgcc agaccatgcc aggtaaggct  11100
ccttgactgt tgacggtccc tgtagcagga gcggtgttgg ccgattgcag gttagtggcc  11160
accgtgccgt actcttctgt ggccactggg ttggtggttt taatttcttc ctcgttggtt  11220
atcataacgt tgtcaaggtc cacgttgcta tttccagctc cctgtttccc aaatattaag  11280
actccgctca tcggaaaaaa tttgtcttcg tcgtccttgt gggttgccat agcgggaccg  11340
ggatttacca gagagtctct gccattcaga tgatacttgg tggcaccggt ccaggcaaag  11400
ttgctgttgt tattttgatt ggttgtcttg gagacgcgtt gctgccggta gcagggcccg  11460
ggtagccagt ttttggcctg attcgccatg ctactaggcc cggcctgaga aaattgcaac  11520
gtccgatttc ctgcggtacc actcgtggtc tgagtccgag acaggtagta caggtactgg  11580
tcgatgaggg ggttcatcag ccggtccagg ctttggctgt gcgcgtagct gctgtgaaaa  11640
ggcacgtcct caaacgtgta gctgaactga aagttgttgc ccgttctcag catttgagaa  11700
ggaaagtatt ccaggcagta gaaggaggaa cggcccacgg cctgactgcc attgttcaga  11760
gtcaggtacc cgtactgagg aatcatgaag acgtccgccg ggaacggagg caggcagccc  11820
tggtgcgcag agccgaggac gtacgggagc tggtattccg agtccgtaaa gacctgaacc  11880
gtgctggtaa ggttattggc gatggtcgtg gtgccatcat tcgtcgtgac ctccttgacc  11940
tggatgttga agagcttgaa gttgagcttc ttgggccgga atccccagtt gttgttgatg  12000
agtcgctgcc agtcacgtgg tgagaagtgg cagtggaatc tgttaaagtc aaaatacccc  12060
cagggggtgc tgtagccgaa gtaggtgttg tcgttggtgc tgcctcccga ttggctggag  12120
atttgcttgt agaggtggtt gttgtaggtg gggagggccc aggttcgggt gctggtggtg  12180
atgactctgt cgcccagcca tgtggaatcg caatgccaat ttcctgaggc gttacccact  12240
ccgtcggcgc cttcgttatt gtctgccatt ggagcgccac cgcctgcagc cattgtatta  12300
gatcccacac cagagggggc tgcggggggt tctccgagtg gttgagggtc gggcactgac  12360
```

-continued

```
tctgagtcgc cagtctgccc aaagttgagt ctctttctcg cgggctgctg gcctttcttg  12420
ccgatgcccg aagaggagtc tggttcctgg ggtgattgct ctaccggtct cttctttcca  12480
ggagccgtct tagcgccttc ctcaaccaga ccgagaggtt cgagaacccg cttcttggcc  12540
tggaagactg ctcgcccgag gttgccccca aaagacgtat cttcttgcag acgctcctga  12600
aactcggcgt cggcgtggtt ataccgcagg tacggattgt cacccgcttt gagctgctgg  12660
tcgtaggcct tgtcgtgctc gagggccgct gcgtccgccg cgttgacggg ctcccccttg  12720
tcgagtccgt tgaagggtcc gaggtacttg tagccaggaa gcaccagacc ccggccgtcg  12780
tcctgctttt gctggttggc tttgggtttc ggggctccag gtttcaagtc ccaccactcg  12840
cgaatgccct cagagaggtt gtcctcgagc caatctggaa gataaccatc ggcagccata  12900
cctgatttaa atcatttatt gttcaaagat gcagtcatcc aaatccacat tgaccagatc  12960
gcaggcagtg caagcgtctg gcacctttcc catgatatga tgaatgtagc acagtttctg  13020
atacgccttt ttgacgacag aaacgggttg agattctgac acgggaaagc actctaaaca  13080
gtctttctgt ccgtgagtga agcagatatt tgaattctga ttcattctct cgcattgtct  13140
gcagggaaac agcatcagat tcatgcccac gtgacgagaa catttgtttt ggtacctgtc  13200
tgcgtagttg atcgaagctt ccgcgtctga cgtcgatggc tgcgcaactg actcgcgcac  13260
ccgtttgggc tcacttatat ctgcgtcact gggggcgggt cttttcttgg ctccaccctt  13320
tttgacgtag aattcatgct ccacctcaac cacgtgatcc tttgcccacc ggaaaaagtc  13380
tttgacttcc tgcttggtga ccttcccaaa gtcatgatcc agacggcggg tgagttcaaa  13440
tttgaacatc cggtcttgca acggctgctg gtgttcgaag gtcgttgagt tcccgtcaat  13500
cacggcgcac atgttggtgt tggaggtgac gatcacggga gtcgggtcta tctgggccga  13560
ggacttgcat ttctggtcca cgcgcacctt gcttcctccg agaatggctt tggccgactc  13620
cacgaccttg gcggtcatct tcccctcctc ccaccagatc accatcttgt cgacacagtc  13680
gttgaaggga aagttctcat tggtccagtt tacgcacccg tagaagggca cagtgtgggc  13740
tatggcctcc gcgatgttgg tcttcccggt agttgcaggc ccaaacagcc agatggtgtt  13800
cctcttgccg aactttttcg tggcccatcc cagaaagacg gaagccgcat attggggatc  13860
gtacccgttt agttccaaaa ttttataaat ccgattgctg gaaatgtcct ccacgggctg  13920
ctggcccacc aggtagtcgg gggcggtttt agtcaggctc ataatctttc ccgcattgtc  13980
caaggcagcc ttgatttggg accgcgagtt ggaggccgca ttgaaggaga tgtatgaggc  14040
ctggtcctcc tggatccact gcttctccga ggtaatcccc ttgtccacga gccacccgac  14100
cagctccatg tacctggctg aagtttttga tctgatcacc ggcgcatcag aattgggatt  14160
ctgattctct ttgttctgct cctgcgtctg cgacacgtgc gtcagatgct gcgccaccaa  14220
ccgtttacgc tccgtgagat tcaaacaggc gctgtggaga gaaaggcaaa gtggatgtca  14280
gtatctctat cactgatagg gagatctcta tcactgatag ggaacttacc ttaaatactg  14340
ttccatatta gtccacgccc actggagctc aggctgggtt ttggggagca agtaattggg  14400
gatgtagcac tcatccacca ccttgttccc gcctccggcg ccatttctgg tctttgtgac  14460
cgcgaaccag tttggcaaag tcggctcgat cccgcggtaa attctctgaa tcagtttttc  14520
gcgaatctga ctcaggaaac gtcccaaaac catggatttc accccggtgg tttccacgag  14580
cacgtgcatg tggaagtagc tctctccctt ctcaaattgc acaaagaaaa gagcctccgg  14640
ggccttactc acacggcgcc attccgtcag aaagtcgcgc tgcagcttct cggccacggt  14700
caggggtgcc tgctcaatca gattcagatc catgtcagaa tctggcggca actcccattc  14760
```

cttctcggcc acccagttca caaagctgtc agaaatgccg ggcagatgct cgtcaaggtc 14820
gctggggacc ttaatcacaa tctcgtaaaa ccccggcatg gcggctgcgc gttcaaacct 14880
cccgcttcaa aatggagacc ctgcgtgctc actcgggcga tctctatcac tgatagggag 14940
atctctatca ctgataggga gattaaatag aatggctagg atccggccgg cctgcaggtg 15000
tcctcacagg aacgaagtcc ctaaagaaac agtggcagcc aggtttagcc ccggaattga 15060
ctggattcct tttttagggc ccattggtat ggctttttcc ccgtatcccc ccaggtgtct 15120
gcaggctcaa agagcagcga gaagcgttca gaggaaagcg atcccgtgcc accttccccg 15180
tgcccgggct gtccccgcac gctgccggct cggggatgcg gggggagcgc cggaccggag 15240
cggagccccg ggcggctcgc tgctgccccc tagcggggga gggacgtaat tacatccctg 15300
ggggctttgg ggggggggctg tccctctaga gcggccgcca ccgcggtgga gctccagctt 15360
ttgttccctt tagtgagggt taattagatc ttaatacgac tcactatagg gcgaattggg 15420
taccgggccc cccctcgagg tcgacggtat cgcctccaag gccagcttcc cacaataagt 15480
tgggtgaatt ttggctcatt cctcctttct ataggattga ggtcagagct ttgtgatggg 15540
aattctgtgg aatgtgtgtc agttagggtg tggaaagtcc cgcgatcgct agcaaacgcc 15600
agcaacgcgg cctttttacg gttcctggcc ttttgctggc cttttgctca catgtcctgc 15660
aggcagctgc gcgctcgctc gctcactgag gccgcccggg caaagcccgg gcgtcgggcg 15720
acctttggtc gcccggcctc agtgagcgag cgagcgcgca gagagggagt ggccaactcc 15780
atcactaggg gttcctgcgg ccgcacgcgt ggagctagtt attaatagta atcaattacg 15840
gggtcattag ttcatagccc atatatggag ttccgcgtta cataacttac ggtaaatggc 15900
ccgcctggct gaccgcccaa cgacccccgc ccattgacgt caataatgac gtatgttccc 15960
atagtaacgt caatagggac tttccattga cgtcaatggg tggagtattt acggtaaact 16020
gcccacttgg cagtacatca agtgtatcat atgccaagta cgccccctat tgacgtcaat 16080
gacggtaaat ggcccgcctg gcattatgcc cagtacatga ccttatggga ctttcctact 16140
tggcagtaca tctacgtatt agtcatcgct attaccatgg tgatgcggtt ttggcagtac 16200
atcaatgggc gtggatagcg gtttgactca cggggatttc caagtctcca ccccattgac 16260
gtcaatggga gtttgttttg caccaaaatc aacgggactt tccaaaatgt cgtaacaact 16320
ccgccccatt gacgcaaatg ggcggtaggc gtgtacggtg ggaggtctat ataagcagag 16380
ctcgtttagt gaaccgtcag atcgcctgga gacgccatcc acgctgtttt gacctccata 16440
gaagacaccg ggaccgatcc agcctccgcg gattcgaatc ccggccggga acggtgcatt 16500
ggaacgcgga ttccccgtgc caagagtgac gtaagtaccg cctatagagt ctataggccc 16560
acaaaaaatg ctttcttctt ttaatatact tttttgttta tcttatttct aatactttcc 16620
ctaatctctt tctttcaggg caataatgat acaatgtatc atgcctcttt gcaccattct 16680
aaagaataac agtgataatt tctgggttaa ggcaatagca atatttctgc atataaatat 16740
ttctgcatat aaattgtaac tgatgtaaga ggtttcatat tgctaatagc agctacaatc 16800
cagctaccat tctgctttta ttttatggtt gggataaggc tggattattc tgagtccaag 16860
ctaggccctt ttgctaatca tgttcatacc tcttatcttc ctcccacagc tcctgggcaa 16920
cgtgctggtc tgtgtgctgg cccatcactt tggcaaagaa ttgggattcg aacatcgatt 16980
gaattctgaa tggtgagcaa gggcgaggag ctgttcaccg ggtggtgcc catcctggtc 17040 gagctggacg gcgacgtaaa cggccacaag ttcagcgtgt ccggcgaggg cgagggcgat 17100

-continued

```
gccacctacg gcaagctgac cctgaagttc atctgcacca ccggcaagct gcccgtgccc  17160
tggcccaccc tcgtgaccac cctgacctac ggcgtgcagt gcttcagccg ctaccccgac  17220
cacatgaagc agcacgactt cttcaagtcc gccatgcccg aaggctacgt ccaggagcgc  17280
accatcttct tcaaggacga cggcaactac aagacccgcg ccgaggtgaa gttcgagggc  17340
gacaccctgg tgaaccgcat cgagctgaag ggcatcgact tcaaggagga cggcaacatc  17400
ctggggcaca agctggagta caactacaac agccacaacg tctatatcat ggccgacaag  17460
cagaagaacg gcatcaaggt gaacttcaag atccgccaca acatcgagga cggcagcgtg  17520
cagctcgccg accactacca gcagaacacc cccatcggcg acggccccgt gctgctgccc  17580
gacaaccact acctgagcac ccagtccgcc ctgagcaaag accccaacga gaagcgcgat  17640
cacatggtcc tgctggagtt cgtgaccgcc gccgggatca ctctcggcat ggacgagctg  17700
tacaagtact cagatctcga gctcaagtag ggatcctcta gagtcgacct gcagaagctt  17760
gcctcgagca gcgctgctcg agagatctac gggtggcatc cctgtgaccc ctccccagtg  17820
cctctcctgg ccctggaagt tgccactcca gtgcccacca gccttgtcct aataaaatta  17880
agttgcatca ttttgtctga ctaggtgtcc ttctataata ttatggggtg gaggggggtg  17940
gtatggagca aggggcaagt tgggaagaca acctgtaggg cctgcggggt ctattgggaa  18000
ccaagctgga gtgcagtggc acaatcttgg ctcactgcaa tctccgcctc ctgggttcaa  18060
gcgattctcc tgcctcagcc tcccgagttg ttgggattcc aggcatgcat gaccaggctc  18120
agctaatttt tgtttttttg gtagagacgg ggtttcacca tattggccag gctggtctcc  18180
aactcctaat ctcaggtgat ctacccacct tggcctccca aattgctggg attacaggcg  18240
tgaaccactg ctcccttccc tgtccttctg attttgtagg taaccacgtg cggaccgagc  18300
ggccgcagga acccctagtg atggagttgg ccactccctc tctgcgcgct cgctcgctca  18360
ctgaggccgg gcgaccaaag gtcgcccgac gcccgggctt tgcccgggcg gcctcagtga  18420
gcgagcgagc gcgcagctgc ctgcaggggc gcctgatgcg gtattttctc cttacgcatc  18480
tgtgcggtat ttcacaccgc atacgtcgta gctgatcaat tggcgcgccg aattcgttaa  18540
caagctttaa ttaacgcgta cgataagctt gatatctata acaagaaaat atatatataa  18600
taagttatca cgtaagtaga acatgaaata acaatataat tatcgtatga gttaaatctt  18660
aaaagtcacg taaaagataa tcatgcgtca ttttgactca cgcggtcgtt atagttcaaa  18720
atcagtgaca cttaccgcat tgacaagcac gcctcacggg agctccaagc ggcgactgag  18780
atgtcctaaa tgcacagcga cggattcgcg ctatttagaa agagagagca atatttcaag  18840
aatgcatgcg tcaattttac gcagactatc tttctagggt taatctagct gcatcaggat  18900
catatcgtcg ggtctttttt ccggctcagt catcgcccaa gctggcgcta tctgggcatc  18960
ggggaggaag aagcccgtgc cttttcccgc gaggttgaag cggcatggaa agagtttgcc  19020
gaggatgact gctgctgcat tgacgttgag cgaaaacgca cgtttaccat gatgattcgg  19080
gaaggtgtgg ccatgcacgc ctttaacggt gaactgttcg ttcaggccac ctgggatacc  19140
agttcgtcgc ggcttttccg gacacagttc cggatggtca gcccgaagcg catcagcaac  19200
ccgaacaata ccggcgacag ccggaactgc cgtgccggtg tgcagattaa tgacagcggt  19260
gcggcgctgg gatattacgt cagcgaggac gggtatcctg gctggatgcc gcagaaatgg  19320
acatggatac cccgtgagtt acccggcggg cgcgcttggc gtaatcatgg tcatagctgt  19380
ttcctgtgtg aaattgttat ccgctcacaa ttccacacaa catacgagcc ggaagcataa  19440
agtgtaaagc ctggggtgcc taatgagtga gctaactcac attaattgcg ttgcgctcac  19500
```

-continued

```
tgcccgcttt ccagtcggga aacctgtcgt gccagctgca ttaatgaatc ggccaacgcg  19560
cggggagagg cggtttgcgt attgggcgct cttccgcttc ctcgctcact gactcgctgc  19620
gctcggtcgt tcggctgcgg cgagcggtat cagctcactc aaaggcggta atacggttat  19680
ccacagaatc aggggataac gcaggaaaga acatgtgagc aaaaggccag caaaaggcca  19740
ggaaccgtaa aaaggccgcg ttgctggcgt ttttccatag gctccgcccc cctgacgagc  19800
atcacaaaaa tcgacgctca agtcagaggt ggcgaaaccc gacaggacta taaagatacc  19860
aggcgtttcc ccctggaagc tccctcgtgc gctctcctgt tccgaccctg ccgcttaccg  19920
gatacctgtc cgcctttctc ccttcgggaa gcgtggcgct ttctcatagc tcacgctgta  19980
ggtatctcag ttcggtgtag gtcgttcgct ccaagctggg ctgtgtgcac gaaccccccg  20040
ttcagcccga ccgctgcgcc ttatccggta actatcgtct tgagtccaac ccggtaagac  20100
acgacttatc gccactggca gcagccactg gtaacaggat tagcagagcg aggtatgtag  20160
gcggtgctac agagttcttg aagtggtggc ctaactacgg ctacactaga aggacagtat  20220
ttggtatctg cgctctgctg aagccagtta ccttcggaaa aagagttggt agctcttgat  20280
ccggcaaaca aaccaccgct ggtagcggtg gtttttttgt ttgcaagcag cagattacgc  20340
gcagaaaaaa aggatctcaa gaagatcctt tgatcttttc tacggggtct gacgctcagt  20400
ggaacgaaaa ctcacgttaa gggattttgg tcatgagatt atcaaaaagg atcttcacct  20460
agatcctttt aaattaaaaa tgaagtttta aatcaatcta aagtatatat gagtaaactt  20520
ggtctgacag ttaccaatgc ttaatcagtg aggcacctat ctcagcgatc tgtctatttc  20580
gttcatccat agttgcctga ctccccgtcg tgtagataac tacgatacgg gagggcttac  20640
catctggccc cagtgctgca atgataccgc gagacccacg ctcaccggct ccagatttat  20700
cagcaataaa ccagccagcc ggaagggccg agcgcagaag tggtcctgca actttatccg  20760
cctccatcca gtctattaat tgttgccggg aagctagagt aagtagttcg ccagttaata  20820
gtttgcgcaa cgttgttgcc attgctacag gcatcgtggt gtcacgctcg tcgtttggta  20880
tggcttcatt cagctccggt tcccaacgat caaggcgagt tacatgatcc cccatgttgt  20940
gcaaaaaagc ggttagctcc ttcggtcctc cgatcgttgt cagaagtaag ttggccgcag  21000
tgttatcact catggttatg gcagcactgc ataattctct tactgtcatg ccatccgtaa  21060
gatgcttttc tgtgactggt gagtactcaa ccaagtcatt ctgagaatag tgtatgcggc  21120
gaccgagttg ctcttgcccg gcgtcaatac gggataatac cgcgccacat agcagaactt  21180
taaaagtgct catcattgga aaacgttctt cggggcgaaa actctcaagg atcttaccgc  21240
tgttgagatc cagttcgatg taacccactc gtgcacccaa ctgatcttca gcatctttta  21300
ctttcaccag cgtttctggg tgagcaaaaa caggaaggca aaatgccgca aaaaagggaa  21360
taagggcgac acggaaatgt tgaatactca t                                 21391
```

<210> SEQ ID NO 14
<211> LENGTH: 21046
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
actcttcctt tttcaatatt attgaagcat ttatcagggt tattgtctca tgagcggata     60
catatttgaa tgtatttaga aaaataaaca aataggggtt ccgcgcacat ttccccgaaa    120
```

-continued

```
agtgccacct aaattgtaag cgttaatatt ttgttaaaat tcgcgttaaa tttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaactttt atcgaattcc tgcagcccgg gggatccact   1140
agttctagag ggacagcccc cccccaaagc ccccagggat gtaattacgt ccctcccccg   1200
ctagggggca gcagcgagcc gcccggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc agatatacgc gttgacattg   1620
attattgact agttattaat agtaatcaat tacggggtca ttagttcata gcccatatat   1680
ggagttccgc gttacataac ttacggtaaa tggcccgcct ggctgaccgc ccaacgaccc   1740
ccgcccattg acgtcaataa tgacgtatgt tcccatagta acgccaatag ggactttcca   1800
ttgacgtcaa tgggtggagt atttacggta aactgcccac ttggcagtac atcaagtgta   1860
tcatatgcca agtacgcccc ctattgacgt caatgacggt aaatggcccg cctggcatta   1920
tgcccagtac atgaccttat gggactttcc tacttggcag tacatctacg tattagtcat   1980
cgctattacc atggtgatgc ggttttggca gtacatcaat gggcgtggat agcggtttga   2040
ctcacgggga tttccaagtc tccaccccat tgacgtcaat gggagtttgt tttggaacca   2100
aaatcaacgg gactttccaa aatgtcgtaa caactccgcc ccattgacgc aaatgggcgg   2160
taggcgtgta cggtgggagg tctatataag cagagctctc cctatcagtg atagagatct   2220
ccctatcagt gatagagatc gtcgacgagc tcgtttagtg aaccgtcaga tcgcctggag   2280
acgccatcca cgctgttttg acctccatag aagacaccgg gaccgatcca gcctccggac   2340
tctagcgttt aaacttaagc ttgccaccat ggccagtcgg gaagaggagc agcgcgaaac   2400
cacccccgag cgcggacgcg gtgcggcgcg acgtccccca accatggagg acgtgtcgtc   2460
```

-continued

```
cccgtccccg tcgccgccgc ctccccgggc gcccccaaaa aagcggatga ggcggcgtat   2520
cgagtccgag gacgaggaag actcatcaca agacgcgctg gtgccgcgca cacccagccc   2580
gcggccatcg acctcggcgg cggatttggc cattgcgccc aagaagaaaa agaagcgccc   2640
ttctcccaag cccgagcgcc cgccatcacc agaggtaatc gtggacagcg aggaagaaag   2700
agaagatgtg gcgctacaaa tggtgggttt cagcaaccca ccggtgctaa tcaagcatgg   2760
caaaggaggt aagcgcacag tgcggcggct gaatgaagac gacccagtgg cgcgtggtat   2820
gcggacgcaa gaggaagagg aagagcccag cgaagcggaa agtgaaatta cggtgatgaa   2880
cccgctgagt gtgccgatcg tgtctgcgtg ggagaagggc atggaggctg cgcgcgcgct   2940
gatggacaag taccacgtgg ataacgatct aaaggcgaac ttcaaactac tgcctgacca   3000
agtggaagct ctggcggccg tatgcaagac ctggctgaac gaggagcacc gcgggttgca   3060
gctgaccttc accagcaaca agacctttgt gacgatgatg gggcgattcc tgcaggcgta   3120
cctgcagtcg tttgcagagg tgacctacaa gcatcacgag cccacgggct gcgcgttgtg   3180
gctgcaccgc tgcgctgaga tcgaaggcga gcttaagtgt ctacacggaa gcattatgat   3240
aaataaggag cacgtgattg aaatggatgt gacgagcgaa aacgggcagc gcgcgctgaa   3300
ggagcagtct agcaaggcca agatcgtgaa gaaccggtgg ggccgaaatg tggtgcagat   3360
ctccaacacc gacgcaaggt gctgcgtgca cgacgcggcc tgtccggcca atcagttttc   3420
cggcaagtct tgcggcatgt tcttctctga aggcgcaaag gctcaggtgg cttttaagca   3480
gatcaaggct tttatgcagg cgctgtatcc taacgcccag accgggcacg gtcacctttt   3540
gatgccacta cggtgcgagt gcaactcaaa gcctgggcac gcgccctttt tgggaaggca   3600
gctaccaaag ttgactccgt tcgccctgag caacgcggag gacctggacg cggatctgat   3660
ctccgacaag agcgtgctgg ccagcgtgca ccacccggcg ctgatagtgt tccagtgctg   3720
caaccctgtg tatcgcaact cgcgcgcgca gggcggaggc cccaactgcg acttcaagat   3780
atcggcgccc gacctgctaa acgcgttggt gatggtgcgc agcctgtgga gtgaaaactt   3840
caccgagctg ccgcggatgg ttgtgcctga gtttaagtgg agcactaaac accagtatcg   3900
caacgtgtcc ctgccagtgg cgcatagcga tgcgcggcag aacccctttg atttttaacc   3960
cgggagttct agggatctgc ccctctccct cccccccccc taacgttact ggccgaagcc   4020
gcttggaata aggccggtgt gcgtttgtct atatgttatt ttccaccata ttgccgtctt   4080
ttggcaatgt gagggcccgg aaacctggcc ctgtcttctt gacgagcatt cctaggggtc   4140
tttcccctct cgccaaagga atgcaaggtc tgttgaatgt cgtgaaggaa gcagttcctc   4200
tggaagcttc ttgaagacaa acaacgtctg tagcgaccct ttgcaggcag cggaaccccc   4260
cacctggcga caggtgcctc tgcggccaaa agccacgtgt ataagataca cctgcaaagg   4320
cggcacaacc ccagtgccac gttgtgagtt ggatagttgt ggaaagagtc aaatggctct   4380
cctcaagcgt attcaacaag gggctgaagg atgcccagaa ggtaccccat tgtatgggat   4440
ctgatctggg gcctcggtgc acatgcttta catgtgttta gtcgaggtta aaaaaacgtc   4500
taggcccccc gaaccacggg gacgtggttt tcctttgaaa aacacgatga taaggatcca   4560
ccggaggcca ccatgactac gtccggcgtt ccatttggca tgacactacg accaacacga   4620
tctcggttgt ctcggcgcac tccgtacagt agggatcgtc tacctccttt tgagacagaa   4680
acccgcgcta ccatactgga ggatcatccg ctgctgcccg aatgtaacac tttgacaatg   4740
cacaacgtga gttacgtgcg aggtcttccc tgcagtgtgg gatttacgct gattcaggaa   4800
tgggttgttc cctgggatat ggttctaacg cgggaggagc ttgtaatcct gaggaagtgt   4860
```

-continued

```
atgcacgtgt gcctgtgttg tgccaacatt gatatcatga cgagcatgat gatccatggt   4920
tacgagtcct gggctctcca ctgtcattgt tccagtcccg gttccctgca gtgtatagcc   4980
ggcgggcagg ttttggccag ctggtttagg atggtggtgg atggcgccat gtttaatcag   5040
aggtttatat ggtaccggga ggtggtgaat tacaacatgc caaaagaggt aatgtttatg   5100
tccagcgtgt ttatgagggg tcgccactta atctacctgc gcttgtggta tgatggccac   5160
gtgggttctg tggtccccgc catgagcttt ggatacagcg ccttgcactg tgggattttg   5220
aacaatattg tggtgctgtg ctgcagttac tgtgctgatt taagtgagat cagggtgcgc   5280
tgctgtgccc ggaggacaag gcgccttatg ctgcgggcgg tgcgaatcat cgctgaggag   5340
accactgcca tgttgtattc ctgcaggacg gagcggcggc ggcagcagtt tattcgcgcg   5400
ctgctgcagc accaccgccc tatcctgatg cacgattatg actctacccc catgtaggcg   5460
gccgctcgag tctagagggc ccgtttaaac ccgctgatca gcctcgactg tgccttctag   5520
ttgccagcca tctgttgttt gcccctcccc cgtgccttcc ttgaccctgg aaggtgccac   5580
tcccactgtc ctttcctaat aaaatgagga aattgcatcg cattgtctga gtaggtgtca   5640
ttctattctg gggggtgggg tggggcagga cagcaagggg gaggattggg aagacaatag   5700
caggcatgct ggggatgcgg tgggctctat ggcttctgag gcggaaagaa ccagctgggg   5760
ctctaggggg tatccccggg gttggggttg cgccttttcc aaggcatcca gcacagtggc   5820
ggccgcaata tttgcatgtc gctatgtgtt ctgggaaatc accataaacg tgaaatccct   5880
atcagtgata gagacttata agttccctat cagtgataga gaaccggtgg gcactcttcc   5940
gtggtctggt ggataaattc gcaagggtat catggcggac gaccggggtt cgagccccgt   6000
atccggccgt ccgccgtgat ccatgcggtt accgcccgcg tgtcgaaccc aggtgtgcga   6060
cgtcagacaa cgggggagtg ctcctttttg aattccactt tggccgcggc tcgagggggt   6120
tggggttgcg ccttttccaa ggcagccctg ggtttgcgca gggacgcggc tgctctgggc   6180
gtggttccgg gaaacgcagc ggcgccgacc ctgggtctcg cacattcttc acgtccgttc   6240
gcagcgtcac ccggatcttc gccgctaccc ttgtgggccc cccggcgacg cttcctgctc   6300
cgcccctaag tcgggaaggt tccttgcggt tcgcggcgtg ccggacgtga caaacggaag   6360
ccgcacgtct cactagtacc ctcgcagacg gacagcgcca gggagcaatg gcagcgcgcc   6420
gaccgcgatg ggctgtggcc aatagcggct gctcagcagg gcgcgccgag agcagcggcc   6480
gggaaggggc ggtgcgggag gcggggtgtg gggcggtagt gtgggccctg ttcctgcccg   6540
cgcggtgttc cgcattctgc aagcctccgg agcgcacgtc ggcagtcggc tccctcgttg   6600
accgaatcac cgacctctct ccccaggggg atctgtgagt ttggggaccc ttgattgttc   6660
tttcttttc gctattgtaa aattcatgtt atatggaggg ggcaaagttt tcagggtgtt    6720
gtttagaatg ggaagatgtc ccttgtatca ccatggaccc tcatgataat tttgtttctt   6780
tcactttcta ctctgttgac aaccattgtc tcctcttatt ttcttttcat tttctgtaac   6840
tttttcgtta aactttagct tgcatttgta acgaattttt aaattcactt ttgtttattt   6900
gtcagattgt aagtactttc tctaatcact ttttttcaa ggcaatcagg gtatattata    6960
ttgtacttca gcacagtttt agagaacaat tgttataatt aaatgataag gtagaatatt   7020
tctgcatata aattctggct ggcgtggaaa tattcttatt ggtagaaaca actacatcct   7080
ggtcatcatc ctgcctttct ctttatggtt acaatgatat acactgtttg agatgaggat   7140
aaaatactct gagtccaaac cgggcccctc tgctaaccat gttcatgcct tcttcttttt   7200
```

cctacagctc ctgggcaacg tgctggttat tgtgctgtct catcattttg gcaaagaatt 7260
gtaatacgac tcactatagg gcgagccacc atggctagat tagataaaag taaagtgatt 7320
aacagcgcat tagagctgct taatgaggtc ggaatcgaag gtttaacaac ccgtaaactc 7380
gcccagaagc taggtgtaga gcagcctaca ttgtattggc atgtaaaaaa taagcgggct 7440
ttgctcgacg ccttagccat tgagatgtta gataggcacc atactcactt ttgccctttta 7500
gaaggggaaa gctggcaaga tttttttacgt aataacgcta aaagttttag atgtgcttta 7560
ctaagtcatc gcgatggagc aaaagtacat ttaggtacac ggcctacaga aaaacagtat 7620
gaaactctcg aaaatcaatt agccttttta tgccaacaag gtttttcact agagaatgcc 7680
ttatatgcac tcagcgccgt ggggcatttt actttaggtt gcgtattgga agatcaagag 7740
catcaagtcg ctaaagaaga aagggaaaca cctactactg atagtatgcc gccattatta 7800
cgacaagcta tcgaattatt tgatcaccaa ggtgcagagc cagccttctt attcggcctt 7860
gaattgatca tatgcggatt agaaaaacaa cttaaatgtg aaagtgggtc cccaaaaaag 7920
aagagaaagg tcgacggcgg tggttcagtt taagcgtaca gcggctcccg ggagttctag 7980
ggatctgccc ctctccctcc ccccccccta acgttactgg ccgaagccgc ttggaataag 8040
gccggtgtgc gtttgtctat atgttatttt ccaccatatt gccgtctttt ggcaatgtga 8100
gggcccggaa acctggccct gtcttcttga cgagcattcc taggggtctt tcccctctcg 8160
ccaaaggaat gcaaggtctg ttgaatgtcg tgaaggaagc agttcctctg gaagcttctt 8220
gaagacaaac aacgtctgta gcgacccttt gcaggcagcg gaacccccca cctggcgaca 8280
ggtgcctctg cggccaaaag ccacgtgtat aagatacacc tgcaaaggcg gcacaacccc 8340
agtgccacgt tgtgagttgg atagttgtgg aaagagtcaa atggctctcc tcaagcgtat 8400
tcaacaaggg gctgaaggat gcccagaagg taccccattg tatgggatct gatctggggc 8460
ctcggtgcac atgctttaca tgtgtttagt cgaggttaaa aaaacgtcta ggccccccga 8520
accacgggga cgtggttttc ctttgaaaaa cacgatgata aggatccacc ggaggccacc 8580
atgaccgagt acaagcccac ggtgcgcctc gccacccgcg acgacgtccc cagggccgta 8640
cgcaccctcg ccgccgcgtt cgccgactac cccgccacgc gccacaccgt cgatccggac 8700
cgccacatcg agcgggtcac cgagctgcaa gaactcttcc tcacgcgcgt cgggctcgac 8760
atcggcaagg tgtgggtcgc ggacgacggc gccgcggtgg cggtctggac cacgccggag 8820
agcgtcgaag cgggggcggt gttcgccgag atcggcccgc gcatggccga gttgagcggt 8880
tcccggctgg ccgcgcagca acagatggaa ggcctcctgg cgccgcaccg gcccaaggag 8940
cccgcgtggt tcctggccac cgtcggcgtc tcgcccgacc accagggcaa gggtctgggc 9000
agcgccgtcg tgctccccgg agtggaggcg gccgagcgcg ccggggtgcc cgccttcctg 9060
gagacctccg cgccccgcaa cctccccttc tacgagcggc tcggcttcac cgtcaccgcc 9120
gacgtcgagg tgcccgaagg accgcgcacc tggtgcatga cccgcaagcc cggtgcctga 9180
ccgcgtctgg aacaatcaac ctctggatta caaaatttgt gaaagattga ctggtattct 9240
taactatgtt gctcctttta cgctatgtgg atacgctgct ttaatgcctt tgtatcatgc 9300
tattgcttcc cgtatggctt tcattttctc ctccttgtat aaatcctggt tgctgtctct 9360
ttatgaggag ttgtggcccg ttgtcaggca acgtggcgtg gtgtgcactg tgtttgctga 9420
cgcaaccccc actggttggg gcattgccac cacctgtcag ctcctttccg ggactttcgc 9480
tttccccctc cctattgcca cggcggaact catcgccgcc tgccttgccc gctgctggac 9540
aggggctcgg ctgttgggca ctgacaattc cgtggtgttg tcggggaagc tgacgtcctt 9600

-continued

```
tccatggctg ctcgcctgtg ttgccacctg gattctgcgc gggacgtcct tctgctacgt   9660
cccttcggcc ctcaatccag cggaccttcc ttcccgcggc ctgctgccgg ctctgcggcc   9720
tcttccgcgt cttcgccttc gccctcagac gagtcggatc tccctttggg ccgcctcccc   9780
gcaaaatgac cgaccaagcg acgcccaacc tgccatcacg agatttcgat tccaccgccg   9840
ccttctatga aaggttgggc ttcggaatcg ttttccggga cgccggctgg atgatcctcc   9900
agcgcgggga tctcatgctg gagttcttcg cccaccccaa cttgtttatt gcagcttata   9960
atggttacaa ataaagcaat agcatcacaa atttcacaaa taaagcattt ttttcactgc  10020
attctagttg tggtttgtcc aaactcatca atgtatctta tcatgtctgt agctgatcaa  10080
ttggcgcgcc gaattcgtta tctgcagaat tcggcttggc ggctgcgcgt tcaaacctcc  10140
cgcttcaaaa tggagaccct gcgtgctcac tcgggcttaa atacccagcg tgaccacatg  10200
gtgtcgcaaa atgtcgcaaa acactcacgt gacctctaat acaggacctc tagagcatgg  10260
aaactagata agaaagaaat acgcagagac caaagttcaa ctgaaacgaa ttaaacggtt  10320
tattgattaa caagcaaact agtttacaga ttacgggtga ggtaacgggt gccgatgggg  10380
cgaggctcag aataaacgcc atttgtgtca acagcaaagt ccacatttgt agatttgttg  10440
tagttggaag tgtattgaat ctctgggttc cagcgtttgc tgttttcttt ctgcagctcc  10500
cattcaattt ccacgctgac ctgtccggtg ctgtactgcg tgatgaacga cgcaaactta  10560
gctggactga aggtagttgg aggattcgcg ggaacaggtg tattcttaat caggatctga  10620
ggaggcgggt gtttcagtcc aaagcctccc atcagcggcg agggatgaaa gtgtccgtcc  10680
gtgtgaggaa tcttggccca gataggaccc tgcaggtaca cgtcccggtc ctgccagacc  10740
atgccaggta aggctccttg actgttgacg gtccctgtag caggagcggt gttggccgat  10800
tgcaggttag tggccaccgt gccgtactct tctgtggcca ctgggttggt ggttttaatt  10860
tcttcctcgt tggttatcat aacgttgtca aggtccacgt tgctatttcc agctccctgt  10920
ttcccaaata ttaagactcc gctcatcgga aaaaatttgt cttcgtcgtc cttgtgggtt  10980
gccatagcgg gaccgggatt taccagagag tctctgccat tcagatgata cttggtggca  11040
ccggtccagg caaagttgct gttgttattt tgattggttg tcttggagac gcgttgctgc  11100
cggtagcagg gcccgggtag ccagtttttg gcctgattcg ccatgctact aggcccggcc  11160
tgagaaaatt gcaacgtccg atttcctgcg gtaccactcg tggtctgagt ccgagacagg  11220
tagtacaggt actggtcgat gagggggttc atcagccggt ccaggctttg gctgtgcgcg  11280
tagctgctgt gaaaaggcac gtcctcaaac gtgtagctga actgaaagtt gttgcccgtt  11340
ctcagcattt gagaaggaaa gtattccagg cagtagaagg aggaacggcc cacggcctga  11400
ctgccattgt tcagagtcag gtacccgtac tgaggaatca tgaagacgtc cgccgggaac  11460
ggaggcaggc agccctggtg cgcagagccg aggacgtacg ggagctggta ttccgagtcc  11520
gtaaagacct gaaccgtgct ggtaaggtta ttggcgatgg tcgtggtgcc atcattcgtc  11580
gtgacctcct tgacctggat gttgaagagc ttgaagttga gcttcttggg ccggaatccc  11640
cagttgttgt tgatgagtcg ctgccagtca cgtggtgaga agtggcagtg gaatctgtta  11700
aagtcaaaat acccccaggg ggtgctgtag ccgaagtagg tgttgtcgtt ggtgctgcct  11760
cccgattggc tggagatttg cttgtagagg tggttgttgt aggtggggag ggcccaggtt  11820
cgggtgctgg tggtgatgac tctgtcgccc agccatgtgg aatcgcaatg ccaatttcct  11880
gaggcgttac ccactccgtc ggcgccttcg ttattgtctg ccattggagc gccaccgcct  11940
```

gcagccattg tattagatcc cacaccagag ggggctgcgg ggggttctcc gagtggttga 12000
gggtcgggca ctgactctga gtcgccagtc tgcccaaagt tgagtctctt tctcgcgggc 12060
tgctggcctt tcttgccgat gcccgaagag gagtctggtt cctggggtga ttgctctacc 12120
ggtctcttct ttccaggagc cgtcttagcg ccttcctcaa ccagaccgag aggttcgaga 12180
acccgcttct tggcctggaa gactgctcgc ccgaggttgc ccccaaaaga cgtatcttct 12240
tgcagacgct cctgaaactc ggcgtcggcg tggttatacc gcaggtacgg attgtcaccc 12300
gctttgagct gctggtcgta ggccttgtcg tgctcgaggg ccgctgcgtc cgccgcgttg 12360
acgggctccc ccttgtcgag tccgttgaag ggtccgaggt acttgtagcc aggaagcacc 12420
agaccccggc cgtcgtcctg cttttgctgg ttggctttgg gtttcggggc tccaggtttc 12480
aagtcccacc actcgcgaat gccctcagag aggttgtcct cgagccaatc tggaagataa 12540
ccatcggcag ccatacctga tttaaatcat ttattgttca aagatgcagt catccaaatc 12600
cacattgacc agatcgcagg cagtgcaagc gtctggcacc tttcccatga tatgatgaat 12660
gtagcacagt ttctgatacg ccttttttgac gacagaaacg ggttgagatt ctgacacggg 12720
aaagcactct aaacagtctt tctgtccgtg agtgaagcag atatttgaat tctgattcat 12780
tctctcgcat tgtctgcagg gaaacagcat cagattcatg cccacgtgac gagaacattt 12840
gttttggtac ctgtctgcgt agttgatcga agcttccgcg tctgacgtcg atggctgcgc 12900
aactgactcg cgcacccgtt tgggctcact tatatctgcg tcactggggg cgggtctttt 12960
cttggctcca cccttttttga cgtagaattc atgctccacc tcaaccacgt gatcctttgc 13020
ccaccggaaa aagtctttga cttcctgctt ggtgaccttc ccaaagtcat gatccagacg 13080
gcgggtgagt tcaaatttga acatccggtc ttgcaacggc tgctggtgtt cgaaggtcgt 13140
tgagttcccg tcaatcacgg cgcacatgtt ggtgttggag gtgacgatca cgggagtcgg 13200
gtctatctgg gccgaggact tgcatttctg gtccacgcgc accttgcttc ctccgagaat 13260
ggctttggcc gactccacga ccttggcggt catcttcccc tcctcccacc agatcaccat 13320
cttgtcgaca cagtcgttga agggaaagtt ctcattggtc cagtttacgc acccgtagaa 13380
gggcacagtg tgggctatgg cctccgcgat gttggtcttc ccggtagttg caggcccaaa 13440
cagccagatg gtgttcctct tgccgaactt tttcgtggcc catcccagaa agacggaagc 13500
cgcatattgg ggatcgtacc cgtttagttc caaaatttta taaatccgat tgctggaaat 13560
gtcctccacg ggctgctggc ccaccaggta gtcgggggcg gttttagtca ggctcataat 13620
ctttcccgca ttgtccaagg cagccttgat ttgggaccgc gagttggagg ccgcattgaa 13680
ggagatgtat gaggcctggt cctcctggat ccactgcttc tccgaggtaa tccccttgtc 13740
cacgagccac ccgaccagct ccatgtacct ggctgaagtt tttgatctga tcaccggcgc 13800
atcagaattg ggattctgat tctctttgtt ctgctcctgc gtctgcgaca cgtgcgtcag 13860
atgctgcgcc accaaccgtt tacgctccgt gagattcaaa caggcgctgt ggagagaaag 13920
gcaaagtgga tgtcagtatc tctatcactg atagggagat ctctatcact gatagggaac 13980
ttaccttaaa tactgttcca tattagtcca cgcccactgg agctcaggct gggttttggg 14040
gagcaagtaa ttggggatgt agcactcatc caccaccttg ttcccgcctc cggcgccatt 14100
tctggtcttt gtgaccgcga accagtttgg caaagtcggc tcgatcccgc ggtaaattct 14160
ctgaatcagt ttttcgcgaa tctgactcag gaaacgtccc aaaaccatgg atttcacccc 14220
ggtggtttcc acgagcacgt gcatgtggaa gtagctctct cccttctcaa attgcacaaa 14280
gaaaagagcc tccggggcct tactcacacg gcgccattcc gtcagaaagt cgcgctgcag 14340
cttctcggcc acggtcaggg gtgcctgctc aatcagattc agatccatgt cagaatctgg 14400
cggcaactcc cattccttct cggccaccca gttcacaaag ctgtcagaaa tgccgggcag 14460
atgctcgtca aggtcgctgg ggaccttaat cacaatctcg taaaaccccg gcatggcggc 14520
tgcgcgttca aacctcccgc ttcaaaatgg agaccctgcg tgctcactcg ggcgatctct 14580
atcactgata gggagatctc tatcactgat agggagatta aatagaatgg ctaggatccg 14640
gccggcctgc aggtgtcctc acaggaacga agtccctaaa gaaacagtgg cagccaggtt 14700
tagccccgga attgactgga ttcctttttt agggcccatt ggtatggctt tttccccgta 14760
tccccccagg tgtctgcagg ctcaaagagc agcgagaagc gttcagagga aagcgatccc 14820
gtgccacctt ccccgtgccc gggctgtccc cgcacgctgc cggctcgggg atgcgggggg 14880
agcgccggac cggagcggag ccccgggcgg ctcgctgctg cccccctagcg ggggagggac 14940
gtaattacat ccctgggggc tttggggggg ggctgtccct ctagagcggc cgccaccgcg 15000
gtggagctcc agcttttgtt ccctttagtg agggttaatt agatcttaat acgactcact 15060
atagggcgaa ttgggtaccg ggcccccccct cgaggtcgac ggtatcgcct ccaaggccag 15120
cttcccacaa taagttgggt gaattttggc tcattcctcc tttctatagg attgaggtca 15180
gagctttgtg atgggaattc tgtggaatgt gtgtcagtta gggtgtggaa agtcccgcga 15240
tcgctagcaa acgccagcaa cgcggccttt ttacggttcc tggccttttg ctggcctttt 15300
gctcacatgt cctgcaggca gctgcgcgct cgctcgctca ctgaggccgc ccgggcaaag 15360
cccgggcgtc gggcgacctt tggtcgcccg gcctcagtga gcgagcgagc gcgcagagag 15420
ggagtggcca actccatcac taggggttcc tgcggccgca cgcgtggagc tagttattaa 15480
tagtaatcaa ttacggggtc attagttcat agcccatata tggagttccg cgttacataa 15540
cttacggtaa atggcccgcc tggctgaccg cccaacgacc cccgcccatt gacgtcaata 15600
atgacgtatg ttcccatagt aacgtcaata gggactttcc attgacgtca atgggtggag 15660
tatttacggt aaactgccca cttggcagta catcaagtgt atcatatgcc aagtacgccc 15720
cctattgacg tcaatgacgg taaatggccc gcctggcatt atgcccagta catgacctta 15780
tgggactttc ctacttggca gtacatctac gtattagtca tcgctattac catggtgatg 15840
cggttttggc agtacatcaa tgggcgtgga tagcggtttg actcacgggg atttccaagt 15900
ctccacccca ttgacgtcaa tgggagtttg ttttgcacca aaatcaacgg gactttccaa 15960
aatgtcgtaa caactccgcc ccattgacgc aaatgggcgg taggcgtgta cggtgggagg 16020
tctatataag cagagctcgt ttagtgaacc gtcagatcgc ctggagacgc catccacgct 16080
gttttgacct ccatagaaga caccgggacc gatccagcct ccgcggattc gaatcccggc 16140
cgggaacggt gcattggaac gcggattccc cgtgccaaga gtgacgtaag taccgcctat 16200
agagtctata ggcccacaaa aaatgctttc ttcttttaat atactttttt gtttatctta 16260
tttctaatac tttccctaat ctctttcttt cagggcaata atgatacaat gtatcatgcc 16320
tctttgcacc attctaaaga ataacagtga taatttctgg gttaaggcaa tagcaatatt 16380
tctgcatata aatatttctg catataaatt gtaactgatg taagaggttt catattgcta 16440
atagcagcta caatccagct accattctgc ttttatttta tggttgggat aaggctggat 16500
tattctgagt ccaagctagg cccttttgct aatcatgttc atacctctta tcttcctccc 16560
acagctcctg ggcaacgtgc tggtctgtgt gctggcccat cactttggca aagaattggg 16620
attcgaacat cgattgaatt ctgaatggtg agcaagggcg aggagctgtt caccggggtg 16680

-continued

```
gtgcccatcc tggtcgagct ggacggcgac gtaaacggcc acaagttcag cgtgtccggc  16740
gagggcgagg gcgatgccac ctacggcaag ctgaccctga agttcatctg caccaccggc  16800
aagctgcccg tgccctggcc caccctcgtg accaccctga cctacggcgt gcagtgcttc  16860
agccgctacc ccgaccacat gaagcagcac gacttcttca agtccgccat gcccgaaggc  16920
tacgtccagg agcgcaccat cttcttcaag gacgacggca actacaagac ccgcgccgag  16980
gtgaagttcg agggcgacac cctggtgaac cgcatcgagc tgaagggcat cgacttcaag  17040
gaggacggca acatcctggg gcacaagctg gagtacaact acaacagcca caacgtctat  17100
atcatggccg acaagcagaa gaacggcatc aaggtgaact tcaagatccg ccacaacatc  17160
gaggacggca gcgtgcagct cgccgaccac taccagcaga acacccccat cggcgacggc  17220
cccgtgctgc tgcccgacaa ccactacctg agcacccagt ccgccctgag caaagacccc  17280
aacgagaagc gcgatcacat ggtcctgctg gagttcgtga ccgccgccgg gatcactctc  17340
ggcatggacg agctgtacaa gtactcagat ctcgagctca agtagggatc ctctagagtc  17400
gacctgcaga agcttgcctc gagcagcgct gctcgagaga tctacgggtg gcatccctgt  17460
gacccctccc cagtgcctct cctggccctg gaagttgcca ctccagtgcc caccagcctt  17520
gtcctaataa aattaagttg catcattttg tctgactagg tgtccttcta taatattatg  17580
gggtggaggg gggtggtatg gagcaagggg caagttggga agacaacctg tagggcctgc  17640
ggggtctatt gggaaccaag ctggagtgca gtggcacaat cttggctcac tgcaatctcc  17700
gcctcctggg ttcaagcgat tctcctgcct cagcctcccg agttgttggg attccaggca  17760
tgcatgacca ggctcagcta atttttgttt ttttggtaga gacggggttt caccatattg  17820
gccaggctgg tctccaactc ctaatctcag gtgatctacc caccttggcc tcccaaattg  17880
ctgggattac aggcgtgaac cactgctccc ttccctgtcc ttctgatttt gtaggtaacc  17940
acgtgcggac cgagcggccg caggaacccc tagtgatgga gttggccact ccctctctgc  18000
gcgctcgctc gctcactgag gccgggcgac caaaggtcgc ccgacgcccg ggctttgccc  18060
gggcggcctc agtgagcgag cgagcgcgca gctgcctgca ggggcgcctg atgcggtatt  18120
ttctccttac gcatctgtgc ggtatttcac accgcatacg tcgtagctga tcaattggcg  18180
cgccgaattc gttaacaagc tttaattaac gcgtacgata agcttgatat ctataacaag  18240
aaaatatata tataataagt tatcacgtaa gtagaacatg aaataacaat ataattatcg  18300
tatgagttaa atcttaaaag tcacgtaaaa gataatcatg cgtcattttg actcacgcgg  18360
tcgttatagt tcaaaatcag tgacacttac cgcattgaca agcacgcctc acgggagctc  18420
caagcggcga ctgagatgtc ctaaatgcac agcgacggat tcgcgctatt tagaaagaga  18480
gagcaatatt tcaagaatgc atgcgtcaat tttacgcaga ctatctttct agggttaatc  18540
tagctgcatc aggatcatat cgtcgggtct tttttccggc tcagtcatcg cccaagctgg  18600
cgctatctgg gcatcgggga ggaagaagcc cgtgcctttt cccgcgaggt tgaagcggca  18660
tggaaagagt ttgccgagga tgactgctgc tgcattgacg ttgagcgaaa acgcacgttt  18720
accatgatga ttcgggaagg tgtggccatg cacgccttta acggtgaact gttcgttcag  18780
gccacctggg ataccagttc gtcgcggctt ttccggacac agttccggat ggtcagcccg  18840
aagcgcatca gcaacccgaa caataccggc gacagccgga actgccgtgc cggtgtgcag  18900
attaatgaca gcggtgcggc gctgggatat tacgtcagcg aggacgggta tcctggctgg  18960
atgccgcaga aatggacatg gataccccgt gagttacccg gcgggcgcgc ttggcgtaat  19020
catggtcata gctgtttcct gtgtgaaatt gttatccgct cacaattcca cacaacatac  19080
```

```
gagccggaag cataaagtgt aaagcctggg gtgcctaatg agtgagctaa ctcacattaa  19140
ttgcgttgcg ctcactgccc gctttccagt cgggaaacct gtcgtgccag ctgcattaat  19200
gaatcggcca acgcgcgggg agaggcggtt tgcgtattgg gcgctcttcc gcttcctcgc  19260
tcactgactc gctgcgctcg gtcgttcggc tgcggcgagc ggtatcagct cactcaaagg  19320
cggtaatacg gttatccaca gaatcagggg ataacgcagg aaagaacatg tgagcaaaag  19380
gccagcaaaa ggccaggaac cgtaaaaagg ccgcgttgct ggcgtttttc cataggctcc  19440
gcccccctga cgagcatcac aaaaatcgac gctcaagtca gaggtggcga aacccgacag  19500
gactataaag ataccaggcg tttccccctg gaagctccct cgtgcgctct cctgttccga  19560
ccctgccgct taccggatac ctgtccgcct ttctcccttc gggaagcgtg gcgctttctc  19620
atagctcacg ctgtaggtat ctcagttcgg tgtaggtcgt tcgctccaag ctgggctgtg  19680
tgcacgaacc ccccgttcag cccgaccgct gcgccttatc cggtaactat cgtcttgagt  19740
ccaacccggt aagacacgac ttatcgccac tggcagcagc cactggtaac aggattagca  19800
gagcgaggta tgtaggcggt gctacagagt tcttgaagtg gtggcctaac tacggctaca  19860
ctagaaggac agtatttggt atctgcgctc tgctgaagcc agttaccttc ggaaaaagag  19920
ttggtagctc ttgatccggc aaacaaacca ccgctggtag cggtggtttt tttgtttgca  19980
agcagcagat tacgcgcaga aaaaaaggat ctcaagaaga tcctttgatc ttttctacgg  20040
ggtctgacgc tcagtggaac gaaaactcac gttaagggat tttggtcatg agattatcaa  20100
aaaggatctt cacctagatc cttttaaatt aaaaatgaag ttttaaatca atctaaagta  20160
tatatgagta aacttggtct gacagttacc aatgcttaat cagtgaggca cctatctcag  20220
cgatctgtct atttcgttca tccatagttg cctgactccc cgtcgtgtag ataactacga  20280
tacgggaggg cttaccatct ggccccagtg ctgcaatgat accgcgagac ccacgctcac  20340
cggctccaga tttatcagca ataaaccagc cagccggaag ggccgagcgc agaagtggtc  20400
ctgcaacttt atccgcctcc atccagtcta ttaattgttg ccgggaagct agagtaagta  20460
gttcgccagt taatagtttg cgcaacgttg ttgccattgc tacaggcatc gtggtgtcac  20520
gctcgtcgtt tggtatggct tcattcagct ccggttccca acgatcaagg cgagttacat  20580
gatcccccat gttgtgcaaa aaagcggtta gctccttcgg tcctccgatc gttgtcagaa  20640
gtaagttggc cgcagtgtta tcactcatgg ttatggcagc actgcataat tctcttactg  20700
tcatgccatc cgtaagatgc ttttctgtga ctggtgagta ctcaaccaag tcattctgag  20760
aatagtgtat gcggcgaccg agttgctctt gcccggcgtc aatacgggat aataccgcgc  20820
cacatagcag aactttaaaa gtgctcatca ttggaaaacg ttcttcgggg cgaaaactct  20880
caaggatctt accgctgttg agatccagtt cgatgtaacc cactcgtgca cccaactgat  20940
cttcagcatc ttttactttc accagcgttt ctgggtgagc aaaaacagga aggcaaaatg  21000
ccgcaaaaaa gggaataagg gcgacacgga aatgttgaat actcat                 21046
```

<210> SEQ ID NO 15
<211> LENGTH: 10497
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15

```
cctcgagggc tagccattct atttaatctc cctatcagtg atagagatct ccctatcagt     60
```

-continued

```
gatagagatc gcccgagtga gcacgcaggg tctccatttt gaagcgggag gtttgaacgc    120
gcagccgcca tgccggggtt ttacgagatt gtgattaagg tccccagcga ccttgacgag    180
catctgcccg gcatttctga cagctttgtg aactgggtgg ccgagaagga atgggagttg    240
ccgccagatt ctgacatgga tctgaatctg attgagcagg cacccctgac cgtggccgag    300
aagctgcagc gcgactttct gacggaatgg cgccgtgtga gtaaggcccc ggaggctctt    360
ttctttgtgc aatttgagaa gggagagagc tacttccaca tgcacgtgct cgtggaaacc    420
accggggtga aatccatggt tttgggacgt ttcctgagtc agattcgcga aaaactgatt    480
cagagaattt accgcgggat cgagccgact ttgccaaact ggttcgcggt cacaaagacc    540
agaaatggcg ccggaggcgg gaacaaggtg gtggatgagt gctacatccc caattacttg    600
ctccccaaaa cccagcctga gctccaatgg gcatggacca acatggaaca gtacctcagc    660
gcctgtttga atctcacgga gcgtaaacgg ttggtggcgc agcatctgac gcacgtgtcg    720
cagacgcagg agcagaacaa agagaatcag aatcccaatt ctgatgcgcc ggtgatcaga    780
tcaaaaactt cagccaggta catggagctg gtcgggtggc tcgtggacaa ggggattacc    840
tcggagaagc agtggatcca ggaggaccag gcctcataca tctccttcaa tgcggcctcc    900
aactcgcggt cccaaatcaa ggctgccttg gacaatgcgg gaaagattat gagcctgact    960
aaaaccgccc ccgactacct ggtgggccag cagcccgtgg aggacatttc cagcaatcgg   1020
atttataaaa ttttggaact aaacgggtac gatccccaat atgcggcttc cgtctttctg   1080
ggatgggcca cgaaaaagtt cggcaagagg aacaccatct ggctgtttgg gcctgcaact   1140
accgggaaga ccaacatcgc ggaggccata gcccacactg tgcccttcta cgggtgcgta   1200
aactggacca atgagaactt tcccttcaac gactgtgtcg acaagatggt gatctggtgg   1260
gaggagggga agatgaccgc caaggtcgtg gagtcggcca aagccattct cggaggaagc   1320
aaggtgcgcg tggaccagaa atgcaagtcc tcggcccaga tagacccgac tcccgtgatc   1380
gtcacctcca acaccaacat gtgcgccgtg attgacggga actcaacgac cttcgaacac   1440
cagcagccgt tgcaagaccg gatgttcaaa tttgaactca cccgccgtct ggatcatgac   1500
tttgggaagg tcaccaagca ggaagtcaaa gactttttcc ggtgggcaaa ggatcacgtg   1560
gttgaggtgg agcatgaatt ctacgtcaaa aagggtggag ccaagaaaag acccgccccc   1620
agtgacgcag atataagtga gcccaaacgg gtgcgcgagt cagttgcgca gccatcgacg   1680
tcagacgcgg aagcttcgat caactacgca gacaggtacc aaaacaaatg ttctcgtcac   1740
gtgggcatga atctgatgct gtttccctgc agacaatgcg agagaatgaa tcagaattca   1800
aatatctgct tcactcacgg acagaaagac tgtttagagt gctttcccgt gtcagaatct   1860
caacccgttt ctgtcgtcaa aaaggcgtat cagaaactgt gctacattca tcatatcatg   1920
ggaaaggtgc cagacgcttg cactgcctgc gatctggtca atgtggattt ggatgactgc   1980
atctttgaac aataaatgat ttaaatcagg tatggctgcc gatggttatc ttccagattg   2040
gctcgaggac aacctctctg agggcattcg cgagtggtgg gacttgaaac ctggagcccc   2100
gaaacccaaa gccaaccagc aaaagcagga cgacggccgg ggtctggtgc ttcctggcta   2160
caagtacctc ggacccttca acggactcga caagggggag cccgtcaacg cggcggacgc   2220
agcggccctc gagcacgaca aggcctacga ccagcagctc aaagcgggtg acaatccgta   2280
cctgcggtat aaccacgccg acgccgagtt tcaggagcgt ctgcaagaag atacgtcttt   2340
tgggggcaac ctcgggcgag cagtcttcca ggccaagaag cgggttctcg aacctctcgg   2400
```

-continued

```
tctggttgag gaaggcgcta agacggctcc tggaaagaag agaccggtag agcaatcacc   2460
ccaggaacca gactcctctt cgggcatcgg caagaaaggc cagcagcccg cgagaaagag   2520
actcaacttt gggcagactg gcgactcaga gtcagtgccc gaccctcaac cactcggaga   2580
accccccgca gccccctctg gtgtgggatc taatacaatg gctgcaggcg gtggcgctcc   2640
aatggcagac aataacgaag gcgccgacgg agtgggtaac gcctcaggaa attggcattg   2700
cgattccaca tggctgggcg acagagtcat caccaccagc acccgaacct gggccctccc   2760
cacctacaac aaccacctct acaagcaaat ctccagccaa tcgggaggca gcaccaacga   2820
caacacctac ttcggctaca gcaccccctg ggggtatttt gactttaaca gattccactg   2880
ccacttctca ccacgtgact ggcagcgact catcaacaac aactggggat tccggcccaa   2940
gaagctcaac ttcaagctct tcaacatcca ggtcaaggag gtcacgacga atgatggcac   3000
cacgaccatc gccaataacc ttaccagcac ggttcaggtc tttacggact cggaatacca   3060
gctcccgtac gtcctcggct ctgcgcacca gggctgcctg cctccgttcc cggcggacgt   3120
cttcatgatt cctcagtacg ggtacctgac tctgaacaat ggcagtcagg ccgtgggccg   3180
ttcctccttc tactgcctgg aatactttcc ttctcaaatg ctgagaacgg gcaacaactt   3240
tcagttcagc tacacgtttg aggacgtgcc ttttcacagc agctacgcgc acagccaaag   3300
cctggaccgg ctgatgaacc ccctcatcga ccagtacctg tactacctgt ctcggactca   3360
gaccacgagt ggtaccgcag gaaatcggac gttgcaattt tctcaggccg ggcctagtag   3420
catggcgaat caggccaaaa actggctacc cgggccctgc taccggcagc aacgcgtctc   3480
caagacaacc aatcaaaata acaacagcaa ctttgcctgg accggtgcca ccaagtatca   3540
tctgaatggc agagactctc tggtaaatcc cggtcccgct atggcaaccc acaaggacga   3600
cgaagacaaa ttttttccga tgagcggagt cttaatattt gggaaacagg gagctggaaa   3660
tagcaacgtg gaccttgaca acgttatgat aaccaacgag gaagaaatta aaaccaccaa   3720
cccagtggcc acagaagagt acggcacggt ggccactaac ctgcaatcgg ccaacaccgc   3780
tcctgctaca gggaccgtca acagtcaagg agccttacct ggcatggtct ggcaggaccg   3840
ggacgtgtac ctgcagggtc ctatctgggc caagattcct cacacggacg gacactttca   3900
tccctcgccg ctgatgggag gctttggact gaaacacccg cctcctcaga tcctgattaa   3960
gaatacacct gttcccgcga atcctccaac taccttcagt ccagctaagt ttgcgtcgtt   4020
catcacgcag tacagcaccg gacaggtcag cgtggaaatt gaatgggagc tgcagaaaga   4080
aaacagcaaa cgctggaacc cagagattca atacacttcc aactacaaca aatctacaaa   4140
tgtggacttt gctgttgaca caaatggcgt ttattctgag cctcgcccca tcggcacccg   4200
ttacctcacc cgtaatctgt aaactagttt gcttgttaat caataaaccg tttaattcgt   4260
ttcagttgaa ctttggtctc tgcgtatttc tttcttatct agtttccatg ctctagaggt   4320
cctgtattag aggtcacgtg agtgttttgc gacattttgc gacaccatgt ggtcacgctg   4380
ggtatttaag cccgagtgag cacgcagggt ctccattttg aagcgggagg tttgaacgcg   4440
cagccgccaa gccgaattct gcagatatcg gggttggggt tgcgcctttt ccaaggcagc   4500
cctgggtttg cgcagggacg cggctgctct gggcgtggtt ccgggaaacg cagcggcgcc   4560
gaccctgggt ctcgcacatt cttcacgtcc gttcgcagcg tcacccggat cttcgccgct   4620
acccttgtgg gccccccggc gacgcttcct gctccgcccc taagtcggga aggttccttg   4680
cggttcgcgg cgtgccggac gtgacaaacg gaagccgcac gtctcactag taccctcgca   4740
gacggacagc gccagggagc aatggcagcg cgccgaccgc gatgggctgt ggccaatagc   4800
```

```
ggctgctcag cagggcgcgc cgagagcagc ggccgggaag gggcggtgcg ggaggcgggg   4860
tgtggggcgg tagtgtgggc cctgttcctg cccgcgcggt gttccgcatt ctgcaagcct   4920
ccggagcgca cgtcggcagt cggctccctc gttgaccgaa tcaccgacct ctctccccag   4980
aagctcccgg gagcttgtat atccattttc ggatctgatc agcacgtgtt gacaattaat   5040
catcggcata gtatatcggc atagtataat acgacaaggt gaggaacgcc accatggcca   5100
agcctttgtc tcaagaagaa tccaccctca ttgaaagagc aacggctaca atcaacagca   5160
tccccatctc tgaagactac agcgtcgcca gcgcagctct ctctagcgac ggccgcatct   5220
tcactggtgt caatgtatat cattttactg ggggaccttg tgcagaactc gtggtgctgg   5280
gcactgctgc tgctgcggca gctggcaacc tgacttgtat cgtcgcgatc ggaaatgaga   5340
acaggggcat cttgagcccc tgcggacggt gccgacaggt gcttctcgat ctgcatcctg   5400
ggatcaaagc catagtgaag gacagtgatg gacagccgac ggcagttggg attcgtgaat   5460
tgctgccctc tggttatgtg tgggagggct aagcacttcg tggccgagga gcaggactga   5520
cacgtgctac gagatttcga ttccaccgcc gccttctatg aaaggttggg cttcggaatc   5580
gttttccggg acgccggctg gatgatcctc cagcgcgggg atctcatgct ggagttcttc   5640
gcccacccca acttgtttat tgcagcttat aatggttaca aataaagcaa tagcatcaca   5700
aatttcacaa ataaagcatt tttttcactg cattctagtt gtggtttgtc caaactcatc   5760
aatgtatctt agcgctcact gcccgctttc cagtcgggaa acctgtcgtg ccagctgcat   5820
taatgaatcg gccaacgcgc ggggagaggc ggtttgcgta ttgggcgctc tcctaggcca   5880
gaaatggcgc cggaggcggg aacaaggtgg tggatgagtg ctacatcccc aattacttgc   5940
tccccaaaac ccagcctgag ctccagtggg cgtggactaa tatggaacag tatttaagcg   6000
cctgtcccta tcagtgatag agatctccct atcagtgata gagatttgaa tctcacggag   6060
cgtaaacggt tggtggcgca gcatctgttt aaacgcagac gcaggagcag aacaaagaga   6120
atcagaatcc caattctgat gcgccggtga tcagatcaaa aacttcagcc aggtacatgg   6180
agctggtcgg gtggctcgtg gacaagggga ttacctcgga gaagcagtgg attcaggagg   6240
accaggcctc atacatctcc ttcaatgcgg cctccaactc gcggtcccaa atcaaggctg   6300
ccttggacaa tgcgggaaag attatgagcc tgactaaaac cgcccccgac tacctggtgg   6360
gccagcagcc cgtggaggac atttccagca atcggattta taaaattttg gaactaaacg   6420
ggtacgatcc ccaatatgcg gcttccgtct ttctgggatg ggccacgaaa aagttcggca   6480
agaggaacac catctggctg tttgggcctg caactaccgg gaagaccaac atcgcggagg   6540
ccatagccca cactgtgccc ttctacgggt gcgtaaactg gaccaatgag aactttccct   6600
tcaacgactg tgtcgacaag atggtgatct ggtgggagga ggggaagatg accgccaagg   6660
tcgtggagtc ggccaaagcc attctcggag gaagcaaggt gcgcgtggac cagaaatgca   6720
agtcctcggc ccagatagac ccgactcccg tgatcgtcac ctccaacacc aacatgtgcg   6780
ccgtgattga cgggaactca acgaccttcg aacaccagca gccgttgcaa gaccggatgt   6840
tcaaatttga actcacccgc cgtctggatc atgactttgg gaaggtcacc aagcaggaag   6900
tcaaagactt tttccggtgg gcaaaggatc acgtggttga ggtggagcat gaattctacg   6960
tcaaaaaggg tggagccaag aaaagacccg cccccagtga cgcagatata agtgagccca   7020
aacgggtgcg cgagtcagtt gcgcagccat cgacgtcaga cgcggaagct tcgatcaact   7080
acgcagacag gtaccaaaac aaatgttctc gtcacgtggg catgaatctg atgctgtttc   7140
```

-continued

```
cctgcagaca atgcgagaga atgaatcaga attcaaatat ctgcttcact cacggacaga   7200
aagactgttt agagtgcttt cccgtgtcag aatctcaacc cgtttctgtc gtcaaaaagg   7260
cgtatcagaa actgtgctac attcatcata tcatgggaaa ggtgccagac gcttgcactg   7320
cctgcgatct ggtcaatgtg gatttggatg actgcatctt tgaacaataa actagtttgc   7380
ttgttaatca ataaaccgtt taattcgttt cagttgaact ttggtctctg cgtatttctt   7440
tcttatctag tttccatgct ctagagtata cgatatccat cacactggcg gccgctcgac   7500
tagagcggcc gccaccgcgg tggagctcca gcttttgttc gcgcgcttgg cgtaatcatg   7560
gtcatagctg tttcctgtgt gaaattccac agcctggggt gcctaattgc gttgcgctca   7620
ctgcccgctt tccagtcggg aaacctgtcg tgccagctgc attaatgaat cggccaacgc   7680
gcggggagag gcggtttgcg tattgggcgc tcttccgctt cctcgctcac tgactcgctg   7740
cgctcggtcg ttcggctgcg gcgagcggta tcagctcact caaaggcggt aatacggtta   7800
tccacagaat caggggataa cgcaggaaag aacatgtgag caaaaggcca gcaaaaggcc   7860
aggaaccgta aaaaggccgc gttgctggcg tttttccata ggctccgccc ccctgacgag   7920
catcacaaaa atcgacgctc aagtcagagg tggcgaaacc cgacaggact ataaagatac   7980
caggcgtttc cccctggaag ctccctcgtg cgctctcctg ttccgaccct gccgcttacc   8040
ggatacctgt ccgcctttct cccttcggga agcgtggcgc tttctcatag ctcacgctgt   8100
aggtatctca gttcggtgta ggtcgttcgc tccaagctgg gctgtgtgca cgaacccccc   8160
gttcagcccg accgctgcgc cttatccggt aactatcgtc ttgagtccaa cccggtaaga   8220
cacgacttat cgccactggc agcagccact ggtaacagga ttagcagagc gaggtatgta   8280
ggcggtgcta cagagttctt gaagtggtgg cctaactacg gctacactag aagaacagta   8340
tttggtatct gcgctctgct gaagccagtt accttcggaa aaagagttgg tagctcttga   8400
tccggcaaac aaaccaccgc tggtagcggt ggtttttttg tttgcaagca gcagattacg   8460
cgcagaaaaa aaggatctca agaagatcct ttgatctttt ctacggggtc tgacgctcag   8520
tggaacgaaa actcacgtta agggattttg gtcatgagat tatcaaaaag gatcttcacc   8580
tagatccttt taaattaaaa atgaagtttt aaatcaatct aaagtatata tgagtaaact   8640
tggtctgaca gaaataataa aaaagccgga ttaataatct ggctttttat attctctctc   8700
tagtatataa acgcagaaag gcccacccga aggtgagcca gtgtgactct agtattatta   8760
gaaaaactca tcgagcatca aatgaaactg caatttattc atatcaggat tatcaatacc   8820
atatttttga aaaagccgtt tctgtaatga aggagaaaac tcaccgaggc agttccaaag   8880
aatggcaagg tcctggtaac ggtctgcgat tccgacccgt ccaacatcaa tacaacctat   8940
taatttcccc tcgtcaaaaa taaggttatc aagtgagaaa tcaccatgag tgacgactga   9000
atccggtgag aatggcaaga gcttgtgcat ttctttccag acttgttcaa caggccagcc   9060
attacgctcg tcatcaaaat cactcgcatc aaccaaaccg ttattcatgc gtgattgcgc   9120
ctgagcaaga cgaaatacac gatcgctgtt aaaaggacaa ttacaaacag gaatcgaatg   9180
taaccggcgc aggaacacgg ccagcgcatc aacaatattt tcacctgaat caggatattc   9240
ttctaatacc tggaaggctg ttttcccagg aatcgcggtg gtgagtaacc acgcatcatc   9300
aggagtacgg ataaaatgct tgatggtcgg gagaggcata aactccgtca gccagttgag   9360
acggaccatc tcatctgtaa catcattggc aacgctacct ttgccatgtt tcagaaacaa   9420
ctctggcgca tcgggcttcc catacaagcg atagattgtc gcacctgatt gcccgacatt   9480
atcgcgagcc catttatacc catataaatc agcgtccatg ttggagttta agcgcggacg   9540
```

```
ggagcaagac gtttcccgtt gaatatggct cataacaccc cttgtattac tgtttatgta   9600
agcagacagt tttattgttc atgatgatat atttttatct tgtgcaatgt aacatcagag   9660
attttgagac acaacgtggc tttgttgaat aaatcgaact tttgctgagt tgaaggatca   9720
gctctagtaa aataataaaa aagccggatt aataatctgg ctttttatat tctctctcta   9780
gtatataaac gcagaaaggc ccacccgaag gtgagccagt gtgacggcac atttccccga   9840
aaagtgccac ctaaattgta agcgttaata ttttgttaaa attcgcgtta aatttttgtt   9900
aaatcagctc attttttaac caataggccg aaatcggcaa aatcccttat aaatcaaaag   9960
aatagaccga gatagggttg agtgttgttc cagtttggaa caagagtcca ctattaaaga  10020
acgtggactc caacgtcaaa gggcgaaaaa ccgtctatca gggcgatggc ccactacgtg  10080
aaccatcacc ctaatcaagt tttttggggt cgaggtgccg taaagcacta aatcggaacc  10140
ctaaagggag cccccgattt agagcttgac ggggaaagcc ggcgaacgtg gcgagaaagg  10200
aagggaagaa agcgaaagga gcgggcgcta gggcgctggc aagtgtagcg gtcacgctgc  10260
gcgtaaccac cacacccgcc gcgcttaatg cgccgctaca gggcgcgtcc cattcgccat  10320
tcaggctgcg caactgttgg gaagggcgat cggtgcgggc ctcttcgcta ttacgccagc  10380
tggcgaaagg gggatgtgct gcaaggcgat taagttgggt aacgccaggg ttttcccagt  10440
cacgacgttg taaaacgacg gccagtgagc gcgcggcgaa ttgggtaccg ggcccc      10497
```

```
<210> SEQ ID NO 16
<211> LENGTH: 10495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

cctcgagggc tagccattct atttaatctc cctatcagtg atagagatcg cccgagtgag     60
cacgcagggt ctccattttg atccctatca gtgatagaga agcgggaggt ttgaacgcgc    120
agccgccatg ccggggtttt acgagattgt gattaaggtc cccagcgacc ttgacgagca    180
tctgcccggc atttctgaca gctttgtgaa ctgggtggcc gagaaggaat gggagttgcc    240
gccagattct gacatggatc tgaatctgat tgagcaggca cccctgaccg tggccgagaa    300
gctgcagcgc gactttctga cggaatggcg ccgtgtgagt aaggccccgg aggctctttt    360
ctttgtgcaa tttgagaagg gagagagcta cttccacatg cacgtgctcg tggaaaccac    420
cggggtgaaa tccatggttt tgggacgttt cctgagtcag attcgcgaaa aactgattca    480
gagaatttac cgcgggatcg agccgacttt gccaaactgg ttcgcggtca caaagaccag    540
aaatggcgcc ggaggcggga acaaggtggt ggatgagtgc tacatcccca attacttgct    600
ccccaaaacc cagcctgagc tccaatgggc atggaccaac atggaacagt acctcagcgc    660
ctgtttgaat ctcacggagc gtaaacggtt ggtggcgcag catctgacgc acgtgtcgca    720
gacgcaggag cagaacaaag agaatcagaa tcccaattct gatgcgccgg tgatcagatc    780
aaaaacttca gccaggtaca tggagctggt cgggtggctc gtggacaagg ggattacctc    840
ggagaagcag tggatccagg aggaccaggc ctcatacatc tccttcaatg cggcctccaa    900
ctcgcggtcc caaatcaagg ctgccttgga caatgcggga aagattatga gcctgactaa    960
aaccgccccc gactacctgg tgggccagca gcccgtggag gacatttcca gcaatcggat   1020
ttataaaatt ttggaactaa acgggtacga tccccaatat gcggcttccg tctttctggg   1080
```

-continued

```
atgggccacg aaaaagttcg gcaagaggaa caccatctgg ctgtttgggc ctgcaactac   1140
cgggaagacc aacatcgcgg aggccatagc ccacactgtg cccttctacg ggtgcgtaaa   1200
ctggaccaat gagaactttc ccttcaacga ctgtgtcgac aagatggtga tctggtggga   1260
ggaggggaag atgaccgcca aggtcgtgga gtcggccaaa gccattctcg gaggaagcaa   1320
ggtgcgcgtg gaccagaaat gcaagtcctc ggcccagata gacccgactc ccgtgatcgt   1380
cacctccaac accaacatgt gcgccgtgat tgacgggaac tcaacgacct tcgaacacca   1440
gcagccgttg caagaccgga tgttcaaatt tgaactcacc cgccgtctgg atcatgactt   1500
tgggaaggtc accaagcagg aagtcaaaga ctttttccgg tgggcaaagg atcacgtggt   1560
tgaggtggag catgaattct acgtcaaaaa gggtggagcc aagaaaagac ccgcccccag   1620
tgacgcagat ataagtgagc ccaaacgggt gcgcgagtca gttgcgcagc catcgacgtc   1680
agacgcggaa gcttcgatca actacgcaga caggtaccaa aacaaatgtt ctcgtcacgt   1740
gggcatgaat ctgatgctgt ttccctgcag acaatgcgag agaatgaatc agaattcaaa   1800
tatctgcttc actcacggac agaaagactg tttagagtgc tttcccgtgt cagaatctca   1860
acccgtttct gtcgtcaaaa aggcgtatca gaaactgtgc tacattcatc atatcatggg   1920
aaaggtgcca gacgcttgca ctgcctgcga tctggtcaat gtggatttgg atgactgcat   1980
ctttgaacaa taaatgattt aaatcaggta tggctgccga tggttatctt ccagattggc   2040
tcgaggacaa cctctctgag ggcattcgcg agtggtggga cttgaaacct ggagccccga   2100
aacccaaagc caaccagcaa aagcaggacg acggccgggg tctggtgctt cctggctaca   2160
agtacctcgg acccttcaac ggactcgaca agggggagcc cgtcaacgcg gcggacgcag   2220
cggccctcga gcacgacaag gcctacgacc agcagctcaa agcgggtgac aatccgtacc   2280
tgcggtataa ccacgccgac gccgagtttc aggagcgtct gcaagaagat acgtcttttg   2340
ggggcaacct cgggcgagca gtcttccagg ccaagaagcg ggttctcgaa cctctcggtc   2400
tggttgagga aggcgctaag acggctcctg gaaagaagag accggtagag caatcacccc   2460
aggaaccaga ctcctcttcg ggcatcggca agaaaggcca gcagcccgcg agaaagagac   2520
tcaactttgg gcagactggc gactcagagt cagtgcccga ccctcaacca ctcggagaac   2580
cccccgcagc cccctctggt gtgggatcta atacaatggc tgcaggcggt ggcgctccaa   2640
tggcagacaa taacgaaggc gccgacggag tgggtaacgc ctcaggaaat tggcattgcg   2700
attccacatg gctgggcgac agagtcatca ccaccagcac ccgaacctgg gccctcccca   2760
cctacaacaa ccacctctac aagcaaatct ccagccaatc gggaggcagc accaacgaca   2820
acacctactt cggctacagc accccctggg ggtattttga ctttaacaga ttccactgcc   2880
acttctcacc acgtgactgg cagcgactca tcaacaacaa ctggggattc cggcccaaga   2940
agctcaactt caagctcttc aacatccagg tcaaggaggt cacgacgaat gatggcacca   3000
cgaccatcgc caataacctt accagcacgg ttcaggtctt tacggactcg gaataccagc   3060
tcccgtacgt cctcggctct gcgcaccagg gctgcctgcc tccgttcccg gcggacgtct   3120
tcatgattcc tcagtacggg tacctgactc tgaacaatgg cagtcaggcc gtgggccgtt   3180
cctccttcta ctgcctggaa tactttcctt ctcaaatgct gagaacgggc aacaactttc   3240
agttcagcta cacgtttgag gacgtgcctt ttcacagcag ctacgcgcac agccaaagcc   3300
tggaccggct gatgaacccc ctcatcgacc agtacctgta ctacctgtct cggactcaga   3360
ccacgagtgg taccgcagga aatcggacgt tgcaattttc tcaggccggg cctagtagca   3420
```

-continued

```
tggcgaatca ggccaaaaac tggctacccg ggccctgcta ccggcagcaa cgcgtctcca   3480
agacaaccaa tcaaaataac aacagcaact ttgcctggac cggtgccacc aagtatcatc   3540
tgaatggcag agactctctg gtaaatcccg gtcccgctat ggcaacccac aaggacgacg   3600
aagacaaatt ttttccgatg agcggagtct taatatttgg gaaacaggga gctggaaata   3660
gcaacgtgga ccttgacaac gttatgataa ccaacgagga agaaattaaa accaccaacc   3720
cagtggccac agaagagtac ggcacggtgg ccactaacct gcaatcggcc aacaccgctc   3780
ctgctacagg gaccgtcaac agtcaaggag ccttacctgg catggtctgg caggaccggg   3840
acgtgtacct gcagggtcct atctgggcca agattcctca cacggacgga cactttcatc   3900
cctcgccgct gatgggaggc tttggactga aacacccgcc tcctcagatc ctgattaaga   3960
atacacctgt tcccgcgaat cctccaacta ccttcagtcc agctaagttt gcgtcgttca   4020
tcacgcagta cagcaccgga caggtcagcg tggaaattga atgggagctg cagaaagaaa   4080
acagcaaacg ctggaaccca gagattcaat acacttccaa ctacaacaaa tctacaaatg   4140
tggactttgc tgttgacaca aatggcgttt attctgagcc tcgccccatc ggcacccgtt   4200
acctcacccg taatctgtaa actagtttgc ttgttaatca ataaaccgtt taattcgttt   4260
cagttgaact ttggtctctg cgtatttctt tcttatctag tttccatgct ctagaggtcc   4320
tgtattagag gtcacgtgag tgttttgcga cattttgcga caccatgtgg tcacgctggg   4380
tatttaagcc cgagtgagca cgcagggtct ccattttgaa gcgggaggtt tgaacgcgca   4440
gccgccaagc cgaattctgc agatatcggg gttggggttg cgccttttcc aaggcagccc   4500
tgggtttgcg cagggacgcg gctgctctgg gcgtggttcc gggaaacgca gcggcgccga   4560
ccctgggtct cgcacattct tcacgtccgt tcgcagcgtc acccggatct tcgccgctac   4620
ccttgtgggc cccccggcga cgcttcctgc tccgccccta agtcgggaag gttccttgcg   4680
gttcgcggcg tgccggacgt gacaaacgga agccgcacgt ctcactagta ccctcgcaga   4740
cggacagcgc cagggagcaa tggcagcgcg ccgaccgcga tgggctgtgg ccaatagcgg   4800
ctgctcagca gggcgcgccg agagcagcgg ccgggaaggg gcggtgcggg aggcggggtg   4860
tggggcggta gtgtgggccc tgttcctgcc cgcgcggtgt tccgcattct gcaagcctcc   4920
ggagcgcacg tcggcagtcg gctccctcgt tgaccgaatc accgacctct ctccccagaa   4980
gctcccggga gcttgtatat ccattttcgg atctgatcag cacgtgttga caattaatca   5040
tcggcatagt atatcggcat agtataatac gacaaggtga ggaacgccac catggccaag   5100
cctttgtctc aagaagaatc caccctcatt gaaagagcaa cggctacaat caacagcatc   5160
cccatctctg aagactacag cgtcgccagc gcagctctct ctagcgacgg ccgcatcttc   5220
actggtgtca atgtatatca ttttactggg ggaccttgtg cagaactcgt ggtgctgggc   5280
actgctgctg ctgcggcagc tggcaacctg acttgtatcg tcgcgatcgg aaatgagaac   5340
aggggcatct tgagcccctg cggacggtgc cgacaggtgc ttctcgatct gcatcctggg   5400
atcaaagcca tagtgaagga cagtgatgga cagccgacgg cagttgggat tcgtgaattg   5460
ctgccctctg gttatgtgtg ggagggctaa gcacttcgtg gccgaggagc aggactgaca   5520
cgtgctacga gatttcgatt ccaccgccgc cttctatgaa aggttgggct tcggaatcgt   5580
tttccgggac gccggctgga tgatcctcca gcgcggggat ctcatgctgg agttcttcgc   5640
ccaccccaac ttgtttattg cagcttataa tggttacaaa taaagcaata gcatcacaaa   5700
tttcacaaat aaagcatttt tttcactgca ttctagttgt ggtttgtcca aactcatcaa   5760
tgtatcttag cgctcactgc ccgctttcca gtcgggaaac ctgtcgtgcc agctgcatta   5820
```

atgaatcggc caacgcgcgg ggagaggcgg tttgcgtatt gggcgctctc ctaggccaga 5880
aatggcgccg gaggcgggaa caaggtggtg gatgagtgct acatccccaa ttacttgctc 5940
cccaaaaccc agcctgagct ccagtgggcg tggactaata tggaacagta tttaagcgcc 6000
tgtccctatc agtgatagag atctccctat cagtgataga gatttgaatc tcacggagcg 6060
taaacggttg gtggcgcagc atctgtttaa acgcagacgc aggagcagaa caaagagaat 6120
cagaatccca attctgatgc gccggtgatc agatcaaaaa cttcagccag gtacatggag 6180
ctggtcgggt ggctcgtgga caaggggatt acctcggaga agcagtggat tcaggaggac 6240
caggcctcat acatctcctt caatgcggcc tccaactcgc ggtcccaaat caaggctgcc 6300
ttggacaatg cgggaaagat tatgagcctg actaaaaccg cccccgacta cctggtgggc 6360
cagcagcccg tggaggacat ttccagcaat cggatttata aaattttgga actaaacggg 6420
tacgatcccc aatatgcggc ttccgtcttt ctgggatggg ccacgaaaaa gttcggcaag 6480
aggaacacca tctggctgtt tgggcctgca actaccggga agaccaacat cgcggaggcc 6540
atagcccaca ctgtgccctt ctacgggtgc gtaaactgga ccaatgagaa ctttcccttc 6600
aacgactgtg tcgacaagat ggtgatctgg tgggaggagg ggaagatgac cgccaaggtc 6660
gtggagtcgg ccaaagccat tctcggagga agcaaggtgc gcgtggacca gaaatgcaag 6720
tcctcggccc agatagaccc gactcccgtg atcgtcacct ccaacaccaa catgtgcgcc 6780
gtgattgacg ggaactcaac gaccttcgaa caccagcagc cgttgcaaga ccggatgttc 6840
aaatttgaac tcacccgccg tctggatcat gactttggga aggtcaccaa gcaggaagtc 6900
aaagactttt tccggtgggc aaaggatcac gtggttgagg tggagcatga attctacgtc 6960
aaaaagggtg gagccaagaa aagacccgcc cccagtgacg cagatataag tgagcccaaa 7020
cgggtgcgcg agtcagttgc gcagccatcg acgtcagacg cggaagcttc gatcaactac 7080
gcagacaggt accaaaacaa atgttctcgt cacgtgggca tgaatctgat gctgtttccc 7140
tgcagacaat gcgagagaat gaatcagaat tcaaatatct gcttcactca cggacagaaa 7200
gactgtttag agtgctttcc cgtgtcagaa tctcaacccg tttctgtcgt caaaaaggcg 7260
tatcagaaac tgtgctacat tcatcatatc atgggaaagg tgccagacgc ttgcactgcc 7320
tgcgatctgg tcaatgtgga tttggatgac tgcatctttg aacaataaac tagtttgctt 7380
gttaatcaat aaaccgttta attcgtttca gttgaacttt ggtctctgcg tatttctttc 7440
ttatctagtt tccatgctct agagtatacg atatccatca cactggcggc cgctcgacta 7500
gagcggccgc caccgcggtg gagctccagc ttttgttcgc gcgcttggcg taatcatggt 7560
catagctgtt tcctgtgtga aattccacag cctggggtgc ctaattgcgt tgcgctcact 7620
gcccgctttc cagtcgggaa acctgtcgtg ccagctgcat taatgaatcg gccaacgcgc 7680
ggggagaggc ggtttgcgta ttgggcgctc ttccgcttcc tcgctcactg actcgctgcg 7740
ctcggtcgtt cggctgcggc gagcggtatc agctcactca aaggcggtaa tacggttatc 7800
cacagaatca ggggataacg caggaaagaa catgtgagca aaaggccagc aaaaggccag 7860
gaaccgtaaa aaggccgcgt tgctggcgtt tttccatagg ctccgccccc ctgacgagca 7920
tcacaaaaat cgacgctcaa gtcagaggtg gcgaaacccg acaggactat aaagatacca 7980
ggcgtttccc cctggaagct ccctcgtgcg ctctcctgtt ccgaccctgc cgcttaccgg 8040
atacctgtcc gcctttctcc cttcgggaag cgtggcgctt tctcatagct cacgctgtag 8100
gtatctcagt tcggtgtagg tcgttcgctc caagctgggc tgtgtgcacg aaccccccgt 8160

-continued

```
tcagcccgac cgctgcgcct tatccggtaa ctatcgtctt gagtccaacc cggtaagaca   8220
cgacttatcg ccactggcag cagccactgg taacaggatt agcagagcga ggtatgtagg   8280
cggtgctaca gagttcttga agtggtggcc taactacggc tacactagaa gaacagtatt   8340
tggtatctgc gctctgctga agccagttac cttcggaaaa agagttggta gctcttgatc   8400
cggcaaacaa accaccgctg gtagcggtgg tttttttgtt tgcaagcagc agattacgcg   8460
cagaaaaaaa ggatctcaag aagatccttt gatcttttct acggggtctg acgctcagtg   8520
gaacgaaaac tcacgttaag ggattttggt catgagatta tcaaaaagga tcttcaccta   8580
gatcctttta aattaaaaat gaagttttaa atcaatctaa agtatatatg agtaaacttg   8640
gtctgacaga aataataaaa aagccggatt aataatctgg ctttttatat tctctctcta   8700
gtatataaac gcagaaaggc ccacccgaag gtgagccagt gtgactctag tattattaga   8760
aaaactcatc gagcatcaaa tgaaactgca atttattcat atcaggatta tcaataccat   8820
atttttgaaa aagccgtttc tgtaatgaag gagaaaactc accgaggcag ttccaaagaa   8880
tggcaaggtc ctggtaacgg tctgcgattc cgacccgtcc aacatcaata caacctatta   8940
atttcccctc gtcaaaaata aggttatcaa gtgagaaatc accatgagtg acgactgaat   9000
ccggtgagaa tggcaagagc ttgtgcattt ctttccagac ttgttcaaca ggccagccat   9060
tacgctcgtc atcaaaatca ctcgcatcaa ccaaaccgtt attcatgcgt gattgcgcct   9120
gagcaagacg aaatacacga tcgctgttaa aaggacaatt acaaacagga atcgaatgta   9180
accggcgcag gaacacggcc agcgcatcaa caatattttc acctgaatca ggatattctt   9240
ctaatacctg gaaggctgtt ttcccaggaa tcgcggtggt gagtaaccac gcatcatcag   9300
gagtacggat aaaatgcttg atggtcggga gaggcataaa ctccgtcagc cagttgagac   9360
ggaccatctc atctgtaaca tcattggcaa cgctaccttt gccatgtttc agaaacaact   9420
ctggcgcatc gggcttccca tacaagcgat agattgtcgc acctgattgc ccgacattat   9480
cgcgagccca tttataccca tataaatcag cgtccatgtt ggagtttaag cgcggacggg   9540
agcaagacgt ttcccgttga atatggctca taacacccct tgtattactg tttatgtaag   9600
cagacagttt tattgttcat gatgatatat ttttatcttg tgcaatgtaa catcagagat   9660
tttgagacac aacgtggctt tgttgaataa atcgaacttt tgctgagttg aaggatcagc   9720
tctagtaaaa taataaaaaa gccggattaa taatctggct ttttatattc tctctctagt   9780
atataaacgc agaaaggccc acccgaaggt gagccagtgt gacggcacat ttccccgaaa   9840
agtgccacct aaattgtaag cgttaatatt ttgttaaaat tcgcgttaaa tttttgttaa   9900
atcagctcat tttttaacca ataggccgaa atcggcaaaa tcccttataa atcaaaagaa   9960
tagaccgaga tagggttgag tgttgttcca gtttggaaca agagtccact attaaagaac  10020
gtggactcca acgtcaaagg gcgaaaaacc gtctatcagg gcgatggccc actacgtgaa  10080
ccatcaccct aatcaagttt tttggggtcg aggtgccgta aagcactaaa tcggaaccct  10140
aaagggagcc cccgatttag agcttgacgg ggaaagccgg cgaacgtggc gagaaaggaa  10200
gggaagaaag cgaaaggagc gggcgctagg gcgctggcaa gtgtagcggt cacgctgcgc  10260
gtaaccacca cacccgccgc gcttaatgcg ccgctacagg gcgcgtccca ttcgccattc  10320
aggctgcgca actgttggga agggcgatcg gtgcgggcct cttcgctatt acgccagctg  10380
gcgaaagggg gatgtgctgc aaggcgatta agttgggtaa cgccagggtt ttcccagtca  10440
cgacgttgta aaacgacggc cagtgagcgc gcggcgaatt gggtaccggg ccccc       10495
```

<210> SEQ ID NO 17
<211> LENGTH: 10493
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
cctcgagggc tagccattct ccctatcagt gatagagatc tatttaagcc cgagtgagca 60
cgcagtccct atcagtgata gagaggtctc cattttgaag cgggaggttt gaacgcgcag 120
ccgccatgcc ggggttttac gagattgtga ttaaggtccc cagcgacctt gacgagcatc 180
tgcccggcat ttctgacagc tttgtgaact gggtggccga gaaggaatgg gagttgccgc 240
cagattctga catggatctg aatctgattg agcaggcacc cctgaccgtg gccgagaagc 300
tgcagcgcga ctttctgacg gaatggcgcc gtgtgagtaa ggccccggag gctcttttct 360
ttgtgcaatt tgagaaggga gagagctact tccacatgca cgtgctcgtg gaaaccaccg 420
gggtgaaatc catggttttg ggacgtttcc tgagtcagat tcgcgaaaaa ctgattcaga 480
gaatttaccg cgggatcgag ccgactttgc caaactggtt cgcggtcaca aagaccagaa 540
atggcgccgg aggcgggaac aaggtggtgg atgagtgcta catccccaat tacttgctcc 600
ccaaaaccca gcctgagctc caatgggcat ggaccaacat ggaacagtac ctcagcgcct 660
gtttgaatct cacggagcgt aaacggttgg tggcgcagca tctgacgcac gtgtcgcaga 720
cgcaggagca gaacaaagag aatcagaatc ccaattctga tgcgccggtg atcagatcaa 780
aaacttcagc caggtacatg gagctggtcg ggtggctcgt ggacaagggg attacctcgg 840
agaagcagtg gatccaggag gaccaggcct catacatctc cttcaatgcg gcctccaact 900
cgcggtccca aatcaaggct gccttggaca atgcgggaaa gattatgagc ctgactaaaa 960
ccgcccccga ctacctggtg ggccagcagc ccgtggagga catttccagc aatcggattt 1020
ataaaatttt ggaactaaac gggtacgatc cccaatatgc ggcttccgtc tttctgggat 1080
gggccacgaa aaagttcggc aagaggaaca ccatctggct gtttgggcct gcaactaccg 1140
ggaagaccaa catcgcggag gccatagccc acactgtgcc cttctacggg tgcgtaaact 1200
ggaccaatga gaactttccc ttcaacgact gtgtcgacaa gatggtgatc tggtgggagg 1260
aggggaagat gaccgccaag gtcgtggagt cggccaaagc cattctcgga ggaagcaagg 1320
tgcgcgtgga ccagaaatgc aagtcctcgg cccagataga cccgactccc gtgatcgtca 1380
cctccaacac caacatgtgc gccgtgattg acgggaactc aacgaccttc gaacaccagc 1440
agccgttgca agaccggatg ttcaaatttg aactcacccg ccgtctggat catgactttg 1500
ggaaggtcac caagcaggaa gtcaaagact tttccggtg ggcaaaggat cacgtggttg 1560
aggtggagca tgaattctac gtcaaaaagg gtggagccaa gaaaagaccc gcccccagtg 1620
acgcagatat aagtgagccc aaacgggtgc gcgagtcagt tgcgcagcca tcgacgtcag 1680
acgcggaagc ttcgatcaac tacgcagaca ggtaccaaaa caaatgttct cgtcacgtgg 1740
gcatgaatct gatgctgttt ccctgcagac aatgcgagag aatgaatcag aattcaaata 1800
tctgcttcac tcacggacag aaagactgtt tagagtgctt tcccgtgtca gaatctcaac 1860
ccgtttctgt cgtcaaaaag gcgtatcaga aactgtgcta cattcatcat atcatgggaa 1920
aggtgccaga cgcttgcact gcctgcgatc tggtcaatgt ggatttggat gactgcatct 1980
ttgaacaata aatgatttaa atcaggtatg gctgccgatg gttatcttcc agattggctc 2040
gaggacaacc tctctgaggg cattcgcgag tggtgggact tgaaacctgg agccccgaaa 2100

```
cccaaagcca accagcaaaa gcaggacgac ggccggggtc tggtgcttcc tggctacaag   2160
tacctcggac ccttcaacgg actcgacaag ggggagcccg tcaacgcggc ggacgcagcg   2220
gccctcgagc acgacaaggc ctacgaccag cagctcaaag cgggtgacaa tccgtacctg   2280
cggtataacc acgccgacgc cgagtttcag gagcgtctgc aagaagatac gtcttttggg   2340
ggcaacctcg ggcgagcagt cttccaggcc aagaagcggg ttctcgaacc tctcggtctg   2400
gttgaggaag gcgctaagac ggctcctgga aagaagagac cggtagagca atcaccccag   2460
gaaccagact cctcttcggg catcggcaag aaaggccagc agcccgcgag aaagagactc   2520
aactttgggc agactggcga ctcagagtca gtgcccgacc ctcaaccact cggagaaccc   2580
cccgcagccc cctctggtgt gggatctaat acaatggctg caggcggtgg cgctccaatg   2640
gcagacaata acgaaggcgc cgacggagtg ggtaacgcct caggaaattg gcattgcgat   2700
tccacatggc tgggcgacag agtcatcacc accagcaccc gaacctgggc cctccccacc   2760
tacaacaacc acctctacaa gcaaatctcc agccaatcgg gaggcagcac caacgacaac   2820
acctacttcg gctacagcac cccctggggg tattttgact ttaacagatt ccactgccac   2880
ttctcaccac gtgactggca gcgactcatc aacaacaact ggggattccg gcccaagaag   2940
ctcaacttca agctcttcaa catccaggtc aaggaggtca cgacgaatga tggcaccacg   3000
accatcgcca ataaccttac cagcacggtt caggtcttta cggactcgga ataccagctc   3060
ccgtacgtcc tcggctctgc gcaccagggc tgcctgcctc cgttcccggc ggacgtcttc   3120
atgattcctc agtacgggta cctgactctg aacaatggca gtcaggccgt gggccgttcc   3180
tccttctact gcctggaata ctttccttct caaatgctga gaacgggcaa caactttcag   3240
ttcagctaca cgtttgagga cgtgcctttt cacagcagct acgcgcacag ccaaagcctg   3300
gaccggctga tgaacccccct catcgaccag tacctgtact acctgtctcg gactcagacc   3360
acgagtggta ccgcaggaaa tcggacgttg caattttctc aggccgggcc tagtagcatg   3420
gcgaatcagg ccaaaaactg gctacccggg ccctgctacc ggcagcaacg cgtctccaag   3480
acaaccaatc aaaataacaa cagcaacttt gcctggaccg gtgccaccaa gtatcatctg   3540
aatggcagag actctctggt aaatcccggt cccgctatgg caacccacaa ggacgacgaa   3600
gacaaatttt ttccgatgag cggagtctta atatttggga aacagggagc tggaaatagc   3660
aacgtggacc ttgacaacgt tatgataacc aacgaggaag aaattaaaac caccaaccca   3720
gtggccacag aagagtacgg cacggtggcc actaacctgc aatcggccaa caccgctcct   3780
gctacaggga ccgtcaacag tcaaggagcc ttacctggca tggtctggca ggaccgggac   3840
gtgtacctgc agggtcctat ctgggccaag attcctcaca cggacggaca ctttcatccc   3900
tcgccgctga tgggaggctt tggactgaaa cacccgcctc ctcagatcct gattaagaat   3960
acacctgttc ccgcgaatcc tccaactacc ttcagtccag ctaagtttgc gtcgttcatc   4020
acgcagtaca gcaccggaca ggtcagcgtg gaaattgaat gggagctgca gaaagaaaac   4080
agcaaacgct ggaacccaga gattcaatac acttccaact acaacaaatc tacaaatgtg   4140
gactttgctg ttgacacaaa tggcgtttat tctgagcctc gccccatcgg cacccgttac   4200
ctcacccgta atctgtaaac tagtttgctt gttaatcaat aaaccgttta attcgtttca   4260
gttgaacttt ggtctctgcg tatttctttc ttatctagtt tccatgctct agaggtcctg   4320
tattagaggt cacgtgagtg ttttgcgaca ttttgcgaca ccatgtggtc acgctgggta   4380
tttaagcccg agtgagcacg cagggtctcc attttgaagc gggaggtttg aacgcgcagc   4440
```

-continued cgccaagccg aattctgcag atatcggggt tggggttgcg ccttttccaa ggcagccctg 4500
ggtttgcgca gggacgcggc tgctctgggc gtggttccgg gaaacgcagc ggcgccgacc 4560
ctgggtctcg cacattcttc acgtccgttc gcagcgtcac ccggatcttc gccgctaccc 4620
ttgtgggccc cccggcgacg cttcctgctc cgcccctaag tcgggaaggt tccttgcggt 4680
tcgcggcgtg ccggacgtga caaacggaag ccgcacgtct cactagtacc ctcgcagacg 4740
gacagcgcca gggagcaatg gcagcgcgcc gaccgcgatg ggctgtggcc aatagcggct 4800
gctcagcagg gcgcgccgag agcagcggcc gggaaggggc ggtgcgggag gcggggtgtg 4860
gggcggtagt gtgggccctg ttcctgcccg cgcggtgttc cgcattctgc aagcctccgg 4920
agcgcacgtc ggcagtcggc tccctcgttg accgaatcac cgacctctct ccccagaagc 4980
tcccgggagc ttgtatatcc attttcggat ctgatcagca cgtgttgaca attaatcatc 5040
ggcatagtat atcggcatag tataatacga caaggtgagg aacgccacca tggccaagcc 5100
tttgtctcaa gaagaatcca ccctcattga aagagcaacg gctacaatca acagcatccc 5160
catctctgaa gactacagcg tcgccagcgc agctctctct agcgacggcc gcatcttcac 5220
tggtgtcaat gtatatcatt ttactggggg accttgtgca gaactcgtgg tgctgggcac 5280
tgctgctgct gcggcagctg gcaacctgac ttgtatcgtc gcgatcggaa atgagaacag 5340
gggcatcttg agcccctgcg gacggtgccg acaggtgctt ctcgatctgc atcctgggat 5400
caaagccata gtgaaggaca gtgatggaca gccgacggca gttgggattc gtgaattgct 5460
gccctctggt tatgtgtggg agggctaagc acttcgtggc cgaggagcag gactgacacg 5520
tgctacgaga tttcgattcc accgccgcct tctatgaaag gttgggcttc ggaatcgttt 5580
tccgggacgc cggctggatg atcctccagc gcggggatct catgctggag ttcttcgccc 5640
accccaactt gtttattgca gcttataatg gttacaaata aagcaatagc atcacaaatt 5700
tcacaaataa agcatttttt tcactgcatt ctagttgtgg tttgtccaaa ctcatcaatg 5760
tatcttagcg ctcactgccc gctttccagt cgggaaacct gtcgtgccag ctgcattaat 5820
gaatcggcca acgcgcgggg agaggcggtt tgcgtattgg gcgctctcct aggccagaaa 5880
tggcgccgga ggcgggaaca aggtggtgga tgagtgctac atccccaatt acttgctccc 5940
caaaacccag cctgagctcc agtgggcgtg gactaatatg gaacagtatt taagcgcctg 6000
tccctatcag tgatagagat ctccctatca gtgatagaga tttgaatctc acggagcgta 6060
aacggttggt ggcgcagcat ctgtttaaac gcagacgcag gagcagaaca aagagaatca 6120
gaatcccaat tctgatgcgc cggtgatcag atcaaaaact tcagccaggt acatggagct 6180
ggtcgggtgg ctcgtggaca aggggattac ctcggagaag cagtggattc aggaggacca 6240
ggcctcatac atctccttca atgcggcctc caactcgcgg tcccaaatca aggctgcctt 6300
ggacaatgcg ggaaagatta tgagcctgac taaaaccgcc cccgactacc tggtgggcca 6360
gcagcccgtg gaggacattt ccagcaatcg gatttataaa attttggaac taaacgggta 6420
cgatccccaa tatgcggctt ccgtctttct gggatgggcc acgaaaaagt tcggcaagag 6480
gaacaccatc tggctgtttg ggcctgcaac taccgggaag accaacatcg cggaggccat 6540
agcccacact gtgcccttct acgggtgcgt aaactggacc aatgagaact ttcccttcaa 6600
cgactgtgtc gacaagatgg tgatctggtg ggaggagggg aagatgaccg ccaaggtcgt 6660
ggagtcggcc aaagccattc tcggaggaag caaggtgcgc gtggaccaga aatgcaagtc 6720
ctcggcccag atagacccga ctcccgtgat cgtcacctcc aacaccaaca tgtgcgccgt 6780
gattgacggg aactcaacga ccttcgaaca ccagcagccg ttgcaagacc ggatgttcaa 6840

-continued

```
atttgaactc acccgccgtc tggatcatga ctttgggaag gtcaccaagc aggaagtcaa   6900
agactttttc cggtgggcaa aggatcacgt ggttgaggtg gagcatgaat tctacgtcaa   6960
aaagggtgga gccaagaaaa gacccgcccc cagtgacgca gatataagtg agcccaaacg   7020
ggtgcgcgag tcagttgcgc agccatcgac gtcagacgcg gaagcttcga tcaactacgc   7080
agacaggtac caaaacaaat gttctcgtca cgtgggcatg aatctgatgc tgtttccctg   7140
cagacaatgc gagagaatga atcagaattc aaatatctgc ttcactcacg gacagaaaga   7200
ctgtttagag tgctttcccg tgtcagaatc tcaacccgtt tctgtcgtca aaaaggcgta   7260
tcagaaactg tgctacattc atcatatcat gggaaaggtg ccagacgctt gcactgcctg   7320
cgatctggtc aatgtggatt tggatgactg catctttgaa caataaacta gtttgcttgt   7380
taatcaataa accgtttaat tcgtttcagt tgaactttgg tctctgcgta tttctttctt   7440
atctagtttc catgctctag agtatacgat atccatcaca ctggcggccg ctcgactaga   7500
gcggccgcca ccgcggtgga gctccagctt ttgttcgcgc gcttggcgta atcatggtca   7560
tagctgtttc ctgtgtgaaa ttccacagcc tggggtgcct aattgcgttg cgctcactgc   7620
ccgctttcca gtcgggaaac ctgtcgtgcc agctgcatta atgaatcggc caacgcgcgg   7680
ggagaggcgg tttgcgtatt gggcgctctt ccgcttcctc gctcactgac tcgctgcgct   7740
cggtcgttcg gctgcggcga gcggtatcag ctcactcaaa ggcggtaata cggttatcca   7800
cagaatcagg ggataacgca ggaaagaaca tgtgagcaaa aggccagcaa aaggccagga   7860
accgtaaaaa ggccgcgttg ctggcgtttt tccataggct ccgcccccct gacgagcatc   7920
acaaaaatcg acgctcaagt cagaggtggc gaaacccgac aggactataa agataccagg   7980
cgtttccccc tggaagctcc ctcgtgcgct ctcctgttcc gaccctgccg cttaccggat   8040
acctgtccgc ctttctccct tcgggaagcg tggcgctttc tcatagctca cgctgtaggt   8100
atctcagttc ggtgtaggtc gttcgctcca agctgggctg tgtgcacgaa ccccccgttc   8160
agcccgaccg ctgcgcctta tccggtaact atcgtcttga gtccaacccg gtaagacacg   8220
acttatcgcc actggcagca gccactggta acaggattag cagagcgagg tatgtaggcg   8280
gtgctacaga gttcttgaag tggtggccta actacggcta cactagaaga acagtatttg   8340
gtatctgcgc tctgctgaag ccagttacct tcggaaaaag agttggtagc tcttgatccg   8400
gcaaacaaac caccgctggt agcggtggtt tttttgtttg caagcagcag attacgcgca   8460
gaaaaaaagg atctcaagaa gatcctttga tcttttctac ggggtctgac gctcagtgga   8520
acgaaaactc acgttaaggg attttggtca tgagattatc aaaaaggatc ttcacctaga   8580
tccttttaaa ttaaaaatga agttttaaat caatctaaag tatatatgag taaacttggt   8640
ctgacagaaa taataaaaaa gccggattaa taatctggct tttatattc tctctctagt   8700
atataaacgc agaaaggccc acccgaaggt gagccagtgt gactctagta ttattagaaa   8760
aactcatcga gcatcaaatg aaactgcaat ttattcatat caggattatc aataccatat   8820
ttttgaaaaa gccgtttctg taatgaagga gaaaactcac cgaggcagtt ccaaagaatg   8880
gcaaggtcct ggtaacggtc tgcgattccg acccgtccaa catcaataca acctattaat   8940
ttcccctcgt caaaaataag gttatcaagt gagaaatcac catgagtgac gactgaatcc   9000
ggtgagaatg gcaagagctt gtgcatttct ttccagactt gttcaacagg ccagccatta   9060
cgctcgtcat caaaatcact cgcatcaacc aaaccgttat tcatgcgtga ttgcgcctga   9120
gcaagacgaa atacacgatc gctgttaaaa ggacaattac aaacaggaat cgaatgtaac   9180
```

```
cggcgcagga acacggccag cgcatcaaca atattttcac ctgaatcagg atattcttct   9240

aatacctgga aggctgtttt cccaggaatc gcggtggtga gtaaccacgc atcatcagga   9300

gtacggataa aatgcttgat ggtcgggaga ggcataaact ccgtcagcca gttgagacgg   9360

accatctcat ctgtaacatc attggcaacg ctacctttgc catgtttcag aaacaactct   9420

ggcgcatcgg gcttcccata caagcgatag attgtcgcac ctgattgccc gacattatcg   9480

cgagcccatt tatacccata taaatcagcg tccatgttgg agtttaagcg cggacgggag   9540

caagacgttt cccgttgaat atggctcata acaccccttg tattactgtt tatgtaagca   9600

gacagtttta ttgttcatga tgatatattt ttatcttgtg caatgtaaca tcagagattt   9660

tgagacacaa cgtggctttg ttgaataaat cgaacttttg ctgagttgaa ggatcagctc   9720

tagtaaaata ataaaaaagc cggattaata atctggcttt ttatattctc tctctagtat   9780

ataaacgcag aaaggcccac ccgaaggtga gccagtgtga cggcacattt ccccgaaaag   9840

tgccacctaa attgtaagcg ttaatatttt gttaaaattc gcgttaaatt tttgttaaat   9900

cagctcattt tttaaccaat aggccgaaat cggcaaaatc ccttataaat caaaagaata   9960

gaccgagata gggttgagtg ttgttccagt ttggaacaag agtccactat taaagaacgt  10020

ggactccaac gtcaaagggc gaaaaaccgt ctatcagggc gatggcccac tacgtgaacc  10080

atcaccctaa tcaagttttt tggggtcgag gtgccgtaaa gcactaaatc ggaaccctaa  10140

agggagcccc cgatttagag cttgacgggg aaagccggcg aacgtggcga gaaaggaagg  10200

gaagaaagcg aaaggagcgg gcgctagggc gctggcaagt gtagcggtca cgctgcgcgt  10260

aaccaccaca cccgccgcgc ttaatgcgcc gctacagggc gcgtcccatt cgccattcag  10320

gctgcgcaac tgttgggaag ggcgatcggt gcgggcctct tcgctattac gccagctggc  10380

gaaaggggga tgtgctgcaa ggcgattaag ttgggtaacg ccagggtttt cccagtcacg  10440

acgttgtaaa acgacggcca gtgagcgcgc ggcgaattgg gtaccgggcc ccc         10493
```

<210> SEQ ID NO 18
<211> LENGTH: 10495
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
cctcgagggc tagccattct atttaatctc cctatcagtg atagagatct ccctatcagt     60

gatagagatc gcccgagtga gcacgcaggg tctccatttt gaagcgggag gtttgaacgc    120

gcagccgcca tgccggggtt ttacgagatt gtgattaagg tccccagcga ccttgacgag    180

catctgcccg gcatttctga cagctttgtg aactgggtgg ccgagaagga atgggagttg    240

ccgccagatt ctgacatgga tctgaatctg attgagcagg cacccctgac cgtggccgag    300

aagctgcagc gcgactttct gacggaatgg cgccgtgtga gtaaggcccc ggaggctctt    360

ttctttgtgc aatttgagaa gggagagagc tacttccaca tgcacgtgct cgtggaaacc    420

accggggtga aatccatggt tttgggacgt ttcctgagtc agattcgcga aaaactgatt    480

cagagaattt accgcgggat cgagccgact ttgccaaact ggttcgcggt cacaaagacc    540

agaaatggcg ccggaggcgg gaacaaggtg gtggatgagt gctacatccc caattacttg    600

ctccccaaaa cccagcctga gctccaatgg gcatggacca acatggaaca gtacctcagc    660

gcctgtttga atctcacgga gcgtaaacgg ttggtggcgc agcatctgac gcacgtgtcg    720
```

-continued cagacgcagg agcagaacaa agagaatcag aatcccaatt ctgatgcgcc ggtgatcaga 780
tcaaaaactt cagccaggta catggagctg gtcgggtggc tcgtggacaa ggggattacc 840
tcggagaagc agtggatcca ggaggaccag gcctcataca tctccttcaa tgcggcctcc 900
aactcgcggt cccaaatcaa ggctgccttg gacaatgcgg gaaagattat gagcctgact 960
aaaaccgccc ccgactacct ggtgggccag cagcccgtgg aggacatttc cagcaatcgg 1020
atttataaaa ttttggaact aaacgggtac gatccccaat atgcggcttc cgtctttctg 1080
ggatgggcca cgaaaaagtt cggcaagagg aacaccatct ggctgtttgg gcctgcaact 1140
accgggaaga ccaacatcgc ggaggccata gcccacactg tgcccttcta cgggtgcgta 1200
aactggacca atgagaactt tcccttcaac gactgtgtcg acaagatggt gatctggtgg 1260
gaggagggga agatgaccgc caaggtcgtg gagtcggcca aagccattct cggaggaagc 1320
aaggtgcgcg tggaccagaa atgcaagtcc tcggcccaga tagacccgac tcccgtgatc 1380
gtcacctcca acaccaacat gtgcgccgtg attgacggga actcaacgac cttcgaacac 1440
cagcagccgt tgcaagaccg gatgttcaaa tttgaactca cccgccgtct ggatcatgac 1500
tttgggaagg tcaccaagca ggaagtcaaa gactttttcc ggtgggcaaa ggatcacgtg 1560
gttgaggtgg agcatgaatt ctacgtcaaa aagggtggag ccaagaaaag acccgccccc 1620
agtgacgcag atataagtga gcccaaacgg gtgcgcgagt cagttgcgca gccatcgacg 1680
tcagacgcgg aagcttcgat caactacgca gacaggtacc aaaacaaatg ttctcgtcac 1740
gtgggcatga atctgatgct gtttccctgc agacaatgcg agagaatgaa tcagaattca 1800
aatatctgct tcactcacgg acagaaagac tgtttagagt gctttcccgt gtcagaatct 1860
caacccgttt ctgtcgtcaa aaaggcgtat cagaaactgt gctacattca tcatatcatg 1920
ggaaaggtgc cagacgcttg cactgcctgc gatctggtca atgtggattt ggatgactgc 1980
atctttgaac aataaatgat ttaaatcagg tatggctgcc gatggttatc ttccagattg 2040
gctcgaggac aacctctctg agggcattcg cgagtggtgg gacttgaaac ctggagcccc 2100
gaaacccaaa gccaaccagc aaaagcagga cgacggccgg ggtctggtgc ttcctggcta 2160
caagtacctc ggacccttca acggactcga caagggggag cccgtcaacg cggcggacgc 2220
agcggccctc gagcacgaca aggcctacga ccagcagctc aaagcgggtg acaatccgta 2280
cctgcggtat aaccacgccg acgccgagtt tcaggagcgt ctgcaagaag atacgtcttt 2340
tgggggcaac ctcgggcgag cagtcttcca ggccaagaag cgggttctcg aacctctcgg 2400
tctggttgag gaaggcgcta agacggctcc tggaaagaag agaccggtag agcaatcacc 2460
ccaggaacca gactcctctt cgggcatcgg caagaaaggc cagcagcccg cgagaaagag 2520
actcaacttt gggcagactg gcgactcaga gtcagtgccc gaccctcaac cactcggaga 2580 acccccgca gccccctctg gtgtgggatc taatacaatg gctgcaggcg gtggcgctcc 2640
aatggcagac aataacgaag gcgccgacgg agtgggtaac gcctcaggaa attggcattg 2700
cgattccaca tggctgggcg acagagtcat caccaccagc acccgaacct gggccctccc 2760
cacctacaac aaccacctct acaagcaaat ctccagccaa tcgggaggca gcaccaacga 2820
caacacctac ttcggctaca gcaccccctg ggggtatttt gactttaaca gattccactg 2880
ccacttctca ccacgtgact ggcagcgact catcaacaac aactggggat tccggcccaa 2940
gaagctcaac ttcaagctct tcaacatcca ggtcaaggag gtcacgacga atgatggcac 3000
cacgaccatc gccaataacc ttaccagcac ggttcaggtc tttacggact cggaatacca 3060
gctcccgtac gtcctcggct ctgcgcacca gggctgcctg cctccgttcc cggcggacgt 3120

-continued

```
cttcatgatt cctcagtacg ggtacctgac tctgaacaat ggcagtcagg ccgtgggccg   3180
ttcctccttc tactgcctgg aatactttcc ttctcaaatg ctgagaacgg gcaacaactt   3240
tcagttcagc tacacgtttg aggacgtgcc ttttcacagc agctacgcgc acagccaaag   3300
cctggaccgg ctgatgaacc ccctcatcga ccagtacctg tactacctgt ctcggactca   3360
gaccacgagt ggtaccgcag gaaatcggac gttgcaattt tctcaggccg ggcctagtag   3420
catggcgaat caggccaaaa actggctacc cgggccctgc taccggcagc aacgcgtctc   3480
caagacaacc aatcaaaata acaacagcaa ctttgcctgg accggtgcca ccaagtatca   3540
tctgaatggc agagactctc tggtaaatcc cggtcccgct atggcaaccc acaaggacga   3600
cgaagacaaa ttttttccga tgagcggagt cttaatattt gggaaacagg gagctggaaa   3660
tagcaacgtg gaccttgaca acgttatgat aaccaacgag gaagaaatta aaaccaccaa   3720
cccagtggcc acagaagagt acggcacggt ggccactaac ctgcaatcgg ccaacaccgc   3780
tcctgctaca gggaccgtca acagtcaagg agccttacct ggcatggtct ggcaggaccg   3840
ggacgtgtac ctgcagggtc ctatctgggc caagattcct cacacggacg gacactttca   3900
tccctcgccg ctgatgggag gctttggact gaaacacccg cctcctcaga tcctgattaa   3960
gaatacacct gttcccgcga atcctccaac taccttcagt ccagctaagt ttgcgtcgtt   4020
catcacgcag tacagcaccg gacaggtcag cgtggaaatt gaatgggagc tgcagaaaga   4080
aaacagcaaa cgctggaacc cagagattca atacacttcc aactacaaca aatctacaaa   4140
tgtggacttt gctgttgaca caaatggcgt ttattctgag cctcgcccca tcggcacccg   4200
ttacctcacc cgtaatctgt aaactagttt gcttgttaat caataaaccg tttaattcgt   4260
ttcagttgaa ctttggtctc tgcgtatttc tttcttatct agtttccatg ctctagaggt   4320
cctgtattag aggtcacgtg agtgttttgc gacattttgc gacaccatgt ggtcacgctg   4380
ggtatttaag cccgagtgag cacgcagggt ctccattttg aagcgggagg tttgaacgcg   4440
cagccgccaa gccgaattct gcagatatcg gggttggggt tgcgcctttt ccaaggcagc   4500
cctgggtttg cgcagggacg cggctgctct gggcgtggtt ccgggaaacg cagcggcgcc   4560
gaccctgggt ctcgcacatt cttcacgtcc gttcgcagcg tcacccggat cttcgccgct   4620
acccttgtgg gccccccggc gacgcttcct gctccgcccc taagtcggga aggttccttg   4680
cggttcgcgg cgtgccggac gtgacaaacg gaagccgcac gtctcactag taccctcgca   4740
gacggacagc gccagggagc aatggcagcg cgccgaccgc gatgggctgt ggccaatagc   4800
ggctgctcag cagggcgcgc cgagagcagc ggccgggaag ggcggtgcg ggaggcgggg    4860
tgtggggcgg tagtgtgggc cctgttcctg cccgcgcggt gttccgcatt ctgcaagcct   4920
ccggagcgca cgtcggcagt cggctccctc gttgaccgaa tcaccgacct ctctccccag   4980
aagctcccgg gagcttgtat atccattttc ggatctgatc agcacgtgtt gacaattaat   5040
catcggcata gtatatcggc atagtataat acgacaaggt gaggaacgcc accatggcca   5100
agcctttgtc tcaagaagaa tccaccctca ttgaaagagc aacggctaca atcaacagca   5160
tccccatctc tgaagactac agcgtcgcca gcgcagctct ctctagcgac ggccgcatct   5220
tcactggtgt caatgtatat cattttactg gggaccttgg tgcagaactc gtggtgctgg   5280
gcactgctgc tgctgcggca gctggcaacc tgacttgtat cgtcgcgatc ggaaatgaga   5340
acaggggcat cttgagcccc tgcggacggt gccgacaggt gcttctcgat ctgcatcctg   5400
ggatcaaagc catagtgaag gacagtgatg gacagccgac ggcagttggg attcgtgaat   5460
```

-continued

```
tgctgccctc tggttatgtg tgggagggct aagcacttcg tggccgagga gcaggactga   5520
cacgtgctac gagatttcga ttccaccgcc gccttctatg aaaggttggg cttcggaatc   5580
gttttccggg acgccggctg gatgatcctc cagcgcgggg atctcatgct ggagttcttc   5640
gcccacccca acttgtttat tgcagcttat aatggttaca aataaagcaa tagcatcaca   5700
aatttcacaa ataaagcatt tttttcactg cattctagtt gtggtttgtc caaactcatc   5760
aatgtatctt agcgctcact gcccgctttc cagtcgggaa acctgtcgtg ccagctgcat   5820
taatgaatcg gccaacgcgc ggggagaggc ggtttgcgta ttgggcgctc tcctaggcca   5880
gaaatggcgc cggaggcggg aacaaggtgg tggatgagtg ctacatcccc aattacttgc   5940
tccccaaaac ccagcctgag tccctatcag tgatagagac tccagtgggc gtggactaat   6000
atggaacagt atttaagcgc ctgtccctat cagtgataga gatttgaatc tcacggagcg   6060
taaacggttg gtggcgcagc atctgtttaa acgcagacgc aggagcagaa caaagagaat   6120
cagaatccca attctgatgc gccggtgatc agatcaaaaa cttcagccag gtacatggag   6180
ctggtcgggt ggctcgtgga caaggggatt acctcggaga agcagtggat tcaggaggac   6240
caggcctcat acatctcctt caatgcggcc tccaactcgc ggtcccaaat caaggctgcc   6300
ttggacaatg cgggaaagat tatgagcctg actaaaaccg cccccgacta cctggtgggc   6360
cagcagcccg tggaggacat ttccagcaat cggatttata aaattttgga actaaacggg   6420
tacgatcccc aatatgcggc ttccgtcttt ctgggatggg ccacgaaaaa gttcggcaag   6480
aggaacacca tctggctgtt tggccctgca actaccggga agaccaacat cgcggaggcc   6540
atagcccaca ctgtgccctt ctacgggtgc gtaaactgga ccaatgagaa ctttcccttc   6600
aacgactgtg tcgacaagat ggtgatctgg tgggaggagg ggaagatgac cgccaaggtc   6660
gtggagtcgg ccaaagccat tctcggagga agcaaggtgc gcgtggacca gaaatgcaag   6720
tcctcggccc agatagaccc gactcccgtg atcgtcacct ccaacaccaa catgtgcgcc   6780
gtgattgacg ggaactcaac gaccttcgaa caccagcagc cgttgcaaga ccggatgttc   6840
aaatttgaac tcacccgccg tctggatcat gactttggga aggtcaccaa gcaggaagtc   6900
aaagactttt tccggtgggc aaaggatcac gtggttgagg tggagcatga attctacgtc   6960
aaaaagggtg gagccaagaa aagacccgcc cccagtgacg cagatataag tgagcccaaa   7020
cgggtgcgcg agtcagttgc gcagccatcg acgtcagacg cggaagcttc gatcaactac   7080
gcagacaggt accaaaacaa atgttctcgt cacgtgggca tgaatctgat gctgtttccc   7140
tgcagacaat gcgagagaat gaatcagaat tcaaatatct gcttcactca cggacagaaa   7200
gactgtttag agtgctttcc cgtgtcagaa tctcaacccg tttctgtcgt caaaaaggcg   7260
tatcagaaac tgtgctacat tcatcatatc atgggaaagg tgccagacgc ttgcactgcc   7320
tgcgatctgg tcaatgtgga tttggatgac tgcatctttg aacaataaac tagtttgctt   7380
gttaatcaat aaaccgttta attcgtttca gttgaacttt ggtctctgcg tatttctttc   7440
ttatctagtt tccatgctct agagtatacg atatccatca cactggcggc cgctcgacta   7500
gagcggccgc caccgcggtg gagctccagc ttttgttcgc gcgcttggcg taatcatggt   7560
catagctgtt tcctgtgtga aattccacag cctggggtgc ctaattgcgt tgcgctcact   7620
gcccgctttc cagtcgggaa acctgtcgtg ccagctgcat taatgaatcg gccaacgcgc   7680
ggggagaggc ggtttgcgta ttgggcgctc ttccgcttcc tcgctcactg actcgctgcg   7740
ctcggtcgtt cggctgcggc gagcggtatc agctcactca aaggcggtaa tacggttatc   7800
cacagaatca ggggataacg caggaaagaa catgtgagca aaaggccagc aaaaggccag   7860
```

-continued gaaccgtaaa aaggccgcgt tgctggcgtt tttccatagg ctccgccccc ctgacgagca 7920
tcacaaaaat cgacgctcaa gtcagaggtg gcgaaacccg acaggactat aaagatacca 7980
ggcgtttccc cctggaagct ccctcgtgcg ctctcctgtt ccgaccctgc cgcttaccgg 8040
atacctgtcc gcctttctcc cttcgggaag cgtggcgctt tctcatagct cacgctgtag 8100
gtatctcagt tcggtgtagg tcgttcgctc caagctgggc tgtgtgcacg aaccccccgt 8160
tcagcccgac cgctgcgcct tatccggtaa ctatcgtctt gagtccaacc cggtaagaca 8220
cgacttatcg ccactggcag cagccactgg taacaggatt agcagagcga ggtatgtagg 8280
cggtgctaca gagttcttga agtggtggcc taactacggc tacactagaa gaacagtatt 8340
tggtatctgc gctctgctga agccagttac cttcggaaaa agagttggta gctcttgatc 8400
cggcaaacaa accaccgctg gtagcggtgg tttttttgtt tgcaagcagc agattacgcg 8460
cagaaaaaaa ggatctcaag aagatccttt gatcttttct acggggtctg acgctcagtg 8520
gaacgaaaac tcacgttaag ggattttggt catgagatta tcaaaaagga tcttcaccta 8580
gatcctttta aattaaaaat gaagttttaa atcaatctaa agtatatatg agtaaacttg 8640
gtctgacaga aataataaaa aagccggatt aataatctgg ctttttatat tctctctcta 8700
gtatataaac gcagaaaggc ccacccgaag gtgagccagt gtgactctag tattattaga 8760
aaaactcatc gagcatcaaa tgaaactgca atttattcat atcaggatta tcaataccat 8820
atttttgaaa aagccgtttc tgtaatgaag gagaaaactc accgaggcag ttccaaagaa 8880
tggcaaggtc ctggtaacgg tctgcgattc cgacccgtcc aacatcaata caacctatta 8940
atttcccctc gtcaaaaata aggttatcaa gtgagaaatc accatgagtg acgactgaat 9000
ccggtgagaa tggcaagagc ttgtgcattt ctttccagac ttgttcaaca ggccagccat 9060
tacgctcgtc atcaaaatca ctcgcatcaa ccaaaccgtt attcatgcgt gattgcgcct 9120
gagcaagacg aaatacacga tcgctgttaa aaggacaatt acaaacagga atcgaatgta 9180
accggcgcag gaacacggcc agcgcatcaa caatattttc acctgaatca ggatattctt 9240
ctaatacctg gaaggctgtt ttcccaggaa tcgcggtggt gagtaaccac gcatcatcag 9300
gagtacggat aaaatgcttg atggtcggga gaggcataaa ctccgtcagc cagttgagac 9360
ggaccatctc atctgtaaca tcattggcaa cgctaccttt gccatgtttc agaaacaact 9420
ctggcgcatc gggcttccca tacaagcgat agattgtcgc acctgattgc ccgacattat 9480
cgcgagccca tttataccca tataaatcag cgtccatgtt ggagtttaag cgcggacggg 9540
agcaagacgt ttcccgttga atatggctca taacacccct tgtattactg tttatgtaag 9600
cagacagttt tattgttcat gatgatatat ttttatcttg tgcaatgtaa catcagagat 9660
tttgagacac aacgtggctt tgttgaataa atcgaacttt tgctgagttg aaggatcagc 9720
tctagtaaaa taataaaaaa gccggattaa taatctggct ttttatattc tctctctagt 9780
atataaacgc agaaaggccc acccgaaggt gagccagtgt gacggcacat ttccccgaaa 9840
agtgccacct aaattgtaag cgttaatatt ttgttaaaat tcgcgttaaa tttttgttaa 9900
atcagctcat ttttaacca ataggccgaa atcggcaaaa tcccttataa atcaaaagaa 9960
tagaccgaga tagggttgag tgttgttcca gtttggaaca agagtccact attaaagaac 10020
gtggactcca acgtcaaagg gcgaaaaacc gtctatcagg gcgatggccc actacgtgaa 10080
ccatcaccct aatcaagttt tttggggtcg aggtgccgta aagcactaaa tcggaaccct 10140
aaagggagcc cccgatttag agcttgacgg ggaaagccgg cgaacgtggc gagaaaggaa 10200
gggaagaaag cgaaaggagc gggcgctagg gcgctggcaa gtgtagcggt cacgctgcgc 10260
gtaaccacca cacccgccgc gcttaatgcg ccgctacagg gcgcgtccca ttcgccattc 10320
aggctgcgca actgttggga agggcgatcg gtgcgggcct cttcgctatt acgccagctg 10380
gcgaaagggg gatgtgctgc aaggcgatta agttgggtaa cgccagggtt ttcccagtca 10440
cgacgttgta aaacgacggc cagtgagcgc gcggcgaatt gggtaccggg ccccc 10495

<210> SEQ ID NO 19
<211> LENGTH: 10493
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
cctcgagggc tagccattct atttaatctc cctatcagtg atagagatcg cccgagtgag 60
cacgcagggt ctccattttg atccctatca gtgatagaga agcgggaggt ttgaacgcgc 120
agccgccatg ccggggtttt acgagattgt gattaaggtc cccagcgacc ttgacgagca 180
tctgcccggc atttctgaca gctttgtgaa ctgggtggcc gagaaggaat gggagttgcc 240
gccagattct gacatggatc tgaatctgat tgagcaggca cccctgaccg tggccgagaa 300
gctgcagcgc gactttctga cggaatggcg ccgtgtgagt aaggccccgg aggctctttt 360
ctttgtgcaa tttgagaagg gagagagcta cttccacatg cacgtgctcg tggaaaccac 420
cggggtgaaa tccatggttt tgggacgttt cctgagtcag attcgcgaaa aactgattca 480
gagaatttac cgcgggatcg agccgacttt gccaaactgg ttcgcggtca caaagaccag 540
aaatggcgcc ggaggcggga acaaggtggt ggatgagtgc tacatcccca attacttgct 600
ccccaaaacc cagcctgagc tccaatgggc atggaccaac atggaacagt acctcagcgc 660
ctgtttgaat ctcacggagc gtaaacggtt ggtggcgcag catctgacgc acgtgtcgca 720
gacgcaggag cagaacaaag agaatcagaa tcccaattct gatgcgccgg tgatcagatc 780
aaaaacttca gccaggtaca tggagctggt cgggtggctc gtggacaagg ggattacctc 840
ggagaagcag tggatccagg aggaccaggc ctcatacatc tccttcaatg cggcctccaa 900
ctcgcggtcc caaatcaagg ctgccttgga caatgcggga aagattatga gcctgactaa 960
aaccgccccc gactacctgg tgggccagca gcccgtggag gacatttcca gcaatcggat 1020
ttataaaatt ttggaactaa acgggtacga tccccaatat gcggcttccg tctttctggg 1080
atgggccacg aaaaagttcg gcaagaggaa caccatctgg ctgtttgggc ctgcaactac 1140
cgggaagacc aacatcgcgg aggccatagc ccacactgtg cccttctacg ggtgcgtaaa 1200
ctggaccaat gagaactttc ccttcaacga ctgtgtcgac aagatggtga tctggtggga 1260
ggaggggaag atgaccgcca aggtcgtgga gtcggccaaa gccattctcg gaggaagcaa 1320
ggtgcgcgtg gaccagaaat gcaagtcctc ggcccagata gacccgactc ccgtgatcgt 1380
cacctccaac accaacatgt gcgccgtgat tgacgggaac tcaacgacct tcgaacacca 1440
gcagccgttg caagaccgga tgttcaaatt tgaactcacc cgccgtctgg atcatgactt 1500
tgggaaggtc accaagcagg aagtcaaaga ctttttccgg tgggcaaagg atcacgtggt 1560
tgaggtggag catgaattct acgtcaaaaa gggtggagcc aagaaaagac ccgcccccag 1620
tgacgcagat ataagtgagc ccaaacgggt gcgcgagtca gttgcgcagc catcgacgtc 1680
agacgcggaa gcttcgatca actacgcaga caggtaccaa aacaaatgtt ctcgtcacgt 1740

-continued

```
gggcatgaat ctgatgctgt ttccctgcag acaatgcgag agaatgaatc agaattcaaa   1800
tatctgcttc actcacggac agaaagactg tttagagtgc tttcccgtgt cagaatctca   1860
acccgtttct gtcgtcaaaa aggcgtatca gaaactgtgc tacattcatc atatcatggg   1920
aaaggtgcca gacgcttgca ctgcctgcga tctggtcaat gtggatttgg atgactgcat   1980
ctttgaacaa taaatgattt aaatcaggta tggctgccga tggttatctt ccagattggc   2040
tcgaggacaa cctctctgag ggcattcgcg agtggtggga cttgaaacct ggagccccga   2100
aacccaaagc caaccagcaa aagcaggacg acggccgggg tctggtgctt cctggctaca   2160
agtacctcgg acccttcaac ggactcgaca agggggagcc cgtcaacgcg gcggacgcag   2220
cggccctcga gcacgacaag gcctacgacc agcagctcaa agcgggtgac aatccgtacc   2280
tgcggtataa ccacgccgac gccgagtttc aggagcgtct gcaagaagat acgtcttttg   2340
ggggcaacct cgggcgagca gtcttccagg ccaagaagcg ggttctcgaa cctctcggtc   2400
tggttgagga aggcgctaag acggctcctg gaaagaagag accggtagag caatcacccc   2460
aggaaccaga ctcctcttcg ggcatcggca agaaaggcca gcagcccgcg agaaaagagac  2520
tcaactttgg gcagactggc gactcagagt cagtgcccga ccctcaacca ctcggagaac   2580
cccccgcagc cccctctggt gtgggatcta atacaatggc tgcaggcggt ggcgctccaa   2640
tggcagacaa taacgaaggc gccgacggag tgggtaacgc ctcaggaaat tggcattgcg   2700
attccacatg gctgggcgac agagtcatca ccaccagcac ccgaacctgg gccctcccca   2760
cctacaacaa ccacctctac aagcaaatct ccagccaatc gggaggcagc accaacgaca   2820
acacctactt cggctacagc accccctggg ggtattttga ctttaacaga ttccactgcc   2880
acttctcacc acgtgactgg cagcgactca tcaacaacaa ctggggattc cggcccaaga   2940
agctcaactt caagctcttc aacatccagg tcaaggaggt cacgacgaat gatggcacca   3000
cgaccatcgc caataacctt accagcacgg ttcaggtctt tacggactcg gaataccagc   3060
tcccgtacgt cctcggctct gcgcaccagg gctgcctgcc tccgttcccg gcggacgtct   3120
tcatgattcc tcagtacggg tacctgactc tgaacaatgg cagtcaggcc gtgggccgtt   3180
cctccttcta ctgcctggaa tactttcctt ctcaaatgct gagaacgggc aacaactttc   3240
agttcagcta cacgtttgag gacgtgcctt ttcacagcag ctacgcgcac agccaaagcc   3300
tggaccggct gatgaacccc ctcatcgacc agtacctgta ctacctgtct cggactcaga   3360
ccacgagtgg taccgcagga aatcggacgt tgcaattttc tcaggccggg cctagtagca   3420
tggcgaatca ggccaaaaac tggctacccg ggccctgcta ccggcagcaa cgcgtctcca   3480
agacaaccaa tcaaaataac aacagcaact ttgcctggac cggtgccacc aagtatcatc   3540
tgaatggcag agactctctg gtaaatcccg gtcccgctat ggcaacccac aaggacgacg   3600
aagacaaatt ttttccgatg agcggagtct taatatttgg gaaacaggga gctggaaata   3660
gcaacgtgga ccttgacaac gttatgataa ccaacgagga agaaattaaa accaccaacc   3720
cagtggccac agaagagtac ggcacggtgg ccactaacct gcaatcggcc aacaccgctc   3780
ctgctacagg gaccgtcaac agtcaaggag ccttacctgg catggtctgg caggaccggg   3840
acgtgtacct gcagggtcct atctgggcca agattcctca cacggacgga cactttcatc   3900
cctcgccgct gatgggaggc tttggactga aacacccgcc tcctcagatc ctgattaaga   3960
atacacctgt tcccgcgaat cctccaacta ccttcagtcc agctaagttt gcgtcgttca   4020
tcacgcagta cagcaccgga caggtcagcg tggaaattga atgggagctg cagaaagaaa   4080
acagcaaacg ctggaaccca gagattcaat acacttccaa ctacaacaaa tctacaaatg   4140
```

```
tggactttgc tgttgacaca aatggcgttt attctgagcc tcgccccatc ggcacccgtt   4200
acctcacccg taatctgtaa actagtttgc ttgttaatca ataaaccgtt taattcgttt   4260
cagttgaact ttggtctctg cgtatttctt tcttatctag tttccatgct ctagaggtcc   4320
tgtattagag gtcacgtgag tgttttgcga cattttgcga caccatgtgg tcacgctggg   4380
tatttaagcc cgagtgagca cgcagggtct ccattttgaa gcgggaggtt tgaacgcgca   4440
gccgccaagc cgaattctgc agatatcggg gttggggttg cgccttttcc aaggcagccc   4500
tgggtttgcg cagggacgcg gctgctctgg gcgtggttcc gggaaacgca gcggcgccga   4560
ccctgggtct cgcacattct tcacgtccgt tcgcagcgtc acccggatct tcgccgctac   4620
ccttgtgggc cccccggcga cgcttcctgc tccgccccta agtcgggaag gttccttgcg   4680
gttcgcggcg tgccggacgt gacaaacgga agccgcacgt ctcactagta ccctcgcaga   4740
cggacagcgc cagggagcaa tggcagcgcg ccgaccgcga tgggctgtgg ccaatagcgg   4800
ctgctcagca gggcgcgccg agagcagcgg ccgggaaggg gcggtgcggg aggcggggtg   4860
tggggcggta gtgtgggccc tgttcctgcc cgcgcggtgt tccgcattct gcaagcctcc   4920
ggagcgcacg tcggcagtcg gctccctcgt tgaccgaatc accgacctct ctccccagaa   4980
gctcccggga gcttgtatat ccattttcgg atctgatcag cacgtgttga caattaatca   5040
tcggcatagt atatcggcat agtataatac gacaaggtga ggaacgccac catggccaag   5100
cctttgtctc aagaagaatc caccctcatt gaaagagcaa cggctacaat caacagcatc   5160
cccatctctg aagactacag cgtcgccagc gcagctctct ctagcgacgg ccgcatcttc   5220
actggtgtca atgtatatca ttttactggg ggaccttgtg cagaactcgt ggtgctgggc   5280
actgctgctg ctgcggcagc tggcaacctg acttgtatcg tcgcgatcgg aaatgagaac   5340
aggggcatct tgagcccctg cggacggtgc cgacaggtgc ttctcgatct gcatcctggg   5400
atcaaagcca tagtgaagga cagtgatgga cagccgacgg cagttgggat tcgtgaattg   5460
ctgccctctg gttatgtgtg ggagggctaa gcacttcgtg gccgaggagc aggactgaca   5520
cgtgctacga gatttcgatt ccaccgccgc cttctatgaa aggttgggct tcggaatcgt   5580
tttccgggac gccggctgga tgatcctcca gcgcggggat ctcatgctgg agttcttcgc   5640
ccaccccaac ttgtttattg cagcttataa tggttacaaa taaagcaata gcatcacaaa   5700
tttcacaaat aaagcatttt tttcactgca ttctagttgt ggtttgtcca aactcatcaa   5760
tgtatcttag cgctcactgc ccgctttcca gtcgggaaac ctgtcgtgcc agctgcatta   5820
atgaatcggc caacgcgcgg ggagaggcgg tttgcgtatt gggcgctctc ctaggccaga   5880
aatggcgccg gaggcgggaa caaggtggtg gatgagtgct acatccccaa ttacttgctc   5940
cccaaaaccc agcctgagtc cctatcagtg atagagactc cagtgggcgt ggactaatat   6000
ggaacagtat ttaagcgcct gtccctatca gtgatagaga tttgaatctc acggagcgta   6060
aacggttggt ggcgcagcat ctgtttaaac gcagacgcag gagcagaaca aagagaatca   6120
gaatcccaat tctgatgcgc cggtgatcag atcaaaaact tcagccaggt acatggagct   6180
ggtcgggtgg ctcgtggaca aggggattac ctcggagaag cagtggattc aggaggacca   6240
ggcctcatac atctccttca atgcggcctc caactcgcgg tcccaaatca aggctgcctt   6300
ggacaatgcg ggaaagatta tgagcctgac taaaaccgcc cccgactacc tggtgggcca   6360
gcagcccgtg gaggacattt ccagcaatcg gatttataaa attttggaac taaacgggta   6420
cgatccccaa tatgcggctt ccgtctttct gggatgggcc acgaaaaagt tcggcaagag   6480
```

-continued

```
gaacaccatc tggctgtttg ggcctgcaac taccgggaag accaacatcg cggaggccat   6540
agcccacact gtgcccttct acgggtgcgt aaactggacc aatgagaact ttcccttcaa   6600
cgactgtgtc gacaagatgg tgatctggtg ggaggagggg aagatgaccg ccaaggtcgt   6660
ggagtcggcc aaagccattc tcggaggaag caaggtgcgc gtggaccaga aatgcaagtc   6720
ctcggcccag atagacccga ctcccgtgat cgtcacctcc aacaccaaca tgtgcgccgt   6780
gattgacggg aactcaacga ccttcgaaca ccagcagccg ttgcaagacc ggatgttcaa   6840
atttgaactc acccgccgtc tggatcatga ctttgggaag gtcaccaagc aggaagtcaa   6900
agactttttc cggtgggcaa aggatcacgt ggttgaggtg gagcatgaat tctacgtcaa   6960
aaagggtgga gccaagaaaa gacccgcccc cagtgacgca gatataagtg agcccaaacg   7020
ggtgcgcgag tcagttgcgc agccatcgac gtcagacgcg gaagcttcga tcaactacgc   7080
agacaggtac caaaacaaat gttctcgtca cgtgggcatg aatctgatgc tgtttccctg   7140
cagacaatgc gagagaatga atcagaattc aaatatctgc ttcactcacg gacagaaaga   7200
ctgtttagag tgctttcccg tgtcagaatc tcaacccgtt tctgtcgtca aaaaggcgta   7260
tcagaaactg tgctacattc atcatatcat gggaaaggtg ccagacgctt gcactgcctg   7320
cgatctggtc aatgtggatt tggatgactg catctttgaa caataaacta gtttgcttgt   7380
taatcaataa accgtttaat tcgtttcagt tgaactttgg tctctgcgta tttctttctt   7440
atctagtttc catgctctag agtatacgat atccatcaca ctggcggccg ctcgactaga   7500
gcggccgcca ccgcggtgga gctccagctt ttgttcgcgc gcttggcgta atcatggtca   7560
tagctgtttc ctgtgtgaaa ttccacagcc tggggtgcct aattgcgttg cgctcactgc   7620
ccgctttcca gtcgggaaac ctgtcgtgcc agctgcatta atgaatcggc caacgcgcgg   7680
ggagaggcgg tttgcgtatt gggcgctctt ccgcttcctc gctcactgac tcgctgcgct   7740
cggtcgttcg gctgcggcga gcggtatcag ctcactcaaa ggcggtaata cggttatcca   7800
cagaatcagg ggataacgca ggaaagaaca tgtgagcaaa aggccagcaa aaggccagga   7860
accgtaaaaa ggccgcgttg ctggcgtttt tccataggct ccgcccccct gacgagcatc   7920
acaaaaatcg acgctcaagt cagaggtggc gaaacccgac aggactataa agataccagg   7980
cgtttccccc tggaagctcc ctcgtgcgct ctcctgttcc gaccctgccg cttaccggat   8040
acctgtccgc ctttctccct tcgggaagcg tggcgctttc tcatagctca cgctgtaggt   8100
atctcagttc ggtgtaggtc gttcgctcca agctgggctg tgtgcacgaa ccccccgttc   8160
agcccgaccg ctgcgcctta tccggtaact atcgtcttga gtccaacccg gtaagacacg   8220
acttatcgcc actggcagca gccactggta acaggattag cagagcgagg tatgtaggcg   8280
gtgctacaga gttcttgaag tggtggccta actacggcta cactagaaga acagtatttg   8340
gtatctgcgc tctgctgaag ccagttacct tcggaaaaag agttggtagc tcttgatccg   8400
gcaaacaaac caccgctggt agcggtggtt tttttgtttg caagcagcag attacgcgca   8460
gaaaaaaagg atctcaagaa gatcctttga tcttttctac ggggtctgac gctcagtgga   8520
acgaaaactc acgttaaggg attttggtca tgagattatc aaaaaggatc ttcacctaga   8580
tccttttaaa ttaaaaatga agttttaaat caatctaaag tatatatgag taaacttggt   8640
ctgacagaaa taataaaaaa gccggattaa taatctggct ttttatattc tctctctagt   8700
atataaacgc agaaaggccc acccgaaggt gagccagtgt gactctagta ttattagaaa   8760
aactcatcga gcatcaaatg aaactgcaat ttattcatat caggattatc aataccatat   8820
ttttgaaaaa gccgtttctg taatgaagga gaaaactcac cgaggcagtt ccaaagaatg   8880
```

```
gcaaggtcct ggtaacggtc tgcgattccg acccgtccaa catcaataca acctattaat   8940

ttcccctcgt caaaaataag gttatcaagt gagaaatcac catgagtgac gactgaatcc   9000

ggtgagaatg gcaagagctt gtgcatttct ttccagactt gttcaacagg ccagccatta   9060

cgctcgtcat caaaatcact cgcatcaacc aaaccgttat tcatgcgtga ttgcgcctga   9120

gcaagacgaa atacacgatc gctgttaaaa ggacaattac aaacaggaat cgaatgtaac   9180

cggcgcagga acacggccag cgcatcaaca atattttcac ctgaatcagg atattcttct   9240

aatacctgga aggctgtttt cccaggaatc gcggtggtga gtaaccacgc atcatcagga   9300

gtacggataa aatgcttgat ggtcgggaga ggcataaact ccgtcagcca gttgagacgg   9360

accatctcat ctgtaacatc attggcaacg ctacctttgc catgtttcag aaacaactct   9420

ggcgcatcgg gcttcccata caagcgatag attgtcgcac ctgattgccc gacattatcg   9480

cgagcccatt tatacccata taaatcagcg tccatgttgg agtttaagcg cggacgggag   9540

caagacgttt cccgttgaat atggctcata acaccccttg tattactgtt tatgtaagca   9600

gacagtttta ttgttcatga tgatatattt ttatcttgtg caatgtaaca tcagagattt   9660

tgagacacaa cgtggctttg ttgaataaat cgaacttttg ctgagttgaa ggatcagctc   9720

tagtaaaata ataaaaaagc cggattaata atctggcttt ttatattctc tctctagtat   9780

ataaacgcag aaaggcccac ccgaaggtga gccagtgtga cggcacattt ccccgaaaag   9840

tgccacctaa attgtaagcg ttaatatttt gttaaaattc gcgttaaatt tttgttaaat   9900

cagctcattt tttaaccaat aggccgaaat cggcaaaatc ccttataaat caaaagaata   9960

gaccgagata gggttgagtg ttgttccagt ttggaacaag agtccactat taaagaacgt  10020

ggactccaac gtcaaagggc gaaaaaccgt ctatcagggc gatggcccac tacgtgaacc  10080

atcaccctaa tcaagttttt tggggtcgag gtgccgtaaa gcactaaatc ggaaccctaa  10140

agggagcccc cgatttagag cttgacgggg aaagccggcg aacgtggcga gaaaggaagg  10200

gaagaaagcg aaaggagcgg gcgctagggc gctggcaagt gtagcggtca cgctgcgcgt  10260

aaccaccaca cccgccgcgc ttaatgcgcc gctacagggc gcgtcccatt cgccattcag  10320

gctgcgcaac tgttgggaag ggcgatcggt gcgggcctct tcgctattac gccagctggc  10380

gaaaggggga tgtgctgcaa ggcgattaag ttgggtaacg ccagggtttt cccagtcacg  10440

acgttgtaaa acgacggcca gtgagcgcgc ggcgaattgg gtaccgggcc ccc         10493
```

```
<210> SEQ ID NO 20
<211> LENGTH: 10491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
```

```
cctcgagggc tagccattct ccctatcagt gatagagatc tatttaagcc cgagtgagca     60

cgcagtccct atcagtgata gagaggtctc cattttgaag cgggaggttt gaacgcgcag    120

ccgccatgcc ggggttttac gagattgtga ttaaggtccc cagcgacctt gacgagcatc    180

tgcccggcat ttctgacagc tttgtgaact gggtggccga gaaggaatgg gagttgccgc    240

cagattctga catggatctg aatctgattg agcaggcacc cctgaccgtg gccgagaagc    300

tgcagcgcga ctttctgacg gaatggcgcc gtgtgagtaa ggccccggag gctcttttct    360

ttgtgcaatt tgagaaggga gagagctact tccacatgca cgtgctcgtg gaaaccaccg    420
```

```
gggtgaaatc catggttttg ggacgtttcc tgagtcagat tcgcgaaaaa ctgattcaga    480
gaatttaccg cgggatcgag ccgactttgc caaactggtt cgcggtcaca aagaccagaa    540
atggcgccgg aggcgggaac aaggtggtgg atgagtgcta catcccccaat tacttgctcc   600
ccaaaaccca gcctgagctc caatgggcat ggaccaacat ggaacagtac ctcagcgcct    660
gtttgaatct cacggagcgt aaacggttgg tggcgcagca tctgacgcac gtgtcgcaga    720
cgcaggagca gaacaaagag aatcagaatc ccaattctga tgcgccggtg atcagatcaa    780
aaacttcagc caggtacatg gagctggtcg ggtggctcgt ggacaagggg attacctcgg    840
agaagcagtg gatccaggag gaccaggcct catacatctc cttcaatgcg gcctccaact    900
cgcggtccca aatcaaggct gccttggaca atgcgggaaa gattatgagc ctgactaaaa    960
ccgcccccga ctacctggtg ggccagcagc ccgtggagga catttccagc aatcggattt   1020
ataaaatttt ggaactaaac gggtacgatc cccaatatgc ggcttccgtc tttctgggat   1080
gggccacgaa aaagttcggc aagaggaaca ccatctggct gtttgggcct gcaactaccg   1140
ggaagaccaa catcgcggag gccatagccc acactgtgcc cttctacggg tgcgtaaact   1200
ggaccaatga gaactttccc ttcaacgact gtgtcgacaa gatggtgatc tggtgggagg   1260
aggggaagat gaccgccaag gtcgtggagt cggccaaagc cattctcgga ggaagcaagg   1320
tgcgcgtgga ccagaaatgc aagtcctcgg cccagataga cccgactccc gtgatcgtca   1380
cctccaacac caacatgtgc gccgtgattg acgggaactc aacgaccttc gaacaccagc   1440
agccgttgca agaccggatg ttcaaatttg aactcacccg ccgtctggat catgactttg   1500
ggaaggtcac caagcaggaa gtcaaagact tttccggtgg ggcaaaggat cacgtggttg   1560
aggtggagca tgaattctac gtcaaaaagg gtggagccaa gaaaagaccc gcccccagtg   1620
acgcagatat aagtgagccc aaacgggtgc gcgagtcagt tgcgcagcca tcgacgtcag   1680
acgcggaagc ttcgatcaac tacgcagaca ggtaccaaaa caaatgttct cgtcacgtgg   1740
gcatgaatct gatgctgttt ccctgcagac aatgcgagag aatgaatcag aattcaaata   1800
tctgcttcac tcacggacag aaagactgtt tagagtgctt tcccgtgtca gaatctcaac   1860
ccgtttctgt cgtcaaaaag gcgtatcaga aactgtgcta cattcatcat atcatgggaa   1920
aggtgccaga cgcttgcact gcctgcgatc tggtcaatgt ggatttggat gactgcatct   1980
ttgaacaata aatgatttaa atcaggtatg gctgccgatg gttatcttcc agattggctc   2040
gaggacaacc tctctgaggg cattcgcgag tggtgggact tgaaacctgg agccccgaaa   2100
cccaaagcca accagcaaaa gcaggacgac ggccggggtc tggtgcttcc tggctacaag   2160
tacctcggac ccttcaacgg actcgacaag ggggagcccg tcaacgcggc ggacgcagcg   2220
gccctcgagc acgacaaggc ctacgaccag cagctcaaag cgggtgacaa tccgtacctg   2280
cggtataacc acgccgacgc cgagtttcag gagcgtctgc aagaagatac gtcttttggg   2340
ggcaacctcg ggcgagcagt cttccaggcc aagaagcggg ttctcgaacc tctcggtctg   2400
gttgaggaag gcgctaagac ggctcctgga aagaagagac cggtagagca atcaccccag   2460
gaaccagact cctcttcggg catcggcaag aaaggccagc agcccgcgag aaaagagactc   2520
aactttgggc agactggcga ctcagagtca gtgcccgacc ctcaaccact cggagaaccc   2580
cccgcagccc cctctggtgt gggatctaat acaatggctg caggcggtgg cgctccaatg   2640
gcagacaata acgaaggcgc cgacggagtg ggtaacgcct caggaaattg gcattgcgat   2700
tccacatggc tgggcgacag agtcatcacc accagcaccc gaacctgggc cctccccacc   2760
```

-continued

```
tacaacaacc acctctacaa gcaaatctcc agccaatcgg gaggcagcac caacgacaac   2820
acctacttcg gctacagcac cccctggggg tattttgact ttaacagatt ccactgccac   2880
ttctcaccac gtgactggca gcgactcatc aacaacaact ggggattccg gcccaagaag   2940
ctcaacttca agctcttcaa catccaggtc aaggaggtca cgacgaatga tggcaccacg   3000
accatcgcca ataaccttac cagcacggtt caggtcttta cggactcgga ataccagctc   3060
ccgtacgtcc tcggctctgc gcaccagggc tgcctgcctc cgttcccggc ggacgtcttc   3120
atgattcctc agtacgggta cctgactctg aacaatggca gtcaggccgt gggccgttcc   3180
tccttctact gcctggaata ctttccttct caaatgctga gaacgggcaa caactttcag   3240
ttcagctaca cgtttgagga cgtgcctttt cacagcagct acgcgcacag ccaaagcctg   3300
gaccggctga tgaaccccct catcgaccag tacctgtact acctgtctcg gactcagacc   3360
acgagtggta ccgcaggaaa tcggacgttg caattttctc aggccgggcc tagtagcatg   3420
gcgaatcagg ccaaaaactg gctacccggg ccctgctacc ggcagcaacg cgtctccaag   3480
acaaccaatc aaaataacaa cagcaacttt gcctggaccg gtgccaccaa gtatcatctg   3540
aatggcagag actctctggt aaatcccggt cccgctatgg caacccacaa ggacgacgaa   3600
gacaaatttt ttccgatgag cggagtctta atatttggga aacagggagc tggaaatagc   3660
aacgtggacc ttgacaacgt tatgataacc aacgaggaag aaattaaaac caccaaccca   3720
gtggccacag aagagtacgg cacggtggcc actaacctgc aatcggccaa caccgctcct   3780
gctacaggga ccgtcaacag tcaaggagcc ttacctggca tggtctggca ggaccgggac   3840
gtgtacctgc agggtcctat ctgggccaag attcctcaca cggacggaca ctttcatccc   3900
tcgccgctga tgggaggctt tggactgaaa cacccgcctc ctcagatcct gattaagaat   3960
acacctgttc ccgcgaatcc tccaactacc ttcagtccag ctaagtttgc gtcgttcatc   4020
acgcagtaca gcaccggaca ggtcagcgtg gaaattgaat gggagctgca gaaagaaaac   4080
agcaaacgct ggaacccaga gattcaatac acttccaact acaacaaatc tacaaatgtg   4140
gactttgctg ttgacacaaa tggcgtttat tctgagcctc gccccatcgg cacccgttac   4200
ctcacccgta atctgtaaac tagtttgctt gttaatcaat aaaccgttta attcgtttca   4260
gttgaacttt ggtctctgcg tatttctttc ttatctagtt tccatgctct agaggtcctg   4320
tattagaggt cacgtgagtg ttttgcgaca ttttgcgaca ccatgtggtc acgctgggta   4380
tttaagcccg agtgagcacg cagggtctcc attttgaagc gggaggtttg aacgcgcagc   4440
cgccaagccg aattctgcag atatcggggt tggggttgcg ccttttccaa ggcagccctg   4500
ggtttgcgca gggacgcggc tgctctgggc gtggttccgg gaaacgcagc ggcgccgacc   4560
ctgggtctcg cacattcttc acgtccgttc gcagcgtcac ccggatcttc gccgctaccc   4620
ttgtgggccc cccggcgacg cttcctgctc cgcccctaag tcgggaaggt tccttgcggt   4680
tcgcggcgtg ccggacgtga caaacggaag ccgcacgtct cactagtacc ctcgcagacg   4740
gacagcgcca gggagcaatg gcagcgcgcc gaccgcgatg ggctgtggcc aatagcggct   4800
gctcagcagg gcgcgccgag agcagcggcc gggaaggggc ggtgcgggag gcggggtgtg   4860
gggcggtagt gtgggccctg ttcctgcccg cgcggtgttc cgcattctgc aagcctccgg   4920
agcgcacgtc ggcagtcggc tccctcgttg accgaatcac cgacctctct ccccagaagc   4980
tcccgggagc ttgtatatcc attttcggat ctgatcagca cgtgttgaca attaatcatc   5040
ggcatagtat atcggcatag tataatacga caaggtgagg aacgccacca tggccaagcc   5100
tttgtctcaa gaagaatcca ccctcattga aagagcaacg gctacaatca acagcatccc   5160
```

catctctgaa gactacagcg tcgccagcgc agctctctct agcgacggcc gcatcttcac 5220
tggtgtcaat gtatatcatt ttactggggg accttgtgca gaactcgtgg tgctgggcac 5280
tgctgctgct gcggcagctg gcaacctgac ttgtatcgtc gcgatcggaa atgagaacag 5340
gggcatcttg agcccctgcg gacggtgccg acaggtgctt ctcgatctgc atcctgggat 5400
caaagccata gtgaaggaca gtgatggaca gccgacggca gttgggattc gtgaattgct 5460
gccctctggt tatgtgtggg agggctaagc acttcgtggc cgaggagcag gactgacacg 5520
tgctacgaga tttcgattcc accgccgcct tctatgaaag gttgggcttc ggaatcgttt 5580
tccgggacgc cggctggatg atcctccagc gcggggatct catgctggag ttcttcgccc 5640
accccaactt gtttattgca gcttataatg gttacaaata aagcaatagc atcacaaatt 5700
tcacaaataa agcatttttt tcactgcatt ctagttgtgg tttgtccaaa ctcatcaatg 5760
tatcttagcg ctcactgccc gctttccagt cgggaaacct gtcgtgccag ctgcattaat 5820
gaatcggcca acgcgcgggg agaggcggtt tgcgtattgg gcgctctcct aggccagaaa 5880
tggcgccgga ggcgggaaca aggtggtgga tgagtgctac atccccaatt acttgctccc 5940
caaaacccag cctgagtccc tatcagtgat agagactcca gtgggcgtgg actaatatgg 6000
aacagtattt aagcgcctgt ccctatcagt gatagagatt tgaatctcac ggagcgtaaa 6060
cggttggtgg cgcagcatct gtttaaacgc agacgcagga gcagaacaaa gagaatcaga 6120
atcccaattc tgatgcgccg gtgatcagat caaaaacttc agccaggtac atggagctgg 6180
tcgggtggct cgtggacaag ggattacct cggagaagca gtggattcag gaggaccagg 6240
cctcatacat ctccttcaat gcggcctcca actcgcggtc ccaaatcaag gctgccttgg 6300
acaatgcggg aaagattatg agcctgacta aaaccgcccc cgactacctg gtgggccagc 6360
agcccgtgga ggacatttcc agcaatcgga tttataaaat tttggaacta aacgggtacg 6420
atccccaata tgcggcttcc gtctttctgg gatgggccac gaaaaagttc ggcaagagga 6480
acaccatctg gctgtttggg cctgcaacta ccgggaagac caacatcgcg gaggccatag 6540
cccacactgt gcccttctac gggtgcgtaa actggaccaa tgagaacttt cccttcaacg 6600
actgtgtcga caagatggtg atctggtggg aggaggggaa gatgaccgcc aaggtcgtgg 6660
agtcggccaa agccattctc ggaggaagca aggtgcgcgt ggaccagaaa tgcaagtcct 6720
cggcccagat agacccgact cccgtgatcg tcacctccaa caccaacatg tgcgccgtga 6780
ttgacgggaa ctcaacgacc ttcgaacacc agcagccgtt gcaagaccgg atgttcaaat 6840
ttgaactcac ccgccgtctg gatcatgact ttgggaaggt caccaagcag gaagtcaaag 6900
actttttccg gtgggcaaag gatcacgtgg ttgaggtgga gcatgaattc tacgtcaaaa 6960
agggtggagc caagaaaaga cccgccccca gtgacgcaga tataagtgag cccaaacggg 7020
tgcgcgagtc agttgcgcag ccatcgacgt cagacgcgga agcttcgatc aactacgcag 7080
acaggtacca aaacaaatgt tctcgtcacg tgggcatgaa tctgatgctg tttccctgca 7140
gacaatgcga gagaatgaat cagaattcaa atatctgctt cactcacgga cagaaagact 7200
gtttagagtg ctttcccgtg tcagaatctc aacccgtttc tgtcgtcaaa aaggcgtatc 7260
agaaactgtg ctacattcat catatcatgg gaaaggtgcc agacgcttgc actgcctgcg 7320
atctggtcaa tgtggatttg gatgactgca tctttgaaca ataaactagt ttgcttgtta 7380
atcaataaac cgtttaattc gtttcagttg aactttggtc tctgcgtatt tctttcttat 7440
ctagtttcca tgctctagag tatacgatat ccatcacact ggcggccgct cgactagagc 7500

-continued

```
ggccgccacc gcggtggagc tccagctttt gttcgcgcgc ttggcgtaat catggtcata   7560
gctgtttcct gtgtgaaatt ccacagcctg gggtgcctaa ttgcgttgcg ctcactgccc   7620
gctttccagt cgggaaacct gtcgtgccag ctgcattaat gaatcggcca acgcgcgggg   7680
agaggcggtt tgcgtattgg gcgctcttcc gcttcctcgc tcactgactc gctgcgctcg   7740
gtcgttcggc tgcggcgagc ggtatcagct cactcaaagg cggtaatacg gttatccaca   7800
gaatcagggg ataacgcagg aaagaacatg tgagcaaaag gccagcaaaa ggccaggaac   7860
cgtaaaaagg ccgcgttgct ggcgtttttc cataggctcc gcccccctga cgagcatcac   7920
aaaaatcgac gctcaagtca gaggtggcga aacccgacag gactataaag ataccaggcg   7980
tttccccctg gaagctccct cgtgcgctct cctgttccga ccctgccgct taccggatac   8040
ctgtccgcct ttctcccttc gggaagcgtg gcgctttctc atagctcacg ctgtaggtat   8100
ctcagttcgg tgtaggtcgt tcgctccaag ctgggctgtg tgcacgaacc ccccgttcag   8160
cccgaccgct gcgccttatc cggtaactat cgtcttgagt ccaacccggt aagacacgac   8220
ttatcgccac tggcagcagc cactggtaac aggattagca gagcgaggta tgtaggcggt   8280
gctacagagt tcttgaagtg gtggcctaac tacggctaca ctagaagaac agtatttggt   8340
atctgcgctc tgctgaagcc agttaccttc ggaaaaagag ttggtagctc ttgatccggc   8400
aaacaaacca ccgctggtag cggtggtttt tttgtttgca agcagcagat tacgcgcaga   8460
aaaaaaggat ctcaagaaga tcctttgatc ttttctacgg ggtctgacgc tcagtggaac   8520
gaaaactcac gttaagggat tttggtcatg agattatcaa aaaggatctt cacctagatc   8580
cttttaaatt aaaaatgaag ttttaaatca atctaaagta tatatgagta aacttggtct   8640
gacagaaata ataaaaaagc cggattaata atctggcttt ttatattctc tctctagtat   8700
ataaacgcag aaaggcccac ccgaaggtga gccagtgtga ctctagtatt attagaaaaa   8760
ctcatcgagc atcaaatgaa actgcaattt attcatatca ggattatcaa taccatattt   8820
ttgaaaaagc cgtttctgta atgaaggaga aaactcaccg aggcagttcc aaagaatggc   8880
aaggtcctgg taacggtctg cgattccgac ccgtccaaca tcaatacaac ctattaattt   8940
cccctcgtca aaaataaggt tatcaagtga gaaatcacca tgagtgacga ctgaatccgg   9000
tgagaatggc aagagcttgt gcatttcttt ccagacttgt tcaacaggcc agccattacg   9060
ctcgtcatca aaatcactcg catcaaccaa accgttattc atgcgtgatt gcgcctgagc   9120
aagacgaaat acacgatcgc tgttaaaagg acaattacaa acaggaatcg aatgtaaccg   9180
gcgcaggaac acggccagcg catcaacaat attttcacct gaatcaggat attcttctaa   9240
tacctggaag gctgttttcc caggaatcgc ggtggtgagt aaccacgcat catcaggagt   9300
acggataaaa tgcttgatgg tcgggagagg cataaactcc gtcagccagt tgagacggac   9360
catctcatct gtaacatcat tggcaacgct acctttgcca tgtttcagaa acaactctgg   9420
cgcatcgggc ttcccataca agcgatagat tgtcgcacct gattgcccga cattatcgcg   9480
agcccattta tacccatata aatcagcgtc catgttggag tttaagcgcg gacgggagca   9540
agacgtttcc cgttgaatat ggctcataac accccttgta ttactgttta tgtaagcaga   9600
cagttttatt gttcatgatg atatattttt atcttgtgca atgtaacatc agagattttg   9660
agacacaacg tggctttgtt gaataaatcg aacttttgct gagttgaagg atcagctcta   9720
gtaaaataat aaaaaagccg gattaataat ctggcttttt atattctctc tctagtatat   9780
aaacgcagaa aggcccaccc gaaggtgagc cagtgtgacg gcacatttcc ccgaaaagtg   9840
ccacctaaat tgtaagcgtt aatattttgt taaaattcgc gttaaatttt tgttaaatca   9900
```

```
gctcattttt taaccaatag gccgaaatcg gcaaaatccc ttataaatca aaagaataga   9960
ccgagatagg gttgagtgtt gttccagttt ggaacaagag tccactatta aagaacgtgg  10020
actccaacgt caaagggcga aaaaccgtct atcagggcga tggcccacta cgtgaaccat  10080
caccctaatc aagttttttg gggtcgaggt gccgtaaagc actaaatcgg aaccctaaag  10140
ggagcccccg atttagagct tgacggggaa agccggcgaa cgtggcgaga aaggaaggga  10200
agaaagcgaa aggagcgggc gctagggcgc tggcaagtgt agcggtcacg ctgcgcgtaa  10260
ccaccacacc cgccgcgctt aatgcgccgc tacagggcgc gtcccattcg ccattcaggc  10320
tgcgcaactg ttgggaaggg cgatcggtgc gggcctcttc gctattacgc cagctggcga  10380
aagggggatg tgctgcaagg cgattaagtt gggtaacgcc agggttttcc cagtcacgac  10440
gttgtaaaac gacggccagt gagcgcgcgg cgaattgggt accgggcccc c           10491
```

```
<210> SEQ ID NO 21
<211> LENGTH: 10495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
```

```
cctcgagggc tagccattct atttaatctc cctatcagtg atagagatct ccctatcagt     60
gatagagatc gcccgagtga gcacgcaggg tctccatttt gaagcgggag gtttgaacgc    120
gcagccgcca tgccggggtt ttacgagatt gtgattaagg tccccagcga ccttgacgag    180
catctgcccg gcatttctga cagctttgtg aactgggtgg ccgagaagga atgggagttg    240
ccgccagatt ctgacatgga tctgaatctg attgagcagg cacccctgac cgtggccgag    300
aagctgcagc gcgactttct gacggaatgg cgccgtgtga gtaaggcccc ggaggctctt    360
ttctttgtgc aatttgagaa gggagagagc tacttccaca tgcacgtgct cgtggaaacc    420
accggggtga aatccatggt tttgggacgt ttcctgagtc agattcgcga aaaactgatt    480
cagagaattt accgcgggat cgagccgact ttgccaaact ggttcgcggt cacaaagacc    540
agaaatggcg ccggaggcgg gaacaaggtg gtggatgagt gctacatccc caattacttg    600
ctccccaaaa cccagcctga gctccaatgg gcatggacca acatggaaca gtacctcagc    660
gcctgtttga atctcacgga gcgtaaacgg ttggtggcgc agcatctgac gcacgtgtcg    720
cagacgcagg agcagaacaa agagaatcag aatcccaatt ctgatgcgcc ggtgatcaga    780
tcaaaaactt cagccaggta catggagctg gtcgggtggc tcgtggacaa ggggattacc    840
tcggagaagc agtggatcca ggaggaccag gcctcataca tctccttcaa tgcggcctcc    900
aactcgcggt cccaaatcaa ggctgccttg gacaatgcgg gaaagattat gagcctgact    960
aaaaccgccc ccgactacct ggtgggccag cagcccgtgg aggacatttc cagcaatcgg   1020
atttataaaa ttttggaact aaacgggtac gatccccaat atgcggcttc cgtctttctg   1080
ggatgggcca cgaaaaagtt cggcaagagg aacaccatct ggctgtttgg gcctgcaact   1140
accgggaaga ccaacatcgc ggaggccata gcccacactg tgcccttcta cgggtgcgta   1200
aactggacca atgagaactt tcccttcaac gactgtgtcg acaagatggt gatctggtgg   1260
gaggagggga agatgaccgc caaggtcgtg gagtcggcca aagccattct cggaggaagc   1320
aaggtgcgcg tggaccagaa atgcaagtcc tcggcccaga tagacccgac tcccgtgatc   1380
gtcacctcca acaccaacat gtgcgccgtg attgacggga actcaacgac cttcgaacac   1440
```

cagcagccgt tgcaagaccg gatgttcaaa tttgaactca cccgccgtct ggatcatgac 1500
tttgggaagg tcaccaagca ggaagtcaaa gactttttcc ggtgggcaaa ggatcacgtg 1560
gttgaggtgg agcatgaatt ctacgtcaaa aagggtggag ccaagaaaag acccgccccc 1620
agtgacgcag atataagtga gcccaaacgg gtgcgcgagt cagttgcgca gccatcgacg 1680
tcagacgcgg aagcttcgat caactacgca gacaggtacc aaaacaaatg ttctcgtcac 1740
gtgggcatga atctgatgct gtttccctgc agacaatgcg agagaatgaa tcagaattca 1800
aatatctgct tcactcacgg acagaaagac tgtttagagt gctttcccgt gtcagaatct 1860
caacccgttt ctgtcgtcaa aaaggcgtat cagaaactgt gctacattca tcatatcatg 1920
ggaaaggtgc cagacgcttg cactgcctgc gatctggtca atgtggattt ggatgactgc 1980
atctttgaac aataaatgat ttaaatcagg tatggctgcc gatggttatc ttccagattg 2040
gctcgaggac aacctctctg agggcattcg cgagtggtgg gacttgaaac ctggagcccc 2100
gaaacccaaa gccaaccagc aaaagcagga cgacggccgg ggtctggtgc ttcctggcta 2160
caagtacctc ggacccttca acggactcga caagggggag cccgtcaacg cggcggacgc 2220
agcggccctc gagcacgaca aggcctacga ccagcagctc aaagcgggtg acaatccgta 2280
cctgcggtat aaccacgccg acgccgagtt tcaggagcgt ctgcaagaag atacgtcttt 2340
tgggggcaac ctcgggcgag cagtcttcca ggccaagaag cgggttctcg aacctctcgg 2400
tctggttgag gaaggcgcta agacggctcc tggaaagaag agaccggtag agcaatcacc 2460
ccaggaacca gactcctctt cgggcatcgg caagaaaggc cagcagcccg cgagaaagag 2520
actcaacttt gggcagactg gcgactcaga gtcagtgccc gaccctcaac cactcggaga 2580
accccccgca gccccctctg gtgtgggatc taatacaatg gctgcaggcg gtggcgctcc 2640
aatggcagac aataacgaag gcgccgacgg agtgggtaac gcctcaggaa attggcattg 2700
cgattccaca tggctgggcg acagagtcat caccaccagc acccgaacct gggccctccc 2760
cacctacaac aaccacctct acaagcaaat ctccagccaa tcgggaggca gcaccaacga 2820
caacacctac ttcggctaca gcaccccctg ggggtatttt gactttaaca gattccactg 2880
ccacttctca ccacgtgact ggcagcgact catcaacaac aactggggat tccggcccaa 2940
gaagctcaac ttcaagctct tcaacatcca ggtcaaggag gtcacgacga atgatggcac 3000
cacgaccatc gccaataacc ttaccagcac ggttcaggtc tttacggact cggaatacca 3060
gctcccgtac gtcctcggct ctgcgcacca gggctgcctg cctccgttcc cggcggacgt 3120
cttcatgatt cctcagtacg ggtacctgac tctgaacaat ggcagtcagg ccgtgggccg 3180
ttcctccttc tactgcctgg aatactttcc ttctcaaatg ctgagaacgg gcaacaactt 3240
tcagttcagc tacacgtttg aggacgtgcc ttttcacagc agctacgcgc acagccaaag 3300
cctggaccgg ctgatgaacc ccctcatcga ccagtacctg tactacctgt ctcggactca 3360
gaccacgagt ggtaccgcag gaaatcggac gttgcaattt tctcaggccg ggcctagtag 3420
catggcgaat caggccaaaa actggctacc cgggccctgc taccggcagc aacgcgtctc 3480
caagacaacc aatcaaaata acaacagcaa ctttgcctgg accggtgcca ccaagtatca 3540
tctgaatggc agagactctc tggtaaatcc cggtcccgct atggcaaccc acaaggacga 3600
cgaagacaaa ttttttccga tgagcggagt cttaatattt gggaaacagg gagctggaaa 3660
tagcaacgtg gaccttgaca acgttatgat aaccaacgag gaagaaatta aaaccaccaa 3720
cccagtggcc acagaagagt acggcacggt ggccactaac ctgcaatcgg ccaacaccgc 3780

-continued

```
tcctgctaca gggaccgtca acagtcaagg agccttacct ggcatggtct ggcaggaccg   3840
ggacgtgtac ctgcagggtc ctatctgggc caagattcct cacacggacg gacactttca   3900
tccctcgccg ctgatgggag gctttggact gaaacacccg cctcctcaga tcctgattaa   3960
gaatacacct gttcccgcga atcctccaac taccttcagt ccagctaagt ttgcgtcgtt   4020
catcacgcag tacagcaccg gacaggtcag cgtggaaatt gaatgggagc tgcagaaaga   4080
aaacagcaaa cgctggaacc cagagattca atacacttcc aactacaaca aatctacaaa   4140
tgtggacttt gctgttgaca caaatggcgt ttattctgag cctcgcccca tcggcacccg   4200
ttacctcacc cgtaatctgt aaactagttt gcttgttaat caataaaccg tttaattcgt   4260
ttcagttgaa ctttggtctc tgcgtatttc tttcttatct agtttccatg ctctagaggt   4320
cctgtattag aggtcacgtg agtgttttgc gacattttgc gacaccatgt ggtcacgctg   4380
ggtatttaag cccgagtgag cacgcagggt ctccattttg aagcgggagg tttgaacgcg   4440
cagccgccaa gccgaattct gcagatatcg ggttggggt tgcgcctttt ccaaggcagc   4500
cctgggtttg cgcagggacg cggctgctct gggcgtggtt ccgggaaacg cagcggcgcc   4560
gaccctgggt ctcgcacatt cttcacgtcc gttcgcagcg tcacccggat cttcgccgct   4620
acccttgtgg gccccccggc gacgcttcct gctccgcccc taagtcggga aggttccttg   4680
cggttcgcgg cgtgccggac gtgacaaacg gaagccgcac gtctcactag taccctcgca   4740
gacggacagc gccagggagc aatggcagcg cgccgaccgc gatgggctgt ggccaatagc   4800
ggctgctcag cagggcgcgc cgagagcagc ggccgggaag gggcggtgcg ggaggcgggg   4860
tgtggggcgg tagtgtgggc cctgttcctg cccgcgcggt gttccgcatt ctgcaagcct   4920
ccggagcgca cgtcggcagt cggctccctc gttgaccgaa tcaccgacct ctctccccag   4980
aagctcccgg gagcttgtat atccattttc ggatctgatc agcacgtgtt gacaattaat   5040
catcggcata gtatatcggc atagtataat acgacaaggt gaggaacgcc accatggcca   5100
agcctttgtc tcaagaagaa tccaccctca ttgaaagagc aacggctaca atcaacagca   5160
tccccatctc tgaagactac agcgtcgcca gcgcagctct ctctagcgac ggccgcatct   5220
tcactggtgt caatgtatat cattttactg ggggaccttg tgcagaactc gtggtgctgg   5280
gcactgctgc tgctgcggca gctggcaacc tgacttgtat cgtcgcgatc ggaaatgaga   5340
acaggggcat cttgagcccc tgcggacggt gccgacaggt gcttctcgat ctgcatcctg   5400
ggatcaaagc catagtgaag gacagtgatg gacagccgac ggcagttggg attcgtgaat   5460
tgctgccctc tggttatgtg tgggagggct aagcacttcg tggccgagga gcaggactga   5520
cacgtgctac gagatttcga ttccaccgcc gccttctatg aaaggttggg cttcggaatc   5580
gttttccggg acgccggctg gatgatcctc cagcgcgggg atctcatgct ggagttcttc   5640
gcccacccca acttgtttat tgcagcttat aatggttaca aataaagcaa tagcatcaca   5700
aatttcacaa ataaagcatt tttttcactg cattctagtt gtggtttgtc caaactcatc   5760
aatgtatctt agcgctcact gcccgctttc cagtcgggaa acctgtcgtg ccagctgcat   5820
taatgaatcg gccaacgcgc ggggagaggc ggtttgcgta ttgggcgctc tcctaggcca   5880
gaaatggcgc cggaggcggg aacaaggtgg tggatgagtg ctacatcccc aattacttgc   5940
tccccaaaac ccagcctgag ctccagtggg cgtggactaa tatggaatcc ctatcagtga   6000
tagagacagt atttaagcgc ctgtccctat cagtgataga gatttgaatc tcacggagcg   6060
taaacggttg gtggcgcagc atctgtttaa acgcagacgc aggagcagaa caaagagaat   6120
cagaatccca attctgatgc gccggtgatc agatcaaaaa cttcagccag gtacatggag   6180
```

ctggtcgggt ggctcgtgga caaggggatt acctcggaga agcagtggat tcaggaggac 6240
caggcctcat acatctcctt caatgcggcc tccaactcgc ggtcccaaat caaggctgcc 6300
ttggacaatg cgggaaagat tatgagcctg actaaaaccg cccccgacta cctggtgggc 6360
cagcagcccg tggaggacat ttccagcaat cggatttata aaattttgga actaaacggg 6420
tacgatcccc aatatgcggc ttccgtcttt ctgggatggg ccacgaaaaa gttcggcaag 6480
aggaacacca tctggctgtt tgggcctgca actaccggga agaccaacat cgcggaggcc 6540
atagcccaca ctgtgccctt ctacgggtgc gtaaactgga ccaatgagaa ctttcccttc 6600
aacgactgtg tcgacaagat ggtgatctgg tgggaggagg ggaagatgac cgccaaggtc 6660
gtggagtcgg ccaaagccat tctcggagga agcaaggtgc gcgtggacca gaaatgcaag 6720
tcctcggccc agatagaccc gactcccgtg atcgtcacct ccaacaccaa catgtgcgcc 6780
gtgattgacg ggaactcaac gaccttcgaa caccagcagc cgttgcaaga ccggatgttc 6840
aaatttgaac tcacccgccg tctggatcat gactttggga aggtcaccaa gcaggaagtc 6900
aaagactttt tccggtgggc aaaggatcac gtggttgagg tggagcatga attctacgtc 6960
aaaaagggtg gagccaagaa aagacccgcc cccagtgacg cagatataag tgagcccaaa 7020
cgggtgcgcg agtcagttgc gcagccatcg acgtcagacg cggaagcttc gatcaactac 7080
gcagacaggt accaaaacaa atgttctcgt cacgtgggca tgaatctgat gctgtttccc 7140
tgcagacaat gcgagagaat gaatcagaat tcaaatatct gcttcactca cggacagaaa 7200
gactgtttag agtgctttcc cgtgtcagaa tctcaacccg tttctgtcgt caaaaaggcg 7260
tatcagaaac tgtgctacat tcatcatatc atgggaaagg tgccagacgc ttgcactgcc 7320
tgcgatctgg tcaatgtgga tttggatgac tgcatctttg aacaataaac tagtttgctt 7380
gttaatcaat aaaccgttta attcgtttca gttgaacttt ggtctctgcg tatttctttc 7440
ttatctagtt tccatgctct agagtatacg atatccatca cactggcggc cgctcgacta 7500
gagcggccgc caccgcggtg gagctccagc ttttgttcgc gcgcttggcg taatcatggt 7560
catagctgtt tcctgtgtga aattccacag cctggggtgc ctaattgcgt tgcgctcact 7620
gcccgctttc cagtcgggaa acctgtcgtg ccagctgcat taatgaatcg gccaacgcgc 7680
ggggagaggc ggtttgcgta ttgggcgctc ttccgcttcc tcgctcactg actcgctgcg 7740
ctcggtcgtt cggctgcggc gagcggtatc agctcactca aaggcggtaa tacggttatc 7800
cacagaatca ggggataacg caggaaagaa catgtgagca aaaggccagc aaaaggccag 7860
gaaccgtaaa aaggccgcgt tgctggcgtt tttccatagg ctccgccccc ctgacgagca 7920
tcacaaaaat cgacgctcaa gtcagaggtg gcgaaacccg acaggactat aaagatacca 7980
ggcgtttccc cctggaagct ccctcgtgcg ctctcctgtt ccgaccctgc cgcttaccgg 8040
atacctgtcc gcctttctcc cttcgggaag cgtggcgctt tctcatagct cacgctgtag 8100
gtatctcagt tcggtgtagg tcgttcgctc caagctgggc tgtgtgcacg aaccccccgt 8160
tcagcccgac cgctgcgcct tatccggtaa ctatcgtctt gagtccaacc cggtaagaca 8220
cgacttatcg ccactggcag cagccactgg taacaggatt agcagagcga ggtatgtagg 8280
cggtgctaca gagttcttga agtggtggcc taactacggc tacactagaa gaacagtatt 8340
tggtatctgc gctctgctga agccagttac cttcggaaaa agagttggta gctcttgatc 8400
cggcaaacaa accaccgctg gtagcggtgg tttttttgtt tgcaagcagc agattacgcg 8460
cagaaaaaaa ggatctcaag aagatccttt gatcttttct acggggtctg acgctcagtg 8520

-continued

```
gaacgaaaac tcacgttaag ggattttggt catgagatta tcaaaaagga tcttcaccta   8580
gatcctttta aattaaaaat gaagttttaa atcaatctaa agtatatatg agtaaacttg   8640
gtctgacaga aataataaaa aagccggatt aataatctgg ctttttatat tctctctcta   8700
gtatataaac gcagaaaggc ccacccgaag gtgagccagt gtgactctag tattattaga   8760
aaaactcatc gagcatcaaa tgaaactgca atttattcat atcaggatta tcaataccat   8820
atttttgaaa aagccgtttc tgtaatgaag gagaaaactc accgaggcag ttccaaagaa   8880
tggcaaggtc ctggtaacgg tctgcgattc cgacccgtcc aacatcaata caacctatta   8940
atttcccctc gtcaaaaata aggttatcaa gtgagaaatc accatgagtg acgactgaat   9000
ccggtgagaa tggcaagagc ttgtgcattt ctttccagac ttgttcaaca ggccagccat   9060
tacgctcgtc atcaaaatca ctcgcatcaa ccaaaccgtt attcatgcgt gattgcgcct   9120
gagcaagacg aaatacacga tcgctgttaa aaggacaatt acaaacagga atcgaatgta   9180
accggcgcag gaacacggcc agcgcatcaa caatattttc acctgaatca ggatattctt   9240
ctaatacctg gaaggctgtt ttcccaggaa tcgcggtggt gagtaaccac gcatcatcag   9300
gagtacggat aaaatgcttg atggtcggga gaggcataaa ctccgtcagc cagttgagac   9360
ggaccatctc atctgtaaca tcattggcaa cgctaccttt gccatgtttc agaaacaact   9420
ctggcgcatc gggcttccca tacaagcgat agattgtcgc acctgattgc ccgacattat   9480
cgcgagccca tttataccca tataaatcag cgtccatgtt ggagtttaag cgcggacggg   9540
agcaagacgt ttcccgttga atatggctca taacacccct tgtattactg tttatgtaag   9600
cagacagttt tattgttcat gatgatatat ttttatcttg tgcaatgtaa catcagagat   9660
tttgagacac aacgtggctt tgttgaataa atcgaacttt tgctgagttg aaggatcagc   9720
tctagtaaaa taataaaaaa gccggattaa taatctggct ttttatattc tctctctagt   9780
atataaacgc agaaaggccc acccgaaggt gagccagtgt gacggcacat ttccccgaaa   9840
agtgccacct aaattgtaag cgttaatatt ttgttaaaat tcgcgttaaa tttttgttaa   9900
atcagctcat tttttaacca ataggccgaa atcggcaaaa tcccttataa atcaaaagaa   9960
tagaccgaga tagggttgag tgttgttcca gtttggaaca agagtccact attaaagaac  10020
gtggactcca acgtcaaagg gcgaaaaacc gtctatcagg gcgatggccc actacgtgaa  10080
ccatcaccct aatcaagttt tttggggtcg aggtgccgta aagcactaaa tcggaaccct  10140
aaagggagcc cccgatttag agcttgacgg ggaaagccgg cgaacgtggc gagaaaggaa  10200
gggaagaaag cgaaaggagc gggcgctagg gcgctggcaa gtgtagcggt cacgctgcgc  10260
gtaaccacca cacccgccgc gcttaatgcg ccgctacagg gcgcgtccca ttcgccattc  10320
aggctgcgca actgttggga agggcgatcg gtgcgggcct cttcgctatt acgccagctg  10380
gcgaaagggg gatgtgctgc aaggcgatta agttgggtaa cgccagggtt ttcccagtca  10440
cgacgttgta aaacgacggc cagtgagcgc gcggcgaatt gggtaccggg ccccc       10495
```

<210> SEQ ID NO 22
<211> LENGTH: 10493
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
cctcgagggc tagccattct atttaatctc cctatcagtg atagagatcg cccgagtgag     60
```

-continued

```
cacgcagggt ctccattttg atccctatca gtgatagaga agcgggaggt ttgaacgcgc    120
agccgccatg ccggggtttt acgagattgt gattaaggtc cccagcgacc ttgacgagca    180
tctgcccggc atttctgaca gctttgtgaa ctgggtggcc gagaaggaat gggagttgcc    240
gccagattct gacatggatc tgaatctgat tgagcaggca cccctgaccg tggccgagaa    300
gctgcagcgc gactttctga cggaatggcg ccgtgtgagt aaggccccgg aggctctttt    360
ctttgtgcaa tttgagaagg gagagagcta cttccacatg cacgtgctcg tggaaaccac    420
cggggtgaaa tccatggttt tgggacgttt cctgagtcag attcgcgaaa aactgattca    480
gagaatttac cgcgggatcg agccgacttt gccaaactgg ttcgcggtca caaagaccag    540
aaatggcgcc ggaggcggga acaaggtggt ggatgagtgc tacatcccca attacttgct    600
ccccaaaacc cagcctgagc tccaatgggc atggaccaac atggaacagt acctcagcgc    660
ctgtttgaat ctcacggagc gtaaacggtt ggtggcgcag catctgacgc acgtgtcgca    720
gacgcaggag cagaacaaag agaatcagaa tcccaattct gatgcgccgg tgatcagatc    780
aaaaacttca gccaggtaca tggagctggt cgggtggctc gtggacaagg ggattacctc    840
ggagaagcag tggatccagg aggaccaggc ctcatacatc tccttcaatg cggcctccaa    900
ctcgcggtcc caaatcaagg ctgccttgga caatgcggga aagattatga gcctgactaa    960
aaccgccccc gactacctgg tgggccagca gcccgtggag gacatttcca gcaatcggat   1020
ttataaaatt ttggaactaa acgggtacga tccccaatat gcggcttccg tctttctggg   1080
atgggccacg aaaaagttcg gcaagaggaa caccatctgg ctgtttgggc ctgcaactac   1140
cgggaagacc aacatcgcgg aggccatagc ccacactgtg cccttctacg ggtgcgtaaa   1200
ctggaccaat gagaactttc ccttcaacga ctgtgtcgac aagatggtga tctggtggga   1260
ggaggggaag atgaccgcca aggtcgtgga gtcggccaaa gccattctcg gaggaagcaa   1320
ggtgcgcgtg gaccagaaat gcaagtcctc ggcccagata gacccgactc ccgtgatcgt   1380
cacctccaac accaacatgt gcgccgtgat tgacgggaac tcaacgacct tcgaacacca   1440
gcagccgttg caagaccgga tgttcaaatt tgaactcacc cgccgtctgg atcatgactt   1500
tgggaaggtc accaagcagg aagtcaaaga ctttttccgg tgggcaaagg atcacgtggt   1560
tgaggtggag catgaattct acgtcaaaaa gggtggagcc aagaaaagac ccgcccccag   1620
tgacgcagat ataagtgagc ccaaacgggt gcgcgagtca gttgcgcagc catcgacgtc   1680
agacgcggaa gcttcgatca actacgcaga caggtaccaa aacaaatgtt ctcgtcacgt   1740
gggcatgaat ctgatgctgt ttccctgcag acaatgcgag agaatgaatc agaattcaaa   1800
tatctgcttc actcacggac agaaagactg tttagagtgc tttcccgtgt cagaatctca   1860
acccgtttct gtcgtcaaaa aggcgtatca gaaactgtgc tacattcatc atatcatggg   1920
aaaggtgcca gacgcttgca ctgcctgcga tctggtcaat gtggatttgg atgactgcat   1980
ctttgaacaa taaatgattt aaatcaggta tggctgccga tggttatctt ccagattggc   2040
tcgaggacaa cctctctgag ggcattcgcg agtggtggga cttgaaacct ggagccccga   2100
aacccaaagc caaccagcaa aagcaggacg acggccgggg tctggtgctt cctggctaca   2160
agtacctcgg acccttcaac ggactcgaca agggggagcc cgtcaacgcg gcggacgcag   2220
cggccctcga gcacgacaag gcctacgacc agcagctcaa agcgggtgac aatccgtacc   2280
tgcggtataa ccacgccgac gccgagtttc aggagcgtct gcaagaagat acgtcttttg   2340
gggcaacct cgggcgagca gtcttccagg ccaagaagcg ggttctcgaa cctctcggtc   2400
tggttgagga aggcgctaag acggctcctg gaaagaagag accggtagag caatcacccc   2460
```

aggaaccaga ctcctcttcg ggcatcggca agaaaggcca gcagcccgcg agaaagagac 2520
tcaactttgg gcagactggc gactcagagt cagtgcccga ccctcaacca ctcggagaac 2580
cccccgcagc cccctctggt gtgggatcta atacaatggc tgcaggcggt ggcgctccaa 2640
tggcagacaa taacgaaggc gccgacggag tgggtaacgc ctcaggaaat tggcattgcg 2700
attccacatg gctgggcgac agagtcatca ccaccagcac ccgaacctgg gccctcccca 2760
cctacaacaa ccacctctac aagcaaatct ccagccaatc gggaggcagc accaacgaca 2820
acacctactt cggctacagc acccccctggg ggtattttga ctttaacaga ttccactgcc 2880
acttctcacc acgtgactgg cagcgactca tcaacaacaa ctggggattc cggcccaaga 2940
agctcaactt caagctcttc aacatccagg tcaaggaggt cacgacgaat gatggcacca 3000
cgaccatcgc caataacctt accagcacgg ttcaggtctt tacggactcg gaataccagc 3060
tcccgtacgt cctcggctct gcgcaccagg gctgcctgcc tccgttcccg gcggacgtct 3120
tcatgattcc tcagtacggg tacctgactc tgaacaatgg cagtcaggcc gtgggccgtt 3180
cctccttcta ctgcctggaa tactttcctt ctcaaatgct gagaacgggc aacaactttc 3240
agttcagcta cacgtttgag gacgtgcctt ttcacagcag ctacgcgcac agccaaagcc 3300
tggaccggct gatgaacccc ctcatcgacc agtacctgta ctacctgtct cggactcaga 3360
ccacgagtgg taccgcagga aatcggacgt tgcaattttc tcaggccggg cctagtagca 3420
tggcgaatca ggccaaaaac tggctacccg ggccctgcta ccggcagcaa cgcgtctcca 3480
agacaaccaa tcaaaataac aacagcaact ttgcctggac cggtgccacc aagtatcatc 3540
tgaatggcag agactctctg gtaaatcccg gtcccgctat ggcaacccac aaggacgacg 3600
aagacaaatt ttttccgatg agcggagtct taatatttgg gaaacaggga gctggaaata 3660
gcaacgtgga ccttgacaac gttatgataa ccaacgagga agaaattaaa accaccaacc 3720
cagtggccac agaagagtac ggcacggtgg ccactaacct gcaatcggcc aacaccgctc 3780
ctgctacagg gaccgtcaac agtcaaggag ccttacctgg catggtctgg caggaccggg 3840
acgtgtacct gcagggtcct atctgggcca agattcctca cacggacgga cactttcatc 3900
cctcgccgct gatgggaggc tttggactga aacacccgcc tcctcagatc ctgattaaga 3960
atacacctgt tcccgcgaat cctccaacta ccttcagtcc agctaagttt gcgtcgttca 4020
tcacgcagta cagcaccgga caggtcagcg tggaaattga atgggagctg cagaaagaaa 4080
acagcaaacg ctggaaccca gagattcaat acacttccaa ctacaacaaa tctacaaatg 4140
tggactttgc tgttgacaca aatggcgttt attctgagcc tcgccccatc ggcacccgtt 4200
acctcacccg taatctgtaa actagtttgc ttgttaatca ataaaccgtt taattcgttt 4260
cagttgaact ttggtctctg cgtatttctt tcttatctag tttccatgct ctagaggtcc 4320
tgtattagag gtcacgtgag tgttttgcga cattttgcga caccatgtgg tcacgctggg 4380
tatttaagcc cgagtgagca cgcagggtct ccattttgaa gcgggaggtt tgaacgcgca 4440
gccgccaagc cgaattctgc agatatcggg gttggggttg cgccttttcc aaggcagccc 4500
tgggtttgcg cagggacgcg gctgctctgg gcgtggttcc gggaaacgca gcggcgccga 4560
ccctgggtct cgcacattct tcacgtccgt tcgcagcgtc acccggatct tcgccgctac 4620
ccttgtgggc cccccggcga cgcttcctgc tccgccccta agtcgggaag gttccttgcg 4680
gttcgcggcg tgccggacgt gacaaacgga agccgcacgt ctcactagta ccctcgcaga 4740
cggacagcgc cagggagcaa tggcagcgcg ccgaccgcga tgggctgtgg ccaatagcgg 4800

-continued

```
ctgctcagca gggcgcgccg agagcagcgg ccgggaaggg gcggtgcggg aggcggggtg   4860
tggggcggta gtgtgggccc tgttcctgcc cgcgcggtgt tccgcattct gcaagcctcc   4920
ggagcgcacg tcggcagtcg gctccctcgt tgaccgaatc accgacctct ctccccagaa   4980
gctcccggga gcttgtatat ccattttcgg atctgatcag cacgtgttga caattaatca   5040
tcggcatagt atatcggcat agtataatac gacaaggtga ggaacgccac catggccaag   5100
cctttgtctc aagaagaatc caccctcatt gaaagagcaa cggctacaat caacagcatc   5160
cccatctctg aagactacag cgtcgccagc gcagctctct ctagcgacgg ccgcatcttc   5220
actggtgtca atgtatatca ttttactggg ggaccttgtg cagaactcgt ggtgctgggc   5280
actgctgctg ctgcggcagc tggcaacctg acttgtatcg tcgcgatcgg aaatgagaac   5340
aggggcatct tgagcccctg cggacggtgc cgacaggtgc ttctcgatct gcatcctggg   5400
atcaaagcca tagtgaagga cagtgatgga cagccgacgg cagttgggat tcgtgaattg   5460
ctgccctctg gttatgtgtg ggagggctaa gcacttcgtg gccgaggagc aggactgaca   5520
cgtgctacga gatttcgatt ccaccgccgc cttctatgaa aggttgggct tcggaatcgt   5580
tttccgggac gccggctgga tgatcctcca gcgcggggat ctcatgctgg agttcttcgc   5640
ccaccccaac ttgtttattg cagcttataa tggttacaaa taaagcaata gcatcacaaa   5700
tttcacaaat aaagcatttt tttcactgca ttctagttgt ggtttgtcca aactcatcaa   5760
tgtatcttag cgctcactgc ccgctttcca gtcgggaaac ctgtcgtgcc agctgcatta   5820
atgaatcggc caacgcgcgg ggagaggcgg tttgcgtatt gggcgctctc ctaggccaga   5880
aatggcgccg gaggcgggaa caaggtggtg gatgagtgct acatccccaa ttacttgctc   5940
cccaaaaccc agcctgagct ccagtgggcg tggactaata tggaatccct atcagtgata   6000
gagacagtat ttaagcgcct gtccctatca gtgatagaga tttgaatctc acggagcgta   6060
aacggttggt ggcgcagcat ctgtttaaac gcagacgcag gagcagaaca aagagaatca   6120
gaatcccaat tctgatgcgc cggtgatcag atcaaaaact tcagccaggt acatggagct   6180
ggtcgggtgg ctcgtggaca aggggattac ctcggagaag cagtggattc aggaggacca   6240
ggcctcatac atctccttca atgcggcctc caactcgcgg tcccaaatca aggctgcctt   6300
ggacaatgcg ggaaagatta tgagcctgac taaaaccgcc cccgactacc tggtgggcca   6360
gcagcccgtg gaggacattt ccagcaatcg gatttataaa attttggaac taaacgggta   6420
cgatccccaa tatgcggctt ccgtctttct gggatgggcc acgaaaaagt tcggcaagag   6480
gaacaccatc tggctgtttg ggcctgcaac taccgggaag accaacatcg cggaggccat   6540
agcccacact gtgcccttct acgggtgcgt aaactggacc aatgagaact ttcccttcaa   6600
cgactgtgtc gacaagatgg tgatctggtg ggaggagggg aagatgaccg ccaaggtcgt   6660
ggagtcggcc aaagccattc tcggaggaag caaggtgcgc gtggaccaga aatgcaagtc   6720
ctcggcccag atagacccga ctcccgtgat cgtcacctcc aacaccaaca tgtgcgccgt   6780
gattgacggg aactcaacga ccttcgaaca ccagcagccg ttgcaagacc ggatgttcaa   6840
atttgaactc acccgccgtc tggatcatga ctttgggaag gtcaccaagc aggaagtcaa   6900
agactttttc cggtgggcaa aggatcacgt ggttgaggtg gagcatgaat tctacgtcaa   6960
aaagggtgga gccaagaaaa gacccgcccc cagtgacgca gatataagtg agcccaaacg   7020
ggtgcgcgag tcagttgcgc agccatcgac gtcagacgcg gaagcttcga tcaactacgc   7080
agacaggtac caaaacaaat gttctcgtca cgtgggcatg aatctgatgc tgtttccctg   7140
cagacaatgc gagagaatga atcagaattc aaatatctgc ttcactcacg gacagaaaga   7200
```

-continued

```
ctgtttagag tgctttcccg tgtcagaatc tcaacccgtt tctgtcgtca aaaaggcgta   7260
tcagaaactg tgctacattc atcatatcat gggaaaggtg ccagacgctt gcactgcctg   7320
cgatctggtc aatgtggatt tggatgactg catctttgaa caataaacta gtttgcttgt   7380
taatcaataa accgtttaat tcgtttcagt tgaactttgg tctctgcgta tttctttctt   7440
atctagtttc catgctctag agtatacgat atccatcaca ctggcggccg ctcgactaga   7500
gcggccgcca ccgcggtgga gctccagctt ttgttcgcgc gcttggcgta atcatggtca   7560
tagctgtttc ctgtgtgaaa ttccacagcc tggggtgcct aattgcgttg cgctcactgc   7620
ccgctttcca gtcgggaaac ctgtcgtgcc agctgcatta atgaatcggc caacgcgcgg   7680
ggagaggcgg tttgcgtatt gggcgctctt ccgcttcctc gctcactgac tcgctgcgct   7740
cggtcgttcg gctgcggcga gcggtatcag ctcactcaaa ggcggtaata cggttatcca   7800
cagaatcagg ggataacgca ggaaagaaca tgtgagcaaa aggccagcaa aaggccagga   7860
accgtaaaaa ggccgcgttg ctggcgtttt tccataggct ccgcccccct gacgagcatc   7920
acaaaaatcg acgctcaagt cagaggtggc gaaacccgac aggactataa agataccagg   7980
cgtttccccc tggaagctcc ctcgtgcgct ctcctgttcc gaccctgccg cttaccggat   8040
acctgtccgc ctttctccct tcgggaagcg tggcgctttc tcatagctca cgctgtaggt   8100
atctcagttc ggtgtaggtc gttcgctcca agctgggctg tgtgcacgaa ccccccgttc   8160
agcccgaccg ctgcgcctta tccggtaact atcgtcttga gtccaacccg gtaagacacg   8220
acttatcgcc actggcagca gccactggta acaggattag cagagcgagg tatgtaggcg   8280
gtgctacaga gttcttgaag tggtggccta actacggcta cactagaaga acagtatttg   8340
gtatctgcgc tctgctgaag ccagttacct tcggaaaaag agttggtagc tcttgatccg   8400
gcaaacaaac caccgctggt agcggtggtt tttttgtttg caagcagcag attacgcgca   8460
gaaaaaaagg atctcaagaa gatcctttga tcttttctac ggggtctgac gctcagtgga   8520
acgaaaactc acgttaaggg attttggtca tgagattatc aaaaaggatc ttcacctaga   8580
tccttttaaa ttaaaaatga agttttaaat caatctaaag tatatatgag taaacttggt   8640
ctgacagaaa taataaaaaa gccggattaa taatctggct tttatattc tctctctagt   8700
atataaacgc agaaaggccc acccgaaggt gagccagtgt gactctagta ttattagaaa   8760
aactcatcga gcatcaaatg aaactgcaat ttattcatat caggattatc aataccatat   8820
ttttgaaaaa gccgtttctg taatgaagga gaaaactcac cgaggcagtt ccaaagaatg   8880
gcaaggtcct ggtaacggtc tgcgattccg acccgtccaa catcaataca acctattaat   8940
ttcccctcgt caaaaataag gttatcaagt gagaaatcac catgagtgac gactgaatcc   9000
ggtgagaatg gcaagagctt gtgcatttct ttccagactt gttcaacagg ccagccatta   9060
cgctcgtcat caaaatcact cgcatcaacc aaaccgttat tcatgcgtga ttgcgcctga   9120
gcaagacgaa atacacgatc gctgttaaaa ggacaattac aaacaggaat cgaatgtaac   9180
cggcgcagga acacggccag cgcatcaaca atattttcac ctgaatcagg atattcttct   9240
aatacctgga aggctgtttt cccaggaatc gcggtggtga gtaaccacgc atcatcagga   9300
gtacggataa aatgcttgat ggtcgggaga ggcataaact ccgtcagcca gttgagacgg   9360
accatctcat ctgtaacatc attggcaacg ctacctttgc catgtttcag aaacaactct   9420
ggcgcatcgg gcttcccata caagcgatag attgtcgcac ctgattgccc gacattatcg   9480
cgagcccatt tatacccata taaatcagcg tccatgttgg agtttaagcg cggacgggag   9540
```

caagacgttt cccgttgaat atggctcata acaccccttg tattactgtt tatgtaagca 9600
gacagtttta ttgttcatga tgatatattt ttatcttgtg caatgtaaca tcagagattt 9660
tgagacacaa cgtggctttg ttgaataaat cgaacttttg ctgagttgaa ggatcagctc 9720
tagtaaaata ataaaaaagc cggattaata atctggcttt ttatattctc tctctagtat 9780
ataaacgcag aaaggcccac ccgaaggtga gccagtgtga cggcacattt ccccgaaaag 9840
tgccacctaa attgtaagcg ttaatatttt gttaaaattc gcgttaaatt tttgttaaat 9900
cagctcattt tttaaccaat aggccgaaat cggcaaaatc ccttataaat caaaagaata 9960
gaccgagata gggttgagtg ttgttccagt ttggaacaag agtccactat taaagaacgt 10020
ggactccaac gtcaaagggc gaaaaaccgt ctatcagggc gatggcccac tacgtgaacc 10080
atcaccctaa tcaagttttt tggggtcgag gtgccgtaaa gcactaaatc ggaaccctaa 10140
agggagcccc cgatttagag cttgacgggg aaagccggcg aacgtggcga gaaaggaagg 10200
gaagaaagcg aaaggagcgg gcgctagggc gctggcaagt gtagcggtca cgctgcgcgt 10260
aaccaccaca cccgccgcgc ttaatgcgcc gctacagggc gcgtcccatt cgccattcag 10320
gctgcgcaac tgttgggaag ggcgatcggt gcgggcctct tcgctattac gccagctggc 10380
gaaaggggga tgtgctgcaa ggcgattaag ttgggtaacg ccagggtttt cccagtcacg 10440
acgttgtaaa acgacggcca gtgagcgcgc ggcgaattgg gtaccgggcc ccc 10493

<210> SEQ ID NO 23
<211> LENGTH: 10491
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
cctcgagggc tagccattct ccctatcagt gatagagatc tatttaagcc cgagtgagca 60
cgcagtccct atcagtgata gagaggtctc cattttgaag cgggaggttt gaacgcgcag 120
ccgccatgcc ggggttttac gagattgtga ttaaggtccc cagcgacctt gacgagcatc 180
tgcccggcat ttctgacagc tttgtgaact gggtggccga gaaggaatgg gagttgccgc 240
cagattctga catggatctg aatctgattg agcaggcacc cctgaccgtg gccgagaagc 300
tgcagcgcga ctttctgacg gaatggcgcc gtgtgagtaa ggccccggag gctcttttct 360
ttgtgcaatt tgagaaggga gagagctact tccacatgca cgtgctcgtg gaaaccaccg 420
gggtgaaatc catggttttg ggacgtttcc tgagtcagat tcgcgaaaaa ctgattcaga 480
gaatttaccg cgggatcgag ccgactttgc caaactggtt cgcggtcaca aagaccagaa 540
atggcgccgg aggcgggaac aaggtggtgg atgagtgcta catccccaat tacttgctcc 600
ccaaaaccca gcctgagctc caatgggcat ggaccaacat ggaacagtac ctcagcgcct 660
gtttgaatct cacggagcgt aaacggttgg tggcgcagca tctgacgcac gtgtcgcaga 720
cgcaggagca gaacaaagag aatcagaatc ccaattctga tgcgccggtg atcagatcaa 780
aaacttcagc caggtacatg gagctggtcg ggtggctcgt ggacaagggg attacctcgg 840
agaagcagtg gatccaggag gaccaggcct catacatctc cttcaatgcg gcctccaact 900
cgcggtccca aatcaaggct gccttggaca atgcgggaaa gattatgagc ctgactaaaa 960
ccgcccccga ctacctggtg ggccagcagc ccgtggagga catttccagc aatcggattt 1020
ataaaatttt ggaactaaac gggtacgatc cccaatatgc ggcttccgtc tttctgggat 1080

-continued gggccacgaa aaagttcggc aagaggaaca ccatctggct gtttgggcct gcaactaccg 1140
ggaagaccaa catcgcggag gccatagccc acactgtgcc cttctacggg tgcgtaaact 1200
ggaccaatga gaactttccc ttcaacgact gtgtcgacaa gatggtgatc tggtgggagg 1260
aggggaagat gaccgccaag gtcgtggagt cggccaaagc cattctcgga ggaagcaagg 1320
tgcgcgtgga ccagaaatgc aagtcctcgg cccagataga cccgactccc gtgatcgtca 1380
cctccaacac caacatgtgc gccgtgattg acgggaactc aacgaccttc gaacaccagc 1440
agccgttgca agaccggatg ttcaaatttg aactcacccg ccgtctggat catgactttg 1500
ggaaggtcac caagcaggaa gtcaaagact ttttccggtg ggcaaaggat cacgtggttg 1560
aggtggagca tgaattctac gtcaaaaagg gtggagccaa gaaaagaccc gcccccagtg 1620
acgcagatat aagtgagccc aaacgggtgc gcgagtcagt tgcgcagcca tcgacgtcag 1680
acgcggaagc ttcgatcaac tacgcagaca ggtaccaaaa caaatgttct cgtcacgtgg 1740
gcatgaatct gatgctgttt ccctgcagac aatgcgagag aatgaatcag aattcaaata 1800
tctgcttcac tcacggacag aaagactgtt tagagtgctt tcccgtgtca gaatctcaac 1860
ccgtttctgt cgtcaaaaag gcgtatcaga aactgtgcta cattcatcat atcatgggaa 1920
aggtgccaga cgcttgcact gcctgcgatc tggtcaatgt ggatttggat gactgcatct 1980
ttgaacaata aatgatttaa atcaggtatg gctgccgatg gttatcttcc agattggctc 2040
gaggacaacc tctctgaggg cattcgcgag tggtgggact tgaaacctgg agccccgaaa 2100
cccaaagcca accagcaaaa gcaggacgac ggccggggtc tggtgcttcc tggctacaag 2160
tacctcggac ccttcaacgg actcgacaag ggggagcccg tcaacgcggc ggacgcagcg 2220
gccctcgagc acgacaaggc ctacgaccag cagctcaaag cgggtgacaa tccgtacctg 2280
cggtataacc acgccgacgc cgagtttcag gagcgtctgc aagaagatac gtcttttggg 2340
ggcaacctcg ggcgagcagt cttccaggcc aagaagcggg ttctcgaacc tctcggtctg 2400
gttgaggaag gcgctaagac ggctcctgga aagaagagac cggtagagca atcaccccag 2460
gaaccagact cctcttcggg catcggcaag aaaggccagc agcccgcgag aaagagactc 2520
aactttgggc agactggcga ctcagagtca gtgcccgacc ctcaaccact cggagaaccc 2580
cccgcagccc cctctggtgt gggatctaat acaatggctg caggcggtgg cgctccaatg 2640
gcagacaata acgaaggcgc cgacggagtg ggtaacgcct caggaaattg gcattgcgat 2700
tccacatggc tgggcgacag agtcatcacc accagcaccc gaacctgggc cctccccacc 2760
tacaacaacc acctctacaa gcaaatctcc agccaatcgg gaggcagcac caacgacaac 2820
acctacttcg gctacagcac cccctggggg tattttgact ttaacagatt ccactgccac 2880
ttctcaccac gtgactggca gcgactcatc aacaacaact ggggattccg gcccaagaag 2940
ctcaacttca agctcttcaa catccaggtc aaggaggtca cgacgaatga tggcaccacg 3000
accatcgcca ataaccttac cagcacggtt caggtcttta cggactcgga ataccagctc 3060
ccgtacgtcc tcggctctgc gcaccagggc tgcctgcctc cgttcccggc ggacgtcttc 3120
atgattcctc agtacgggta cctgactctg aacaatggca gtcaggccgt gggccgttcc 3180
tccttctact gcctggaata ctttccttct caaatgctga gaacgggcaa caactttcag 3240
ttcagctaca cgtttgagga cgtgcctttt cacagcagct acgcgcacag ccaaagcctg 3300
gaccggctga tgaacccccct catcgaccag tacctgtact acctgtctcg gactcagacc 3360
acgagtggta ccgcaggaaa tcggacgttg caattttctc aggccgggcc tagtagcatg 3420
gcgaatcagg ccaaaaactg gctacccggg ccctgctacc ggcagcaacg cgtctccaag 3480

-continued acaaccaatc aaaataacaa cagcaacttt gcctggaccg gtgccaccaa gtatcatctg 3540
aatggcagag actctctggt aaatcccggt cccgctatgg caacccacaa ggacgacgaa 3600
gacaaatttt ttccgatgag cggagtctta atatttggga aacagggagc tggaaatagc 3660
aacgtggacc ttgacaacgt tatgataacc aacgaggaag aaattaaaac caccaaccca 3720
gtggccacag aagagtacgg cacggtggcc actaacctgc aatcggccaa caccgctcct 3780
gctacaggga ccgtcaacag tcaaggagcc ttacctggca tggtctggca ggaccgggac 3840
gtgtacctgc agggtcctat ctgggccaag attcctcaca cggacggaca ctttcatccc 3900
tcgccgctga tgggaggctt tggactgaaa cacccgcctc ctcagatcct gattaagaat 3960
acacctgttc ccgcgaatcc tccaactacc ttcagtccag ctaagtttgc gtcgttcatc 4020
acgcagtaca gcaccggaca ggtcagcgtg gaaattgaat gggagctgca gaaagaaaac 4080
agcaaacgct ggaacccaga gattcaatac acttccaact acaacaaatc tacaaatgtg 4140
gactttgctg ttgacacaaa tggcgtttat tctgagcctc gccccatcgg cacccgttac 4200
ctcacccgta atctgtaaac tagtttgctt gttaatcaat aaaccgttta attcgtttca 4260
gttgaacttt ggtctctgcg tatttctttc ttatctagtt tccatgctct agaggtcctg 4320
tattagaggt cacgtgagtg ttttgcgaca ttttgcgaca ccatgtggtc acgctgggta 4380
tttaagcccg agtgagcacg cagggtctcc attttgaagc gggaggtttg aacgcgcagc 4440
cgccaagccg aattctgcag atatcggggt tggggttgcg ccttttccaa ggcagccctg 4500
ggtttgcgca gggacgcggc tgctctgggc gtggttccgg gaaacgcagc ggcgccgacc 4560
ctgggtctcg cacattcttc acgtccgttc gcagcgtcac ccggatcttc gccgctaccc 4620
ttgtgggccc cccggcgacg cttcctgctc cgcccctaag tcgggaaggt tccttgcggt 4680
tcgcggcgtg ccggacgtga caaacggaag ccgcacgtct cactagtacc ctcgcagacg 4740
gacagcgcca gggagcaatg gcagcgcgcc gaccgcgatg ggctgtggcc aatagcggct 4800
gctcagcagg gcgcgccgag agcagcggcc gggaaggggc ggtgcgggag gcggggtgtg 4860
gggcggtagt gtgggccctg ttcctgcccg cgcggtgttc cgcattctgc aagcctccgg 4920
agcgcacgtc ggcagtcggc tccctcgttg accgaatcac cgacctctct ccccagaagc 4980
tcccgggagc ttgtatatcc attttcggat ctgatcagca cgtgttgaca attaatcatc 5040
ggcatagtat atcggcatag tataatacga caaggtgagg aacgccacca tggccaagcc 5100
tttgtctcaa gaagaatcca ccctcattga aagagcaacg gctacaatca acagcatccc 5160
catctctgaa gactacagcg tcgccagcgc agctctctct agcgacggcc gcatcttcac 5220
tggtgtcaat gtatatcatt ttactggggg accttgtgca gaactcgtgg tgctgggcac 5280
tgctgctgct gcggcagctg gcaacctgac ttgtatcgtc gcgatcggaa atgagaacag 5340
gggcatcttg agcccctgcg gacggtgccg acaggtgctt ctcgatctgc atcctgggat 5400
caaagccata gtgaaggaca gtgatggaca gccgacggca gttgggattc gtgaattgct 5460
gccctctggt tatgtgtggg agggctaagc acttcgtggc cgaggagcag gactgacacg 5520
tgctacgaga tttcgattcc accgccgcct tctatgaaag gttgggcttc ggaatcgttt 5580
tccgggacgc cggctggatg atcctccagc gcggggatct catgctggag ttcttcgccc 5640
accccaactt gtttattgca gcttataatg gttacaaata aagcaatagc atcacaaatt 5700
tcacaaataa agcatttttt tcactgcatt ctagttgtgg tttgtccaaa ctcatcaatg 5760
tatcttagcg ctcactgccc gctttccagt cgggaaacct gtcgtgccag ctgcattaat 5820

-continued

```
gaatcggcca acgcgcgggg agaggcggtt tgcgtattgg gcgctctcct aggccagaaa   5880
tggcgccgga ggcgggaaca aggtggtgga tgagtgctac atccccaatt acttgctccc   5940
caaaacccag cctgagctcc agtgggcgtg gactaatatg gaatccctat cagtgataga   6000
gacagtattt aagcgcctgt ccctatcagt gatagagatt tgaatctcac ggagcgtaaa   6060
cggttggtgg cgcagcatct gtttaaacgc agacgcagga gcagaacaaa gagaatcaga   6120
atcccaattc tgatgcgccg gtgatcagat caaaaacttc agccaggtac atggagctgg   6180
tcgggtggct cgtggacaag ggattacct cggagaagca gtggattcag gaggaccagg   6240
cctcatacat ctccttcaat gcggcctcca actcgcggtc ccaaatcaag gctgccttgg   6300
acaatgcggg aaagattatg agcctgacta aaaccgcccc cgactacctg gtgggccagc   6360
agcccgtgga ggacatttcc agcaatcgga tttataaaat tttggaacta aacgggtacg   6420
atccccaata tgcggcttcc gtctttctgg gatgggccac gaaaaagttc ggcaagagga   6480
acaccatctg gctgtttggg cctgcaacta ccgggaagac caacatcgcg gaggccatag   6540
cccacactgt gcccttctac gggtgcgtaa actggaccaa tgagaacttt cccttcaacg   6600
actgtgtcga caagatggtg atctggtggg aggaggggaa gatgaccgcc aaggtcgtgg   6660
agtcggccaa agccattctc ggaggaagca aggtgcgcgt ggaccagaaa tgcaagtcct   6720
cggcccagat agacccgact cccgtgatcg tcacctccaa caccaacatg tgcgccgtga   6780
ttgacgggaa ctcaacgacc ttcgaacacc agcagccgtt gcaagaccgg atgttcaaat   6840
ttgaactcac ccgccgtctg gatcatgact ttgggaaggt caccaagcag gaagtcaaag   6900
actttttccg gtgggcaaag gatcacgtgg ttgaggtgga gcatgaattc tacgtcaaaa   6960
agggtggagc caagaaaaga cccgccccca gtgacgcaga tataagtgag cccaaacggg   7020
tgcgcgagtc agttgcgcag ccatcgacgt cagacgcgga agcttcgatc aactacgcag   7080
acaggtacca aaacaaatgt tctcgtcacg tgggcatgaa tctgatgctg tttccctgca   7140
gacaatgcga gagaatgaat cagaattcaa atatctgctt cactcacgga cagaaagact   7200
gtttagagtg ctttcccgtg tcagaatctc aacccgtttc tgtcgtcaaa aaggcgtatc   7260
agaaactgtg ctacattcat catatcatgg gaaaggtgcc agacgcttgc actgcctgcg   7320
atctggtcaa tgtggatttg gatgactgca tctttgaaca ataaactagt ttgcttgtta   7380
atcaataaac cgtttaattc gtttcagttg aactttggtc tctgcgtatt tctttcttat   7440
ctagtttcca tgctctagag tatacgatat ccatcacact ggcggccgct cgactagagc   7500
ggccgccacc gcggtggagc tccagctttt gttcgcgcgc ttggcgtaat catggtcata   7560
gctgtttcct gtgtgaaatt ccacagcctg gggtgcctaa ttgcgttgcg ctcactgccc   7620
gctttccagt cgggaaacct gtcgtgccag ctgcattaat gaatcggcca acgcgcgggg   7680
agaggcggtt tgcgtattgg gcgctcttcc gcttcctcgc tcactgactc gctgcgctcg   7740
gtcgttcggc tgcggcgagc ggtatcagct cactcaaagg cggtaatacg gttatccaca   7800
gaatcagggg ataacgcagg aaagaacatg tgagcaaaag gccagcaaaa ggccaggaac   7860
cgtaaaaagg ccgcgttgct ggcgtttttc cataggctcc gcccccctga cgagcatcac   7920
aaaaatcgac gctcaagtca gaggtggcga aacccgacag gactataaag ataccaggcg   7980
tttccccctg gaagctccct cgtgcgctct cctgttccga ccctgccgct taccggatac   8040
ctgtccgcct ttctcccttc gggaagcgtg gcgctttctc atagctcacg ctgtaggtat   8100
ctcagttcgg tgtaggtcgt tcgctccaag ctgggctgtg tgcacgaacc ccccgttcag   8160
cccgaccgct gcgccttatc cggtaactat cgtcttgagt ccaacccggt aagacacgac   8220
```

```
ttatcgccac tggcagcagc cactggtaac aggattagca gagcgaggta tgtaggcggt   8280
gctacagagt tcttgaagtg gtggcctaac tacggctaca ctagaagaac agtatttggt   8340
atctgcgctc tgctgaagcc agttaccttc ggaaaaagag ttggtagctc ttgatccggc   8400
aaacaaacca ccgctggtag cggtggtttt tttgtttgca agcagcagat tacgcgcaga   8460
aaaaaaggat ctcaagaaga tcctttgatc ttttctacgg ggtctgacgc tcagtggaac   8520
gaaaactcac gttaagggat tttggtcatg agattatcaa aaaggatctt cacctagatc   8580
cttttaaatt aaaaatgaag ttttaaatca atctaaagta tatatgagta aacttggtct   8640
gacagaaata ataaaaaagc cggattaata atctggcttt ttatattctc tctctagtat   8700
ataaacgcag aaaggcccac ccgaaggtga gccagtgtga ctctagtatt attagaaaaa   8760
ctcatcgagc atcaaatgaa actgcaattt attcatatca ggattatcaa taccatattt   8820
ttgaaaaagc cgtttctgta atgaaggaga aaactcaccg aggcagttcc aaagaatggc   8880
aaggtcctgg taacggtctg cgattccgac ccgtccaaca tcaatacaac ctattaattt   8940
cccctcgtca aaaataaggt tatcaagtga gaaatcacca tgagtgacga ctgaatccgg   9000
tgagaatggc aagagcttgt gcatttcttt ccagacttgt tcaacaggcc agccattacg   9060
ctcgtcatca aaatcactcg catcaaccaa accgttattc atgcgtgatt gcgcctgagc   9120
aagacgaaat acacgatcgc tgttaaaagg acaattacaa acaggaatcg aatgtaaccg   9180
gcgcaggaac acggccagcg catcaacaat attttcacct gaatcaggat attcttctaa   9240
tacctggaag gctgttttcc caggaatcgc ggtggtgagt aaccacgcat catcaggagt   9300
acggataaaa tgcttgatgg tcgggagagg cataaactcc gtcagccagt tgagacggac   9360
catctcatct gtaacatcat tggcaacgct acctttgcca tgtttcagaa acaactctgg   9420
cgcatcgggc ttcccataca agcgatagat tgtcgcacct gattgcccga cattatcgcg   9480
agcccattta tacccatata aatcagcgtc catgttggag tttaagcgcg gacgggagca   9540
agacgtttcc cgttgaatat ggctcataac accccttgta ttactgttta tgtaagcaga   9600
cagttttatt gttcatgatg atatattttt atcttgtgca atgtaacatc agagattttg   9660
agacacaacg tggctttgtt gaataaatcg aacttttgct gagttgaagg atcagctcta   9720
gtaaaataat aaaaaagccg gattaataat ctggcttttt atattctctc tctagtatat   9780
aaacgcagaa aggcccaccc gaaggtgagc cagtgtgacg gcacatttcc ccgaaaagtg   9840
ccacctaaat tgtaagcgtt aatattttgt taaaattcgc gttaaatttt tgttaaatca   9900
gctcattttt taaccaatag gccgaaatcg gcaaaatccc ttataaatca aaagaataga   9960
ccgagatagg gttgagtgtt gttccagttt ggaacaagag tccactatta aagaacgtgg  10020
actccaacgt caaagggcga aaaaccgtct atcagggcga tggcccacta cgtgaaccat  10080
caccctaatc aagttttttg gggtcgaggt gccgtaaagc actaaatcgg aaccctaaag  10140
ggagcccccg atttagagct tgacggggaa agccggcgaa cgtggcgaga aaggaaggga  10200
agaaagcgaa aggagcgggc gctagggcgc tggcaagtgt agcggtcacg ctgcgcgtaa  10260
ccaccacacc cgccgcgctt aatgcgccgc tacagggcgc gtcccattcg ccattcaggc  10320
tgcgcaactg ttgggaaggg cgatcggtgc gggcctcttc gctattacgc cagctggcga  10380
aagggggatg tgctgcaagg cgattaagtt gggtaacgcc agggttttcc cagtcacgac  10440
gttgtaaaac gacggccagt gagcgcgcgg cgaattgggt accgggcccc c          10491
```

<210> SEQ ID NO 24

<211> LENGTH: 7567
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24

```
cctcgagggc tagccattct atttaatctc cctatcagtg atagagatct ccctatcagt     60

gatagagatc gcccgagtga gcacgcaggg tctccatttt gaagcgggag gtttgaacgc    120

gcagccgcca tgccggggtt ttacgagatt gtgattaagg tccccagcga ccttgacgag    180

catctgcccg gcatttctga cagctttgtg aactgggtgg ccgagaagga atgggagttg    240

ccgccagatt ctgacatgga tctgaatctg attgagcagg cacccctgac cgtggccgag    300

aagctgcagc gcgactttct gacggaatgg cgccgtgtga gtaaggcccc ggaggctctt    360

ttctttgtgc aatttgagaa gggagagagc tacttccaca tgcacgtgct cgtggaaacc    420

accggggtga aatccatggt tttgggacgt ttcctgagtc agattcgcga aaaactgatt    480

cagagaattt accgcgggat cgagccgact ttgccaaact ggttcgcggt cacaaagacc    540

agaaatggcg ccggaggcgg gaacaaggtg gtggatgagt gctacatccc caattacttg    600

ctccccaaaa cccagcctga gctccagtgg gcgtggacta atatggaaca gtatttaagg    660

taagttccct atcagtgata gagatctccc tatcagtgat agagatactg acatccactt    720

tgcctttctc tccacagcgc ctgtttgaat ctcacggagc gtaaacggtt ggtggcgcag    780

catctgacgc acgtgtcgca gacgcaggag cagaacaaag agaatcagaa tcccaattct    840

gatgcgccgg tgatcagatc aaaaacttca gccaggtaca tggagctggt cgggtggctc    900

gtggacaagg ggattacctc ggagaagcag tggatccagg aggaccaggc ctcatacatc    960

tccttcaatg cggcctccaa ctcgcggtcc caaatcaagg ctgccttgga caatgcggga   1020

aagattatga gcctgactaa aaccgccccc gactacctgg tgggccagca gcccgtggag   1080

gacatttcca gcaatcggat ttataaaatt ttggaactaa acgggtacga tccccaatat   1140

gcggcttccg tctttctggg atgggccacg aaaaagttcg gcaagaggaa caccatctgg   1200

ctgtttgggc ctgcaactac cgggaagacc aacatcgcgg aggccatagc ccacactgtg   1260

cccttctacg ggtgcgtaaa ctggaccaat gagaactttc ccttcaacga ctgtgtcgac   1320

aagatggtga tctggtggga ggaggggaag atgaccgcca aggtcgtgga gtcggccaaa   1380

gccattctcg gaggaagcaa ggtgcgcgtg gaccagaaat gcaagtcctc ggcccagata   1440

gacccgactc ccgtgatcgt cacctccaac accaacatgt gcgccgtgat tgacgggaac   1500

tcaacgacct tcgaacacca gcagccgttg caagaccgga tgttcaaatt tgaactcacc   1560

cgccgtctgg atcatgactt tgggaaggtc accaagcagg aagtcaaaga ctttttccgg   1620

tgggcaaagg atcacgtggt tgaggtggag catgaattct acgtcaaaaa gggtggagcc   1680

aagaaaagac ccgcccccag tgacgcagat ataagtgagc ccaaacgggt gcgcgagtca   1740

gttgcgcagc catcgacgtc agacgcggaa gcttcgatca actacgcaga caggtaccaa   1800

aacaaatgtt ctcgtcacgt gggcatgaat ctgatgctgt ttccctgcag acaatgcgag   1860

agaatgaatc agaattcaaa tatctgcttc actcacggac agaaagactg tttagagtgc   1920

tttcccgtgt cagaatctca acccgtttct gtcgtcaaaa aggcgtatca gaaactgtgc   1980

tacattcatc atatcatggg aaaggtgcca gacgcttgca ctgcctgcga tctggtcaat   2040

gtggatttgg atgactgcat ctttgaacaa taaatgattt aaatcaggta tggctgccga   2100
```

-continued tggttatctt ccagattggc tcgaggacaa cctctctgag ggcattcgcg agtggtggga 2160
cttgaaacct ggagccccga aacccaaagc caaccagcaa aagcaggacg acggccgggg 2220
tctggtgctt cctggctaca agtacctcgg acccttcaac ggactcgaca agggggagcc 2280
cgtcaacgcg gcggacgcag cggccctcga gcacgacaag gcctacgacc agcagctcaa 2340
agcgggtgac aatccgtacc tgcggtataa ccacgccgac gccgagtttc aggagcgtct 2400
gcaagaagat acgtcttttg ggggcaacct cgggcgagca gtcttccagg ccaagaagcg 2460
ggttctcgaa cctctcggtc tggttgagga aggcgctaag acggctcctg gaaagaagag 2520
accggtagag caatcacccc aggaaccaga ctcctcttcg ggcatcggca agaaaggcca 2580
gcagcccgcg agaaagagac tcaactttgg gcagactggc gactcagagt cagtgcccga 2640
ccctcaacca ctcggagaac ccccgcagc cccctctggt gtgggatcta atacaatggc 2700
tgcaggcggt ggcgctccaa tggcagacaa taacgaaggc gccgacggag tgggtaacgc 2760
ctcaggaaat tggcattgcg attccacatg gctgggcgac agagtcatca ccaccagcac 2820
ccgaacctgg gccctcccca cctacaacaa ccacctctac aagcaaatct ccagccaatc 2880
gggaggcagc accaacgaca acacctactt cggctacagc accccctggg ggtattttga 2940
ctttaacaga ttccactgcc acttctcacc acgtgactgg cagcgactca tcaacaacaa 3000
ctggggattc cggcccaaga agctcaactt caagctcttc aacatccagg tcaaggaggt 3060
cacgacgaat gatggcacca cgaccatcgc caataacctt accagcacgg ttcaggtctt 3120
tacggactcg gaataccagc tcccgtacgt cctcggctct gcgcaccagg gctgcctgcc 3180
tccgttcccg gcggacgtct tcatgattcc tcagtacggg tacctgactc tgaacaatgg 3240
cagtcaggcc gtgggccgtt cctccttcta ctgcctggaa tactttcctt ctcaaatgct 3300
gagaacgggc aacaactttc agttcagcta cacgtttgag gacgtgcctt ttcacagcag 3360
ctacgcgcac agccaaagcc tggaccggct gatgaacccc ctcatcgacc agtacctgta 3420
ctacctgtct cggactcaga ccacgagtgg taccgcagga aatcggacgt tgcaattttc 3480
tcaggccggg cctagtagca tggcgaatca ggccaaaaac tggctacccg ggccctgcta 3540
ccggcagcaa cgcgtctcca agacaaccaa tcaaaataac aacagcaact ttgcctggac 3600
cggtgccacc aagtatcatc tgaatggcag agactctctg gtaaatcccg gtcccgctat 3660
ggcaacccac aaggacgacg aagacaaatt ttttccgatg agcggagtct taatatttgg 3720
gaaacaggga gctggaaata gcaacgtgga ccttgacaac gttatgataa ccaacgagga 3780
agaaattaaa accaccaacc cagtggccac agaagagtac ggcacggtgg ccactaacct 3840
gcaatcggcc aacaccgctc ctgctacagg gaccgtcaac agtcaaggag ccttacctgg 3900
catggtctgg caggaccggg acgtgtacct gcagggtcct atctgggcca agattcctca 3960
cacggacgga cactttcatc cctcgccgct gatgggaggc tttggactga aacacccgcc 4020
tcctcagatc ctgattaaga atacacctgt tcccgcgaat cctccaacta ccttcagtcc 4080
agctaagttt gcgtcgttca tcacgcagta cagcaccgga caggtcagcg tggaaattga 4140
atgggagctg cagaaagaaa acagcaaacg ctggaaccca gagattcaat acacttccaa 4200
ctacaacaaa tctacaaatg tggactttgc tgttgacaca aatggcgttt attctgagcc 4260
tcgccccatc ggcacccgtt acctcacccg taatctgtaa actagtttgc ttgttaatca 4320
ataaaccgtt taattcgttt cagttgaact ttggtctctg cgtatttctt tcttatctag 4380
tttccatgct ctagaggtcc tgtattagag gtcacgtgag tgttttgcga cattttgcga 4440
caccatgtgg tcacgctggg tatttaagcc cgagtgagca cgcagggtct ccattttgaa 4500
gcgggaggtt tgaacgcgca gccgccaagc cgaattctgc agatatccat cacactggcg 4560
gccgctcgac tagagcggcc gccaccgcgg tggagctcca gcttttgttc gcgcgcttgg 4620
cgtaatcatg gtcatagctg tttcctgtgt gaaattccac agcctggggt gcctaattgc 4680
gttgcgctca ctgcccgctt tccagtcggg aaacctgtcg tgccagctgc attaatgaat 4740
cggccaacgc gcggggagag gcggtttgcg tattgggcgc tcttccgctt cctcgctcac 4800
tgactcgctg cgctcggtcg ttcggctgcg gcgagcggta tcagctcact caaaggcggt 4860
aatacggtta tccacagaat caggggataa cgcaggaaag aacatgtgag caaaaggcca 4920
gcaaaaggcc aggaaccgta aaaaggccgc gttgctggcg tttttccata ggctccgccc 4980
ccctgacgag catcacaaaa atcgacgctc aagtcagagg tggcgaaacc cgacaggact 5040
ataaagatac caggcgtttc cccctggaag ctccctcgtg cgctctcctg ttccgaccct 5100
gccgcttacc ggatacctgt ccgcctttct cccttcggga agcgtggcgc tttctcatag 5160
ctcacgctgt aggtatctca gttcggtgta ggtcgttcgc tccaagctgg gctgtgtgca 5220
cgaacccccc gttcagcccg accgctgcgc cttatccggt aactatcgtc ttgagtccaa 5280
cccggtaaga cacgacttat cgccactggc agcagccact ggtaacagga ttagcagagc 5340
gaggtatgta ggcggtgcta cagagttctt gaagtggtgg cctaactacg gctacactag 5400
aagaacagta tttggtatct gcgctctgct gaagccagtt accttcggaa aaagagttgg 5460
tagctcttga tccggcaaac aaaccaccgc tggtagcggt ggtttttttg tttgcaagca 5520
gcagattacg cgcagaaaaa aaggatctca agaagatcct ttgatctttt ctacggggtc 5580
tgacgctcag tggaacgaaa actcacgtta agggattttg gtcatgagat tatcaaaaag 5640
gatcttcacc tagatccttt taaattaaaa atgaagtttt aaatcaatct aaagtatata 5700
tgagtaaact tggtctgaca gaaataataa aaaagccgga ttaataatct ggctttttat 5760
attctctctc tagtatataa acgcagaaag gcccacccga aggtgagcca gtgtgactct 5820
agtattatta gaaaaactca tcgagcatca aatgaaactg caatttattc atatcaggat 5880
tatcaatacc atatttttga aaaagccgtt tctgtaatga aggagaaaac tcaccgaggc 5940
agttccaaag aatggcaagg tcctggtaac ggtctgcgat tccgacccgt ccaacatcaa 6000
tacaacctat taatttcccc tcgtcaaaaa taaggttatc aagtgagaaa tcaccatgag 6060
tgacgactga atccggtgag aatggcaaga gcttgtgcat ttctttccag acttgttcaa 6120
caggccagcc attacgctcg tcatcaaaat cactcgcatc aaccaaaccg ttattcatgc 6180
gtgattgcgc ctgagcaaga cgaaatacac gatcgctgtt aaaaggacaa ttacaaacag 6240
gaatcgaatg taaccggcgc aggaacacgg ccagcgcatc aacaatattt tcacctgaat 6300
caggatattc ttctaatacc tggaaggctg ttttcccagg aatcgcggtg gtgagtaacc 6360
acgcatcatc aggagtacgg ataaaatgct tgatggtcgg gagaggcata aactccgtca 6420
gccagttgag acggaccatc tcatctgtaa catcattggc aacgctacct ttgccatgtt 6480
tcagaaacaa ctctggcgca tcgggcttcc catacaagcg atagattgtc gcacctgatt 6540
gcccgacatt atcgcgagcc catttatacc catataaatc agcgtccatg ttggagttta 6600
agcgcggacg ggagcaagac gtttcccgtt gaatatggct cataacaccc cttgtattac 6660
tgtttatgta agcagacagt tttattgttc atgatgatat atttttatct tgtgcaatgt 6720
aacatcagag attttgagac acaacgtggc tttgttgaat aaatcgaact tttgctgagt 6780
tgaaggatca gctctagtaa aataataaaa aagccggatt aataatctgg ctttttatat 6840
tctctctcta gtatataaac gcagaaaggc ccacccgaag gtgagccagt gtgacggcac 6900
atttccccga aaagtgccac ctaaattgta agcgttaata ttttgttaaa attcgcgtta 6960
aatttttgtt aaatcagctc attttttaac caataggccg aaatcggcaa aatcccttat 7020
aaatcaaaag aatagaccga gatagggttg agtgttgttc cagtttggaa caagagtcca 7080
ctattaaaga acgtggactc caacgtcaaa gggcgaaaaa ccgtctatca gggcgatggc 7140
ccactacgtg aaccatcacc ctaatcaagt tttttggggt cgaggtgccg taaagcacta 7200
aatcggaacc ctaaagggag cccccgattt agagcttgac ggggaaagcc ggcgaacgtg 7260
gcgagaaagg aagggaagaa agcgaaagga gcgggcgcta gggcgctggc aagtgtagcg 7320
gtcacgctgc gcgtaaccac cacacccgcc gcgcttaatg cgccgctaca gggcgcgtcc 7380
cattcgccat tcaggctgcg caactgttgg gaagggcgat cggtgcgggc ctcttcgcta 7440
ttacgccagc tggcgaaagg gggatgtgct gcaaggcgat taagttgggt aacgccaggg 7500
ttttcccagt cacgacgttg taaaacgacg gccagtgagc gcgcggcgaa ttgggtaccg 7560
ggcccc 7567

<210> SEQ ID NO 25
<211> LENGTH: 7567
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
cctcgagggc tagccattct atttaatctc cctatcagtg atagagatct ccctatcagt 60
gatagagatc gcccgagtga gcacgcaggg tctccatttt gaagcgggag gtttgaacgc 120
gcagccgcca tgccggggtt ttacgagatt gtgattaagg tccccagcga ccttgacgag 180
catctgcccg gcatttctga cagctttgtg aactgggtgg ccgagaagga atgggagttg 240
ccgccagatt ctgacatgga tctgaatctg attgagcagg caccccctgac cgtggccgag 300 aagctgcagc gcgactttct gacggaatgg cgccgtgtga gtaaggcccc ggaggctctt 360
ttctttgtgc aatttgagaa gggagagagc tacttccaca tgcacgtgct cgtggaaacc 420
accggggtga aatccatggt tttgggacgt ttcctgagtc agattcgcga aaaactgatt 480
cagagaattt accgcgggat cgagccgact ttgccaaact ggttcgcggt cacaaagacc 540
agaaatggcg ccggaggcgg gaacaaggtg gtggatgagt gctacatccc caattacttg 600
ctccccaaaa cccagcctga gctccagtgg gcgtggacta atatggaaca gtatttaagc 660
gcctgtttga atctcacgga aaggtaagtt ccctatcagt gatagagatc tccctatcag 720
tgatagagat actgacatcc actttgcctt tctctccaca ggaaacggtt ggtggcgcag 780
catctgacgc acgtgtcgca gacgcaggag cagaacaaag agaatcagaa tcccaattct 840
gatgcgccgg tgatcagatc aaaaacttca gccaggtaca tggagctggt cgggtggctc 900
gtggacaagg ggattacctc ggagaagcag tggatccagg aggaccaggc ctcatacatc 960
tccttcaatg cggcctccaa ctcgcggtcc caaatcaagg ctgccttgga caatgcggga 1020
aagattatga gcctgactaa aaccgccccc gactacctgg tgggccagca gcccgtggag 1080
gacatttcca gcaatcggat ttataaaatt ttggaactaa acgggtacga tccccaatat 1140
gcggcttccg tctttctggg atgggccacg aaaaagttcg gcaagaggaa caccatctgg 1200
ctgtttgggc ctgcaactac cgggaagacc aacatcgcgg aggccatagc ccacactgtg 1260

-continued

```
cccttctacg ggtgcgtaaa ctggaccaat gagaactttc ccttcaacga ctgtgtcgac   1320
aagatggtga tctggtggga ggaggggaag atgaccgcca aggtcgtgga gtcggccaaa   1380
gccattctcg gaggaagcaa ggtgcgcgtg gaccagaaat gcaagtcctc ggcccagata   1440
gacccgactc ccgtgatcgt cacctccaac accaacatgt gcgccgtgat tgacgggaac   1500
tcaacgacct tcgaacacca gcagccgttg caagaccgga tgttcaaatt tgaactcacc   1560
cgccgtctgg atcatgactt tgggaaggtc accaagcagg aagtcaaaga ctttttccgg   1620
tgggcaaagg atcacgtggt tgaggtggag catgaattct acgtcaaaaa gggtggagcc   1680
aagaaaagac ccgcccccag tgacgcagat ataagtgagc ccaaacgggt gcgcgagtca   1740
gttgcgcagc catcgacgtc agacgcggaa gcttcgatca actacgcaga caggtaccaa   1800
aacaaatgtt ctcgtcacgt gggcatgaat ctgatgctgt ttccctgcag acaatgcgag   1860
agaatgaatc agaattcaaa tatctgcttc actcacggac agaaagactg tttagagtgc   1920
tttcccgtgt cagaatctca acccgtttct gtcgtcaaaa aggcgtatca gaaactgtgc   1980
tacattcatc atatcatggg aaaggtgcca gacgcttgca ctgcctgcga tctggtcaat   2040
gtggatttgg atgactgcat ctttgaacaa taaatgattt aaatcaggta tggctgccga   2100
tggttatctt ccagattggc tcgaggacaa cctctctgag ggcattcgcg agtggtggga   2160
cttgaaacct ggagccccga aacccaaagc caaccagcaa aagcaggacg acggccgggg   2220
tctggtgctt cctggctaca agtacctcgg acccttcaac ggactcgaca agggggagcc   2280
cgtcaacgcg gcggacgcag cggccctcga gcacgacaag gcctacgacc agcagctcaa   2340
agcgggtgac aatccgtacc tgcggtataa ccacgccgac gccgagtttc aggagcgtct   2400
gcaagaagat acgtcttttg gggcaacct cgggcgagca gtcttccagg ccaagaagcg   2460
ggttctcgaa cctctcggtc tggttgagga aggcgctaag acggctcctg gaaagaagag   2520
accggtagag caatcacccc aggaaccaga ctcctcttcg ggcatcggca agaaaggcca   2580
gcagcccgcg agaaagagac tcaactttgg gcagactggc gactcagagt cagtgcccga   2640
ccctcaacca ctcggagaac cccccgcagc cccctctggt gtgggatcta atacaatggc   2700
tgcaggcggt ggcgctccaa tggcagacaa taacgaaggc gccgacggag tgggtaacgc   2760
ctcaggaaat tggcattgcg attccacatg gctgggcgac agagtcatca ccaccagcac   2820
ccgaacctgg gccctcccca cctacaacaa ccacctctac aagcaaatct ccagccaatc   2880
gggaggcagc accaacgaca acacctactt cggctacagc accccctggg ggtattttga   2940
ctttaacaga ttccactgcc acttctcacc acgtgactgg cagcgactca tcaacaacaa   3000
ctggggattc cggcccaaga agctcaactt caagctcttc aacatccagg tcaaggaggt   3060
cacgacgaat gatggcacca cgaccatcgc caataacctt accagcacgg ttcaggtctt   3120
tacggactcg gaataccagc tcccgtacgt cctcggctct gcgcaccagg gctgcctgcc   3180
tccgttcccg gcggacgtct tcatgattcc tcagtacggg tacctgactc tgaacaatgg   3240
cagtcaggcc gtgggccgtt cctccttcta ctgcctggaa tactttcctt ctcaaatgct   3300
gagaacgggc aacaactttc agttcagcta cacgtttgag gacgtgcctt ttcacagcag   3360
ctacgcgcac agccaaagcc tggaccggct gatgaacccc ctcatcgacc agtacctgta   3420
ctacctgtct cggactcaga ccacgagtgg taccgcagga aatcggacgt tgcaattttc   3480
tcaggccggg cctagtagca tggcgaatca ggccaaaaac tggctacccg ggccctgcta   3540
ccggcagcaa cgcgtctcca agacaaccaa tcaaaataac aacagcaact ttgcctggac   3600
cggtgccacc aagtatcatc tgaatggcag agactctctg gtaaatcccg gtcccgctat   3660
```

-continued

```
ggcaacccac aaggacgacg aagacaaatt ttttccgatg agcggagtct taatatttgg   3720
gaaacaggga gctggaaata gcaacgtgga ccttgacaac gttatgataa ccaacgagga   3780
agaaattaaa accaccaacc cagtggccac agaagagtac ggcacggtgg ccactaacct   3840
gcaatcggcc aacaccgctc ctgctacagg gaccgtcaac agtcaaggag ccttacctgg   3900
catggtctgg caggaccggg acgtgtacct gcagggtcct atctgggcca agattcctca   3960
cacggacgga cactttcatc cctcgccgct gatgggaggc tttggactga aacacccgcc   4020
tcctcagatc ctgattaaga atacacctgt tcccgcgaat cctccaacta ccttcagtcc   4080
agctaagttt gcgtcgttca tcacgcagta cagcaccgga caggtcagcg tggaaattga   4140
atgggagctg cagaaagaaa acagcaaacg ctggaaccca gagattcaat acacttccaa   4200
ctacaacaaa tctacaaatg tggactttgc tgttgacaca aatggcgttt attctgagcc   4260
tcgccccatc ggcacccgtt acctcacccg taatctgtaa actagtttgc ttgttaatca   4320
ataaaccgtt taattcgttt cagttgaact ttggtctctg cgtatttctt tcttatctag   4380
tttccatgct ctagaggtcc tgtattagag gtcacgtgag tgttttgcga cattttgcga   4440
caccatgtgg tcacgctggg tatttaagcc cgagtgagca cgcagggtct ccattttgaa   4500
gcgggaggtt tgaacgcgca gccgccaagc cgaattctgc agatatccat cacactggcg   4560
gccgctcgac tagagcggcc gccaccgcgg tggagctcca gcttttgttc gcgcgcttgg   4620
cgtaatcatg gtcatagctg tttcctgtgt gaaattccac agcctggggt gcctaattgc   4680
gttgcgctca ctgcccgctt tccagtcggg aaacctgtcg tgccagctgc attaatgaat   4740
cggccaacgc gcggggagag gcggtttgcg tattgggcgc tcttccgctt cctcgctcac   4800
tgactcgctg cgctcggtcg ttcggctgcg gcgagcggta tcagctcact caaaggcggt   4860
aatacggtta tccacagaat caggggataa cgcaggaaag aacatgtgag caaaaggcca   4920
gcaaaaggcc aggaaccgta aaaaggccgc gttgctggcg tttttccata ggctccgccc   4980
ccctgacgag catcacaaaa atcgacgctc aagtcagagg tggcgaaacc cgacaggact   5040
ataaagatac caggcgtttc cccctggaag ctccctcgtg cgctctcctg ttccgaccct   5100
gccgcttacc ggatacctgt ccgcctttct cccttcggga agcgtggcgc tttctcatag   5160
ctcacgctgt aggtatctca gttcggtgta ggtcgttcgc tccaagctgg gctgtgtgca   5220
cgaacccccc gttcagcccg accgctgcgc cttatccggt aactatcgtc ttgagtccaa   5280
cccggtaaga cacgacttat cgccactggc agcagccact ggtaacagga ttagcagagc   5340
gaggtatgta ggcggtgcta cagagttctt gaagtggtgg cctaactacg gctacactag   5400
aagaacagta tttggtatct gcgctctgct gaagccagtt accttcggaa aaagagttgg   5460
tagctcttga tccggcaaac aaaccaccgc tggtagcggt ggtttttttg tttgcaagca   5520
gcagattacg cgcagaaaaa aaggatctca agaagatcct ttgatctttt ctacggggtc   5580
tgacgctcag tggaacgaaa actcacgtta agggattttg gtcatgagat tatcaaaaag   5640
gatcttcacc tagatccttt taaattaaaa atgaagtttt aaatcaatct aaagtatata   5700
tgagtaaact tggtctgaca gaaataataa aaaagccgga ttaataatct ggctttttat   5760
attctctctc tagtatataa acgcagaaag gcccacccga aggtgagcca gtgtgactct   5820
agtattatta gaaaaactca tcgagcatca aatgaaactg caatttattc atatcaggat   5880
tatcaatacc atatttttga aaaagccgtt tctgtaatga aggagaaaac tcaccgaggc   5940
agttccaaag aatggcaagg tcctggtaac ggtctgcgat tccgacccgt ccaacatcaa   6000
```

```
tacaacctat taatttcccc tcgtcaaaaa taaggttatc aagtgagaaa tcaccatgag   6060

tgacgactga atccggtgag aatggcaaga gcttgtgcat ttctttccag acttgttcaa   6120

caggccagcc attacgctcg tcatcaaaat cactcgcatc aaccaaaccg ttattcatgc   6180

gtgattgcgc ctgagcaaga cgaaatacac gatcgctgtt aaaaggacaa ttacaaacag   6240

gaatcgaatg taaccggcgc aggaacacgg ccagcgcatc aacaatattt tcacctgaat   6300

caggatattc ttctaatacc tggaaggctg ttttcccagg aatcgcggtg gtgagtaacc   6360

acgcatcatc aggagtacgg ataaaatgct tgatggtcgg gagaggcata aactccgtca   6420

gccagttgag acggaccatc tcatctgtaa catcattggc aacgctacct ttgccatgtt   6480

tcagaaacaa ctctggcgca tcgggcttcc catacaagcg atagattgtc gcacctgatt   6540

gcccgacatt atcgcgagcc catttatacc catataaatc agcgtccatg ttggagttta   6600

agcgcggacg ggagcaagac gtttcccgtt gaatatggct cataacaccc cttgtattac   6660

tgtttatgta agcagacagt tttattgttc atgatgatat atttttatct tgtgcaatgt   6720

aacatcagag attttgagac acaacgtggc tttgttgaat aaatcgaact tttgctgagt   6780

tgaaggatca gctctagtaa aataataaaa aagccggatt aataatctgg ctttttatat   6840

tctctctcta gtatataaac gcagaaaggc ccacccgaag gtgagccagt gtgacggcac   6900

atttccccga aaagtgccac ctaaattgta agcgttaata ttttgttaaa attcgcgtta   6960

aatttttgtt aaatcagctc atttttaac caataggccg aaatcggcaa aatcccttat   7020

aaatcaaaag aatagaccga gatagggttg agtgttgttc cagtttggaa caagagtcca   7080

ctattaaaga acgtggactc caacgtcaaa gggcgaaaaa ccgtctatca gggcgatggc   7140

ccactacgtg aaccatcacc ctaatcaagt tttttggggt cgaggtgccg taaagcacta   7200

aatcggaacc ctaaagggag cccccgattt agagcttgac ggggaaagcc ggcgaacgtg   7260

gcgagaaagg aagggaagaa agcgaaagga gcgggcgcta gggcgctggc aagtgtagcg   7320

gtcacgctgc gcgtaaccac cacacccgcc gcgcttaatg cgccgctaca gggcgcgtcc   7380

cattcgccat tcaggctgcg caactgttgg gaagggcgat cggtgcgggc ctcttcgcta   7440

ttacgccagc tggcgaaagg gggatgtgct gcaaggcgat taagttgggt aacgccaggg   7500

ttttcccagt cacgacgttg taaaacgacg gccagtgagc gcgcggcgaa ttgggtaccg   7560

ggccccc                                                             7567
```

```
<210> SEQ ID NO 26
<211> LENGTH: 11801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct aaattgtaag cgttaatatt ttgttaaaat tcgcgttaaa tttttgttaa    180

atcagctcat tttttaacca ataggccgaa atcggcaaaa tcccttataa atcaaaagaa    240

tagaccgaga tagggttgag tgttgttcca gtttggaaca agagtccact attaaagaac    300

gtggactcca acgtcaaagg gcgaaaaacc gtctatcagg gcgatggccc actacgtgaa    360

ccatcaccct aatcaagttt tttggggtcg aggtgccgta aagcactaaa tcggaaccct    420
```

-continued

```
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaactttt atcgaattcc tgcagcccgg gggatccact   1140
agttctagag ggacagcccc cccccaaagc ccccagggat gtaattacgt ccctcccccg   1200
ctagggggca gcagcgagcc gcccggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcgtttaaac ttaagcttgg taccgagctc ggatccacta   1560
gtccagtgtg gtggaattcc tgcttcgcga tgtacgggcc agatatacgc gttgacattg   1620
attattgact agttattaat agtaatcaat tacggggtca ttagttcata gcccatatat   1680
ggagttccgc gttacataac ttacggtaaa tggcccgcct ggctgaccgc ccaacgaccc   1740
ccgcccattg acgtcaataa tgacgtatgt tcccatagta acgccaatag ggactttcca   1800
ttgacgtcaa tgggtggagt atttacggta aactgcccac ttggcagtac atcaagtgta   1860
tcatatgcca agtacgcccc ctattgacgt caatgacggt aaatggcccg cctggcatta   1920
tgcccagtac atgaccttat gggactttcc tacttggcag tacatctacg tattagtcat   1980
cgctattacc atggtgatgc ggttttggca gtacatcaat gggcgtggat agcggtttga   2040
ctcacgggga tttccaagtc tccaccccat tgacgtcaat gggagtttgt tttggaacca   2100
aaatcaacgg gactttccaa aatgtcgtaa caactccgcc ccattgacgc aaatgggcgg   2160
taggcgtgta cggtgggagg tctatataag cagagctctc cctatcagtg atagagatct   2220
ccctatcagt gatagagatc gtcgacgagc tcgtttagtg aaccgtcaga tcgcctggag   2280
acgccatcca cgctgttttg acctccatag aagacaccgg gaccgatcca gcctccggac   2340
tctagcgttt aaacttaagc ttgccaccat ggccagtcgg gaagaggagc agcgcgaaac   2400
cacccccgag cgcggacgcg gtgcggcgcg acgtccccca accatggagg acgtgtcgtc   2460
cccgtccccg tcgccgccgc ctccccgggc gcccccaaaa aagcggatga ggcggcgtat   2520
cgagtccgag gacgaggaag actcatcaca agacgcgctg gtgccgcgca cacccagccc   2580
gcggccatcg acctcggcgg cggatttggc cattgcgccc aagaagaaaa agaagcgccc   2640
ttctcccaag cccgagcgcc cgccatcacc agaggtaatc gtggacagcg aggaagaaag   2700
agaagatgtg gcgctacaaa tggtgggttt cagcaaccca ccggtgctaa tcaagcatgg   2760
caaaggaggt aagcgcacag tgcggcggct gaatgaagac gacccagtgg cgcgtggtat   2820
```

-continued gcggacgcaa gaggaagagg aagagcccag cgaagcggaa agtgaaatta cggtgatgaa 2880
cccgctgagt gtgccgatcg tgtctgcgtg ggagaagggc atggaggctg cgcgcgcgct 2940
gatggacaag taccacgtgg ataacgatct aaaggcgaac ttcaaactac tgcctgacca 3000
agtggaagct ctggcggccg tatgcaagac ctggctgaac gaggagcacc gcgggttgca 3060
gctgaccttc accagcaaca agacctttgt gacgatgatg gggcgattcc tgcaggcgta 3120
cctgcagtcg tttgcagagg tgacctacaa gcatcacgag cccacgggct gcgcgttgtg 3180
gctgcaccgc tgcgctgaga tcgaaggcga gcttaagtgt ctacacggaa gcattatgat 3240
aaataaggag cacgtgattg aaatggatgt gacgagcgaa aacgggcagc gcgcgctgaa 3300
ggagcagtct agcaaggcca agatcgtgaa gaaccggtgg ggccgaaatg tggtgcagat 3360
ctccaacacc gacgcaaggt gctgcgtgca cgacgcggcc tgtccggcca atcagttttc 3420
cggcaagtct tgcggcatgt tcttctctga aggcgcaaag gctcaggtgg cttttaagca 3480
gatcaaggct tttatgcagg cgctgtatcc taacgcccag accgggcacg gtcacctttt 3540
gatgccacta cggtgcgagt gcaactcaaa gcctgggcac gcgccctttt tgggaaggca 3600
gctaccaaag ttgactccgt tcgccctgag caacgcggag gacctggacg cggatctgat 3660
ctccgacaag agcgtgctgg ccagcgtgca ccacccggcg ctgatagtgt tccagtgctg 3720
caaccctgtg tatcgcaact cgcgcgcgca gggcggaggc cccaactgcg acttcaagat 3780
atcggcgccc gacctgctaa acgcgttggt gatggtgcgc agcctgtgga gtgaaaactt 3840
caccgagctg ccgcggatgg ttgtgcctga gtttaagtgg agcactaaac accagtatcg 3900
caacgtgtcc ctgccagtgg cgcatagcga tgcgcggcag aacccctttg atttttaacc 3960
cgggagttct agggatctgc cctctccct cccccccccc taacgttact ggccgaagcc 4020
gcttggaata aggccggtgt gcgtttgtct atatgttatt ttccaccata ttgccgtctt 4080
ttggcaatgt gagggcccgg aaacctggcc ctgtcttctt gacgagcatt cctaggggtc 4140
tttcccctct cgccaaagga atgcaaggtc tgttgaatgt cgtgaaggaa gcagttcctc 4200
tggaagcttc ttgaagacaa acaacgtctg tagcgaccct ttgcaggcag cggaaccccc 4260
cacctggcga caggtgcctc tgcggccaaa agccacgtgt ataagataca cctgcaaagg 4320
cggcacaacc ccagtgccac gttgtgagtt ggatagttgt ggaaagagtc aaatggctct 4380
cctcaagcgt attcaacaag gggctgaagg atgcccagaa ggtaccccat tgtatgggat 4440
ctgatctggg gcctcggtgc acatgcttta catgtgttta gtcgaggtta aaaaaacgtc 4500
taggcccccc gaaccacggg gacgtggttt tcctttgaaa aacacgatga taaggatcca 4560
ccggaggcca ccatgactac gtccggcgtt ccatttggca tgacactacg accaacacga 4620
tctcggttgt ctcggcgcac tccgtacagt agggatcgtc tacctccttt tgagacagaa 4680
acccgcgcta ccatactgga ggatcatccg ctgctgcccg aatgtaacac tttgacaatg 4740
cacaacgtga gttacgtgcg aggtcttccc tgcagtgtgg gatttacgct gattcaggaa 4800
tgggttgttc cctgggatat ggttctaacg cgggaggagc ttgtaatcct gaggaagtgt 4860
atgcacgtgt gcctgtgttg tgccaacatt gatatcatga cgagcatgat gatccatggt 4920
tacgagtcct gggctctcca ctgtcattgt tccagtcccg gttccctgca gtgtatagcc 4980
ggcgggcagg ttttggccag ctggtttagg atggtggtgg atggcgccat gtttaatcag 5040
aggtttatat ggtaccggga ggtggtgaat tacaacatgc caaaagaggt aatgtttatg 5100
tccagcgtgt ttatgagggg tcgccactta atctacctgc gcttgtggta tgatggccac 5160

-continued

```
gtgggttctg tggtccccgc catgagcttt ggatacagcg ccttgcactg tgggattttg   5220
aacaatattg tggtgctgtg ctgcagttac tgtgctgatt taagtgagat cagggtgcgc   5280
tgctgtgccc ggaggacaag gcgccttatg ctgcgggcgg tgcgaatcat cgctgaggag   5340
accactgcca tgttgtattc ctgcaggacg gagcggcggc ggcagcagtt tattcgcgcg   5400
ctgctgcagc accaccgccc tatcctgatg cacgattatg actctacccc catgtaggcg   5460
gccgtcgagt ctagagggcc cgtttaaacc cgctgatcag cctcgactgt gccttctagt   5520
tgccagccat ctgttgtttg cccctccccc gtgccttcct tgaccctgga aggtgccact   5580
cccactgtcc tttcctaata aaatgaggaa attgcatcgc attgtctgag taggtgtcat   5640
tctattctgg ggggtggggt ggggcaggac agcaaggggg aggattggga agacaatagc   5700
aggcatgctg gggatgcggt gggctctatg gcttctgagg cggaaagaac cagctggggc   5760
tctagggggt atccccggcg cgccggggtt gagctattcc agaagtagtg aagaggcttt   5820
tttggaggcc taggcttttg caaaaagctc cggatcgatt ggggttgcgc cttttccaag   5880
gcttttcccc gtatcccccc aggtgtctgc aggctcaaag agcagcgaga agcgttcaga   5940
ggaaagcgat cccgtgccac cttccccgtg cccgggctgt ccccgcacgc tgccggctcg   6000
gggatgcggg gggagcgccg gaccggagcg gagccccggg cggctcgctg ctgcccccta   6060
gcgggggagg gacgtaatta catccctggg ggctttgggg gggggctgtc cctctagggg   6120
atcctctagg gcctctgagc tattccagaa gtagtgaaga ggcttttttg gaggcctagg   6180
cttttgcaaa aagctccgga tcgatcgagc ggatccagca cagtggcggc cgcaatattt   6240
gcatgtcgct atgtgttctg ggaaatcacc ataaacgtga aatccctatc agtgatagag   6300
acttataagt tccctatcag tgatagagaa ccggtgggca ctcttccgtg gtctggtgga   6360
taaattcgca agggtatcat ggcggacgac cggggttcga gccccgtatc cggccgtccg   6420
ccgtgatcca tgcggttacc gcccgcgtgt cgaacccagg tgtgcgacgt cagacaacgg   6480
gggagtgctc ctttttgaat tccactttgg ccgcggctcg agtgagctat tccagaagta   6540
gtgaagaggc tttttggag gcctaggctt ttgcaaaaag ctccggatcg atgcccgggg   6600
gatccactag ttctagaggg acagcccccc cccaaagccc ccagggatgt aattacgtcc   6660
ctcccccgct agggggcagc agcgagccgc ccggggctcc gctccggtcc ggcgctcccc   6720
ccgcatcccc gagccggcag cgtgcgggga cagcccgggc acggggaagg tggcacggga   6780
tcgctttcct ctgaacgctt ctcgctgctc tttgagcctg cagacacctg gggggatacg   6840
gggaaaaggc ctccaaggcc agcttcccac aataagttgg gtgaattttg gctgagctat   6900
tccagaagta gtgaagaggc tttttggag gcctaggctt ttgcaaaaag ctccggatcg   6960
atcatatatg gcagatatac gcgttgacat tgattattga ctagttatta atagtaatca   7020
attacggggt cattagttca tagcccatat atggagttcc gcgttacata acttacggta   7080
aatggcccgc ctggctgacc gcccaacgac ccccgcccat tgacgtcaat aatgacgtat   7140
gttcccatag taacgccaat agggactttc cattgacgtc aatgggtgga gtatttacgg   7200
taaactgccc acttggcagt acatcaagtg tatcatatgc caagtacgcc ccctattgac   7260
gtcaatgacg gtaaatggcc cgcctggcat tatgcccagt acatgacctt atgggacttt   7320
cctacttggc agtacatcta cgtattagtc atcgctatta ccatggtgat gcggttttgg   7380
cagtacatca atgggcgtgg atagcggttt gactcacggg gatttccaag tctccacccc   7440
attgacgtca atgggagttt gttttggcac caaaatcaac gggactttcc aaaatgtcgt   7500
aacaactccg ccccattgac gcaaatgggc ggtaggcgtg tacggtggga ggtctatata   7560
```

```
agcagagctc tctggctaac tatcgtcgac gagctcgttt agtgaaccgt cagatcgcct   7620
ggagacgcca tccacgctgt tttgacctcc atagaagaca ccgggaccga tccagcctcc   7680
ggactctagc gtttaaactt aagcttgcca ccatgaccga gtacaagccc acggtgcgcc   7740
tcgccacccg cgacgacgtc cccagggccg tacgcaccct cgccgccgcg ttcgccgact   7800
accccgccac gcgccacacc gtcgatccgg accgccacat cgagcgggtc accgagctgc   7860
aagaactctt cctcacgcgc gtcgggctcg acatcggcaa ggtgtgggtc gcggacgacg   7920
gcgccgcggt ggcggtctgg accacgccgg agagcgtcga agcgggggcg gtgttcgccg   7980
agatcggccc gcgcatggcc gagttgagcg gttcccggct ggccgcgcag caacagatgg   8040
aaggcctcct ggcgccgcac cggcccaagg agcccgcgtg gttcctggcc accgtcggcg   8100
tctcgcccga ccaccagggc aagggtctgg gcagcgccgt cgtgctcccc ggagtggagg   8160
cggccgagcg cgccggggtg cccgccttcc tggagacctc cgcgccccgc aacctcccct   8220
tctacgagcg gctcggcttc accgtcaccg ccgacgtcga ggtgcccgaa ggaccgcgca   8280
cctggtgcat gacccgcaag cccggtgcct gaagcgcggg gatctcatgc tggagttctt   8340
cgcccacccc aacttgttta ttgcagctta taatggttac aaataaagca atagcatcac   8400
aaatttcaca aataaagcat ttttttcact gcattctagt tgtggtttgt ccaaactcat   8460
caatgtatct tatcatgtct gtagctgatg tatacctagg atccggccgg cctgcaggtg   8520
tcctcacagg aacgaagtcc ctaaagaaac agtggcagcc aggtttagcc ccggaattga   8580
ctggattcct tttttagggc ccattggtat ggctttttcc ccgtatcccc ccaggtgtct   8640
gcaggctcaa agagcagcga gaagcgttca gaggaaagcg atcccgtgcc accttccccg   8700
tgcccgggct gtccccgcac gctgccggct cggggatgcg gggggagcgc cggaccggag   8760
cggagccccg ggcggctcgc tgctgccccc tagcggggga gggacgtaat tacatccctg   8820
ggggctttgg ggggggggctg tccctctaga gcggccgcca ccgcggtgga gctccagctt   8880
ttgttccctt tagtgagggt taattagatc ttaatacgac tcactatagg gcgaattggg   8940
taccgggccc cccctcgagg tcgacggtat cgataagctt gatatctata acaagaaaat   9000
atatatataa taagttatca cgtaagtaga acatgaaata acaatataat tatcgtatga   9060
gttaaatctt aaaagtcacg taaaagataa tcatgcgtca ttttgactca cgcggtcgtt   9120
atagttcaaa atcagtgaca cttaccgcat tgacaagcac gcctcacggg agctccaagc   9180
ggcgactgag atgtcctaaa tgcacagcga cggattcgcg ctatttagaa agagagagca   9240
atatttcaag aatgcatgcg tcaattttac gcagactatc tttctagggt taatctagct   9300
gcatcaggat catatcgtcg ggtctttttt ccggctcagt catcgcccaa gctggcgcta   9360
tctgggcatc ggggaggaag aagcccgtgc cttttcccgc gaggttgaag cggcatggaa   9420
agagtttgcc gaggatgact gctgctgcat tgacgttgag cgaaaacgca cgtttaccat   9480
gatgattcgg gaaggtgtgg ccatgcacgc ctttaacggt gaactgttcg ttcaggccac   9540
ctgggatacc agttcgtcgc ggcttttccg gacacagttc cggatggtca gcccgaagcg   9600
catcagcaac ccgaacaata ccggcgacag ccggaactgc cgtgccggtg tgcagattaa   9660
tgacagcggt gcggcgctgg gatattacgt cagcgaggac gggtatcctg gctggatgcc   9720
gcagaaatgg acatggatac cccgtgagtt acccggcggg cgcgcttggc gtaatcatgg   9780
tcatagctgt ttcctgtgtg aaattgttat ccgctcacaa ttccacacaa catacgagcc   9840
ggaagcataa agtgtaaagc ctggggtgcc taatgagtga gctaactcac attaattgcg   9900
```

-continued

```
ttgcgctcac tgcccgcttt ccagtcggga aacctgtcgt gccagctgca ttaatgaatc   9960
ggccaacgcg cggggagagg cggtttgcgt attgggcgct cttccgcttc ctcgctcact  10020
gactcgctgc gctcggtcgt tcggctgcgg cgagcggtat cagctcactc aaaggcggta  10080
atacggttat ccacagaatc aggggataac gcaggaaaga acatgtgagc aaaaggccag  10140
caaaaggcca ggaaccgtaa aaaggccgcg ttgctggcgt ttttccatag gctccgcccc  10200
cctgacgagc atcacaaaaa tcgacgctca agtcagaggt ggcgaaaccc gacaggacta  10260
taaagatacc aggcgtttcc ccctggaagc tccctcgtgc gctctcctgt tccgaccctg  10320
ccgcttaccg gatacctgtc cgcctttctc ccttcgggaa gcgtggcgct ttctcatagc  10380
tcacgctgta ggtatctcag ttcggtgtag gtcgttcgct ccaagctggg ctgtgtgcac  10440
gaaccccccg ttcagcccga ccgctgcgcc ttatccggta actatcgtct tgagtccaac  10500
ccggtaagac acgacttatc gccactggca gcagccactg gtaacaggat tagcagagcg  10560
aggtatgtag gcggtgctac agagttcttg aagtggtggc ctaactacgg ctacactaga  10620
aggacagtat ttggtatctg cgctctgctg aagccagtta ccttcggaaa aagagttggt  10680
agctcttgat ccggcaaaca aaccaccgct ggtagcggtg gtttttttgt ttgcaagcag  10740
cagattacgc gcagaaaaaa aggatctcaa gaagatcctt tgatcttttc tacggggtct  10800
gacgctcagt ggaacgaaaa ctcacgttaa gggattttgg tcatgagatt atcaaaaagg  10860
atcttcacct agatcctttt aaattaaaaa tgaagtttta aatcaatcta aagtatatat  10920
gagtaaactt ggtctgacag ttaccaatgc ttaatcagtg aggcacctat ctcagcgatc  10980
tgtctatttc gttcatccat agttgcctga ctccccgtcg tgtagataac tacgatacgg  11040
gagggcttac catctggccc cagtgctgca atgataccgc gagacccacg ctcaccggct  11100
ccagatttat cagcaataaa ccagccagcc ggaagggccg agcgcagaag tggtcctgca  11160
actttatccg cctccatcca gtctattaat tgttgccggg aagctagagt aagtagttcg  11220
ccagttaata gtttgcgcaa cgttgttgcc attgctacag gcatcgtggt gtcacgctcg  11280
tcgtttggta tggcttcatt cagctccggt tcccaacgat caaggcgagt tacatgatcc  11340
cccatgttgt gcaaaaaagc ggttagctcc ttcggtcctc cgatcgttgt cagaagtaag  11400
ttggccgcag tgttatcact catggttatg gcagcactgc ataattctct tactgtcatg  11460
ccatccgtaa gatgcttttc tgtgactggt gagtactcaa ccaagtcatt ctgagaatag  11520
tgtatgcggc gaccgagttg ctcttgcccg gcgtcaatac gggataatac cgcgccacat  11580
agcagaactt taaaagtgct catcattgga aaacgttctt cggggcgaaa actctcaagg  11640
atcttaccgc tgttgagatc cagttcgatg taacccactc gtgcacccaa ctgatcttca  11700
gcatctttta ctttcaccag cgtttctggg tgagcaaaaa caggaaggca aaatgccgca  11760
aaaaagggaa taagggcgac acggaaatgt tgaatactca t                      11801
```

<210> SEQ ID NO 27
<211> LENGTH: 7798
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27

```
actcttcctt tttcaatatt attgaagcat ttatcagggt tattgtctca tgagcggata     60
catatttgaa tgtatttaga aaaataaaca aataggggtt ccgcgcacat ttccccgaaa    120
```

-continued

```
agtgccacct aaattgtaag cgttaatatt ttgttaaaat tcgcgttaaa tttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaactttt atcgaattcc tgcagcccgg gggatccact   1140
agttctagag ggacagcccc cccccaaagc ccccagggat gtaattacgt ccctcccccg   1200
ctagggggca gcagcgagcc gcccggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tgggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcaaacgcca gcaacgcggc ctttttacgg ttcctggcct   1560
tttgctggcc ttttgctcac atgtcctgca ggcagctgcg cgctcgctcg ctcactgagg   1620
ccgcccgggc aaagcccggg cgtcgggcga cctttggtcg cccggcctca gtgagcgagc   1680
gagcgcgcag agagggagtg gccaactcca tcactagggg ttcctgcggc cgcacgcgtg   1740
gagctagtta ttaatagtaa tcaattacgg ggtcattagt tcatagccca tatatggagt   1800
tccgcgttac ataacttacg gtaaatggcc cgcctggctg accgcccaac gacccccgcc   1860
cattgacgtc aataatgacg tatgttccca tagtaacgtc aatagggact ttccattgac   1920
gtcaatgggt ggagtattta cggtaaactg cccacttggc agtacatcaa gtgtatcata   1980
tgccaagtac gccccctatt gacgtcaatg acggtaaatg gcccgcctgg cattatgccc   2040
agtacatgac cttatgggac tttcctactt ggcagtacat ctacgtatta gtcatcgcta   2100
ttaccatggt gatgcggttt tggcagtaca tcaatgggcg tggatagcgg tttgactcac   2160
ggggatttcc aagtctccac cccattgacg tcaatgggag tttgttttgc accaaaatca   2220
acgggacttt ccaaaatgtc gtaacaactc cgccccattg acgcaaatgg gcggtaggcg   2280
tgtacggtgg gaggtctata taagcagagc tcgtttagtg aaccgtcaga tcgcctggag   2340
acgccatcca cgctgttttg acctccatag aagacaccgg gaccgatcca gcctccgcgg   2400
attcgaatcc cggccgggaa cggtgcattg gaacgcggat tccccgtgcc aagagtgacg   2460
taagtaccgc ctatagagtc tataggccca caaaaaatgc tttcttcttt taatatactt   2520
```

```
ttttgtttat cttatttcta atactttccc taatctcttt ctttcagggc aataatgata   2580
caatgtatca tgcctctttg caccattcta aagaataaca gtgataattt ctgggttaag   2640
gcaatagcaa tatttctgca tataaatatt tctgcatata aattgtaact gatgtaagag   2700
gtttcatatt gctaatagca gctacaatcc agctaccatt ctgcttttat tttatggttg   2760
ggataaggct ggattattct gagtccaagc taggcccttt tgctaatcat gttcatacct   2820
cttatcttcc tcccacagct cctgggcaac gtgctggtct gtgtgctggc ccatcacttt   2880
ggcaaagaat tgggattcga acatcgattg aattctgaat ggtgagcaag ggcgaggagc   2940
tgttcaccgg ggtggtgccc atcctggtcg agctggacgg cgacgtaaac ggccacaagt   3000
tcagcgtgtc cggcgagggc gagggcgatg ccacctacgg caagctgacc ctgaagttca   3060
tctgcaccac cggcaagctg cccgtgccct ggcccaccct cgtgaccacc ctgacctacg   3120
gcgtgcagtg cttcagccgc taccccgacc acatgaagca gcacgacttc ttcaagtccg   3180
ccatgcccga aggctacgtc caggagcgca ccatcttctt caaggacgac ggcaactaca   3240
agacccgcgc cgaggtgaag ttcgagggcg acaccctggt gaaccgcatc gagctgaagg   3300
gcatcgactt caaggaggac ggcaacatcc tggggcacaa gctggagtac aactacaaca   3360
gccacaacgt ctatatcatg gccgacaagc agaagaacgg catcaaggtg aacttcaaga   3420
tccgccacaa catcgaggac ggcagcgtgc agctcgccga ccactaccag cagaacaccc   3480
ccatcggcga cggccccgtg ctgctgcccg acaaccacta cctgagcacc cagtccgccc   3540
tgagcaaaga ccccaacgag aagcgcgatc acatggtcct gctggagttc gtgaccgccg   3600
ccgggatcac tctcggcatg gacgagctgt acaagtactc agatctcgag ctcaagtagg   3660
gatcctctag agtcgacctg cagaagcttg cctcgagcag cgctgctcga gagatctacg   3720
ggtggcatcc ctgtgacccc tccccagtgc ctctcctggc cctggaagtt gccactccag   3780
tgcccaccag ccttgtccta ataaaattaa gttgcatcat tttgtctgac taggtgtcct   3840
tctataatat tatggggtgg aggggggtgg tatggagcaa ggggcaagtt gggaagacaa   3900
cctgtagggc ctgcggggtc tattgggaac caagctggag tgcagtggca caatcttggc   3960
tcactgcaat ctccgcctcc tgggttcaag cgattctcct gcctcagcct cccgagttgt   4020
tgggattcca ggcatgcatg accaggctca gctaattttt gtttttttgg tagagacggg   4080
gtttcaccat attggccagg ctggtctcca actcctaatc tcaggtgatc tacccacctt   4140
ggcctcccaa attgctggga ttacaggcgt gaaccactgc tcccttccct gtccttctga   4200
ttttgtaggt aaccacgtgc ggaccgagcg gccgcaggaa cccctagtga tggagttggc   4260
cactccctct ctgcgcgctc gctcgctcac tgaggccggg cgaccaaagg tcgcccgacg   4320
cccgggcttt gcccgggcgg cctcagtgag cgagcgagcg cgcagctgcc tgcaggggcg   4380
cctgatgcgg tattttctcc ttacgcatct gtgcggtatt tcacaccgca tacgtcgtag   4440
ctgatcaatt ggcgcgccga attcgttaac aagctttaat taacgcgtat acctaggatc   4500
cggccggcct gcaggtgtcc tcacaggaac gaagtcccta aagaaacagt ggcagccagg   4560
tttagccccg gaattgactg gattcctttt ttagggccca ttggtatggc tttttccccg   4620
tatcccccca ggtgtctgca ggctcaaaga gcagcgagaa gcgttcagag gaaagcgatc   4680
ccgtgccacc ttccccgtgc ccgggctgtc cccgcacgct gccggctcgg ggatgcgggg   4740
ggagcgccgg accggagcgg agccccgggc ggctcgctgc tgccccctag cgggggaggg   4800
acgtaattac atccctgggg gctttggggg ggggctgtcc ctctagagcg gccgccaccg   4860
```

-continued

```
cggtggagct ccagcttttg ttccctttag tgagggttaa ttagatctta atacgactca   4920
ctatagggcg aattgggtac cgggcccccc ctcgaggtcg acggtatcga taagcttgat   4980
atctataaca agaaaatata tatataataa gttatcacgt aagtagaaca tgaaataaca   5040
atataattat cgtatgagtt aaatcttaaa agtcacgtaa aagataatca tgcgtcattt   5100
tgactcacgc ggtcgttata gttcaaaatc agtgacactt accgcattga caagcacgcc   5160
tcacgggagc tccaagcggc gactgagatg tcctaaatgc acagcgacgg attcgcgcta   5220
tttagaaaga gagagcaata tttcaagaat gcatgcgtca attttacgca gactatcttt   5280
ctagggttaa tctagctgca tcaggatcat atcgtcgggt ctttttttccg gctcagtcat   5340
cgcccaagct ggcgctatct gggcatcggg gaggaagaag cccgtgcctt ttcccgcgag   5400
gttgaagcgg catggaaaga gtttgccgag gatgactgct gctgcattga cgttgagcga   5460
aaacgcacgt ttaccatgat gattcgggaa ggtgtggcca tgcacgcctt taacggtgaa   5520
ctgttcgttc aggccacctg ggataccagt tcgtcgcggc ttttccggac acagttccgg   5580
atggtcagcc cgaagcgcat cagcaacccg aacaataccg gcgacagccg gaactgccgt   5640
gccggtgtgc agattaatga cagcggtgcg gcgctgggat attacgtcag cgaggacggg   5700
tatcctggct ggatgccgca gaaatggaca tggataccccc gtgagttacc cggcgggcgc   5760
gcttggcgta atcatggtca tagctgtttc ctgtgtgaaa ttgttatccg ctcacaattc   5820
cacacaacat acgagccgga agcataaagt gtaaagcctg gggtgcctaa tgagtgagct   5880
aactcacatt aattgcgttg cgctcactgc ccgctttcca gtcgggaaac ctgtcgtgcc   5940
agctgcatta atgaatcggc caacgcgcgg ggagaggcgg tttgcgtatt gggcgctctt   6000
ccgcttcctc gctcactgac tcgctgcgct cggtcgttcg gctgcggcga gcggtatcag   6060
ctcactcaaa ggcggtaata cggttatcca cagaatcagg ggataacgca ggaaagaaca   6120
tgtgagcaaa aggccagcaa aaggccagga accgtaaaaa ggccgcgttg ctggcgtttt   6180
tccataggct ccgcccccct gacgagcatc acaaaaatcg acgctcaagt cagaggtggc   6240
gaaacccgac aggactataa agataccagg cgtttccccc tggaagctcc ctcgtgcgct   6300
ctcctgttcc gaccctgccg cttaccggat acctgtccgc ctttctccct tcgggaagcg   6360
tggcgctttc tcatagctca cgctgtaggt atctcagttc ggtgtaggtc gttcgctcca   6420
agctgggctg tgtgcacgaa ccccccgttc agcccgaccg ctgcgcctta tccggtaact   6480
atcgtcttga gtccaacccg gtaagacacg acttatcgcc actggcagca gccactggta   6540
acaggattag cagagcgagg tatgtaggcg gtgctacaga gttcttgaag tggtggccta   6600
actacggcta cactagaagg acagtatttg gtatctgcgc tctgctgaag ccagttacct   6660
tcggaaaaag agttggtagc tcttgatccg gcaaacaaac caccgctggt agcggtggtt   6720
tttttgtttg caagcagcag attacgcgca gaaaaaaagg atctcaagaa gatcctttga   6780
tcttttctac ggggtctgac gctcagtgga acgaaaactc acgttaaggg attttggtca   6840
tgagattatc aaaaaggatc ttcacctaga tccttttaaa ttaaaaatga agttttaaat   6900
caatctaaag tatatatgag taaacttggt ctgacagtta ccaatgctta atcagtgagg   6960
cacctatctc agcgatctgt ctatttcgtt catccatagt tgcctgactc cccgtcgtgt   7020
agataactac gatacgggag ggcttaccat ctggccccag tgctgcaatg ataccgcgag   7080
acccacgctc accggctcca gatttatcag caataaacca gccagccgga agggccgagc   7140
gcagaagtgg tcctgcaact ttatccgcct ccatccagtc tattaattgt tgccgggaag   7200
ctagagtaag tagttcgcca gttaatagtt tgcgcaacgt tgttgccatt gctacaggca   7260
```

```
tcgtggtgtc acgctcgtcg tttggtatgg cttcattcag ctccggttcc caacgatcaa   7320

ggcgagttac atgatccccc atgttgtgca aaaaagcggt tagctccttc ggtcctccga   7380

tcgttgtcag aagtaagttg gccgcagtgt tatcactcat ggttatggca gcactgcata   7440

attctcttac tgtcatgcca tccgtaagat gcttttctgt gactggtgag tactcaacca   7500

agtcattctg agaatagtgt atgcggcgac cgagttgctc ttgcccggcg tcaatacggg   7560

ataataccgc gccacatagc agaactttaa aagtgctcat cattggaaaa cgttcttcgg   7620

ggcgaaaact ctcaaggatc ttaccgctgt tgagatccag ttcgatgtaa cccactcgtg   7680

cacccaactg atcttcagca tcttttactt tcaccagcgt ttctgggtga gcaaaaacag   7740

gaaggcaaaa tgccgcaaaa aagggaataa gggcgacacg gaaatgttga atactcat     7798
```

<210> SEQ ID NO 28
<211> LENGTH: 9399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct aaattgtaag cgttaatatt ttgttaaaat tcgcgttaaa tttttgttaa    180

atcagctcat tttttaacca ataggccgaa atcggcaaaa tcccttataa atcaaaagaa    240

tagaccgaga tagggttgag tgttgttcca gtttggaaca agagtccact attaaagaac    300

gtggactcca acgtcaaagg gcgaaaaacc gtctatcagg gcgatggccc actacgtgaa    360

ccatcaccct aatcaagttt tttggggtcg aggtgccgta aagcactaaa tcggaaccct    420

aaagggagcc cccgatttag agcttgacgg ggaaagccgg cgaacgtggc gagaaaggaa    480

gggaagaaag cgaaaggagc gggcgctagg gcgctggcaa gtgtagcggt cacgctgcgc    540

gtaaccacca cacccgccgc gcttaatgcg ccgctacagg gcgcgtccca ttcgccattc    600

aggctgcgca actgttggga agggcgatcg gtgcgggcct cttcgctatt acgccagctg    660

gcgaaagggg gatgtgctgc aaggcgatta agttgggtaa cgccagggtt ttcccagtca    720

cgacgttgta aaacgacggc cagtgagcgc gcctcgttca ttcacgtttt tgaacccgtg    780

gaggacgggc agactcgcgg tgcaaatgtg ttttacagcg tgatggagca gatgaagatg    840

ctcgacacgc tgcagaacac gcagctagat taaccctaga aagataatca tattgtgacg    900

tacgttaaag ataatcatgc gtaaaattga cgcatgtgtt ttatcggtct gtatatcgag    960

gtttatttat taatttgaat agatattaag ttttattata tttacactta catactaata   1020

ataaattcaa caaacaattt atttatgttt atttatttat taaaaaaaaa caaaaactca   1080

aaatttcttc tataaagtaa caaaactttt atcgaattcc tgcagcccgg gggatccact   1140

agttctagag ggacagcccc cccccaaagc ccccagggat gtaattacgt ccctcccccg   1200

ctagggggca gcagcgagcc gcccggggct ccgctccggt ccggcgctcc ccccgcatcc   1260

ccgagccggc agcgtgcggg gacagcccgg gcacggggaa ggtggcacgg gatcgctttc   1320

ctctgaacgc ttctcgctgc tctttgagcc tgcagacacc tggggggata cggggaaaag   1380

gcctccaagg ccagcttccc acaataagtt gggtgaattt tggctcattc ctcctttcta   1440

taggattgag gtcagagctt tgtgatggga attctgtgga atgtgtgtca gttagggtgt   1500
```

-continued

```
ggaaagtccc gcgatcgcta gcttaagcgc tgatcaattg gcgcgccgaa ttcgttatct   1560
gcagaattcg gcttggcggc tgcgcgttca aacctcccgc ttcaaaatgg agaccctgcg   1620
tgctcactcg ggcttaaata cccagcgtga ccacatggtg tcgcaaaatg tcgcaaaaca   1680
ctcacgtgac ctctaataca ggacctctag agcatggaaa ctagataaga aagaaatacg   1740
cagagaccaa agttcaactg aaacgaatta aacggtttat tgattaacaa gcaaactagt   1800
ttacagatta cgggtgaggt aacgggtgcc aatggggcgg ggttcagagt acacgccttc   1860
tgtattaaca gcaaagtcca cacttgtaga tttgtagtag ttggaggtgt actggatctc   1920
ggggttccag cgcttgctgt ttccttctg cagctcccat tcaatttcca cgctgacctg    1980
tccggtgctg tattgcgtga tgaaagagtt cagctttgac tggttgaagg tggtcggagg   2040
atccgcaggt acaggcgtgt tcttgatcag gatctgaggc ggaggatgtt tcaggccaaa   2100
gccgcccatc agcggagacg ggtggaagtt gccgtccgtg tgaggaatct tggcccagat   2160
gggaccctgc aggtacacgt cccggttctg ccagaccata ccgggtaagg ccccctggct   2220
gttgacagtt ccaatttgag gagccgtgtt ttgctgctgc aagttatctg ccacgatacc   2280
gtattcctct gtagccacag ggttagtggt tttgatttct tcctcgctgg tgagcatgac   2340
atcgctgtaa tccgcattgt ctctggcagc attttgtttg ccaaaaatca ggatcccgtt   2400
actgggaaaa aaacgctcct cgtcgtcttt gtgtgttgcc atagcgatgc caggattagc   2460
caatgaattt cttccattca gatggtattt ggtcccagca gtccaggcaa agttgctatt   2520
gttgttttgc ccggttgtcg ttgagacgcg ttgttggcgg taacagggtc ctggcagcca   2580
gttctttgcc tgattggcca ttgtattagg cccaccttgg ctgaagccca gagtctgcgt   2640
atttgccgtg cctcctgttg tttgagtccg agacaagtag tacaggtact ggtcaatcag   2700
aggattcatc agccggtcca agctctggct gtgggcgtag ctgctgtgga aaggcacgtc   2760
ctcgaaggtg taagtaaact ggaagttgtt gccggttctc agcatctgcg aaggaaagta   2820
ttccaggcag tagaaggagg agcgtcccac ggcctgacta ccgttgttga gtgttaggta   2880
gccgtactgg ggaatcatga acacgtccgc cgggaacgga ggcaggcagc cctggtgggc   2940
agagccgaga acgtacggca gctggtactc cgagtccgta aacacctgga tggtgctggt   3000
gaggttattg gcgatggtct tggtgccttc attctgcgtg acctccttga cctggatgtt   3060
gaagagcttg aagctgagtc tcttgggccg gaatccccag ttgttgttga tgagtcgctg   3120
ccagtcacgt ggtgaaaagt ggcagtggaa tctgttaaag tcaaaatacc cccagggggt   3180
gctgtagccg aagtaggtgt tgtcgttggt ggctcctccc gatgtcccgt tggagatttg   3240
cttgtagagg tggttgttgt aggtgggcag ggcccaggtt cgggtgctgg tggtgatgac   3300
tctgtcgccc agccatgtgg aatcgcaatg ccaatttccc gaggaactac ccactccgtc   3360
ggcgccttcg ttattgtctg ccattggtgc gccaccgcct gcagccattg tattaggtcc   3420
cacaccagag ggcgctgctg gaggttctcc gagaggttga gggtctggaa ctgactctga   3480
gtcgccagtc tgaccaaaat tgagtctttt tctggcgggc tgttggcctt tcttgccgat   3540
gcccgtagag gagtctggag aacgctgggg tgatggctct accggtctct tctttccagg   3600
agccgtctta gcgccttcct caaccagacc gagaggttcg agaacccgct tcttggcctg   3660
gaagactgct cgcccgaggt tgcccccaaa agacgtatct tcttgcagac gctcctgaaa   3720
ctcggcgtcg gcgtggttat accgcaggta cggattgtca cccgcctgca gctgctggtc   3780
gtaggccttg tcgtgctcga gggccgctgc gtccgccgcg ttgacgggct ccccccttgtc   3840
```

-continued

```
gagtccgttg aagggtccga ggtacttgta gccaggaagc accagacccc ggccgtcgtc   3900
ctgcttttgc tggttggctt tgggcttcgg ggctccaggt ttcagcgccc accactcgcg   3960
aatgccctca gagaggttgt cctcgagcca atctggaaga taaccatcgg cagccatacc   4020
tgatttaaat catttattgt tcaaagatgc agtcatccaa atccacattg accagatcgc   4080
aggcagtgca agcgtctggc acctttccca tgatatgatg aatgtagcac agtttctgat   4140
acgccttttt gacgacagaa acgggttgag attctgacac gggaaagcac tctaaacagt   4200
ctttctgtcc gtgagtgaag cagatatttg aattctgatt cattctctcg cattgtctgc   4260
agggaaacag catcagattc atgcccacgt gacgagaaca tttgttttgg tacctgtctg   4320
cgtagttgat cgaagcttcc gcgtctgacg tcgatggctg cgcaactgac tcgcgcaccc   4380
gtttgggctc acttatatct gcgtcactgg gggcgggtct ttcttggct ccaccctttt   4440
tgacgtagaa ttcatgctcc acctcaacca cgtgatcctt tgcccaccgg aaaaagtctt   4500
tgacttcctg cttggtgacc ttcccaaagt catgatccag acggcgggtg agttcaaatt   4560
tgaacatccg gtcttgcaac ggctgctggt gttcgaaggt cgttgagttc ccgtcaatca   4620
cggcgcacat gttggtgttg gaggtgacga tcacgggagt cgggtctatc tgggccgagg   4680
acttgcattt ctggtccacg cgcaccttgc ttcctccgag aatggctttg gccgactcca   4740
cgaccttggc ggtcatcttc cctcctccc accagatcac catcttgtcg acacagtcgt   4800
tgaagggaaa gttctcattg gtccagttta cgcacccgta gaagggcaca gtgtgggcta   4860
tggcctccgc gatgttggtc ttcccggtag ttgcaggccc aaacagccag atggtgttcc   4920
tcttgccgaa ctttttcgtg gcccatccca gaaagacgga agccgcatat tggggatcgt   4980
acccgtttag ttccaaaatt ttataaatcc gattgctgga aatgtcctcc acgggctgct   5040
ggcccaccag gtagtcgggg gcggttttag tcaggctcat aatctttccc gcattgtcca   5100
aggcagcctt gatttgggac cgcgagttgg aggccgcatt gaaggagatg tatgaggcct   5160
ggtcctcctg gatccactgc ttctccgagg taatcccctt gtccacgagc cacccgacca   5220
gctccatgta cctggctgaa gtttttgatc tgatcaccgg cgcatcagaa ttgggattct   5280
gattctcttt gttctgctcc tgcgtctgcg acacgtgcgt cagatgctgc gccaccaacc   5340
gtttacgctc cgtgagattc aaacaggcgc tgtggagaga aaggcaaagt ggatgtcagt   5400
atctctatca ctgataggga gatctctatc actgataggg aacttacctt aaatactgtt   5460
ccatattagt ccacgcccac tggagctcag gctgggtttt ggggagcaag taattgggga   5520
tgtagcactc atccaccacc ttgttcccgc ctccggcgcc atttctggtc tttgtgaccg   5580
cgaaccagtt tggcaaagtc ggctcgatcc cgcggtaaat tctctgaatc agtttttcgc   5640
gaatctgact caggaaacgt cccaaaacca tggatttcac cccggtggtt tccacgagca   5700
cgtgcatgtg gaagtagctc tctcccttct caaattgcac aaagaaaaga gcctccgggg   5760
ccttactcac acggcgccat tccgtcagaa agtcgcgctg cagcttctcg gccacggtca   5820
ggggtgcctg ctcaatcaga ttcagatcca tgtcagaatc tggcggcaac tcccattcct   5880
tctcggccac ccagttcaca aagctgtcag aaatgccggg cagatgctcg tcaaggtcgc   5940
tggggacctt aatcacaatc tcgtaaaacc ccggcatggc ggctgcgcgt tcaaacctcc   6000
cgcttcaaaa tggagaccct gcgtgctcac tcgggcgatc tctatcactg atagggagat   6060
ctctatcact gatagggaga ttaaatagaa tggctaggat ccggccggcc tgcaggtgtc   6120
ctcacaggaa cgaagtccct aaagaaacag tggcagccag gtttagcccc ggaattgact   6180
ggattccttt tttagggccc attggtatgg ctttttcccc gtatcccccc aggtgtctgc   6240
```

```
aggctcaaag agcagcgaga agcgttcaga ggaaagcgat cccgtgccac cttccccgtg   6300
cccgggctgt ccccgcacgc tgccggctcg gggatgcggg gggagcgccg gaccggagcg   6360
gagccccggg cggctcgctg ctgcccccta gcgggggagg gacgtaatta catccctggg   6420
ggctttgggg gggggctgtc cctctagagc ggccgccacc gcggtggagc tccagctttt   6480
gttcccttta gtgagggtta attagatctt aatacgactc actatagggc gaattgggta   6540
ccgggccccc cctcgaggtc gacggtatcg ataagcttga tatctataac aagaaaatat   6600
atatataata agttatcacg taagtagaac atgaaataac aatataatta tcgtatgagt   6660
taaatcttaa aagtcacgta aaagataatc atgcgtcatt ttgactcacg cggtcgttat   6720
agttcaaaat cagtgacact taccgcattg acaagcacgc ctcacgggag ctccaagcgg   6780
cgactgagat gtcctaaatg cacagcgacg gattcgcgct atttagaaag agagagcaat   6840
atttcaagaa tgcatgcgtc aattttacgc agactatctt tctagggtta atctagctgc   6900
atcaggatca tatcgtcggg tctttttttcc ggctcagtca tcgcccaagc tggcgctatc   6960
tgggcatcgg ggaggaagaa gcccgtgcct tttcccgcga ggttgaagcg gcatggaaag   7020
agtttgccga ggatgactgc tgctgcattg acgttgagcg aaaacgcacg tttaccatga   7080
tgattcggga aggtgtggcc atgcacgcct ttaacggtga actgttcgtt caggccacct   7140
gggataccag ttcgtcgcgg cttttccgga cacagttccg gatggtcagc ccgaagcgca   7200
tcagcaaccc gaacaatacc ggcgacagcc ggaactgccg tgccggtgtg cagattaatg   7260
acagcggtgc ggcgctggga tattacgtca gcgaggacgg gtatcctggc tggatgccgc   7320
agaaatggac atggataccc cgtgagttac ccggcgggcg cgcttggcgt aatcatggtc   7380
atagctgttt cctgtgtgaa attgttatcc gctcacaatt ccacacaaca tacgagccgg   7440
aagcataaag tgtaaagcct ggggtgccta atgagtgagc taactcacat taattgcgtt   7500
gcgctcactg cccgctttcc agtcgggaaa cctgtcgtgc cagctgcatt aatgaatcgg   7560
ccaacgcgcg gggagaggcg gtttgcgtat tgggcgctct tccgcttcct cgctcactga   7620
ctcgctgcgc tcggtcgttc ggctgcggcg agcggtatca gctcactcaa aggcggtaat   7680
acggttatcc acagaatcag gggataacgc aggaaagaac atgtgagcaa aaggccagca   7740
aaaggccagg aaccgtaaaa aggccgcgtt gctggcgttt ttccataggc tccgcccccc   7800
tgacgagcat cacaaaaatc gacgctcaag tcagaggtgg cgaaacccga caggactata   7860
aagataccag gcgtttcccc ctggaagctc cctcgtgcgc tctcctgttc cgaccctgcc   7920
gcttaccgga tacctgtccg cctttctccc ttcgggaagc gtggcgcttt ctcatagctc   7980
acgctgtagg tatctcagtt cggtgtaggt cgttcgctcc aagctgggct gtgtgcacga   8040
accccccgtt cagcccgacc gctgcgcctt atccggtaac tatcgtcttg agtccaaccc   8100
ggtaagacac gacttatcgc cactggcagc agccactggt aacaggatta gcagagcgag   8160
gtatgtaggc ggtgctacag agttcttgaa gtggtggcct aactacggct acactagaag   8220
gacagtattt ggtatctgcg ctctgctgaa gccagttacc ttcggaaaaa gagttggtag   8280
ctcttgatcc ggcaaacaaa ccaccgctgg tagcggtggt ttttttgttt gcaagcagca   8340
gattacgcgc agaaaaaaag gatctcaaga agatcctttg atcttttcta cggggtctga   8400
cgctcagtgg aacgaaaact cacgttaagg gattttggtc atgagattat caaaaaggat   8460
cttcacctag atccttttaa attaaaaatg aagttttaaa tcaatctaaa gtatatatga   8520
gtaaacttgg tctgacagtt accaatgctt aatcagtgag gcacctatct cagcgatctg   8580
```

tctatttcgt tcatccatag ttgcctgact ccccgtcgtg tagataacta cgatacggga 8640
gggcttacca tctggcccca gtgctgcaat gataccgcga gacccacgct caccggctcc 8700
agatttatca gcaataaacc agccagccgg aagggccgag cgcagaagtg gtcctgcaac 8760
tttatccgcc tccatccagt ctattaattg ttgccgggaa gctagagtaa gtagttcgcc 8820
agttaatagt ttgcgcaacg ttgttgccat tgctacaggc atcgtggtgt cacgctcgtc 8880
gtttggtatg gcttcattca gctccggttc ccaacgatca aggcgagtta catgatcccc 8940
catgttgtgc aaaaaagcgg ttagctcctt cggtcctccg atcgttgtca gaagtaagtt 9000
ggccgcagtg ttatcactca tggttatggc agcactgcat aattctctta ctgtcatgcc 9060
atccgtaaga tgcttttctg tgactggtga gtactcaacc aagtcattct gagaatagtg 9120
tatgcggcga ccgagttgct cttgcccggc gtcaatacgg gataataccg cgccacatag 9180
cagaacttta aaagtgctca tcattggaaa acgttcttcg gggcgaaaac tctcaaggat 9240
cttaccgctg ttgagatcca gttcgatgta acccactcgt gcacccaact gatcttcagc 9300
atcttttact ttcaccagcg tttctgggtg agcaaaaaca ggaaggcaaa atgccgcaaa 9360
aaagggaata agggcgacac ggaaatgttg aatactcat 9399

<210> SEQ ID NO 29
<211> LENGTH: 9393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct aaattgtaag cgttaatatt ttgttaaaat tcgcgttaaa tttttgttaa 180
atcagctcat tttttaacca ataggccgaa atcggcaaaa tcccttataa atcaaaagaa 240
tagaccgaga tagggttgag tgttgttcca gtttggaaca agagtccact attaaagaac 300
gtggactcca acgtcaaagg gcgaaaaacc gtctatcagg gcgatggccc actacgtgaa 360
ccatcaccct aatcaagttt tttggggtcg aggtgccgta aagcactaaa tcggaaccct 420
aaagggagcc cccgatttag agcttgacgg ggaaagccgg cgaacgtggc gagaaaggaa 480
gggaagaaag cgaaaggagc gggcgctagg gcgctggcaa gtgtagcggt cacgctgcgc 540
gtaaccacca cacccgccgc gcttaatgcg ccgctacagg gcgcgtccca ttcgccattc 600
aggctgcgca actgttggga agggcgatcg gtgcgggcct cttcgctatt acgccagctg 660
gcgaaagggg gatgtgctgc aaggcgatta agttgggtaa cgccagggtt ttcccagtca 720
cgacgttgta aaacgacggc cagtgagcgc gcctcgttca ttcacgtttt tgaacccgtg 780
gaggacgggc agactcgcgg tgcaaatgtg ttttacagcg tgatggagca gatgaagatg 840
ctcgacacgc tgcagaacac gcagctagat taaccctaga aagataatca tattgtgacg 900
tacgttaaag ataatcatgc gtaaaattga cgcatgtgtt ttatcggtct gtatatcgag 960
gtttatttat taatttgaat agatattaag ttttattata tttacactta catactaata 1020
ataaattcaa caaacaattt atttatgttt atttatttat taaaaaaaaa caaaaactca 1080
aaatttcttc tataaagtaa caaaactttt atcgaattcc tgcagcccgg gggatccact 1140
agttctagag ggacagcccc cccccaaagc ccccagggat gtaattacgt ccctcccccg 1200

-continued

```
ctagggggca gcagcgagcc gcccggggct ccgctccggt ccggcgctcc ccccgcatcc   1260
ccgagccggc agcgtgcggg gacagcccgg gcacggggaa ggtggcacgg gatcgctttc   1320
ctctgaacgc ttctcgctgc tctttgagcc tgcagacacc tggggggata cggggaaaag   1380
gcctccaagg ccagcttccc acaataagtt gggtgaattt tggctcattc ctcctttcta   1440
taggattgag gtcagagctt tgtgatggga attctgtgga atgtgtgtca gttagggtgt   1500
ggaaagtccc gcgatcgcta gcttaagcgc tgatcaattg gcgcgccgaa ttcgttatct   1560
gcagaattcg gcttggcggc tgcgcgttca aacctcccgc ttcaaaatgg agaccctgcg   1620
tgctcactcg ggcttaaata cccagcgtga ccacatggtg tcgcaaaatg tcgcaaaaca   1680
ctcacgtgac ctctaataca ggacctctag agcatggaaa ctagataaga aagaaatacg   1740
cagagaccaa agttcaactg aaacgaatta aacggtttat tgattaacaa gcaaactagt   1800
ttacagatta cgagtcaggt atctggtgcc aatggggcgg ggttcactat atacaccttc   1860
agtattaaca gcaaattcaa cattattaga cttgtaatag ttggaagtgt actggatctc   1920
cgggttccag cgcttgctgt tttccttctg cagctcccac tcgatctcca cgctgacttg   1980
gccagtagaa tactgggtga tgaaagagtt cagcttgtcc ttgttgaagg ccgttggagg   2040
atccgcaggt acaggtgtgt ttttgatgag gatctgagga ggcgggtgct tcattccaaa   2100
ccctcccatc agcggagaag ggtgaaagtt gccgtccgtg tgaggaattt tggcccaaat   2160
gggtccttgc aggtacacat ctctgtcctg ccaaaccata cccggaagta ttccttggtt   2220
ttgaacccag ccggtctgcg cctgtgcttg ggcactctgg tggtttgtgg ccacttgtcc   2280
ataggactcc gttgctaccg ggttagtagt tttaatttct tcttcgttgg ttatcatgac   2340
tttgtccgca tccacgttgt ctcttccagt tccttgtttg ccaaaaaatta aagatccaga   2400
caaaggaaag aaacggtcct ctccttcttt gtggctggcc atagcaggtc caggattcat   2460
caagctatta cgtccattga gagcccaaga agaagctcca ggccaagcaa attcgctgtt   2520
gttgttttga gtcacagtgg ttgagacacg ttgttgtcgg tagctgggtc caggtatgta   2580
gtttcttccc tggacagcca tgttgctggg tccggccaca ctgaatttta gcgtttgttg   2640
attctgtcca gaaccgttaa tagtctttga gagatagtac aagtattggt cgatgagtgg   2700
attcattagt cggtccaggc tttggctgtg agcgtagctg ctatggaaag gtacgttctc   2760
aaactcgtag ctgaactgga agttgttacc cgttcttagc atttgcgacg ggaaatattc   2820
caggcagtaa aaggacgaac gacccacggc ctggcttcca tcattaagcg tcagataccc   2880
gtactgagga atcatgaaaa cgtccgctgg gaacggcggg aggcagccct cgtgagccga   2940
cccgagcacg tacgggagct gatagtctga gtccgtgaag acctggaccg tgctggtaag   3000
gttattggcg atggtcttga ctccattgtt gtccgtaacc tctttgacct gaatgttgaa   3060
gagcttgaag ttgagtcgct taggccggaa tccccagttg ttgttgatga gtcgctgcca   3120
gtcacgtggt gagaagtggc agtggaatct gttgaagtca aaatacccccc agggggtgct   3180
gtagccgaag taggcgttgt catttgaaga tcctccagat gtgctgttgg agatttgctt   3240
gtagaggtga ttgttgtagg tgggcagggc ccaggttcgg gtgctggtgg tgatgactct   3300
gtcccccagc cattgggaat cgcaatgcca atttcccgag gaactaccca ctccatcggc   3360
accttcgtta ttgtctgcca ctggtgcgcc accacctgaa gccattgtaa gagatcccac   3420
acctgagggg gctgcgggag gttctccgat tggttgaggg tctgggactg actctgtgtc   3480
gccagtctga ccgaaattga gtctcttttt agcgggctgt gcacccgatt tgccaatacc   3540
cgcggaggag tccggttcct gaggagactg ctctacaggc ctcttctttc caggagccgt   3600
```

-continued

```
cttagccgct tcctcaacca gaccaagagg ttcaagaagc ctctttttgg cctggaagac   3660
tgctcgcccg aggttgcccc caaaagacgt atcttctttg agccgctcct ggaactcggc   3720
gtcggcgtgg ttgtacttga ggtacgggtt gtctccggcc ttgagctgct ggtcgtaggc   3780
cttgtcgtgc tcgagggccg ccgcgtctgc tgcgttgacc ggctccccct tgtcgagtcc   3840
gttgccgggt ccaaggtatt tgtaacccgg aagcacaaga cctcgagcgt tgtcttgatg   3900
ttgttgattt gccttgggtt gaggggctcc aggtttcaaa gcccaccact cgcgaattcc   3960
ttcactaagg ttgtcctcga gccaatctgg aagataacca tcggcagcca tacctgattt   4020
aaatcattta ttgttcaaag atgcagtcat ccaaatccac attgaccaga tcgcaggcag   4080
tgcaagcgtc tggcaccttt cccatgatat gatgaatgta gcacagtttc tgatacgcct   4140
ttttgacgac agaaacgggt tgagattctg acacgggaaa gcactctaaa cagtctttct   4200
gtccgtgagt gaagcagata tttgaattct gattcattct ctcgcattgt ctgcagggaa   4260
acagcatcag attcatgccc acgtgacgag aacatttgtt ttggtacctg tctgcgtagt   4320
tgatcgaagc ttccgcgtct gacgtcgatg gctgcgcaac tgactcgcgc acccgtttgg   4380
gctcacttat atctgcgtca ctgggggcgg gtcttttctt ggctccaccc tttttgacgt   4440
agaattcatg ctccacctca accacgtgat cctttgccca ccggaaaaag tctttgactt   4500
cctgcttggt gaccttccca aagtcatgat ccagacggcg ggtgagttca aatttgaaca   4560
tccggtcttg caacggctgc tggtgttcga aggtcgttga gttcccgtca atcacggcgc   4620
acatgttggt gttggaggtg acgatcacgg gagtcgggtc tatctgggcc gaggacttgc   4680
atttctggtc cacgcgcacc ttgcttcctc cgagaatggc tttggccgac tccacgacct   4740
tggcggtcat cttcccctcc tcccaccaga tcaccatctt gtcgacacag tcgttgaagg   4800
gaaagttctc attggtccag tttacgcacc cgtagaaggg cacagtgtgg gctatggcct   4860
ccgcgatgtt ggtcttcccg gtagttgcag gcccaaacag ccagatggtg ttcctcttgc   4920
cgaacttttt cgtggcccat cccagaaaga cggaagccgc atattgggga tcgtacccgt   4980
ttagttccaa aattttataa atccgattgc tggaaatgtc ctccacgggc tgctggccca   5040
ccaggtagtc gggggcggtt ttagtcaggc tcataatctt tcccgcattg tccaaggcag   5100
ccttgatttg ggaccgcgag ttggaggccg cattgaagga gatgtatgag gcctggtcct   5160
cctggatcca ctgcttctcc gaggtaatcc ccttgtccac gagccacccg accagctcca   5220
tgtacctggc tgaagttttt gatctgatca ccggcgcatc agaattggga ttctgattct   5280
ctttgttctg ctcctgcgtc tgcgacacgt gcgtcagatg ctgcgccacc aaccgtttac   5340
gctccgtgag attcaaacag gcgctgtgga gagaaaggca aagtggatgt cagtatctct   5400
atcactgata gggagatctc tatcactgat agggaactta ccttaaatac tgttccatat   5460
tagtccacgc ccactggagc tcaggctggg ttttggggag caagtaattg gggatgtagc   5520
actcatccac caccttgttc ccgcctccgg cgccatttct ggtctttgtg accgcgaacc   5580
agtttggcaa agtcggctcg atcccgcggt aaattctctg aatcagtttt tcgcgaatct   5640
gactcaggaa acgtcccaaa accatggatt tcaccccggt ggtttccacg agcacgtgca   5700
tgtggaagta gctctctccc ttctcaaatt gcacaaagaa aagagcctcc ggggccttac   5760
tcacacggcg ccattccgtc agaaagtcgc gctgcagctt ctcggccacg gtcaggggtg   5820
cctgctcaat cagattcaga tccatgtcag aatctggcgg caactcccat tccttctcgg   5880
ccacccagtt cacaaagctg tcagaaatgc cgggcagatg ctcgtcaagg tcgctgggga   5940
```

-continued

```
ccttaatcac aatctcgtaa aaccccggca tggcggctgc gcgttcaaac ctcccgcttc   6000
aaaatggaga ccctgcgtgc tcactcgggc gatctctatc actgataggg agatctctat   6060
cactgatagg gagattaaat agaatggcta ggatccggcc ggcctgcagg tgtcctcaca   6120
ggaacgaagt ccctaaagaa acagtggcag ccaggtttag ccccggaatt gactggattc   6180
ctttttttagg gcccattggt atggcttttt ccccgtatcc ccccaggtgt ctgcaggctc   6240
aaagagcagc gagaagcgtt cagaggaaag cgatcccgtg ccaccttccc cgtgcccggg   6300
ctgtccccgc acgctgccgg ctcggggatg cggggggagc gccggaccgg agcggagccc   6360
cgggcggctc gctgctgccc cctagcgggg gagggacgta attacatccc tgggggcttt   6420
gggggggggc tgtccctcta gagcggccgc caccgcggtg gagctccagc ttttgttccc   6480
tttagtgagg gttaattaga tcttaatacg actcactata gggcgaattg ggtaccgggc   6540
ccccctcga ggtcgacggt atcgataagc ttgatatcta taacaagaaa atatatatat   6600
aataagttat cacgtaagta gaacatgaaa taacaatata attatcgtat gagttaaatc   6660
ttaaaagtca cgtaaaagat aatcatgcgt cattttgact cacgcggtcg ttatagttca   6720
aaatcagtga cacttaccgc attgacaagc acgcctcacg ggagctccaa gcggcgactg   6780
agatgtccta aatgcacagc gacggattcg cgctatttag aaagagagag caatatttca   6840
agaatgcatg cgtcaatttt acgcagacta tctttctagg gttaatctag ctgcatcagg   6900
atcatatcgt cgggtctttt ttccggctca gtcatcgccc aagctggcgc tatctgggca   6960
tcggggagga agaagcccgt gccttttccc gcgaggttga agcggcatgg aaagagtttg   7020
ccgaggatga ctgctgctgc attgacgttg agcgaaaacg cacgtttacc atgatgattc   7080
gggaaggtgt ggccatgcac gcctttaacg gtgaactgtt cgttcaggcc acctgggata   7140
ccagttcgtc gcggcttttc cggacacagt tccggatggt cagcccgaag cgcatcagca   7200
acccgaacaa taccggcgac agccggaact gccgtgccgg tgtgcagatt aatgacagcg   7260
gtgcggcgct gggatattac gtcagcgagg acgggtatcc tggctggatg ccgcagaaat   7320
ggacatggat accccgtgag ttacccggcg ggcgcgcttg gcgtaatcat ggtcatagct   7380
gtttcctgtg tgaaattgtt atccgctcac aattccacac aacatacgag ccggaagcat   7440
aaagtgtaaa gcctggggtg cctaatgagt gagctaactc acattaattg cgttgcgctc   7500
actgcccgct ttccagtcgg gaaacctgtc gtgccagctg cattaatgaa tcggccaacg   7560
cgcggggaga ggcggtttgc gtattgggcg ctcttccgct tcctcgctca ctgactcgct   7620
gcgctcggtc gttcggctgc ggcgagcggt atcagctcac tcaaaggcgg taatacggtt   7680
atccacagaa tcaggggata acgcaggaaa gaacatgtga gcaaaaggcc agcaaaaggc   7740
caggaaccgt aaaaaggccg cgttgctggc gtttttccat aggctccgcc cccctgacga   7800
gcatcacaaa aatcgacgct caagtcagag gtggcgaaac ccgacaggac tataaagata   7860
ccaggcgttt ccccctggaa gctccctcgt gcgctctcct gttccgaccc tgccgcttac   7920
cggatacctg tccgcctttc tcccttcggg aagcgtggcg ctttctcata gctcacgctg   7980
taggtatctc agttcggtgt aggtcgttcg ctccaagctg ggctgtgtgc acgaaccccc   8040
cgttcagccc gaccgctgcg ccttatccgg taactatcgt cttgagtcca acccggtaag   8100
acacgactta tcgccactgg cagcagccac tggtaacagg attagcagag cgaggtatgt   8160
aggcggtgct acagagttct tgaagtggtg gcctaactac ggctacacta gaaggacagt   8220
atttggtatc tgcgctctgc tgaagccagt taccttcgga aaaagagttg gtagctcttg   8280
atccggcaaa caaaccaccg ctggtagcgg tggttttttt gtttgcaagc agcagattac   8340
```

```
gcgcagaaaa aaaggatctc aagaagatcc tttgatcttt tctacggggt ctgacgctca   8400
gtggaacgaa aactcacgtt aagggatttt ggtcatgaga ttatcaaaaa ggatcttcac   8460
ctagatcctt ttaaattaaa aatgaagttt taaatcaatc taaagtatat atgagtaaac   8520
ttggtctgac agttaccaat gcttaatcag tgaggcacct atctcagcga tctgtctatt   8580
tcgttcatcc atagttgcct gactccccgt cgtgtagata actacgatac gggagggctt   8640
accatctggc cccagtgctg caatgatacc gcgagaccca cgctcaccgg ctccagattt   8700
atcagcaata aaccagccag ccggaagggc cgagcgcaga agtggtcctg caactttatc   8760
cgcctccatc cagtctatta attgttgccg ggaagctaga gtaagtagtt cgccagttaa   8820
tagtttgcgc aacgttgttg ccattgctac aggcatcgtg gtgtcacgct cgtcgtttgg   8880
tatggcttca ttcagctccg gttcccaacg atcaaggcga gttacatgat cccccatgtt   8940
gtgcaaaaaa gcggttagct ccttcggtcc tccgatcgtt gtcagaagta agttggccgc   9000
agtgttatca ctcatggtta tggcagcact gcataattct cttactgtca tgccatccgt   9060
aagatgcttt tctgtgactg gtgagtactc aaccaagtca ttctgagaat agtgtatgcg   9120
gcgaccgagt tgctcttgcc cggcgtcaat acgggataat accgcgccac atagcagaac   9180
tttaaaagtg ctcatcattg gaaaacgttc ttcggggcga aaactctcaa ggatcttacc   9240
gctgttgaga tccagttcga tgtaacccac tcgtgcaccc aactgatctt cagcatcttt   9300
tactttcacc agcgtttctg ggtgagcaaa aacaggaagg caaaatgccg caaaaaaggg   9360
aataagggcg acacggaaat gttgaatact cat                                9393
```

<210> SEQ ID NO 30
<211> LENGTH: 9393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
actcttcctt tttcaatatt attgaagcat ttatcagggt tattgtctca tgagcggata     60
catatttgaa tgtatttaga aaaataaaca aataggggtt ccgcgcacat ttccccgaaa    120
agtgccacct aaattgtaag cgttaatatt ttgttaaaat tcgcgttaaa tttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
```

gtttatttat taatttgaat agatattaag ttttattata tttacactta catactaata 1020
ataaattcaa caaacaattt atttatgttt atttatttat taaaaaaaaa caaaaactca 1080
aaatttcttc tataaagtaa caaaactttt atcgaattcc tgcagcccgg gggatccact 1140
agttctagag ggacagcccc cccccaaagc ccccagggat gtaattacgt ccctcccccg 1200
ctagggggca gcagcgagcc gcccggggct ccgctccggt ccggcgctcc ccccgcatcc 1260
ccgagccggc agcgtgcggg gacagcccgg gcacggggaa ggtggcacgg gatcgctttc 1320
ctctgaacgc ttctcgctgc tctttgagcc tgcagacacc tggggggata cggggaaaag 1380
gcctccaagg ccagcttccc acaataagtt gggtgaattt tggctcattc ctcctttcta 1440
taggattgag gtcagagctt tgtgatggga attctgtgga atgtgtgtca gttagggtgt 1500
ggaaagtccc gcgatcgcta gcttaagcgc tgatcaattg gcgcgccgaa ttcgttatct 1560
gcagaattcg gcttggcggc tgcgcgttca aacctcccgc ttcaaaatgg agaccctgcg 1620
tgctcactcg ggcttaaata cccagcgtga ccacatggtg tcgcaaaatg tcgcaaaaca 1680
ctcacgtgac ctctaataca ggacctctag agcatggaaa ctagataaga aagaaatacg 1740
cagagaccaa agttcaactg aaacgaatta aacggtttat tgattaacaa gcaaactagt 1800
ttacagatta cgggtgaggt aacgggtgcc gatggggcga ggctcagaat aaacgccatt 1860
tgtgtcaaca gcaaagtcca catttgtaga tttgttgtag ttggaagtgt attgaatctc 1920
tgggttccag cgtttgctgt ttctttctg cagctcccat tcaatttcca cgctgacctg 1980
tccggtgctg tactgcgtga tgaacgacgc aaacttagct ggactgaagg tagttggagg 2040
attcgcggga acaggtgtat tcttaatcag gatctgagga ggcgggtgtt tcagtccaaa 2100
gcctcccatc agcggcgagg gatgaaagtg tccgtccgtg tgaggaatct tggcccagat 2160
aggaccctgc aggtacacgt cccggtcctg ccagaccatg ccaggtaagg ctccttgact 2220
gttgacggtc cctgtagcag gagcggtgtt ggccgattgc aggttagtgg ccaccgtgcc 2280
gtactcttct gtggccactg ggttggtggt tttaatttct tcctcgttgg ttatcataac 2340
gttgtcaagg tccacgttgc tatttccagc tccctgtttc ccaaatatta agactccgct 2400
catcggaaaa aatttgtctt cgtcgtcctt gtgggttgcc atagcgggac cgggatttac 2460
cagagagtct ctgccattca gatgatactt ggtggcaccg gtccaggcaa agttgctgtt 2520
gttattttga ttggttgtct tggagacgcg ttgctgccgg tagcagggcc cgggtagcca 2580
gtttttggcc tgattcgcca tgctactagg cccggcctga gaaaattgca acgtccgatt 2640
tcctgcggta ccactcgtgg tctgagtccg agacaggtag tacaggtact ggtcgatgag 2700
ggggttcatc agccggtcca ggctttggct gtgcgcgtag ctgctgtgaa aaggcacgtc 2760
ctcaaacgtg tagctgaact gaaagttgtt gcccgttctc agcatttgag aaggaaagta 2820
ttccaggcag tagaaggagg aacggcccac ggcctgactg ccattgttca gagtcaggta 2880
cccgtactga ggaatcatga agacgtccgc cgggaacgga ggcaggcagc cctggtgcgc 2940
agagccgagg acgtacggga gctggtattc cgagtccgta aagacctgaa ccgtgctggt 3000
aaggttattg gcgatggtcg tggtgccatc attcgtcgtg acctccttga cctggatgtt 3060
gaagagcttg aagttgagct tcttgggccg gaatccccag ttgttgttga tgagtcgctg 3120
ccagtcacgt ggtgagaagt ggcagtggaa tctgttaaag tcaaaatacc cccagggggt 3180
gctgtagccg aagtaggtgt tgtcgttggt gctgcctccc gattggctgg agatttgctt 3240
gtagaggtgg ttgttgtagg tggggagggc ccaggttcgg gtgctggtgg tgatgactct 3300

-continued

```
gtcgcccagc catgtggaat cgcaatgcca atttcctgag gcgttaccca ctccgtcggc   3360
gccttcgtta ttgtctgcca ttggagcgcc accgcctgca gccattgtat tagatcccac   3420
accagagggg gctgcggggg gttctccgag tggttgaggg tcgggcactg actctgagtc   3480
gccagtctgc ccaaagttga gtctctttct cgcgggctgc tggcctttct tgccgatgcc   3540
cgaagaggag tctggttcct ggggtgattg ctctaccggt ctcttctttc caggagccgt   3600
cttagcgcct tcctcaacca gaccgagagg ttcgagaacc cgcttcttgg cctggaagac   3660
tgctcgcccg aggttgcccc caaaagacgt atcttcttgc agacgctcct gaaactcggc   3720
gtcggcgtgg ttataccgca ggtacggatt gtcacccgct ttgagctgct ggtcgtaggc   3780
cttgtcgtgc tcgagggccg ctgcgtccgc cgcgttgacg ggctccccct tgtcgagtcc   3840
gttgaagggt ccgaggtact tgtagccagg aagcaccaga ccccggccgt cgtcctgctt   3900
ttgctggttg gctttgggtt tcggggctcc aggtttcaag tcccaccact cgcgaatgcc   3960
ctcagagagg ttgtcctcga gccaatctgg aagataacca tcggcagcca tacctgattt   4020
aaatcattta ttgttcaaag atgcagtcat ccaaatccac attgaccaga tcgcaggcag   4080
tgcaagcgtc tggcaccttt cccatgatat gatgaatgta gcacagtttc tgatacgcct   4140
ttttgacgac agaaacgggt tgagattctg acacgggaaa gcactctaaa cagtctttct   4200
gtccgtgagt gaagcagata tttgaattct gattcattct ctcgcattgt ctgcagggaa   4260
acagcatcag attcatgccc acgtgacgag aacatttgtt ttggtacctg tctgcgtagt   4320
tgatcgaagc ttccgcgtct gacgtcgatg gctgcgcaac tgactcgcgc acccgtttgg   4380
gctcacttat atctgcgtca ctgggggcgg gtcttttctt ggctccaccc tttttgacgt   4440
agaattcatg ctccacctca accacgtgat cctttgccca ccggaaaaag tctttgactt   4500
cctgcttggt gaccttccca aagtcatgat ccagacggcg ggtgagttca aatttgaaca   4560
tccggtcttg caacggctgc tggtgttcga aggtcgttga gttcccgtca atcacggcgc   4620
acatgttggt gttggaggtg acgatcacgg gagtcgggtc tatctgggcc gaggacttgc   4680
atttctggtc cacgcgcacc ttgcttcctc cgagaatggc tttggccgac tccacgacct   4740
tggcggtcat cttcccctcc tcccaccaga tcaccatctt gtcgacacag tcgttgaagg   4800
gaaagttctc attggtccag tttacgcacc cgtagaaggg cacagtgtgg gctatggcct   4860
ccgcgatgtt ggtcttcccg gtagttgcag gcccaaacag ccagatggtg ttcctcttgc   4920
cgaacttttt cgtggcccat cccagaaaga cggaagccgc atattgggga tcgtacccgt   4980
ttagttccaa aattttataa atccgattgc tggaaatgtc ctccacgggc tgctggccca   5040
ccaggtagtc gggggcggtt ttagtcaggc tcataatctt tcccgcattg tccaaggcag   5100
ccttgatttg ggaccgcgag ttggaggccg cattgaagga gatgtatgag gcctggtcct   5160
cctggatcca ctgcttctcc gaggtaatcc ccttgtccac gagccacccg accagctcca   5220
tgtacctggc tgaagttttt gatctgatca ccggcgcatc agaattggga ttctgattct   5280
ctttgttctg ctcctgcgtc tgcgacacgt gcgtcagatg ctgcgccacc aaccgtttac   5340
gctccgtgag attcaaacag gcgctgtgga gagaaaggca aagtggatgt cagtatctct   5400
atcactgata gggagatctc tatcactgat agggaactta ccttaaatac tgttccatat   5460
tagtccacgc ccactggagc tcaggctggg ttttggggag caagtaattg gggatgtagc   5520
actcatccac caccttgttc ccgcctccgg cgccatttct ggtctttgtg accgcgaacc   5580
agtttggcaa agtcggctcg atcccgcggt aaattctctg aatcagtttt tcgcgaatct   5640
gactcaggaa acgtcccaaa accatggatt tcaccccggt ggtttccacg agcacgtgca   5700
```

-continued

```
tgtggaagta gctctctccc ttctcaaatt gcacaaagaa aagagcctcc ggggccttac   5760
tcacacggcg ccattccgtc agaaagtcgc gctgcagctt ctcggccacg gtcaggggtg   5820
cctgctcaat cagattcaga tccatgtcag aatctggcgg caactcccat tccttctcgg   5880
ccacccagtt cacaaagctg tcagaaatgc cgggcagatg ctcgtcaagg tcgctgggga   5940
ccttaatcac aatctcgtaa aaccccggca tggcggctgc gcgttcaaac ctcccgcttc   6000
aaaatggaga ccctgcgtgc tcactcgggc gatctctatc actgataggg agatctctat   6060
cactgatagg gagattaaat agaatggcta ggatccggcc ggcctgcagg tgtcctcaca   6120
ggaacgaagt ccctaaagaa acagtggcag ccaggtttag ccccggaatt gactggattc   6180
ctttttagg gcccattggt atggcttttt ccccgtatcc ccccaggtgt ctgcaggctc   6240
aaagagcagc gagaagcgtt cagaggaaag cgatcccgtg ccaccttccc cgtgcccggg   6300
ctgtccccgc acgctgccgg ctcggggatg cgggggggagc gccggaccgg agcggagccc   6360
cgggcggctc gctgctgccc cctagcgggg gagggacgta attacatccc tgggggcttt   6420
gggggggggc tgtccctcta gagcggccgc caccgcggtg gagctccagc ttttgttccc   6480
tttagtgagg gttaattaga tcttaatacg actcactata gggcgaattg ggtaccgggc   6540
ccccctcga ggtcgacggt atcgataagc ttgatatcta taacaagaaa atatatatat   6600
aataagttat cacgtaagta gaacatgaaa taacaatata attatcgtat gagttaaatc   6660
ttaaaagtca cgtaaaagat aatcatgcgt cattttgact cacgcggtcg ttatagttca   6720
aaatcagtga cacttaccgc attgacaagc acgcctcacg ggagctccaa gcggcgactg   6780
agatgtccta aatgcacagc gacggattcg cgctatttag aaagagagag caatatttca   6840
agaatgcatg cgtcaatttt acgcagacta tctttctagg gttaatctag ctgcatcagg   6900
atcatatcgt cgggtctttt ttccggctca gtcatcgccc aagctggcgc tatctgggca   6960
tcggggagga agaagcccgt gccttttccc gcgaggttga agcggcatgg aaagagtttg   7020
ccgaggatga ctgctgctgc attgacgttg agcgaaaacg cacgtttacc atgatgattc   7080
gggaaggtgt ggccatgcac gcctttaacg gtgaactgtt cgttcaggcc acctgggata   7140
ccagttcgtc gcggcttttc cggacacagt tccggatggt cagcccgaag cgcatcagca   7200
acccgaacaa taccggcgac agccggaact gccgtgccgg tgtgcagatt aatgacagcg   7260
gtgcggcgct gggatattac gtcagcgagg acgggtatcc tggctggatg ccgcagaaat   7320
ggacatggat accccgtgag ttacccggcg ggcgcgcttg gcgtaatcat ggtcatagct   7380
gtttcctgtg tgaaattgtt atccgctcac aattccacac aacatacgag ccggaagcat   7440
aaagtgtaaa gcctggggtg cctaatgagt gagctaactc acattaattg cgttgcgctc   7500
actgcccgct ttccagtcgg gaaacctgtc gtgccagctg cattaatgaa tcggccaacg   7560
cgcggggaga ggcggtttgc gtattgggcg ctcttccgct tcctcgctca ctgactcgct   7620
gcgctcggtc gttcggctgc ggcgagcggt atcagctcac tcaaaggcgg taatacggtt   7680
atccacagaa tcaggggata acgcaggaaa gaacatgtga gcaaaaggcc agcaaaaggc   7740
caggaaccgt aaaaaggccg cgttgctggc gtttttccat aggctccgcc cccctgacga   7800
gcatcacaaa aatcgacgct caagtcagag gtggcgaaac ccgacaggac tataaagata   7860
ccaggcgttt ccccctggaa gctccctcgt gcgctctcct gttccgaccc tgccgcttac   7920
cggatacctg tccgcctttc tcccttcggg aagcgtggcg ctttctcata gctcacgctg   7980
taggtatctc agttcggtgt aggtcgttcg ctccaagctg ggctgtgtgc acgaaccccc   8040
```

```
cgttcagccc gaccgctgcg ccttatccgg taactatcgt cttgagtcca acccggtaag   8100
acacgactta tcgccactgg cagcagccac tggtaacagg attagcagag cgaggtatgt   8160
aggcggtgct acagagttct tgaagtggtg gcctaactac ggctacacta gaaggacagt   8220
atttggtatc tgcgctctgc tgaagccagt taccttcgga aaaagagttg gtagctcttg   8280
atccggcaaa caaaccaccg ctggtagcgg tggttttttt gtttgcaagc agcagattac   8340
gcgcagaaaa aaaggatctc aagaagatcc tttgatcttt tctacggggt ctgacgctca   8400
gtggaacgaa aactcacgtt aagggatttt ggtcatgaga ttatcaaaaa ggatcttcac   8460
ctagatcctt ttaaattaaa aatgaagttt taaatcaatc taaagtatat atgagtaaac   8520
ttggtctgac agttaccaat gcttaatcag tgaggcacct atctcagcga tctgtctatt   8580
tcgttcatcc atagttgcct gactccccgt cgtgtagata actacgatac gggagggctt   8640
accatctggc cccagtgctg caatgatacc gcgagaccca cgctcaccgg ctccagattt   8700
atcagcaata aaccagccag ccggaagggc cgagcgcaga agtggtcctg caactttatc   8760
cgcctccatc cagtctatta attgttgccg ggaagctaga gtaagtagtt cgccagttaa   8820
tagtttgcgc aacgttgttg ccattgctac aggcatcgtg gtgtcacgct cgtcgtttgg   8880
tatggcttca ttcagctccg gttcccaacg atcaaggcga gttacatgat cccccatgtt   8940
gtgcaaaaaa gcggttagct ccttcggtcc tccgatcgtt gtcagaagta agttggccgc   9000
agtgttatca ctcatggtta tggcagcact gcataattct cttactgtca tgccatccgt   9060
aagatgcttt tctgtgactg gtgagtactc aaccaagtca ttctgagaat agtgtatgcg   9120
gcgaccgagt tgctcttgcc cggcgtcaat acgggataat accgcgccac atagcagaac   9180
tttaaaagtg ctcatcattg gaaaacgttc ttcggggcga aaactctcaa ggatcttacc   9240
gctgttgaga tccagttcga tgtaacccac tcgtgcaccc aactgatctt cagcatcttt   9300
tactttcacc agcgtttctg ggtgagcaaa aacaggaagg caaaatgccg caaaaaaggg   9360
aataagggcg acacggaaat gttgaatact cat                               9393
```

<210> SEQ ID NO 31
<211> LENGTH: 7147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gacggatcgg gagatctgag ctcacgggga cagcccccc ccaaagcccc cagggatgta     60
attacgtccc tcccccgcta gggggcagca gcgagccgcc cggggctccg ctccggtccg    120
gcgctccccc cgcatccccg agccggcagc gtgcggggac agcccgggca cggggaaggt    180
ggcacgggat cgctttcctc tgaacgcttc tcgctgctct ttgagcctgc agacacctgg    240
ggggatacgg ggaaaaagct ttaggctgaa agagagattt agaatgacag aatcatagaa    300
cggcctgggt tgcaaaggag cacagtgctc atccagatcc aaccccctgc tatgtgcagg    360
gtcatcaacc agcagcccag gctgcccaga gccacatcca gcctggcctt gaatgcctgc    420
aggcccgatc ccctatggtc gactctcagt acaatctgct ctgatgccgc atagttaagc    480
cagtatctgc tccctgcttg tgtgttggag gtcgctgagt agtgcgcgag caaaatttaa    540
gctacaacaa ggcaaggctt gaccgacaat tgcatgaaga atctgcttag ggttaggcgt    600
tttgcgctgc ttcgcgatgt acgggccaga tatacgcgtt gacattgatt attgactagt    660
```

```
tattaatagt aatcaattac ggggtcatta gttcatagcc catatatgga gttccgcgtt    720
acataactta cggtaaatgg cccgcctggc tgaccgccca acgacccccg cccattgacg    780
tcaataatga cgtatgttcc catagtaacg ccaataggga ctttccattg acgtcaatgg    840
gtggactatt tacggtaaac tgcccacttg gcagtacatc aagtgtatca tatgccaagt    900
acgcccccta ttgacgtcaa tgacggtaaa tggcccgcct ggcattatgc ccagtacatg    960
accttatggg actttcctac ttggcagtac atctacgtat tagtcatcgc tattaccatg   1020
gtgatgcggt tttggcagta catcaatggg cgtggatagc ggtttgactc acggggattt   1080
ccaagtctcc accccattga cgtcaatggg agtttgtttt ggcaccaaaa tcaacgggac   1140
tttccaaaat gtcgtaacaa ctccgcccca ttgacgcaaa tgggcggtag gcgtgtacgg   1200
tgggaggtct atataagcag agctctctgg ctaactagag aacccactgc ttactggctt   1260
atcgaaatta atacgactca ctatagggag acccaagctg gctagcgttt aaacttaagc   1320
tttctgtgag tttggggacc cttgattgtt ctttcttttt cgctattgta aaattcatgt   1380
tatatggagg gggcaaagtt ttcagggtgt tgtttagaat gggaagatgt cccttgtatc   1440
accatggacc ctcatgataa ttttgtttct ttcactttct actctgttga caaccattgt   1500
ctcctcttat tttcttttca ttttctgtaa ctttttcgtt aaactttagc ttgcatttgt   1560
aacgaatttt taaattcact tttgtttatt tgtcagattg taagtacttt ctctaatcac   1620
tttttttca aggcaatcag ggtatattat attgtacttc agcacagttt tagagaacaa   1680
ttgttataat taaatgataa ggtagaatat ttctgcatat aaattctggc tggcgtggaa   1740
atattcttat tggtagaaac aactacatcc tggtcatcat cctgcctttc tctttatggt   1800
tacaatgata tacactgttt gagatgagga taaaatactc tgagtccaaa ccgggcccct   1860
ctgctaacca tgttcatgcc ttcttctttt tcctacagct cctgggcaac gtgctggtta   1920
ttgtgctgtc tcatcatttt ggcaaagaat tgtaatacga ctcactatag ggcgagccac   1980
catggctaga ttagataaaa gtaaagtgat taacagcgca ttagagctgc ttaatgaggt   2040
cggaatcgaa ggtttaacaa cccgtaaact cgcccagaag ctaggtgtag agcagcctac   2100
attgtattgg catgtaaaaa ataagcgggc tttgctcgac gccttagcca ttgagatgtt   2160
agataggcac catactcact tttgcccttt agaaggggaa agctggcaag atttttacg    2220
taataacgct aaaagtttta gatgtgcttt actaagtcat cgcgatggag caaaagtaca   2280
tttaggtaca cggcctacag aaaaacagta tgaaactctc gaaaatcaat tagccttttt   2340
atgccaacaa ggtttttcac tagagaatgc cttatatgca ctcagcgccg tggggcattt   2400
tactttaggt tgcgtattgg aagatcaaga gcatcaagtc gctaaagaag aaagggaaac   2460
acctactact gatagtatgc cgccattatt acgacaagct atcgaattat ttgatcacca   2520
aggtgcagag ccagccttct tattcggcct tgaattgatc atatgcggat tagaaaaaca   2580
acttaaatgt gaaagtgggt ccccaaaaaa gaagagaaag gtcgacggcg gtggttcagt   2640
ttaagcgtac agcgggatcc actagtccag tgtggtggaa ttctgcagat atccagcaca   2700
gtggcggccg ctcgagtcta gagggcccgt ttaaacccgc tgatcagcct cgactgtgcc   2760
ttctagttgc cagccatctg ttgtttgccc ctcccccgtg ccttccttga ccctggaagg   2820
tgccactccc actgtccttt cctaataaaa tgaggaaatt gcatcgcatt gtctgagtag   2880
gtgtcattct attctggggg gtggggtggg gcaggacagc aagggggagg attgggaaga   2940
caatagcagg catgctgggg atgcggtggg ctctatggct tctgaggcgg aaagaaccag   3000
ctggggctct agggggtatc cccacgcgcc ctgtagcggc gcattaagcg cggcgggtgt   3060
```

-continued

```
ggtggttacg cgcagcgtga ccgctacact tgccagcgcc ctagcgcccg ctcctttcgc   3120
tttcttccct tcctttctcg ccacgttcgc cggctttccc cgtcaagctc taaatcgggg   3180
catcccttta gggttccgat ttagtgcttt acggcacctc gaccccaaaa aacttgatta   3240
gggtgatggt tcacgtagtg ggccatcgcc ctgatagacg gtttttcgcc ctttgacgtt   3300
ggagtccacg ttctttaata gtggactctt gttccaaact ggaacaacac tcaaccctat   3360
ctcggtctat tcttttgatt tataagggat tttggggatt tcggcctatt ggttaaaaaa   3420
tgagctgatt taacaaaaat ttaacgcgaa ttaattctgt ggaatgtgtg tcagttaggg   3480
tgtggaaagt ccccaggctc cccaggcagg cagaagtatg caaagcatgc atctcaatta   3540
gtcagcaacc aggtgtggaa agtccccagg ctccccagca ggcagaagta tgcaaagcat   3600
gcatctcaat tagtcagcaa ccatagtccc gcccctaact ccgcccatcc cgcccctaac   3660
tccgcccagt tccgcccatt ctccgcccca tggctgacta atttttttta tttatgcaga   3720
ggccgaggcc gcctctgcct ctgagctatt ccagaagtag tgaggaggct tttttggagg   3780
cctaggcttt tgcaaaaagc tcccgggagc ttgtatatcc attttcggat ctgatcagca   3840
cgtgttgaca attaatcatc ggcatagtat atcggcatag tataatacga caaggtgagg   3900
aactaaacca tggccaagtt gaccagtgcc gttccggtgc tcaccgcgcg cgacgtcgcc   3960
ggagcggtcg agttctggac cgaccggctc gggttctccc gggacttcgt ggaggacgac   4020
ttcgccggtg tggtccggga cgacgtgacc ctgttcatca gcgcggtcca ggaccaggtg   4080
gtgccggaca acaccctggc ctgggtgtgg gtgcgcggcc tggacgagct gtacgccgag   4140
tggtcggagg tcgtgtccac gaacttccgg gacgcctccg ggccggccat gaccgagatc   4200
ggcgagcagc cgtgggggcg ggagttcgcc ctgcgcgacc cggccggcaa ctgcgtgcac   4260
ttcgtggccg aggagcagga ctgacacgtg ctacgagatt tcgattccac cgccgccttc   4320
tatgaaaggt tgggcttcgg aatcgttttc cgggacgccg gctggatgat cctccagcgc   4380
ggggatctca tgctggagtt cttcgcccac cccaacttgt ttattgcagc ttataatggt   4440
tacaaataaa gcaatagcat cacaaatttc acaaataaag cattttttc actgcattct   4500
agttgtggtt tgtccaaact catcaatgta tcttatcatg tctgtatacc gtcgacctct   4560
agctagagct tggcgtaatc atggtcatag ctgtttcctg tgtgaaattg ttatccgctc   4620
acaattccac acaacatacg agccggaagc ataaagtgta aagcctgggg tgcctaatga   4680
gtgagctaac tcacattaat tgcgttgcgc tcactgcccg ctttccagtc gggaaacctg   4740
tcgtgccagc tgcattaatg aatcggccaa cgcgcgggga gaggcggttt gcgtattggg   4800
cgctcttccg cttcctcgct cactgactcg ctgcgctcgg tcgttcggct gcggcgagcg   4860
gtatcagctc actcaaaggc ggtaatacgg ttatccacag aatcagggga taacgcagga   4920
aagagagctc acggggacag ccccccccca aagcccccag ggatgtaatt acgtccctcc   4980
cccgctaggg ggcagcagcg agccgcccgg ggctccgctc cggtccggcg ctcccccgc   5040
atccccgagc cggcagcgtg cggggacagc ccgggcacgg ggaaggtggc acgggatcgc   5100
tttcctctga acgcttctcg ctgctctttg agcctgcaga cacctggggg gatacgggga   5160
aaaagcttta ggctgaaaga gagatttaga atgacagaat catagaacgg cctgggttgc   5220
aaaggagcac agtgctcatc cagatccaac cccctgctat gtgcagggtc atcaaccagc   5280
agcccaggct gcccagagcc acatccagcc tggccttgaa tgcctgcagg acatgtgagc   5340
aaaaggccag caaaaggcca ggaaccgtaa aaaggccgcg ttgctggcgt ttttccatag   5400
```

gctccgcccc cctgacgagc atcacaaaaa tcgacgctca agtcagaggt ggcgaaaccc 5460
gacaggacta taaagatacc aggcgtttcc ccctggaagc tccctcgtgc gctctcctgt 5520
tccgaccctg ccgcttaccg gatacctgtc cgcctttctc ccttcgggaa gcgtggcgct 5580
ttctcaatgc tcacgctgta ggtatctcag ttcggtgtag gtcgttcgct ccaagctggg 5640
ctgtgtgcac gaaccccccg ttcagcccga ccgctgcgcc ttatccggta actatcgtct 5700
tgagtccaac ccggtaagac acgacttatc gccactggca gcagccactg gtaacaggat 5760
tagcagagcg aggtatgtag gcggtgctac agagttcttg aagtggtggc ctaactacgg 5820
ctacactaga aggacagtat ttggtatctg cgctctgctg aagccagtta ccttcggaaa 5880
aagagttggt agctcttgat ccggcaaaca aaccaccgct ggtagcggtg gtttttttgt 5940
ttgcaagcag cagattacgc gcagaaaaaa aggatctcaa gaagatcctt tgatcttttc 6000
tacggggtct gacgctcagt ggaacgaaaa ctcacgttaa gggattttgg tcatgagatt 6060
atcaaaaagg atcttcacct agatcctttt aaattaaaaa tgaagtttta aatcaatcta 6120
aagtatatat gagtaaactt ggtctgacag ttaccaatgc ttaatcagtg aggcacctat 6180
ctcagcgatc tgtctatttc gttcatccat agttgcctga ctccccgtcg tgtagataac 6240
tacgatacgg gagggcttac catctggccc cagtgctgca atgataccgc gagacccacg 6300
ctcaccggct ccagatttat cagcaataaa ccagccagcc ggaagggccg agcgcagaag 6360
tggtcctgca actttatccg cctccatcca gtctattaat tgttgccggg aagctagagt 6420
aagtagttcg ccagttaata gtttgcgcaa cgttgttgcc attgctacag gcatcgtggt 6480
gtcacgctcg tcgtttggta tggcttcatt cagctccggt tcccaacgat caaggcgagt 6540
tacatgatcc cccatgttgt gcaaaaaagc ggttagctcc ttcggtcctc cgatcgttgt 6600
cagaagtaag ttggccgcag tgttatcact catggttatg gcagcactgc ataattctct 6660
tactgtcatg ccatccgtaa gatgcttttc tgtgactggt gagtactcaa ccaagtcatt 6720
ctgagaatag tgtatgcggc gaccgagttg ctcttgcccg gcgtcaatac gggataatac 6780
cgcgccacat agcagaactt taaaagtgct catcattgga aaacgttctt cggggcgaaa 6840
actctcaagg atcttaccgc tgttgagatc cagttcgatg taacccactc gtgcacccaa 6900
ctgatcttca gcatctttta ctttcaccag cgtttctggg tgagcaaaaa caggaaggca 6960
aaatgccgca aaaaagggaa taagggcgac acggaaatgt tgaatactca tactcttcct 7020
ttttcaatat tattgaagca tttatcaggg ttattgtctc atgagcggat acatatttga 7080
atgtatttag aaaaataaac aaataggggt tccgcgcaca tttccccgaa aagtgccacc 7140
tgacgtc 7147

<210> SEQ ID NO 32
<211> LENGTH: 7493
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
gacggatcgg gagatctgag ctcacgggga cagccccccc ccaaagcccc cagggatgta 60
attacgtccc tcccccgcta gggggcagca gcgagccgcc cggggctccg ctccggtccg 120
gcgctccccc cgcatccccg agccggcagc gtgcggggac agcccgggca cggggaaggt 180
ggcacgggat cgctttcctc tgaacgcttc tcgctgctct ttgagcctgc agacacctgg 240

```
ggggatacgg ggaaaaagct ttaggctgaa agagagattt agaatgacag aatcatagaa    300
cggcctgggt tgcaaaggag cacagtgctc atccagatcc aaccccctgc tatgtgcagg    360
gtcatcaacc agcagcccag gctgcccaga gccacatcca gcctggcctt gaatgcctgc    420
aggcccgatc ccctatggtc gactctcagt acaatctgct ctgatgccgc atagttaagc    480
cagtatctgc tccctgcttg tgtgttggag gtcgctgagt agtgcgcgag caaaatttaa    540
gctacaacaa ggcaaggctt gaccgacaat tgcatgaaga atctgcttag ggttaggcgt    600
tttgcgctgc ttcgcgatgt acgggccaga tatacgcgtt gacattgatt attgactagt    660
tattaatagt aatcaattac ggggtcatta gttcatagcc catatatgga gttccgcgtt    720
acataactta cggtaaatgg cccgcctggc tgaccgccca acgacccccg cccattgacg    780
tcaataatga cgtatgttcc catagtaacg ccaataggga ctttccattg acgtcaatgg    840
gtggactatt tacggtaaac tgcccacttg gcagtacatc aagtgtatca tatgccaagt    900
acgcccccta ttgacgtcaa tgacggtaaa tggcccgcct ggcattatgc ccagtacatg    960
accttatggg actttcctac ttggcagtac atctacgtat tagtcatcgc tattaccatg   1020
gtgatgcggt tttggcagta catcaatggg cgtggatagc ggtttgactc acggggattt   1080
ccaagtctcc accccattga cgtcaatggg agtttgtttt ggcaccaaaa tcaacgggac   1140
tttccaaaat gtcgtaacaa ctccgcccca ttgacgcaaa tgggcggtag gcgtgtacgg   1200
tgggaggtct atataagcag agctctctgg ctaactagag aacccactgc ttactggctt   1260
atcgaaatta atacgactca ctatagggag acccaagctg gctagcgttt aaacttaagc   1320
tttctgtgag tttggggacc cttgattgtt ctttcttttt cgctattgta aaattcatgt   1380
tatatggagg gggcaaagtt ttcagggtgt tgtttagaat gggaagatgt cccttgtatc   1440
accatggacc ctcatgataa ttttgtttct ttcactttct actctgttga caaccattgt   1500
ctcctcttat tttcttttca ttttctgtaa ctttttcgtt aaactttagc ttgcatttgt   1560
aacgaatttt taaattcact tttgtttatt tgtcagattg taagtacttt ctctaatcac   1620
tttttttca aggcaatcag ggtatattat attgtacttc agcacagttt tagagaacaa   1680
ttgttataat taaatgataa ggtagaatat ttctgcatat aaattctggc tggcgtggaa   1740
atattcttat tggtagaaac aactacatcc tggtcatcat cctgcctttc tctttatggt   1800
tacaatgata tacactgttt gagatgagga taaaatactc tgagtccaaa ccgggcccct   1860
ctgctaacca tgttcatgcc ttcttctttt tcctacagct cctgggcaac gtgctggtta   1920
ttgtgctgtc tcatcatttt ggcaaagaat tgtaatacga ctcactatag ggcgagccac   1980
catggctaga ttagataaaa gtaaagtgat taacagcgca ttagagctgc ttaatgaggt   2040
cggaatcgaa ggtttaacaa cccgtaaact cgcccagaag ctaggtgtag agcagcctac   2100
attgtattgg catgtaaaaa ataagcgggc tttgctcgac gccttagcca ttgagatgtt   2160
agataggcac catactcact tttgcccttt agaaggggaa agctggcaag atttttttacg   2220
taataacgct aaaagtttta gatgtgcttt actaagtcat cgcgatggag caaaagtaca   2280
tttaggtaca cggcctacag aaaaacagta tgaaactctc gaaaatcaat tagccttttt   2340
atgccaacaa ggtttttcac tagagaatgc cttatatgca ctcagcgccg tggggcattt   2400
tactttaggt tgcgtattgg aagatcaaga gcatcaagtc gctaaagaag aaagggaaac   2460
acctactact gatagtatgc cgccattatt acgacaagct atcgaattat ttgatcacca   2520
aggtgcagag ccagccttct tattcggcct tgaattgatc atatgcggat tagaaaaaca   2580
acttaaatgt gaaagtgggt ccccaaaaaa gaagagaaag gtcgacggcg gtggtgcttt   2640
```

```
gtctcctcag cactctgctg tcactcaagg aagtatcatc aagaacaagg agggcatgga   2700
tgctaagtca ctaactgcct ggtcccggac actggtgacc ttcaaggatg tatttgtgga   2760
cttcaccagg gaggagtgga agctgctgga cactgctcag cagatcgtgt acagaaatgt   2820
gatgctggag aactataaga acctggtttc cttgggttat cagcttacta agccagatgt   2880
gatcctccgg ttggagaagg gagaagagcc ctggctggtg gagagagaaa ttcaccaaga   2940
gacccatcct gattcagaga ctgcatttga aatcaaatca tcagtttaag cgtacagcgg   3000
ggatccacta gtccagtgtg gtggaattct gcagatatcc agcacagtgg cggccgctcg   3060
agtctagagg gcccgtttaa acccgctgat cagcctcgac tgtgccttct agttgccagc   3120
catctgttgt ttgcccctcc cccgtgcctt ccttgaccct ggaaggtgcc actcccactg   3180
tcctttccta ataaaatgag gaaattgcat cgcattgtct gagtaggtgt cattctattc   3240
tggggggtgg ggtggggcag gacagcaagg gggaggattg ggaagacaat agcaggcatg   3300
ctggggatgc ggtgggctct atggcttctg aggcggaaag aaccagctgg ggctctaggg   3360
ggtatcccca cgcgccctgt agcggcgcat taagcgcggc gggtgtggtg gttacgcgca   3420
gcgtgaccgc tacacttgcc agcgccctag cgcccgctcc tttcgctttc ttcccttcct   3480
ttctcgccac gttcgccggc tttccccgtc aagctctaaa tcgggggcatc cctttagggt   3540
tccgatttag tgctttacgg cacctcgacc ccaaaaaact tgattagggt gatggttcac   3600
gtagtgggcc atcgccctga tagacggttt ttcgcccttt gacgttggag tccacgttct   3660
ttaatagtgg actcttgttc caaactggaa caacactcaa ccctatctcg gtctattctt   3720
ttgatttata agggattttg gggatttcgg cctattggtt aaaaaatgag ctgatttaac   3780
aaaaatttaa cgcgaattaa ttctgtggaa tgtgtgtcag ttagggtgtg gaaagtcccc   3840
aggctcccca ggcaggcaga agtatgcaaa gcatgcatct caattagtca gcaaccaggt   3900
gtggaaagtc cccaggctcc ccagcaggca gaagtatgca aagcatgcat ctcaattagt   3960
cagcaaccat agtcccgccc ctaactccgc ccatcccgcc cctaactccg cccagttccg   4020
cccattctcc gccccatggc tgactaattt tttttattta tgcagaggcc gaggccgcct   4080
ctgcctctga gctattccag aagtagtgag gaggcttttt tggaggccta ggcttttgca   4140
aaaagctccc gggagcttgt atatccattt tcggatctga tcagcacgtg ttgacaatta   4200
atcatcggca tagtatatcg gcatagtata atacgacaag gtgaggaact aaaccatggc   4260
caagttgacc agtgccgttc cggtgctcac cgcgcgcgac gtcgccggag cggtcgagtt   4320
ctggaccgac cggctcgggt tctcccggga cttcgtggag gacgacttcg ccggtgtggt   4380
ccgggacgac gtgaccctgt tcatcagcgc ggtccaggac caggtggtgc cggacaacac   4440
cctggcctgg gtgtgggtgc gcggcctgga cgagctgtac gccgagtggt cggaggtcgt   4500
gtccacgaac ttccgggacg cctccgggcc ggccatgacc gagatcggcg agcagccgtg   4560
gggggcggag ttcgccctgc gcgacccggc cggcaactgc gtgcacttcg tggccgagga   4620
gcaggactga cacgtgctac gagatttcga ttccaccgcc gccttctatg aaaggttggg   4680
cttcggaatc gttttccggg acgccggctg gatgatcctc cagcgcgggg atctcatgct   4740
ggagttcttc gcccacccca acttgtttat tgcagcttat aatggttaca aataaagcaa   4800
tagcatcaca aatttcacaa ataaagcatt tttttcactg cattctagtt gtggtttgtc   4860
caaactcatc aatgtatctt atcatgtctg tataccgtcg acctctagct agagcttggc   4920
gtaatcatgg tcatagctgt ttcctgtgtg aaattgttat ccgctcacaa ttccacacaa   4980
```

-continued

```
catacgagcc ggaagcataa agtgtaaagc ctggggtgcc taatgagtga gctaactcac   5040
attaattgcg ttgcgctcac tgcccgcttt ccagtcggga aacctgtcgt gccagctgca   5100
ttaatgaatc ggccaacgcg cggggagagg cggtttgcgt attgggcgct cttccgcttc   5160
ctcgctcact gactcgctgc gctcggtcgt tcggctgcgg cgagcggtat cagctcactc   5220
aaaggcggta atacggttat ccacagaatc aggggataac gcaggaaaga gagctcacgg   5280
ggacagcccc cccccaaagc ccccagggat gtaattacgt ccctcccccg ctagggggca   5340
gcagcgagcc gcccggggct ccgctccggt ccggcgctcc ccccgcatcc ccgagccggc   5400
agcgtgcggg gacagcccgg gcacggggaa ggtggcacgg gatcgctttc ctctgaacgc   5460
ttctcgctgc tctttgagcc tgcagacacc tggggggata cggggaaaaa gctttaggct   5520
gaaagagaga tttagaatga cagaatcata gaacggcctg ggttgcaaag gagcacagtg   5580
ctcatccaga tccaaccccc tgctatgtgc agggtcatca accagcagcc caggctgccc   5640
agagccacat ccagcctggc cttgaatgcc tgcaggacat gtgagcaaaa ggccagcaaa   5700
aggccaggaa ccgtaaaaag gccgcgttgc tggcgttttt ccataggctc cgcccccctg   5760
acgagcatca caaaaatcga cgctcaagtc agaggtggcg aaacccgaca ggactataaa   5820
gataccaggc gtttccccct ggaagctccc tcgtgcgctc tcctgttccg accctgccgc   5880
ttaccggata cctgtccgcc tttctccctt cgggaagcgt ggcgctttct caatgctcac   5940
gctgtaggta tctcagttcg gtgtaggtcg ttcgctccaa gctgggctgt gtgcacgaac   6000
cccccgttca gcccgaccgc tgcgccttat ccggtaacta tcgtcttgag tccaacccgg   6060
taagacacga cttatcgcca ctggcagcag ccactggtaa caggattagc agagcgaggt   6120
atgtaggcgg tgctacagag ttcttgaagt ggtggcctaa ctacggctac actagaagga   6180
cagtatttgg tatctgcgct ctgctgaagc cagttacctt cggaaaaaga gttggtagct   6240
cttgatccgg caaacaaacc accgctggta gcggtggttt ttttgtttgc aagcagcaga   6300
ttacgcgcag aaaaaaagga tctcaagaag atcctttgat cttttctacg gggtctgacg   6360
ctcagtggaa cgaaaactca cgttaaggga ttttggtcat gagattatca aaaaggatct   6420
tcacctagat ccttttaaat taaaaatgaa gttttaaatc aatctaaagt atatatgagt   6480
aaacttggtc tgacagttac caatgcttaa tcagtgaggc acctatctca gcgatctgtc   6540
tatttcgttc atccatagtt gcctgactcc ccgtcgtgta gataactacg atacgggagg   6600
gcttaccatc tggccccagt gctgcaatga taccgcgaga cccacgctca ccggctccag   6660
atttatcagc aataaaccag ccagccggaa gggccgagcg cagaagtggt cctgcaactt   6720
tatccgcctc catccagtct attaattgtt gccgggaagc tagagtaagt agttcgccag   6780
ttaatagttt gcgcaacgtt gttgccattg ctacaggcat cgtggtgtca cgctcgtcgt   6840
ttggtatggc ttcattcagc tccggttccc aacgatcaag gcgagttaca tgatccccca   6900
tgttgtgcaa aaaagcggtt agctccttcg gtcctccgat cgttgtcaga agtaagttgg   6960
ccgcagtgtt atcactcatg gttatggcag cactgcataa ttctcttact gtcatgccat   7020
ccgtaagatg cttttctgtg actggtgagt actcaaccaa gtcattctga gaatagtgta   7080
tgcggcgacc gagttgctct tgcccggcgt caatacggga taataccgcg ccacatagca   7140
gaactttaaa agtgctcatc attggaaaac gttcttcggg gcgaaaactc tcaaggatct   7200
taccgctgtt gagatccagt tcgatgtaac ccactcgtgc acccaactga tcttcagcat   7260
cttttacttt caccagcgtt tctgggtgag caaaaacagg aaggcaaaat gccgcaaaaa   7320
agggaataag ggcgacacgg aaatgttgaa tactcatact cttccttttt caatattatt   7380
```

-continued

```
gaagcattta tcagggttat tgtctcatga gcggatacat atttgaatgt atttagaaaa   7440

ataaacaaat aggggttccg cgcacatttc cccgaaaagt gccacctgac gtc          7493
```